US012668599B2

(12) United States Patent
Eastman et al.

(10) Patent No.: US 12,668,599 B2
(45) Date of Patent: Jun. 30, 2026

(54) HETEROBIFUNCTIONAL COMPOUNDS AND METHODS OF TREATING DISEASE

(71) Applicant: Halda Therapeutics OpCo, Inc., New Haven, CT (US)

(72) Inventors: Kyle J. Eastman, Killingworth, CT (US); Katherine J. Kayser-Bricker, Branford, CT (US); James John Mousseau, Salem, CT (US); Kanak Shail Raina, Branford, CT (US)

(73) Assignee: Halda Therapeutics OpCo, Inc., New Haven, CT (US)

( * ) Notice: Subject to any disclaimer, the term of this patent is extended or adjusted under 35 U.S.C. 154(b) by 0 days.

(21) Appl. No.: 18/920,528

(22) Filed: Oct. 18, 2024

(65) Prior Publication Data

US 2025/0136611 A1 May 1, 2025

Related U.S. Application Data

(60) Provisional application No. 63/563,000, filed on Mar. 8, 2024, provisional application No. 63/618,075, filed on Jan. 5, 2024, provisional application No. 63/544,710, filed on Oct. 18, 2023.

(51) Int. Cl.

| | |
|---|---|
| ***C07D 495/14*** | (2006.01) |
| ***A61K 31/551*** | (2006.01) |
| ***A61P 35/00*** | (2006.01) |
| ***C07D 519/00*** | (2006.01) |

(52) U.S. Cl.

CPC .......... *C07D 495/14* (2013.01); *A61K 31/551* (2013.01); *A61P 35/00* (2018.01); *C07D 519/00* (2013.01)

(58) Field of Classification Search

CPC .. C07D 495/14; C07D 519/00; A61K 31/551; A61P 35/00

See application file for complete search history.

(56) References Cited

U.S. PATENT DOCUMENTS

| | | | |
|---|---|---|---|
| 4,133,814 A | 1/1979 | Jones et al. | |
| 7,344,699 B2 | 3/2008 | Lappin et al. | |
| 7,390,784 B2 | 6/2008 | Briesewitz et al. | |
| 9,597,343 B2 | 3/2017 | Chimmanamada et al. | |
| 10,772,962 B2 | 9/2020 | Qian et al. | |
| 10,836,749 B1 | 11/2020 | Fan et al. | |
| 11,572,371 B2 | 2/2023 | Fan et al. | |
| 2006/0116364 A1 | 6/2006 | Hamaoka et al. | |
| 2014/0357661 A1 | 12/2014 | Bradbury et al. | |
| 2016/0175284 A1 | 6/2016 | Labadie et al. | |
| 2016/0175289 A1 | 6/2016 | Labadie et al. | |
| 2016/0272639 A1 | 9/2016 | Crew et al. | |
| 2016/0367526 A1 | 12/2016 | Govek et al. | |
| 2017/0065719 A1 | 3/2017 | Qian et al. | |
| 2017/0129855 A1 | 5/2017 | Liang et al. | |
| 2017/0281784 A1 | 10/2017 | Wang et al. | |
| 2017/0327469 A1 | 11/2017 | Crew et al. | |
| 2018/0015087 A1 | 1/2018 | Liu et al. | |
| 2018/0021316 A1 | 1/2018 | Scott et al. | |
| 2018/0099940 A1 | 4/2018 | Crew et al. | |
| 2018/0111931 A1 | 4/2018 | Barlaam et al. | |
| 2018/0155322 A1 | 6/2018 | Crew et al. | |
| 2018/0215731 A1 | 8/2018 | Crew et al. | |
| 2018/0228907 A1 | 8/2018 | Crew et al. | |
| 2018/0291019 A1 | 10/2018 | Guan et al. | |
| 2018/0346461 A1 | 12/2018 | Crew et al. | |
| 2019/0119243 A1 | 4/2019 | Strum | |
| 2019/0375732 A1 | 12/2019 | Hung et al. | |
| 2020/0095205 A1 | 3/2020 | Crew et al. | |
| 2020/0155521 A1 | 5/2020 | Schwartz et al. | |
| 2020/0155689 A1 | 5/2020 | Crew et al. | |
| 2020/0255450 A1* | 8/2020 | Fan | A61P 31/00 |
| 2021/0085700 A1 | 3/2021 | Chimmanamada et al. | |
| 2021/0087169 A1 | 3/2021 | Fan et al. | |
| 2021/0187108 A1 | 6/2021 | Qian et al. | |
| 2021/0196710 A1 | 7/2021 | Snyder et al. | |
| 2021/0220475 A1 | 7/2021 | Crew et al. | |
| 2021/0284654 A1 | 9/2021 | Yamazaki et al. | |
| 2022/0079931 A1 | 3/2022 | Wang et al. | |
| 2022/0259154 A1 | 8/2022 | Berlin et al. | |
| 2023/0135173 A1 | 5/2023 | Fan et al. | |
| 2023/0183209 A1 | 6/2023 | Crew et al. | |
| 2023/0203030 A1 | 6/2023 | Crew et al. | |
| 2023/0263893 A1 | 8/2023 | Qian et al. | |
| 2023/0331681 A1 | 10/2023 | Berlin et al. | |
| 2023/0406837 A1 | 12/2023 | London et al. | |
| 2024/0059686 A1 | 2/2024 | Crew et al. | |

(Continued)

FOREIGN PATENT DOCUMENTS

| | | |
|---|---|---|
| AU | 2020259946 B2 | 5/2023 |
| CN | 108379591 A | 8/2018 |

(Continued)

OTHER PUBLICATIONS

Meanwell, N.A., "Synopsis of some recent tactical application of bioisosteres in drug design." Journal of medicinal chemistry 54.8 (2011): 2529-2591.*

Raina, Kanak et al. "PROTAC-Induced BET Protein Degradation as a Therapy for Castration-Resistant Prostate Cancer." Proceedings of the National Academy of Sciences—PNAS 113.26 (2016): 7124-7129. (Year: 2016).*

Noblejas-López, M.d.M et al. TACKling Cancer by Targeting Selective Protein Degradation. Pharmaceutics 2023, 15, 2442. https://doi.org/10.3390/pharmaceutics15102442 (Year: 2023).*

Liu Z et al. An overview of PROTACs: a promising drug discovery paradigm. Mol Biomed. Dec. 20, 2022;3(1):46. doi: 10.1186/s43556-022-00112-0. PMID: 36536188; PMCID: PMC9763089 (Year: 2022).*

Choudhary D et al. Target protein degradation by protacs: A budding cancer treatment strategy. Pharmacol Ther. Oct. 2023;250: 108525. doi: 10.1016/j.pharmthera.2023.108525. Epub Sep. 9, 2023. PMID: 37696366. (Year: 2023).*

(Continued)

*Primary Examiner* — Renee Claytor
*Assistant Examiner* — Elena V Vishnyakova
(74) *Attorney, Agent, or Firm* — Morgan, Lewis & Bockius LLP

(57) ABSTRACT

The invention provides heterobifunctional compounds, pharmaceutical compositions, and their use treating disease, such as cancer.

30 Claims, 24 Drawing Sheets

(56) References Cited

U.S. PATENT DOCUMENTS

| | | | |
|---|---|---|---|
| 2024/0059711 | A1 | 2/2024 | Wang et al. |
| 2024/0066032 | A1 | 2/2024 | Chirnomas et al. |
| 2024/0076295 | A1 | 3/2024 | Crew et al. |
| 2024/0131023 | A1 | 4/2024 | Snyder et al. |
| 2024/0139326 | A1 | 5/2024 | London et al. |
| 2024/0180900 | A1 | 6/2024 | Peck et al. |
| 2024/0238424 | A1 | 7/2024 | Gerritz et al. |
| 2024/0299366 | A1 | 9/2024 | Crew et al. |
| 2024/0325547 | A1 | 10/2024 | Berlin et al. |
| 2024/0408093 | A1 | 12/2024 | Gerritz et al. |
| 2025/0009737 | A1 | 1/2025 | Zhang et al. |
| 2025/0082763 | A1 | 3/2025 | Li et al. |
| 2025/0082764 | A1 | 3/2025 | Li et al. |
| 2025/0099596 | A1 | 3/2025 | Yang et al. |
| 2025/0136611 | A1 | 5/2025 | Eastman et al. |
| 2025/0136619 | A1 | 5/2025 | Gerritz et al. |
| 2025/0281623 | A1 | 9/2025 | Eastman et al. |

FOREIGN PATENT DOCUMENTS

| | | | | |
|---|---|---|---|---|
| CN | 112574278 | A | 3/2021 | |
| CN | 113582974 | A | 11/2021 | |
| CN | 113896669 | A | 1/2022 | |
| CN | 114105977 | A | 3/2022 | |
| CN | 114181277 | A | 3/2022 | |
| CN | 116354933 | A | 6/2023 | |
| EP | 3699167 | A1 | 8/2020 | |
| EP | 3957633 | A1 | 2/2022 | |
| EP | 4166550 | A1 | 4/2023 | |
| WO | WO-2001077093 | A1 | 10/2001 | |
| WO | WO-2004022561 | A1 | 3/2004 | |
| WO | WO-2009063054 | A1 | 5/2009 | |
| WO | WO-2011156518 | A2 | 12/2011 | |
| WO | WO-2015160845 | A2 | 10/2015 | |
| WO | WO-2015160845 | A3 | 12/2015 | |
| WO | WO-2016073903 | A1 | 5/2016 | |
| WO | WO-2016118666 | A1 | 7/2016 | |
| WO | WO-2016149668 | A1 | 9/2016 | |
| WO | WO-2017059139 | A1 | 4/2017 | |
| WO | WO-2017136688 | A1 | 8/2017 | |
| WO | WO-2017140669 | A1 | 8/2017 | |
| WO | WO-2017201069 | A1 | 11/2017 | |
| WO | WO-2017204445 | A2 | 11/2017 | |
| WO | WO-2018033556 | A1 | 2/2018 | |
| WO | WO-2018071606 | A1 | 4/2018 | |
| WO | WO-2018119441 | A1 | 6/2018 | |
| WO | WO-2018144649 | A1 | 8/2018 | |
| WO | WO-2018178060 | A1 | 10/2018 | |
| WO | WO-2018191199 | A1 | 10/2018 | |
| WO | WO-2019020559 | A1 | 1/2019 | |
| WO | WO-2019023553 | A1 | 1/2019 | |
| WO | WO-2019040274 | A1 | 2/2019 | |
| WO | WO-2019052519 | A1 * | 3/2019 | ........... A61K 31/551 |
| WO | WO-2019079701 | A1 | 4/2019 | |
| WO | WO-2019114770 | A1 | 6/2019 | |
| WO | WO-2019144132 | A1 | 7/2019 | |
| WO | WO-2019173224 | A1 | 9/2019 | |
| WO | WO-2019195609 | A2 | 10/2019 | |
| WO | WO-2019199816 | A1 | 10/2019 | |
| WO | WO-2019215488 | A1 | 11/2019 | |
| WO | WO-2019222272 | A1 | 11/2019 | |
| WO | WO-2020049150 | A1 | 3/2020 | |
| WO | WO-2020049153 | A1 | 3/2020 | |
| WO | WO-2020081450 | A1 | 4/2020 | |
| WO | WO-2020206137 | A1 | 10/2020 | |
| WO | WO-2020211822 | A1 | 10/2020 | |
| WO | WO-2020214952 | A1 | 10/2020 | |
| WO | WO-2020225375 | A1 | 11/2020 | |
| WO | WO-2020232119 | A1 | 11/2020 | |
| WO | WO-2021026153 | A1 | 2/2021 | |
| WO | WO-2021063967 | A1 | 4/2021 | |
| WO | WO-2021091575 | A1 | 5/2021 | |
| WO | WO-2021097046 | A1 | 5/2021 | |
| WO | WO-2021113557 | A1 | 6/2021 | |
| WO | WO-2021116074 | A1 | 6/2021 | |
| WO | WO-2021127039 | A1 | 6/2021 | |
| WO | WO-2021127042 | A1 | 6/2021 | |
| WO | WO-2021127043 | A1 | 6/2021 | |
| WO | WO-2021127046 | A1 | 6/2021 | |
| WO | WO-2021127443 | A1 | 6/2021 | |
| WO | WO-2021170793 | A1 | 9/2021 | |
| WO | WO-2021178846 | A1 | 9/2021 | |
| WO | WO-2021214253 | A1 | 10/2021 | |
| WO | WO-2021214254 | A1 | 10/2021 | |
| WO | WO-2021231927 | A1 | 11/2021 | |
| WO | WO-2021249534 | A1 | 12/2021 | |
| WO | WO-2022011205 | A1 | 1/2022 | |
| WO | WO-2022025640 | A1 | 2/2022 | |
| WO | WO-2022048527 | A1 | 3/2022 | |
| WO | WO-2022087125 | A1 | 4/2022 | |
| WO | WO-2022106711 | A1 | 5/2022 | |
| WO | WO-2022109395 | A2 | 5/2022 | |
| WO | WO-2022125969 | A1 | 6/2022 | |
| WO | WO-2022133446 | A1 | 6/2022 | |
| WO | WO-2022166980 | A1 | 8/2022 | |
| WO | WO-2022187392 | A1 | 9/2022 | |
| WO | WO-2022187588 | A1 | 9/2022 | |
| WO | WO-2022218956 | A1 | 10/2022 | |
| WO | WO-2022218958 | A1 | 10/2022 | |
| WO | WO-2022235585 | A1 | 11/2022 | |
| WO | WO-2022235698 | A1 | 11/2022 | |
| WO | WO-2022251588 | A1 | 12/2022 | |
| WO | WO-2023287938 | A1 | 1/2023 | |
| WO | WO-2023023531 | A1 | 2/2023 | |
| WO | WO-2023059581 | A1 | 4/2023 | |
| WO | WO-2023059582 | A1 | 4/2023 | |
| WO | WO-2023059583 | A1 | 4/2023 | |
| WO | WO-2023059605 | A1 | 4/2023 | |
| WO | WO-2023059609 | A1 | 4/2023 | |
| WO | WO-2023175477 | A1 | 9/2023 | |
| WO | WO-2023180388 | A1 | 9/2023 | |
| WO | WO-2023187086 | A1 | 10/2023 | |
| WO | WO-2023212599 | A2 | 11/2023 | |
| WO | WO-2023215311 | A1 | 11/2023 | |
| WO | WO-2024006781 | A1 | 1/2024 | |
| WO | WO-2024033513 | A1 | 2/2024 | |
| WO | WO-2024054602 | A1 | 3/2024 | |
| WO | WO-2024054603 | A1 * | 3/2024 | ............. A61P 35/00 |
| WO | WO-2024054604 | A1 | 3/2024 | |
| WO | WO-2024054952 | A1 | 3/2024 | |
| WO | WO-2024054953 | A1 | 3/2024 | |
| WO | WO-2024054954 | A1 | 3/2024 | |
| WO | WO-2024054955 | A1 | 3/2024 | |
| WO | WO-2024054956 | A1 | 3/2024 | |
| WO | WO-2024083716 | A1 | 4/2024 | |
| WO | WO-2024097775 | A1 | 5/2024 | |
| WO | WO-2024102784 | A1 | 5/2024 | |
| WO | WO-2024105147 | A1 | 5/2024 | |
| WO | WO-2024138077 | A1 | 6/2024 | |
| WO | WO-2024146617 | A1 | 7/2024 | |
| WO | WO-2024197429 | A1 | 10/2024 | |
| WO | WO-2024211684 | A1 | 10/2024 | |
| WO | WO-2025011623 | A1 | 1/2025 | |
| WO | WO-2025040147 | A1 | 2/2025 | |
| WO | WO-2025081082 | A1 | 4/2025 | |
| WO | WO-2025081091 | A1 | 4/2025 | |
| WO | WO-2025085738 | A1 | 4/2025 | |
| WO | WO-2025189056 | A1 | 9/2025 | |
| WO | WO-2025189057 | A1 | 9/2025 | |

OTHER PUBLICATIONS

Ma Z et al. RIPTACs: A groundbreaking approach to drug discovery. Drug Discov Today. Nov. 2023;28(11):103774. doi: 10.1016/j.drudis.2023.103774. Epub Sep. 19, 2023. PMID: 37734702; PMCID: PMC11144445. (Year: 2023).*

Gerry et al. "Unifying principles of bifunctional, proximity-inducing small molecules", Nat Chem Biol. Apr. 2020 ; 16(4): 369-378. (Year: 2020).*

Abdel-Magid, A. F. "Combination of Cyclin-Dependent Kinase 4 Inhibitors and Androgen Receptor Inhibitors as Cancer Therapy," ACS Medicinal Chemistry Letters, 2022, 13(9), 1408-1410.

(56) References Cited

OTHER PUBLICATIONS

Barchéchath, S. et al. "Rational Design of Multitargeted Tyrosine Kinase Inhibitors: A Novel Approach," Chem. Biol. Drug Des., 2009, 73, 380-387.
Beckers, T. et al. "Chimerically designed HDAC- and tyrosine kinase inhibitors. A series of erlotinib hybrids as dual-selective inhibitors of EGFR, HER2 and histone deacetylases," Med. Chem. Commun., 2012, 3, 829-835.
Duan, Y. et al. "Targeting Brd4 for cancer therapy: inhibitors and degraders," Med. Chem. Commun., 2018, 9, 1779-1802.
Filippakopoulos, P. et al. "Selective Inhibition of BET Bromodomains," Nature, 2010, 468 (7327), 1067-1073.
Gourisankar, S. et al. "Rewiring Cancer Drivers to Activate Apoptosis," bioRxiv reprints, Dec. 7, 2022, retrieved from https://doi.org/10.1101/2022.12.04.517548, 36 pages.
Guo, J. et al. "BCL6 confers KRAS-mutant non-small-cell lung cancer resistance to BET inhibitors," J. Clin. Invest., 2021, 131(1), e133090.
Han, X. et al. "Discovery of ARD-69 as a highly potent proteolysis targeting chimera (PROTAC) degrader of androgen receptor (AR) for the treatment of prostate cancer," Journal of Medicinal Chemistry, 2019, 62(2), 941-964.
Hu, J. et al. "Discovery of ERD-308 as a highly potent proteolysis targeting chimera (PROTAC) degrader of estrogen receptor (ER)," Journal of Medicinal Chemistry, 2019, 62(3), 1420-1442.
International Search Report for International Application No. PCT/US2022/031280 dated Aug. 31, 2022 (11 pages).
International Search Report for International Application No. PCT/US2022/045603 dated Jan. 10, 2023 (8 pages).
International Search Report for International Application No. PCT/US2022/045604 dated Dec. 19, 2022 (6 pages).
International Search Report for International Application No. PCT/US2022/045606 dated Jan. 10, 2023 (7 pages).
International Search Report for International Application No. PCT/US2022/045631 dated Jan. 9, 2023 (6 pages).
International Search Report for International Application No. PCT/US2022/045637 dated Jan. 10, 2023 (7 pages).
International Search Report for International Application No. PCT/US2023/032248 dated Oct. 31, 2023 (10 pages).
International Search Report for International Application No. PCT/US2023/032252 dated Dec. 1, 2023 (8 pages).
International Search Report for International Application No. PCT/US2023/032254 dated Dec. 6, 2023 (7 pages).
International Search Report for International Application No. PCT/US2023/073694 dated Nov. 28, 2023 (8 pages).
International Search Report for International Application No. PCT/US2023/073695 dated Nov. 15, 2023 (7 pages).
International Search Report for International Application No. PCT/US2023/073696 dated Nov. 16, 2023 (9 pages).
International Search Report for International Application No. PCT/US2023/073697 dated Dec. 5, 2023 (8 pages).
International Search Report for International Application No. PCT/US2023/073698 dated Dec. 7, 2023 (7 pages).
International Search Report for International Application No. PCT/US2024/023239 dated Jun. 27, 2024 (6 pages).
International Search Report for International Application No. PCT/US2024/051958 dated Jan. 17, 2025 (7 pages).
Kerres, N. et al. "Chemically Induced Degradation of the Oncogenic Transcription Factor BCL6," Cell Reports, 2017, 20, 2860-2875.
Mu, X. et al. "Protein targeting chimeric molecules specific for dual bromodomain 4 (BRD4) and Polo-like kinase 1 (PLK1) proteins in acute myeloid leukemia cells," Biochemical and Biophysical Research Communications, 2020, 521, 833-839.
Ogitani, Y. et al. "Bystander killing effect of DS-8201a, a novel anti-human epidermal growth factor receptor 2 antibody-drug conjugate, in tumors with human epidermal growth factor receptor 2 heterogeneity," Cancer Sci., 2016, 107, 1039-1046.
Powell, C. E. et al. "Selective degradation of GSPT1 by cereblon modulators identified via a focused combinatorial library," ACS Chemical Biology, 2020, 15(10), 2722-2730.
Reddi, R. N. et al. "Tunable Methacrylamides for Covalent Ligand Directed Release Chemistry," JACS, 2021, 143, 4979-4992.
Sheppard, G. S. et al. "Discovery of N-Ethyl-4-[2-(4-fluoro-2,6-dimethyl-phenoxy)-5-(1-hydroxy-1-methyl-ethyl)phenyl]-6-methyl-7-oxo-1H-pyrrolo[2,3-c]pyridine-2-carboxamide (ABBV-744), a BET Bromodomain Inhibitor with Selectivity for the Second Bromodomain," J. Med. Chem., 2020, 63, 5585-5623.
Skidmore, L. et al. "ARX788, a Site-specific Anti-HER2 Antibody-Drug Conjugate, Demonstrates Potent and Selective Activity in HER2-low and T-DM1-resistant Breast and Gastric Cancers," Mol. Cancer Ther., 2020, 19, 1833-1843.
Stazi, G. et al. "Histone deacetylases as an epigenetic pillar for the development of hybrid inhibitors in cancer," Current Opinion in Chemical Biology, 2019, 50, 89-100.
Tang, P. et al. "Targeting Bromodomain and Extraterminal Proteins for Drug Discovery: From Current Progress to Technological Development," J. Med. Chem., 2021, 64, 2419-2435.
Tinworth, C. P. et al. "PROTAC-mediated degradation of Bruton's Tyrosine Kinase is inhibited by covalent binding," ACS Chemical Biology, 2019, 14(3), 342-347.
Trabucco, S. E. et al. "Inhibition of Bromodomain Proteins for the Treatment of Human Diffuse Large B-cell Lymphoma," Clinical Cancer Research, 2014, 21(1), 113-122.
Written Opinion for International Application No. PCT/US2022/031280 dated Aug. 31, 2022 (9 pages).
Written Opinion for International Application No. PCT/US2022/045603 dated Jan. 10, 2023 (11 pages).
Written Opinion for International Application No. PCT/US2022/045604 dated Dec. 19, 2022 (7 pages).
Written Opinion for International Application No. PCT/US2022/045606 dated Jan. 10, 2023 (8 pages).
Written Opinion for International Application No. PCT/US2022/045631 dated Jan. 9, 2023 (8 pages).
Written Opinion for International Application No. PCT/US2022/045637 dated Jan. 10, 2023 (6 pages).
Written Opinion for International Application No. PCT/US2023/032248 dated Oct. 31, 2023 (6 pages).
Written Opinion for International Application No. PCT/US2023/032252 dated Dec. 1, 2023 (9 pages).
Written Opinion for International Application No. PCT/US2023/032254 dated Dec. 6, 2023 (6 pages).
Written Opinion for International Application No. PCT/US2023/073694 dated Nov. 28, 2023 (10 pages).
Written Opinion for International Application No. PCT/US2023/073695 dated Nov. 15, 2023 (10 pages).
Written Opinion for International Application No. PCT/US2023/073696 dated Nov. 16, 2023 (10 pages).
Written Opinion for International Application No. PCT/US2023/073697 dated Dec. 5, 2023 (10 pages).
Written Opinion for International Application No. PCT/US2023/073698 dated Dec. 7, 2023 (9 pages).
Written Opinion for International Application No. PCT/US2024/023239 dated Jun. 27, 2024 (10 pages).
Written Opinion for International Application No. PCT/US2024/051958 dated Jan. 17, 2025 (6 pages).
Yu, X. et al. "Exploring Degradation of Mutant and Wild-Type Epidermal Growth Factor Receptors Induced by Proteolysis-Targeting Chimeras," J. Med. Chem., 2022, 65, 8416-8443.
Zhang, Q. et al. "Light-mediated multi-target protein degradation using arylazopyrazole photoswitchable PROTACs (AP-PROTACs)," Chemical Communications, 2022, 58(78), 10933-10936.
Ha, S. et al. "A Comprehensive Overview of Small-Molecule Androgen Receptor Degraders: Recent Progress and Future Perspectives," *J. Med. Chem.*, 2022, vol. 65, p. 16128-16154.
Kargbo, Robert B. "Targeted Degradation of Androgen Receptor for the Potential Treatment of Prostate Cancer," *ACS Med. Chem. Lett.*, 2022, vol. 13, p. 1558-1560.
Zhang, S. et al. "Design, Synthesis, and Biological Evaluation of Androgen Receptor (AR) Antagonist-Heat Shock Protein 90 (Hsp90) Inhibitor Conjugates for Targeted Therapy of Castration-Resistant Prostate Cancer," *J. Med. Chem.*, 2023, vol. 66, p. 4784-4801.

(56) References Cited

OTHER PUBLICATIONS

Bowry, A. et al. "BET Inhibition Induces HEXIM1- and RAD51-Dependent Conflicts between Transcription and Replication" *Cell Reports* 2018;25:2061-2069.
Donati, B. et al., "BRD4 and Cancer: going beyond transcriptional regulation," *Mol. Cancer* 2018;17:164.
Eischer, N. et al., "Emerging roles of BET proteins in transcription and co-transcriptional RNA processing," *WIREs RNA* 2023; 14(1):e1734.
Faivre, E. J. et al., "Selective inhibition of the BD2 bromodomain of BET proteins in prostate cancer," *Nature* 2020;578:306-310.
Nagarajan, S. et al., "Bromodomain Protein BRD4 Is Required for Estrogen Receptor-Dependent Enhancer Activation and Gene Transcription" *Cell Reports* 2014;8:460-469.
Shorstova, T. et al., "Achieving clinical success with BET inhibitors as anti-cancer agents," *Br. J. Cancer* 2021; 124: 1478-1490.
Winter, G. E. et al., "BET Bromodomain Proteins Function as Master Transcription Elongation Factors Independent of CDK9 Recruitment," *Molecular Cell* 2017:67:5-18.
Zhang, B. et al., "BRCA1 deficiency sensitizes breast cancer cells to bromodomain and extra-terminal domain (BET) inhibition," *Oncogene* 2018;37:6341-6356.
Zhang, S. and Roeder, R. G., "Resistance of estrogen receptor function to BET bromodomain inhibition is mediated by transcriptional coactivator cooperativity," *Nat. Struct. Mol. Biol.* 2025;32:98-112.
Zheng, Z. et al., "Super-enhancer-controlled positive feedback loop BRD4/ERα-RET-ERα promotes ERα-positive breast cancer," *Nucleic Acids Research* 2022;50(18):10230-10248.
Bauer, K. et al., "Degradation of BRD4—a promising treatment approach not only for hematologic but also for solid cancer," *Am. J. Cancer Res.* 2021;11(2):530-545.
Devaraj, S. G. T. et al., "HEXIM1 induction is mechanistically involved in mediating anti-AML activity of BET protein bromodomain antagonist," *Leukemia* 2016;30:504-508.
Feng, Q. et al., "An epigenomic approach to therapy for tamoxifen-resistant breast cancer," *Cell Res.* 2014;24:809-819.
Lin, X. et al., "HEXIM1 as a Robust Pharmacodynamic Marker for Monitoring Target Engagement of BET Family Bromodomain Inhibitors in Tumors and Surrogate Tissues," *Mol. Cancer Ther.* 2017;16(2):388-396.
Marcotte, R. et al. "Functional Genomic Landscape of Human Breast Cancer Drivers, Vulnerabilities, and Resistance" *Cell* 2016;164:293-309.
Murakami, S. et al., "Distinct Roles for BET Family Members in Estrogen Receptor a Enhancer Function and Gene Regulation in Breast Cancer Cells," *Mol. Cancer Res.* 2019;17(12):2356-2368.
Shao, H. et al., "HEXIM1 controls P-TEFb processing and regulates drug sensitivity in triple-negative breast cancer," *Mol. Biol. Cell.* 2020;31:1867-1878.
Udden. S. N. et al., "Targeting ESR1 mutation-induced transcriptional addiction in breast cancer with BET inhibition," *JCI Insight.* 2022; 7(17):e151851.
Wang, C. et al., "Estrogen induces c-myc gene expression via an upstream enhancer activated by the estrogen receptor and the AP-1 transcription factor," *Mol. Endocrinol.* 2011;25(9):1527-38.
Yeh, T. et al., "Identification of CCR2 and CD180 as Robust Pharmacodynamic Tumor and Blood Biomarkers for Clinical Use with BRD4/BET Inhibitors," *Clin. Cancer Res.* 2017;23(4):1025-1035.
Chung, G. G. et al., "Quantitative analysis of estrogen receptor heterogeneity in breast cancer," *Lab. Invest.* 2007;87:662-669.
Guglielmi, G. et al., "Pharmacological insights on novel oral selective estrogen receptor degraders in breast cancer," *Eur. J. Pharmacology*, 2024;969:176424.
Liang, J. et al., "GDC-9545 (Giredestrant): A Potent and Orally Bioavailable Selective Estrogen Receptor Antagonist and Degrader with an Exceptional Preclinical Profile for ER+ Breast Cancer," *J. Med. Chem.* 2021;64:11841-11856.
Luo, G. et al., "Development of novel tetrahydroisoquinoline-hydroxamate conjugates as potent dual SERDs/HDAC inhibitors for the treatment of breast cancer," *Eur. J. Med. Chem.* 2021;226:113870.
Miller, M. M. et al., "Development of an In vitro Assay Measuring Uterine-Specific Estrogenic Responses for Use in Chemical Safety Assessment," *Toxicological Sciences* 2016;154(1):162-173.
Ogba, N. et al., "HEXIM1 regulates 17beta-estradiol/estrogen receptor-alpha-mediated expression of cyclin D1 in mammary cells via modulation of P-TEFb," *Cancer Res.* 2008;68(17):7015-7024.
Rich, R. L. et al., "Kinetic analysis of estrogen receptor/ligand interactions," *Proc. Natl. Acad. Sci. U. S. A.* 2002;99(13):8562-8567.
Sengupta, S. et al., "Inhibition of BET proteins impairs estrogen-mediated growth and transcription in breast cancers by pausing RNA polymerase advancement," *Breast Cancer Res. Treat.* 2015; 150:265-278.
Wang, Y.-C. et al. "Different mechanisms for resistance to trastuzumab versus lapatinib in HER2-positive breast cancers—role of estrogen receptor and HER2 reactivation," *Breast Cancer Res.* 2011;13:R121.
Welsh, A. W. et al., "Standardization of estrogen receptor measurement in breast cancer suggests false-negative results are a function of threshold intensity rather than percentage of positive cells," *J. Clin. Oncol.* 2011;29(22):2978-2984.
Bardia, A. et al. "AMEERA-5: a randomized, double-blind phase 3 study of amcenestrant plus palbociclib versus letrozole plus palbociclib for previously untreated ER+/HER2-advanced breast cancer," *Ther. Adv. Med. Oncol.* 2022;14:1-12.
Bardia, A. et al., "AMEERA-1 phase 1/2 study of amcenestrant, SAR439859, in postmenopausal women with ER-positive/HER2-negative advanced breast cancer," *Nat. Commun.* 2022;13:4116.
Besret, L. et al., "Translational strategy using multiple nuclear imaging biomarkers to evaluate target engagement and early therapeutic efficacy of SAR439859, a novel selective estrogen receptor degrader," *EJNMMI Res.* 2020;10:70.
Campone, M. et al., "AMEERA-4: a randomized, preoperative window-of-opportunity study of amcenestrant versus letrozole in early breast cancer," *Breast Cancer Res.* 2023;25:141.
Chen, Y.-C. et al., "Latest generation estrogen receptor degraders for the treatment of hormone receptor-positive breast cancer," *Expert Opin. Investigational Drugs*, 2021;31(6):515-529.
El-Ahmad, Y. et al., "Discovery of 6-(2,4-Dichlorophenyl)-5-[4-[(3S)-1-(3-fluoropropyl)pyrrolidin-3-yl]oxyphenyl]-8,9-dihydro-7H-benzo[7]annulene-2-carboxylic acid (SAR439859), a Potent and Selective Estrogen Receptor Degrader (SERD) for the Treatment of Estrogen-Receptor-Positive Breast Cancer," *J. Med. Chem.* 2020;63:512-528.
Lawson, M. et al., "The Next-Generation Oral Selective Estrogen Receptor Degrader Camizestrant (AZD9833) Suppresses ER+ Breast Cancer Growth and Overcomes Endocrine and CDK4/6 Inhibitor Resistance," *Cancer Res.* 2023;83:3989-4004.
Rej, R. K. et al., "Targeting the Estrogen Receptor for the Treatment of Breast Cancer: Recent Advances and Challenges" *J. Med. Chem.* 2023;66(13):8339-8381.
Scott, J. S. et al., "Discovery of AZD9833, a Potent and Orally Bioavailable Selective Estrogen Receptor Degrader and Antagonist," *J. Med. Chem.* 2020;63:14530-14559.
Shomali, M. et al., "SAR439859, a Novel Selective Estrogen Receptor Degrader (SERD), Demonstrates Effective and Broad Antitumor Activity in Wild-Type and Mutant ER-Positive Breast Cancer Models," *Mol. Cancer Ther.* 2021;20:250-262.
Chen, Z. et al., "Discovery of ERD-3111 as a Potent and Orally Efficacious Estrogen Receptor PROTAC Degrader with Strong Antitumor Activity," *J. Med. Chem.* 2023;66:12559-12585.
De Savi, C. et al., "Optimization of a Novel Binding Motif to (E)-3-(3,5-Difluoro-4-((1R,3R)-2-(2 fluoro-2-methylpropyl)-3-methyl-2,3,4,9-tetrahydro-1H-pyrido[3,4-b]indol-1-yl)phenyl)acrylic Acid (AZD9496), a Potent and Orally Bioavailable Selective Estrogen Receptor Downregulator and Antagonist," *J. Med. Chem.* 2015;58:8128-8140.
Hamilton, E. et al., "A phase I dose escalation and expansion trial of the next-generation oral SERD camizestrant in women with ER-positive, HER2-negative advanced breast cancer: SERENA-1 monotherapy results," *Ann. Oncology*, 2024;35(8):707-717.

(56) References Cited

OTHER PUBLICATIONS

Joseph, J. D. et al., "The selective estrogen receptor downregulator GDC-0810 is efficacious in diverse models of ER+ breast cancer," *eLife* 2016;5:e15828.

Nagasawa, J. et al., "Identification of an Orally Bioavailable Chromene-Based Selective Estrogen Receptor Degrader (SERD) That Demonstrates Robust Activity in a Model of Tamoxifen-Resistant Breast Cancer," *J. Med. Chem.* 2018;61:7917-7928.

Tatton, M. R. et al. "First Multikilogram Synthesis of the Next-Generation Oral Selective ERα Degrader Camizestrant," *Org. Process Res. Dev.* 2024;28:2334-2342.

Turner, N. et al., "Design of SERENA-6, a phase III switching trial of camizestrant in ESR1-mutant breast cancer during first-line treatment," *Future Oncol.* 2023; 19(8):559-573.

Welsh, A. W. et al., "Quantitative Analysis of Estrogen Receptor Expression Shows SP1 Antibody Is More Sensitive Than 1D5," *Appl. Immunohistochem. Mol. Morphol.* 2013;21(2):139-147.

Will, M. et al. "Therapeutic resistance to anti-oestrogen therapy in breast cancer," Nat. Rev. Cancer 2023;23:673-685.

Zhou, F. et al., "SCR-6852, an oral and highly brain-penetrating estrogen receptor degrader (SERD), effectively shrinks tumors both in intracranial and subcutaneous ER + breast cancer models," Breast Cancer Res. 2023;25:96.

Collier, A. et al., "Exploratory biomarker analysis of acelERA Breast Cancer (BC): Phase II study of giredestrant vs. physician's choice of endocrine therapy (PCET) for previously treated, estrogen receptor-positive, HER2-negative advanced BC (ER+, HER2-aBC)," Poster presented on Jun. 3, 2023 at the American Society of Clinical Oncology Annual Meeting.

Eikesdal, H. P. et al., "Olaparib monotherapy as primary treatment in unselected triple negative breast cancer," *Ann. Oncology*, 2021;32(2):240-249.

Grese, T. A. et al., "Structure-Activity Relationships of Selective Estrogen Receptor Modulators: Modifications to the 2-Arylbenzothiophene Core of Raloxifene," *J. Med. Chem.* 1997;40:146-167.

Von Angerer, E. and Strohmeier, J. "2-Phenylindoles. Effect of N-Benzylation on Estrogen Receptor Affinity, Estrogenic Properties, and Mammary Tumor Inhibiting Activity" *J. Med. Chem.* 1987;30(1):131-136.

Yu, D. et al., "Hydrogen Peroxide-Inducible PROTACs for Targeted Protein Degradation in Cancer Cells," *ChemBioChem* 2023;24(17):e202300422.

International Search Report and Written Opinion for International Application No. PCT/US2025/018835, dated Jun. 12, 2025 (14 pages).

International Search Report and Written Opinion for International Application No. PCT/US2025/018836, dated Jun. 4, 2025 (17 pages).

* cited by examiner

HETEROBIFUNCTIONAL COMPOUNDS AND METHODS OF TREATING DISEASE

CROSS REFERENCE TO RELATED APPLICATIONS

This application claims the benefit of and priority to Chinese Patent Application serial number 202411404732.7, filed Oct. 9, 2024; U.S. Provisional Patent Application Ser. No. 63/563,000, filed Mar. 8, 2024; U.S. Provisional Patent Application Ser. No. 63/618,075, filed Jan. 5, 2024; and U.S. Provisional Patent Application Ser. No. 63/544,710, filed Oct. 18, 2023; the contents of each of which are hereby incorporated by reference in their entirety.

FIELD OF THE INVENTION

The invention provides heterobifunctional compounds, pharmaceutical compositions, and their use treating disease, such as cancer.

BACKGROUND

Cancer continues to be a significant health problem despite the substantial research efforts and scientific advances reported in the literature for treating this disease. Solid tumors, including prostate cancer, breast cancer, and lung cancer remain highly prevalent among the world population. The incidence of prostate cancer increases with age, and with increasing longevity of human subjects, there continues to be a corresponding rise in the number of patients suffering from prostate cancer. Breast cancer is one of the most common cancers among women and is a leading cause of death for women between ages 50-55. Lung cancer is a leading cause of death among cancer patients, where over 85% of lung cancers are non-small cell lung cancer (NSCLC). Many lung cancers are attributed to tobacco smoking. Current treatment options for these cancers are not effective for all patients and/or can have substantial adverse side effects.

New therapies are needed to address this unmet need in cancer therapy. In particular, new therapies are needed that achieve an anti-cancer effect through a different mechanism than commonly available therapies. Exemplary mechanisms for common anti-cancer therapies include (a) alkylation of DNA which limits ability of the cell to reproduce, (b) topoisomerase inhibition, in which the therapeutic agent inhibits the activity of a topoisomerase thereby limiting separation of strands of DNA, and (c) mitotic inhibition, where the therapeutic agent reduces ability of the cell to divide. New therapies that achieve an anti-cancer effect through a different mechanism present an opportunity to treat cancers more effectively and/or to treat cancers that have become resistant to currently available medicines.

The present invention addresses the foregoing needs and provides other related advantages.

SUMMARY

The invention provides heterobifunctional compounds, pharmaceutical compositions, and their use treating disease, such as cancer. In particular, one aspect of the invention provides a collection of heterobifunctional compounds, such as a compound represented by Formula I:

(I)

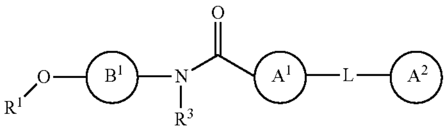

or a pharmaceutically acceptable salt thereof, where the variables are as defined in the detailed description. Further description of additional collections of heterobifunctional compounds are described in the detailed description. The compounds may be part of a pharmaceutical composition comprising a pharmaceutically acceptable carrier.

Another aspect of the invention provides a crystalline compound of Formula II-5:

(II-5)

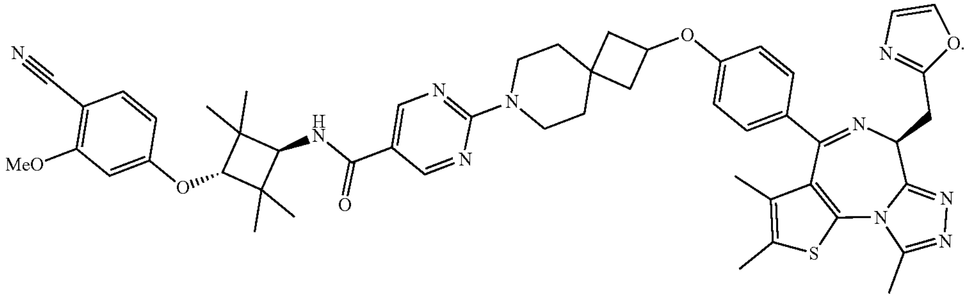

The compound may be part or a pharmaceutical composition comprising a pharmaceutically acceptable carrier.

Another aspect of the invention provides a method of treating cancer. The method comprises administering to a patient in need thereof a therapeutically effective amount of a compound described herein, such as a compound of Formula I, to treat the cancer.

Another aspect of the invention provides a method of causing death of a cancer cell. The method comprises contacting a cancer cell with an effective amount of a compound described herein, such as a compound of Formula I, to cause death of the cancer cell.

DETAILED DESCRIPTION

Figure 1:
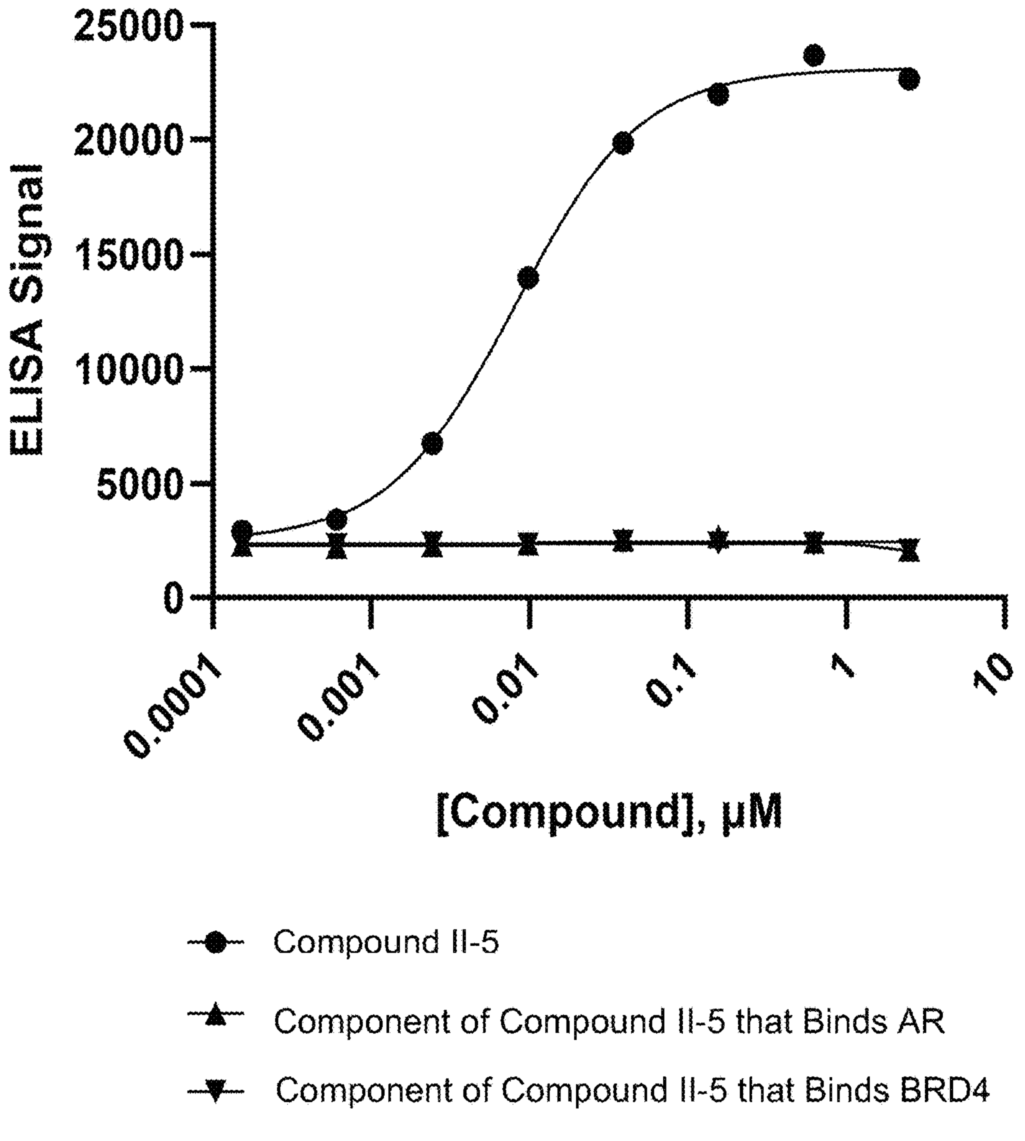
FIG. 1 is a graph showing detected ternary complex formation between test compound, androgen receptor, and BRD4 protein, as further described in Example 67.

The invention provides heterobifunctional compounds, pharmaceutical compositions, and their use treating disease, such as cancer. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

Compounds of the present invention include those described generally herein, and are further illustrated by the classes, subclasses, and species disclosed herein. As used herein, the following definitions shall apply unless otherwise indicated. These definitions apply regardless of whether a term is used by itself or in combination with other terms, unless otherwise indicated. Hence, the definition of "alkyl" applies to "alkyl" as well as the "alkyl" portions of "—O-alkyl" etc. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e., carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

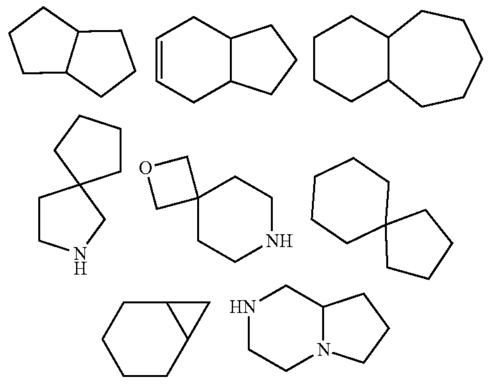

Exemplary bridged bicyclics include:

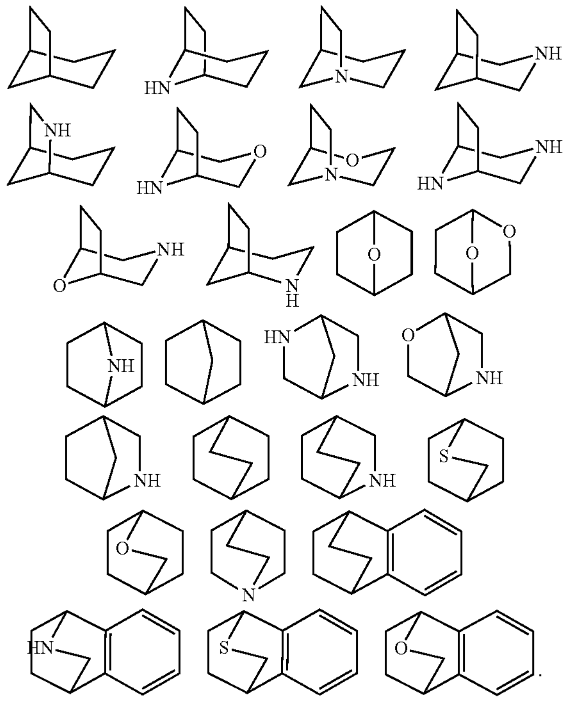

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $—(CH_2)_n—$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "—($C_0$ alkylene)-" refers to a bond. Accordingly, the term "—($C_{0-3}$ alkylene)-" encompasses a bond (i.e., $C_0$) and a —($C_{1-3}$ alkylene)- group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "haloaryl" refers to an aryl group that is substituted with at least one halogen. Exemplary haloaryl groups include chlorophenyl (e.g., 3-chlorophenyl, 4-chlorophenyl), fluorophenyl, and the like. The term "phenylene" refers to a bivalent phenyl group.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted. The term "haloheteroaryl" refers to a heteroaryl group that is substituted with at least one halogen. Exemplary haloheteroaryl groups include chloropyridine, fluoropyridine, chloropyrazole, fluoropyrazole, and the like. The term "heteroarylene" refers to a bivalent heteroaryl group. Similarly, the terms "pyrazolylene", "imidazolylene", and "pyrrolylene", respectively refer to bivalent pyrazolyl, imidazolyl, and pyrrolyl groups. Similarly, the terms "pyridazinylene," "pyrimidinylene," "pyrazinylene," and "pyridinylene," respectively refer to bivalent pyridazinyl, pyrimidinyl, pyrazinyl, and pyridinyl groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted. The term "heterocyclylene" refers to a bivalent heterocyclyl group. The terms "piperidinylene," "piperazinylene," and "azetidinylene", respectively refer to bivalent piperidinyl, piperazinyl, and azetidinyl groups.

As used herein, the term "heterocycloalkyl" refers to a saturated heterocyclyl. The term "heterocycloalkylene" refers to a bivalent heterocycloalkyl group.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $—(CH_2)_{0-4}R^o$; $—(CH_2)_{0-4}OR^o$; $—O(CH_2)_{0-4}R^o$, $—O—(CH_2)_{0-4}C(O)OR^o$; $—(CH_2)_{0-4}CH(OR^o)_2$; $—(CH_2)_{0-4}SR^o$; $—(CH_2)_{0-4}Ph$, which may be substituted with $R^o$; $—(CH_2)_{0-4}O(CH_2)_{0-1}Ph$ which may be substituted with $R^o$; —CH═CHPh, which may be substituted with $R^o$; $—(CH_2)_{0-40}$ $(CH_2)_{0-1}$-pyridyl which may be substituted with $R^o$; $—NO_2$; —CN; $—N_3$; $—(CH_2)_{0-4}N(R^o)_2$; $—(CH_2)_{0-4}N(R^o)C(O)R^o)$; $—N(R^o)C(S)R^o$; $—(CH_2)_{0-4}N(R^o)C(O)NR^o_2$; $—N(R^o)C(S)NR^o_2$; $—(CH_2)_{0-4}N(R^o)C(O)OR^o$; $—N(R^o)N(R^o)C(O)R^o$; $—N(R^o)N(R^o)C(O)NR^o_2$; $—N(R^o)N(R^o)C(O)OR^o$; $—(CH_2)_{0-4}C(O)R^o$; $—C(S)R^o$; $—(CH_2)_{0-4}C(O)OR^o$; $—(CH_2)_{0-4}C(O)SR^o$; $—(CH_2)_{0-4}C(O)OSiR^o_3$; $—(CH_2)_{0-4}OC(O)R^o$; $—OC(O)(CH_2)_{0-4}SR—$, $SC(S)SR^o$; $—(CH_2)_{0-4}SC(O)R^o$; $(CH_2)_{0-4}C(O)NR^o_2$; $—C(S)$ $NR^o_2$; $—C(S)SR^o$; $—SC(S)SR^o$, $—(CH_2)_{0-40}C(O)NR^o_2$; $—C(O)N(OR^o)R^o$; $—C(O)C(O)R^o$; $—C(O)CH_2C(O)R^o$; $—C(NOR^o)R^o$; $—(CH_2)_{0-4}SSR^o$; $—(CH_2)_{0-4}S(O)_2R^o$; $—(CH_2)_{0-4}S(O)_2OR^o$; $—(CH_2)_{0-4}OS(O)_2R^o$; $—S(O)_2NR^o_2$; $—S(O)(NR^o)R^o$; $—S(O)_2N═C(NR^o_2)_2$; $—(CH_2)_{0-4}S(O)R^o$; $—N(R^o)S(O)_2NR^o_2$; $—N(R^o)S(O)_2R^o$; $—N(OR^o)$ $R^o$; $—C(NH)NR^o_2$; $—P(O)_2R^o$; $—P(O)R^o_2$; $—OP(O)R^o_2$; $—OP(O)(OR^o)_2$; $SiR^o_3$; $—(C_{1-4}$ straight or branched) alkylene)$O—N(R^o_2$; or $—(C_{1-4}$ straight or branched) alkylene) $C(O)O—N(R^o_2$.

Each $R^o$ is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^o$ selected from ═O and ═S; or each $R^o$ is optionally substituted with a monovalent substituent independently selected from halogen, $—(CH_2)_{0-2}R^{\bullet}$, -(halo$R^{\bullet}$), $—(CH_2)_{0-2}OH$, $—(CH_2)_{0-2}OR^o$, $—(CH_2)_{0-2}CH(OR^{\bullet})_2$; —O(halo$R^{\bullet}$), —CN, $—N_3$, $—(CH_2)_{0-2}C(O)R^o$, $—(CH_2)_{0-2}C(O)OH$, $—(CH_2)_{0-2}C(O)OR^{\bullet}$, $—(CH_2)_{0-2}SR^{\bullet}$, $—(CH_2)_{0-2}SH$, $—(CH_2)_{0-2}NH_2$, $—(CH_2)_{0-2}NHR^{\bullet}$, $—(CH_2)_{0-2}NR^{\bullet}_2$, $—NO_2$, $—SiR^{\bullet}_3$, $—OSiR^{\bullet}_3$, $—C(O)SR^{\bullet}$, $—(C_{1-4}$ straight or branched alkylene) $C(O)OR^{\bullet}$, or $—SSR^{\bullet}$.

Each $R^{\bullet}$ is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens; or wherein an optional substituent on a saturated carbon is a divalent substituent independently selected from ═O, ═S, $═NNR^*_2$, $═NNHC(O)R^*$, $═NNHC(O)OR^*$, $═NNHS(O)_2$ $R^*$, $═NR^*$, $═NOR^*$, $—O(C(R^*_2))_{2-3}O—$, or $—S(C(R^*_2))_{2-3}S—$, or a divalent substituent bound to vicinal substitutable carbons of an "optionally substituted" group is $—O(CR^*_2)_{2-3}O—$, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, $—R^o$, -(halo$R^{\bullet}$), —OH, $—OR^{\bullet}$, —O (halo$R^{\bullet}$), —CN, —C(O) OH, —C(O) OR', $—NH_2$, $—NHR^{\bullet}$, $—NR^{\bullet}_2$, or $—NO_2$, wherein each $R^{\bullet}$ is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

An optional substituent on a substitutable nitrogen is independently $—R^{\dagger}$, $—NR^{\dagger}_2$, $—C(O)R^{\dagger}$, $—C(O)OR^{\dagger}$, $—C(O)CO)R^{\dagger}$, $—C(O)CH_2C(O)R^{\dagger}$, $—S(O)_2R^{\dagger}$, $—S(O)_2NR^{\dagger}_2$, $—C(S)NR^{\dagger}_2$, $—C(NH)NR^{\dagger}_2$, or $—N(R^{\dagger})S(O)_2R^{\dagger}$; wherein each $R^{\dagger}$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^{\dagger}$ is $C_{1-6}$ aliphatic, $R^{\dagger}$ is optionally substituted with halogen, $—R^{\bullet}$, -(halo$R^{\bullet}$), —OH, $—OR^{\bullet}$, —O(halo$R^{\bullet}$), —CN, —C(O)OH, $—C(O)OR^{\bullet}$, $—NH_2$, $—NHR^{\bullet}$, $—NR^{\bullet}_2$, or $—NO_2$, wherein each $R^o$ is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., Journal of Pharmaceutical Sciences (1977) 66 (1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. The invention includes compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples and tables herein is assumed to have the sufficient number of hydrogen atom(s) to satisfy the valences.

The terms "a" and "an" as used herein mean "one or more" and include the plural unless the context is inappropriate.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, tert-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "cycloalkylene" refers to a bivalent cycloalkyl group.

The term "haloalkyl" refers to an alkyl group that is substituted with at least one halogen. Exemplary haloalkyl groups include $-CH_2F$, $-CHF_2$, $-CF_3$, $-CH_2CF_3$, $-CF_2CF_3$, and the like. The term "chloroalkyl" refers to an alkyl group that is substituted with at least one chloro. The term "bromoalkyl" refers to an alkyl group that is substituted with at least one bromo. The term "haloalkylene" refers to a bivalent haloalkyl group.

The term "hydroxyalkyl" refers to an alkyl group that is substituted with at least one hydroxyl. Exemplary hydroxyalkyl groups include $-CH_2CH_2OH$, $-C(H)(OH)CH_3$, $-CH_2C(H)(OH)CH_2CH_2OH$, and the like.

The term "heteroalkyl" refers to an alkyl group in which one or more carbon atoms has been replaced by a heteroatom (e.g., N, O, or S). Exemplary heteroalkyl groups include $-OCH_3$, $-CH_2OCH_3$, $-CH_2CH_2N(CH_3)_2$, and $-CH_2CH_2OH$. The heteroalkyl group may contain, for example, from 2-4, 2-6, or 2-8 atoms selected from the group consisting of carbon and a heteroatom (e.g., N, O, or S). The phrase 3-8 membered heteroalkyl refers to a heteroalkyl group having from 3 to 8 atoms selected from the group consisting of carbon and a heteroatom. The term "heteroalkylene" refers to a bivalent heteroalkyl group.

The terms "alkenyl" and "alkynyl" are art-recognized and refer to unsaturated aliphatic groups analogous in length and possible substitution to the alkyls described above, but that contain at least one double or triple bond respectively. The term "haloalkenyl" refers to an alkenyl group that is substituted with at least one halogen. The term "fluoroalkenyl" refers to an alkenyl group that is substituted with at least one fluoro. The term "nitroalkenyl" refers to an alkenyl group that is substituted with at least one nitro.

The term "carbocyclylene" refers to a bivalent cycloaliphatic group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. The term "haloalkoxyl" refers to an alkoxyl group that is substituted with at least one halogen. Exemplary haloalkoxyl groups include $-OCH_2F$, $-OCHF_2$, $-OCF_3$, $-OCH_2CF_3$, $-OCF_2CF_3$, and the like.

The term "oxo" is art-recognized and refers to a "=O" substituent. For example, a cyclopentane substituted with an oxo group is cyclopentanone.

The term "amino" is art-recognized and refers to both unsubstituted and substituted amines, e.g., a moiety that may be represented by the general formulas:

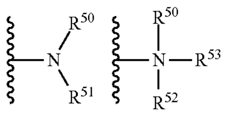

wherein $R^{50}$, $R^{51}$, $R^{52}$ and $R^{53}$ each independently represent a hydrogen, an alkyl, an alkenyl, $-(CH_2)_m-R^{61}$, or $R^{50}$ and $R^{51}$, taken together with the N atom to which they are attached complete a heterocycle having from 4 to 8 atoms in the ring structure; $R^{61}$ represents an aryl, a 3-7 membered cycloalkyl, a 4-7 membered cycloalkenyl, 5-10 membered heteroaryl, or 3-10 membered heterocyclyl; and m is zero or an integer in the range of 1 to 8.

The term "amido" is art-recognized and refers to both unsubstituted and substituted amides, e.g., a moiety that may be represented by the general formulas:

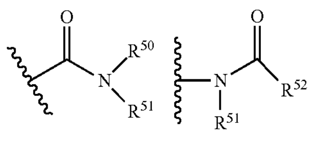

wherein $R^{50}$ and $R^{51}$ each independently represent a hydrogen, an alkyl, an alkenyl, $-(CH_2)_m-R^{61}$, or $R^{50}$ and $R^{51}$, taken together with the N atom to which they are attached complete a heterocycle having from 4 to 8 atoms in the ring structure; $R^{61}$ represents an aryl, a 3-7 membered cycloalkyl, a 4-7 membered cycloalkenyl, 5-10 membered heteroaryl, or 3-10 membered heterocyclyl; and m is zero or an integer in the range of 1 to 8; and $R^{52}$ is an alkyl, an alkenyl, or $-(CH_2)_m-R^{61}$.

The symbol "" indicates a point of attachment.

When any substituent or variable occurs more than one time in any constituent or the compound of the invention, its definition on each occurrence is independent of its definition at every other occurrence, unless otherwise indicated.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

The term "$IC_{50}$" is art-recognized and refers to the concentration of a compound that is required to achieve 50% inhibition of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. Heterobifunctional Compounds

One aspect of the invention provides heterobifunctional compounds. The compounds may be used in the pharmaceutical compositions and therapeutic methods described herein. Exemplary compounds are described in the following sections, along with exemplary procedures for making the compounds. Without being bound by theory, the compounds can facilitate therapeutic effects by binding to both an androgen receptor and BRD4 (bromodomain-containing protein 4).

Part A: Compound of Formula I

One aspect of the invention provides a compound represented by Formula I:

(I)

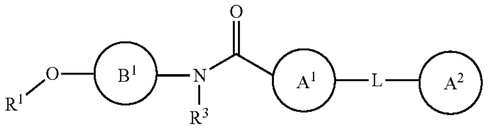

or a pharmaceutically acceptable salt thereof, wherein:

$R^1$ is phenyl substituted by (i) cyano and m occurrences of $R^4$, and (ii) $C_{1-4}$ alkoxyl or $C_{1-4}$ haloalkoxyl;

$R^2$ represents independently for each occurrence $C_{1-4}$ alkyl;

$R^3$ is hydrogen or $C_{1-4}$ alkyl;

$R^4$ is $C_{1-4}$ alkyl;

$R^5$ represents independently for each occurrence $C_{1-4}$ alkyl or halogen;

$A^1$ is a pyrimidinylene, pyridazinylene, pyrazinylene, pyridinylene, or phenylene, each of which is substituted with n occurrences of $R^5$;

L is a linker; and $A^2$ is one of the following:

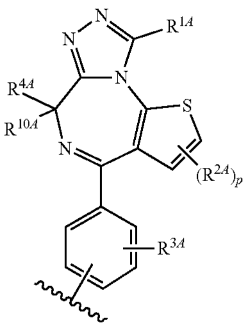

or

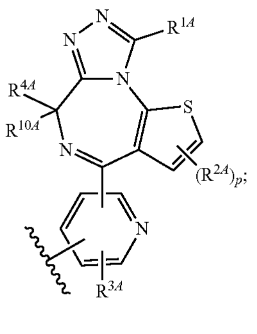

$B^1$ is (i) cyclobutylene substituted by 1, 2, 3, or 4 occurrences of $R^2$ or (ii) cyclohexylene substituted by 0, 1, or 2 occurrences of $R^2$;

$R^{1A}$ is $C_{1-4}$ alkyl or $C_{3-4}$ cycloalkyl;

$R^{2A}$ represents independently for each occurrence $C_{1-4}$ alkyl or $C_{3-4}$ cycloalkyl;

$R^{3A}$ is hydrogen, halo, $C_{1-4}$ alkyl, $C_{1-4}$ haloalkyl, or $C_{1-4}$ alkoxyl;

$R^{4A}$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^{5A}$)($R^{6A}$), —($C_{1-6}$ alkylene)-N($R^{5A}$)C(O)$R^{7A}$, —($C_{1-6}$ alkylene)-$CO_2R^{7A}$, —($C_{1-6}$ cycloalkyl, or hydrogen; or $R^{4A}$ and $R^{10A}$ taken together with the carbon atom to which they are attached form a $C_{3-5}$ saturated carbocyclic ring;

$R^{5A}$ and $R^{6A}$ are independently hydrogen, $C_{1-6}$ alkyl, or $C_{3-6}$ cycloalkyl; or $R^{5A}$ and $R^{6A}$ are taken together with the nitrogen atom to which they are attached to form a 3-7 membered ring containing 1 nitrogen atom;

$R^{7A}$ is $C_{1-6}$ alkyl, —($C_{1-6}$ alkylene)-($C_{3-6}$ cycloalkyl), or $C_{3-6}$ cycloalkyl;

$R^{10A}$ is hydrogen or $C_{1-4}$ alkyl; and m, n, and p are independently 0, 1, or 2.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula I.

As define generally above, $R^1$ is phenyl substituted by (i) cyano and m occurrences of $R^4$, and (ii) $C_{1-4}$ alkoxyl or $C_{1-4}$ haloalkoxyl. In certain embodiments, $R^1$ is phenyl substituted by (i) cyano and m occurrences of $R^4$, and (ii) $C_{1-4}$ alkoxyl. In certain embodiments, $R^1$ is phenyl substituted by cyano and $C_{1-4}$ alkoxyl. In certain embodiments, $R^1$ is phenyl substituted by cyano and methoxy. In certain embodiments, $R^1$ is

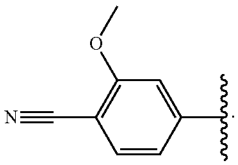 [SMILES: *c1ccc(C#N)c(OC)c1]

In certain embodiments, $R^1$ is phenyl substituted by (i) cyano and m occurrences of $R^4$, and (ii) $C_{1-4}$ haloalkoxyl. In certain embodiments, $R^1$ is phenyl substituted by cyano and $C_{1-4}$ haloalkoxyl. In certain embodiments, $R^1$ is phenyl substituted by cyano and $C_{1-4}$ fluoroalkoxyl. In certain embodiments, $R^1$ is phenyl substituted by cyano and trifluoromethoxy. In certain embodiments, $R^1$ is

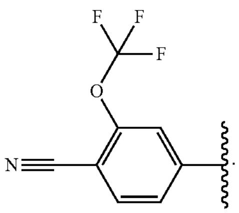 [SMILES: *c1ccc(C#N)c(OC(F)(F)F)c1]

In certain embodiments, $R^1$ is selected from the groups depicted in the compounds in Table 1 or 2 below.

As defined generally above, $R^2$ represents independently for each occurrence $C_{1-4}$ alkyl. In certain embodiments, $R^2$ is methyl. In certain embodiments, $R^2$ is selected from the groups depicted in the compounds in Table 1 or 2 below.

As defined generally above, $R^3$ is hydrogen or $C_{1-4}$ alkyl. In certain embodiments, $R^3$ is hydrogen. In certain embodiments, $R^3$ is $C_{1-4}$ alkyl. In certain embodiments, $R^3$ is selected from the groups depicted in the compounds in Table 1 or 2 below.

As defined generally above, $A^1$ is a pyrimidinylene, pyridazinylene, pyrazinylene, pyridinylene, or phenylene, each of which is substituted with n occurrences of $R^5$. In certain embodiments, $A^1$ is pyridazinylene substituted with n occurrences of $R^5$. In certain embodiments, $A^1$ is

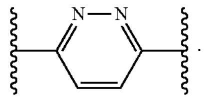 [SMILES: *c1ccc(*)nn1]

In certain embodiments, $A^1$ is pyrimidinylene substituted with n occurrences of $R^5$. In certain embodiments, $A^1$ is

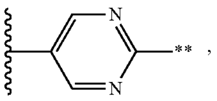

where *** is the point of attachment to L. In certain embodiments, $A^1$ is

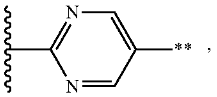

where *** is the point of attachment to L. In certain embodiments, $A^1$ is pyrazinylene substituted with n occurrences of $R^5$. In certain embodiments, $A^1$ is

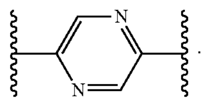 [SMILES: *c1cnc(*)cn1]

In certain embodiments, $A^1$ is pyridinylene substituted with n occurrences of $R^5$. In certain embodiments, $A^1$ is

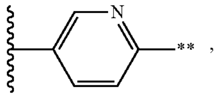

where *** is the point of attachment to L. In certain embodiments, $A^1$ is phenylene substituted with n occurrences of $R^5$. In certain embodiments, $A^1$ is

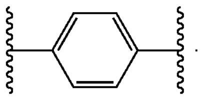 [SMILES: *c1ccc(*)cc1]

In certain embodiments, $A^1$ is a pyridazinylene substituted with 0 occurrences of $R^5$. In certain embodiments, $A^1$ is a pyrimidinylene substituted with 0 occurrences of $R^5$. In certain embodiments, $A^1$ is a pyrazinylene substituted with 0 occurrences of $R^5$. In certain embodiments, $A^1$ is a pyridinylene, substituted with 0 occurrences of $R^5$. In certain embodiments, $A^1$ is a phenylene substituted with 0 occurrences of $R^5$. In certain embodiments, $A^1$ is selected from the groups depicted in the compounds in Table 1 or 2 below.

As defined generally above, $A^2$ is

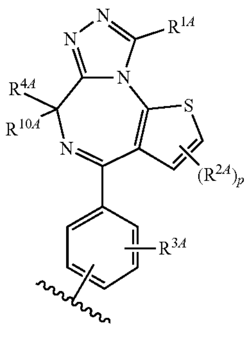

or

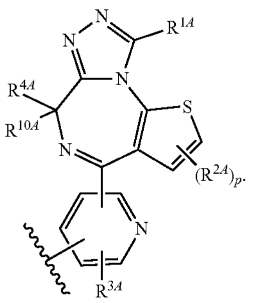

In certain embodiments, $A^2$ is

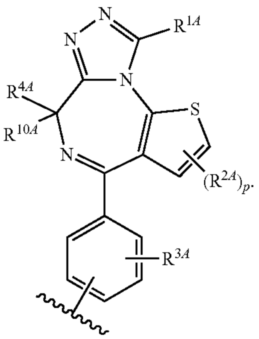

In certain embodiments, $A^2$ is
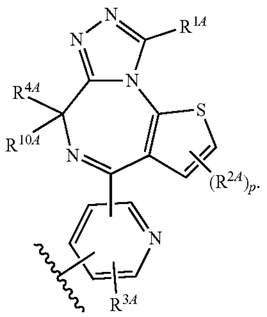
In certain embodiments, $A^2$ is
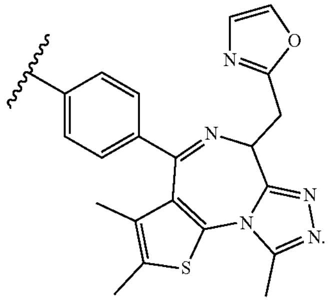 [SMILES: *c1ccc(C2=NC(Cc3ncco3)c3nnc(C)n3-c3sc(C)c(C)c32)cc1]
In certain embodiments, $A^2$ is
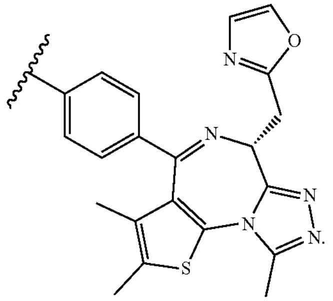 [SMILES: *c1ccc(C2=N[C@H](Cc3ncco3)c3nnc(C)n3-c3sc(C)c(C)c32)cc1]
In certain embodiments, $A^2$ is
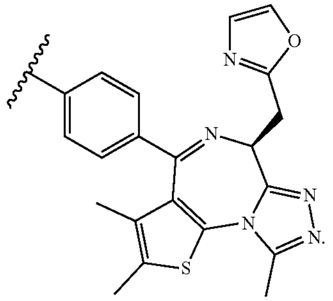 [SMILES: *c1ccc(C2=N[C@@H](Cc3ncco3)c3nnc(C)n3-c3sc(C)c(C)c32)cc1]
In certain embodiments, $A^2$ is
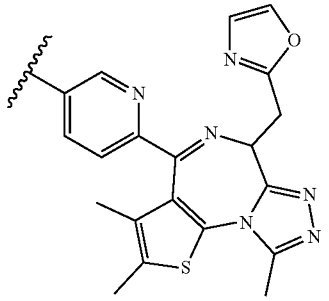
or
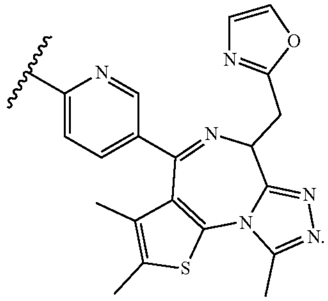
In certain embodiments, $A^2$ is
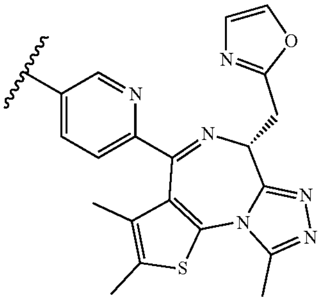
or
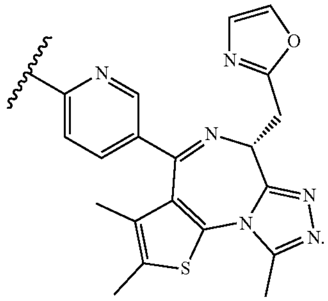
In certain embodiments, $A^2$ is
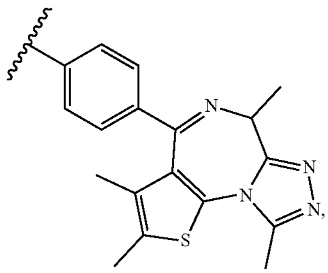

-continued
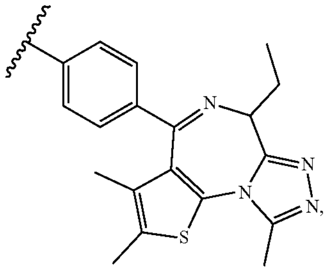
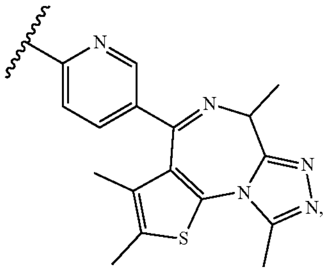
or
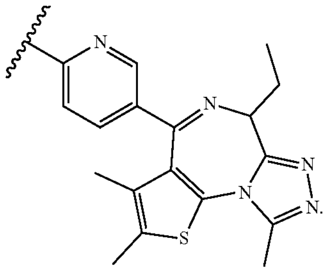
In certain embodiments, $A^2$ is
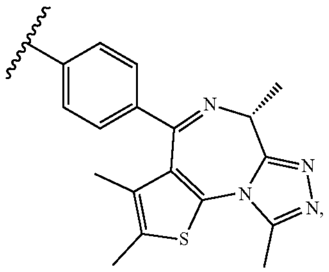
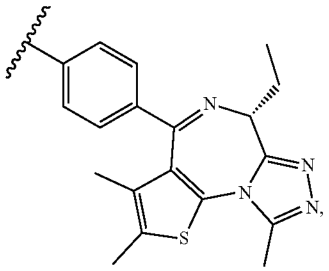
-continued
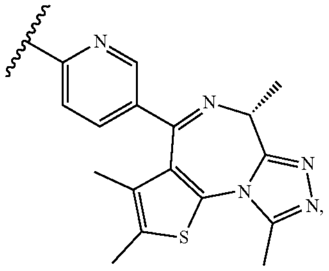
or
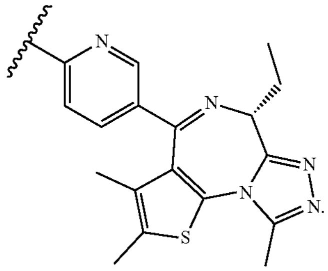
In certain embodiments, $A^2$ is
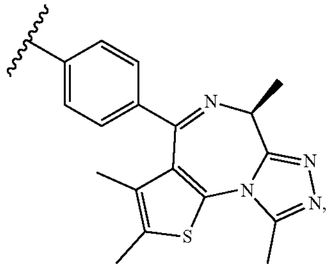
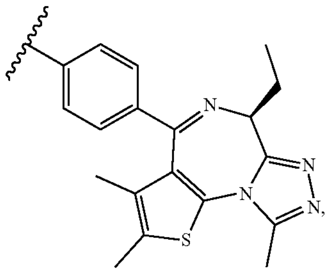
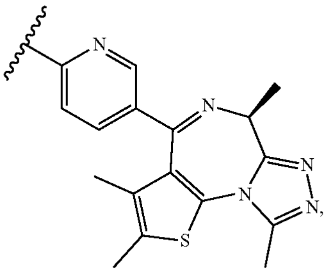
or -continued
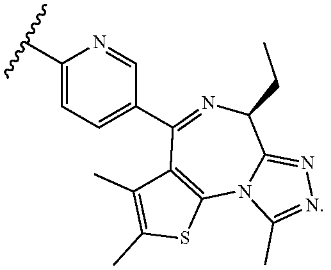
In certain embodiments, $A^2$ is
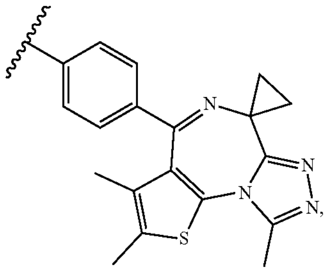
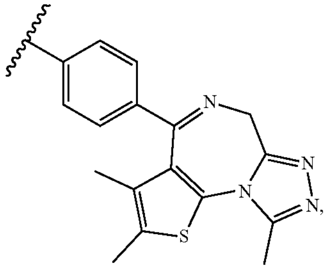
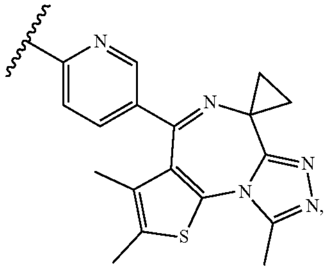
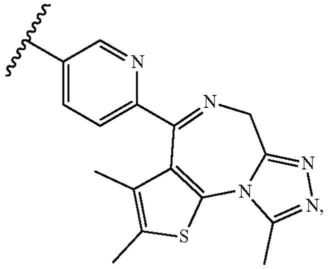
-continued
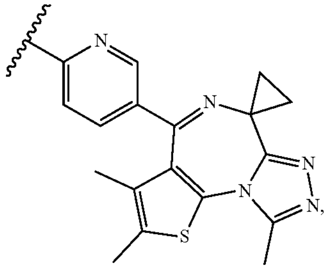
or
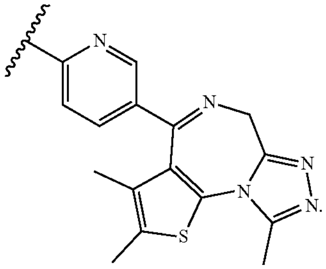
In certain embodiments, $A^2$ is
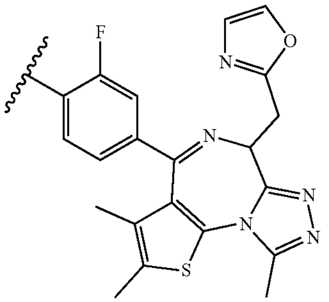
or
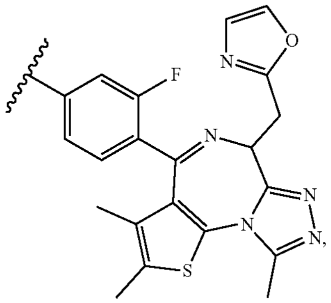
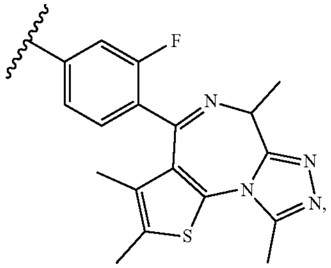

-continued
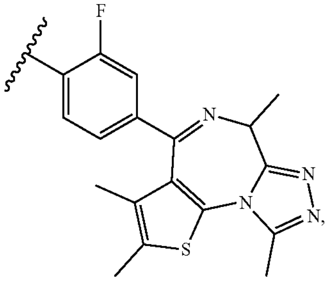
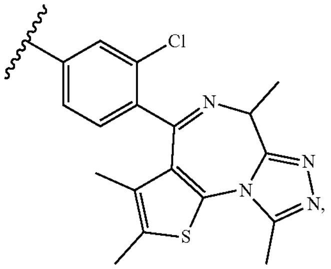
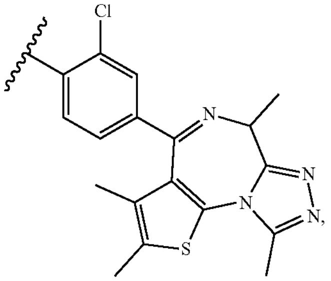
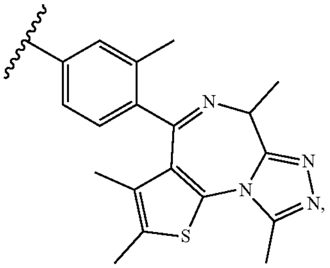
or
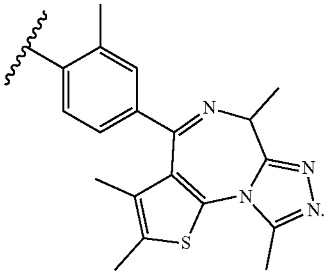
In certain embodiments, $A^2$ is
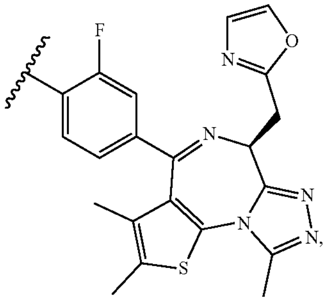
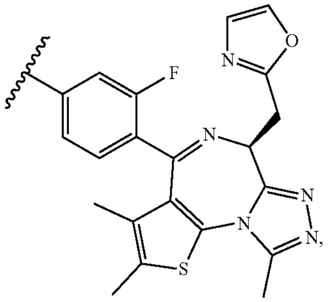
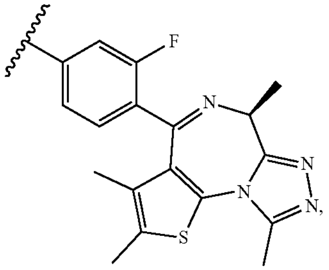
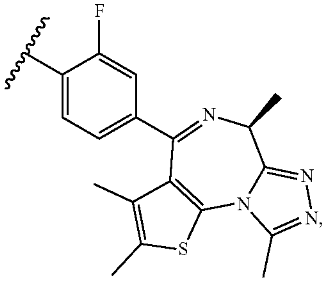
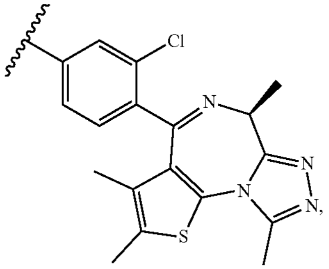

-continued
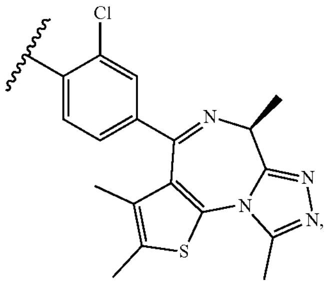
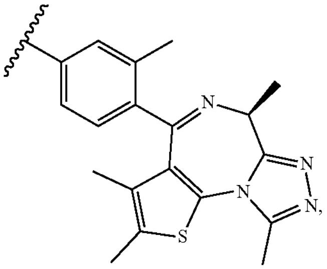
or
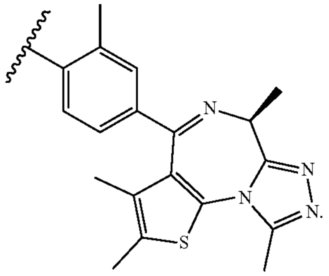
In certain embodiments, $A^2$ is one of the following:
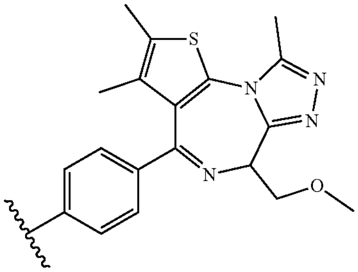
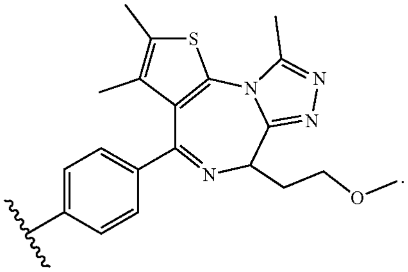
In certain embodiments, $A^2$ is one of the following:
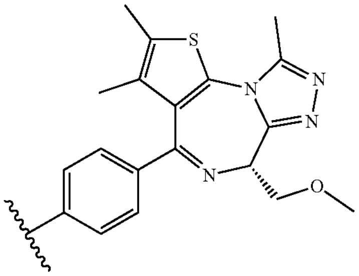
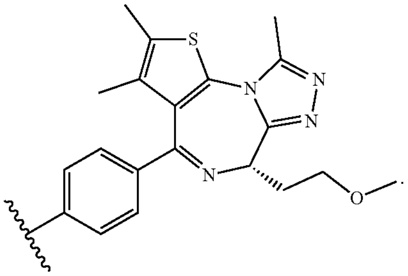
In certain embodiments, $A^2$ is
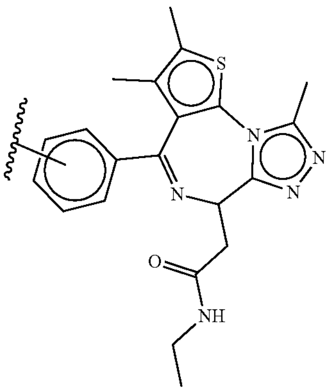
or
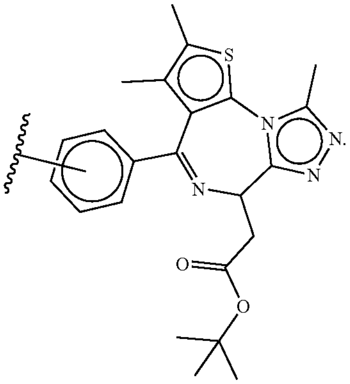

In certain embodiments, $A^2$ is

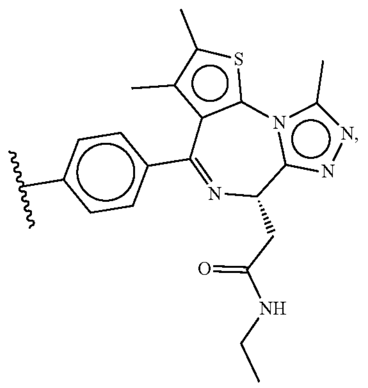

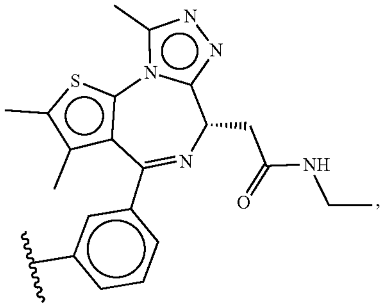

, or

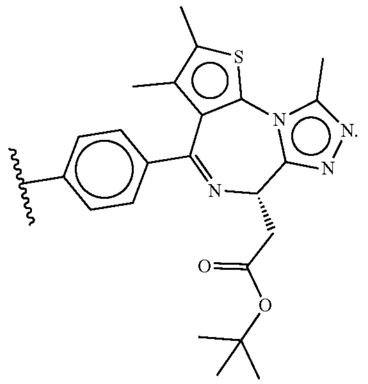

In certain embodiments, $A^2$ is

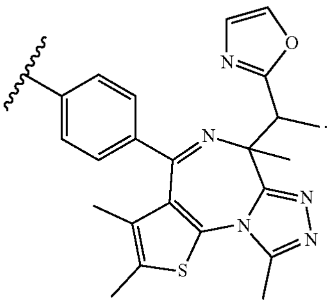 [SMILES: *c1ccc(C2=NC(C)(C(C)c3ncco3)c3nnc(C)n3-c3sc(C)c(C)c32)cc1]

In certain embodiments, $A^2$ is

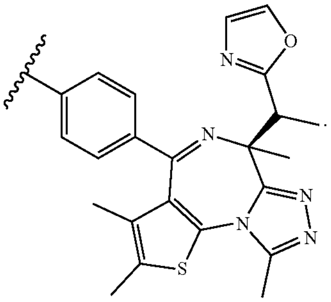 [SMILES: *c1ccc(C2=N[C@@](C)(C(C)c3ncco3)c3nnc(C)n3-c3sc(C)c(C)c32)cc1]

In certain embodiments, $A^2$ is

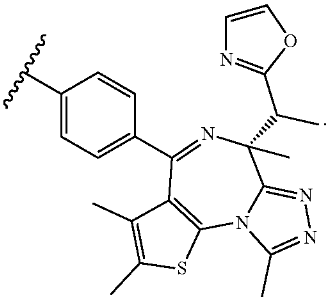 [SMILES: *c1ccc(C2=N[C@](C)(C(C)c3ncco3)c3nnc(C)n3-c3sc(C)c(C)c32)cc1]

In certain embodiments, $A^2$ is selected from the groups depicted in the compounds in Table 1 or 2 below.

As defined generally above, $B^1$ is (i) cyclobutylene substituted by 1, 2, 3, or 4 occurrences of $R^2$ or (ii) cyclohexylene substituted by 0, 1, or 2 occurrences of $R^2$. In certain embodiments, $B^1$ is cyclobutylene substituted by 1, 2, 3, or 4 occurrences of $R^2$. In certain embodiments, $B^1$ is cyclobutylene substituted by 4 occurrences of $R^2$. In certain embodiments, $B^1$ is cyclohexylene substituted by 0, 1, or 2 occurrences of $R^2$. In certain embodiments, $B^1$ is cyclohexylene substituted by 0 occurrences of $R^2$ (that is, $B^1$ is cyclohexylene). In certain embodiments, $B^1$ is selected from the groups depicted in the compounds in Table 1 or 2 below.

As defined generally above, $R^{1A}$ is $C_{1-4}$ alkyl or $C_{3-4}$ cycloalkyl. In certain embodiments, $R^{1A}$ is $C_{1-4}$ alkyl. In certain embodiments, $R^{1A}$ is methyl. In certain embodiments, $R^{1A}$ is $C_{3-4}$ cycloalkyl. In certain embodiments, $R^{1A}$ is selected from the groups depicted in the compounds in Table 1 or 2 below.

As defined generally above, $R^{2A}$ represents independently for each occurrence $C_{1-4}$ alkyl or $C_{3-4}$ cycloalkyl. In certain embodiments, $R^{2A}$ is $C_{1-4}$ alkyl. In certain embodiments, $R^{2A}$ is methyl. In certain embodiments, $R^{2A}$ is $C_{3-4}$ cycloalkyl. In certain embodiments, $R^{2A}$ is selected from the groups depicted in the compounds in Table 1 or 2 below.

As defined generally above, $R^{3A}$ is hydrogen, halo, $C_{1-4}$ alkyl, $C_{1-4}$ haloalkyl, or $C_{1-4}$ alkoxyl. In certain embodiments, $R^{3A}$ is hydrogen, halo, $C_{1-4}$ alkyl, or $C_{1-4}$ alkoxyl. In certain embodiments, $R^{3A}$ is hydrogen. In certain embodiments, $R^{3A}$ is halo. In certain embodiments, $R^{3A}$ is fluoro. In certain embodiments, $R^{3A}$ is chloro. In certain embodiments, $R^{3A}$ is $C_{1-4}$ alkyl. In certain embodiments, $R^{3A}$ is methyl. In certain embodiments, $R^{3A}$ is $C_{1-4}$ alkoxyl. In certain embodiments, $R^{3A}$ is methoxy. In certain embodiments, $R^{3A}$ is $C_{1-4}$ haloalkyl. In certain embodiments, $R^{3A}$ is trifluoromethyl. In certain embodiments, $R^{3A}$ is halo, $C_{1-4}$ alkyl, or $C_{1-4}$ alkoxyl. In certain embodiments, $R^{3A}$ is selected from the groups depicted in the compounds in Table 1 or 2 below.

As defined generally above, $R^{4A}$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^{5A}$)($R^{6A}$), —($C_{1-6}$ alkylene)-N($R^{5A}$)C(O)$R^{7A}$, —($C_{1-6}$ alkylene)-$CO_2R^{7A}$, —($C_{1-6}$ alkylene)-OC(O)$R^{7A}$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^{4A}$ and $R^{10A}$ taken together with the carbon atom to which they are attached form a $C_{3-5}$ saturated carbocyclic ring. In certain embodiments, $R^{4A}$ is —($C_{1-6}$ alkylene)-C(O)N($R^{5A}$)($R^{6A}$), —($C_{1-6}$ alkylene)-N($R^{5A}$)C(O)$R^{7A}$, —($C_{1-6}$ alkylene)-$CO_2R^{7A}$, —($C_{1-6}$ alkylene)-OC(O)$R^{7A}$, or —($C_{0-6}$ alkylene)-(5-6 membered heteroaryl containing 1, 2, or 3 heteroatoms independently selected from nitrogen, oxygen, and sulfur). In certain embodiments, $R^{4A}$ is —($C_{1-6}$ alkylene)-C(O)N($R^{5A}$)($R^{6A}$), —($C_{1-6}$ alkylene)-N($R^{5A}$)C(O)$R^{7A}$, —($C_{1-6}$ alkylene)-$CO_2R^{7A}$, or —($C_{1-6}$ alkylene)-OC(O)$R^{7A}$. In certain embodiments, $R^{4A}$ is hydrogen. In certain embodiments, $R^{4A}$ is —($C_{1-6}$ alkylene)-cyano. In certain embodiments, $R^{4A}$ is $C_{1-6}$ alkyl. In certain embodiments, $R^{4A}$ is methyl. In certain embodiments, $R^{4A}$ is —($C_{1-6}$ alkylene)-C(O)N($R^{5A}$)($R^{6A}$). In certain embodiments, $R^{4A}$ is —($C_{1-6}$ alkylene)-$CO_2R^{7A}$. In certain embodiments, $R^{4A}$ is —($C_{1-6}$ alkylene)-N($R^{5A}$)C(O)$R^{7A}$. In certain embodiments, $R^{4A}$ is —($C_{1-6}$ alkylene)-OC(O)$R^{7A}$.

In certain embodiments, $R^{4A}$ is —($C_{0-6}$ alkylene)-(5-6 membered heteroaryl containing 1, 2, or 3 heteroatoms independently selected from nitrogen, oxygen, and sulfur). In certain embodiments, $R^{4A}$ is —($C_{0-6}$ alkylene)-(5-6 membered heteroaryl containing 1, 2, or 3 heteroatoms independently selected from nitrogen, oxygen, and sulfur). In certain embodiments, $R^{4A}$ is —($C_{1-2}$ alkylene)-(5-6 membered heteroaryl containing 1, 2, or 3 heteroatoms independently selected from nitrogen, oxygen, and sulfur). In certain embodiments, $R^{4A}$ is —($C_{1-2}$ alkylene)-(5-membered heteroaryl containing 1 or 2 heteroatoms independently selected from nitrogen, oxygen, and sulfur). In certain embodiments, $R^{4A}$ is —($C_{1-2}$ alkylene)-(oxazolyl).

In certain embodiments, $R^{4A}$ is —($C_{1-6}$ alkylene)-O—($C_{1-6}$ alkyl). In certain embodiments, $R^{4A}$ is —($C_{1-2}$ alkylene)-O—($C_{1-2}$ alkyl).

In certain embodiments, $R^{4A}$ and $R^{10A}$ taken together with the carbon atom to which they are attached form a $C_{3-5}$ saturated carbocyclic ring.

In certain embodiments, $R^{4A}$ is selected from the groups depicted in the compounds in Table 1 or 2 below.

As defined generally above, $R^{5A}$ and $R^{6A}$ are independently hydrogen, $C_{1-6}$ alkyl, or $C_{3-6}$ cycloalkyl; or $R^{5A}$ and $R^{6A}$ are taken together with the nitrogen atom to which they are attached to form a 3-7 membered ring containing 1 nitrogen atom. In certain embodiments, $R^{5A}$ and $R^{6A}$ are independently hydrogen, $C_{1-6}$ alkyl, or $C_{3-6}$ cycloalkyl. In certain embodiments, $R^{5A}$ is hydrogen. In certain embodiments, $R^{5A}$ is $C_{1-6}$ alkyl. In certain embodiments, $R^{5A}$ is $C_{3-6}$ cycloalkyl. In certain embodiments, $R^{6A}$ is hydrogen. In certain embodiments, $R^{6A}$ is $C_{1-6}$ alkyl. In certain embodiments, $R^{6A}$ is $C_{3-6}$ cycloalkyl. In certain embodiments, $R^{5A}$ and $R^{6A}$ are taken together with the nitrogen atom to which they are attached to form a 3-7 membered ring containing 1 nitrogen atom. In certain embodiments, $R^{5A}$ and $R^{6A}$ are taken together with the nitrogen atom to which they are attached to form a 3-membered ring containing 1 nitrogen atom. In certain embodiments, $R^{5A}$ and $R^{6A}$ are taken together with the nitrogen atom to which they are attached to form a 4-membered ring containing 1 nitrogen atom. In certain embodiments, $R^{5A}$ and $R^{6A}$ are taken together with the nitrogen atom to which they are attached to form a 5-membered ring containing 1 nitrogen atom. In certain embodiments, $R^{5A}$ and $R^{6A}$ are taken together with the nitrogen atom to which they are attached to form a 6-membered ring containing 1 nitrogen atom. In certain embodiments, $R^{5A}$ and $R^{6A}$ are taken together with the nitrogen atom to which they are attached to form a 7-membered ring containing 1 nitrogen atom. In certain embodiments, $R^{5A}$ is selected from the groups depicted in the compounds in Table 1 or 2 below. In certain embodiments, $R^{6A}$ is selected from the groups depicted in the compounds in Table 1 or 2 below.

As defined generally above, $R^{7A}$ is $C_{1-6}$ alkyl, —($C_{1-6}$ alkylene)-($C_{3-6}$ cycloalkyl), or $C_{3-6}$ cycloalkyl. In certain embodiments, $R^{7A}$ is $C_{1-6}$ alkyl. In certain embodiments, $R^{7A}$ is —($C_{1-6}$ alkylene)-($C_{3-6}$ cycloalkyl). In certain embodiments, $R^{7A}$ is $C_{3-6}$ cycloalkyl. In certain embodiments, $R^{7A}$ is selected from the groups depicted in the compounds in Table 1 or 2 below.

As defined generally above, $R^{10A}$ is hydrogen or $C_{1-4}$ alkyl. In certain embodiments, $R^{10A}$ is hydrogen. In certain embodiments, $R^{10A}$ is $C_{1-4}$ alkyl. In certain embodiments, $R^{10A}$ is methyl. In certain embodiments, $R^{10A}$ is selected from the groups depicted in the compounds in Table 1 or 2 below.

As defined generally above, m, n, and p are independently 0, 1, or 2. In certain embodiments, p is 2. In certain embodiments, p is 1. In certain embodiments, p is 0. In certain embodiments, m is 0. In certain embodiments, m is 1. In certain embodiments, m is 2. In certain embodiments, n is 0. In certain embodiments, n is 1. In certain embodiments, q is 0. In certain embodiments, q is 1. In certain embodiments, q is 2. In certain embodiments, p is selected from the corresponding value in the groups depicted in the compounds in Table 1 or 2 below. In certain embodiments, m is selected from the corresponding value in the groups depicted in the compounds in Table 1 or 2 below. In certain embodiments, n is selected from the corresponding value in the groups depicted in the compounds in Table 1 or 2 below.

In certain embodiments, the compound of Formula I is further defined by Formula Ia (Ia)

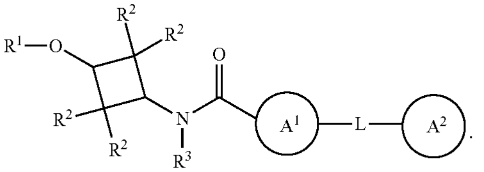

In certain embodiments, the definition of variables $R^1$, $R^2$, $R^3$, $A^1$, and $A^2$ is one of the embodiments described above in connection with Formula I.

In certain embodiments, the compound of Formula I is further defined by Formula Ib or Ic, or a pharmaceutically acceptable salt thereof:

(Ib)

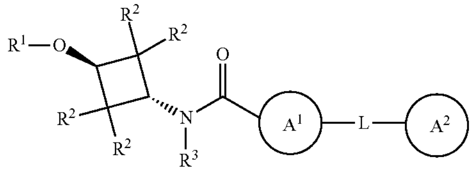

-continued (Ic)

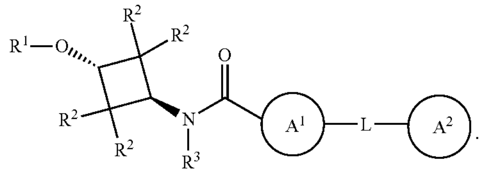

In certain embodiments, the definition of variables $R^1$, $R^2$, $R^3$, $A^1$, and $A^2$ is one of the embodiments described above in connection with Formula I. In certain embodiments, the compound is a compound of Formula Ib or a pharmaceutically acceptable salt thereof. In certain embodiments, the compound is a compound of Formula Ic or a pharmaceutically acceptable salt thereof.

In certain embodiments, the compound of Formula I is further defined by Formula Id or a pharmaceutically acceptable salt thereof:

(Id)

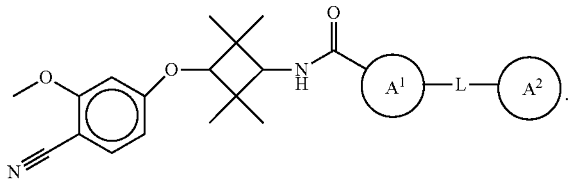

In certain embodiments, the definition of variables $A^1$ and $A^2$ is one of the embodiments described above in connection with Formula I.

In certain embodiments, the compound of Formula I is further defined by Formula Ie (Ie)

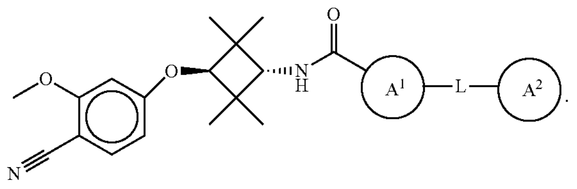

In certain embodiments, the definition of variables $A^1$ and $A^2$ is one of the embodiments described above in connection with Formula I.

In certain embodiments, the compound of Formula I is further defined by Formula If or a pharmaceutically acceptable salt thereof:

(If)

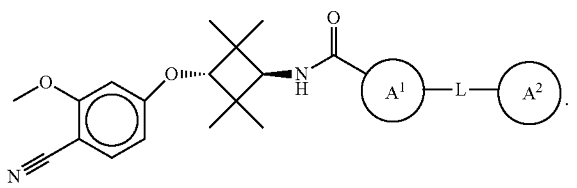

In certain embodiments, the definition of variables $A^1$ and $A^2$ is one of the embodiments described above in connection with Formula I.

In certain embodiments, the compound of Formula I is further defined by Formula Ig or a pharmaceutically acceptable salt thereof:

(Ig)

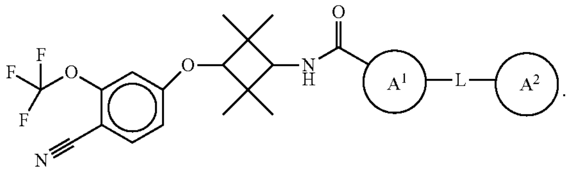

In certain embodiments, the definition of variables $A^1$ and $A^2$ is one of the embodiments described above in connection with Formula I.

In certain embodiments, the compound of Formula I is further defined by Formula Ih (Ih)

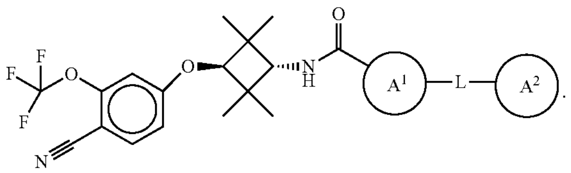

In certain embodiments, the definition of variables $A^1$ and $A^2$ is one of the embodiments described above in connection with Formula I.

In certain embodiments, the compound of Formula I is further defined by Formula Ii or a pharmaceutically acceptable salt thereof:

(Ii)

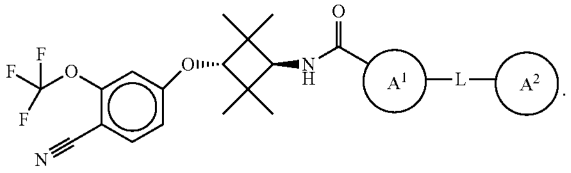

In certain embodiments, the definition of variables $A^1$ and $A^2$ is one of the embodiments described above in connection with Formula I.

In certain embodiments, the compound of Formula I is further defined by Formula Ij or a pharmaceutically acceptable salt thereof:

(Ij)

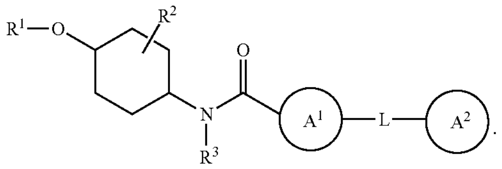

In certain embodiments, the definition of variables $A^1$ and $A^2$ is one of the embodiments described above in connection with Formula I. In certain embodiments, the definition of variables $R^1$, $R^2$, and $R^3$ is one of the embodiments described above in connection with Formula I.

In certain embodiments, the compound of Formula I is further defined by Formula Ik (Ik)

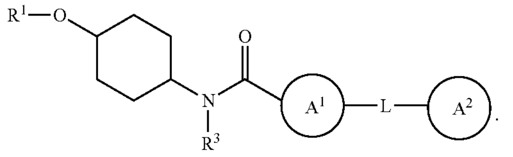

In certain embodiments, the definition of variables $A^1$ and $A^2$ is one of the embodiments described above in connection with Formula I. In certain embodiments, the definition of variables $R^1$ and $R^3$ is one of the embodiments described above in connection with Formula I.

In certain embodiments, the compound of Formula I is further defined by Formula Il or Im. or a pharmaceutically acceptable salt thereof:

(Il)

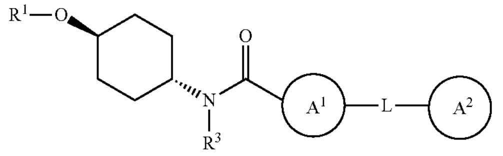

(Im)

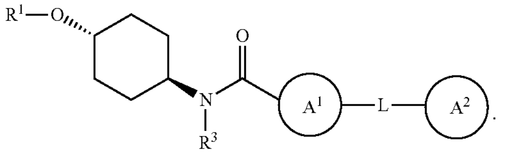

In certain embodiments, the definition of variables $A^1$ and $A^2$ is one of the embodiments described above in connection with Formula I. In certain embodiments, the definition of variables $R^1$ and $R^3$ is one of the embodiments described above in connection with Formula I. In certain embodiments, the compound is a compound of Formula Il or a pharmaceutically acceptable salt thereof. In certain embodiments, the compound is a compound of Formula Im or a pharmaceutically acceptable salt thereof.

In certain embodiments, the compound of Formula I is further defined by Formula In or a pharmaceutically acceptable salt thereof:

(In)

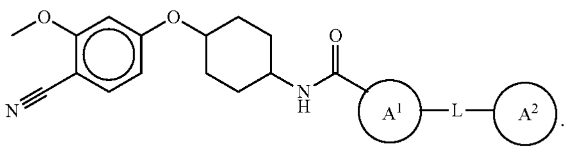

In certain embodiments, the definition of variables $A^1$ and $A^2$ is one of the embodiments described above in connection with Formula I.

In certain embodiments, the compound of Formula I is further defined by Formula Io or Ip, or a pharmaceutically acceptable salt thereof:

(Io)

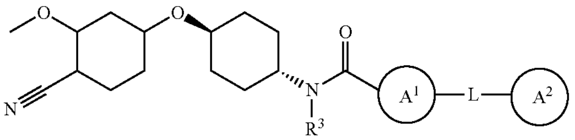

(Ip)

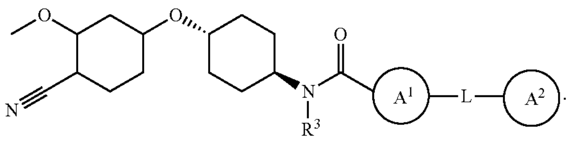

In certain embodiments, the definition of variables $A^1$ and $A^2$ is one of the embodiments described above in connection with Formula I. In certain embodiments, the definition of variable $R^3$ is one of the embodiments described above in connection with Formula I. In certain embodiments, the compound is a compound of Formula Io or a pharmaceutically acceptable salt thereof. In certain embodiments, the compound is a compound of Formula Ip or a pharmaceutically acceptable salt thereof.

In certain embodiments, the compound of Formula I is further defined by Formula Iq or a pharmaceutically acceptable salt thereof:

(Iq)

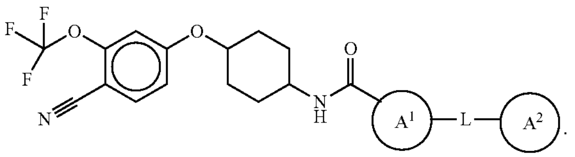

In certain embodiments, the definition of variables $A^1$ and $A^2$ is one of the embodiments described above in connection with Formula I.

In certain embodiments, the compound of Formula I is further defined by Formula Ir or Is, or a pharmaceutically acceptable salt thereof:

(Ir)

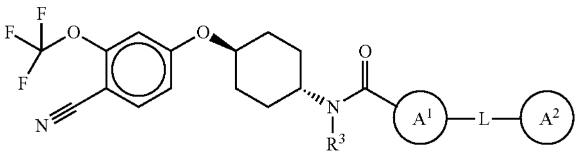

(Is)

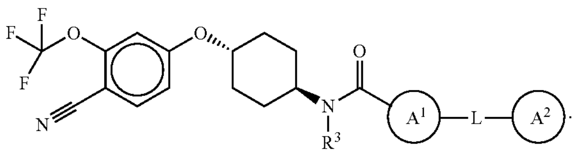

In certain embodiments, the definition of variables $A^1$ and $A^2$ is one of the embodiments described above in connection with Formula I. In certain embodiments, the definition of variable $R^3$ is one of the embodiments described above in connection with Formula I. In certain embodiments, the compound is a compound of Formula Ir or a pharmaceutically acceptable salt thereof. In certain embodiments, the compound is a compound of Formula Is or a pharmaceutically acceptable salt thereof.

Another aspect of the invention provides a compound represented by Formula It, Iu, Iv, or Iw, or a pharmaceutically acceptable salt thereof:

(It)

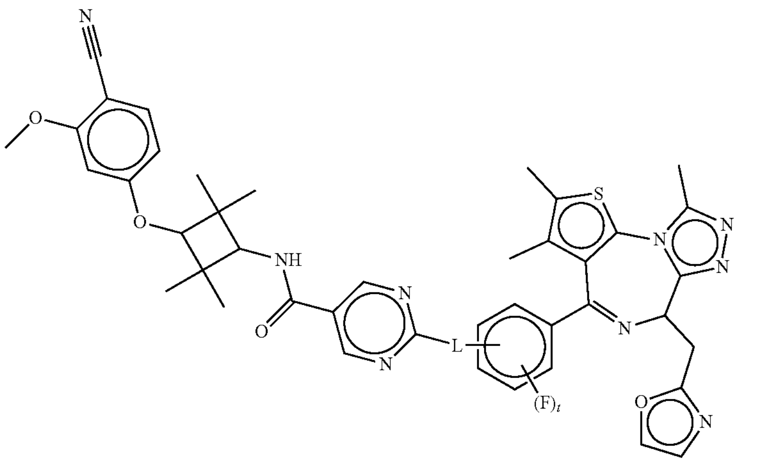

(Iu)

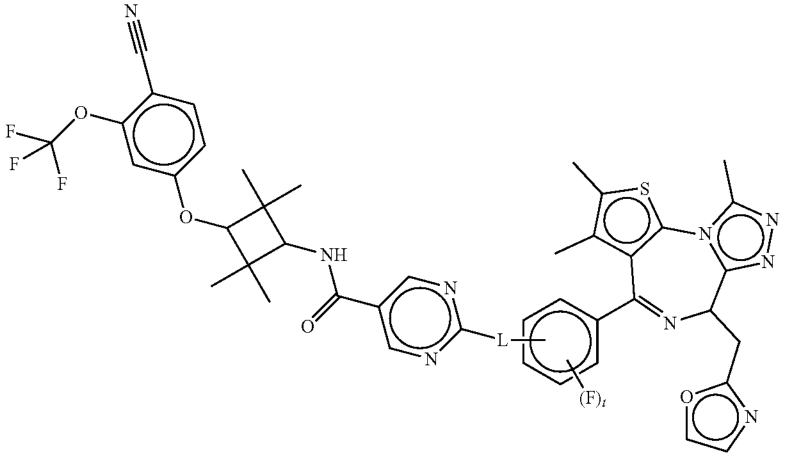

(Iv)

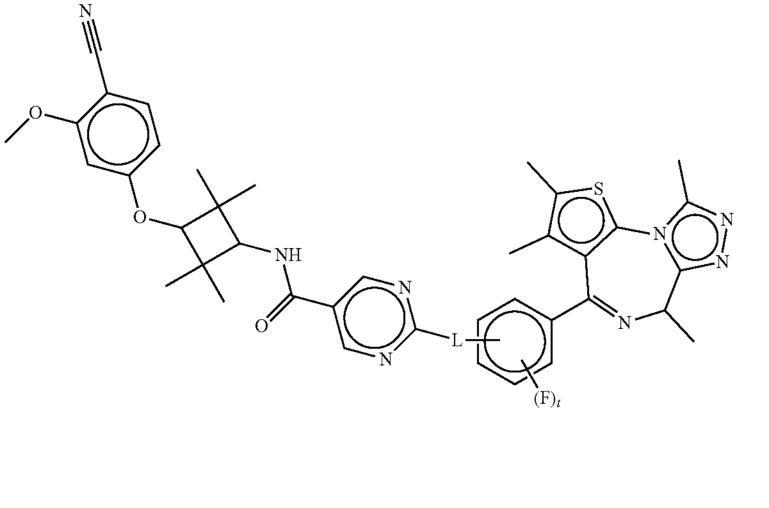

-continued (Iw)

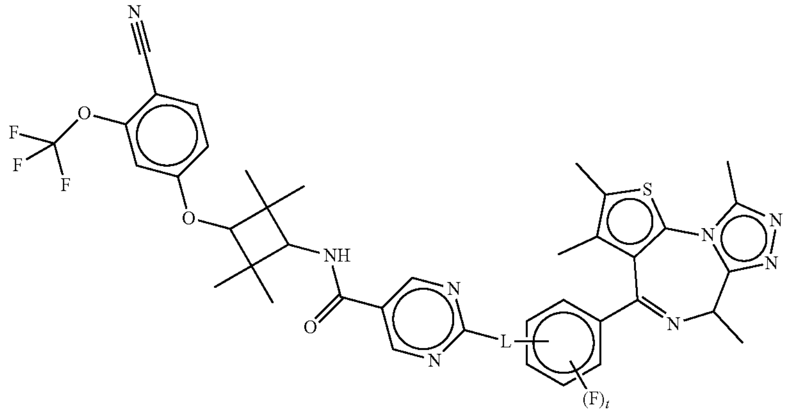

wherein

L is one of the following:

(i)-(7-11 membered spirocyclic or fused bicyclic saturated heterocyclic ring containing 1, 2, or 3 heteroatoms independently selected from nitrogen and oxygen)-O—*, wherein * is the point of attachment to the phenylene group in said formula;

(ii) a 7-11 membered spirocyclic or fused bicyclic saturated heterocyclic ring containing 1, 2, or 3 heteroatoms independently selected from nitrogen and oxygen; or (iii)-(7-11 membered spirocyclic saturated heterocyclic ring containing 1 or 2 heteroatoms selected from nitrogen)-($C_{2-4}$ alkynylene)-*, wherein * is the point of attachment to the phenylene group in said formula; and t is 0 or 1.

In certain embodiments, t is 0. In certain embodiments, t is 1.

Another aspect of the invention provides a compound represented by Formula Ix, Iy, Iz, or Iaa, or a pharmaceutically acceptable salt thereof:

(Ix)

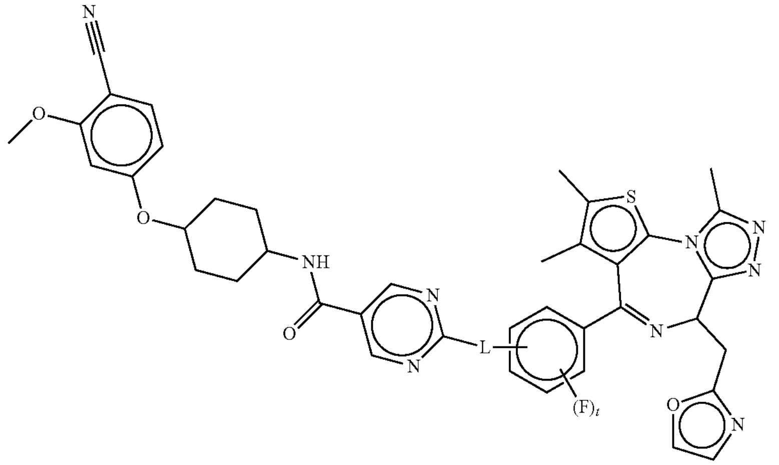

-continued (Iy)

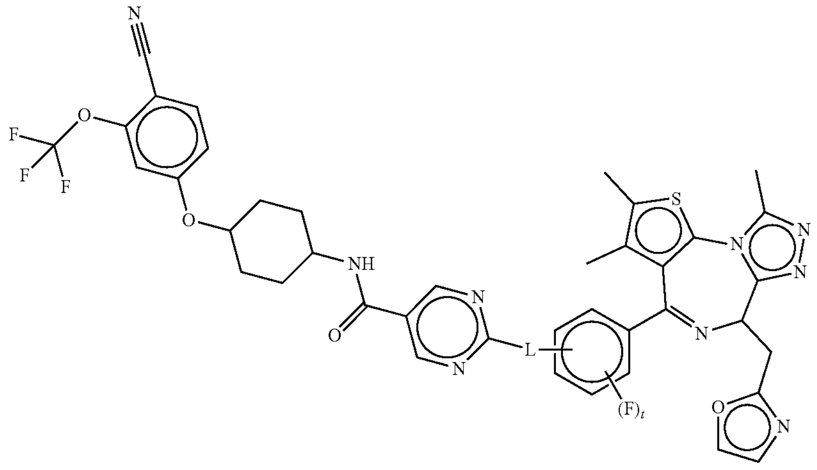

(Iz)

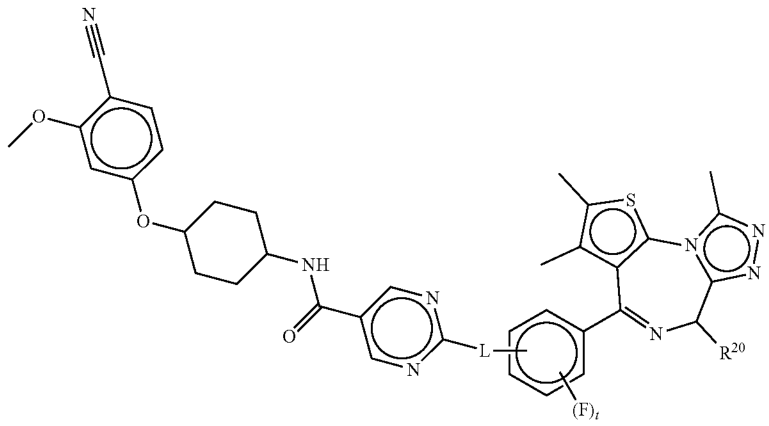

(Iaa)

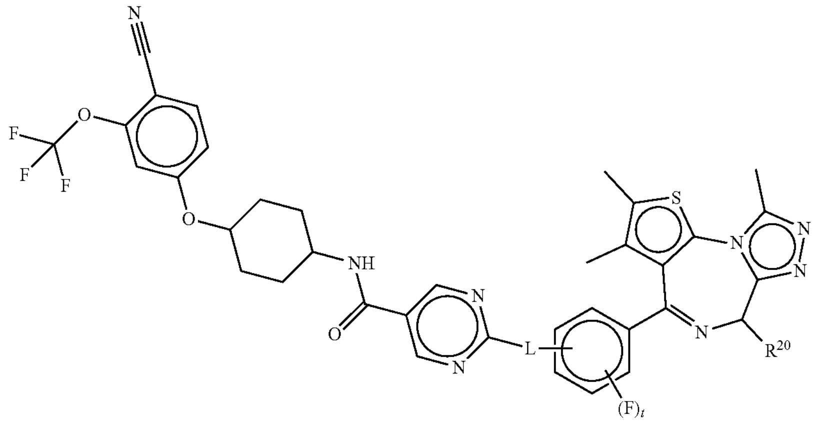

wherein:

$R^{20}$ is methyl, ethyl, $-CH_2-O-CH_3$, or $-(CH_2)_2-O-CH_3$;

L is one of the following:

(i)-(7-11 membered spirocyclic or fused bicyclic saturated heterocyclic ring containing 1, 2, or 3 heteroatoms independently selected from nitrogen and oxygen)-O—*, wherein * is the point of attachment to the phenylene group in said formula;

(ii) a 7-11 membered spirocyclic or fused bicyclic saturated heterocyclic ring containing 1, 2, or 3 heteroatoms independently selected from nitrogen and oxygen; or (iii)-(7-11 membered spirocyclic saturated heterocyclic ring containing 1 or 2 heteroatoms selected from nitrogen)-($C_{2-4}$ alkynylene)-*, wherein * is the point of attachment to the phenylene group in said formula; and t is 0 or 1.

In certain embodiments, t is 0. In certain embodiments, t is 1. In certain embodiments, $R^{20}$ is methyl or ethyl. In certain embodiments, $R^{20}$ is $—CH_2—O—CH_3$ or $—(CH_2)_2—O—CH_3$.

In certain embodiments, L is a -(7-11 membered spirocyclic or fused bicyclic saturated heterocyclic ring containing 1, 2, or 3 heteroatoms independently selected from nitrogen and oxygen)-O—*, wherein * is the point of attachment to the phenylene group in said formula. In certain embodiments, L is a 7-11 membered spirocyclic or fused bicyclic saturated heterocyclic ring containing 1, 2, or 3 heteroatoms independently selected from nitrogen and oxygen. In certain embodiments, L is -(7-11 membered spirocyclic saturated heterocyclic ring containing 1 or 2 heteroatoms selected from nitrogen)-($C_{2-4}$ alkynylene)-* wherein * is the point of attachment to the phenylene group in said formula. In certain embodiments, L is one of the following:

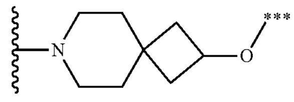
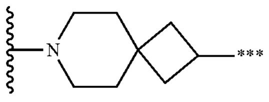
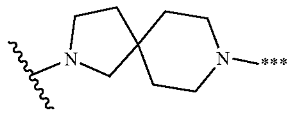
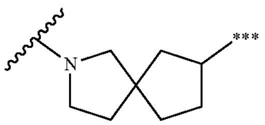
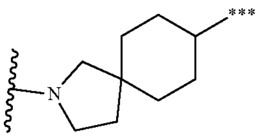
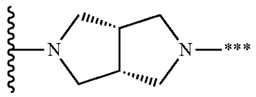

-continued

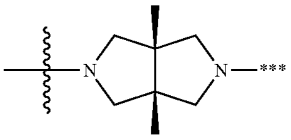
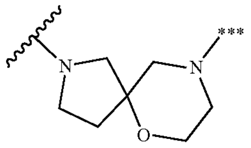
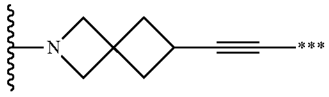

wherein *** is the point of attachment to the phenylene group in said formula. In certain embodiments, L is

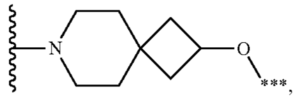

wherein *** is the point of attachment to the phenylene group in said formula. In certain embodiments, L

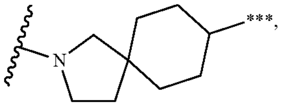

is wherein *** is the point of attachment to the phenylene group in said formula.

The compounds may be further characterized according to, for example, the identity of L according to exemplary further embodiments for L provided in Part C below.

In certain embodiments, the compound is represented by Formula Iab or a pharmaceutically acceptable salt thereof:

(Iab)

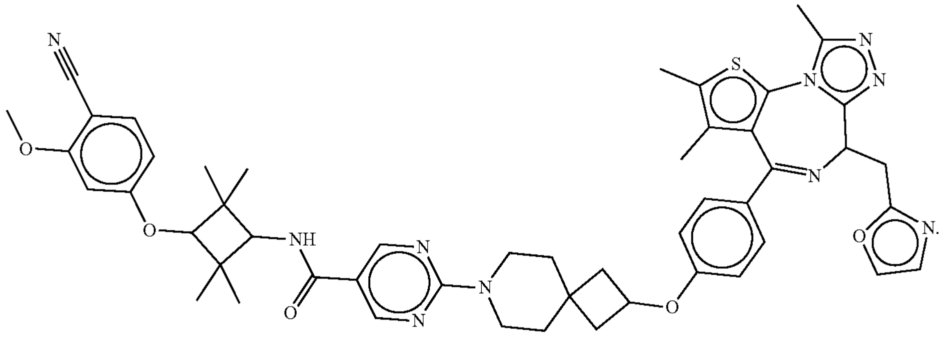

In certain embodiments, the compound is represented by Formula Iac or a pharmaceutically acceptable salt thereof:

(Iac)

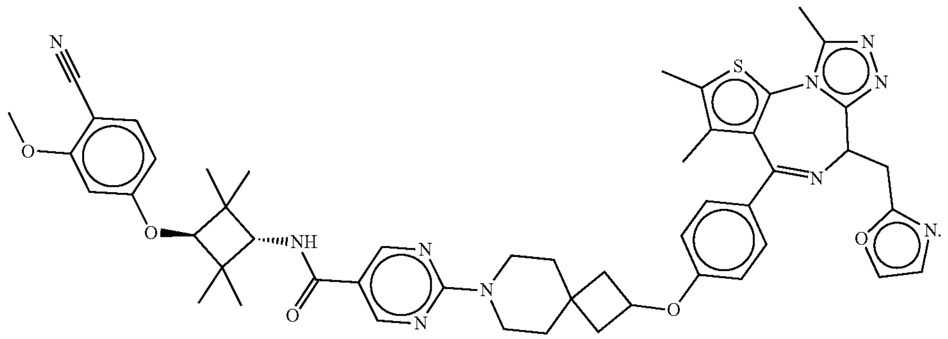

In certain embodiments, the compound is represented by Formula Iad or a pharmaceutically acceptable salt thereof:

(Iad)

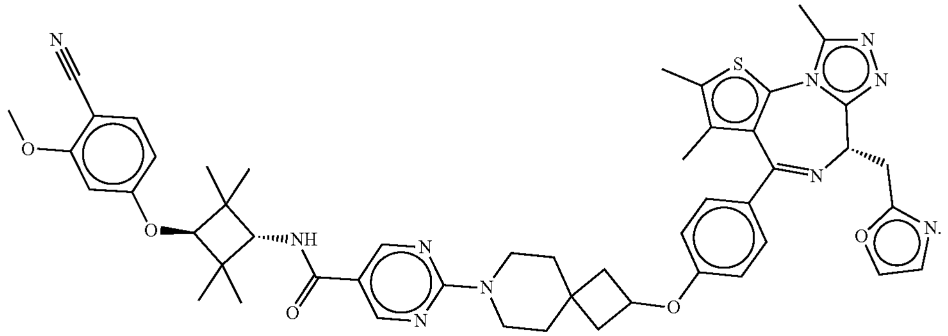

In certain embodiments, the compound is represented by Formula Iae or a pharmaceutically acceptable salt thereof:

(Iae)

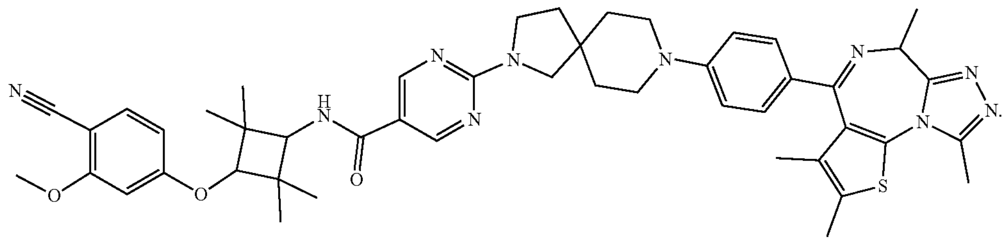

In certain embodiments, the compound is represented by Formula Iaf or a pharmaceutically acceptable salt thereof:

(Iaf)

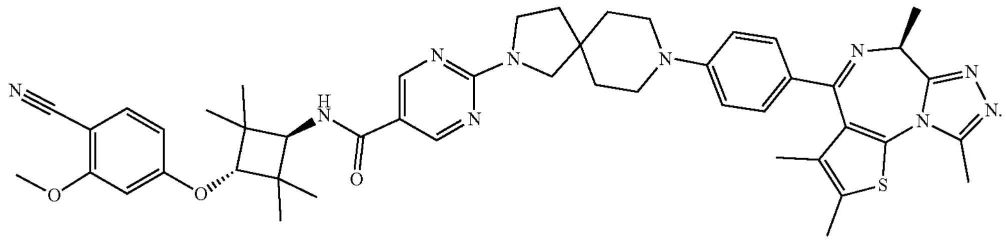

In certain embodiments, the compound is represented by Formula Iag or a pharmaceutically acceptable salt thereof:

(Iag)

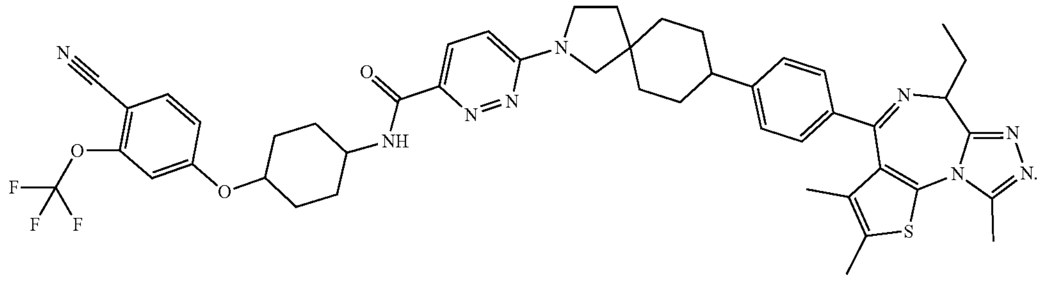

In certain embodiments, the compound is represented by Formula Iah or a pharmaceutically acceptable salt thereof:

(Iah)

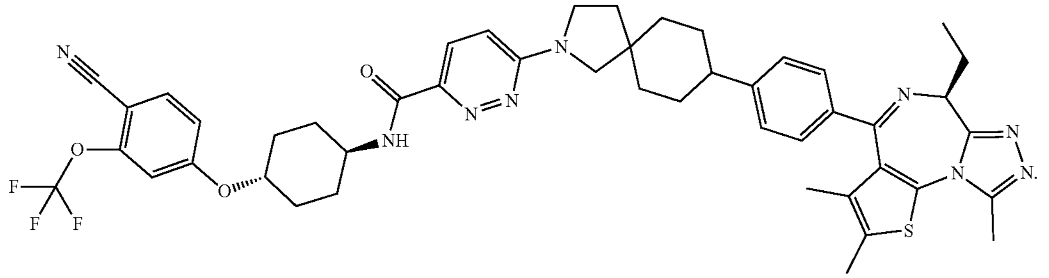

Part B: Compounds of Formula II

Another aspect of the invention provides a compound represented by Formula II:

(II)

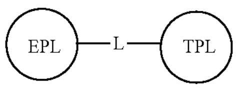

or a pharmaceutically acceptable salt thereof, wherein:

TPL is a group defined by Formula II-1 that is substituted by one occurrence of $R^{II-1A}$, wherein Formula II-1 is represented by:

(II-1)

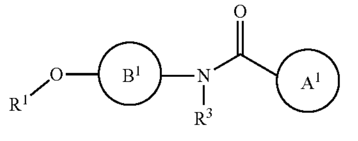

or a pharmaceutically acceptable salt thereof, wherein:

$R^{II-1A}$ is a bond to L;

$R^1$ is phenyl substituted by (i) cyano and m occurrences of $R^4$, and (ii) $C_{1-4}$ alkoxyl or $C_{1-4}$ haloalkoxyl;

$R^2$ represents independently for each occurrence $C_{1-4}$ alkyl;

$R^3$ is hydrogen or $C_{1-4}$ alkyl;

$R^4$ is $C_{1-4}$ alkyl;

$R^5$ represents independently for each occurrence $C_{1-4}$ alkyl or halogen;

$A^1$ is a pyridazinyl, pyrimidinyl, pyrazinyl, pyridinyl, or phenyl, each of which is substituted with n occurrences of $R^5$;

$B^1$ is (i) cyclobutylene substituted by 1, 2, 3, or 4 occurrences of $R^2$ or (ii) cyclohexylene substituted by 0, 1, or 2 occurrences of $R^2$;

L is a linker;

EPL is a moiety that binds to BRD4; and m and n are independently 0, 1, or 2.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula II.

As defined generally above, $R^1$ is phenyl substituted by (i) cyano and m occurrences of $R^4$, and (ii) $C_{1-4}$ alkoxyl or $C_{1-4}$ haloalkoxyl. In certain embodiments, $R^1$ is phenyl substituted by (i) cyano and m occurrences of $R^4$, and (ii) $C_{1-4}$ alkoxyl. In certain embodiments, $R^1$ is phenyl substituted by cyano and $C_{1-4}$ alkoxyl. In certain embodiments, $R^1$ is phenyl substituted by cyano and methoxy. In certain embodiments, $R^1$ is

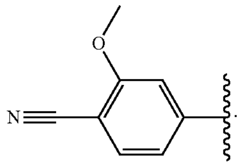 [SMILES: *c1ccc(C#N)c(OC)c1]

In certain embodiments, $R^1$ is phenyl substituted by (i) cyano and m occurrences of $R^4$, and (ii) $C_{1-4}$ haloalkoxyl. In certain embodiments, $R^1$ is phenyl substituted by cyano and $C_{1-4}$ haloalkoxyl. In certain embodiments, $R^1$ is phenyl substituted by cyano and $C_{1-4}$ fluoroalkoxyl. In certain embodiments, $R^1$ is phenyl substituted by cyano and trifluoromethoxy. In certain embodiments, $R^1$ is

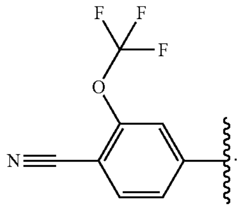 [SMILES: *c1ccc(C#N)c(OC(F)(F)F)c1]

In certain embodiments, $R^1$ is selected from the groups depicted in the compounds in Table 1 or 2 below.

As defined generally above, $R^2$ represents independently for each occurrence $C_{1-4}$ alkyl. In certain embodiments, $R^2$ is methyl. In certain embodiments, $R^2$ is selected from the groups depicted in the compounds in Table 1 or 2 below.

As defined generally above, $R^3$ is hydrogen or $C_{1-4}$ alkyl. In certain embodiments, $R^3$ is hydrogen. In certain embodiments, $R^3$ is $C_{1-4}$ alkyl. In certain embodiments, $R^3$ is selected from the groups depicted in the compounds in Table 1 or 2 below.

As defined generally above, $A^1$ is a pyridazinyl, pyrimidinyl, pyrazinyl, pyridinyl, or phenyl, each of which is substituted with n occurrences of $R^5$. In certain embodiments, $A^1$ is pyridazinyl substituted with n occurrences of $R^5$. In certain embodiments, $A^1$ is pyrimidinyl substituted with n occurrences of $R^5$. In certain embodiments, $A^1$ is pyrazinyl substituted with n occurrences of $R^5$. In certain embodiments, $A^1$ is pyridinyl substituted with n occurrences of $R^5$. In In certain embodiments, $A^1$ is phenyl substituted with n occurrences of $R^5$. In certain embodiments, $A^1$ is selected from the groups depicted in the compounds in Table 1 or 2 below.

As defined generally above, $B^1$ is (i) cyclobutylene substituted by 1, 2, 3, or 4 occurrences of $R^2$ or (ii) cyclohexylene substituted by 0, 1, or 2 occurrences of $R^2$. In certain embodiments, $B^1$ is cyclobutylene substituted by 1, 2, 3, or 4 occurrences of $R^2$. In certain embodiments, $B^1$ is cyclobutylene substituted by 4 occurrences of $R^2$. In certain embodiments, $B^1$ is cyclohexylene substituted by 0, 1, or 2 occurrences of $R^2$. In certain embodiments, $B^1$ is cyclohexylene substituted by 0 occurrences of $R^2$ (that is, $B^1$ is cyclohexylene). In certain embodiments, $B^1$ is selected from the groups depicted in the compounds in Table 1 or 2 below.

In certain embodiments, m is 0. In certain embodiments, m is 1. In certain embodiments, m is 2. In certain embodiments, n is 0. In certain embodiments, n is 1. In certain embodiments, n is 2. In certain embodiments, m is selected from the corresponding value in the groups depicted in the compounds in Table 1 or 2 below. In certain embodiments, n is selected from the corresponding value in the groups depicted in the compounds in Table 1 or 2 below.

In certain embodiments, the TPL is

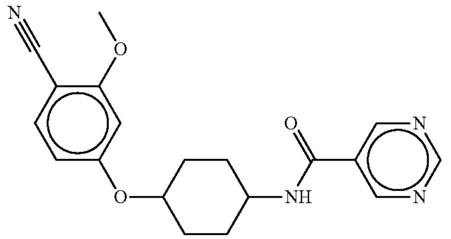

that is substituted by one occurrence of $R^{II-1A}$. In certain embodiments, the TPL is

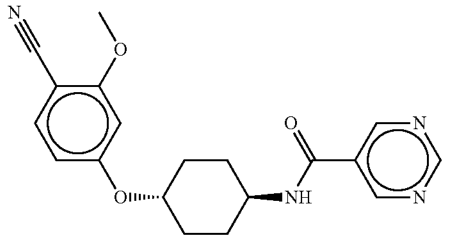

that is substituted by one occurrence of $R^{II-1A}$. In certain embodiments, the TPL is

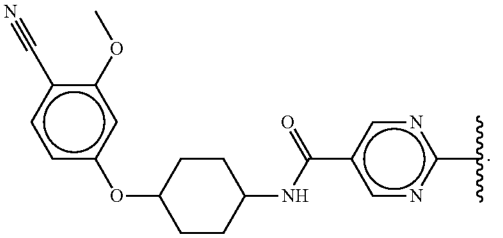

In certain embodiments, the TPL is

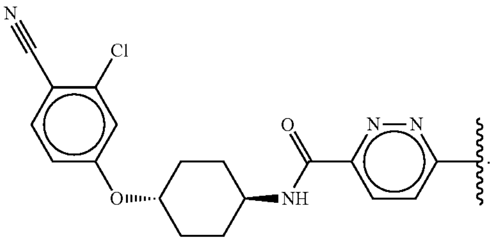

In certain embodiments, the TPL is

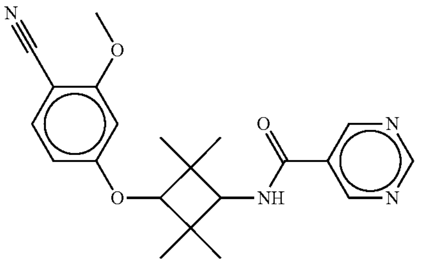

that is substituted by one occurrence of $R^{II-1A}$. In certain embodiments, the TPL is

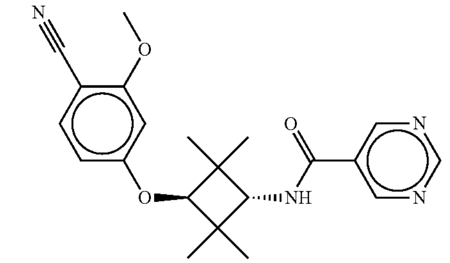

that is substituted by one occurrence of $R^{II\text{-}1A}$. In certain embodiments, the TPL is

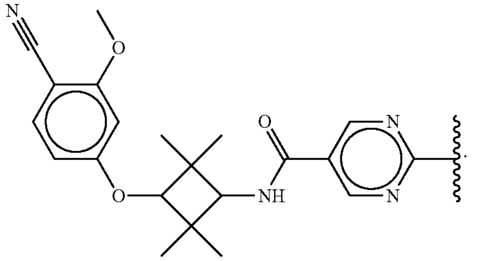

In certain embodiments, the TPL is

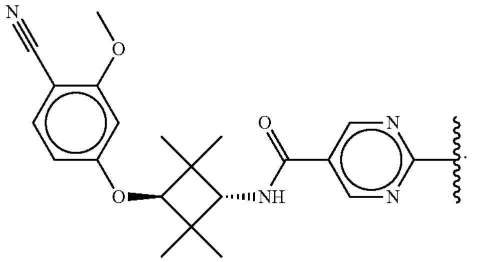

In certain embodiments, the EPL is defined by Formula II-2 that is substituted by one occurrence of $R^{II\text{-}2A}$, wherein Formula II-2 is represented by:

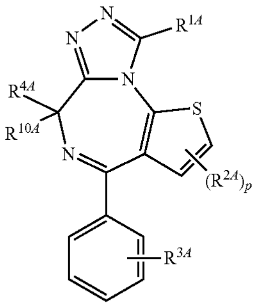

or

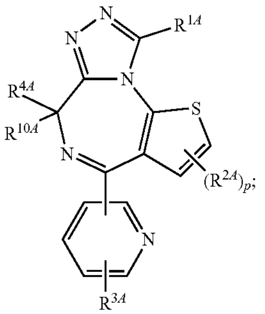

wherein $R^{II\text{-}2A}$ is a bond to L;

$R^{1A}$ is $C_{1\text{-}4}$ alkyl or $C_{3\text{-}4}$ cycloalkyl;

$R^{2A}$ represents independently for each occurrence $C_{1\text{-}4}$ alkyl or $C_{3\text{-}4}$ cycloalkyl;

$R^{3A}$ is hydrogen, halo, $C_{1\text{-}4}$ alkyl, or $C_{1\text{-}4}$ alkoxyl;

$R^{4A}$ is —($C_{0\text{-}6}$ alkylene)-(5-6 membered heteroaryl containing 1, 2, or 3 heteroatoms independently selected from nitrogen, oxygen, and sulfur), —($C_{1\text{-}6}$ alkylene)-C(O)N($R^{5A}$)($R^{6A}$), —($C_{1\text{-}6}$ alkylene)-N($R^{5A}$)C(O)$R^{7A}$, —($C_{1\text{-}6}$ alkylene)-$CO_2R^{7A}$, —($C_{1\text{-}6}$ cycloalkyl, or hydrogen; or $R^{4A}$ and $R^{10A}$ taken together with the carbon atom to which they are attached form a $C_{3\text{-}5}$ saturated carbocyclic ring;

$R^{5A}$ and $R^{6A}$ are independently hydrogen, $C_{1\text{-}6}$ alkyl, or $C_{3\text{-}6}$ cycloalkyl; or $R^{5A}$ and $R^{6A}$ are taken together with the nitrogen atom to which they are attached to form a 3-7 membered ring containing 1 nitrogen atom;

$R^{7A}$ is $C_{1\text{-}6}$ alkyl, —($C_{1\text{-}6}$ alkylene)-($C_{3\text{-}6}$ cycloalkyl), or $C_{3\text{-}6}$ cycloalkyl;

$R^{10A}$ is hydrogen or $C_{1\text{-}4}$ alkyl; and m, n, and p are independently 0, 1, or 2.

In certain embodiments, the EPL is defined by Formula II-2 that is substituted by one occurrence of $R^{II\text{-}2A}$, wherein Formula II-2 is represented by:

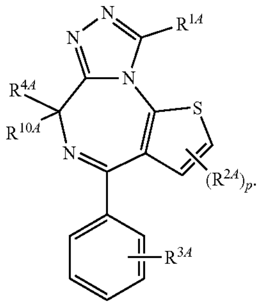

In certain embodiments, the EPL is

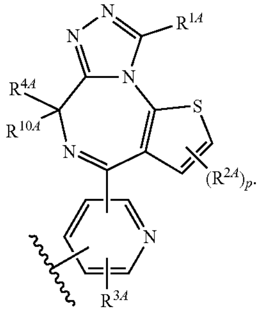

In certain embodiments, EPL is

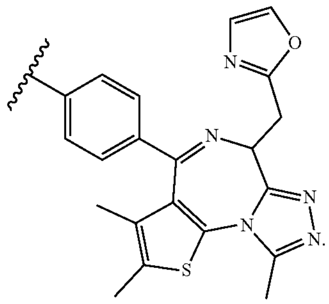 [SMILES: *c1ccc(C2=NC(Cc3ncco3)c3nnc(C)n3-c3sc(C)c(C)c32)cc1]

In certain embodiments, EPL is
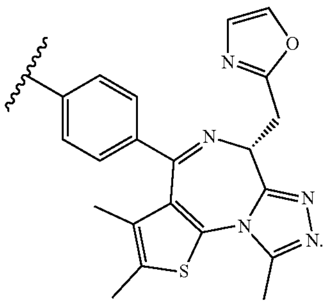 [SMILES: *c1ccc(C2=N[C@H](Cc3ncco3)c3nnc(C)n3-c3sc(C)c(C)c32)cc1]
In certain embodiments, EPL is
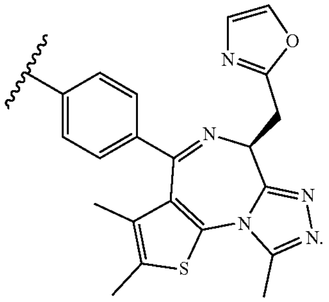 [SMILES: *c1ccc(C2=N[C@@H](Cc3ncco3)c3nnc(C)n3-c3sc(C)c(C)c32)cc1]
In certain embodiments, EPL is
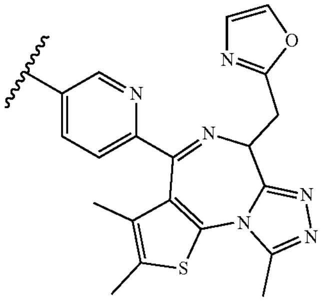
or
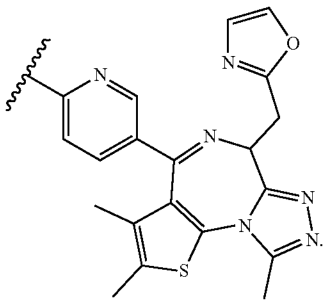
In certain embodiments, EPL is
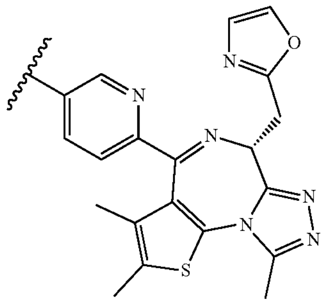
or
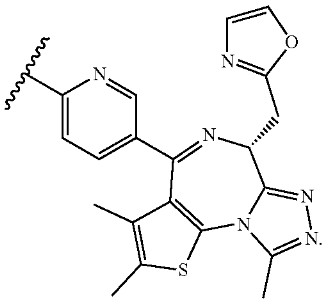
In certain embodiments, EPL is
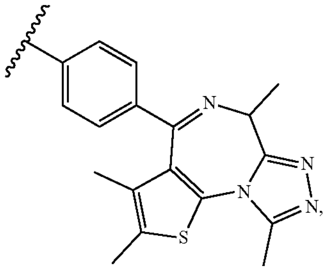
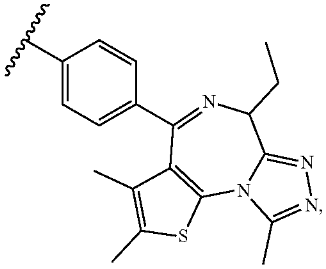
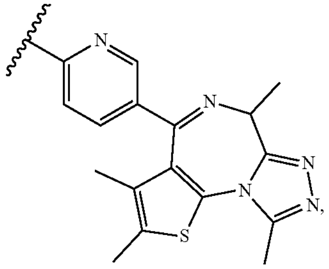
or -continued
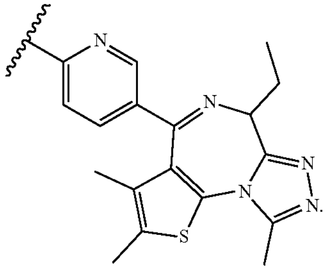
In certain embodiments, EPL is
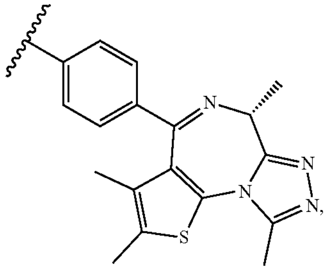
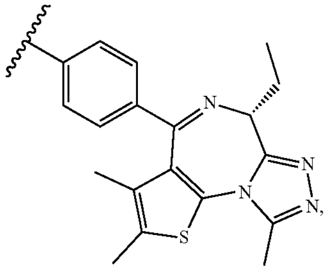
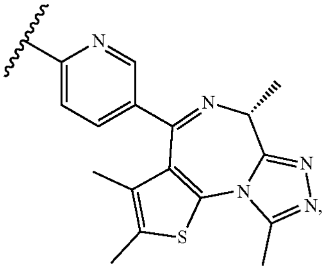
or
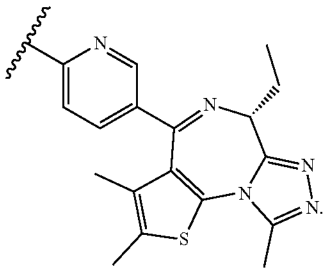
In certain embodiments, EPL is
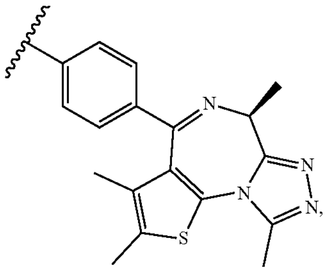
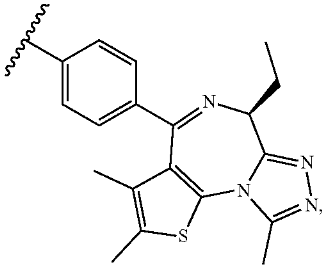
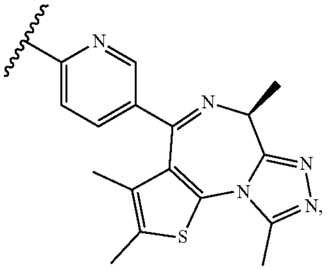
or
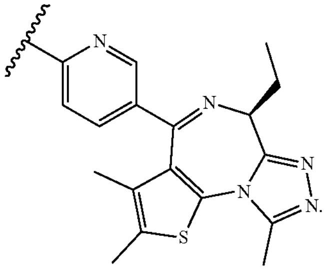
In certain embodiments, EPL is
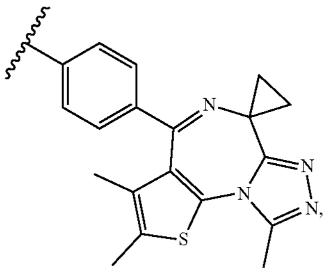

-continued
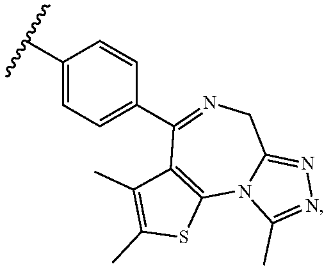
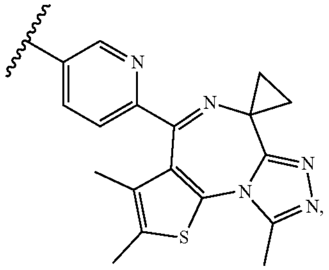
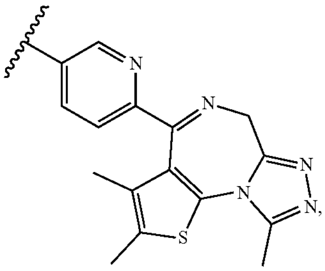
,
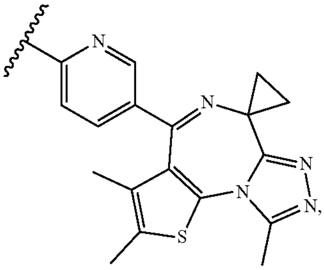
or
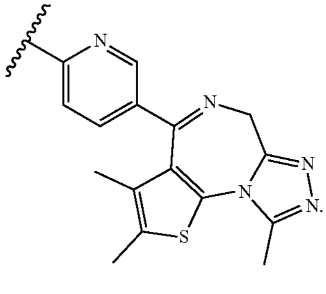
In certain embodiments, EPL is
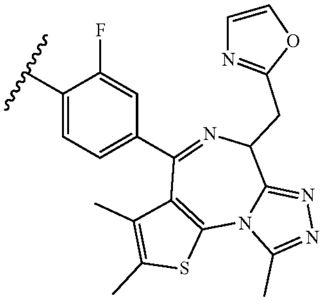
or
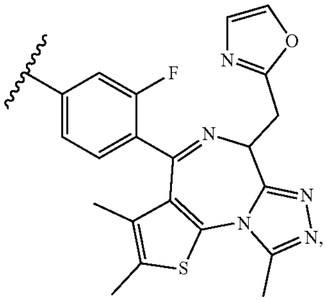
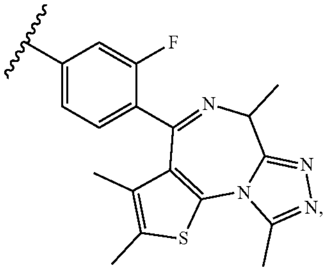
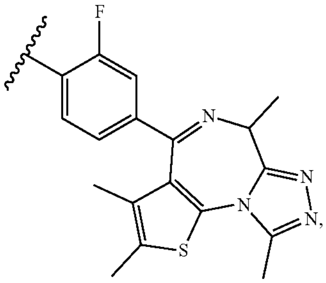
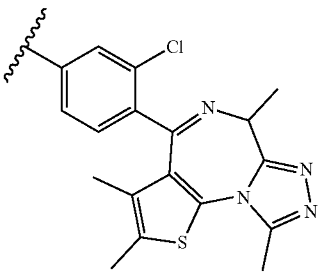

-continued
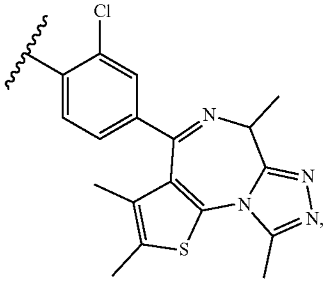
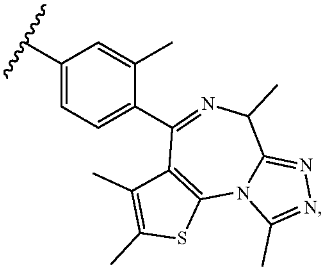
or
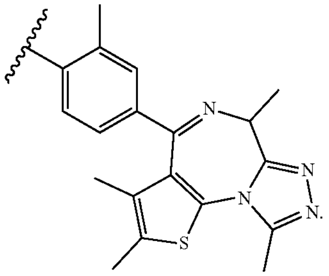
In certain embodiments, EPL is
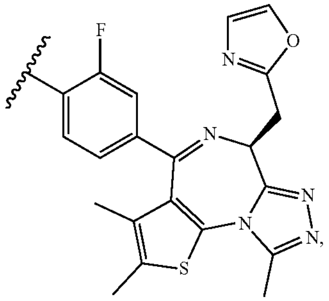
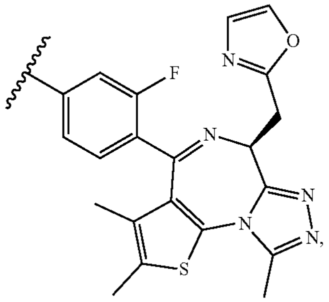
-continued
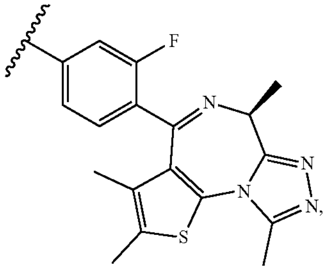
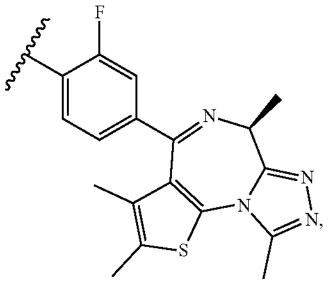
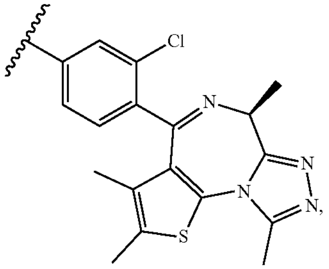
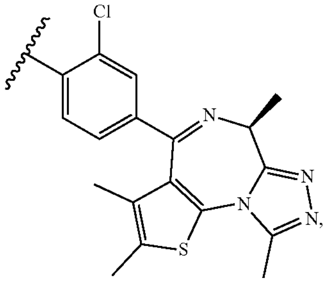
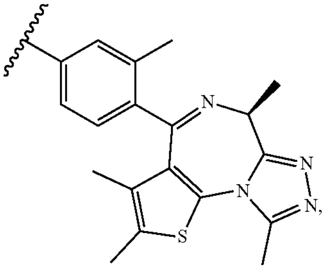
or
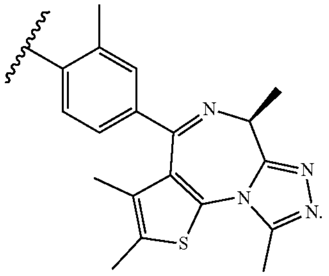

In certain embodiments, EPL is one of the following:
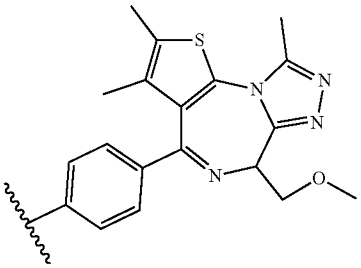
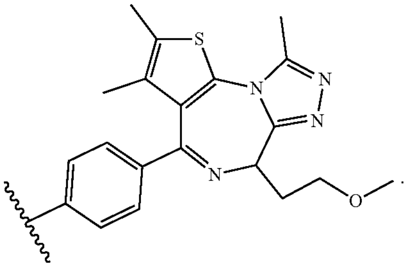
In certain embodiments, EPL is one of the following:
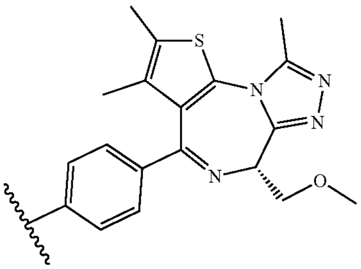
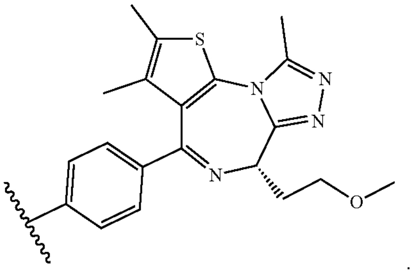
In certain embodiments, EPL is
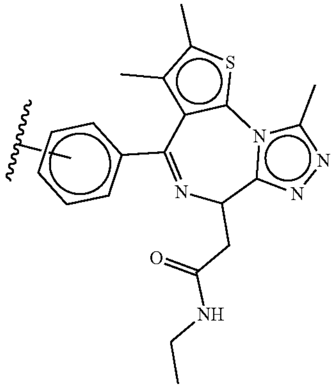
or
-continued
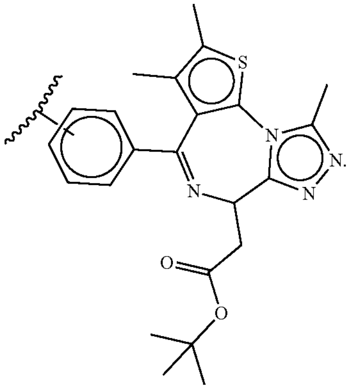
In certain embodiments, EPL is
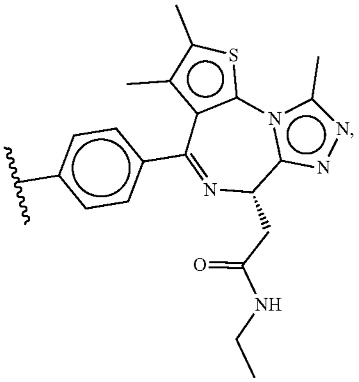
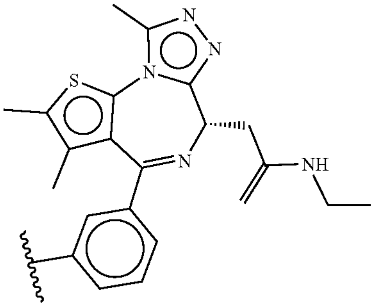
, or
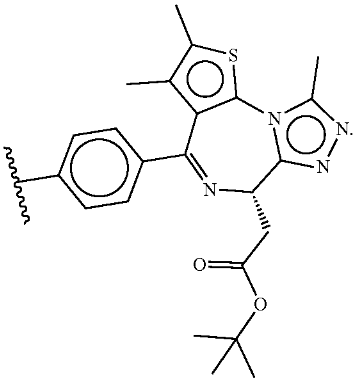

In certain embodiments, EPL is

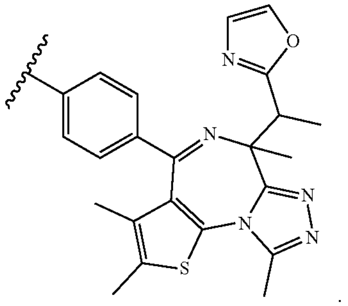 [SMILES: *c1ccc(C2=NC(C)(C(C)c3ncco3)c3nnc(C)n3-c3sc(C)c(C)c32)cc1]

In certain embodiments, EPL is

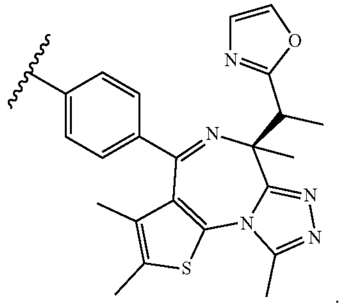 [SMILES: *c1ccc(C2=N[C@@](C)(C(C)c3ncco3)c3nnc(C)n3-c3sc(C)c(C)c32)cc1]

In certain embodiments, EPL is

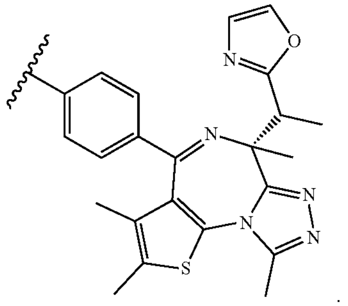 [SMILES: *c1ccc(C2=N[C@](C)(C(C)c3ncco3)c3nnc(C)n3-c3sc(C)c(C)c32)cc1]

In certain embodiments, EPL is selected from the groups depicted in the compounds in Table 1 or 2 below.

As defined generally above, $R^{1A}$ is $C_{1-4}$ alkyl or $C_{3-4}$ cycloalkyl. In certain embodiments, $R^{1A}$ is $C_{1-4}$ alkyl. In certain embodiments, $R^{1A}$ is methyl. In certain embodiments, $R^{1A}$ is $C_{3-4}$ cycloalkyl. In certain embodiments, $R^{1A}$ is selected from the groups depicted in the compounds in Table 1 or 2 below.

As defined generally above, $R^{2A}$ represents independently for each occurrence $C_{1-4}$ alkyl or $C_{3-4}$ cycloalkyl. In certain embodiments, $R^{2A}$ is $C_{1-4}$ alkyl. In certain embodiments, $R^{2A}$ is methyl. In certain embodiments, $R^{2A}$ is $C_{3-4}$ cycloalkyl. In certain embodiments, $R^{2A}$ is selected from the groups depicted in the compounds in Table 1 or 2 below.

As defined generally above, $R^{3A}$ is hydrogen, halo, $C_{1-4}$ alkyl, or $C_{1-4}$ alkoxyl. In certain embodiments, $R^{3A}$ is hydrogen. In certain embodiments, $R^{3A}$ is halo. In certain embodiments, $R^{3A}$ is fluoro. In certain embodiments, $R^{3A}$ is chloro. In certain embodiments, $R^{3A}$ is $C_{1-4}$ alkyl. In certain embodiments, $R^{3A}$ is methyl. In certain embodiments, $R^{3A}$ is $C_{1-4}$ alkoxyl. In certain embodiments, $R^{3A}$ is methoxy. In certain embodiments, $R^{3A}$ is halo, $C_{1-4}$ alkyl, or $C_{1-4}$ alkoxyl. In certain embodiments, $R^{3A}$ is selected from the groups depicted in the compounds in Table 1 or 2 below.

As defined generally above, $R^{4A}$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^{5A}$)($R^{6A}$), —($C_{1-6}$ alkylene)-N($R^{5A}$)C(O)$R^{7A}$, —($C_{1-6}$ alkylene)-$CO_2R^{7A}$, —($C_{1-6}$ alkylene)-OC(O)$R^{7A}$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^{4A}$ and $R^{10A}$ taken together with the carbon atom to which they are attached form a $C_{3-5}$ saturated carbocyclic ring. In certain embodiments, $R^{4A}$ is —($C_{1-6}$ alkylene)-C(O)N($R^{5A}$)($R^{6A}$), —($C_{1-6}$ alkylene)-N($R^{5A}$)C(O)$R^{7A}$, —($C_{1-6}$ alkylene)-$CO_2R^{7A}$, —($C_{1-6}$ alkylene)-OC(O)$R^{7A}$, or —($C_{0-6}$ alkylene)-(5-6 membered heteroaryl containing 1, 2, or 3 heteroatoms independently selected from nitrogen, oxygen, and sulfur). In certain embodiments, $R^{4A}$ is —($C_{1-6}$ alkylene)-C(O)N($R^{5A}$)($R^{6A}$), —($C_{1-6}$ alkylene)-N($R^{5A}$)C(O)$R^{7A}$, —($C_{1-6}$ alkylene)-$CO_2R^{7A}$, or —($C_{1-6}$ alkylene)-OC(O)$R^{7A}$. In certain embodiments, $R^{4A}$ is hydrogen. In certain embodiments, $R^{4A}$ is —($C_{1-6}$ alkylene)-cyano. In certain embodiments, $R^{4A}$ is $C_{1-6}$ alkyl. In certain embodiments, $R^{4A}$ is methyl. In certain embodiments, $R^{4A}$ is —($C_{1-6}$ alkylene)-C(O)N($R^{5A}$)($R^{6A}$). In certain embodiments, $R^{4A}$ is —($C_{1-6}$ alkylene)-$CO_2R^{7A}$. In certain embodiments, $R^{4A}$ is —($C_{1-6}$ alkylene)-N($R^{5A}$)C(O)$R^{7A}$. In certain embodiments, $R^{4A}$ is —($C_{1-6}$ alkylene)-OC(O)$R^{7A}$.

In certain embodiments, $R^{4A}$ is —($C_{0-6}$ alkylene)-(5-6 membered heteroaryl containing 1, 2, or 3 heteroatoms independently selected from nitrogen, oxygen, and sulfur). In certain embodiments, $R^{4A}$ is —($C_{0-6}$ alkylene)-(5-6 membered heteroaryl containing 1, 2, or 3 heteroatoms independently selected from nitrogen, oxygen, and sulfur). In certain embodiments, $R^{4A}$ is —($C_{1-2}$ alkylene)-(5-6 membered heteroaryl containing 1, 2, or 3 heteroatoms independently selected from nitrogen, oxygen, and sulfur). In certain embodiments, $R^{4A}$ is —($C_{1-2}$ alkylene)-(5-membered heteroaryl containing 1 or 2 heteroatoms independently selected from nitrogen, oxygen, and sulfur). In certain embodiments, $R^{4A}$ is —($C_{1-2}$ alkylene)-(oxazolyl).

In certain embodiments, $R^{4A}$ is —($C_{1-6}$ alkylene)-O—($C_{1-6}$ alkyl). In certain embodiments, $R^{4A}$ is —($C_{1-2}$ alkylene)-O—($C_{1-2}$ alkyl).

In certain embodiments, $R^{4A}$ and $R^{10A}$ taken together with the carbon atom to which they are attached form a $C_{3-5}$ saturated carbocyclic ring.

In certain embodiments, $R^{4A}$ is selected from the groups depicted in the compounds in Table 1 or 2 below.

As defined generally above, $R^{5A}$ and $R^{6A}$ are independently hydrogen, $C_{1-6}$ alkyl, or $C_{3-6}$ cycloalkyl; or $R^{5A}$ and $R^{6A}$ are taken together with the nitrogen atom to which they are attached to form a 3-7 membered ring containing 1 nitrogen atom. In certain embodiments, $R^{5A}$ and $R^{6A}$ are independently hydrogen, $C_{1-6}$ alkyl, or $C_{3-6}$ cycloalkyl. In certain embodiments, $R^{5A}$ is hydrogen. In certain embodiments, $R^{5A}$ is $C_{1-6}$ alkyl. In certain embodiments, $R^{5A}$ is $C_{3-6}$ cycloalkyl. In certain embodiments, $R^{6A}$ is hydrogen. In certain embodiments, $R^{6A}$ is $C_{1-6}$ alkyl. In certain embodiments, $R^{6A}$ is $C_{3-6}$ cycloalkyl. In certain embodiments, $R^{5A}$ and $R^{6A}$ are taken together with the nitrogen atom to which they are attached to form a 3-7 membered ring containing 1 nitrogen atom. In certain embodiments, $R^{5A}$ and $R^{6A}$ are taken together with the nitrogen atom to which they are attached to form a 3-membered ring containing 1 nitrogen atom. In certain embodiments, $R^{5A}$ and $R^{6A}$ are taken together with the nitrogen atom to which they are attached to form a 4-membered ring containing 1 nitrogen atom. In certain embodiments, $R^{5A}$ and $R^{6A}$ are taken together with the nitrogen atom to which they are attached to form a 5-membered ring containing 1 nitrogen atom. In certain embodiments, $R^{5A}$ and $R^{6A}$ are taken together with the nitrogen atom to which they are attached to form a 6-membered ring containing 1 nitrogen atom. In certain embodiments, $R^{5A}$ and $R^{6A}$ are taken together with the nitrogen atom to which they are attached to form a 7-membered ring containing 1 nitrogen atom. In certain embodiments, $R^{5A}$ is selected from the groups depicted in the compounds in Table 1 or 2 below. In certain embodiments, $R^{6A}$ is selected from the groups depicted in the compounds in Table 1 or 2 below.

As defined generally above, $R^{7A}$ is $C_{1-6}$ alkyl, —($C_{1-6}$ alkylene)-($C_{3-6}$ cycloalkyl), or $C_{3-6}$ cycloalkyl. In certain embodiments, $R^{7A}$ is $C_{1-6}$ alkyl. In certain embodiments, $R^{7A}$ is —($C_{1-6}$ alkylene)-($C_{3-6}$ cycloalkyl). In certain embodiments, $R^{7A}$ is $C_{3-6}$ cycloalkyl. In certain embodiments, $R^{7A}$ is selected from the groups depicted in the compounds in Table 1 or 2 below.

As defined generally above, $R^{10A}$ is hydrogen or $C_{1-4}$ alkyl. In certain embodiments, $R^{10A}$ is hydrogen. In certain embodiments, $R^{10A}$ is $C_{1-4}$ alkyl. In certain embodiments, $R^{10A}$ is methyl. In certain embodiments, $R^{10A}$ is selected from the groups depicted in the compounds in Table 1 or 2 below.

As defined generally above, m, n, and p are independently 0, 1, or 2. In certain embodiments, p is 2. In certain embodiments, p is 1. In certain embodiments, p is 0. In certain embodiments, m is 0. In certain embodiments, m is 1. In certain embodiments, m is 2. In certain embodiments, n is 0. In certain embodiments, n is 1. In certain embodiments, q is 0. In certain embodiments, q is 1. In certain embodiments, q is 2. In certain embodiments, p is selected from the corresponding value in the groups depicted in the compounds in Table 1 or 2 below. In certain embodiments, m is selected from the corresponding value in the groups depicted in the compounds in Table 1 or 2 below. In certain embodiments, n is selected from the corresponding value in the groups depicted in the compounds in Table 1 or 2 below.

In certain embodiments, the EPL is defined by variable $A^2$ set forth above in connection with Formula I. In certain embodiments, the EPL is defined by one or more of the embodiments for variable $A^2$ set forth in connection with Formula I.

The compounds may be further characterized according to, for example, the identity of L. Exemplary further embodiments for L are provided in Part C below.

Part C: Exemplary Further Description of Linker (L) Component of Compounds of Formula I and II Compounds of Formula I and II may be further characterized according to, for example, the identity of the linker (L) component. A variety of linkers are known to one of skill in the art and may be used in the heterobifunctional compounds described herein. For example, in certain embodiments, L comprises one or more optionally substituted groups selected from amino acids, polyether chains, aliphatic groups, and any combinations thereof. In certain embodiments, L consists of one or more optionally substituted groups selected from amino acids, polyether chains, aliphatic groups, and any combinations thereof. In certain embodiments, L consists of one or more groups selected from amino acids, polyether chains, aliphatic groups, and any combinations thereof.

In some embodiments, L is symmetrical. In some embodiments, L is asymmetric. In certain embodiments, L is a bond.

In certain embodiments, L is a covalent bond or a bivalent $C_{1-30}$ saturated or unsaturated, straight or branched, hydrocarbon chain, wherein 1-15 methylene units of L are optionally and independently replaced by cyclopropylene, —N(H)—, —N($C_{1-4}$ alkyl)-, —N($C_{3-5}$ cycloalkyl)-, —O—, —C(O)—, —OC(O)—, —C(O)O—, —S—, —S(O)—, —$S(O)_2$—, —$S(O)_2$N(H)—, —$S(O)_2$N($C_{1-4}$ alkyl)-, —$S(O)_2$ N($C_{3-5}$ cycloalkyl)-, —N(H)C(O)—, —N($C_{1-4}$ alkyl) C(O)—, —N($C_{3-5}$ cycloalkyl) C(O)—, —C(O)N(H)—, —C(O)N($C_{1-4}$ alkyl)-, —C(O)N($C_{3-5}$ cycloalkyl)-, phenylene, an 8-10 membered bicyclic arylene, a 4-7 membered saturated or partially unsaturated carbocyclylene, an 8-10 membered bicyclic saturated or partially unsaturated carbocyclylene, a 3-7 membered saturated or partially unsaturated heterocyclylene having 1-2 heteroatoms independently selected from nitrogen, oxygen, and sulfur, an 8-10 membered bicyclic saturated or partially unsaturated heterocyclylene having 1-2 heteroatoms independently selected from nitrogen, oxygen, and sulfur, a 5-6 membered heteroarylene having 1-4 heteroatoms independently selected from nitrogen, oxygen, and sulfur, or an 8-10 membered bicyclic heteroarylene having 1-5 heteroatoms independently selected from nitrogen, oxygen, or sulfur.

In certain embodiments, L is a bivalent, saturated or unsaturated, straight or branched $C_{1-60}$ hydrocarbon chain, wherein 0-20 methylene units of the hydrocarbon are independently replaced with —O—, —S—, —N(R)—, —OC(O)—, —C(O)O—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—, optionally substituted 3-10 membered carbocyclyl, or optionally substituted 3-10 membered heterocyclyl containing 1, 2, 3, or 4 heteroatoms independently selected from nitrogen, oxygen, and sulfur, wherein R represents independently for each occurrence hydrogen, $C_{1-6}$ alkyl, or $C_{3-6}$ cycloalkyl.

In certain embodiments, L is a bivalent, saturated or unsaturated, straight or branched $C_{1-60}$ hydrocarbon chain, wherein 0-20 methylene units of the hydrocarbon are independently replaced with —O—, —S—, —N(H)—, —N($C_{1-6}$ alkyl)-, —OC(O)—, —C(O)O—, —S(O)—, —$S(O)_2$—, —N(H) $S(O)_2$—, —N($C_{1-6}$ alkyl) $S(O)_2$—, —$S(O)_2$N(H)—, —$S(O)_2$N($C_{1-6}$ alkyl)-, —N(H)C(O)—, —N($C_{1-6}$ alkyl) C(O)—, —C(O)N(H)—, —C(O)N($C_{1-6}$ alkyl)-, —OC(O)N(H)—, —OC(O)N($C_{1-6}$ alkyl)-, —N(H) C(O)O—, —N($C_{1-6}$ alkyl) C(O)O—, optionally substituted 3-10 membered carbocyclyl, or optionally substituted 3-10 membered heterocyclyl containing 1, 2, 3, or 4 heteroatoms independently selected from nitrogen, oxygen, and sulfur.

In certain embodiments, L is a bivalent, saturated, straight or branched $C_{3-30}$ hydrocarbon chain, wherein 0-15 methylene units of the hydrocarbon are independently replaced with —O—, —N(H)—, —N($C_{1-6}$ alkyl)-, —OC(O)—, —C(O)O—, —N(H)C(O)—, —N($C_{1-6}$ alkyl) C(O)—, —C(O)N(H)—, —C(O)N($C_{1-6}$ alkyl)-, 3-10 membered carbocyclyl, or 3-10 membered heterocyclyl containing 1, 2, or 3 heteroatoms independently selected from nitrogen, oxygen, and sulfur.

In certain embodiments, L is a bivalent, saturated, straight or branched $C_{3-30}$ hydrocarbon chain, wherein 0-15 methylene units of the hydrocarbon are independently replaced with —O—, —N(H)—, —N($C_{1-6}$ alkyl)-, —OC(O)—, —C(O)O—, —N(H)C(O)—, —N($C_{1-6}$ alkyl) C(O)—, —C(O)N(H)—, or —C(O)N($C_{1-6}$ alkyl)-.

In yet other embodiments, L comprises a polyethylene glycol chain ranging in size from about 1 to about 12 ethylene glycol units, from about 1 to about 10 ethylene glycol units, from about 2 to about 6 ethylene glycol units, from about 2 to about 5 ethylene glycol units, or from about 2 to about 4 ethylene glycol units. In yet other embodiments, L is a diradical of a polyethylene glycol chain ranging in size from about 1 to about 12 ethylene glycol units, from about 1 to about 10 ethylene glycol units, from about 2 to about 6 ethylene glycol units, from about 2 to about 5 ethylene glycol units, or from about 2 to about 4 ethylene glycol units.

In certain embodiments, L is a heteroalkylene having from 4 to 30 atoms selected from carbon, oxygen, nitrogen, and sulfur. In certain embodiments, L is a heteroalkylene having from 4 to 20 atoms selected from carbon, oxygen, nitrogen, and sulfur. In certain embodiments, L is a heteroalkylene having from 4 to 10 atoms selected from carbon, oxygen, nitrogen, and sulfur. In certain embodiments, L is a heteroalkylene having from 4 to 30 atoms selected from carbon, oxygen, and nitrogen. In certain embodiments, L is a heteroalkylene having from 4 to 20 atoms selected from carbon, oxygen, and nitrogen. In certain embodiments, L is a heteroalkylene having from 4 to 10 atoms selected from carbon, oxygen, and nitrogen. In certain embodiments, L is a heteroalkylene having from 4 to 30 atoms selected from carbon and oxygen. In certain embodiments, L is a heteroalkylene having from 4 to 20 atoms selected from carbon and oxygen. In certain embodiments, L is a heteroalkylene having from 4 to 10 atoms selected from carbon and oxygen.

In additional embodiments, the L is an optionally substituted (poly)ethyleneglycol having between 1 and about 100 ethylene glycol units, between about 1 and about 50 ethylene glycol units, between 1 and about 25 ethylene glycol units, between about 1 and about 10 ethylene glycol units, between 1 and about 8 ethylene glycol units, between 1 and about 6 ethylene glycol units, between 2 and about 4 ethylene glycol units, or optionally substituted alkyl groups interdispersed with optionally substituted, O, N, S, P or Si atoms. In certain embodiments, L is substituted with an aryl, phenyl, benzyl, alkyl, alkylene, or heterocycle group.

In certain embodiments, L is a bivalent, saturated or unsaturated, straight or branched $C_{1-45}$ hydrocarbon chain, wherein 0-10 methylene units of the hydrocarbon are independently replaced with —O—, —S—, —N(R)—, —OC(O)—, —C(O)O—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—, optionally substituted carbocyclyl, or optionally substituted heterocyclyl, wherein R represents independently for each occurrence hydrogen, $C_{1-6}$ alkyl, or $C_{3-6}$ cycloalkyl.

In certain embodiments, L is a bivalent, saturated or unsaturated, straight or branched $C_{1-45}$ hydrocarbon chain, wherein 0-10 methylene units of the hydrocarbon are independently replaced with —O—, —S—, —N(R)—, —OC(O)—, —C(O)O—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—, optionally substituted 3-10 membered carbocyclyl, or optionally substituted 3-10 membered heterocyclyl containing 1, 2, 3, or 4 heteroatoms selected from nitrogen, oxygen, and sulfur, wherein R represents independently for each occurrence hydrogen, $C_{1-6}$ alkyl, or $C_{3-6}$ cycloalkyl.

In certain embodiments, L has the formula-N(R)-(optionally substituted 3-20 membered heteroalkylene)$_p$-$CH_2$—C(O)—, wherein R is hydrogen or optionally substituted $C_1$-$C_6$ alkyl, and p is 0 or 1.

In certain embodiments, L has the formula-N(R)-(3-20 membered heteroalkylene)$_p$-$CH_2$—C(O)—; wherein the 3-20 membered heteroalkylene is optionally substituted with 1, 2, 3, or 4 substituents independently selected from halogen, $C_1$-$C_6$ haloalkyl, $C_3$-$C_6$ cycloalkyl, hydroxyl, and cyano; R is hydrogen or optionally substituted $C_1$-$C_6$ alkyl; and p is 0 or 1.

In certain embodiments, L has the formula-N(R)-(3-20 membered heteroalkylene)$_p$-$CH_2$—C(O)—; wherein the 3-20 membered heteroalkylene is optionally substituted with 1, 2, or 3 substituents independently selected from halogen and $C_1$-$C_6$ haloalkyl; R is hydrogen or $C_1$-$C_6$ alkyl; and p is 0 or 1.

In certain embodiments, L is a bivalent, saturated or unsaturated, straight or branched $C_{1-60}$ hydrocarbon chain, wherein 0-20 methylene units of the hydrocarbon are independently replaced with —O—, —S—, —N(H)—, —N($C_{1-6}$ alkyl)-, —OC(O)—, —C(O)O—, —S(O)—, —$S(O)_2$—, —N(H) $S(O)_2$—, —N($C_{1-6}$ alkyl) $S(O)_2$—, —$S(O)_2$N(H)—, —$S(O)_2$N($C_{1-6}$ alkyl)-, —N(H)C(O)—, —N($C_{1-6}$ alkyl) C(O)—, —C(O)N(H)—, —C(O)N($C_{1-6}$ alkyl)-, —OC(O)N(H)—, —OC(O)N($C_{1-6}$ alkyl)-, —N(H) C(O)O—, —N($C_{1-6}$ alkyl) C(O)O—, optionally substituted 3-10 membered carbocyclyl, or optionally substituted 3-10 membered heterocyclyl containing 1, 2, 3, or 4 heteroatoms independently selected from nitrogen, oxygen, and sulfur.

In certain embodiments, L is a bivalent, saturated, straight or branched $C_{3-30}$ hydrocarbon chain, wherein 0-15 methylene units of the hydrocarbon are independently replaced with —O—, —N(H)—, —N($C_{1-6}$ alkyl)-, —OC(O)—, —C(O)O—, —N(H)C(O)—, —N($C_{1-6}$ alkyl) C(O)—, —C(O)N(H)—, —C(O)N($C_{1-6}$ alkyl)-, 3-10 membered carbocyclyl, or 3-10 membered heterocyclyl containing 1, 2, or 3 heteroatoms independently selected from nitrogen, oxygen, and sulfur.

In certain embodiments, L is a bivalent, saturated, straight or branched $C_{3-30}$ hydrocarbon chain, wherein 0-15 methylene units of the hydrocarbon are independently replaced with —O—, —N(H)—, —N($C_{1-6}$ alkyl)-, —OC(O)—, —C(O)O—, —N(H)C(O)—, —N($C_{1-6}$ alkyl) C(O)—, —C(O)N(H)—, or —C(O)N($C_{1-6}$ alkyl)-.

In certain embodiments, L is a bivalent, saturated or unsaturated, straight or branched $C_{5-40}$ hydrocarbon chain, wherein 1-20 methylene units of the hydrocarbon are independently replaced with —O—, —N(H)—, —N($C_{1-6}$ alkyl)-, —N(H)C(O)—, —N($C_{1-6}$ alkyl) C(O)—, —C(O)N(H)—, —C(O)N($C_{1-6}$ alkyl)-, optionally substituted 3-10 membered carbocyclyl, or optionally substituted 3-10 membered heterocyclyl containing 1, 2, 3, or 4 heteroatoms independently selected from nitrogen, oxygen, and sulfur.

In certain embodiments, L is -(7-11 membered spirocyclic or fused bicyclic saturated heterocyclic ring containing 1, 2, or 3 heteroatoms selected from nitrogen and oxygen)-$X^1$—* wherein $X^1$ is $C_{0-4}$ alkylene, $C_{2-4}$ alkynylene, or O, wherein * is the point of attachment to $A^2$.

In certain embodiments, L is -(8-10 membered spirocyclic or fused bicyclic saturated heterocyclic ring containing 1, 2, or 3 heteroatoms selected from nitrogen and oxygen, wherein the heterocyclic ring is substituted by 0, 1, or 2 occurrences of $C_{1-4}$ alkyl or halo)-$X^1$—*, wherein $X^1$ is $C_{0-4}$ alkylene, $C_{2-4}$ alkynylene, or O, wherein *** is the point of attachment to $A^2$.

In certain embodiments, L is -(10-13 membered spirocyclic saturated heterocyclic ring containing 1, 2, or 3 heteroatoms selected from nitrogen and oxygen)-$X^1$—*, wherein $X^1$ is $C_{0-4}$ alkylene, $C_{2-4}$ alkynylene, or O, wherein * is the point of attachment to $A^2$.

In certain embodiments, $X^1$ is $C_{1-4}$ alkylene. In certain embodiments, $X^1$ is $C_{2-4}$ alkynylene. In certain embodiments, $X^1$ is —C≡C—. In certain embodiments, $X^1$ is O.

In certain embodiments, L is -(8-10 membered spirocyclic, bicyclic saturated heterocyclic ring containing 1 or 2 heteroatoms selected from nitrogen and oxygen)-O—* wherein * is the point of attachment to $A^2$.

In certain embodiments, L is a 7-11 membered spirocyclic or fused bicyclic saturated heterocyclic ring containing 1, 2, or 3 heteroatoms selected from nitrogen and oxygen.

In certain embodiments, L is -(8-10 membered fused bicyclic saturated heterocyclic ring containing 1, 2, or 3 heteroatoms selected from nitrogen and oxygen, wherein the heterocyclic ring is substituted by 0, 1, or 2 occurrences of $C_{1-4}$ alkyl)-.

In certain embodiments, L is -(9-13 membered tricyclic saturated heterocyclic ring containing 1, 2, or 3 heteroatoms selected from nitrogen and oxygen)-($C_{0-4}$ alkylene)-*, wherein * is the point of attachment to $A^2$.

In certain embodiments, L is an 8-10 membered fused aromatic or partially unsaturated ring containing 1, 2, or 3 heteroatoms selected from nitrogen and oxygen.

In certain embodiments, L is a 7-8 membered spirocyclic or fused bicyclic saturated heterocyclic ring containing 2 heteroatoms selected from nitrogen.

In certain embodiments, L is -(3-7 membered monocyclic saturated heterocyclic ring containing 1 or 2 heteroatoms selected from nitrogen)-$X^3$-(3-7 membered monocyclic saturated heterocyclic ring containing 1 or 2 heteroatoms selected from nitrogen)-, wherein $X^3$ is $C_{1-10}$ alkylene, —O—, —N(H)—, —N($C_{1-4}$ alkyl)-, or a bond.

In certain embodiments, L is -(piperidinylene)-($C_{1-5}$ alkylene)-(piperazinylene)-* wherein * is the point of attachment to $A^2$. In certain embodiments, L is -(piperazinylene)-(azetidinylene)-* or -(azetidinylene)-(piperazinylene)-*, wherein *** is the point of attachment to $A^2$.

In certain embodiments, L is a -(7-11 membered spirocyclic or fused bicyclic saturated heterocyclic ring containing 1, 2, or 3 heteroatoms independently selected from nitrogen and oxygen)-O—*, wherein * is the point of attachment to the phenylene group in said formula.

In certain embodiments, L is a 7-11 membered spirocyclic or fused bicyclic saturated heterocyclic ring containing 1, 2, or 3 heteroatoms independently selected from nitrogen and oxygen.

In certain embodiments, L is -(7-11 membered spirocyclic saturated heterocyclic ring containing 1 or 2 heteroatoms selected from nitrogen)-($C_{2-4}$ alkynylene)-*, wherein * is the point of attachment to the phenylene group in said formula.

In certain embodiments, L is one of the following:

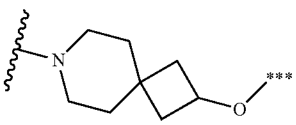
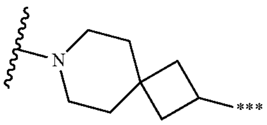
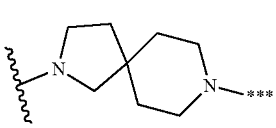
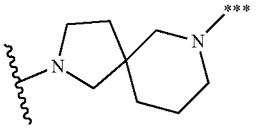
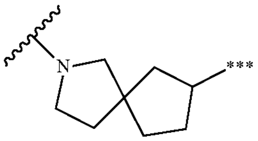
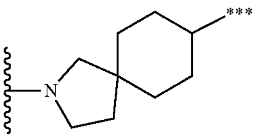

-continued

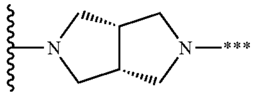
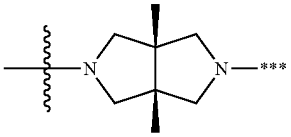
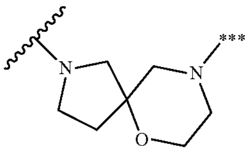
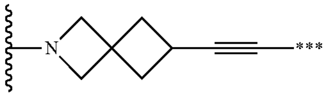
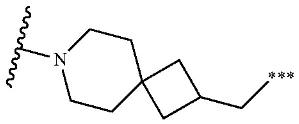

wherein *** is the point of attachment to $A^4$.

In certain embodiments, L is one of the following:

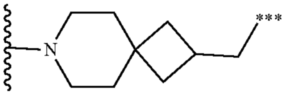
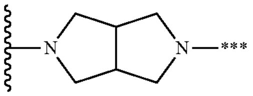
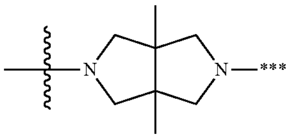
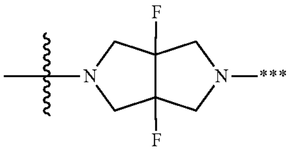
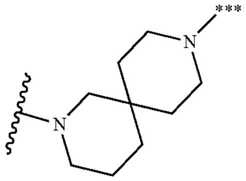
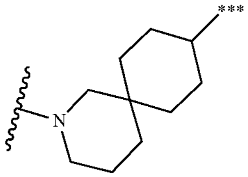
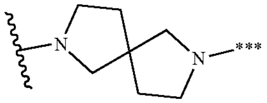
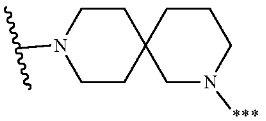
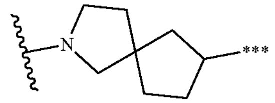
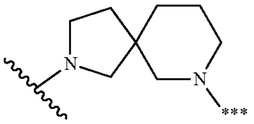
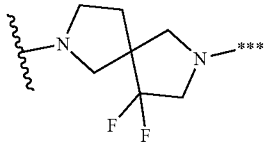
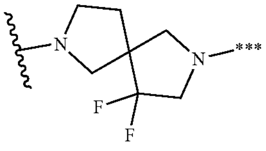
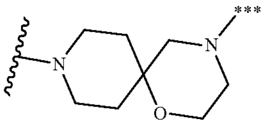

-continued

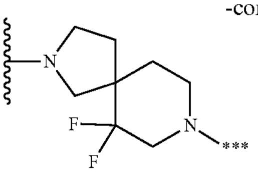
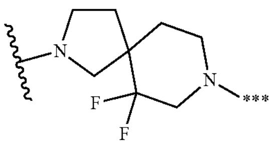
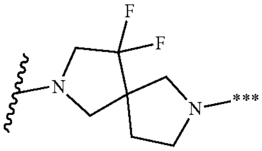
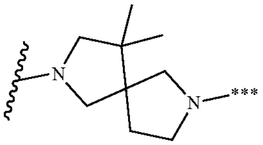
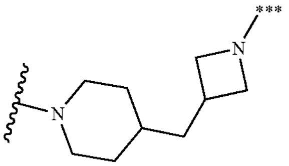
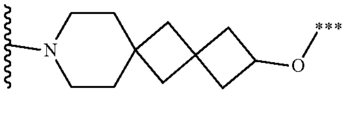

wherein *** is the point of attachment to $A^2$.

In certain embodiments, L is

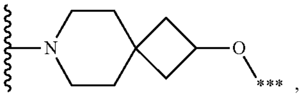

wherein *** is the point of attachment to $A^2$. In certain embodiments, L is

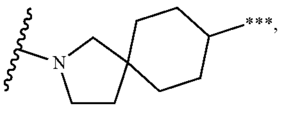

wherein *** is the point of attachment to $A^2$.

Additional Exemplary Embodiments for L

In certain embodiments, L is -(3-7 membered, monocyclic, saturated heterocyclic ring containing 1 or 2 heteroatoms selected from nitrogen)-$(OCH_2CH_2)_{1-15}$—O—*, wherein * is the point of attachment to $A^2$.

In certain embodiments, L is -(3-7 membered, monocyclic, saturated heterocyclic ring containing 1 or 2 heteroatoms selected from nitrogen)-$(OCH_2CH_2)_{1-5}$—O—*, wherein * is the point of attachment to $A^2$.

In certain embodiments, L is -(3-7 membered, monocyclic, saturated heterocyclic ring containing 1 or 2 heteroatoms selected from nitrogen)-$(OCH_2CH_2)_{6-10}$—O—*, wherein * is the point of attachment to $A^2$ In certain embodiments, L is -piperidinylene-$(OCH_2CH_2)_{1-15}$—O—*, wherein * is the point of attachment to $A^2$.

In certain embodiments, L is

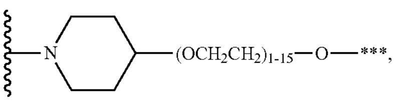

wherein *** is the point of attachment to $A^2$. In certain embodiments, L is

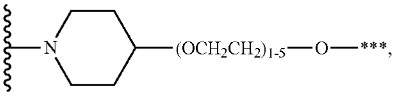

wherein *** is the point of attachment to $A^2$. In certain embodiments, L is

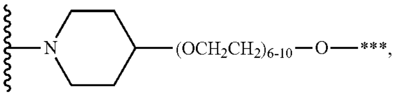

wherein *** is the point of attachment to $A^2$.

In certain embodiments, L is -(3-7 membered, monocyclic, saturated heterocyclic ring containing 1 or 2 heteroatoms selected from nitrogen)-$(OCH_2CH_2)_{1-15}$—N(H)C(O)—$C_{1-10}$ alkylene-*, -(3-7 membered, monocyclic, saturated heterocyclic ring containing 1 or 2 heteroatoms selected from nitrogen)-$(OCH_2CH_2)_{1-15}$—N($C_{1-4}$ alkyl)C(O)—$C_{1-10}$ alkylene-*, -(3-7 membered, monocyclic, saturated heterocyclic ring containing 1 or 2 heteroatoms selected from nitrogen)-$(OCH_2CH_2)_{1-15}$—C(O)N(H)—$C_{1-10}$ alkylene-*, or -(3-7 membered, monocyclic, saturated heterocyclic ring containing 1 or 2 heteroatoms selected from nitrogen)-$(OCH_2CH_2)_{1-15}$—C(O)N($C_{1-4}$ alkyl)-$C_{1-10}$ alkylene-*, wherein *** is the point of attachment to $A^2$.

In certain embodiments, L is -(3-7 membered, monocyclic, saturated heterocyclic ring containing 1 or 2 heteroatoms selected from nitrogen)-$(OCH_2CH_2)_{1-10}$—N(H)C(O)—$C_{1-5}$ alkylene-*, -(3-7 membered, monocyclic, saturated heterocyclic ring containing 1 or 2 heteroatoms selected from nitrogen)-$(OCH_2CH_2)_{1-10}$—N($C_{1-4}$ alkyl)C(O)—$C_{1-5}$ alkylene-*, -(3-7 membered, monocyclic, saturated heterocyclic ring containing 1 or 2 heteroatoms selected from nitrogen)-$(OCH_2CH_2)_{1-10}$—C(O)N(H)—$C_{1-5}$ alkylene-*, or -(3-7 membered, monocyclic, saturated heterocyclic ring containing 1 or 2 heteroatoms selected from nitrogen)-$OCH_2CH_2)_{1-10}$—C(O)N($C_{1-4}$ alkyl)-$C_{1-5}$ alkylene-*, wherein *** is the point of attachment to $A^2$.

In certain embodiments, L is -piperidinylene-$(OCH_2CH_2)_{1-5}$—N(H)C(O)—$C_{1-5}$ alkylene-*, -piperidinylene-$(OCH_2CH_2)_{1-5}$—N($C_{1-4}$ alkyl) C(O)—$C_{1-5}$ alkylene-*, -piperidinylene-$(OCH_2CH_2)_{1-5}$—C(O)N(H)—$C_{1-5}$ alkylene-*, or -piperidinylene-$(OCH_2CH_2)_{1-5}$—C(O)N($C_{1-4}$ alkyl)-$C_{1-5}$ alkylene-*, wherein *** is the point of attachment to $A^2$.

In certain embodiments, L is -(3-7 membered, monocyclic, saturated heterocyclic ring containing 1 or 2 heteroatoms selected from nitrogen)-$(OCH_2CH_2)_{1-10}$—*, -(3-7 membered, monocyclic, saturated heterocyclic ring containing 1 or 2 heteroatoms selected from nitrogen)-($C_{0-10}$ alkylene)-O—*, or -(3-7 membered, monocyclic, saturated heterocyclic ring containing 1 or 2 heteroatoms selected from nitrogen)-$C_{1-10}$ alkylene, wherein *** is the point of attachment to $A^2$.

In certain embodiments, L is -piperidinylene-$(OCH_2CH_2)_{1-5}$—*, -piperidinylene-($C_{0-5}$ alkylene)-O—*, or -piperidinylene-($C_{1-5}$ alkylene)-*, wherein * is the point of attachment to $A^2$.

In certain embodiments, L is -(3-7 membered monocyclic saturated heterocyclic ring containing 1 or 2 heteroatoms selected from nitrogen)-$X^1$—*, wherein * is the point of attachment to $A^2$, and $X^1$ is (i) $C_{1-10}$ alkylene where 1 or 2 methylene groups are optionally replaced by —O—, —N(H)—, or —N($C_{1-4}$ alkyl)-, (ii) a 3-7 membered monocyclic saturated heterocyclic ring containing 1 or 2 heteroatoms selected from nitrogen, or (iii)-(3-7 membered monocyclic saturated heterocyclic ring containing 1 or 2 heteroatoms selected from nitrogen)-($C_{1-10}$ alkylene)-.

In certain embodiments, L is -(piperidinylene)-$X^1$—*, wherein * is the point of attachment to $A^2$, and $X^1$ is (i) $C_{1-5}$ alkylene where 1 or 2 methylene groups are optionally replaced by —O—, —N(H)—, or —N($C_{1-4}$ alkyl)-, (ii) a 3-4 membered monocyclic saturated heterocyclic ring containing 1 heteroatom selected from nitrogen, or (iii)-(3-4 membered monocyclic saturated heterocyclic ring containing 1 heteroatom selected from nitrogen)-($C_{1-5}$ alkylene)-.

In certain embodiments, L is

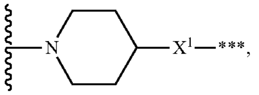

wherein *** is the point of attachment to $A^2$, and $X^1$ is (i) $C_{1-10}$ alkylene where 1 or 2 methylene groups are optionally replaced by —O—, —N(H)—, or —N($C_{1-4}$ alkyl)-, (ii) a 3-7 membered monocyclic saturated heterocyclic ring containing 1 or 2 heteroatoms selected from nitrogen, or (iii)-(3-7 membered monocyclic saturated heterocyclic ring containing 1 or 2 heteroatoms selected from nitrogen)-($C_{1-10}$ alkylene)-.

In certain embodiments, L is -(piperazinylene)-$X^1$—*, wherein * is the point of attachment to $A^2$, and $X^1$ is (i) $C_{1-5}$ alkylene where 1 or 2 methylene groups are optionally replaced by —O—, (ii) a 3-4 membered monocyclic saturated heterocyclic ring containing 1 heteroatom selected from nitrogen, or (iii)-(3-4 membered monocyclic saturated heterocyclic ring containing 1 heteroatom selected from nitrogen)-($C_{1-5}$ alkylene)-.

In certain embodiments, L is

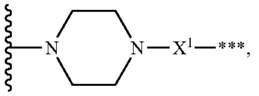

wherein *** is the point of attachment to $A^2$, and $X^1$ is (i) $C_{1-10}$ alkylene where 1 or 2 methylene groups are optionally replaced by —O—, (ii) a 3-7 membered monocyclic saturated heterocyclic ring containing 1 or 2 heteroatoms selected from nitrogen, or (iii)-(3-7 membered monocyclic saturated heterocyclic ring containing 1 or 2 heteroatoms selected from nitrogen)-($C_{1-10}$ alkylene)-.

In certain embodiments, L is -(3-7 membered monocyclic saturated heterocyclic ring containing 1 or 2 heteroatoms selected from nitrogen)-$X^2$—($C_{1-10}$ alkylene)-*, wherein * is the point of attachment to $A^2$, and $X^2$ is —O—, —N(H)—, or —N($C_{1-6}$ alkyl)-. In certain embodiments, L is -(3-7 membered monocyclic saturated heterocyclic ring containing 1 or 2 heteroatoms selected from nitrogen)-$X^2$—($C_{1-10}$ alkylene)-*, wherein * is the point of attachment to $A^2$, and $X^2$ is —O—.

In certain embodiments, L is -(piperidinylene)-$X^2$—($C_{1-10}$ alkylene)-*, wherein is the point of attachment to $A^2$, and $X^2$ is —O—, —N(H)—, or —N($C_{1-6}$ alkyl)-. In certain embodiments, L is -(piperidinylene)-$X^2$—($C_{1-10}$ alkylene)-*, wherein *** is the point of attachment to $A^2$, and $X^2$ is —O—.

In certain embodiments, L is -(piperidinylene)-$X^2$-(a 3-7 membered monocyclic saturated heterocyclic ring containing 1 or 2 heteroatoms selected from nitrogen)-*, wherein is the point of attachment to $A^2$, and $X^2$ is —O—, —N(H)—, or —N($C_{1-6}$ alkyl)-. In certain embodiments, L is -(piperidinylene)-$X^2$-(a 3-7 membered monocyclic saturated heterocyclic ring containing 1 or 2 heteroatoms selected from nitrogen)-*, wherein *** is the point of attachment to $A^2$, and $X^2$ is —O—.

In certain embodiments, L is

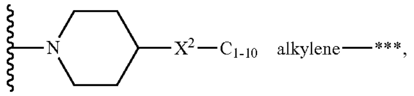

wherein *** is the point of attachment to $A^2$, and $X^2$ is —O—, —N(H)—, or —N($C_{1-6}$ alkyl)-. In certain embodiments, L is

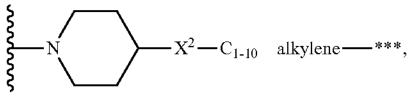

wherein *** is the point of attachment to $A^2$, and $X^2$ is —O—.

In certain embodiments, L is

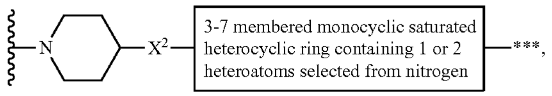

wherein is the point of attachment to $A^2$, and $X^2$ is —O—, —N(H)—, or —N($C_{1-6}$ alkyl)-. In certain embodiments, L is

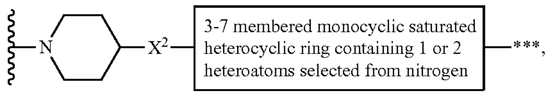

wherein *** is the point of attachment to $A^2$, and $X^2$ is —O—.

In certain embodiments, L is -(3-7 membered monocyclic saturated heterocyclic ring containing 1 or 2 heteroatoms selected from nitrogen)-$X^1$—*, wherein * is the point of attachment to $A^2$, and $X^1$ is —$(OCH_2CH_2)_{1-10}$ where 1 $CH_2$ group is optionally replaced with —C(H)($C_{3-6}$ cycloalkyl)-.

In certain embodiments, L is a 7-11 membered spirocyclic or fused bicyclic saturated heterocyclic ring containing 1, 2, or 3 heteroatoms selected from nitrogen and oxygen. In certain embodiments, L is a 7-8 membered spirocyclic or fused bicyclic saturated heterocyclic ring containing 2 heteroatoms selected from nitrogen.

In certain embodiments, L is -(3-7 membered monocyclic saturated heterocyclic ring containing 1 or 2 heteroatoms selected from nitrogen)-$X^3$-(3-7 membered monocyclic saturated heterocyclic ring containing 1 or 2 heteroatoms selected from nitrogen)-, wherein $X^3$ is $C_{1-10}$ alkylene, —O—, —N(H)—, —N($C_{1-4}$ alkyl)-, or a bond.

In certain embodiments, L is -(piperidinylene)-($C_{1-5}$ alkylene)-(piperazinylene)-*, wherein * is the point of attachment to $A^2$.

In certain embodiments, L is -(piperazinylene)-(azetidinylene)-* or (azetidinylene)-(piperazinylene)-*, wherein *** is the point of attachment to $A^2$.

In certain embodiments, L is -(3-7 membered monocyclic saturated heterocyclic ring containing 1 or 2 heteroatoms selected from nitrogen)-$X^3$—($C_{3-6}$ cycloalkylene)-O—*, -(3-7 membered monocyclic saturated heterocyclic ring containing 1 or 2 heteroatoms selected from nitrogen)-$X^3$—($C_{3-6}$ cycloalkylene)-N(H)—*, or -(3-7 membered monocyclic saturated heterocyclic ring containing 1 or 2 heteroatoms selected from nitrogen)-$X^3$—($C_{3-6}$ cycloalkylene)-N($C_{1-4}$ alkyl)-*, wherein * is the point of attachment to $A^2$, and $X^3$ is $C_{1-10}$ alkylene, —O—, —N(H)—, —N($C_{1-4}$ alkyl)-, or a bond.

In certain embodiments, L is -(piperidinylene)-$X^3$—($C_{3-6}$ cycloalkylene)-O—*, -(piperidinylene)-$X^3$—($C_{3-6}$ cycloalkylene)-N(H)—*, or -(piperidinylene)-$X^3$—($C_{3-6}$ cycloalkylene)-*, wherein * is the point of attachment to $A^2$, and $X^3$ is $C_{1-10}$ alkylene, —O—, —N(H)—, —N($C_{1-4}$ alkyl)-, or a bond.

In certain embodiments, L has the formula-($C_{0-12}$ alkylene)-(optionally substituted 3-40 membered heteroalkylene)-($C_{0-12}$ alkylene)-.

In certain embodiments, L is

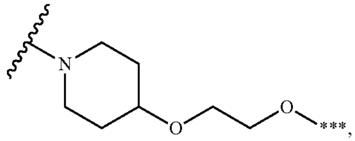,
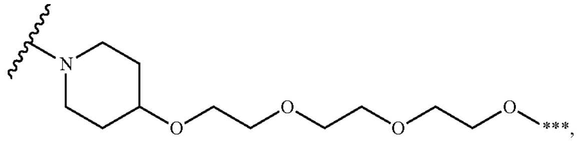,
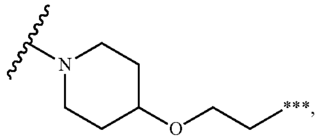,
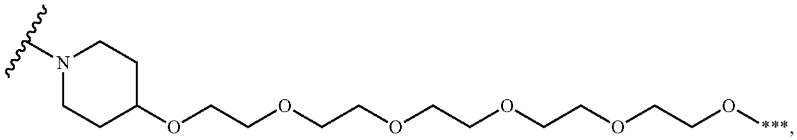,
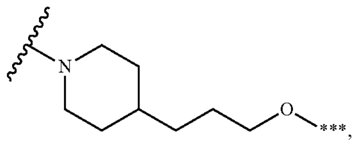,
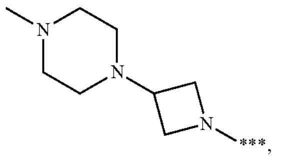,
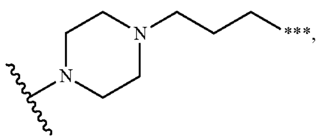, or
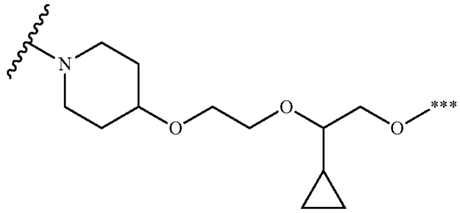

wherein is the point of attachment to $A^2$.

In certain embodiments, L is

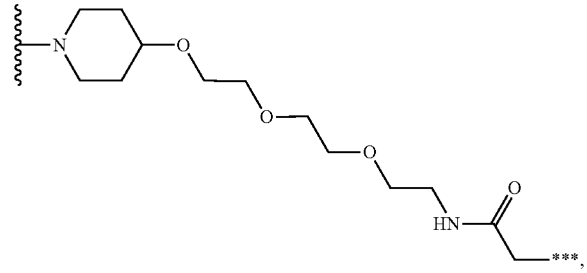,

-continued

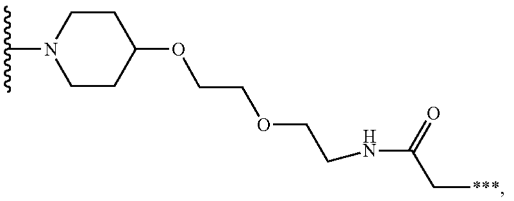

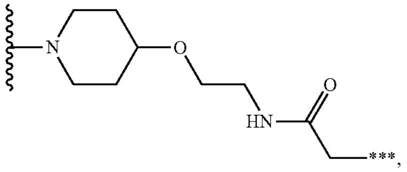

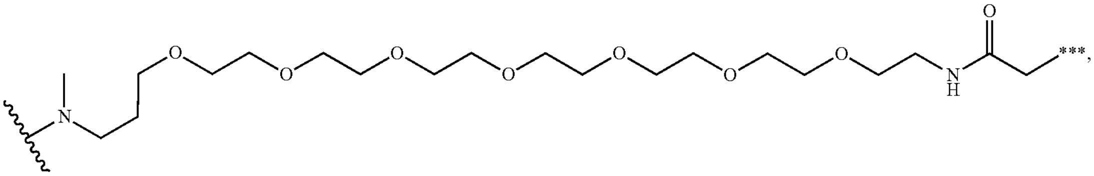

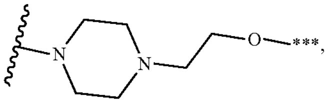

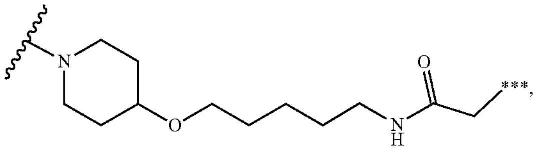

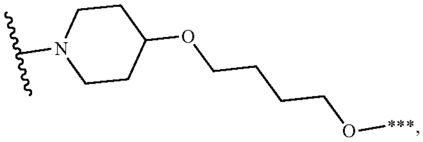

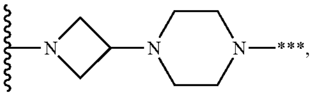

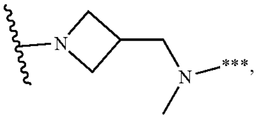

or

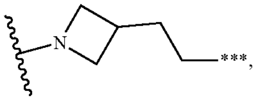

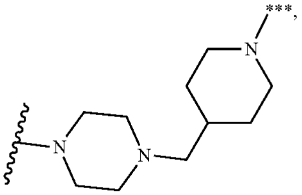

wherein *** is the point of attachment to $A^2$.

In certain embodiments, L is

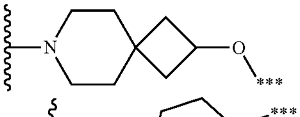

or

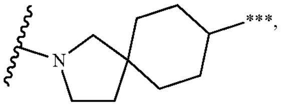

wherein *** is the point of attachment to $A^2$.

In certain embodiments, L is

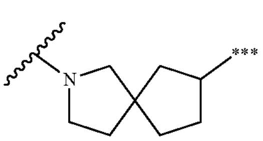

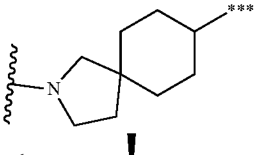

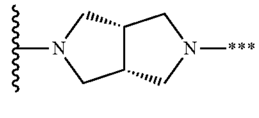

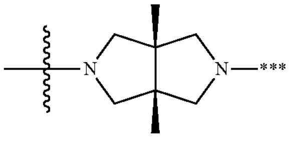

-continued

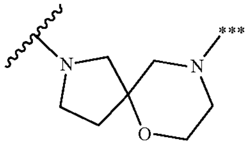

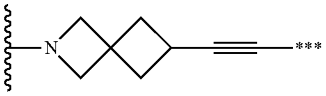

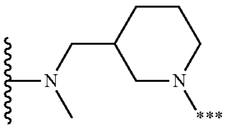

wherein *** is the point of attachment to $A^2$

In certain embodiments, L is -(8-12 membered spirocyclic heterocyclyl containing 1, 2 or 3 heteroatoms independently selected from nitrogen and oxygen)-($C_{3-4}$ cycloalkylene)-*, -(8-12 membered spirocyclic heterocyclyl containing 1, 2 or 3 heteroatoms independently selected from nitrogen and oxygen)-($C_{0-4}$ alkylene)-*, -(8-12 membered spirocyclic heterocyclyl containing 1, 2 or 3 heteroatoms independently selected from nitrogen and oxygen)-C(O)—($C_{1-4}$ alkylene)-*, -(5-6 membered saturated monocyclic heterocyclylene containing 1 or 2 heteroatoms independently selected from nitrogen and oxygen)-(3-5 membered saturated monocyclic heterocyclylene containing 1 or 2 heteroatoms independently selected from nitrogen and oxygen)-*, -(5-6 membered saturated monocyclic heterocyclylene containing 1 or 2 heteroatoms independently selected from nitrogen and oxygen)-O—*, -(5-6 membered saturated monocyclic heterocyclylene containing 1 or 2 heteroatoms independently selected from nitrogen and oxygen)-($C_{0-4}$ alkylene)-*, -(5-6 membered saturated monocyclic heterocyclylene containing 1 or 2 heteroatoms)-($C_{0-4}$ alkylene)-O—*, -(8-12 membered spirocyclic heterocyclyl containing 1, 2 or 3 heteroatoms independently selected from nitrogen and oxygen)-C(O))—*, -(8-12 membered spirocyclic heterocyclyl containing 1 or 2 heteroatoms selected from nitrogen)-O—($C_{0-6}$ alkylene)-*, -(8-12 membered spirocyclic heterocyclyl containing 1 or 2 heteroatoms selected from nitrogen)-($C_{1-6}$ alkylene)-O—($C_{0-6}$ alkylene)-*, -(5-6 membered saturated monocyclic heterocyclylene containing 1 or 2 heteroatoms)-C(O)N(H)—($C_{0-6}$ alkylene)-*, —N($C_{1-6}$ alkyl)-($C_{0-6}$ alkylene)-C(O)N(H)—($C_{0-6}$ alkylene)-*, -(8-12 membered spirocyclic heterocyclyl containing 1, 2 or 3 heteroatoms independently selected from nitrogen and oxygen)-($C_{2-4}$ alkynylene)-*, -(5-6 membered saturated monocyclic heterocyclylene containing 1 or 2 heteroatoms independently selected from nitrogen and oxygen)-($C_{1-6}$ alkyl)-(3-5 membered saturated monocyclic heterocyclylene containing 1 or 2 heteroatoms independently selected from nitrogen and oxygen)-*, -(5-6 membered saturated monocyclic heterocyclylene containing 1 or 2 heteroatoms selected from nitrogen)-C(O)N(H)—($C_{0-6}$ alkylene)-N(H))—*, —(C(O)N(H)—($C_{0-6}$ alkylene)-(5-6 membered saturated monocyclic heterocyclylene containing 1 or 2 heteroatoms)-*, -(5-6 membered saturated monocyclic heterocyclylene containing 1 or 2 heteroatoms independently selected from nitrogen and oxygen)-N($C_{1-6}$ alkyl)-(5-6 membered saturated monocyclic heterocyclylene containing 1 or 2 heteroatoms independently selected from nitrogen and oxygen)-O—*, —C(O)-(5-6 membered saturated monocyclic heterocyclylene containing 1 or 2 heteroatoms selected from nitrogen)-C(O)—*, —($C_{0-6}$ alkylene)-(5-6 membered saturated monocyclic heterocyclylene containing 1 or 2 heteroatoms selected from nitrogen)-C(O)—*, -(5-6 membered saturated monocyclic heterocyclylene containing 1 or 2 heteroatoms selected from nitrogen)-C(O)—($C_{0-6}$ alkylene) *, —C(O)-(5-6 membered saturated monocyclic heterocyclylene containing 1 or 2 heteroatoms selected from nitrogen)-($C_{1-6}$ alkylene)-*, —(C(O)N(H)—($C_{1-6}$ alkylene)-C(O)N(H)—($C_{0-6}$ alkylene)-*, or -(8-11 membered fused bicyclic heterocyclyl containing 1, 2 or 3 heteroatoms independently selected from nitrogen and oxygen)-($C_{1-4}$ alkylene)-*, wherein * is the point of attachment to $A^2$.

In certain embodiments, L is —N($C_{1-6}$ alkyl)-(5-6 membered saturated monocyclic heterocyclylene containing 1 or 2 heteroatoms selected from nitrogen)-C(O)—($C_{0-6}$ alkylene)-* (5-6 membered saturated monocyclic heterocyclylene containing 1 or 2 heteroatoms selected from nitrogen)-(5-6 membered saturated monocyclic heterocyclylene containing 1 or 2 heteroatoms selected from nitrogen)-($C_{0-4}$ alkylene)-O—*, —($C_{0-6}$ alkylene)-N(H)C(O)N(H)—($C_{0-6}$ alkylene)-*, —N(H)—($C_{0-6}$ alkylene)-(5-6 membered saturated monocyclic heterocyclylene containing 1 or 2 heteroatoms selected from nitrogen)-($C_{0-6}$ alkylene)-*, —($C_{0-6}$ alkylene)-C(O)-(5-6 membered saturated monocyclic heterocyclylene containing 1 or 2 heteroatoms selected from nitrogen)-($C_{0-6}$ alkylene)-*, —($C_{0-6}$ alkylene)-(5-6 membered saturated monocyclic heterocyclylene containing 1 or 2 heteroatoms selected from nitrogen)-C(O)N($C_{1-6}$ alkyl)-($C_{0-6}$ alkylene)-*, —($C_{0-6}$ alkylene)-(5-6 membered saturated monocyclic heterocyclylene containing 1 or 2 heteroatoms selected from nitrogen)-($C_{0-6}$ alkylene)-N($C_{1-6}$ alkyl)-(3-6 membered saturated monocyclic heterocyclylene containing 1 or 2 heteroatoms selected from nitrogen)-*, -(4-6 membered monocyclic heterocyclyl containing 1 or 2 heteroatoms selected from nitrogen)-($C_{0-6}$ alkylene)-O-(5-6 membered heteroaryl containing 1 or 2 heteroatoms selected from nitrogen)-O—*, -(4-6 membered monocyclic heterocyclyl containing 1 or 2 heteroatoms selected from nitrogen)-($C_{0-6}$ alkylene)-(5-6 membered heteroaryl containing 1 or 2 heteroatoms selected from nitrogen)-O—*, -(4-6 membered monocyclic heterocyclyl containing 1 or 2 heteroatoms selected from nitrogen)-($C_{0-6}$ alkylene)-(5-6 membered heteroaryl containing 1 or 2 heteroatoms selected from nitrogen)-*, -(8-12 membered spirocyclic heterocyclyl substituted with 1 or 2 fluoro containing 1, 2 or 3 heteroatoms independently selected from nitrogen and oxygen)-($C_{1-4}$ alkylene)-*, -(5-6 membered saturated monocyclic heterocyclylene containing 1 or 2 heteroatoms selected from nitrogen)-($C_{0-4}$ alkylene)-($C_{3-6}$ cycloalkylene)-($C_{0-4}$ alkylene)-O—*, -(5-6 membered saturated monocyclic heterocyclylene containing 1 or 2 heteroatoms selected from nitrogen)-($C_{0-4}$ alkylene)-($C_{3-6}$ cycloalkylene)-($C_{0-4}$ alkylene)-*, —($C_{0-4}$ alkylene)-(8-12 membered spirocyclic heterocyclyl containing 1, 2 or 3 heteroatoms independently selected from nitrogen and oxygen)-*, —($C_{0-4}$ alkylene)-($C_{3-6}$ cycloalkylene)-($C_{2-4}$ alkynylene)-*, —($C_{0-4}$ alkylene)-(8-10 membered fused bicyclic heterocyclyl substituted with 1 or two fluoro containing 1 or 2 heteroatoms selected from nitrogen)-($C_{0-4}$ alkylene)-*, -(8-12 membered spirocyclic heterocyclyl containing 1, 2 or 3 heteroatoms independently selected from nitrogen and oxygen)-O—*, -(8-12 membered spirocyclic heterocyclyl containing 1, 2 or 3 heteroatoms independently selected from nitrogen and oxygen)-($C_{0-4}$ alkylene)-(5-6 membered saturated monocyclic heterocyclylene containing 1 or 2 heteroatoms selected from nitrogen)-*, —($C_{0-4}$ alkylene)-(4-6 membered saturated heterocyclyl containing 1 or 2 heteroatoms selected from nitrogen)-(phenylene substituted with trifluoromethyl)-($C_{0-4}$ alkylene)-N(H)—*, or is -(5-6 membered saturated monocyclic heterocyclylene containing 1 or 2 heteroatoms selected from nitrogen)-C(O)-(5-6 membered saturated monocyclic heterocyclylene containing 1 or 2 heteroatoms selected from nitrogen)-($C_{0-6}$ alkylene)-*, —($C_{3-6}$ cycloalkylene)-C(O)N($C_{1-6}$ alkyl) ($C_{0-6}$ alkylene)-*, -(5-6 membered saturated monocyclic heterocyclylene containing 1 or 2 heteroatoms selected from nitrogen)-(phenylene substituted with 0 or 1 occurrence of methyl or halo)-($C_{0-6}$ alkylene)-*, -(5-6 membered saturated monocyclic heterocyclylene containing 1 or 2 heteroatoms selected from nitrogen)-($C_{0-6}$ alkylene)-(5-6 membered saturated monocyclic oxo-substituted heterocyclylene containing 1 or 2 heteroatoms selected from nitrogen)-($C_{0-6}$ alkylene)-*, -(8-12 membered spirocyclic $C_{1-4}$ alkyl substituted heterocyclyl containing 1, 2 or 3 heteroatoms independently selected from nitrogen and oxygen)-($C_{0-6}$ alkylene)-$(O)_{0-1}$*, —($C_{2-4}$ alkynylene)-(8-12 membered spirocyclic heterocyclyl containing 1, 2 or 3 heteroatoms independently selected from nitrogen and oxygen)-($C_{0-4}$ alkylene)-*, —($C_{0-4}$ alkylene)-($C_{3-7}$ cycloalkylene)-($C_{2-4}$ alkynylene)-*, —($C_{1-4}$ alkylene)-(8-12 membered spirocyclic heterocyclyl containing 1, 2 or 3 heteroatoms independently selected from nitrogen and oxygen)-($C_{0-4}$ alkylene)-*, —($C_{1-4}$ alkylene)-(5-7 membered saturated heterocyclyl containing 1, 2 or 3 heteroatoms independently selected from nitrogen and oxygen)-($C_{0-4}$ alkylene)-*, —($C_{0-4}$ alkylene)-(5-7 membered saturated heterocyclyl containing 1 or 2 heteroatoms independently selected from nitrogen and oxygen)-($C_{2-4}$ alkenylene)-*, or —($C_{0-4}$ alkylene)-(6-8 membered saturated heterocyclyl substituted with 1 or 2 fluoro containing 1 or 2 heteroatoms independently selected from nitrogen and oxygen)-($C_{0-4}$ alkylene)-*, wherein * is the point of attachment to $A^2$.

In certain embodiments, L is —N(H)—($C_{2-9}$ alkylene)-O—($C_{1-6}$ alkylene)-C(O)—*, —N(H)—($C_{10-20}$ alkylene)-O—($C_{1-6}$ alkylene)-C(O)—*, —N(H)—[($C_{2-4}$ alkylene)-O-]$_{2-6}$-($C_{1-6}$ alkylene)-C(O)—*, —N(H)—[($C_{2-4}$ alkylene)-O-]$_{7-15}$-($C_{1-6}$ alkylene)-C(O)—*, —N(H)—($C_{1-6}$ alkylene)-C(O)—*, —N(H)—($C_{7-15}$ alkylene)-C(O)—*, —N(H)—[($C_{2-4}$ alkylene)-O-]$_{2-6}$-($C_{1-6}$ alkylene)-*, —N(H)—[($C_{2-4}$ alkylene)-O-]$_{7-15}$-($C_{1-6}$ alkylene)-*, —N(H)—($C_{2-9}$ alkylene)-O—($C_{1-6}$ alkylene)-C(O)N($C_{1-6}$ alkyl)-($C_{1-6}$ alkylene)-*, —N(H)—($C_{2-9}$ alkylene)-O—($C_{1-6}$ alkylene)-C(O)N(H)—($C_{1-6}$ alkylene)-*, —N(H)—[($C_{2-4}$ alkylene)-O-]$_{2-6}$-($C_{1-6}$ alkylene)-N(H)—($C_{1-6}$ alkylene)-*, —N(H)—[($C_{2-4}$ alkylene)-O-]$_{7-15}$-($C_{1-6}$ alkylene)-N(H)—($C_{1-6}$ alkylene)-*, —N(H)—[($C_{2-4}$ alkylene)-O-]$_{2-6}$-($C_{1-6}$ alkylene)-N($C_{1-6}$ alkyl)-($C_{1-6}$ alkylene)-*, or —N(H)—[($C_{2-4}$ alkylene)-O-]$_{7-15}$-($C_{1-6}$ alkylene)-N($C_{1-6}$ alkyl)-($C_{1-6}$ alkylene)-*, where *** is a point of attachment to $A^2$.

In certain embodiments, L is —N(H)—($C_{2-9}$ alkylene)-O—($C_{1-6}$ alkylene)-C(O)—*, —N(H)—($C_{10-20}$ alkylene)-O—($C_{1-6}$ alkylene)-C(O)—*, —N(H)—[$CH_2CH_2$—O-]$_{2-6}$-($C_{1-6}$ alkylene)-C(O)—*, —N(H)—[$CH_2CH_2$—O-]$_{7-15}$-($C_{1-6}$ alkylene)-C(O)—*, —N(H)—($C_{1-6}$ alkylene)-C(O)—*, —N(H)—($C_{7-15}$ alkylene)-C(O)—*, —N(H)—[$CH_2CH_2$—O-]$_{2-6}$-($C_{1-6}$ alkylene)-*, —N(H)—[$CH_2CH_2$—O-]$_{7-15}$-($C_{1-6}$ alkylene)-*, —N(H)—($C_{2-9}$ alkylene)-O—($C_{1-6}$ alkylene)-C(O)N($C_{1-6}$ alkyl)-($C_{1-6}$ alkylene)-*, —N(H)—($C_{2-9}$ alkylene)-O—($C_{1-6}$ alkylene)-C(O)N(H)—($C_{1-6}$ alkylene)-*, —N(H)—[$CH_2CH_2$—O-]$_{12-6}$-($C_{1-6}$ alkylene)-N(H)—($C_{1-6}$ alkylene)-*, —N(H)—[$CH_2CH_2$—O-]$_{7-15}$-($C_{1-6}$ alkylene)-N(H)—($C_{1-6}$ alkylene)-*, —N(H)—[$CH_2CH_2$—O-]$_{2-6}$-($C_{1-6}$ alkylene)-N($C_{1-6}$ alkyl)-($C_{1-6}$ alkylene)-*, or —N(H)—[$CH_2CH_2$—O-]$_{7-15}$-($C_{1-6}$ alkylene)-N($C_{1-6}$ alkyl)-($C_{1-6}$ alkylene)-*, where *** is a point of attachment to $A^2$.

In certain embodiments, L is —N(H)—[($C_{2-4}$ alkylene)-O-]$_{2-6}$-($C_{1-6}$ alkylene)-C(O)—*, —N(H)—[($C_{2-4}$ alkylene)-O-]$_{7-15}$-($C_{1-6}$ alkylene)-C(O)—*, —N(H)—($C_{1-6}$ alkylene)-N($C_{1-6}$ alkyl) C(O)—($C_{1-6}$ alkylene) *, —N(H)—($C_{1-6}$ alkylene)-N(H)C(O)—($C_{1-6}$ alkylene) *, —N(H)—($C_{2-6}$ alkylene)-*, —N(H)—($C_{7-15}$ alkylene)-*, —N($C_{1-6}$ alkyl)-($C_{2-6}$ alkylene)-*, —N($C_{1-6}$ alkyl)-($C_{7-15}$ alkylene)-*, —N(H)—[($C_{2-4}$ alkylene)-O-]$_{2-6}$-($C_{1-6}$ alkylene)-*, —N(H)—[($C_{2-4}$ alkylene)-O-]$_{7-15}$-($C_{1-6}$ alkylene)-*, —N(H)—($C_{1-6}$ alkylene)-(3-6 membered heterocycloalkylene)-($C_{1-6}$ alkylene)-N($C_{1-6}$ alkyl)-($C_{1-6}$ alkylene)-*, —N(H)—($C_{1-6}$ alkylene)-(3-6 membered heterocycloalkylene)-($C_{1-6}$ alkylene)-N(H)—($C_{1-6}$ alkylene)-*, —N(H)—($C_{2-6}$ alkylene)-N(H)—($C_{1-6}$ alkylene)-*, or —N(H)—($C_{2-6}$ alkylene)-N($C_{1-6}$ alkyl)-($C_{1-6}$ alkylene)-*, where *** is a point of attachment to $A^2$.

In certain embodiments, L is —N(H)—[$CH_2CH_2$—O-]$_{2-6}$-($C_{1-6}$ alkylene)-C(O)—*, —N(H)—[$CH_2CH_2$—O-]$_{7-15}$-($C_{1-6}$ alkylene)-C(O)—*, —N(H)—($C_{1-6}$ alkylene)-N($C_{1-6}$ alkyl) C(O)—($C_{1-6}$ alkylene) *, —N(H)—($C_{1-6}$ alkylene)-N(H)C(O)—($C_{1-6}$ alkylene) *, —N(H)—($C_{2-6}$ alkylene)-*, —N(H)—($C_{7-15}$ alkylene)-*, —N($C_{1-6}$ alkyl)-($C_{2-6}$ alkylene)-*, —N($C_{1-6}$ alkyl)-($C_{7-15}$ alkylene)-*, —N(H)—[$CH_2CH_2$—O-]$_{2-6}$-($C_{1-6}$ alkylene)-*, —N(H)—[$CH_2CH_2$—O-]$_{7-15}$-($C_{1-6}$ alkylene)-*, —N(H)—($C_{1-6}$ alkylene)-(3-6 membered heterocycloalkylene)-($C_{1-6}$ alkylene)-N($C_{1-6}$ alkyl)-($C_{1-6}$ alkylene)-*, —N(H)—($C_{1-6}$ alkylene)-(3-6 membered heterocycloalkylene)-($C_{1-6}$ alkylene)-N(H)—($C_{1-6}$ alkylene)-*, —N(H)—($C_{2-6}$ alkylene)-N(H)—($C_{1-6}$ alkylene)-*, or —N(H)—($C_{2-6}$ alkylene)-N($C_{1-6}$ alkyl)-($C_{1-6}$ alkylene)-*, where *** is a point of attachment to $A^2$.

In certain embodiments, L is —[($C_{2-4}$ alkylene)-O-]$_{2-6}$-($C_{1-6}$ alkylene)-*, —[($C_{2-4}$ alkylene)-O-]$_{7-15}$-($C_{1-6}$ alkylene)-*, —[($C_{2-4}$ alkylene)-O-]$_{2-6}$-($C_{1-6}$ alkylene)-N($C_{1-6}$ alkyl) ($C_{1-6}$ alkylene)-*, —[($C_{2-4}$ alkylene)-O-]$_{7-15}$-($C_{1-6}$ alkylene)-N($C_{1-6}$ alkyl) ($C_{1-6}$ alkylene)-*, —[($C_{2-4}$ alkylene)-O-]$_{2-6}$-($C_{1-6}$ alkylene)-N(H) ($C_{1-6}$ alkylene)-*, —[($C_{2-4}$ alkylene)-O-]$_{7-15}$-($C_{1-6}$ alkylene)-N(H) ($C_{1-6}$ alkylene)-*, —($C_{1-9}$ alkylene)-C(O)N(H)—($C_{1-6}$ alkylene)-*, —($C_{1-9}$ alkylene)-N(H)C(O)—($C_{1-6}$ alkylene)-*, —($C_{1-9}$ alkylene)-C(O)N(H)—[($C_{2-4}$ alkylene)-O-]$_{2-6}$-($C_{1-6}$ alkylene)-*, —($C_{1-9}$ alkylene)-N(H)C(O)—[($C_{2-4}$ alkylene)-O-]$_{2-6}$-($C_{1-6}$ alkylene)-*, —($C_{1-9}$ alkylene)-C(O)N(H)—[($C_{2-4}$ alkylene)-O-]$_{7-15}$-($C_{1-6}$ alkylene)-*, —($C_{1-9}$ alkylene)-N(H)C(O)—[($C_{2-4}$ alkylene)-O-]$_{7-15}$-($C_{1-6}$ alkylene)-*, —($C_{1-9}$ alkylene)-C(O)N(H)—[($C_{2-4}$ alkylene)-O-]$_{2-6}$-($C_{1-6}$ alkylene)-N($C_{1-6}$ alkyl)-($C_{1-6}$ alkylene)-*, —($C_{1-9}$ alkylene)-N(H)C(O)—[($C_{2-4}$ alkylene)-O-]$_{2-6}$-($C_{1-6}$ alkylene)-N($C_{1-6}$ alkyl)-($C_{1-6}$ alkylene)-*, —($C_{1-9}$ alkylene)-C(O)N(H)—[($C_{2-4}$ alkylene)-O-]$_{7-15}$-($C_{1-6}$ alkylene)-N($C_{1-6}$ alkyl)-($C_{1-6}$ alkylene)-*, or —($C_{1-9}$ alkylene)-N(H)C(O)—[($C_{2-4}$ alkylene)-O-]$_{7-15}$-($C_{1-6}$ alkylene)-N($C_{1-6}$ alkyl)-($C_{1-6}$ alkylene)-*, where *** is a point of attachment to $A^2$.

In certain embodiments, L is —[$CH_2CH_2$—O-]$_{2-6}$-($C_{1-6}$ alkylene)-*, —[$CH_2CH_2$—O-]$_{7-15}$-($C_{1-6}$ alkylene)-*, —[$CH_2CH_2$—O-]$_{2-6}$-($C_{1-6}$ alkylene)-N($C_{1-6}$ alkyl) ($C_{1-6}$ alkylene)-*, —[$CH_2CH_2$—O-]$_{7-15}$-($C_{1-6}$ alkylene)-N($C_{1-6}$ alkyl) ($C_{1-6}$ alkylene)-*, —[$CH_2CH_2$—O-]$_{2-6}$-($C_{1-6}$ alkylene)-N(H) ($C_{1-6}$ alkylene)-*, —[$CH_2CH_2$—O-]$_{7-15}$-($C_{1-6}$ alkylene)-N(H) ($C_{1-6}$ alkylene)-*, —($C_{1-9}$ alkylene)-C(O)N(H)—($C_{1-6}$ alkylene)-*, —($C_{1-9}$ alkylene)-N(H)C(O)—($C_{1-6}$ alkylene)-*, —($C_{1-9}$ alkylene)-C(O)N(H)—[$CH_2CH_2$—O-]$_{2-6}$-($C_{1-6}$ alkylene)-*, —($C_{1-9}$ alkylene)-N(H)C(O)—[$CH_2CH_2$—O-]$_{2-6}$-($C_{1-6}$ alkylene)-*, —($C_{1-9}$ alkylene)-C(O)N(H)—[$CH_2CH_2$—O-]$_{7-15}$-($C_{1-6}$ alkylene)-*, —($C_{1-9}$ alkylene)-N(H)C(O)—[$CH_2CH_2$—O-]$_{7-15}$-($C_{1-6}$ alkylene)-*, —($C_{1-9}$ alkylene)-C(O)N(H)—[$CH_2CH_2$—O-]$_{2-6}$-($C_{1-6}$ alkylene)-N($C_{1-6}$ alkyl)-($C_{1-6}$ alkylene)-*, —($C_{1-9}$ alkylene)-N(H)C(O)—[$CH_2CH_2$—O-]$_{2-6}$-($C_{1-6}$ alkylene)-N($C_{1-6}$ alkyl)-($C_{1-6}$ alkylene)-*, —($C_{1-9}$ alkylene)-C(O)N(H)—[$CH_2CH_2$—O-]$_{7-15}$-($C_{1-6}$ alkylene)-N($C_{1-6}$ alkyl)-($C_{1-6}$ alkylene)-*, or —($C_{1-9}$ alkylene)-N(H)C(O)—[($CH_2CH_2$—O-]$_{7-15}$-($C_{1-6}$ alkylene)-N($C_{1-6}$ alkyl)-($C_{1-6}$ alkylene)-*, where *** is a point of attachment to $A^2$.

In certain embodiments, L is —N(H)—[($C_{2-4}$ alkylene)-O-]$_{2-6}$-($C_{1-6}$ alkylene)-N(H)—*, —N(H)—[($C_{2-4}$ alkylene)-O-]$_{7-15}$-($C_{1-6}$ alkylene)-N(H)—*, —N($C_{1-6}$ alkyl)-[($C_{2-4}$ alkylene)-O-]$_{2-6}$-($C_{1-6}$ alkylene)-N(H)—*, —N($C_{1-6}$ alkyl)-[($C_{2-4}$ alkylene)-O-]$_{7-15}$-($C_{1-6}$ alkylene)-N(H)—*, —N($C_{1-6}$ alkyl)-[($C_{2-4}$ alkylene)-O-]$_{2-6}$-($C_{1-6}$ alkylene)-N($C_{1-6}$ alkyl)-*, or —N($C_{1-6}$ alkyl)-[($C_{2-4}$ alkylene)-O-]$_{7-15}$-($C_{1-6}$ alkylene)-N($C_{1-6}$ alkyl)-*, where *** is a point of attachment to $A^2$.

In certain embodiments, L is —N(H)—[$CH_2CH_2$—O-]$_{2-6}$-($C_{1-6}$ alkylene)-N(H)—*, —N(H)—[$CH_2CH_2$—O-]$_{7-15}$-($C_{1-6}$ alkylene)-N(H)—*, —N($C_{1-6}$ alkyl)-[$CH_2CH_2$—O-]$_{2-6}$-($C_{1-6}$ alkylene)-N(H)—*, —N($C_{1-6}$ alkyl)-[$CH_2CH_2$—O-]$_{7-15}$-($C_{1-6}$ alkylene)-N(H)—*, —N($C_{1-6}$ alkyl)-[$CH_2CH_2$—O-]$_{2-6}$-($C_{1-6}$ alkylene)-N($C_{1-6}$ alkyl)-*, or —N($C_{1-6}$ alkyl)-[$CH_2CH_2$—O-]$_{7-15}$-($C_{1-6}$ alkylene)-N($C_{1-6}$ alkyl)-*, where *** is a point of attachment to $A^2$.

In some embodiments, L is one of the following:
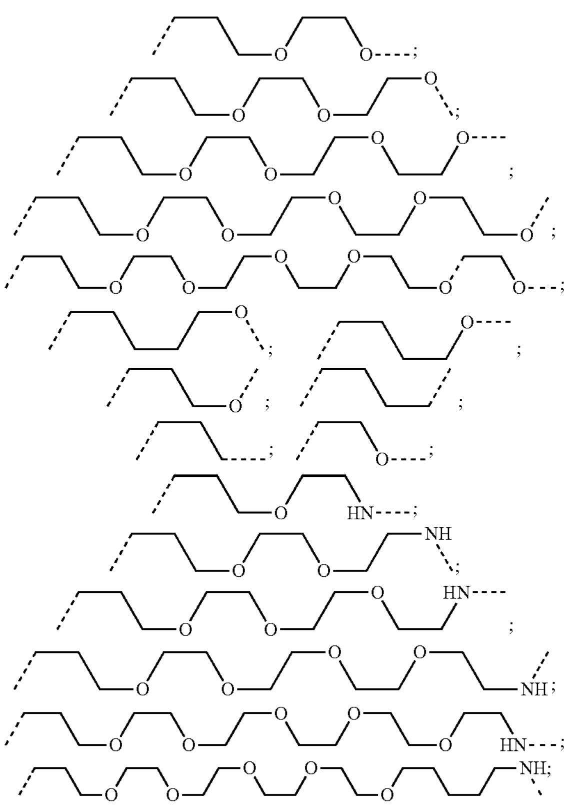
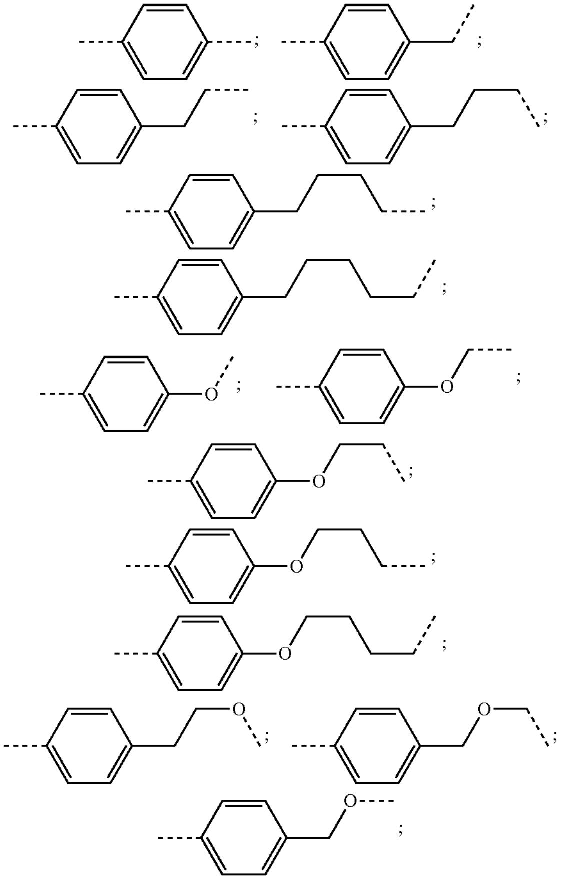
-continued
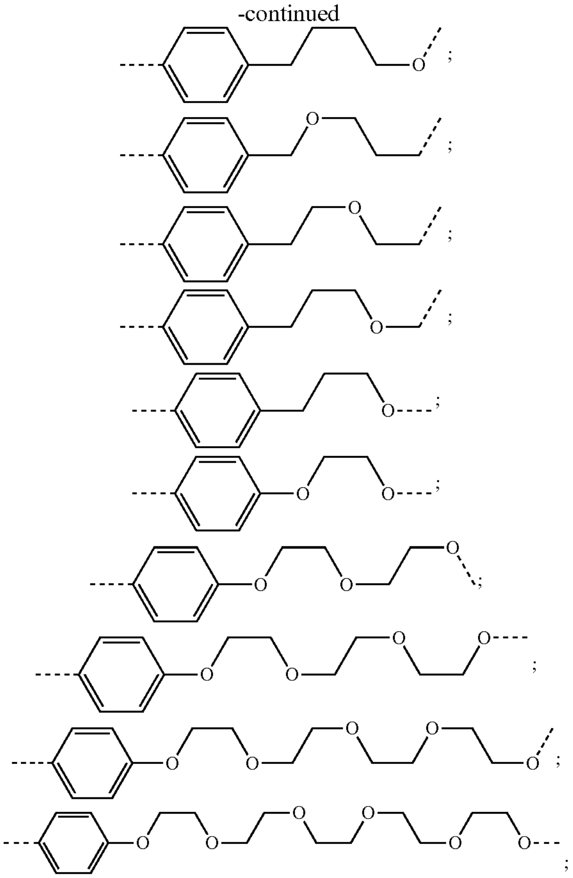
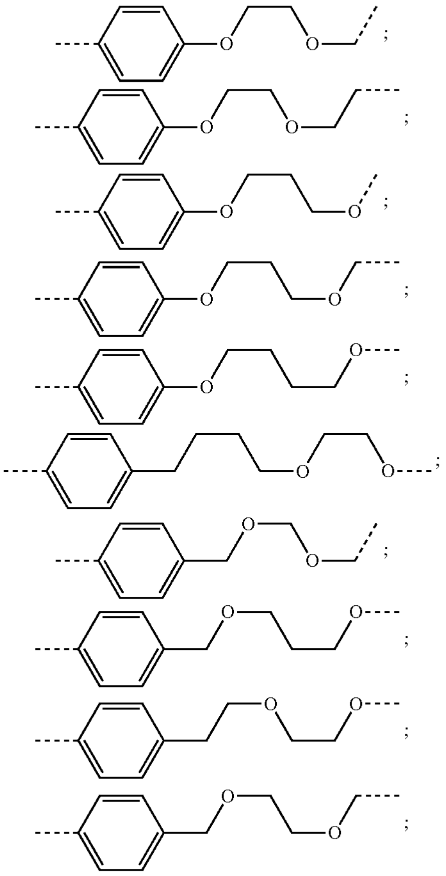

-continued
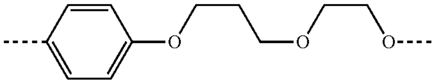
;
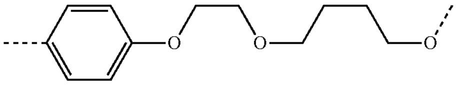
;
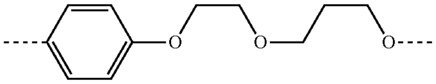
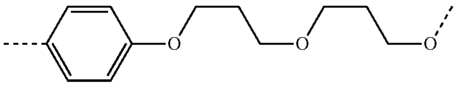
;
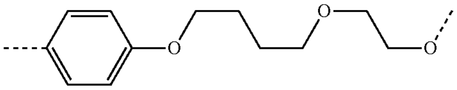
;
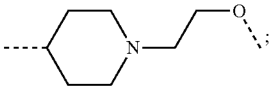
;
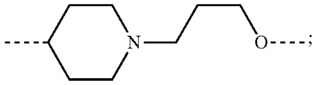
;
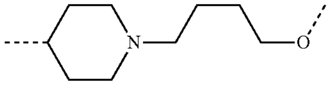
;
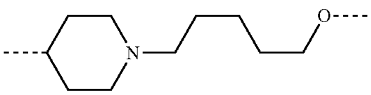
;
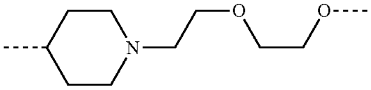
;
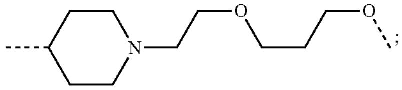
;
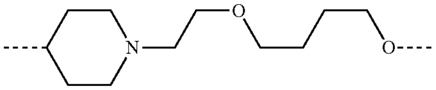
;
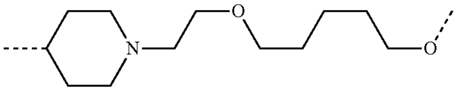
;
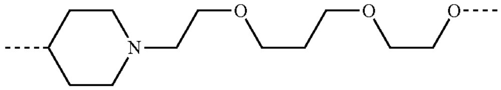
;
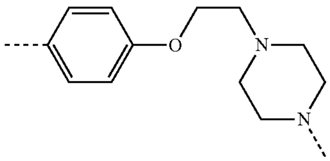
;
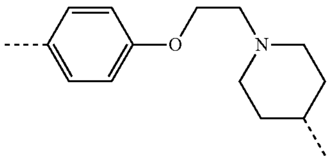
;
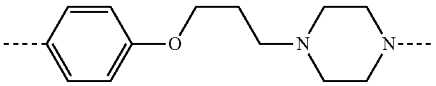
;
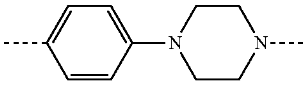
;
-continued
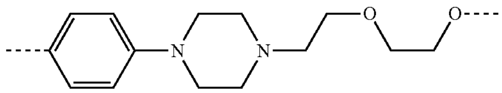
;
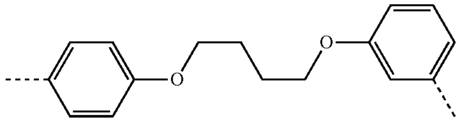
;
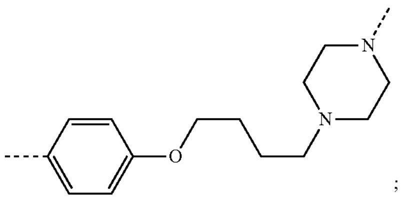
;
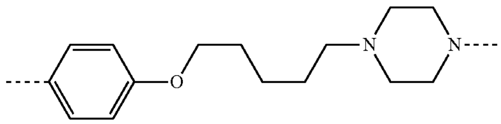
;
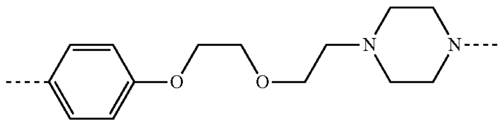
;
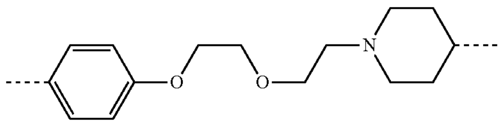
;
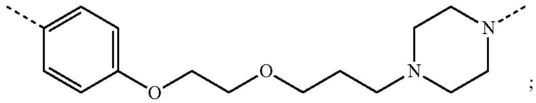
;
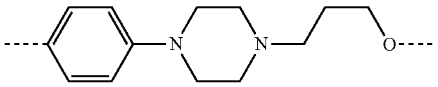
;
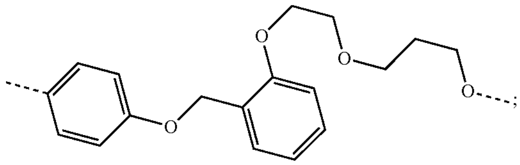
;
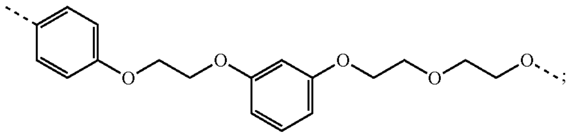
;
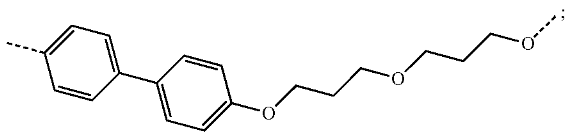
;
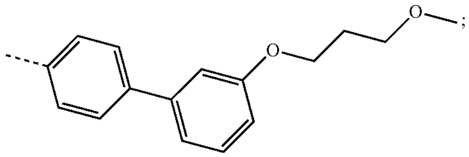
;
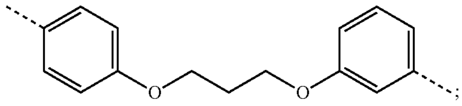
;

-continued
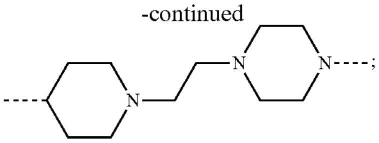;
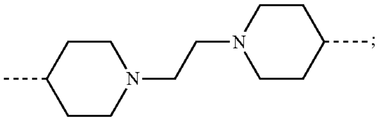;
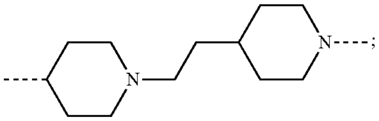;
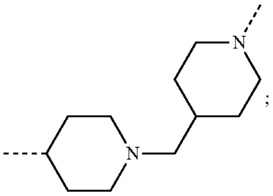;
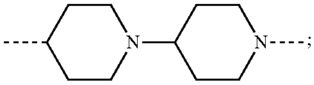;
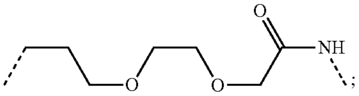;
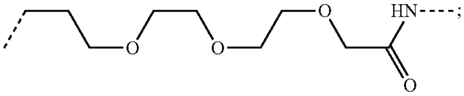;
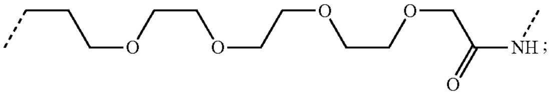;
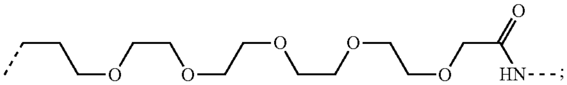;
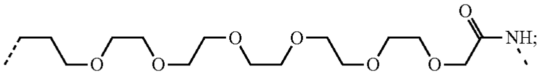;
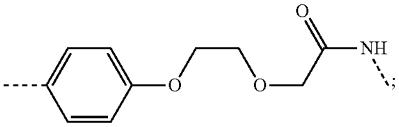;
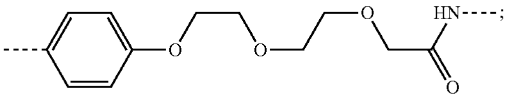;
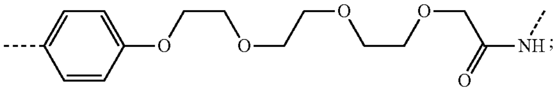;
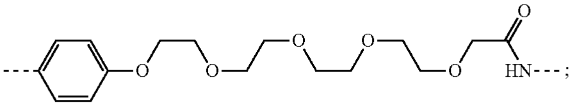;
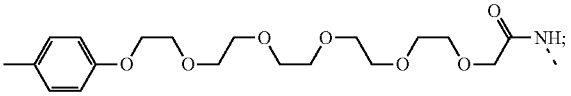;
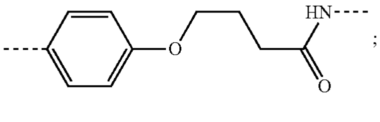;
-continued
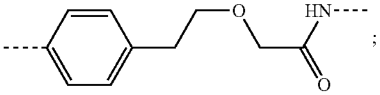;
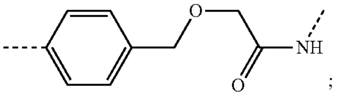;
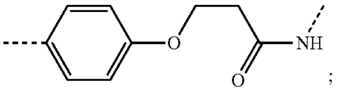;
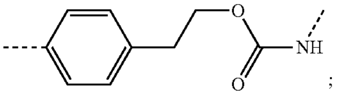;
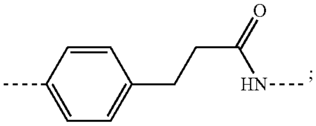;
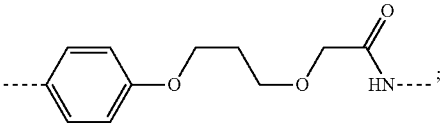;
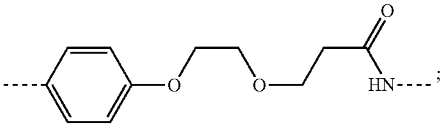;
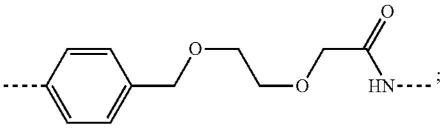;
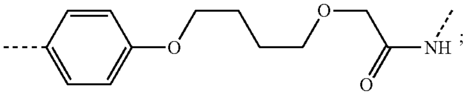;
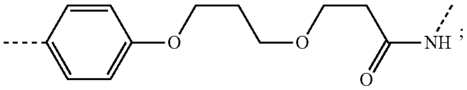;
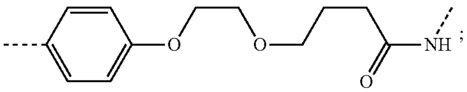;
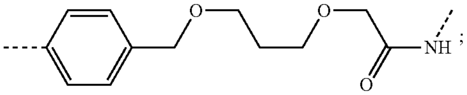;
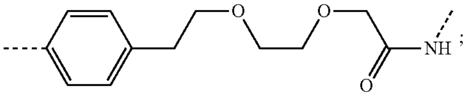;
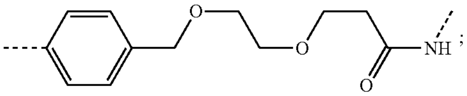;
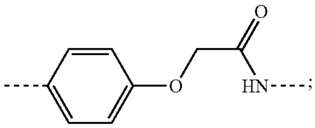;
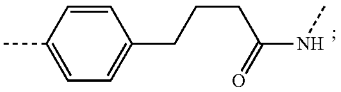;

-continued
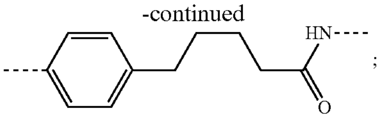
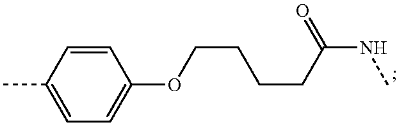
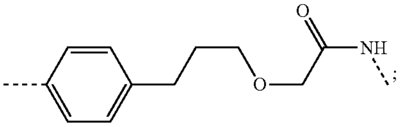
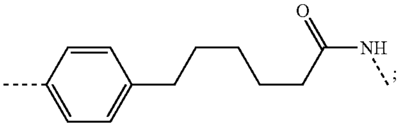
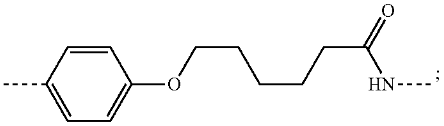
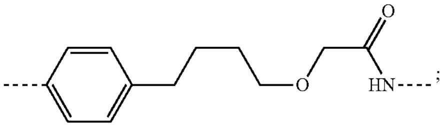
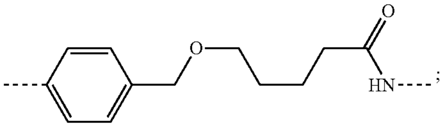
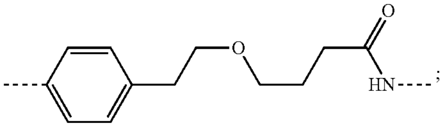
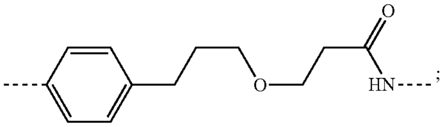
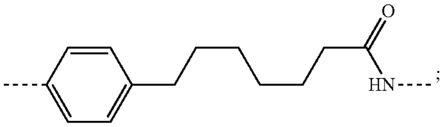
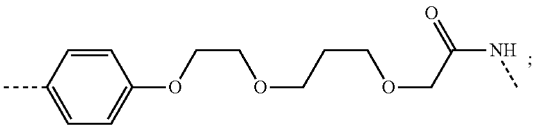
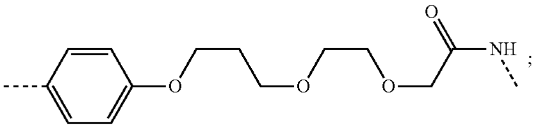
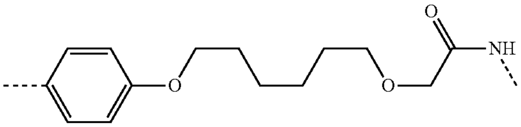
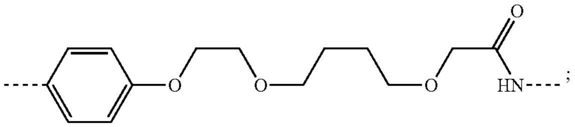
-continued
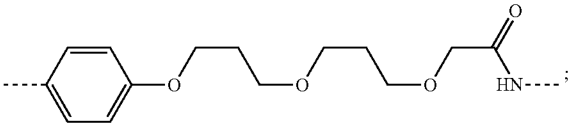
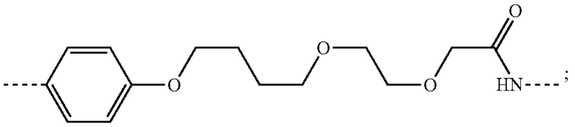
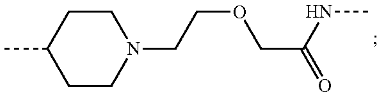
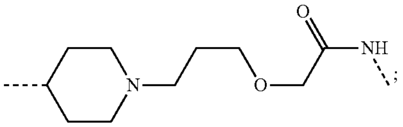
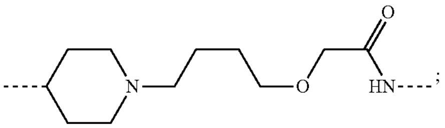
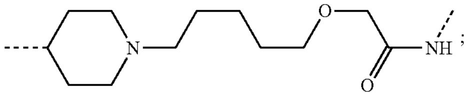
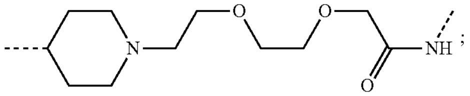
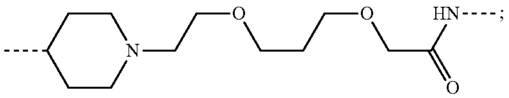
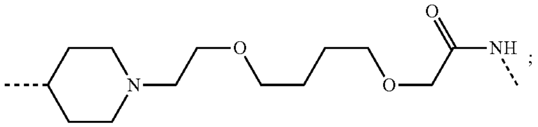
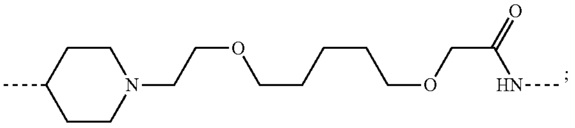
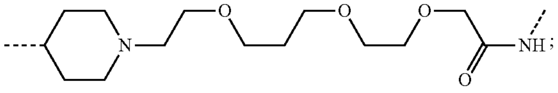
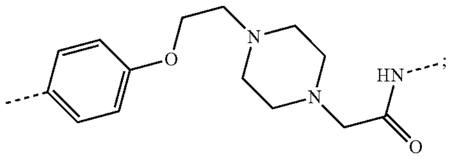
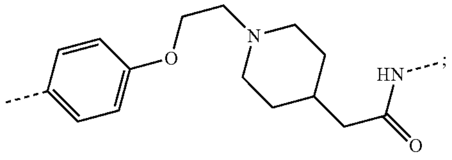
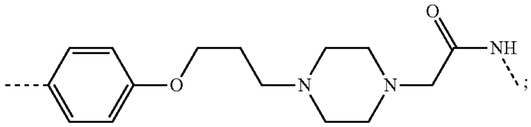

-continued
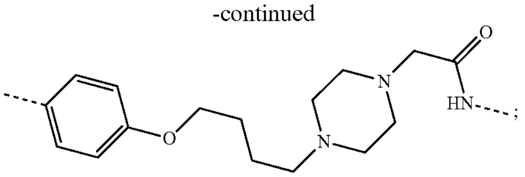
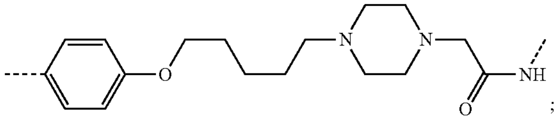
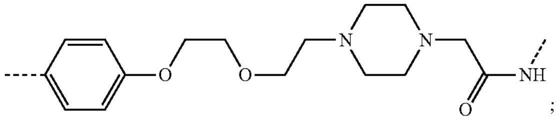
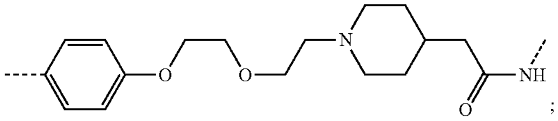
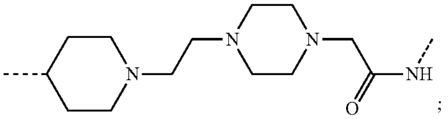
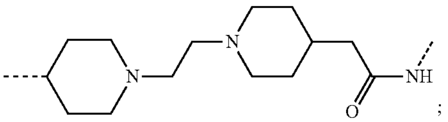
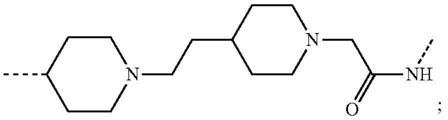
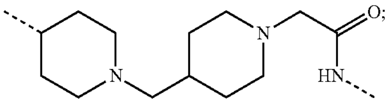
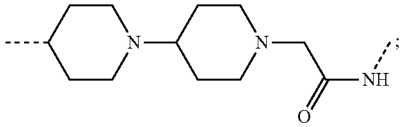
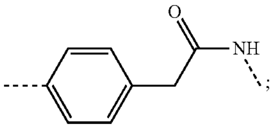
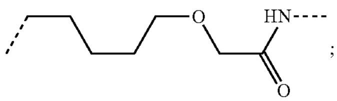
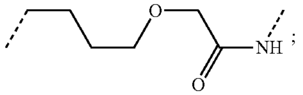
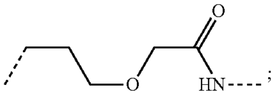
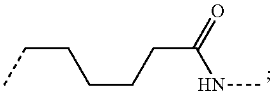
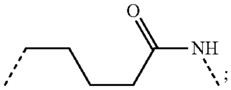
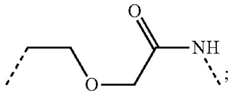
-continued
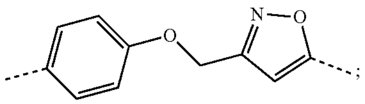
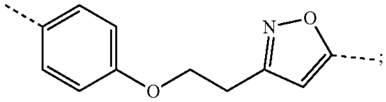
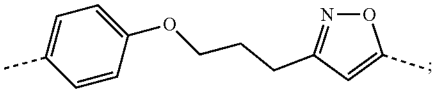
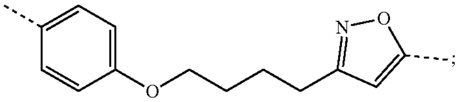
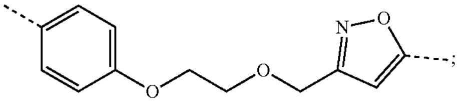
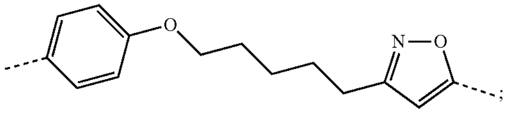
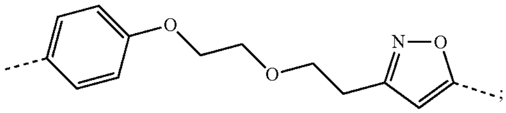
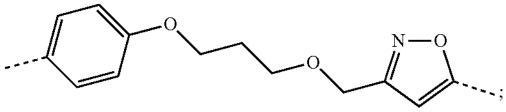
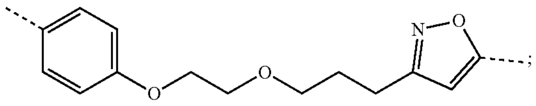
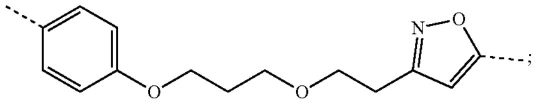
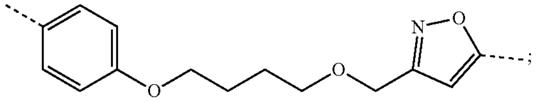
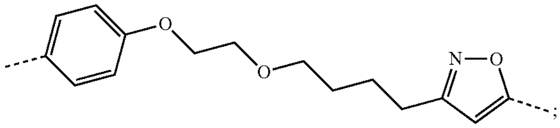
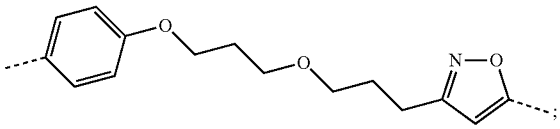
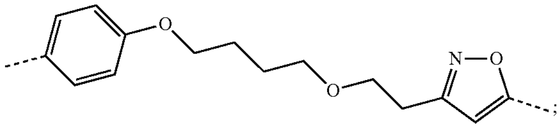
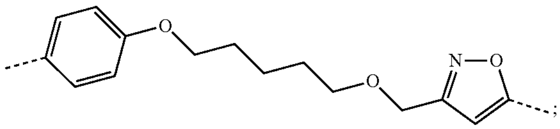

-continued
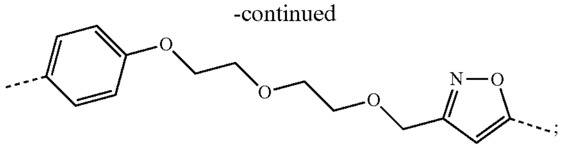
;
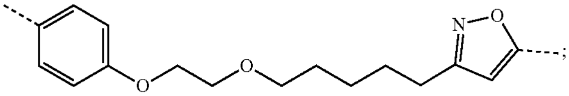
;
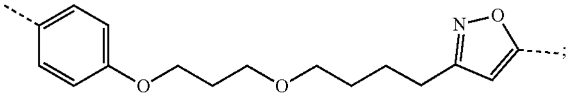
;
-continued
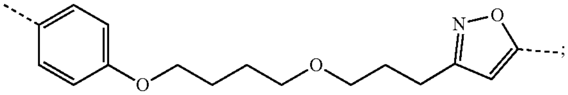
;
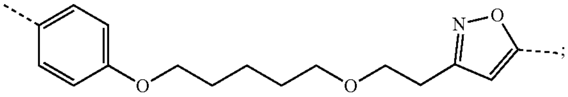
;
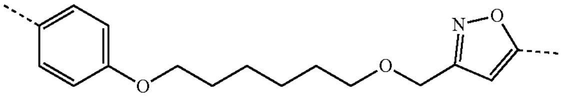
;
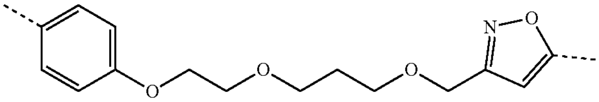
;
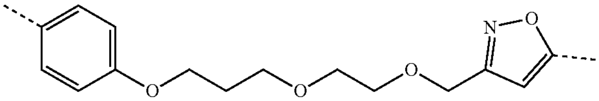
;
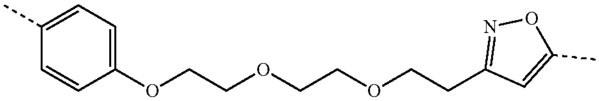
;
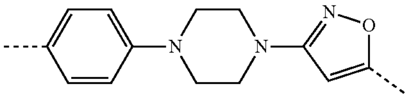
;
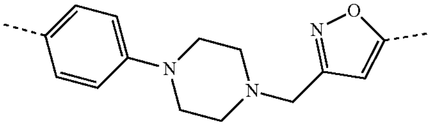
;
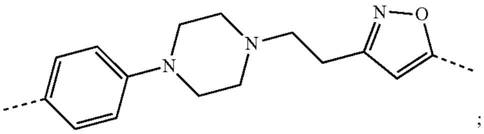
;
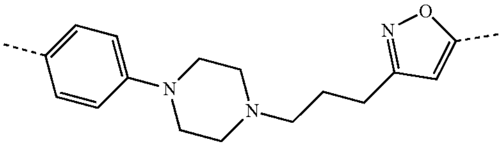
;
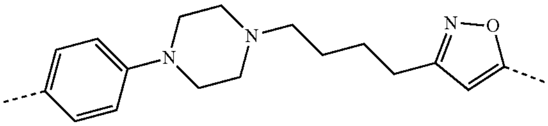
;
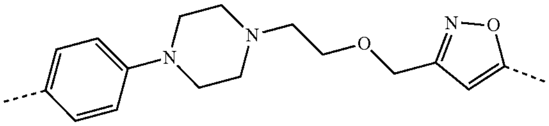
;
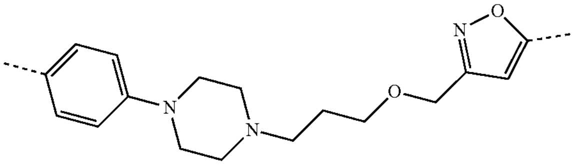
;
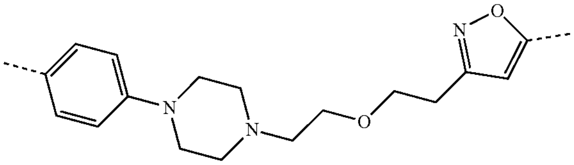
;
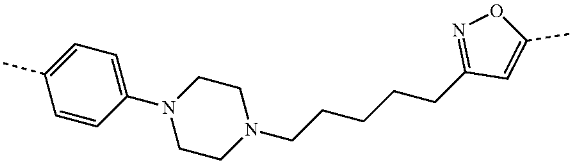
;
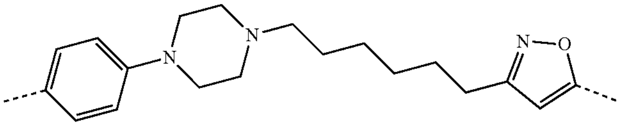
;
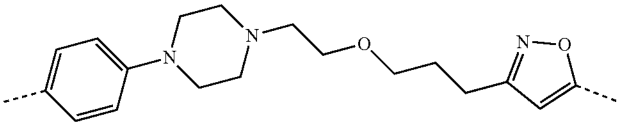
;
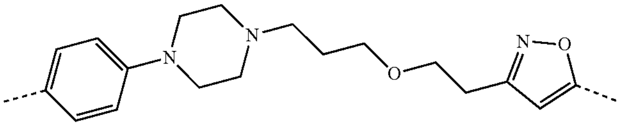
;

-continued
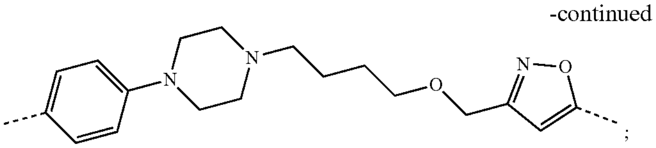
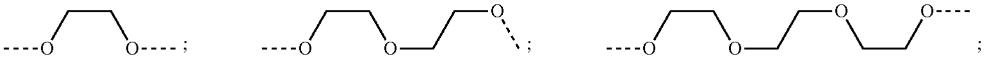
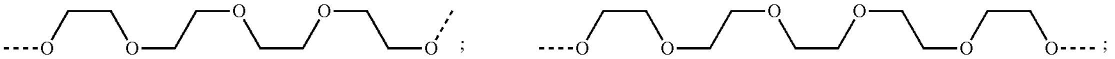
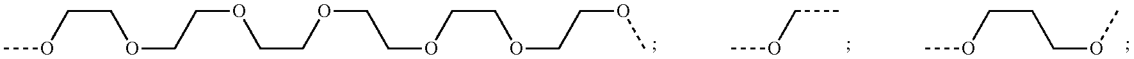
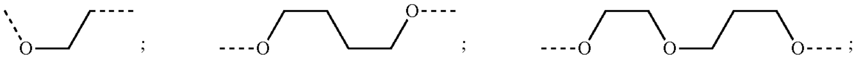
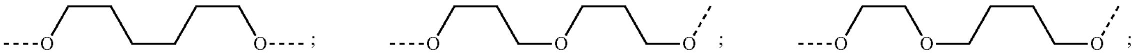
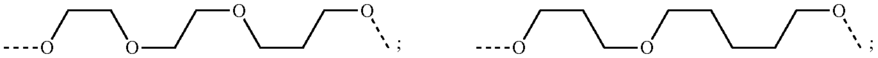
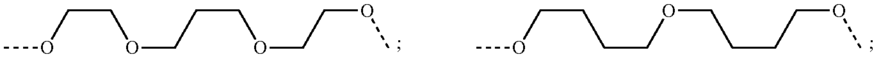
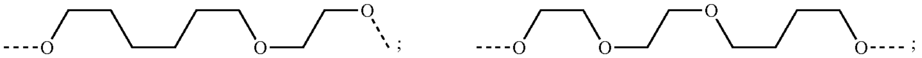
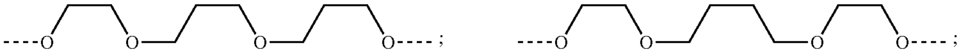
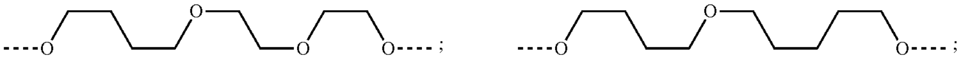
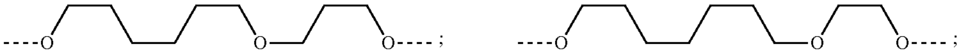
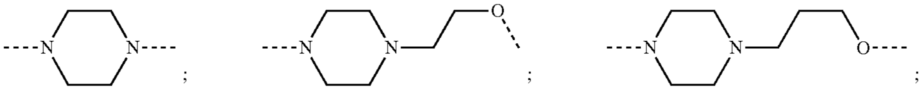
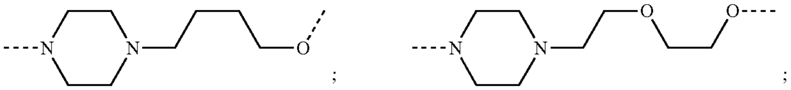
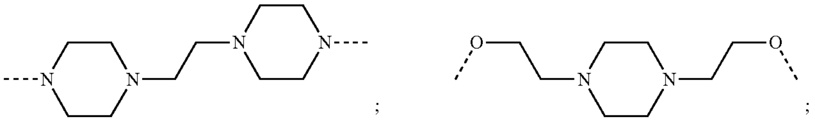
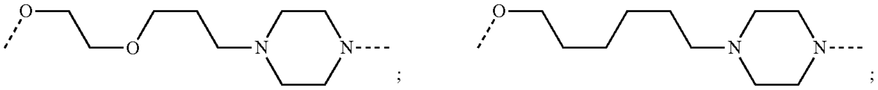
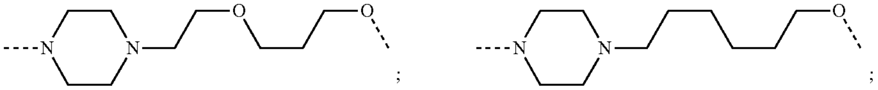
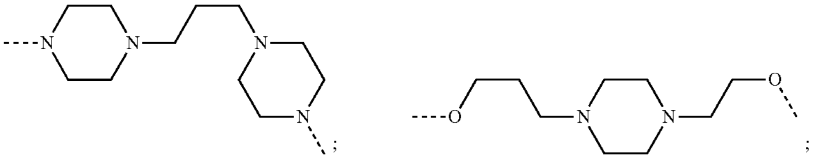
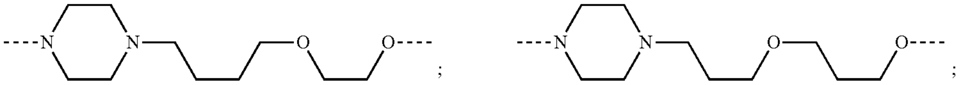
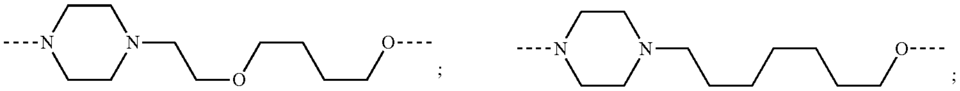
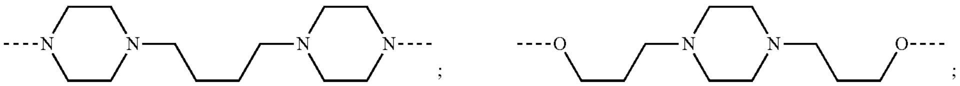
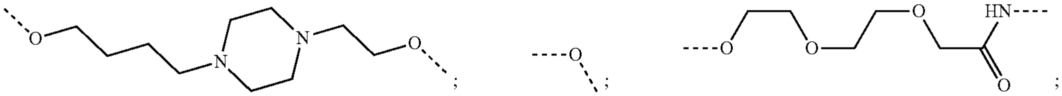

-continued
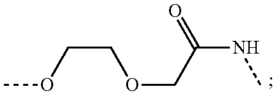 ; 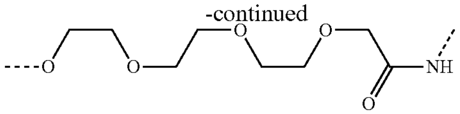 ;
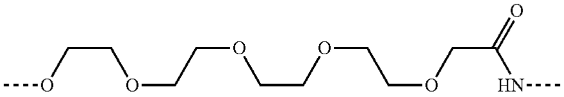 ;
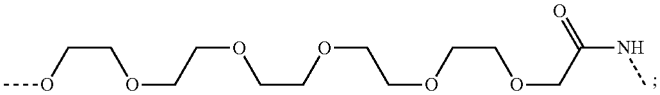 ;
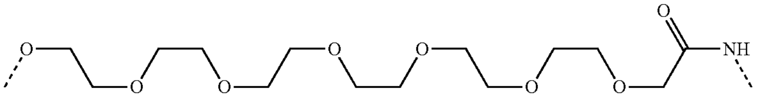 ; 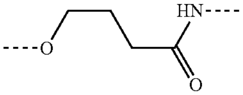 ;
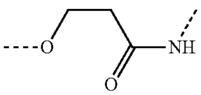 ; 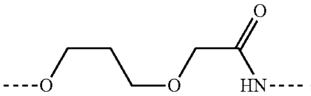 ; 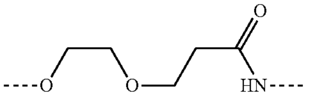 ;
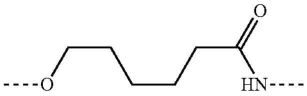 ; 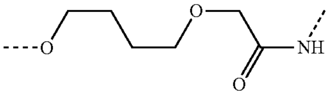 ; 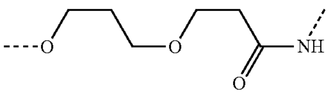 ;
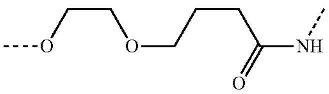 ; 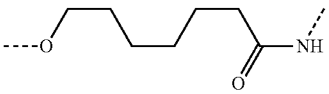 ; 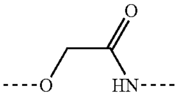 ;
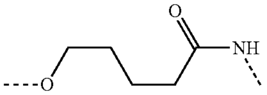 ; 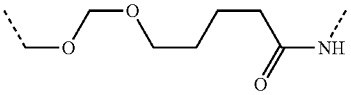 ; 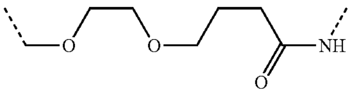 ;
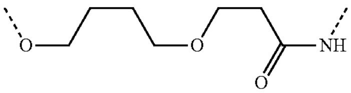 ; 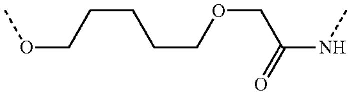 ;
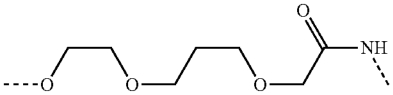 ; 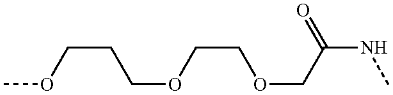 ;
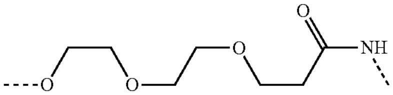 ; 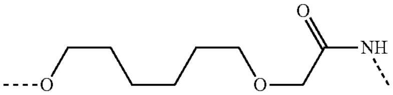 ;
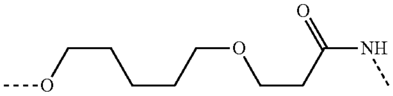 ; 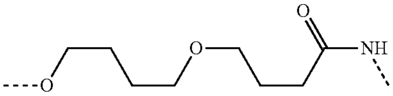 ;
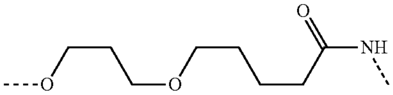 ; 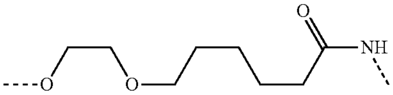 ;
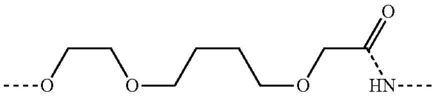 ; 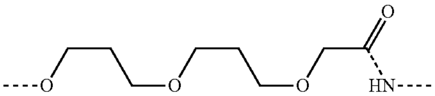 ;
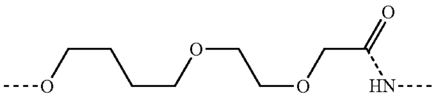 ; 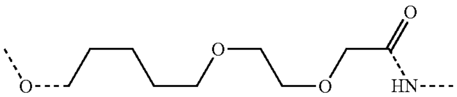 ;
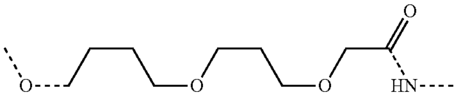 ; 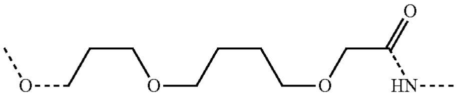 ;
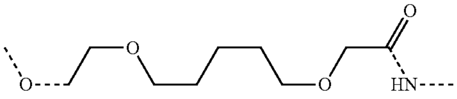 ; 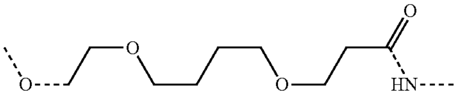 ;
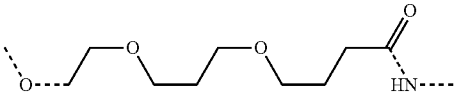 ; 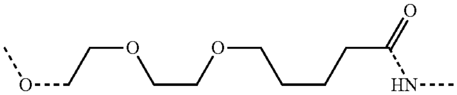 ;

-continued
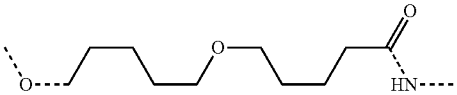 ; 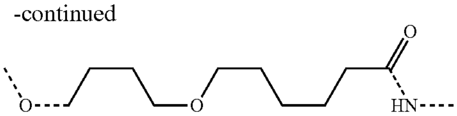 ;
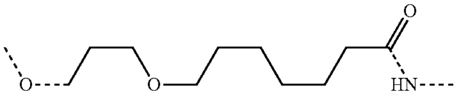 ; 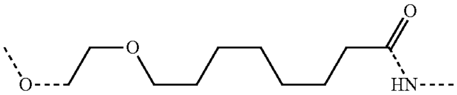 ;
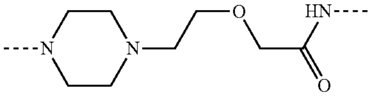 ; 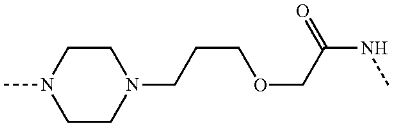 ;
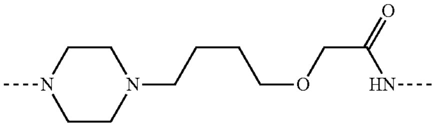 ; 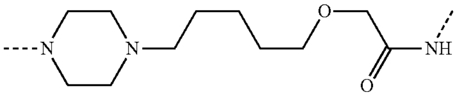 ;
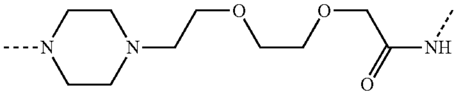 ; 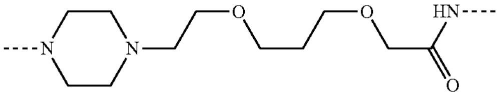 ;
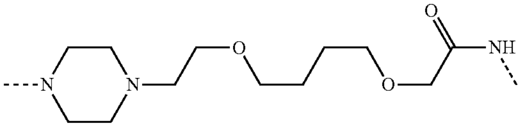 ; 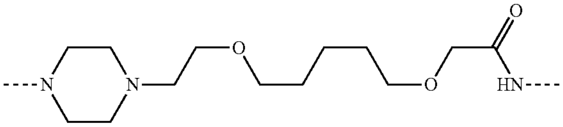 ;
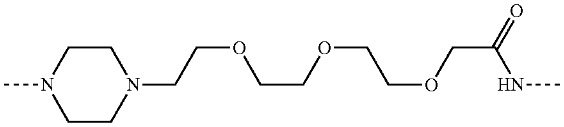 ; 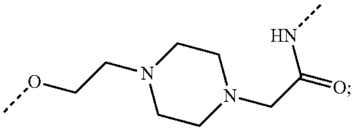 ;
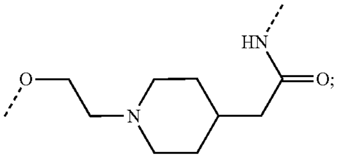 ; 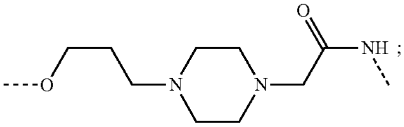 ;
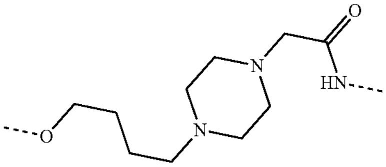 ; 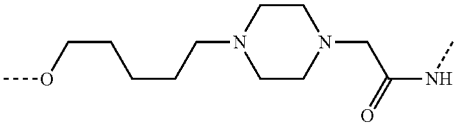 ;
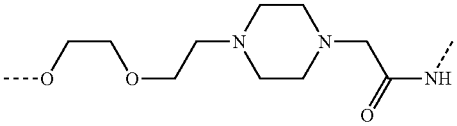 ; 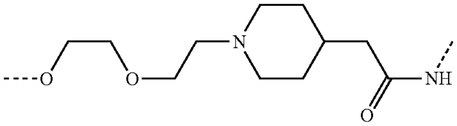 ;
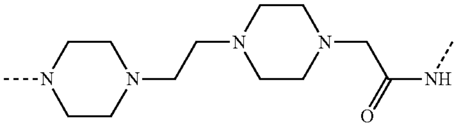 ; 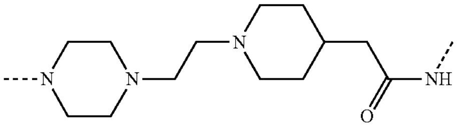 ;
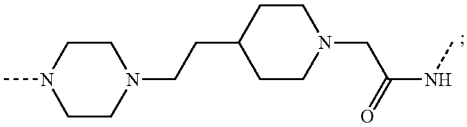 ; 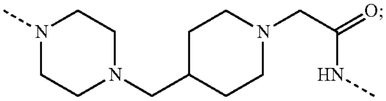 ;
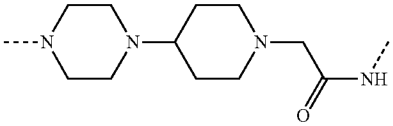 ; 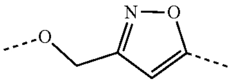 ; 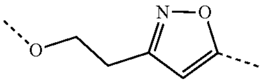 ;
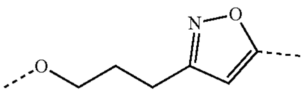 ; 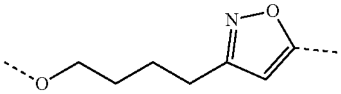 ; 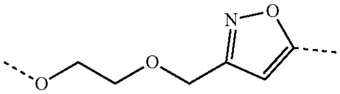 ;

-continued
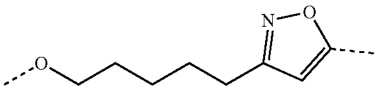 ; 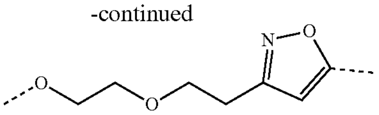 ;
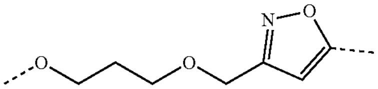 ; 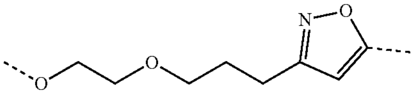 ;
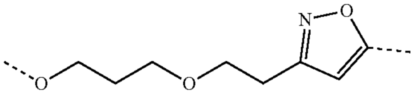 ; 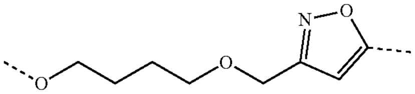 ;
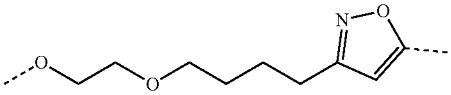 ; 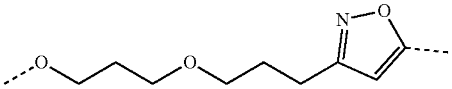 ;
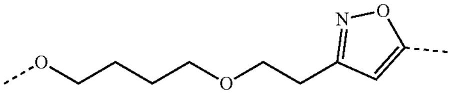 ; 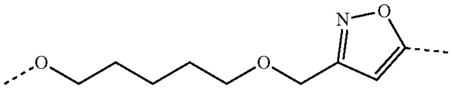 ;
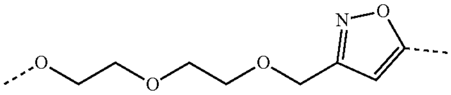 ; 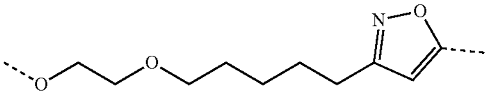 ;
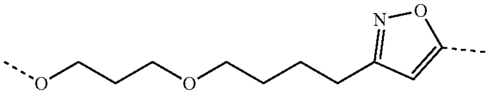 ; 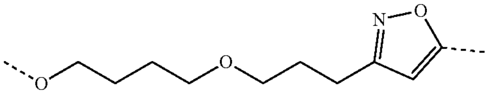 ;
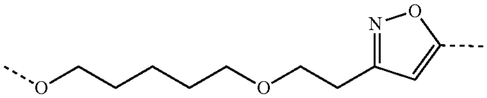 ; 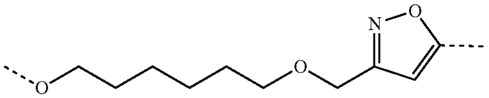 ;
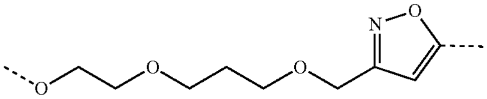 ; 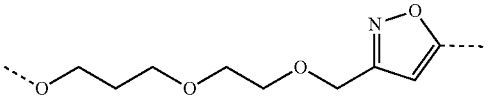 ;
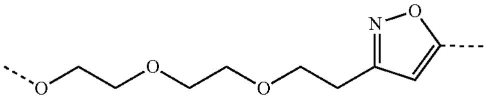 ; 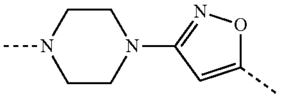 ;
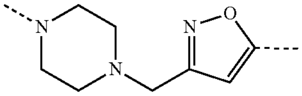 ; 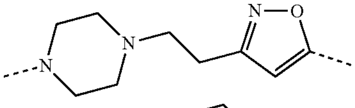 ; 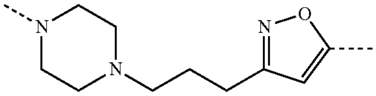 ;
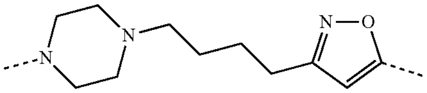 ; 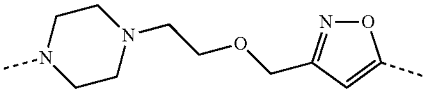 ;
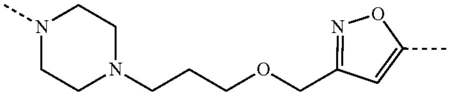 ; 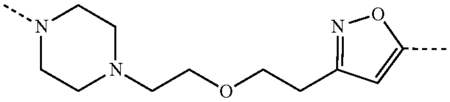 ;
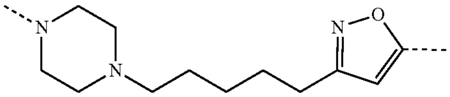 ; 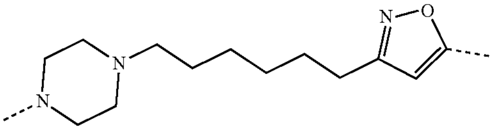 ;
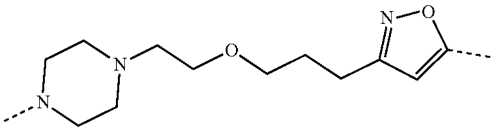 ; 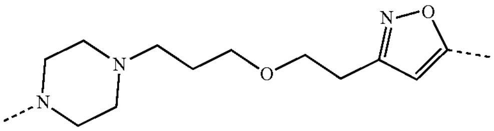 ;
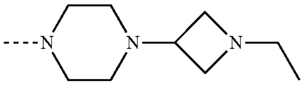 ; and 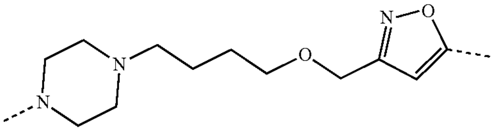 ;
wherein a dashed bond indicates a point of attachment.

In certain embodiments, L is —C(H)($R^{100}$)—, —C($R^{100}$)$_2$—, O, —N($R^{101}$)—, —S(O)$_2$—, an optionally substituted $C_{3-7}$ cycloalkylene, an optionally substituted $C_{4-7}$ cycloalkenylene, or an optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl, and $R^{101}$ is hydrogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is —$CH_2$—$Y^{20}$, —C(H)($R^{100}$)—$Y^{20}$, —C($R^{100}$)$_2$-$Y^{20}$—, —O—$Y^{20}$, —N($R^{101}$)—$Y^{20}$—, —S(O)$_2$—$Y^{20}$—, —C(O)—$Y^{20}$—, -(optionally substituted $C_{3-7}$ cycloalkylene)-$Y^{20}$—, -(optionally substituted $C_{4-7}$ cycloalkenylene)-$Y^{20}$—, -(optionally substituted 3-7 membered heterocyclylene containing 1, 2 or 3 heteroatoms selected from oxygen, nitrogen, and sulfur)-$Y^{20}$—, —$Y^{20}$—$CH_2$—, —$Y^{20}$—C(H)($R^{100}$)—, —$Y^{20}$C($R^{100}$)$_2$—, —$Y^{20}$—O—, —$Y^{20}$—N($R^{101}$)—, —$Y^{20}$—S(O)$_2$—, —$Y^{20}$—C(O)—, -$Y^{20}$-(optionally substituted $C_{3-7}$ cycloalkylene)-, -$Y^{20}$-(optionally substituted $C_{4-7}$ cycloalkenylene)-, or —$Y^{20}$-(optionally substituted 3-7 membered heterocyclylene containing 1, 2 or 3 heteroatoms selected from oxygen, nitrogen, and sulfur)-; wherein $R^{100}$ represents independently for each occurrence hydrogen, halogen, $C_{1-6}$ alkyl, or $C_{3-6}$ cycloalkyl, and R 101 is hydrogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

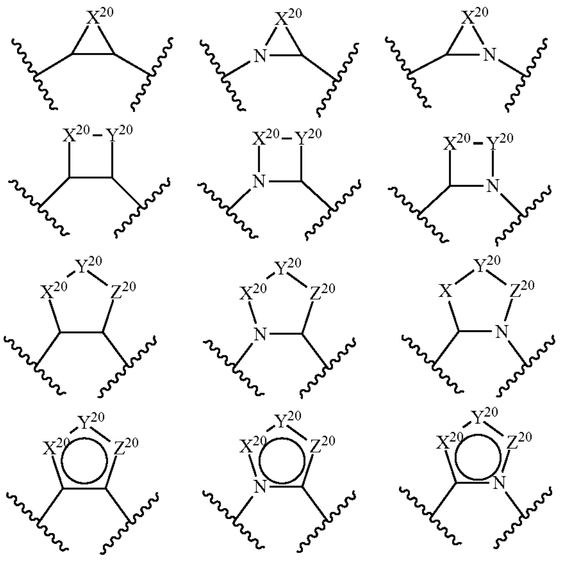

wherein $X^{20}$, $Y^{20}$, and $Z^{20}$ are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, or an optionally substituted $C_{4-7}$ cycloalkenylene; wherein $R^{100}$ represents independently for each occurrence hydrogen, halogen, $C_{1-6}$ alkyl, or $C_{3-6}$ cycloalkyl, and $R^{101}$ is hydrogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

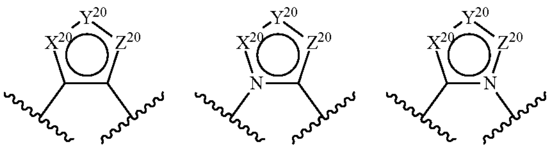

wherein $X^{20}$, $Y^{20}$, and $Z^{20}$ are independently —C($R^{100}$)— or —N—; wherein $R^{100}$ represents independently for each occurrence hydrogen, halogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl.

In certain embodiments, L is -$X^{20}$-$Y^{20}$-$Z^{20}$-, wherein $X^{20}$, $Y^{20}$, and $Z^{20}$ are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl, and $R^{101}$ is hydrogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is —$X^{20}$═$Y^{20}$—$Z^{21}$—, wherein $X^{20}$ and $Y^{20}$ are independently —C($R^{100}$)— or —N—, and $Z^{21}$ is —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, or an optionally substituted $C_{4-7}$ cycloalkenylene; wherein $R^{100}$ represents independently for each occurrence hydrogen, halogen, $C_{1-6}$ alkyl, or $C_{3-6}$ cycloalkyl, and $R^{101}$ is hydrogen, $C_{1-6}$ alkyl, or $C_{3-6}$ cycloalkyl. In certain embodiments, R 100 represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is —C≡C—$Z^{20}$—, wherein $Z^{20}$ is —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, or an optionally substituted $C_{4-7}$ cycloalkenylene; wherein $R^{100}$ represents independently for each occurrence hydrogen, halogen, $C_{1-6}$ alkyl, or $C_{3-6}$ cycloalkyl, and $R^{101}$ is hydrogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl. In certain embodiments, L is one of the following:

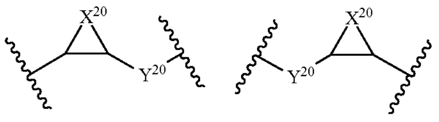

-continued

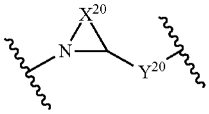
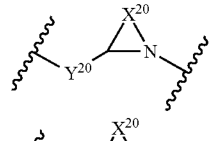
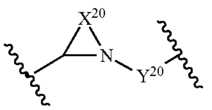
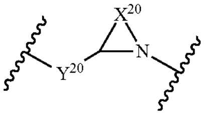
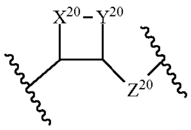
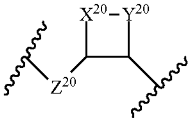
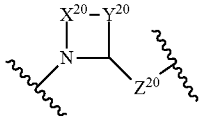
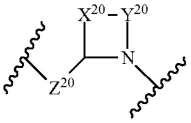
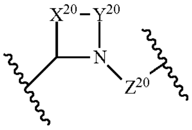
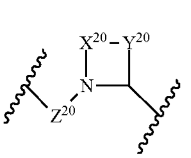
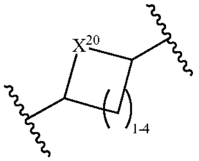
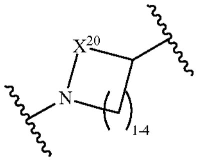
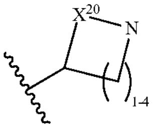
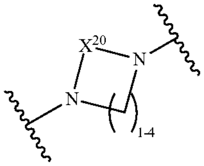
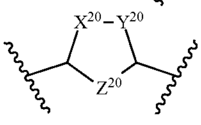
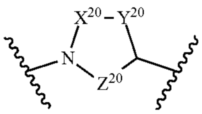
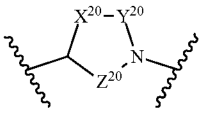
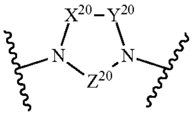

wherein $X^{20}$, $Y^{20}$, and $Z^{20}$ are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl, and $R^{101}$ is hydrogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

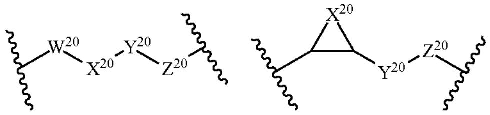
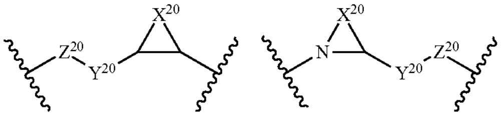
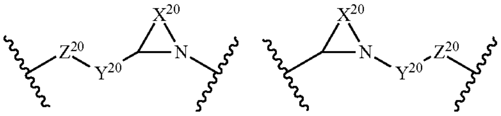
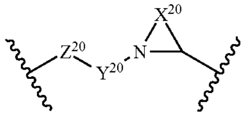
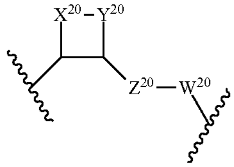
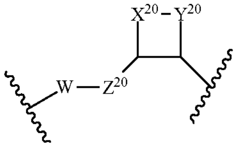
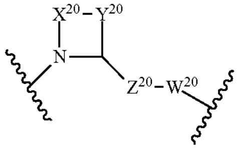
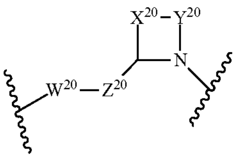
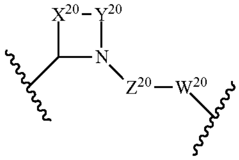
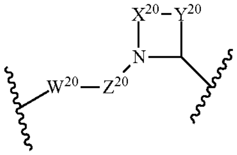
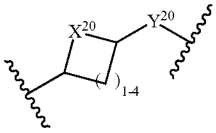
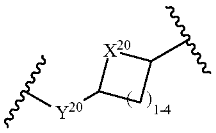
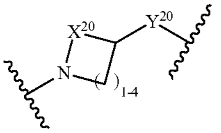
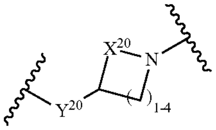
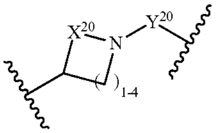
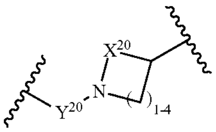
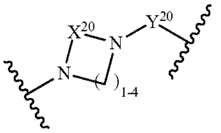
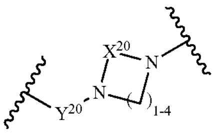
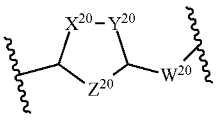
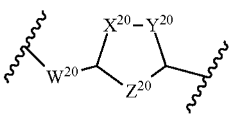
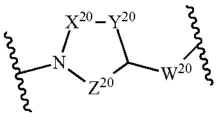

-continued

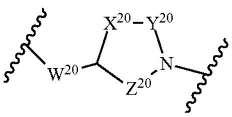 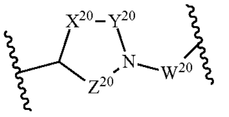

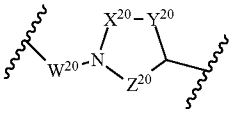 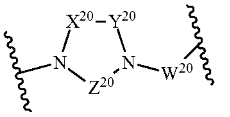

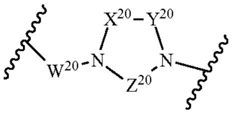 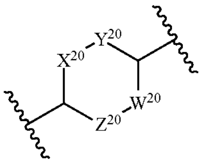

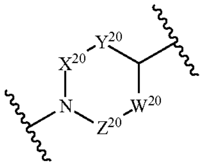 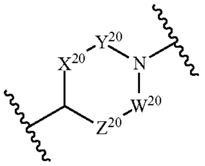

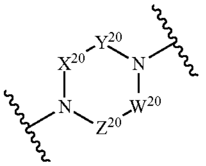 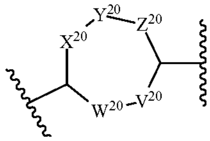

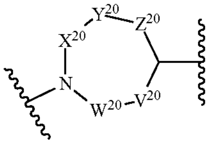 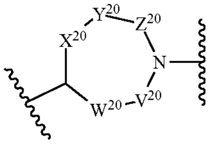

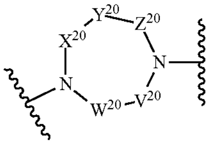

wherein $V^{20}$, $W^{20}$, $X^{20}$, $Y^{20}$, and $Z^{20}$ are independently $—CH_2—$, $—C(H)(R^{100})—$, $—C(R^{100})_2—$, O, $—N(R^{101})—$, $—S(O)_2—$, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl, and $R^{101}$ is hydrogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

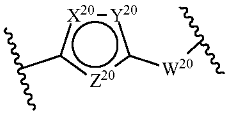 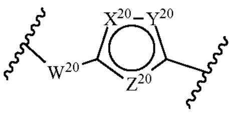

-continued

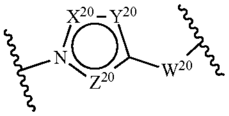 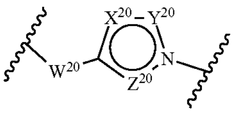

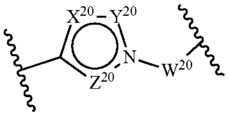 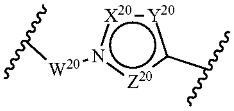

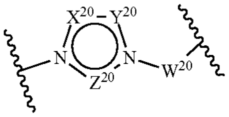 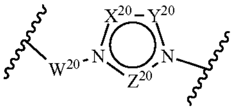

wherein $W^{20}$, $X^{20}$, $Y^{20}$, and $Z^{20}$ are independently $—C(R^{100})—$ or —N—; wherein $R^{100}$ represents independently for each occurrence hydrogen, halogen, $C_{1-6}$ alkyl, or $C_{3-6}$ cycloalkyl. In certain embodiments, R 100 represents independently for each occurrence hydrogen, methyl, ethyl, isopropyl, cyclopropyl, cyclobutyl, or cyclopentyl.

In certain embodiments, L is one of the following:

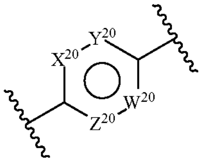 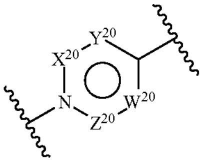

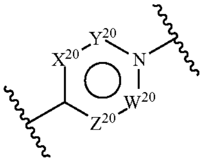 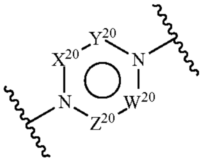

wherein $W^{20}$, $X^{20}$, $Y^{20}$, and $Z^{20}$ are independently $—C(R^{100})—$ or —N—; wherein $R^{100}$ represents independently for each occurrence hydrogen, halogen, $C_{1-6}$ alkyl, or $C_{3-6}$ cycloalkyl. In certain embodiments, $R^{100}$ represents independently for each occurrence hydrogen, methyl, ethyl, isopropyl, cyclopropyl, cyclobutyl, or cyclopentyl.

In certain embodiments, L is one of the following:

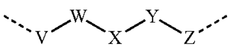 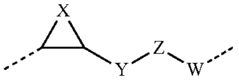

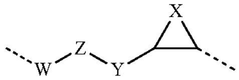 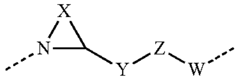

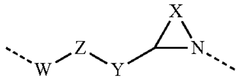 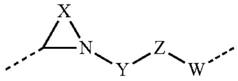

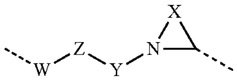 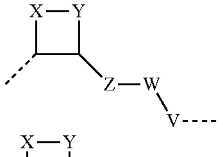

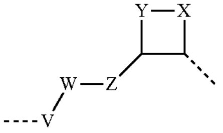 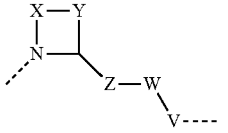

-continued

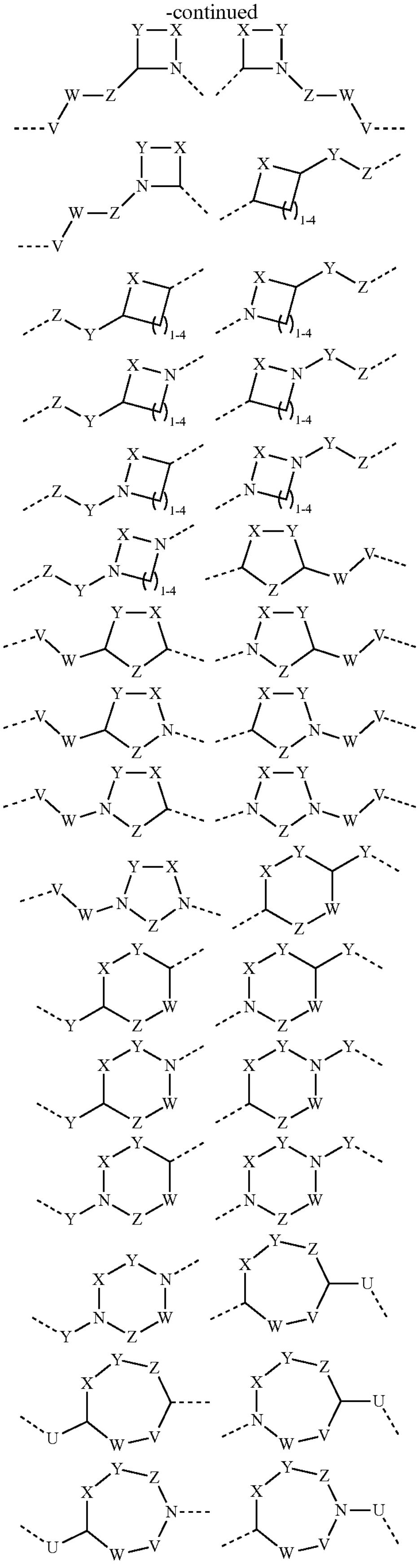

-continued

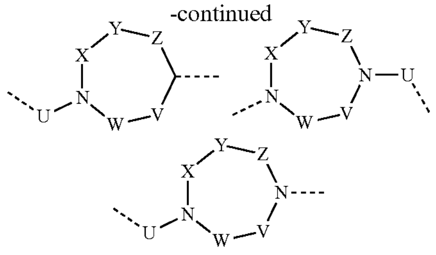

wherein U, V, W, X, Y, and Z are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl; $R^{101}$ is hydrogen, $C_{1-6}$ alkyl, or $C_{3-6}$ cycloalkyl; and a dashed bond indicates a point of attachment. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

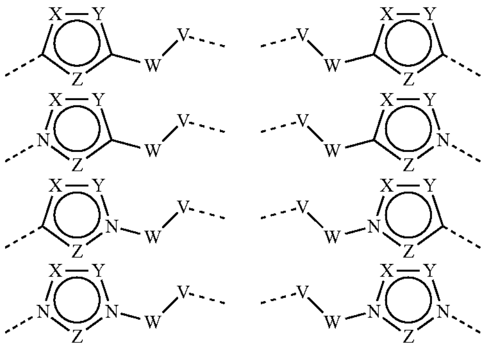

wherein X, Y, and Z are independently —C($R^{100}$)— or —N—; V and W are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl; $R^{101}$ is hydrogen, $C_{1-6}$ alkyl, or $C_{3-6}$ cycloalkyl; and a dashed bond indicates a point of attachment. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

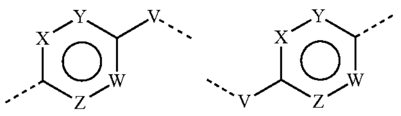

-continued

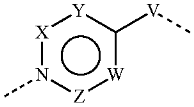
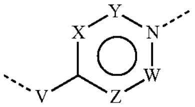
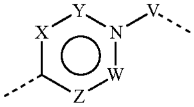
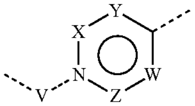
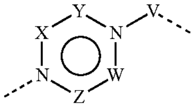
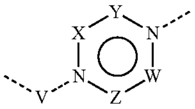

wherein W, X, Y, and Z are independently —C($R^{100}$)— or —N—; V is —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl; $R^{101}$ is hydrogen, $C_{1-6}$ alkyl, or $C_{3-6}$ cycloalkyl; and a dashed bond indicates a point of attachment. In certain embodiments, $R^{100}$ represents independently for each occurrence hydrogen, methyl, ethyl, isopropyl, cyclopropyl, cyclobutyl, or cyclopentyl. In certain embodiments, R 101 is hydrogen, methyl, ethyl, isopropyl, cyclopropyl, cyclobutyl, or cyclopentyl.

In certain embodiments, L is one of the following:

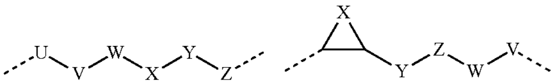
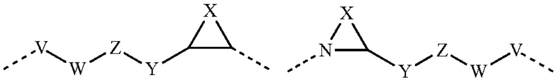
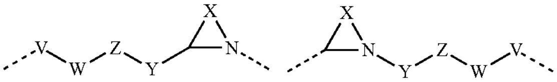
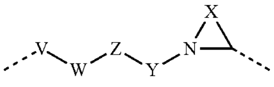
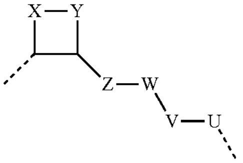
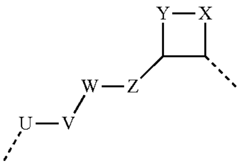
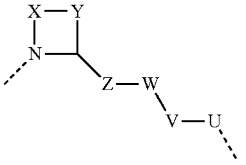
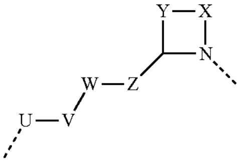
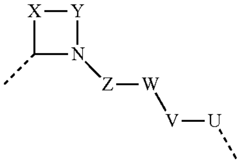
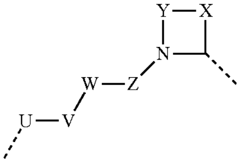
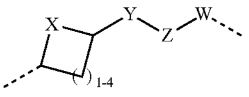
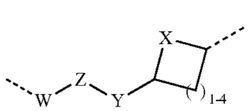
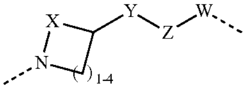
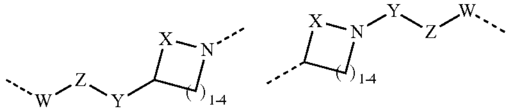

-continued

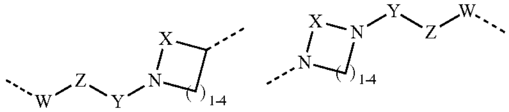
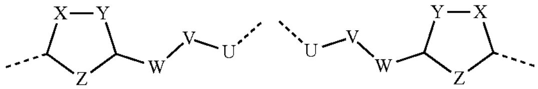
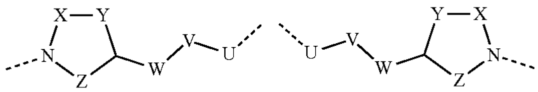
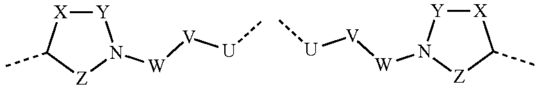
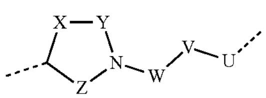
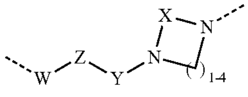
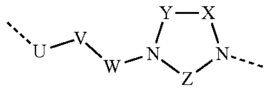
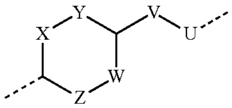
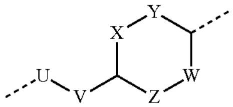
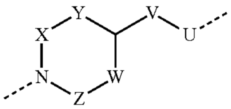
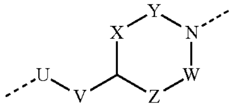
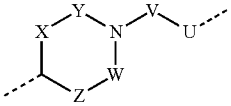
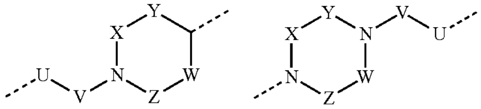
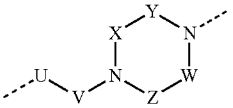
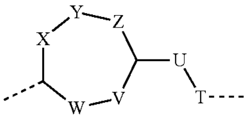
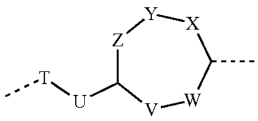
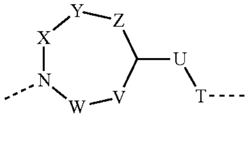
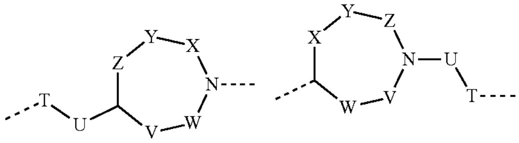
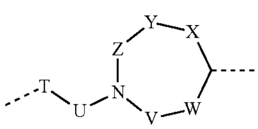
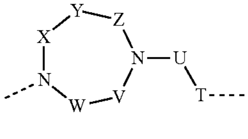

-continued

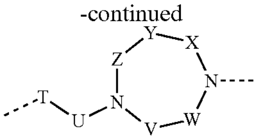

wherein T, U, V, W, X, Y, and Z are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl; $R^{101}$ is hydrogen, $C_{1-6}$ alkyl, or $C_{3-6}$ cycloalkyl; and a dashed bond indicates a point of attachment. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

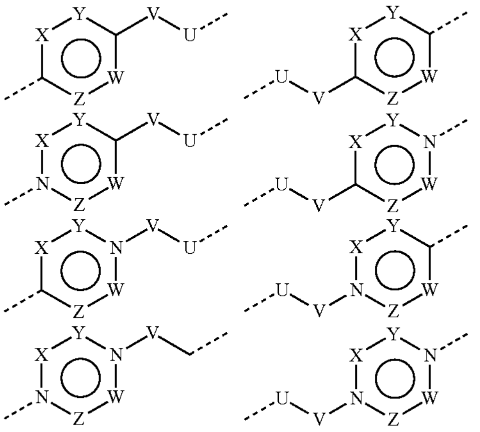

wherein W, X, Y, and Z are independently —C($R^{100}$)— or —N—; U and V are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; $R^{100}$ represents independently for each occurrence hydrogen, halogen, $C_{1-6}$ alkyl, or $C_{3-6}$ cycloalkyl; $R^{101}$ is hydrogen, $C_{1-6}$ alkyl, or $C_{3-6}$ cycloalkyl; and a dashed bond indicates a point of attachment. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

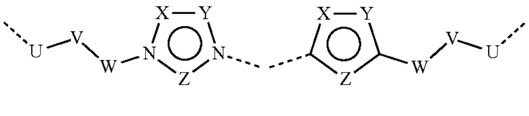

-continued

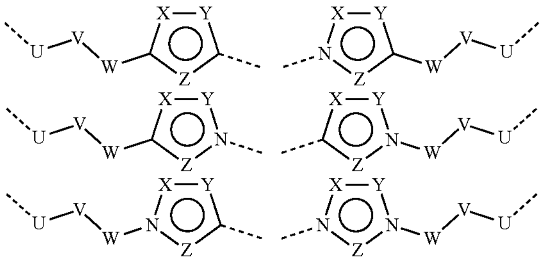

wherein X, Y, and Z are independently —C($R^{100}$)— or —N—; U, V, and W are independently —$CH_2$—, —C(H)($R^{100}$)—, —C($R^{100}$)$_2$—, O, —N($R^{101}$)—, —S(O)$_2$—, —C(O)—, an optionally substituted $C_{3-7}$ cycloalkylene, an optionally substituted $C_{4-7}$ cycloalkenylene, or optionally substituted 3-7 membered heterocyclylene containing 1, 2 or 3 heteroatoms selected from oxygen, nitrogen, and sulfur; wherein $R^{100}$ represents independently for each occurrence hydrogen, halogen, $C_{1-6}$ alkyl, or $C_{3-6}$ cycloalkyl; $R^{101}$ is hydrogen, $C_{1-6}$ alkyl, or $C_{3-6}$ cycloalkyl; and a dashed bond indicates a point of attachment. In certain embodiments, $R^{100}$ represents independently for each occurrence hydrogen, methyl, ethyl, isopropyl, cyclopropyl, cyclobutyl, or cyclopentyl. In certain embodiments, $R^{101}$ is hydrogen, methyl, ethyl, isopropyl, cyclopropyl, cyclobutyl, or cyclopentyl.

In certain embodiments, L is one of the following:

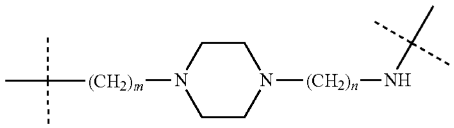
;

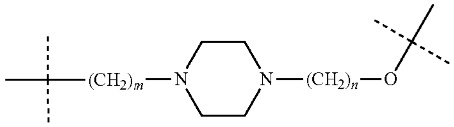
;

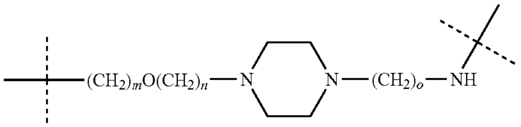
;

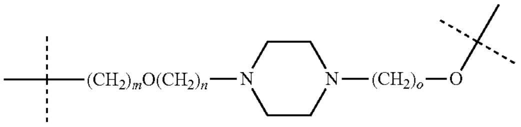
;

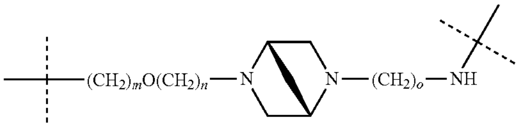
;

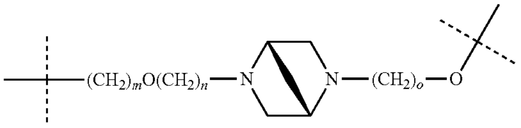
;

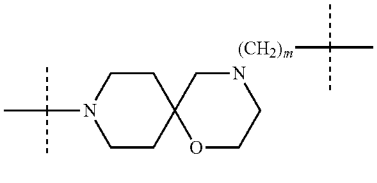
;

-continued
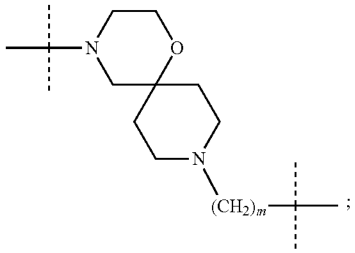
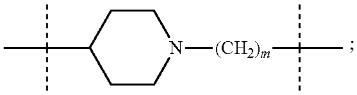
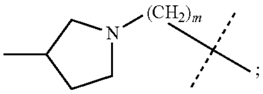
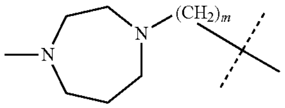
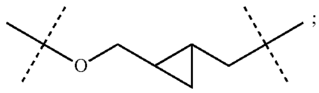
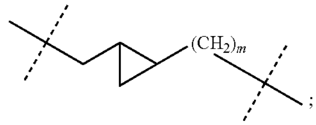
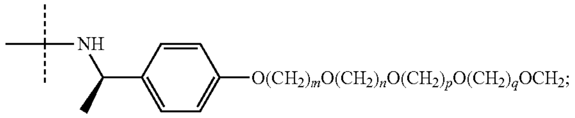
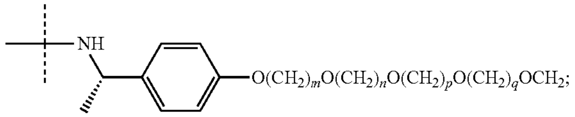
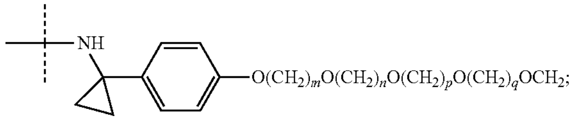
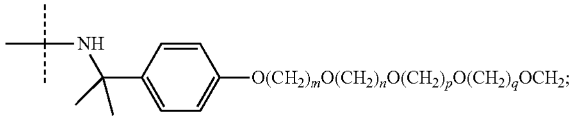
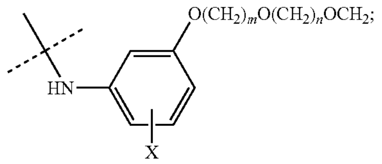
and
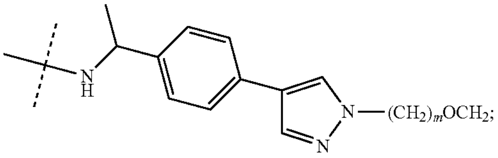
wherein variables m, n, o, p, and q are independently 0, 1, 2, 3, 4, 5, 6, 7, 8, 9, 10, 11, 12, 13, 14, 15, 16, 17, 18, 19, or 20.
In certain embodiments, L is one of the following:
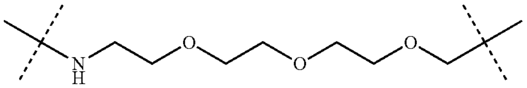
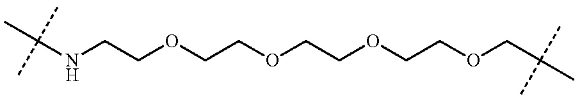
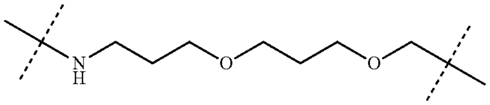
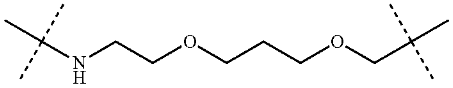
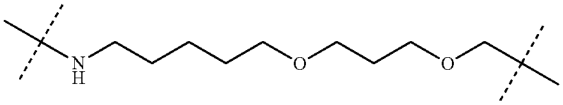
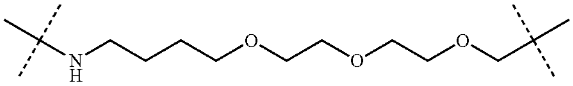
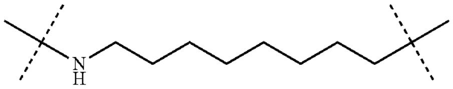
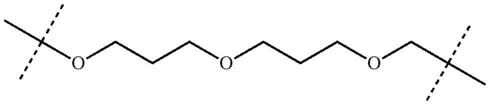
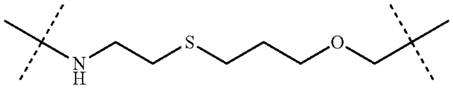
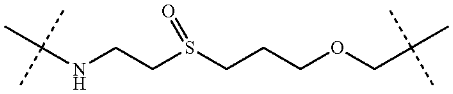
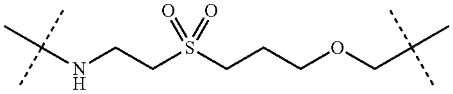
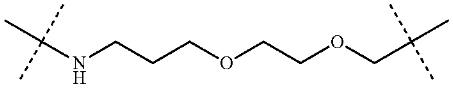
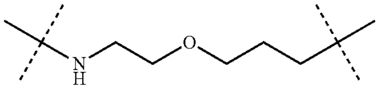
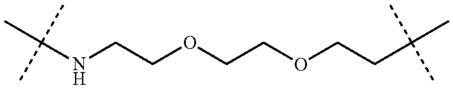
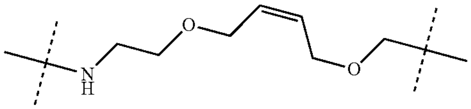
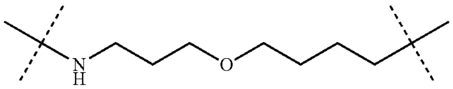
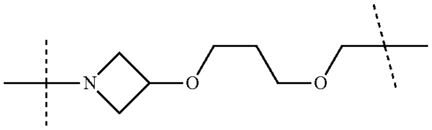

-continued
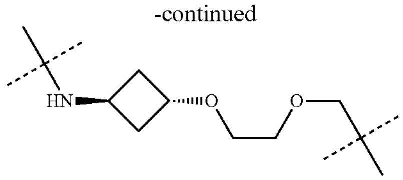
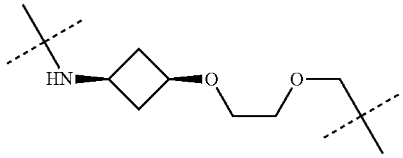
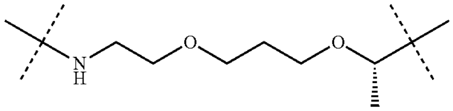
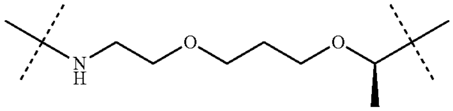
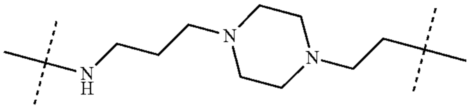
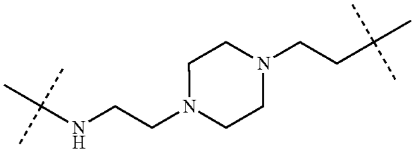
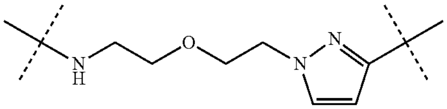
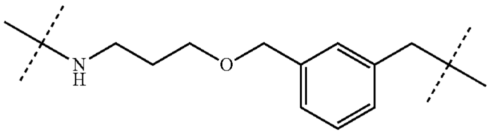
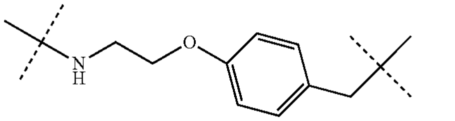
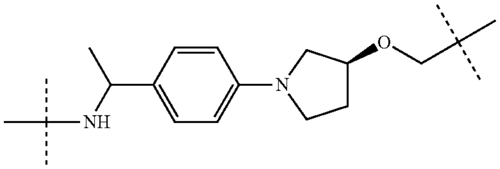
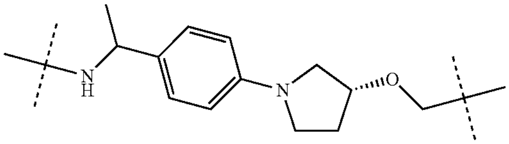
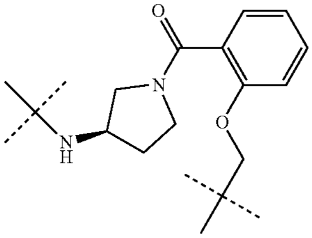
-continued
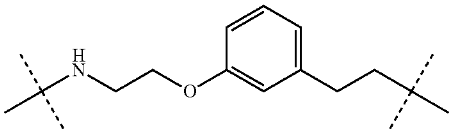
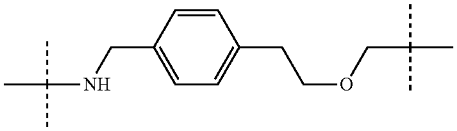
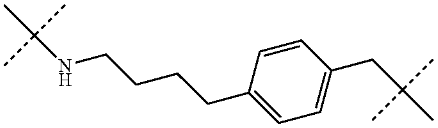
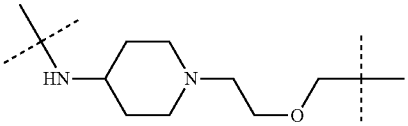
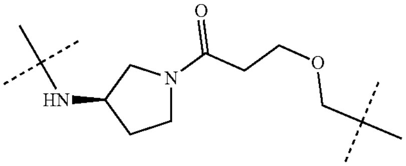
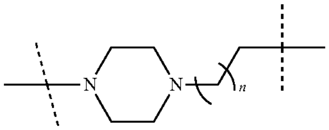
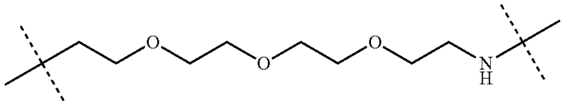
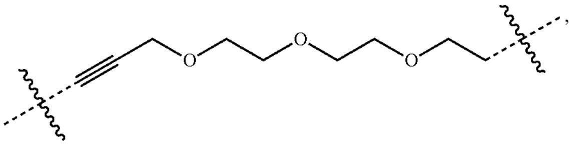
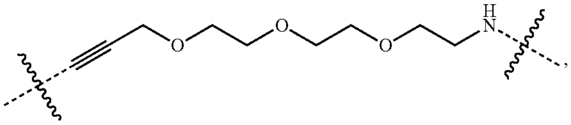
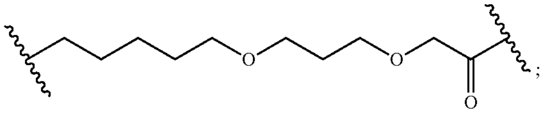
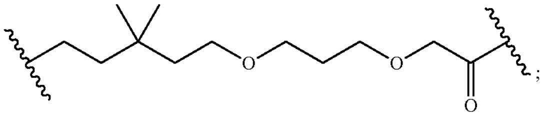
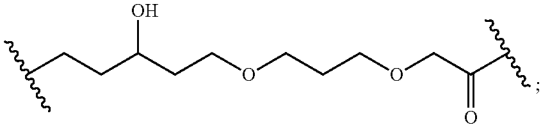
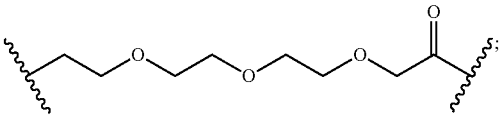

-continued
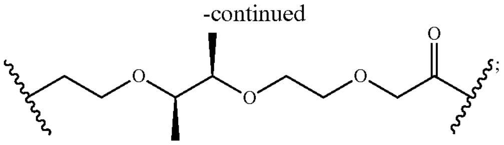
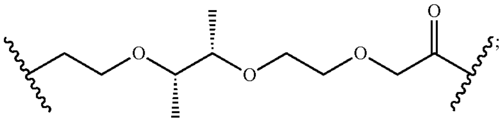
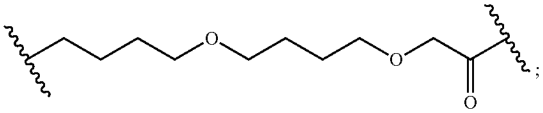
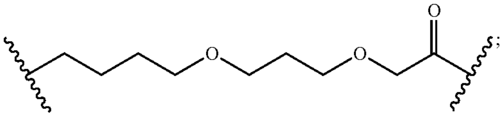
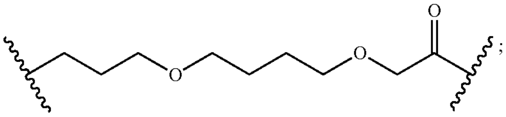
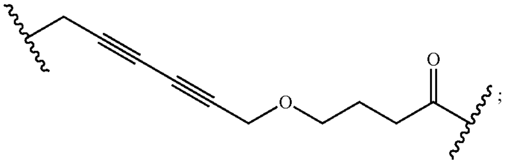
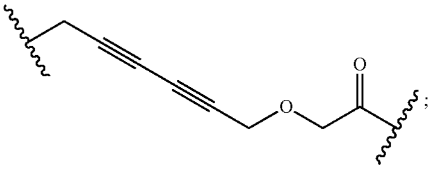
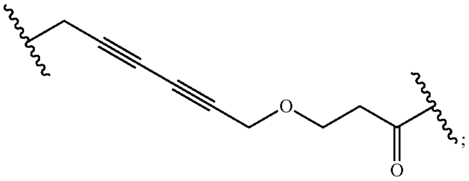
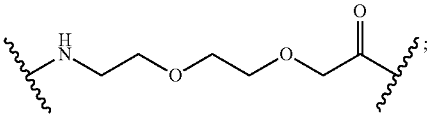
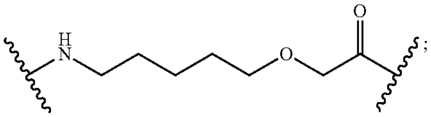
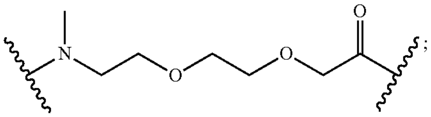
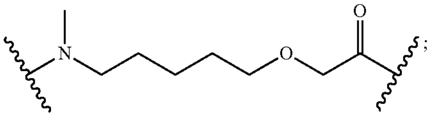
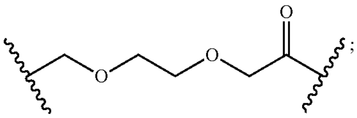
-continued
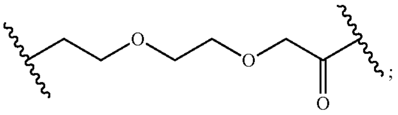
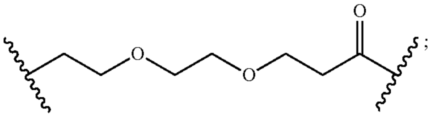
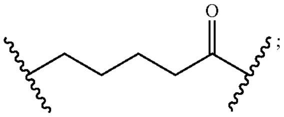
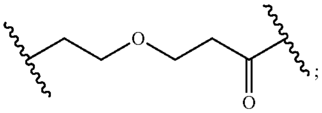
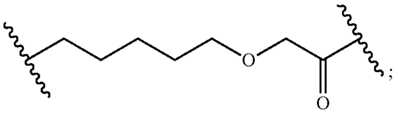
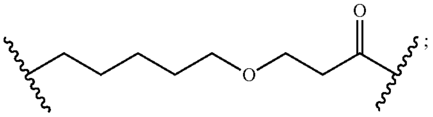
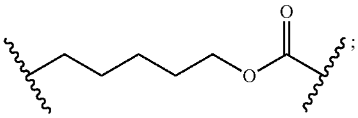
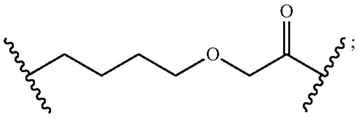
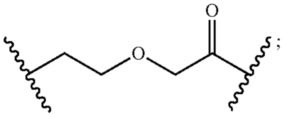
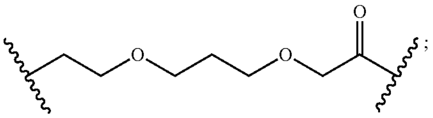
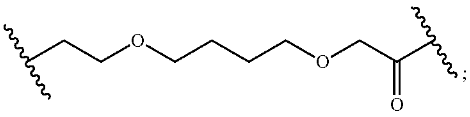
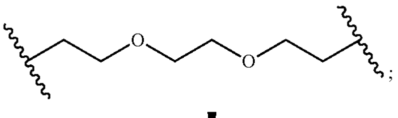
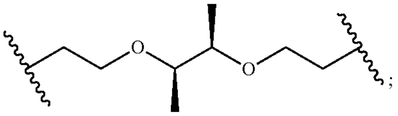
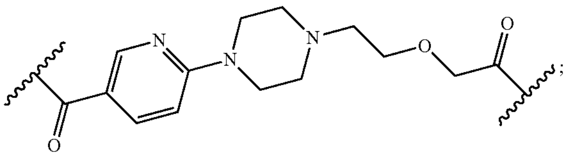

-continued
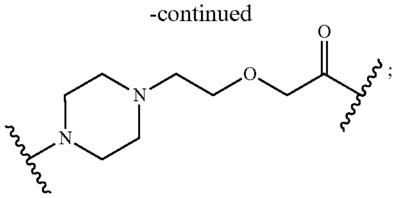
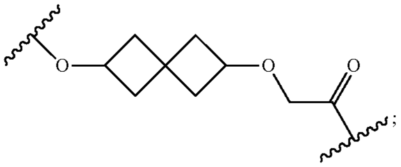
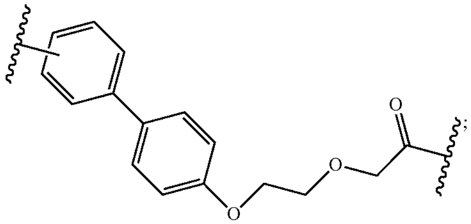
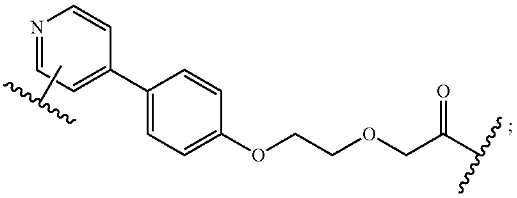
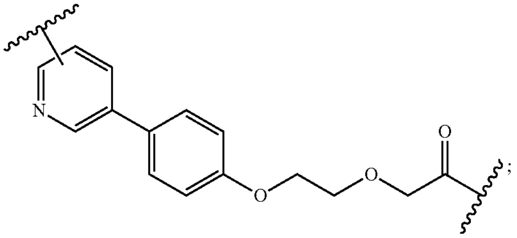
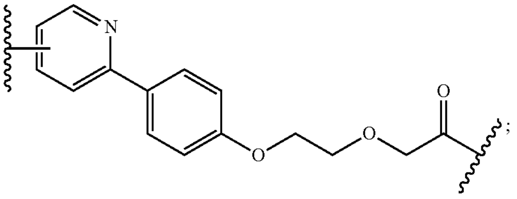
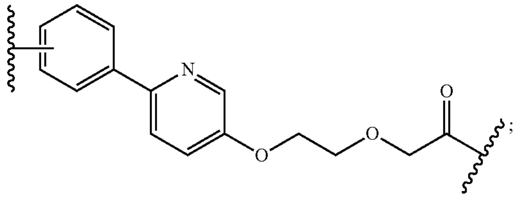
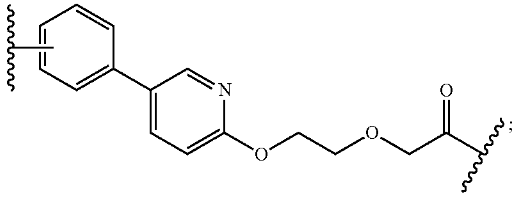
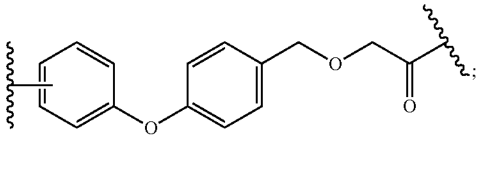
-continued
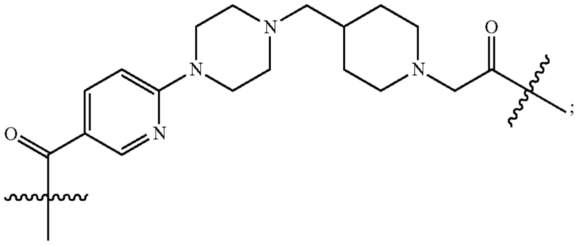
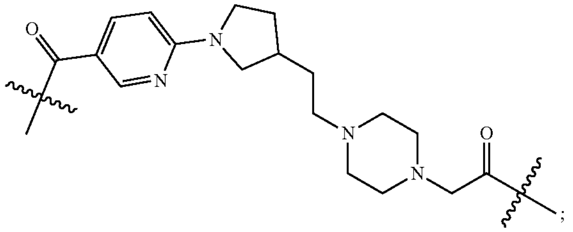
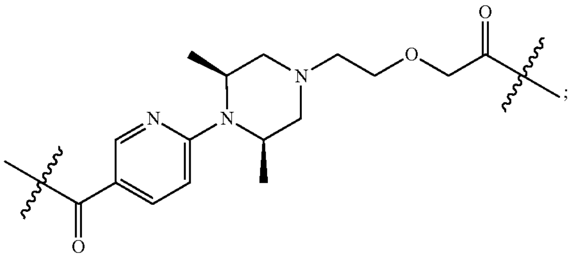
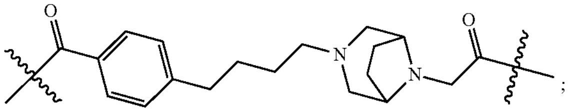
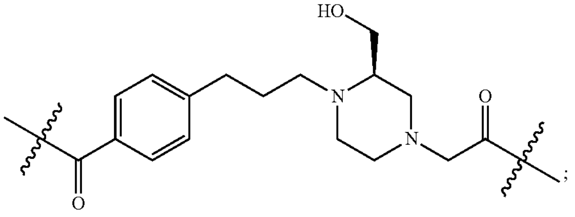
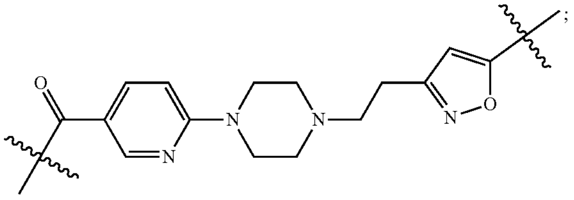
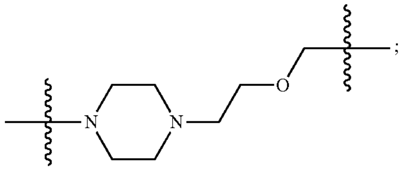
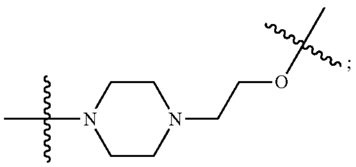
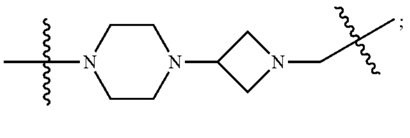

-continued
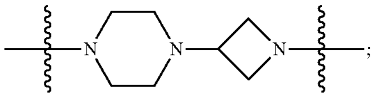
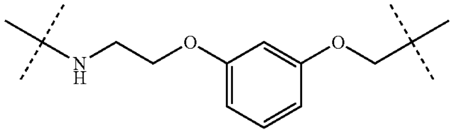
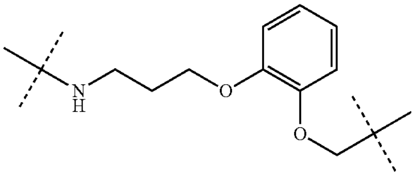
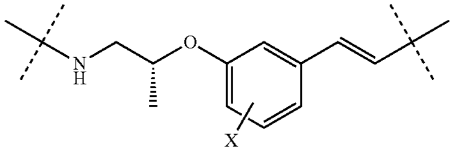
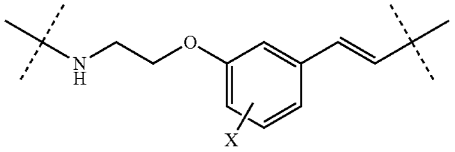
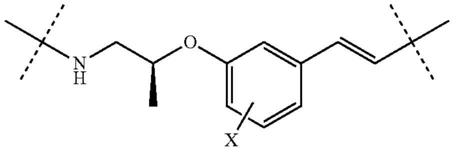
X = H, F
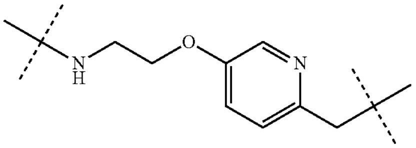
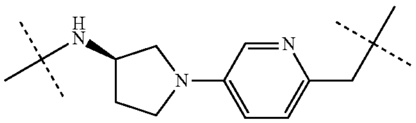
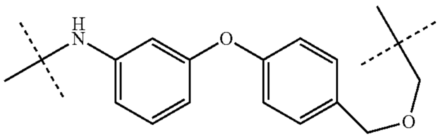
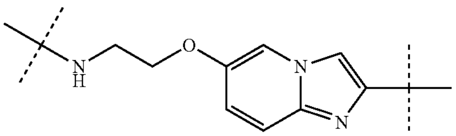
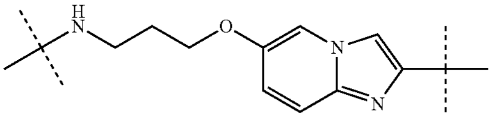
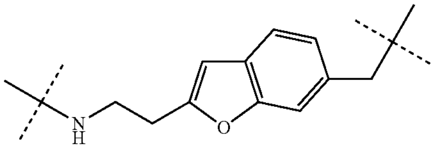
-continued
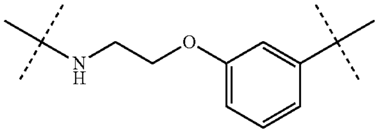
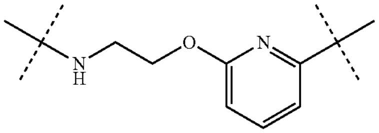
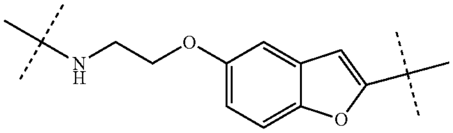
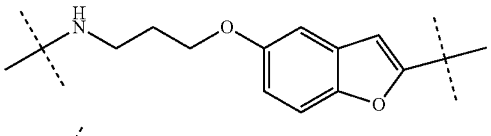
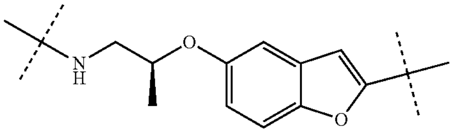
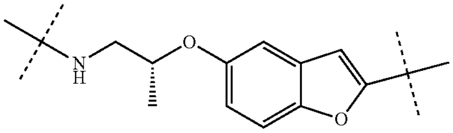
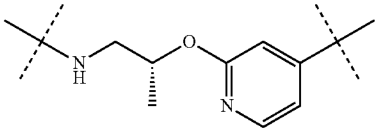
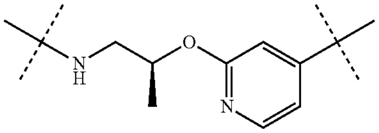
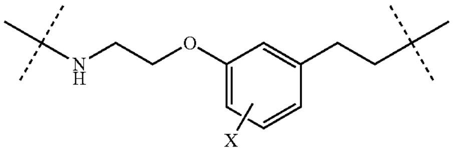
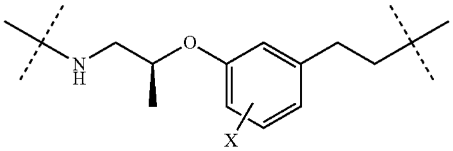
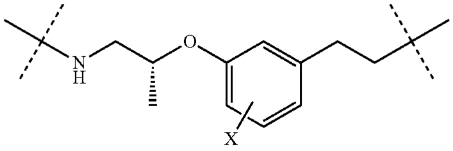
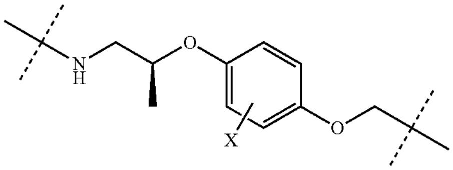

-continued
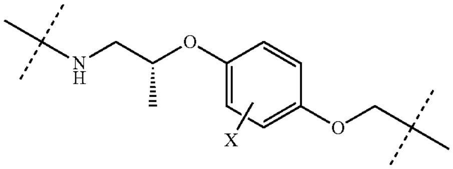
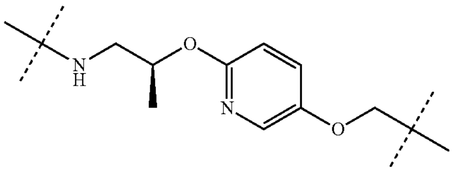
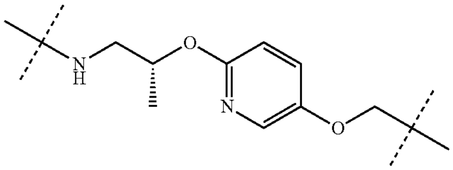
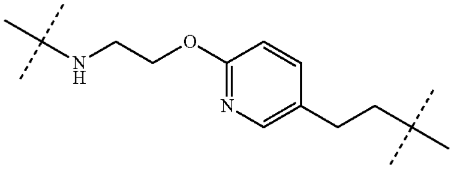
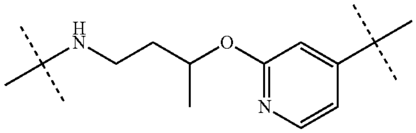
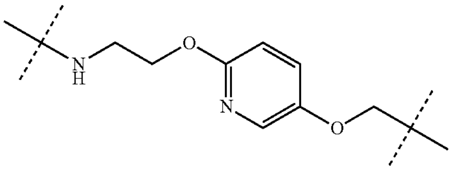
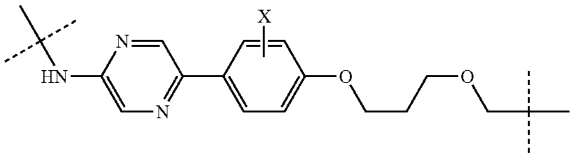
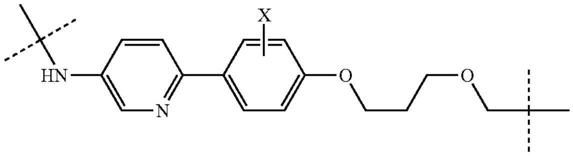
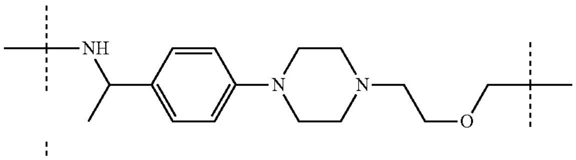
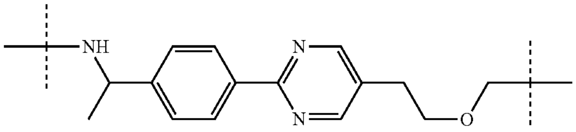
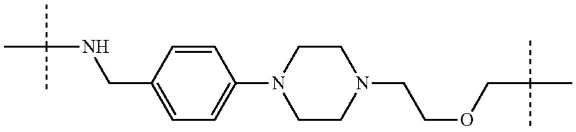
-continued
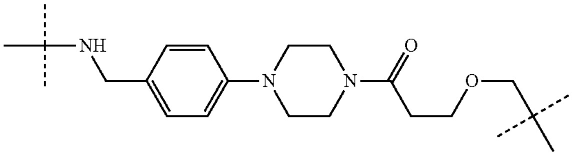
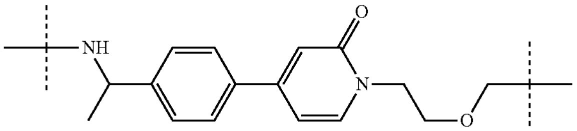
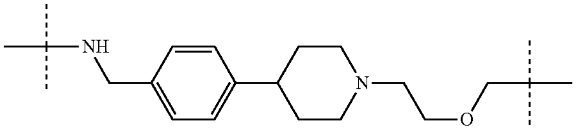
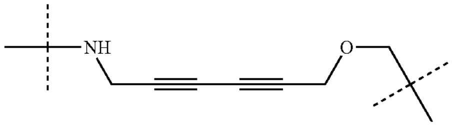
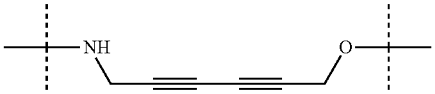
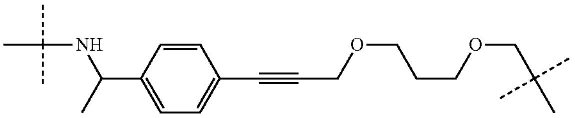
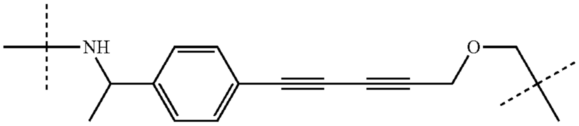
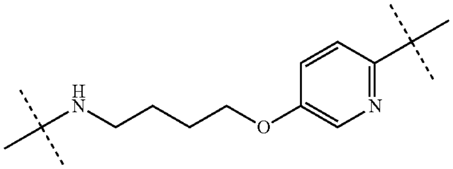
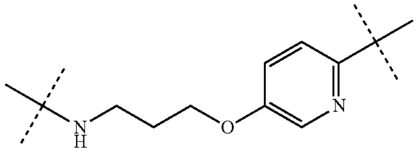
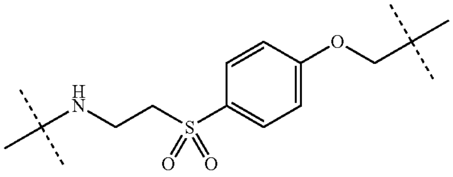
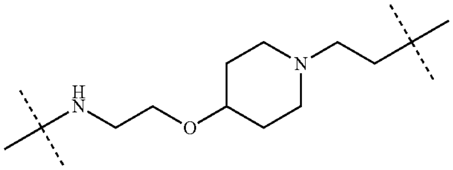
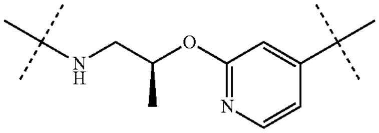

-continued
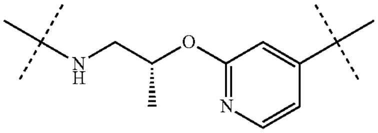
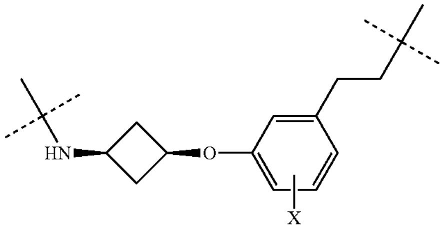
X = H, F
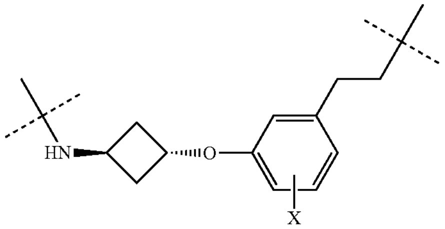
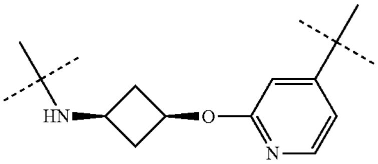
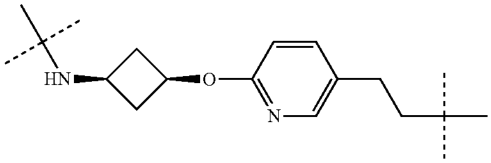
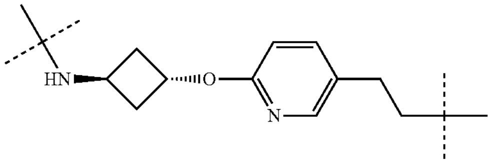
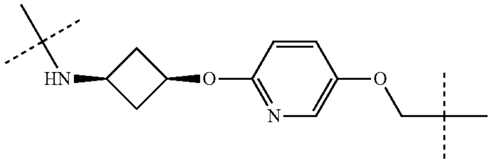
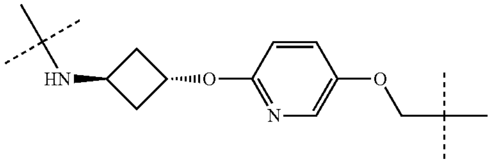
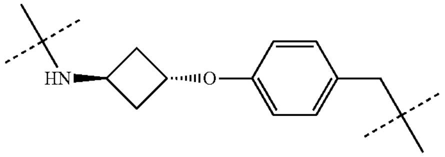
-continued
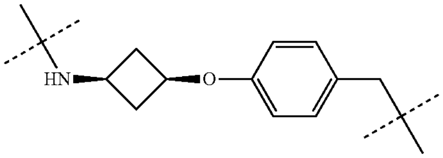
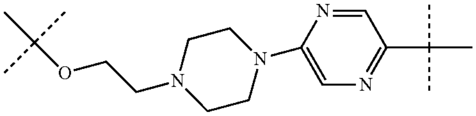
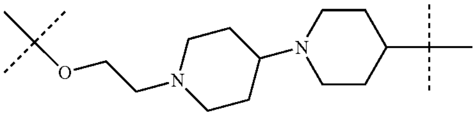
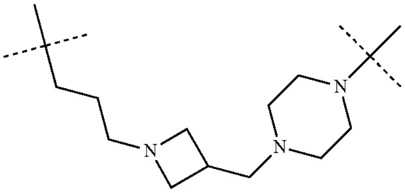
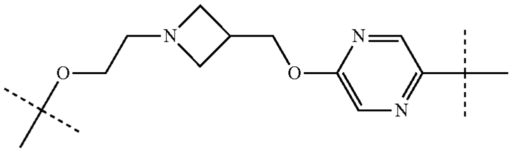
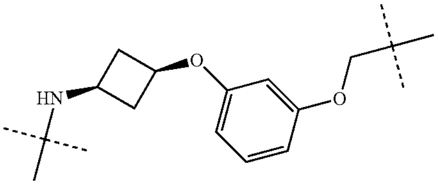
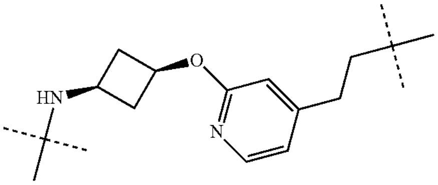
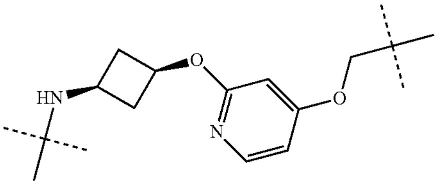
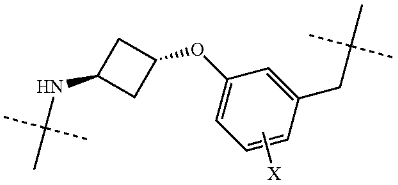
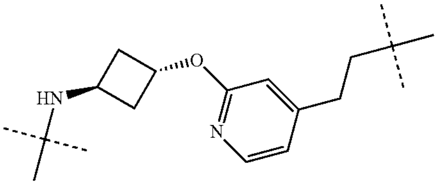

-continued
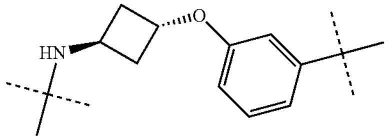
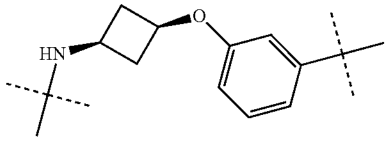
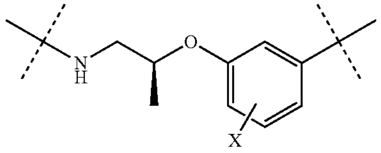
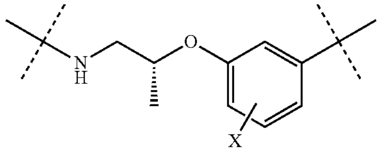
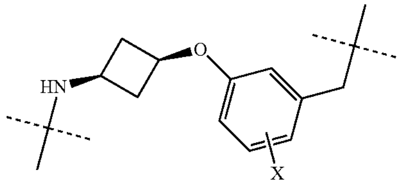
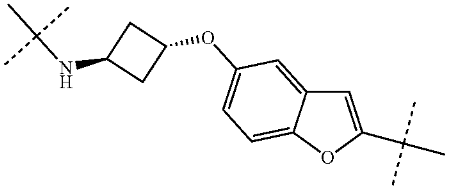
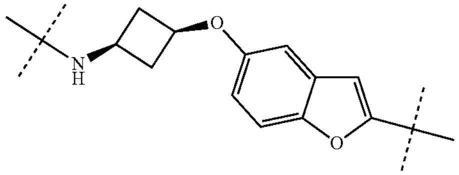
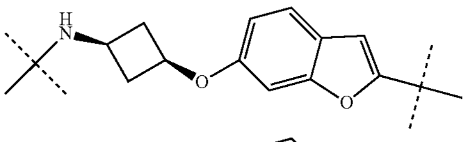
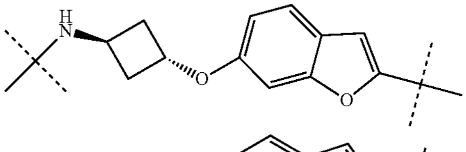
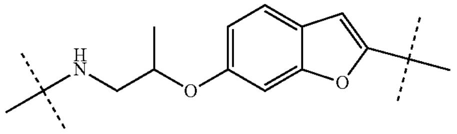
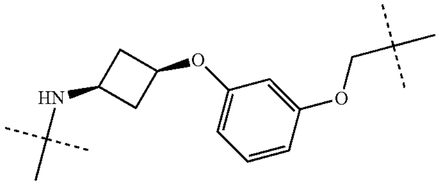
-continued
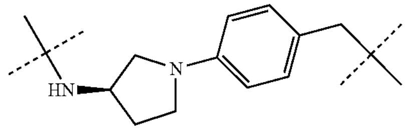
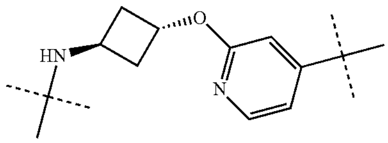
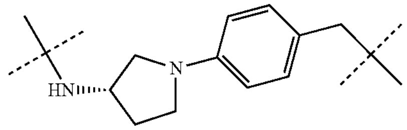
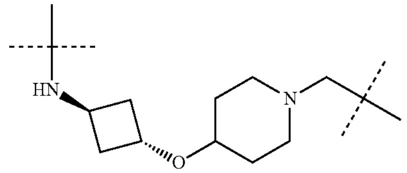
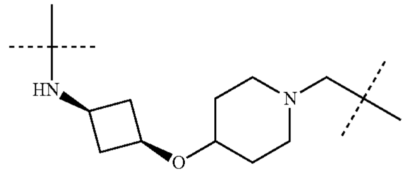
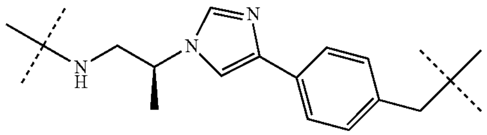
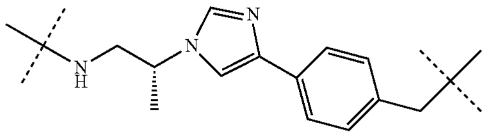
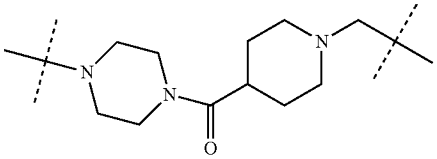
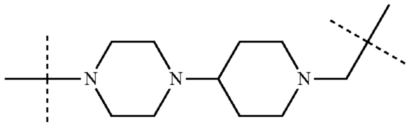
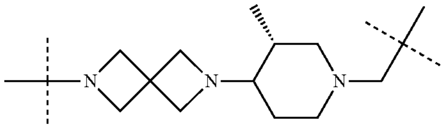
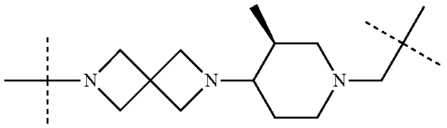

-continued
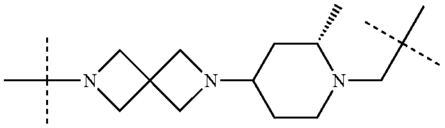
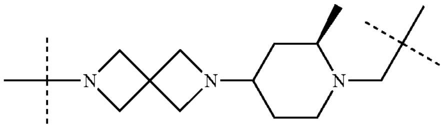
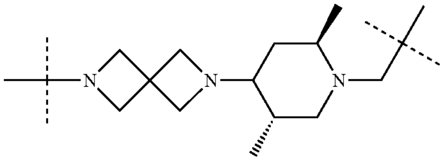
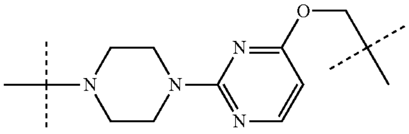
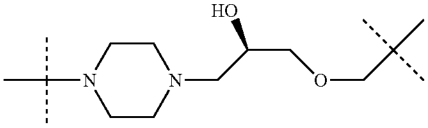
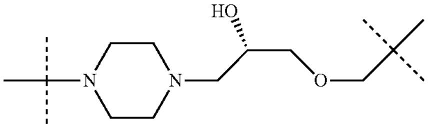
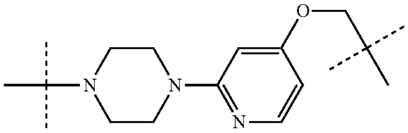
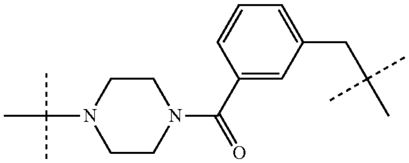
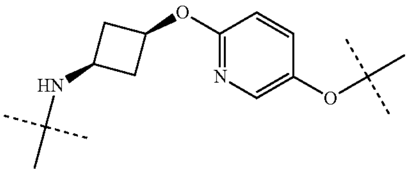
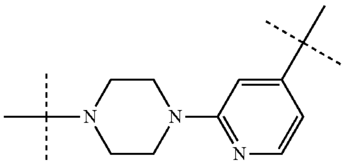
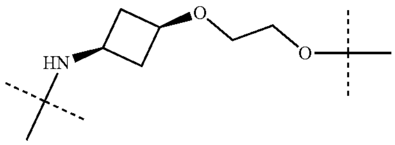
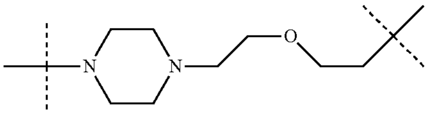
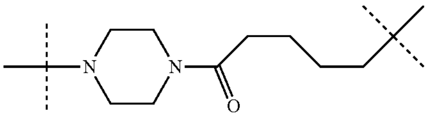
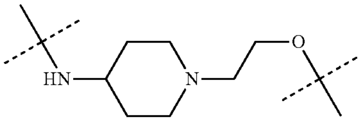
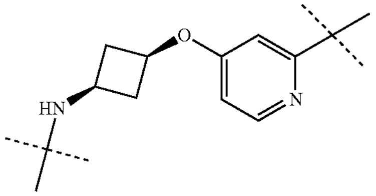
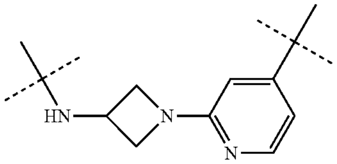
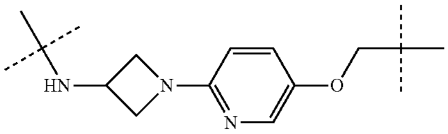
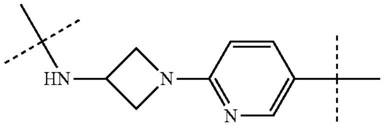
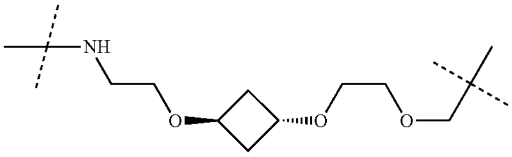
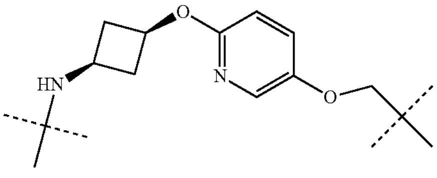
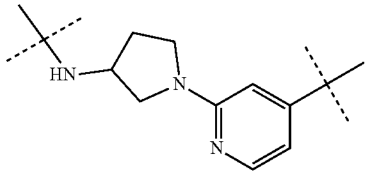
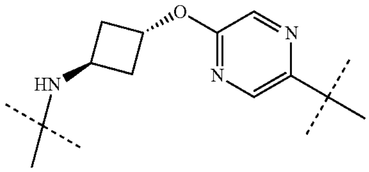
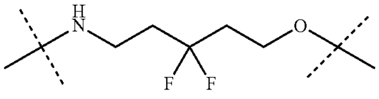
wherein any m or n are independently 0, 1, 2, 3, 4, 5, or 6; and any X is H or F.

In certain embodiments, L is one of the following:
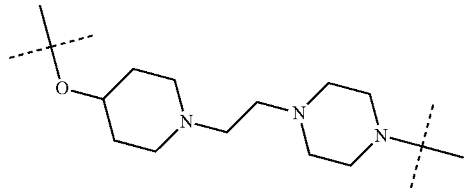
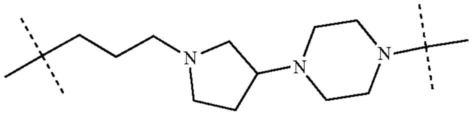
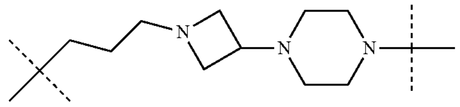
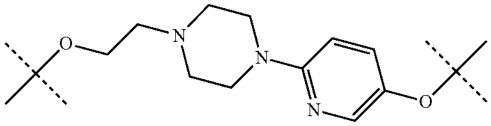
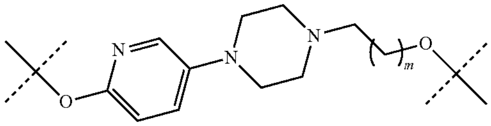
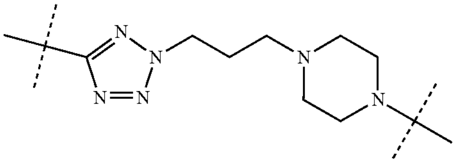
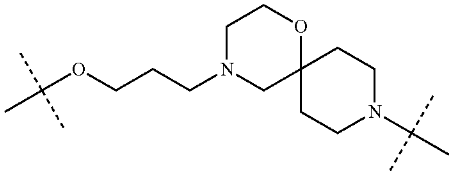
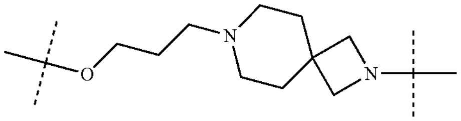
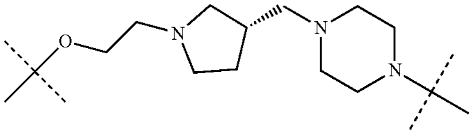
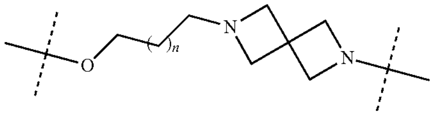
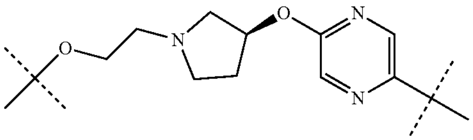
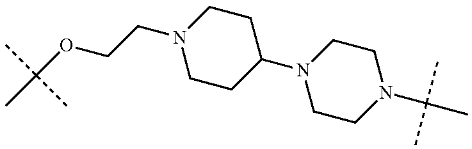
-continued
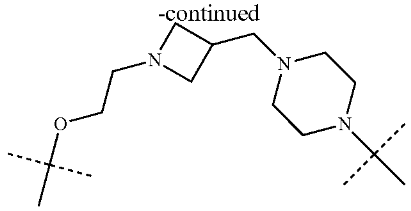
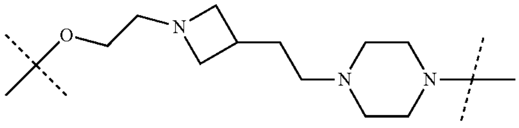
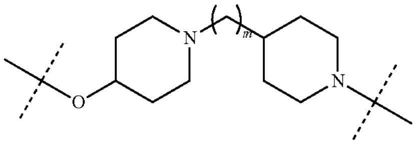
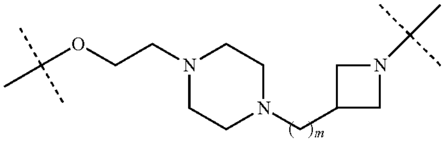
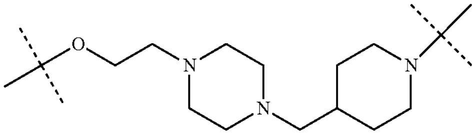
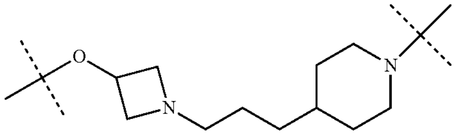
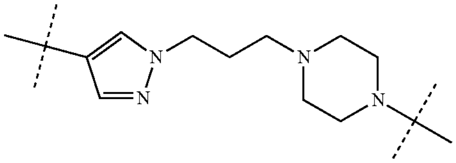
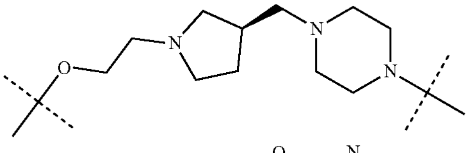
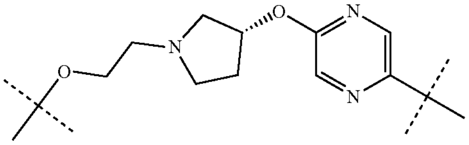
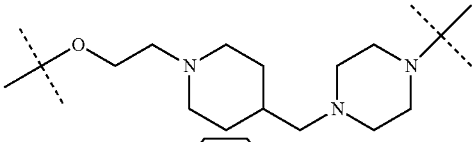
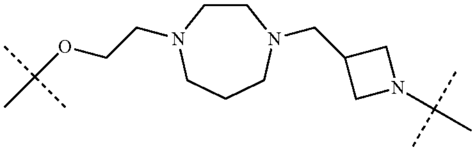
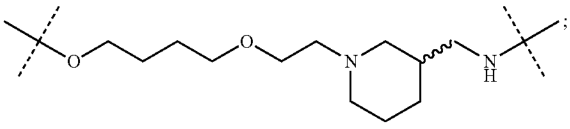;

-continued
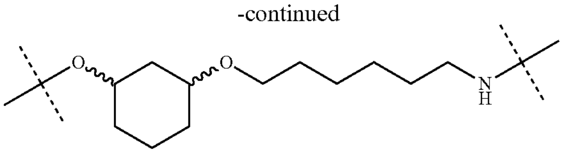
;
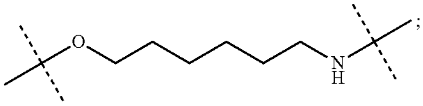
;
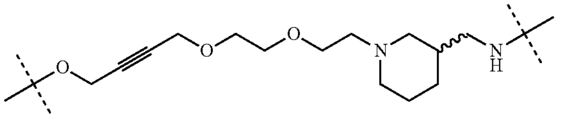
;
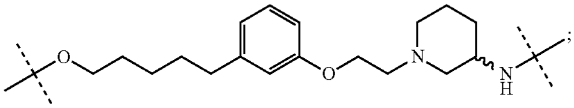
;
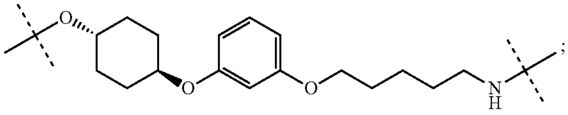
;
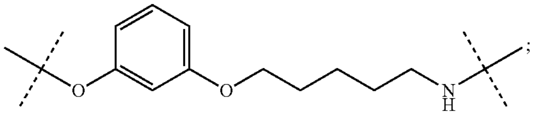
;
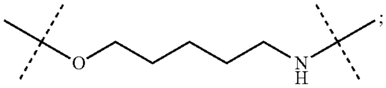
;
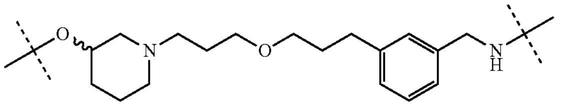
;
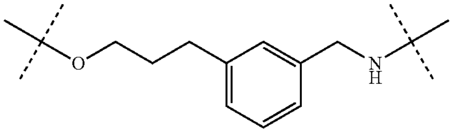
;
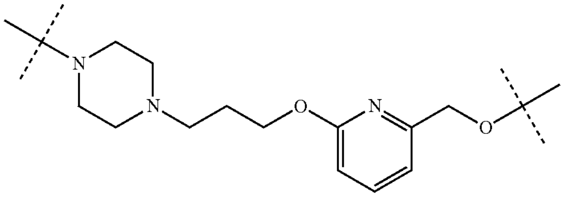
;
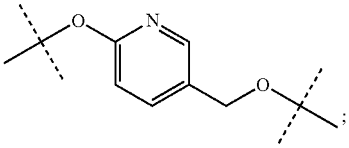
;
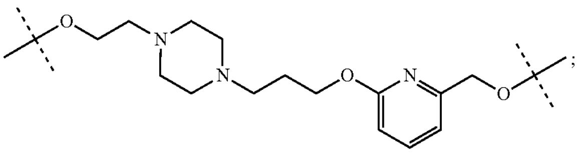
;
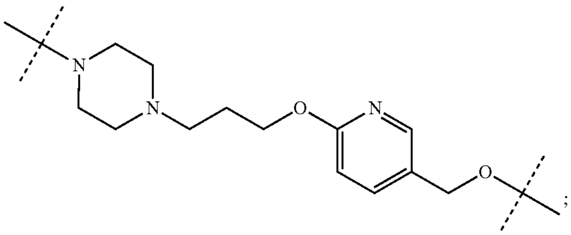
;
-continued
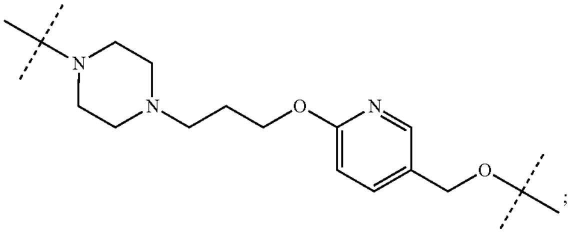
;
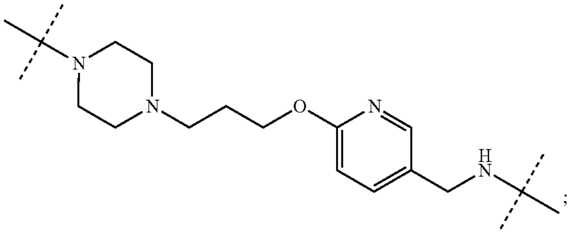
;
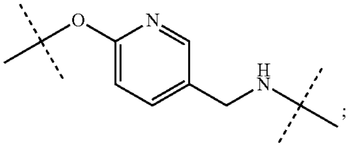
;
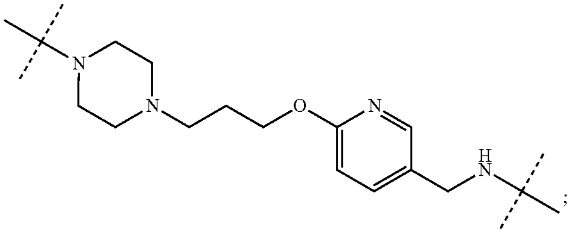
;
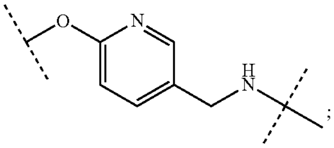
;
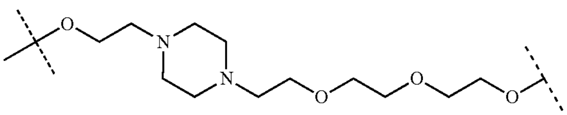
;
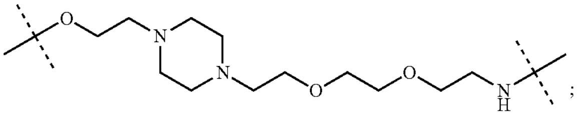
;
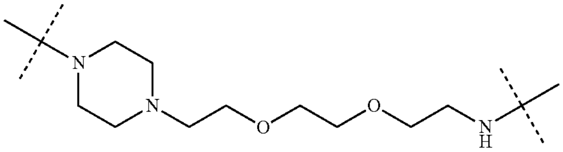
;
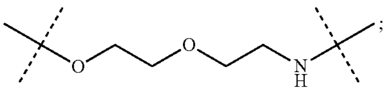
;
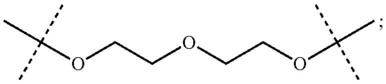
;

-continued
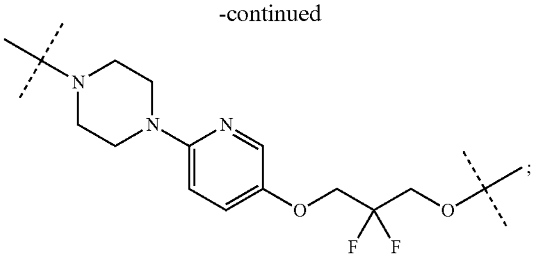
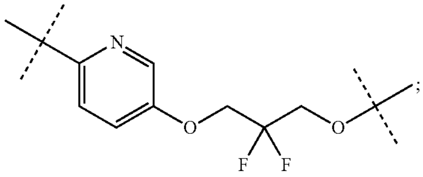
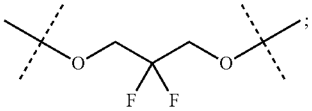
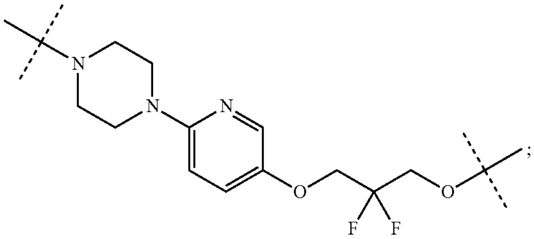
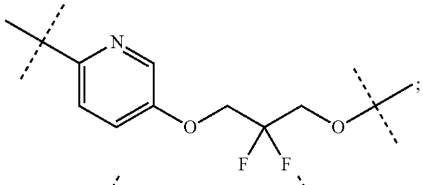
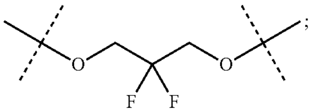
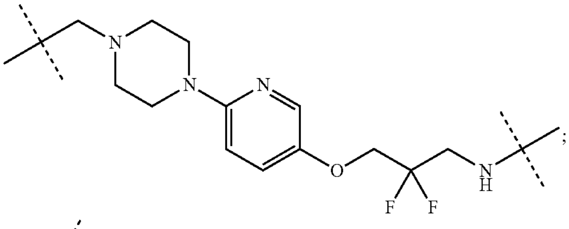
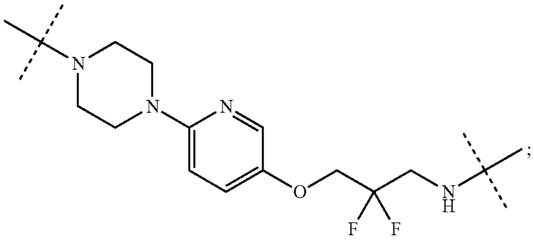
-continued
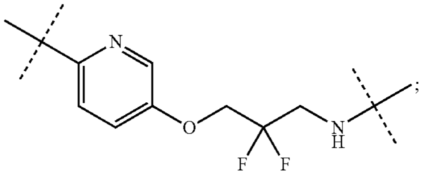
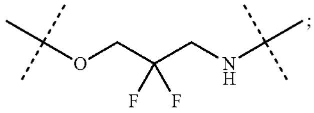
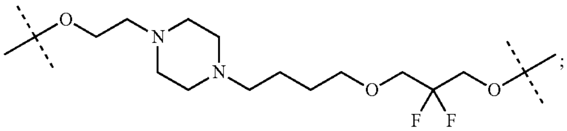
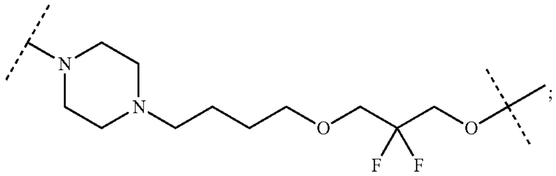
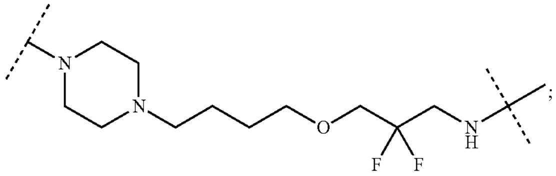
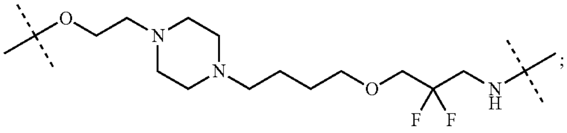
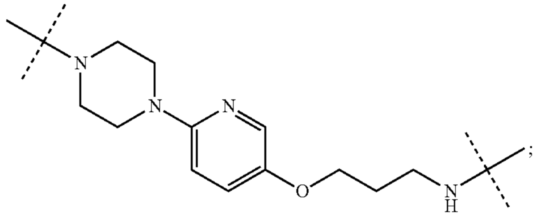
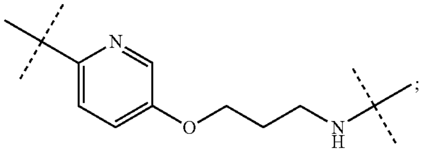
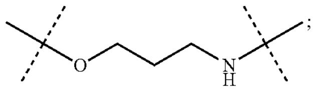
wherein any m or n are independently 0, 1, 2, 3, 4, 5, or 6.
In certain embodiments, L is one of the following:
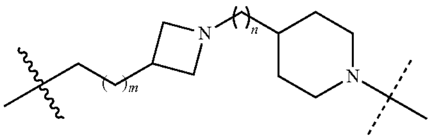
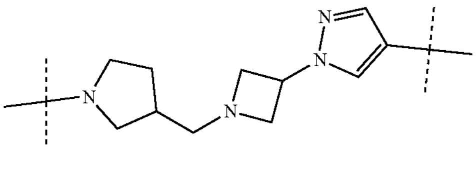

-continued
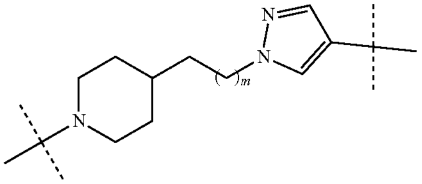
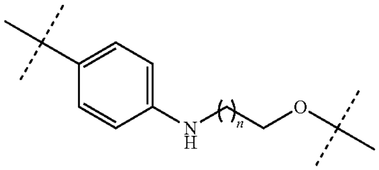
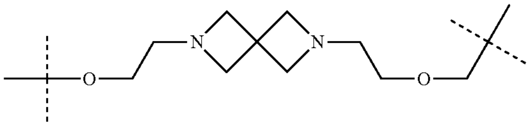
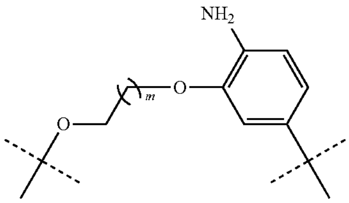
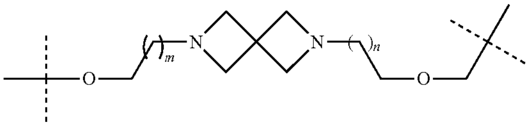
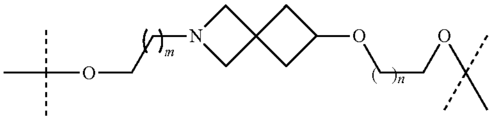
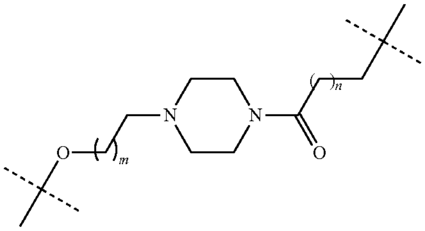
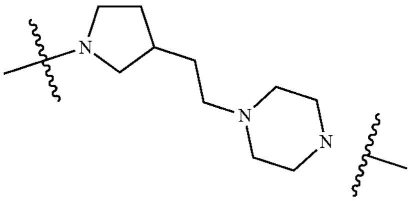
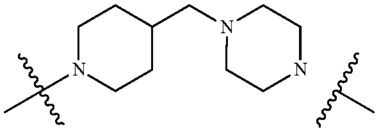
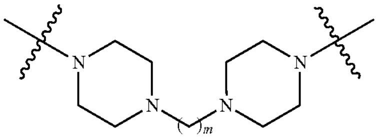
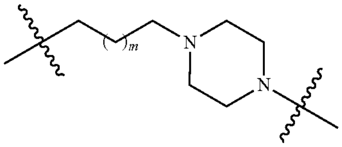
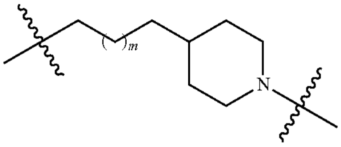
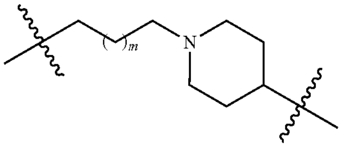
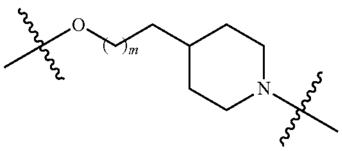
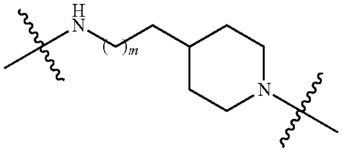
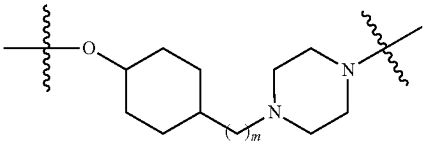
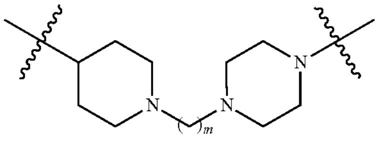
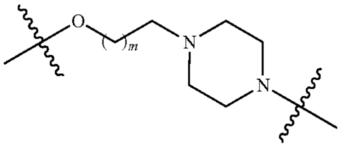
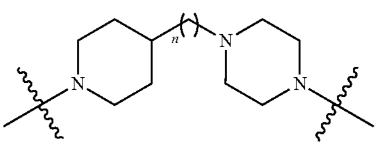
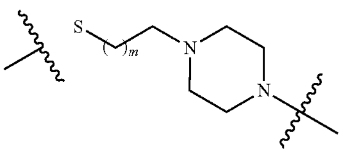
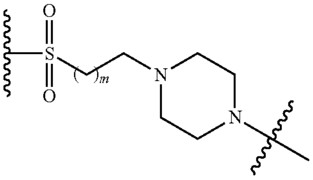
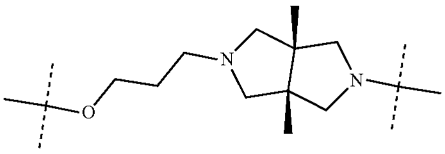

-continued
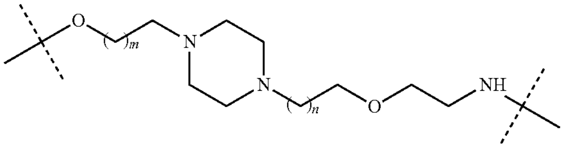
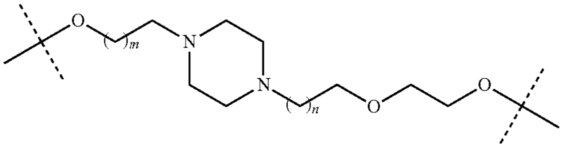
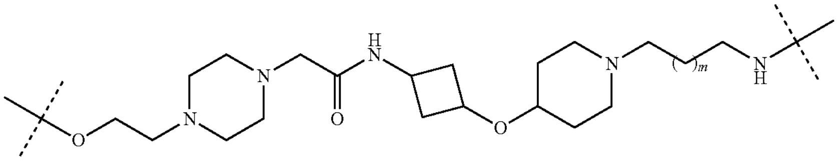
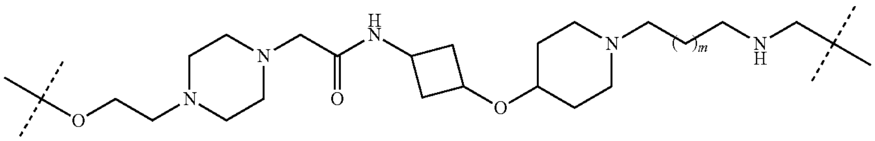
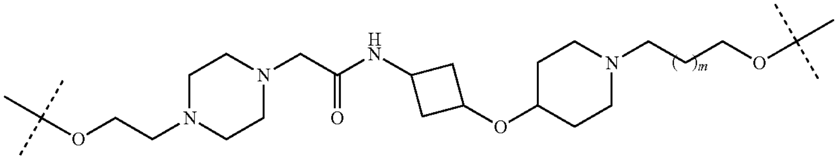
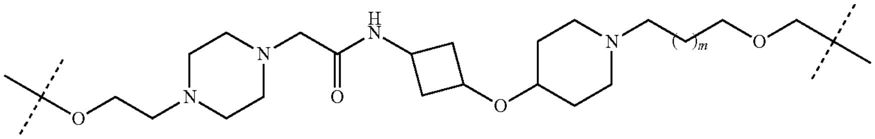
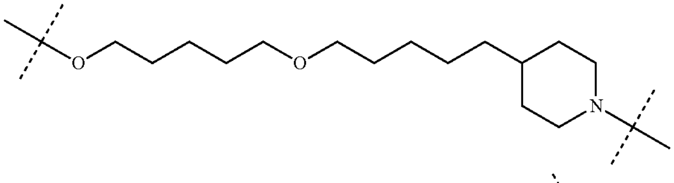
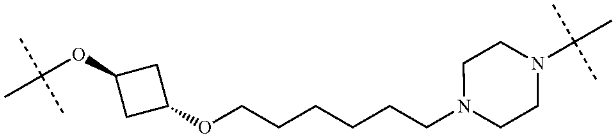
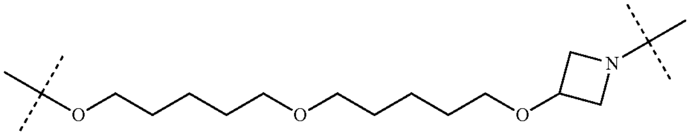
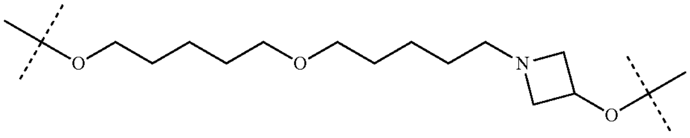
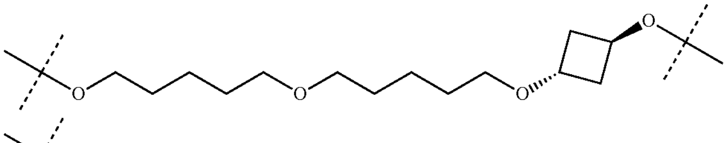
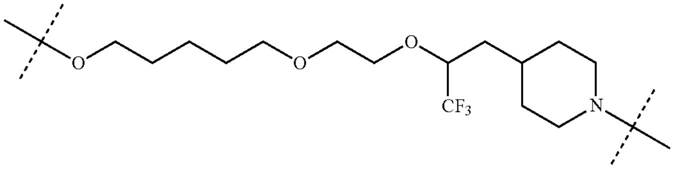
wherein any m or n are independently 0, 1, 2, 3, 4, 5, or 6.

In certain embodiments, L is one of the following:
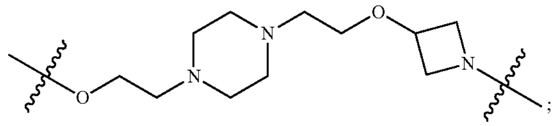
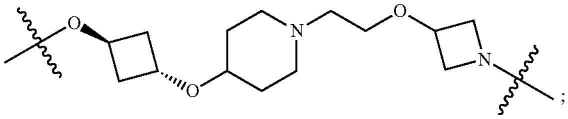
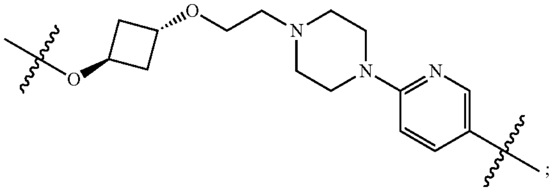
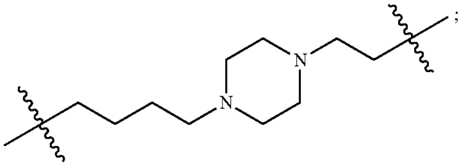
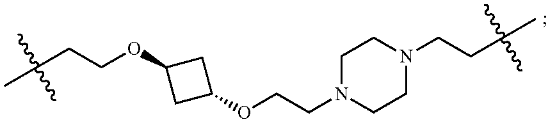
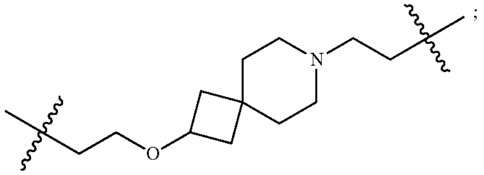
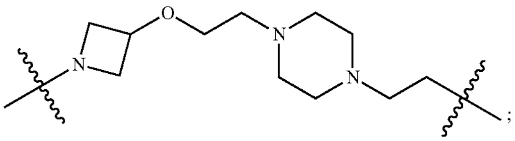
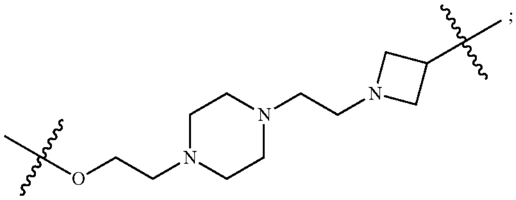
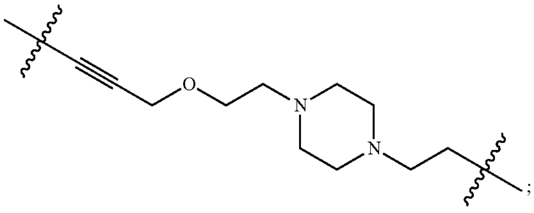
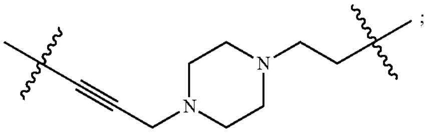
-continued
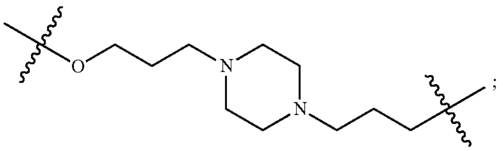
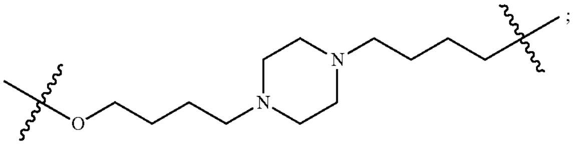
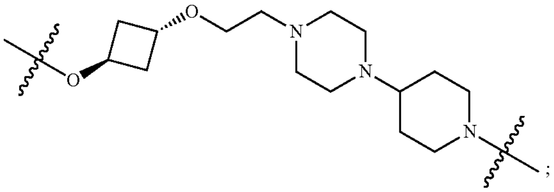
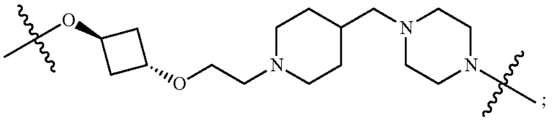
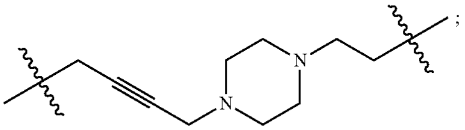
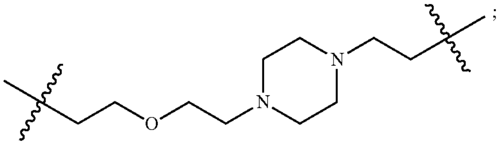
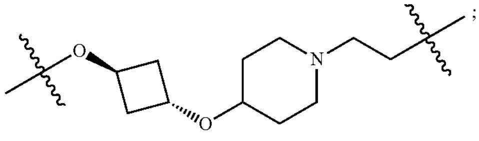
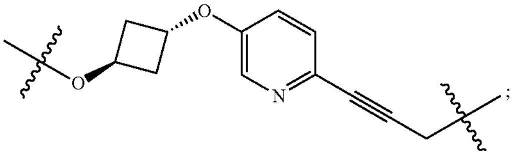
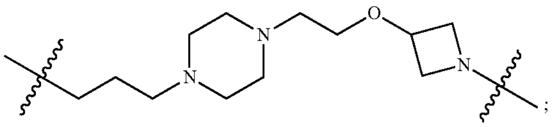
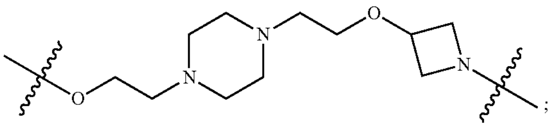
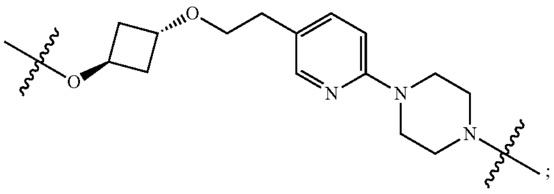

-continued
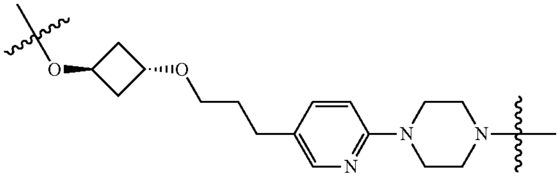
;
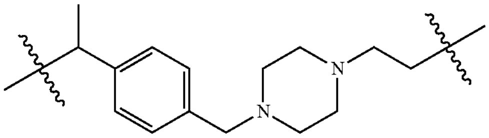
;
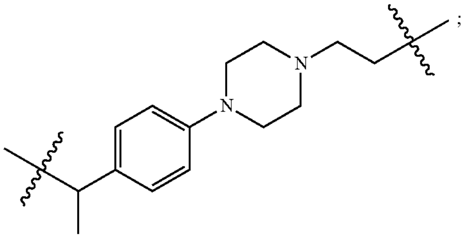
;
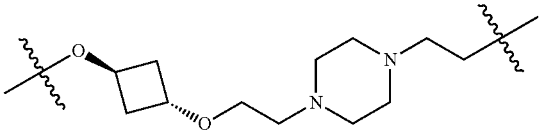
;
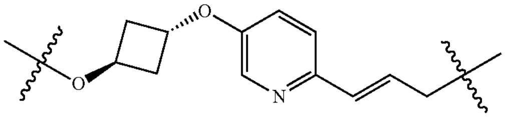
;
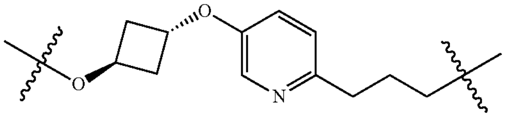
;
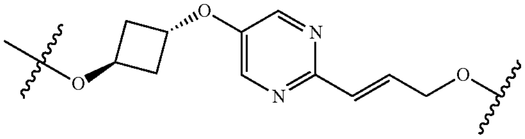
;
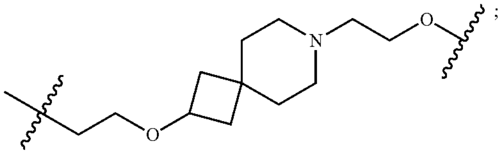
;
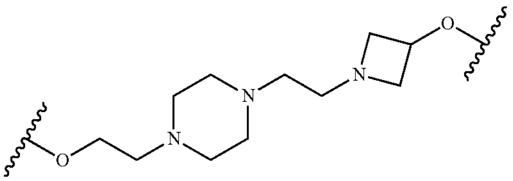
;
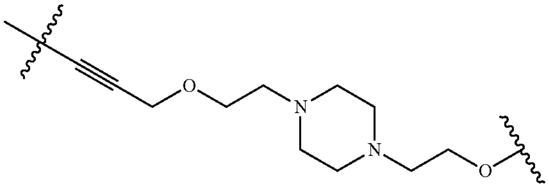
;
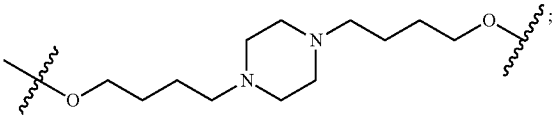
;
-continued
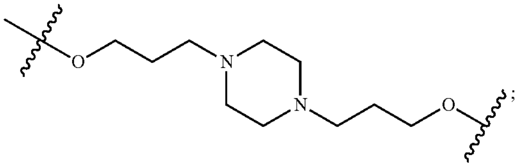
;
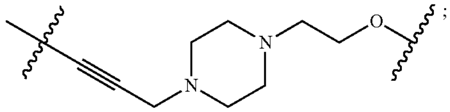
;
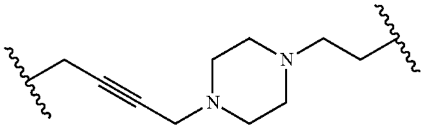
;
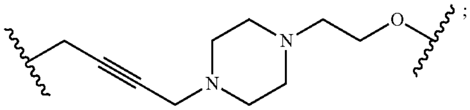
;
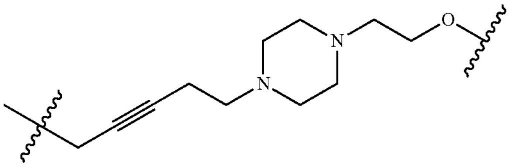
;
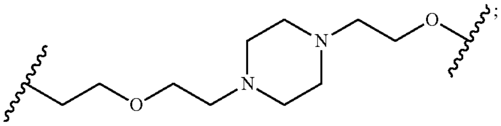
;
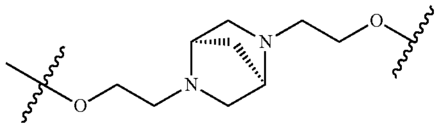
;
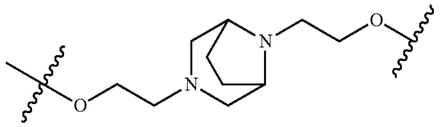
;
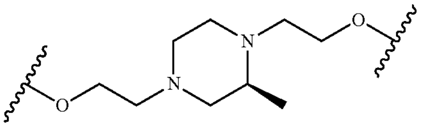
;
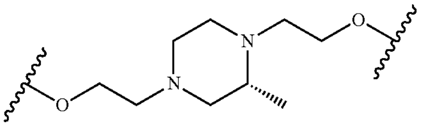
;
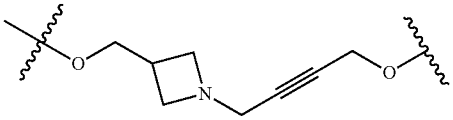
;
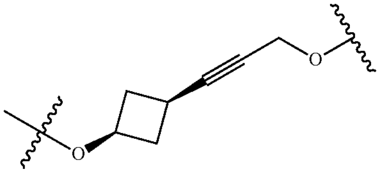
;

-continued
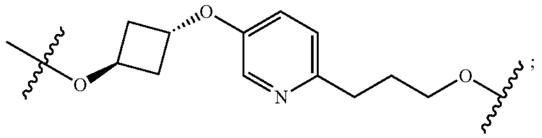
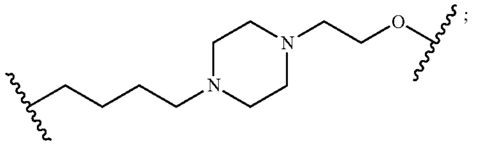
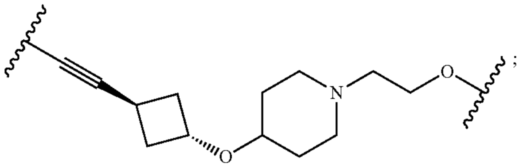
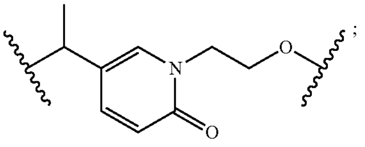
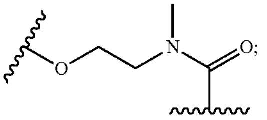
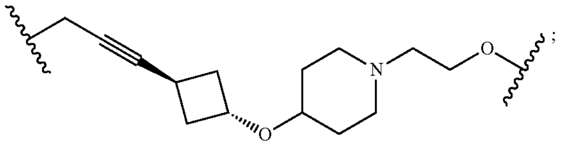
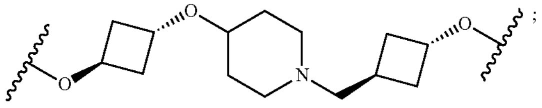
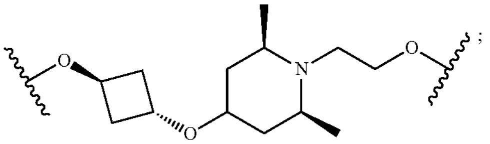
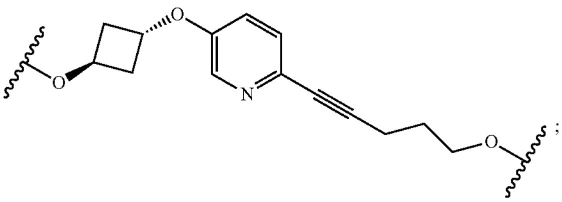
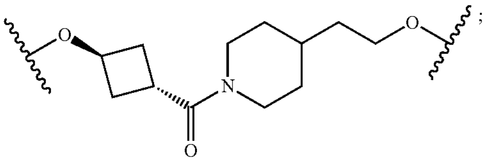
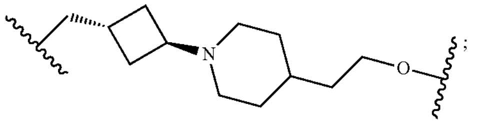
-continued
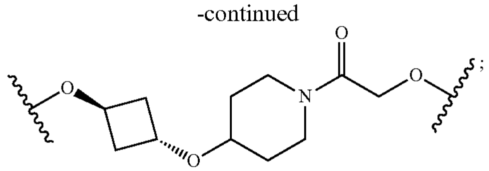
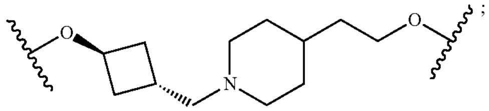
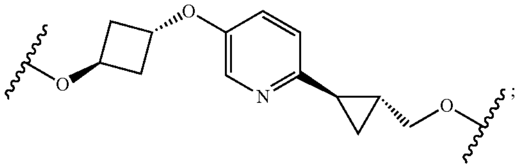
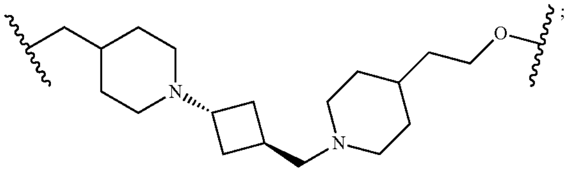
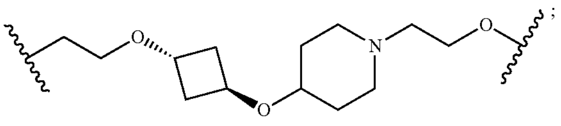
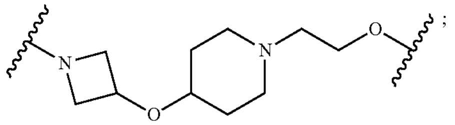
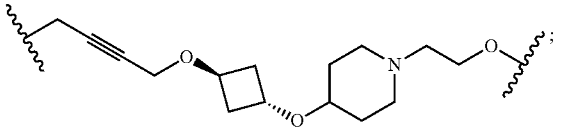
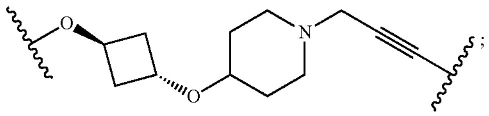
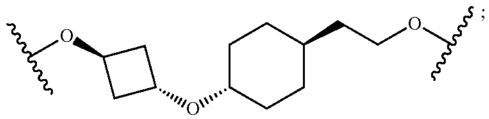
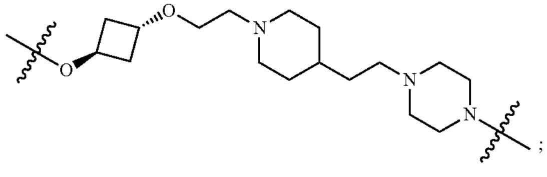
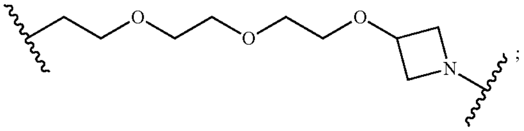
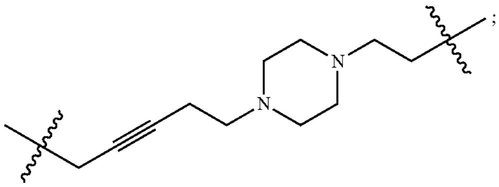

-continued
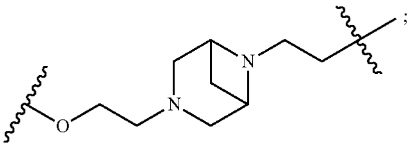
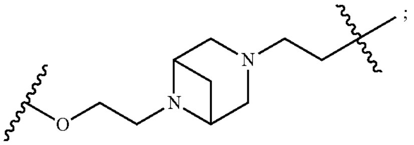
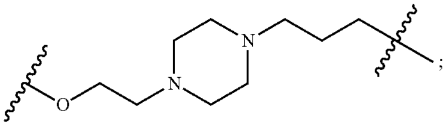
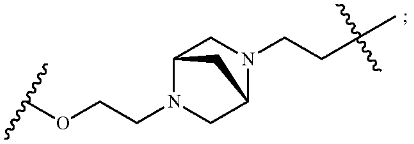
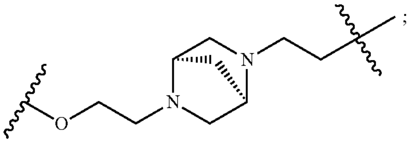
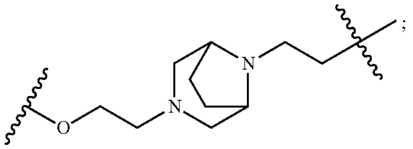
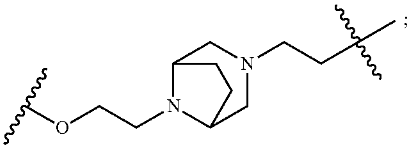
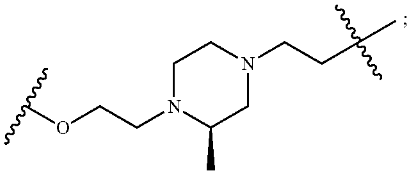
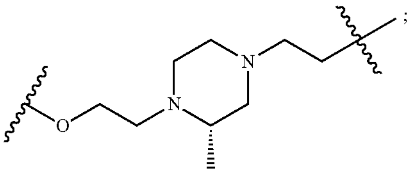
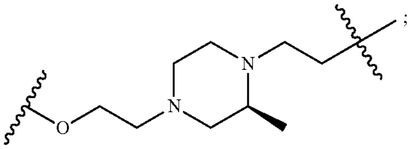
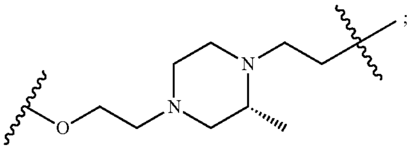
-continued
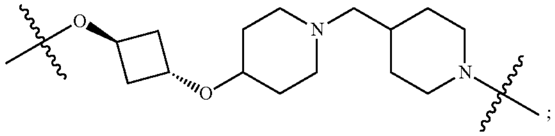
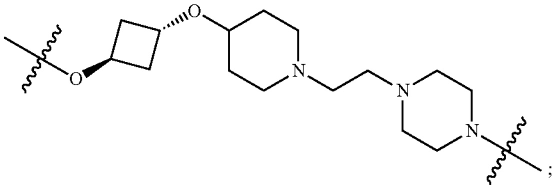
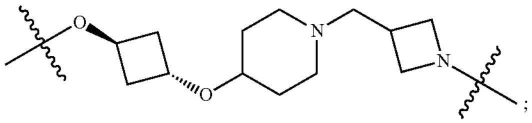
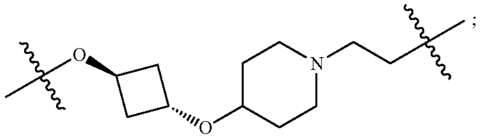
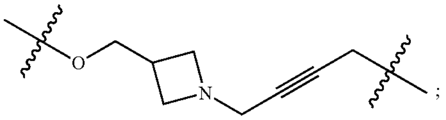
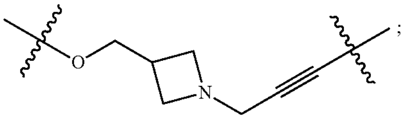
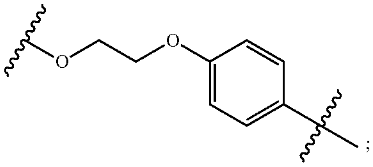
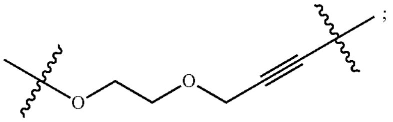
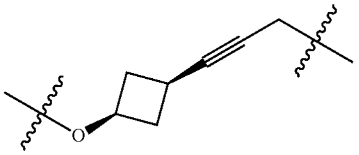
and
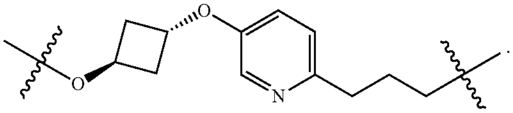
In certain embodiments, L is one of the following:
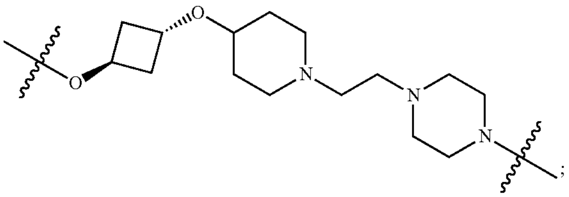

-continued
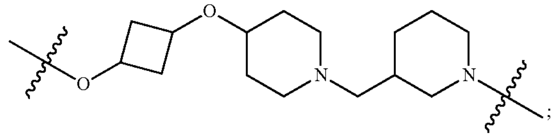
;
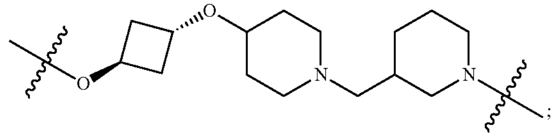
;
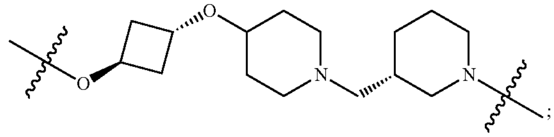
;
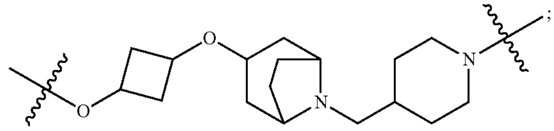
;
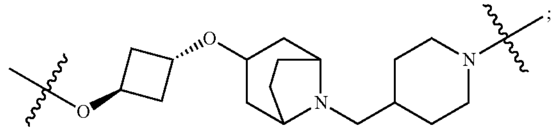
;
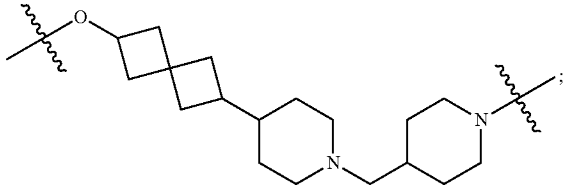
;
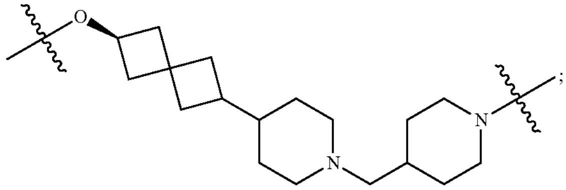
;
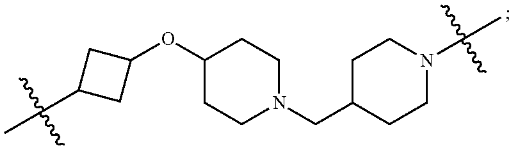
;
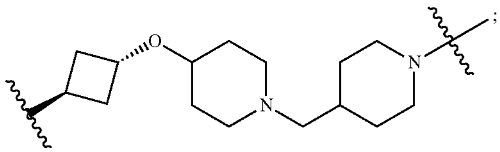
;
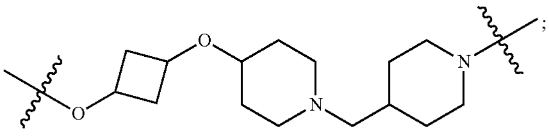
;
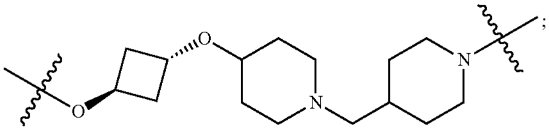
;
-continued
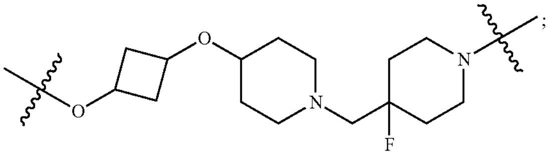
;
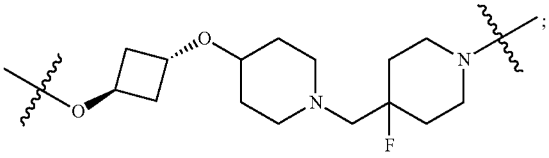
;
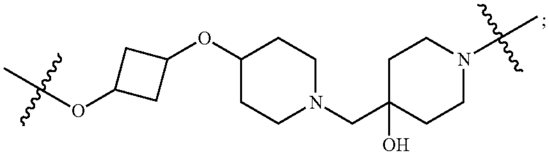
;
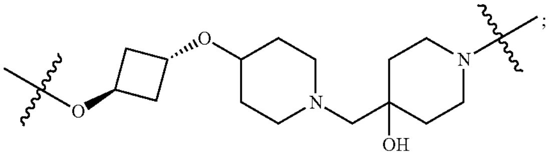
;
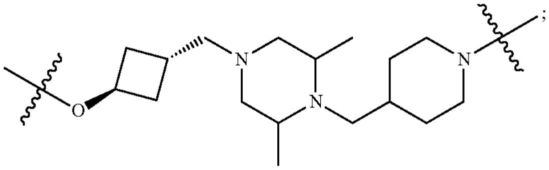
;
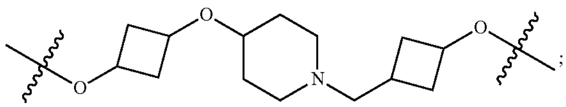
;
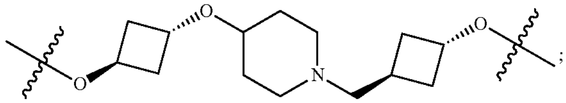
;
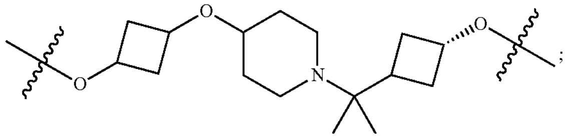
;
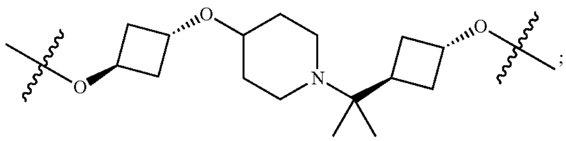
;
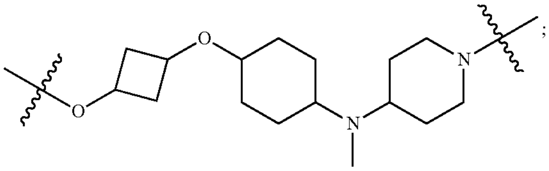
;
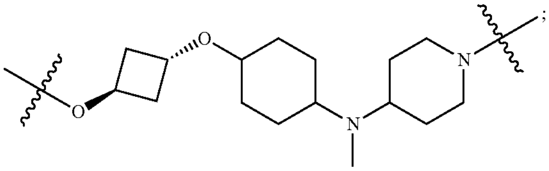
;

-continued
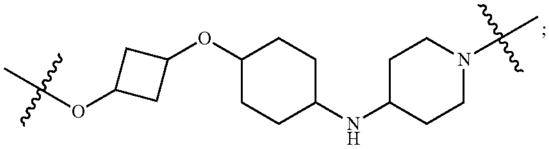
;
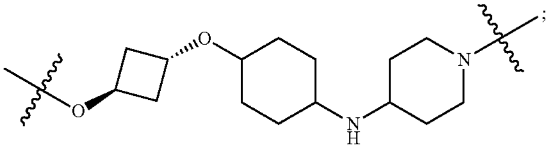
;
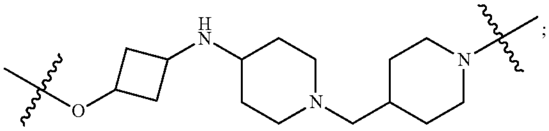
;
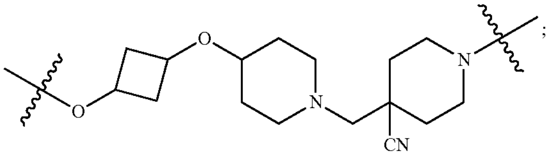
;
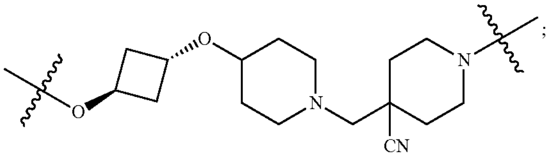
;
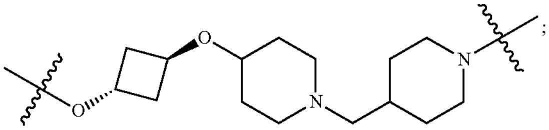
;
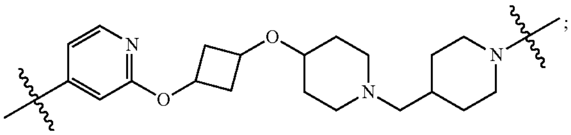
;
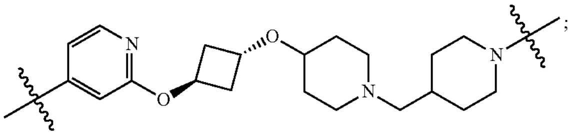
;
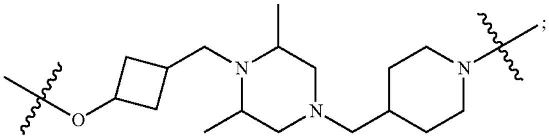
;
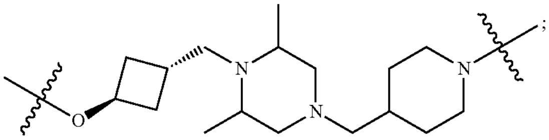
;
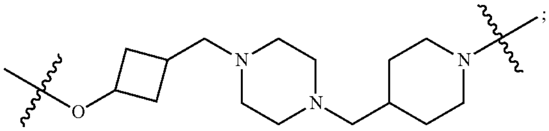
;
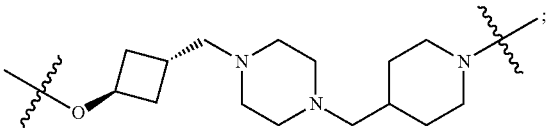
;
-continued
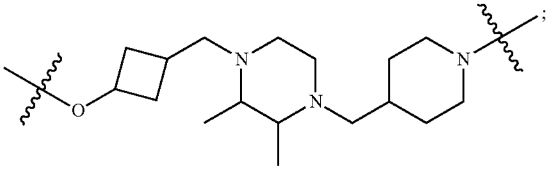
;
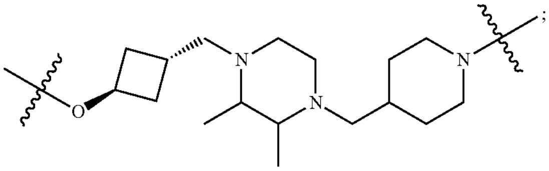
;
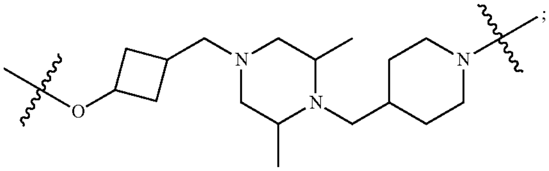
;
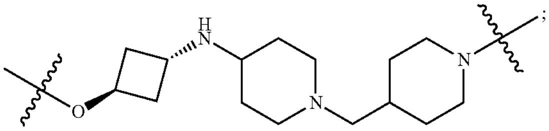
;
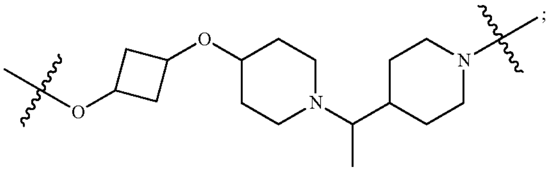
;
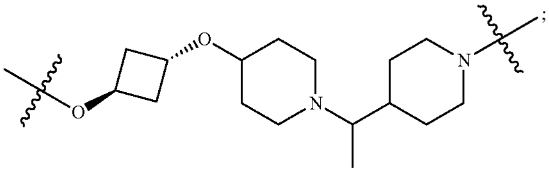
;
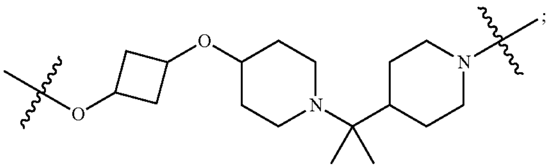
;
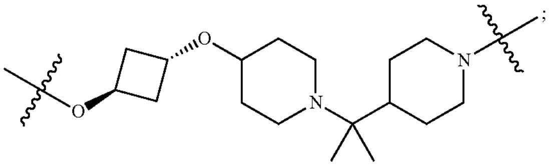
;
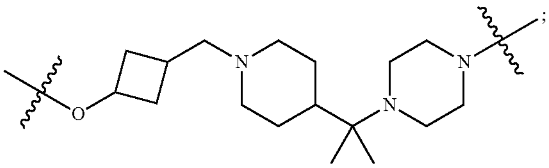
;
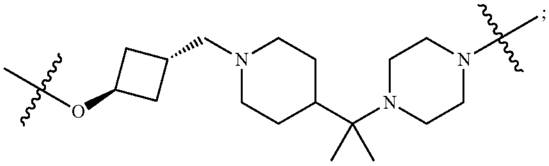
;

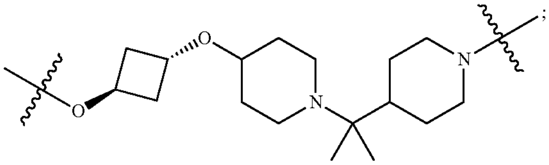
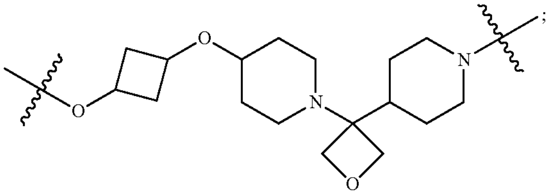
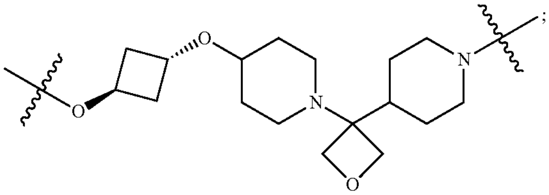
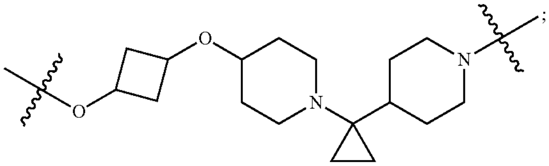
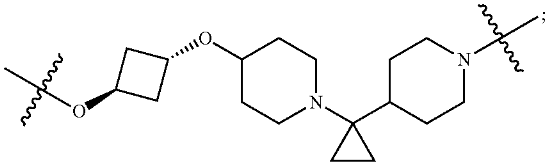
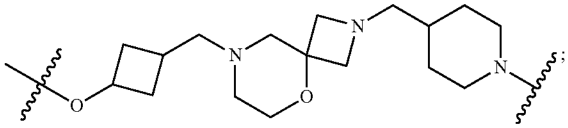
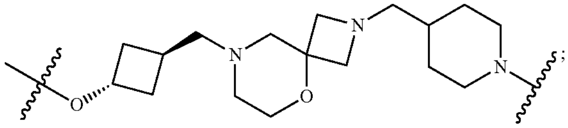
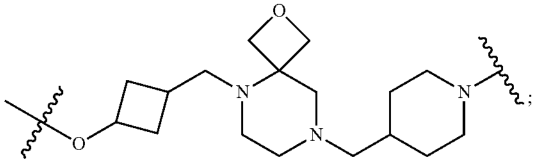
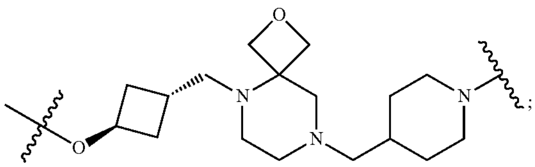
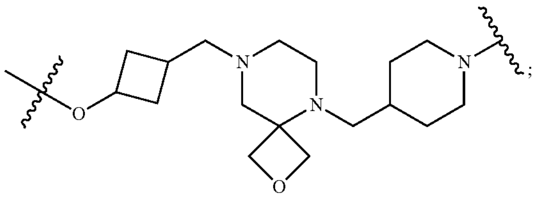
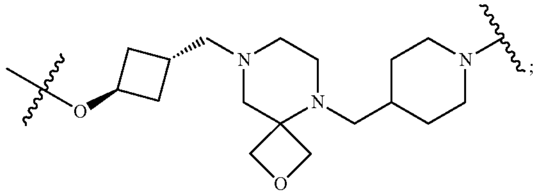
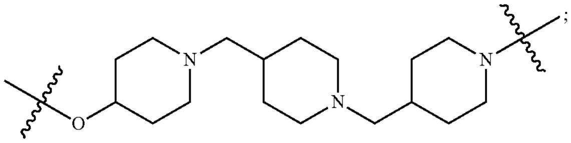
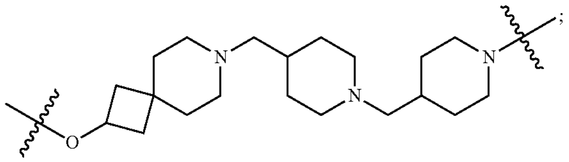
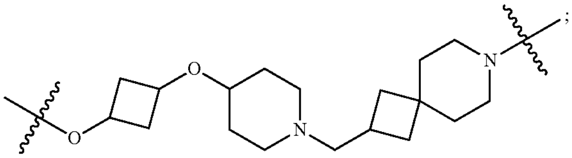
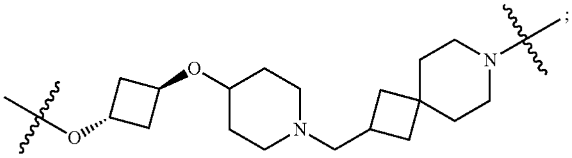
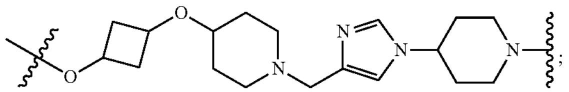
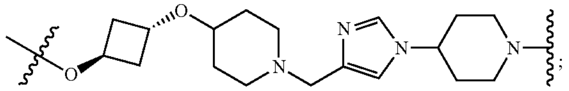
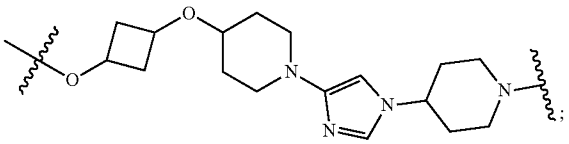
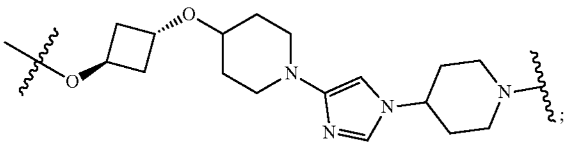
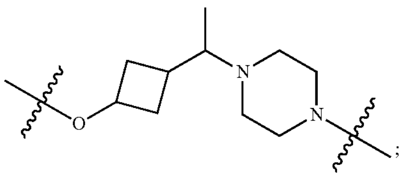
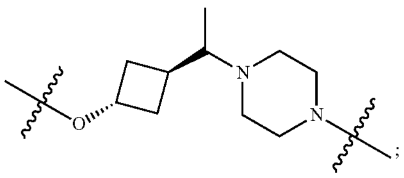

-continued
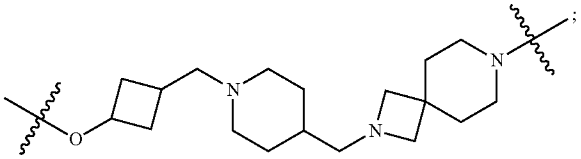
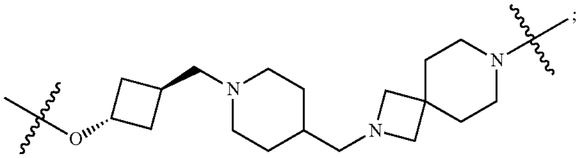
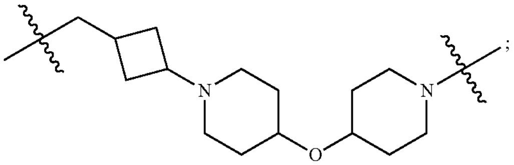
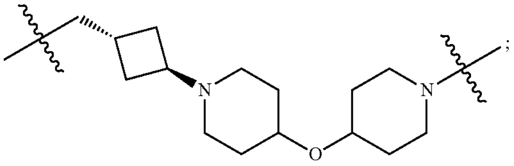
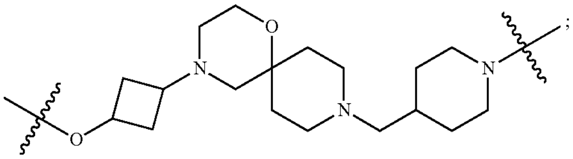
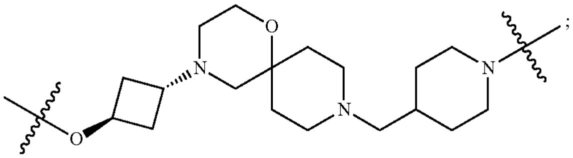
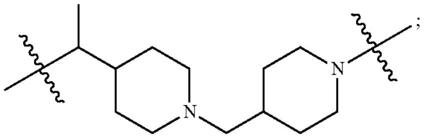
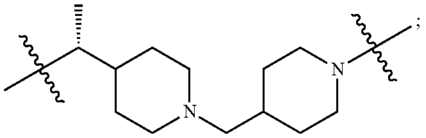
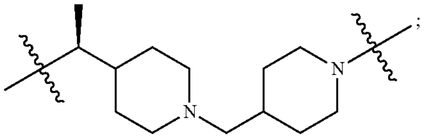
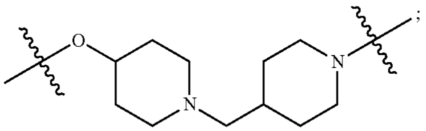
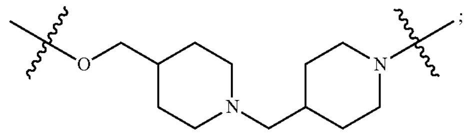
-continued
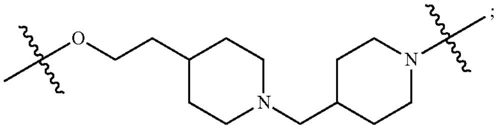
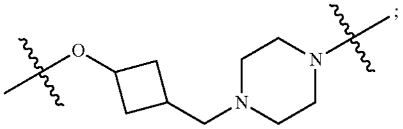
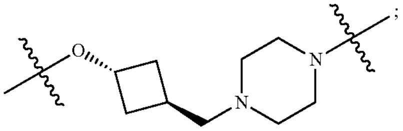
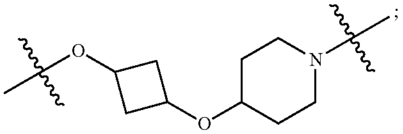
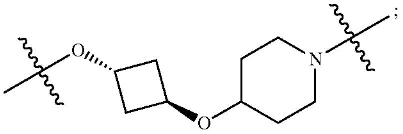
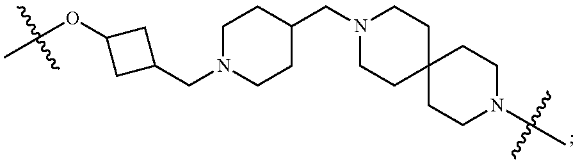
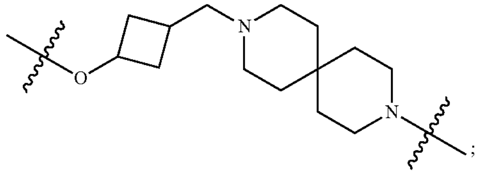
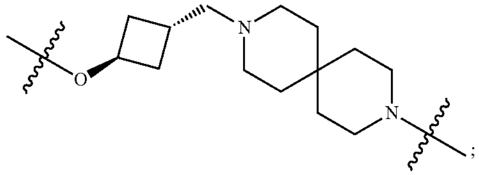
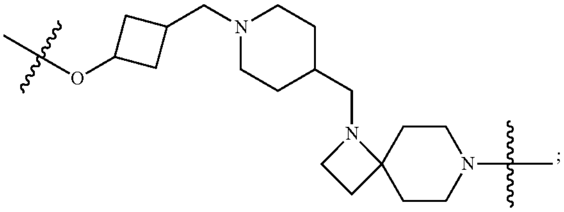
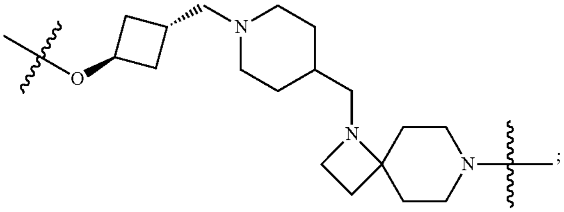

-continued

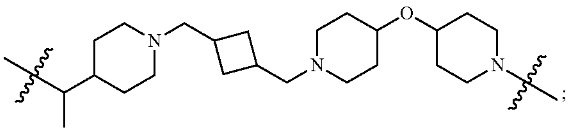
;

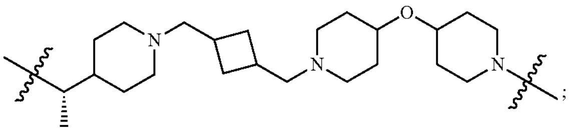
;

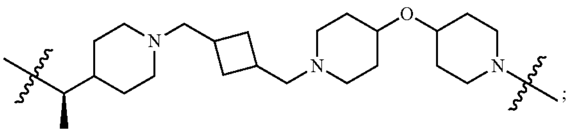
;

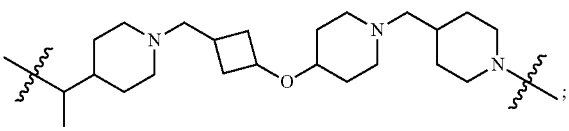
;

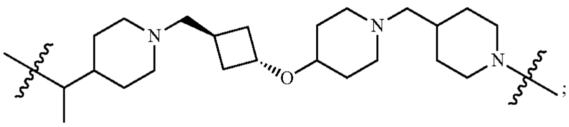
;

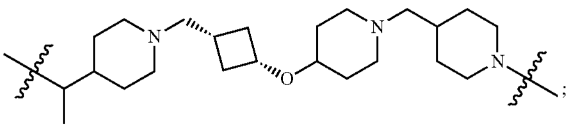
;

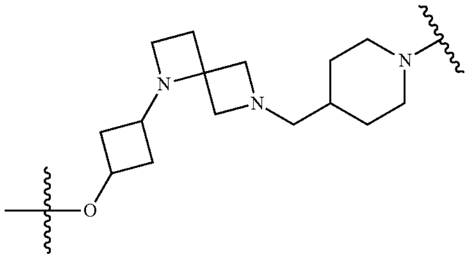
;

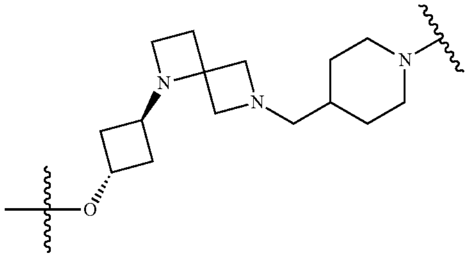
;

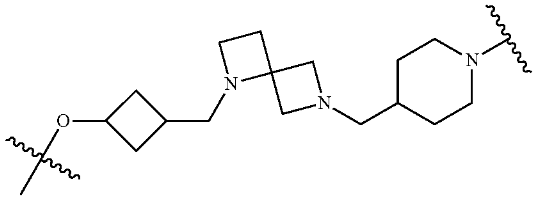
;

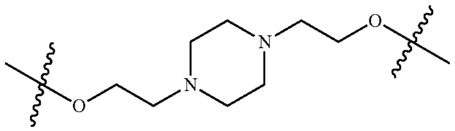
;

-continued

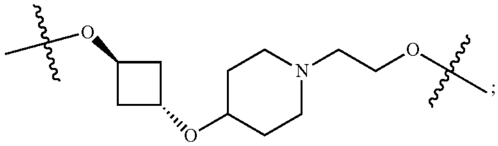
;

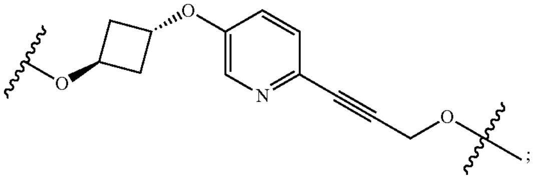
;

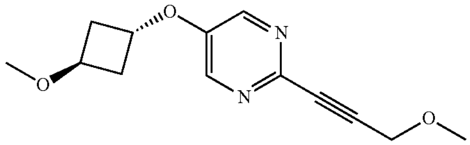
;

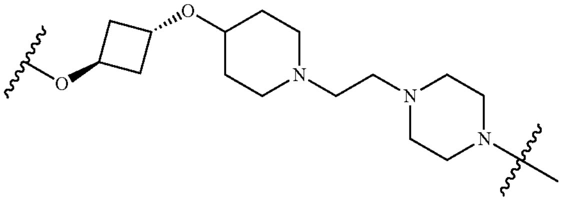
;

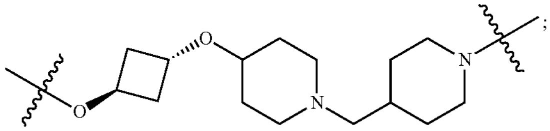
;

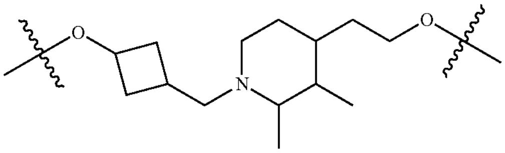
;

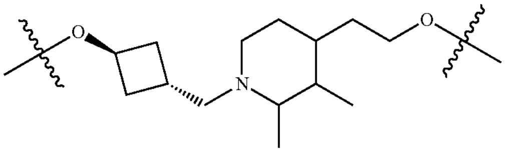
;

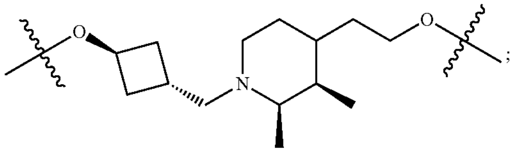
; and

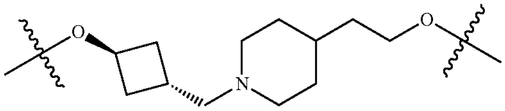
.

In certain embodiments, L has the formula-($C_{0-12}$ alkylene)-(optionally substituted 3-40 membered heteroalkylene)-($C_{0-12}$ alkylene)-. In certain embodiments, L is $C_{4-14}$ alkylene. In certain embodiments, L is $—(CH_2)_{6-10}—$.

In certain embodiments, L is $—CH_2CH_2$ $(OCH_2CH_2)—$*, $—CH_2CH_2$ $(OCH_2CH_2)_2—$*, $—CH_2CH_2$ $(OCH_2CH_2)_3—$*, $—CH_2CH_2$ $(OCH_2CH_2)_4—$*, $—CH_2CH_2$ $(OCH_2CH_2)_5—$*$—CH_2CH_2$ $(OCH_2CH_2)_6—$*, $—CH_2CH_2$ $(OCH_2CH_2)_7—$*, $—CH_2CH_2$ $(OCH_2CH_2)_8—$*, $—CH_2CH_2$ $(OCH_2CH_2)_9—$*, $—CH_2CH_2$ $(OCH_2CH_2)_{10}—$*, $—CH_2CH_2$ $(OCH_2CH_2)_{11}$ —*, $—CH_2CH_2$ $(OCH_2CH_2)_{12}—$*, $—CH_2CH_2$ $(OCH_2CH_2)_{13}—$*, $—CH_2CH_2$ $(OCH_2CH_2)_{14}—$*, —$CH_2CH_2$ $(OCH_2CH_2)_{15}$—*, or —$CH_2CH_2$ $(OCH_2CH_2)_{16-20}$—*, where *** is a point of attachment to $A^2$.

In certain embodiments, L is —($C_{2-20}$ alkylene)-$(OCH_2CH_2)_{2-4}$—($C_{0-4}$ alkylene)-*, —($C_{2-20}$ alkylene)-$(OCH_2CH_2)_{5-7}$—($C_{0-4}$ alkylene)-*, —($C_{2-20}$ alkylene)-$(OCH_2CH_2)_{8-10}$—($C_{0-4}$ alkylene)-*, —($C_{2-20}$ alkylene)-$(OCH_2CH_2)_{11-13}$—($C_{0-4}$ alkylene)-*, —($C_{2-20}$ alkylene)-$(OCH_2CH_2)_{14-16}$—($C_{0-4}$ alkylene)-*, —($C_{2-20}$ alkylene)-$(OCH_2CH_2)_{17-20}$—($C_{0-4}$ alkylene)-*, —($C_{1-20}$ alkylene)-$(OCH_2CH_2)_{1-10}$—($C_{0-4}$ alkylene)-C(O)—*, or —($C_{1-20}$ alkylene)-$(OCH_2CH_2)_{11-20}$—($C_{0-4}$ alkylene)-C(O)—*, where *** is a point of attachment to $A^2$.

In certain embodiments, L is —$O(CH_2CH_2O)_{2-4}$—($C_{0-4}$ alkylene)-*, —$O(CH_2CH_2O)_{5-7}$—($C_{0-4}$ alkylene)-*, —$O(CH_2CH_2O)_{8-10}$—($C_{0-4}$ alkylene)-*, —$O(CH_2CH_2O)_{11-13}$—($C_{0-4}$ alkylene)-*, —$O(CH_2CH_2O)_{14-16}$—($C_{0-4}$ alkylene)-*, —$O(CH_2CH_2O)_{16-20}$—($C_{0-4}$ alkylene)-*, —$O(CH_2CH_2O)_{2-10}$—($C_{0-4}$ alkylene) C(O)—*, or —$O(CH_2CH_2O)_{11-20}$—($C_{0-4}$ alkylene) C(O)—*, where *** is a point of attachment to $A^2$.

In certain embodiments, L is —($C_{0-20}$ alkylene)-$(OCH_2CH_2)_{1-10}$—(N($C_{1-4}$ alkyl))-*, —($C_{0-20}$ alkylene)-$(OCH_2CH_2)_{11-20}$—(N($C_{1-4}$ alkyl))-*, —($C_{0-20}$ alkylene)-$(CH_2CH_2O)_{1-10}$—($C_{2-10}$ alkylene)-(N($C_{1-4}$ alkyl))-($C_{0-10}$ alkylene)-*, or —($C_{0-20}$ alkylene)-$(CH_2CH_2O)_{11-20}$—($C_{2-10}$ alkylene)-(N($C_{1-4}$ alkyl))-($C_{0-10}$ alkylene)-*, where *** is a point of attachment to $A^2$.

In certain embodiments, L is selected from those depicted in the compounds in Table 1, below.

Exemplary Specific Compounds

In certain embodiments, the compound is a compound in Table 1 or 2, or a pharmaceutically acceptable salt thereof. In certain embodiments, the compound is a compound in Table 1 or 2. In certain embodiments, the compound is a compound in Table 1, or a pharmaceutically acceptable salt thereof. In certain embodiments, the compound is a compound in Table 1. In certain embodiments, the compound is any one of compounds I-1 to I-124 in Table 1 or any one of compounds II-1 to II-12 in Table 2, or a pharmaceutically acceptable salt thereof. In certain embodiments, the compound is any one of compounds I-1 to I-124 in Table 1 or any one of compounds II-1 to II-12 in Table 2. In certain embodiments, the compound is any one of compounds I-1 to I-124 in Table 1, or a pharmaceutically acceptable salt thereof. In certain embodiments, the compound is any one of compounds I-1 to I-124 in Table 1. In certain embodiments, the compound is any one of compounds II-1 to II-12 in Table 2, or a pharmaceutically acceptable salt thereof. In certain embodiments, the compound is any one of compounds II-1 to II-12 in Table 2. In certain embodiments, the compound is any one of compounds I-1 to I-137 in Table 1, or a pharmaceutically acceptable salt thereof. In certain embodiments, the compound is any one of compounds I-1 to I-137 in Table 1. In certain embodiments, the compound is a compound in Table 3, or a pharmaceutically acceptable salt thereof. In certain embodiments, the compound is a compound in Table 3.

TABLE 1

| Compound No. | Chemical Structure |
|---|---|
| I-1 | 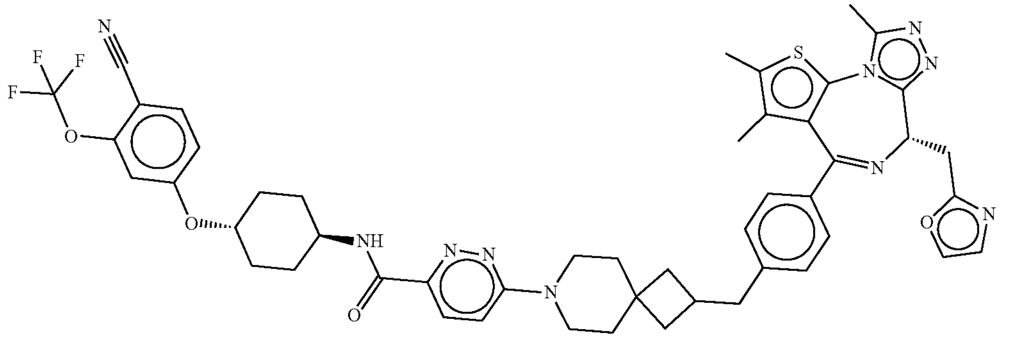 |
| I-2 | 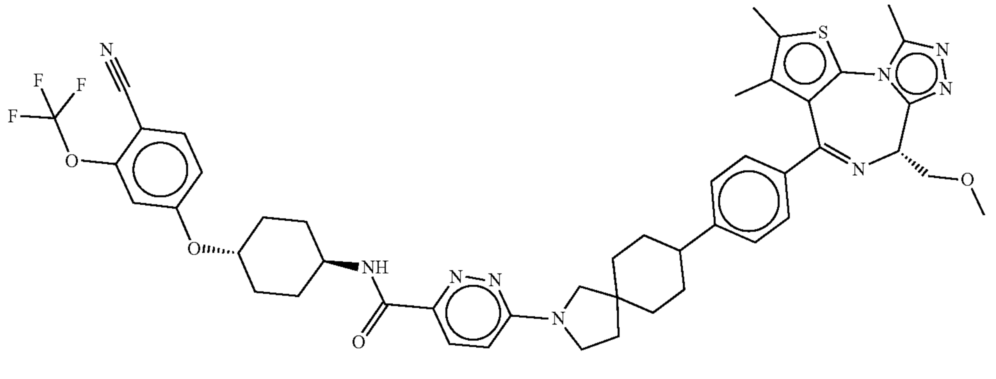 |

TABLE 1-continued
| Compound No. | Chemical Structure |
| --- | --- |
| I-3 | 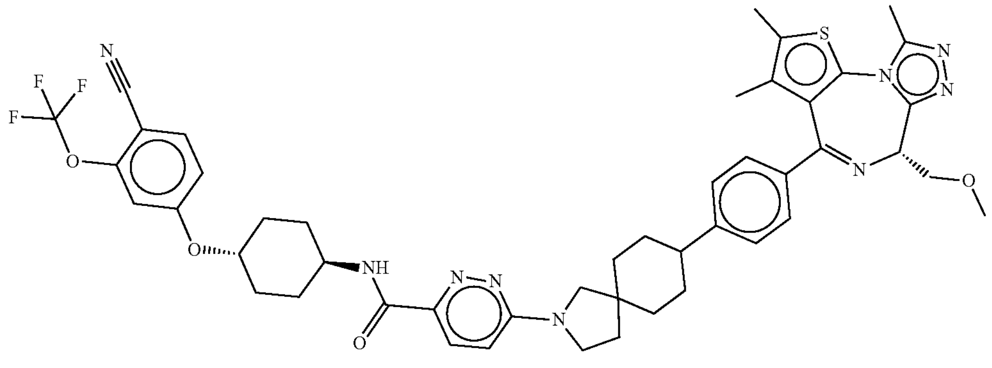 |
| I-4 | 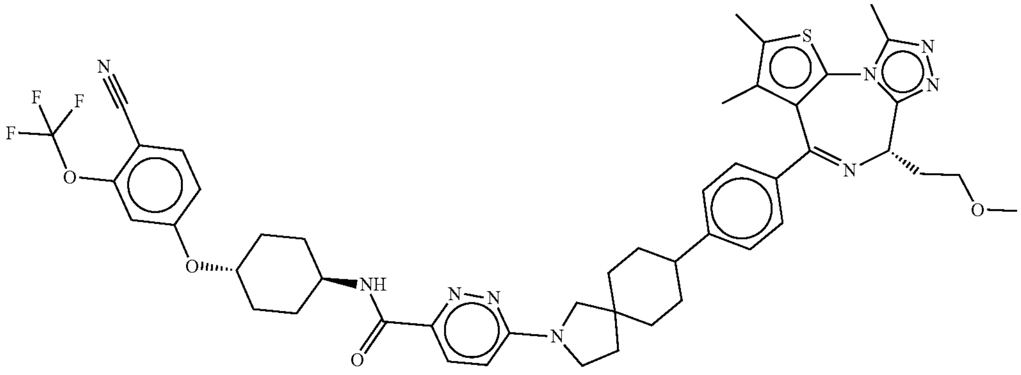 |
| I-5 | 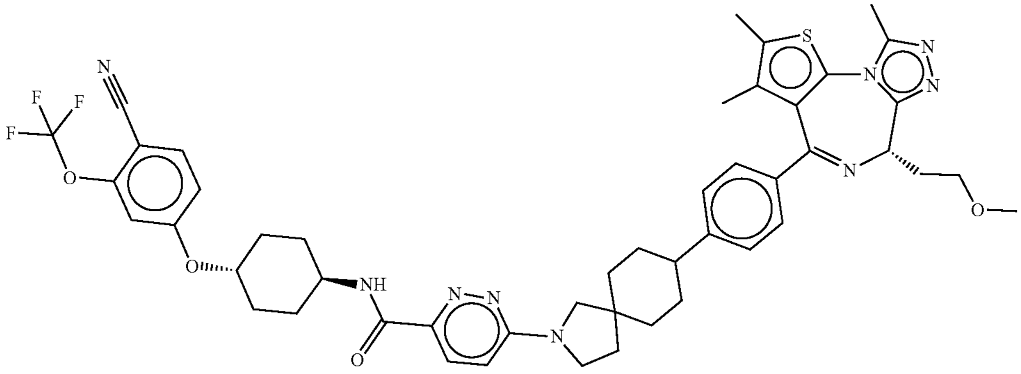 |
| I-6 | 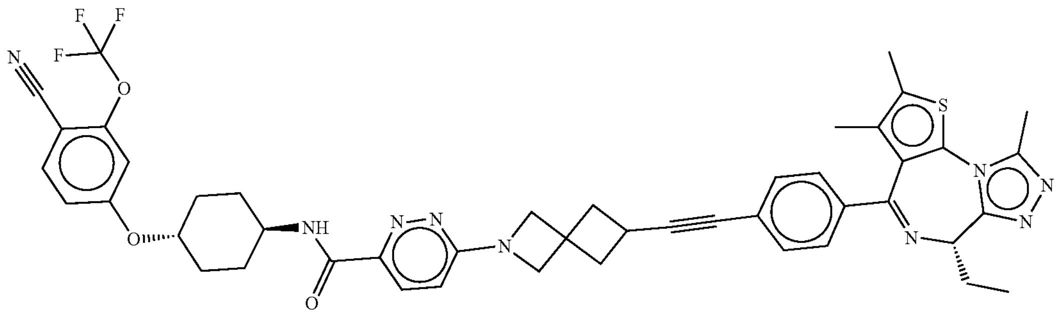 |

TABLE 1-continued
| Compound No. | Chemical Structure |
|---|---|
| I-7 | 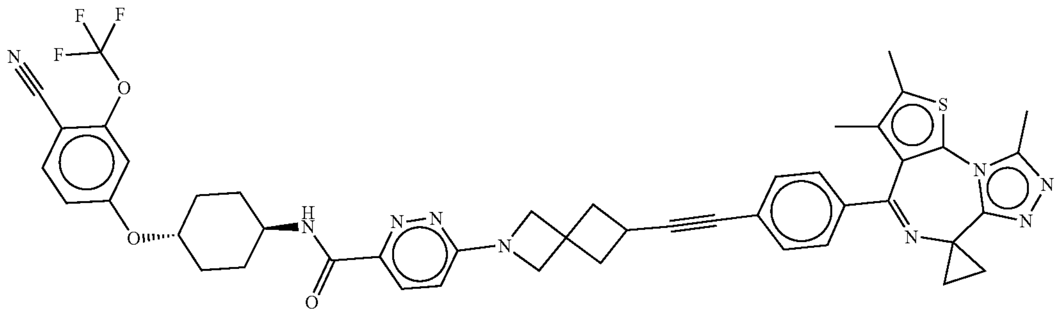 |
| I-8 | 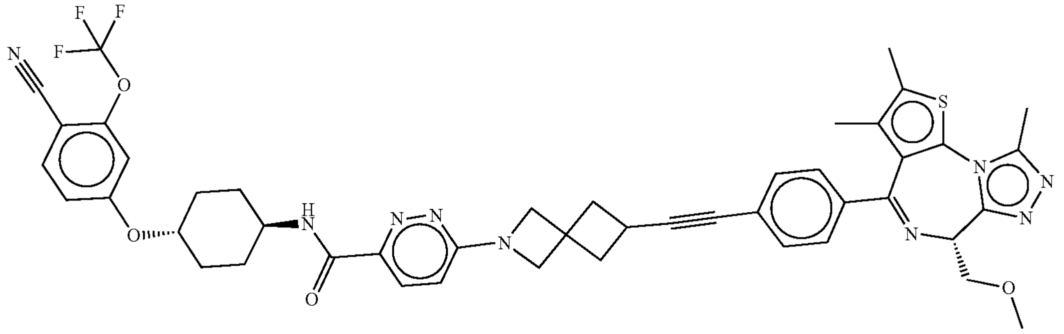 |
| I-9 | 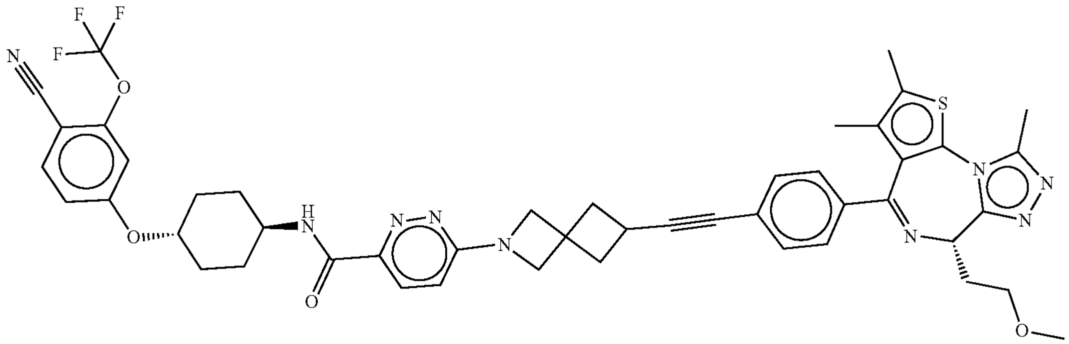 |
| I-10 | 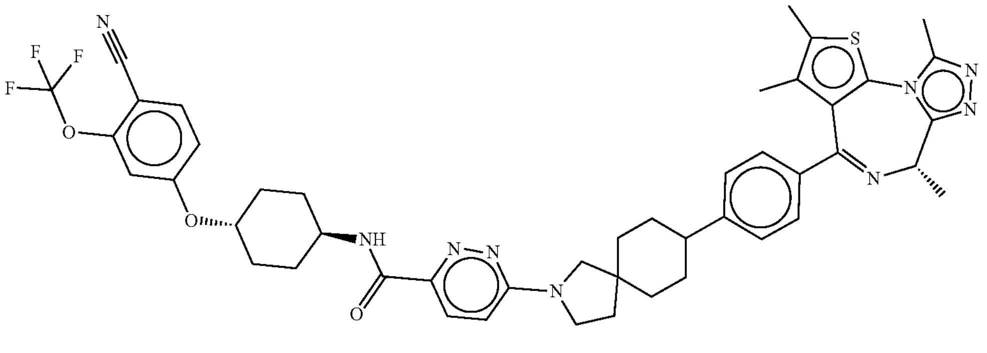 |

TABLE 1-continued
| Compound No. | Chemical Structure |
|---|---|
| I-11 | 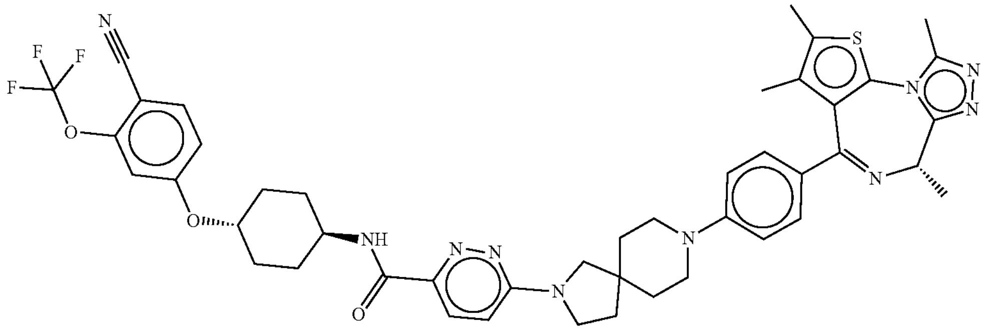 |
| I-12 | 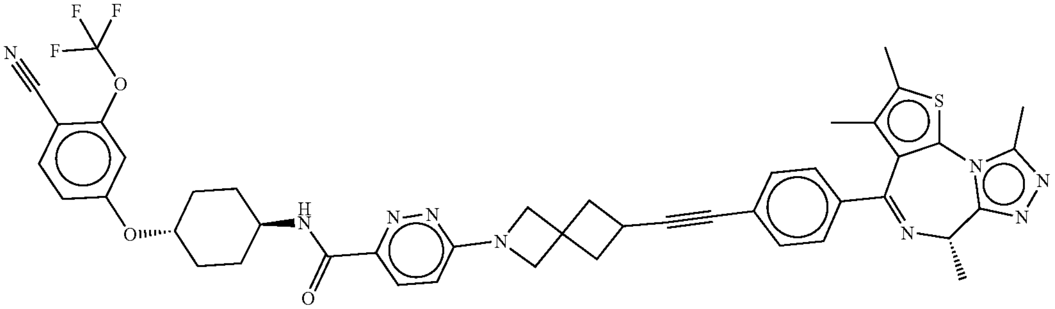 |
| I-13 | 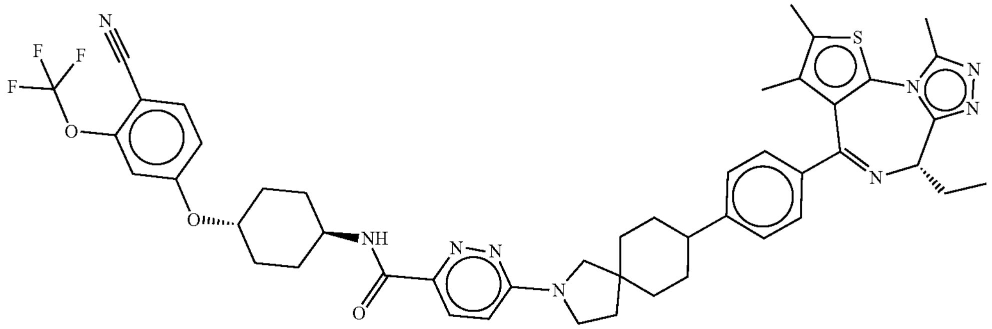 |
| I-14 | 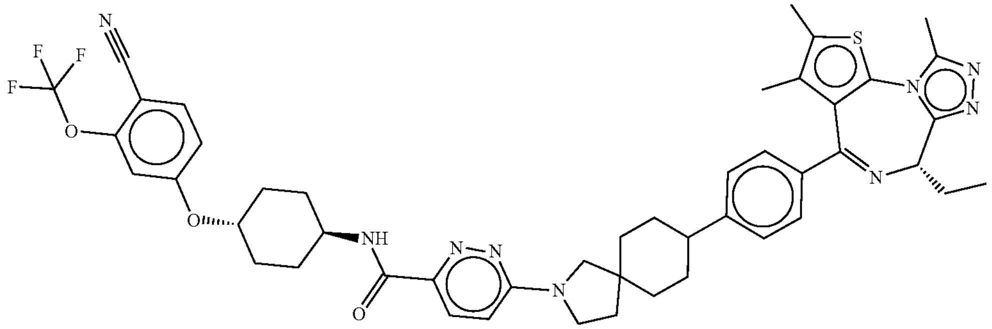 |

TABLE 1-continued
| Compound No. | Chemical Structure |
|---|---|
| I-15 | 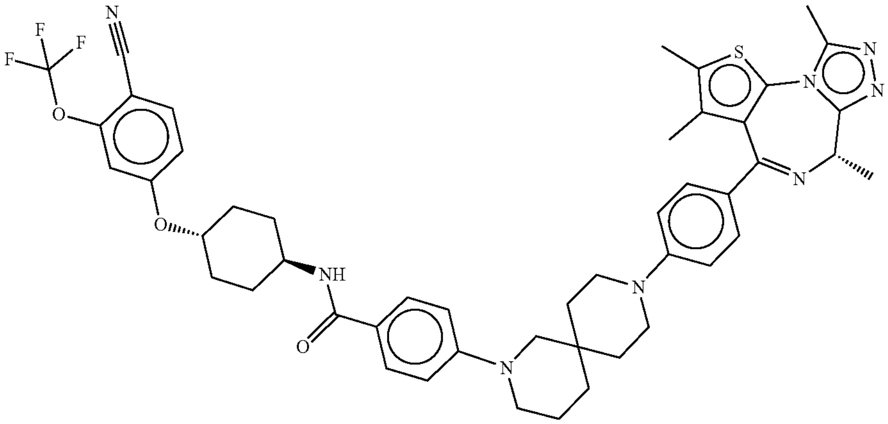 |
| I-16 | 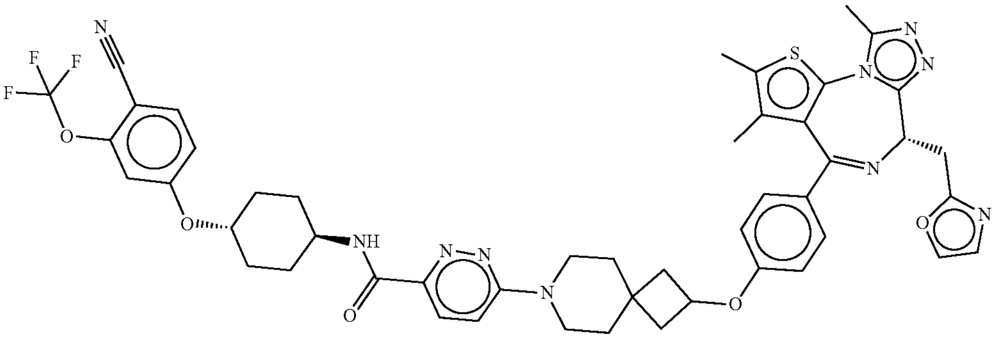 |
| I-17 | 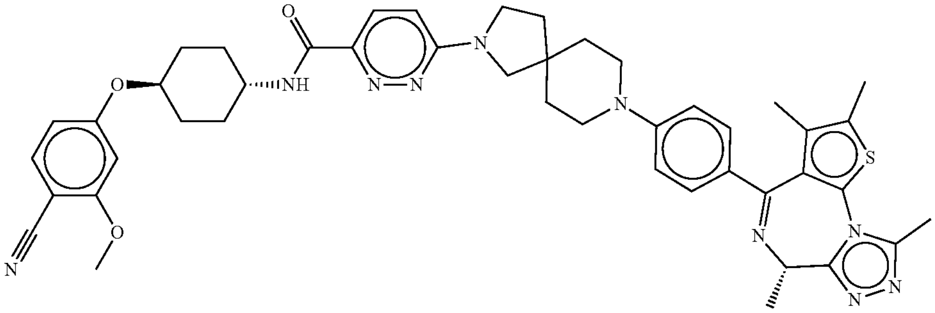 |
| I-18 | 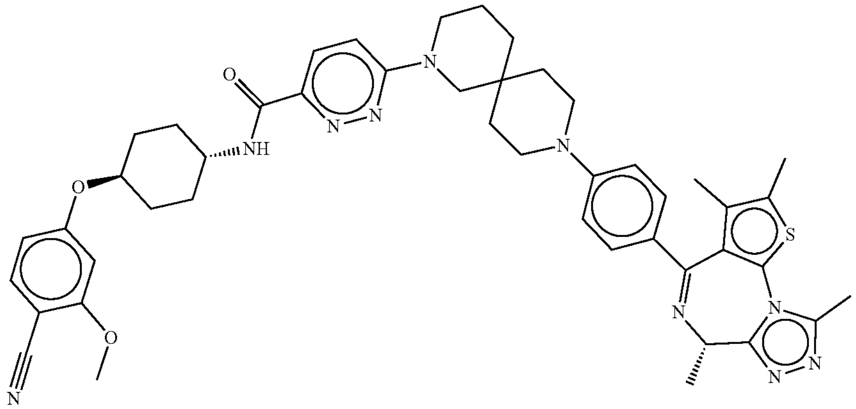 |

TABLE 1-continued
| Compound No. | Chemical Structure |
|---|---|
| I-19 | 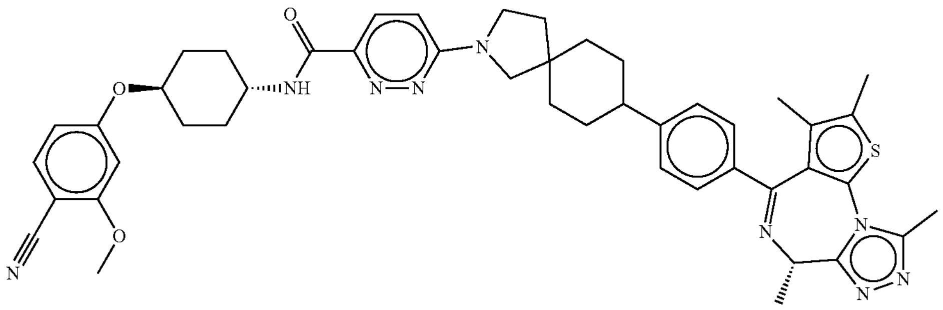 |
| I-20 | 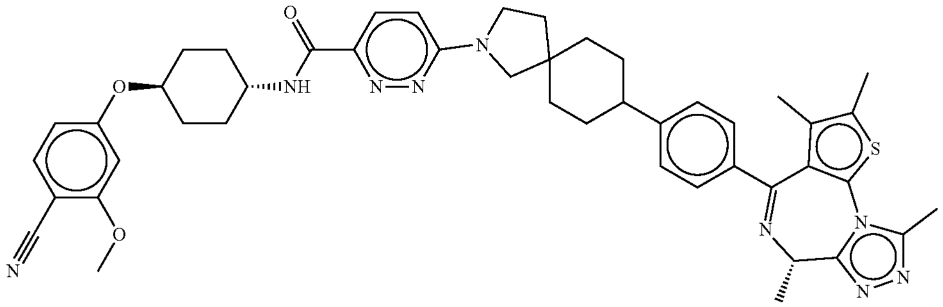 |
| I-21 | 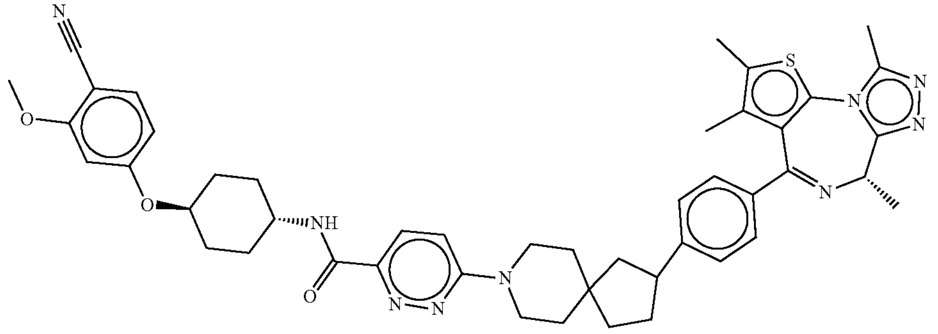 |
| I-22 | 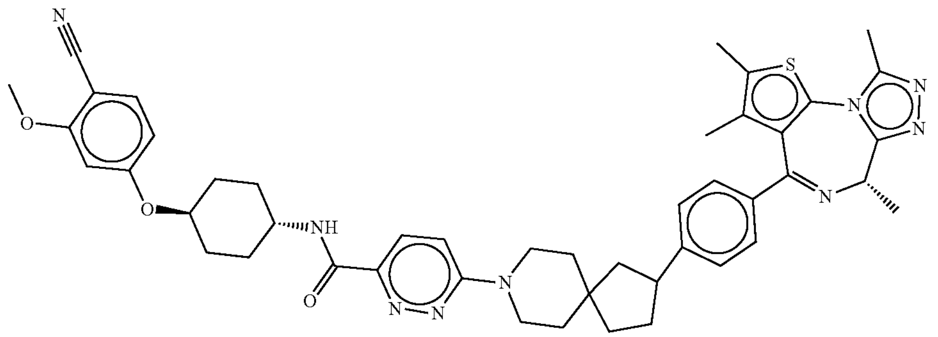 |

TABLE 1-continued
| Compound No. | Chemical Structure |
|---|---|
| I-23 | 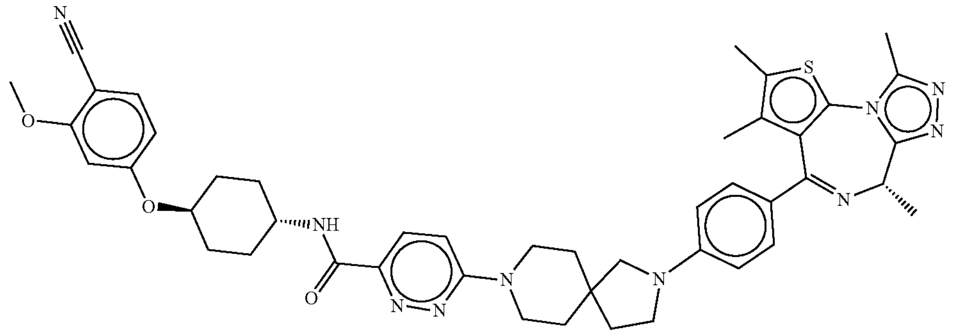 |
| I-24 | 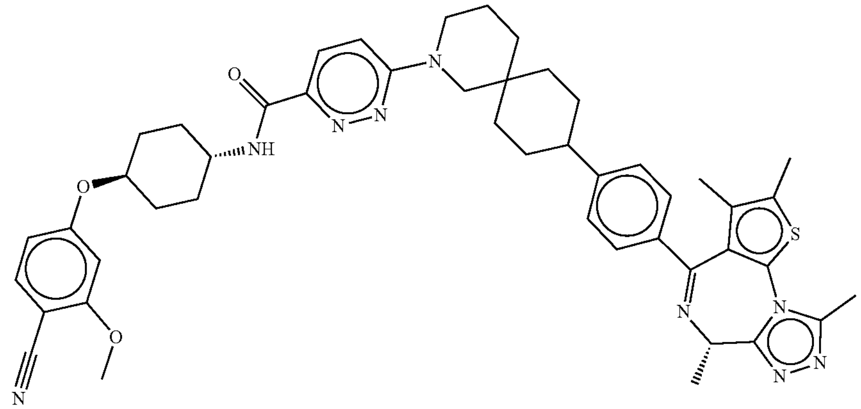 |
| I-25 | 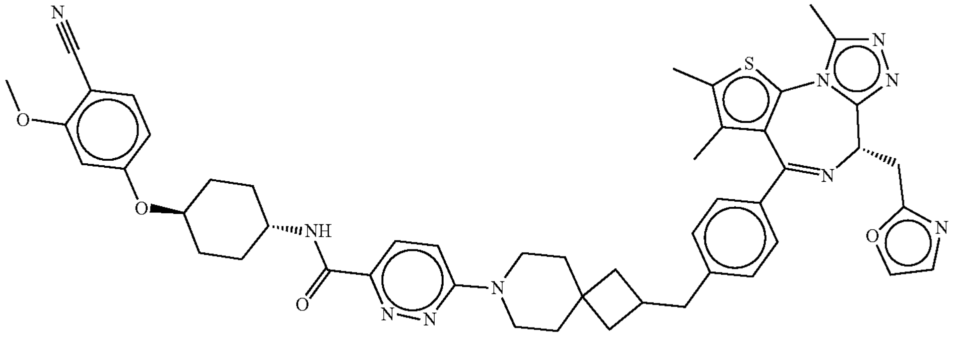 |
| I-26 | 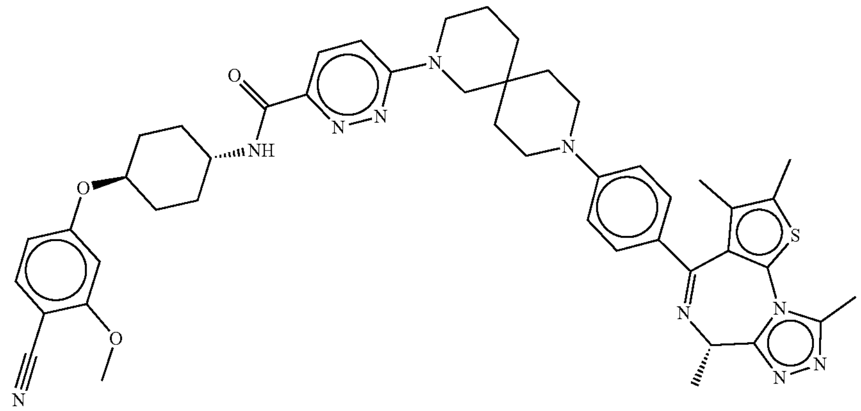 |

TABLE 1-continued
| Compound No. | Chemical Structure |
|---|---|
| I-27 | 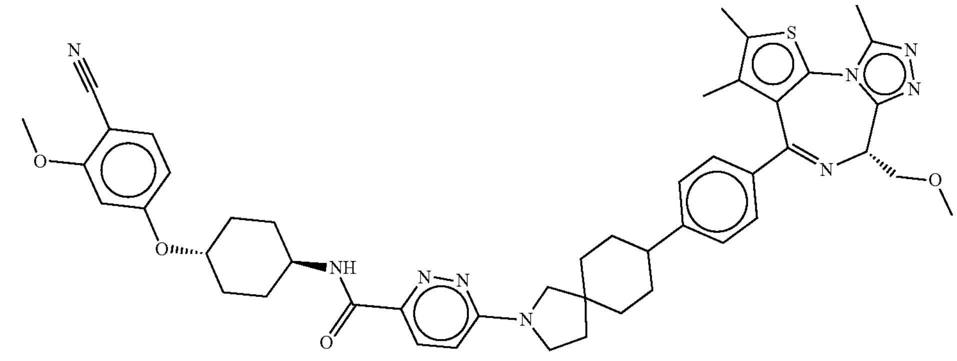 |
| I-28 | 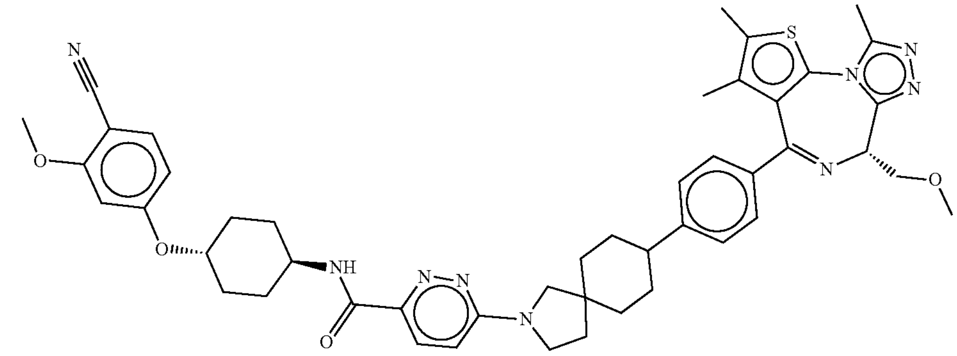 |
| I-29 | 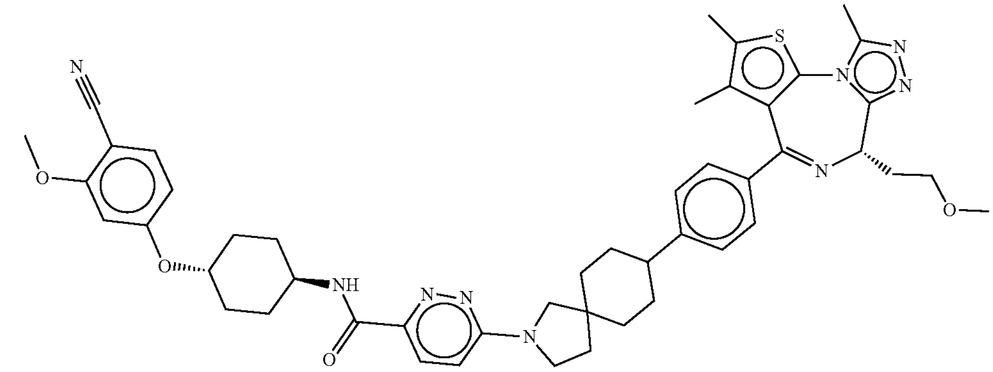 |
| I-30 | 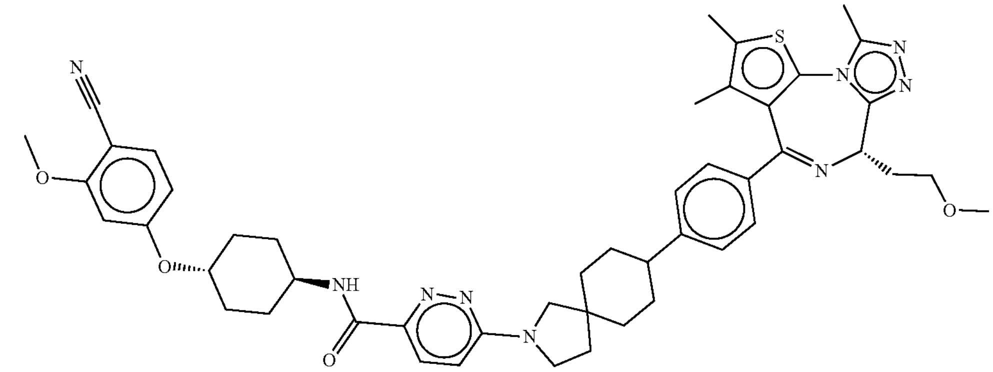 |

TABLE 1-continued
| Compound No. | Chemical Structure |
|---|---|
| I-31 | 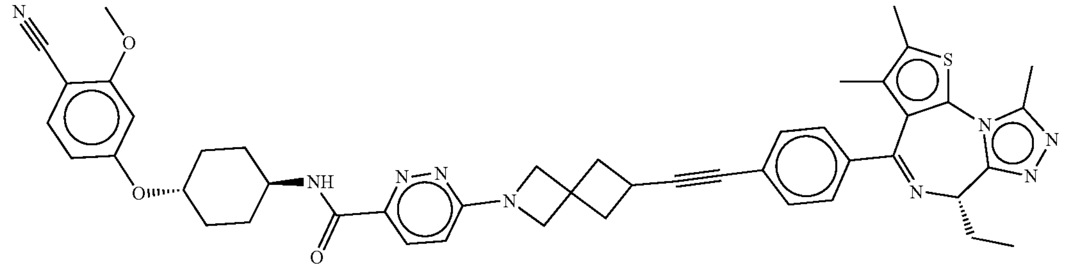 |
| I-32 | 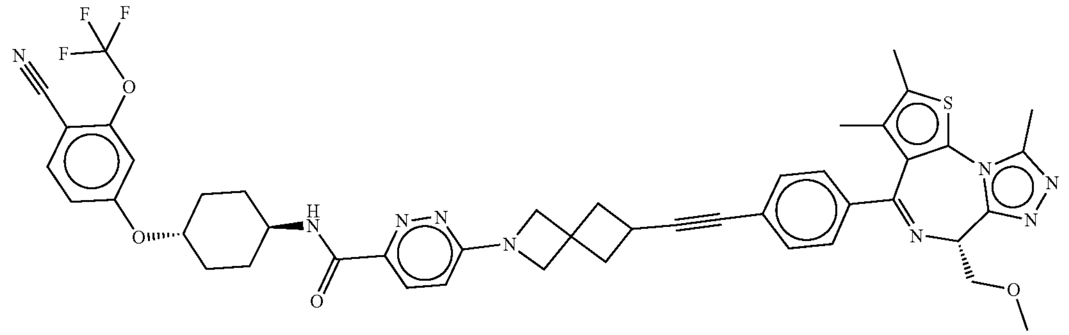 |
| I-33 | 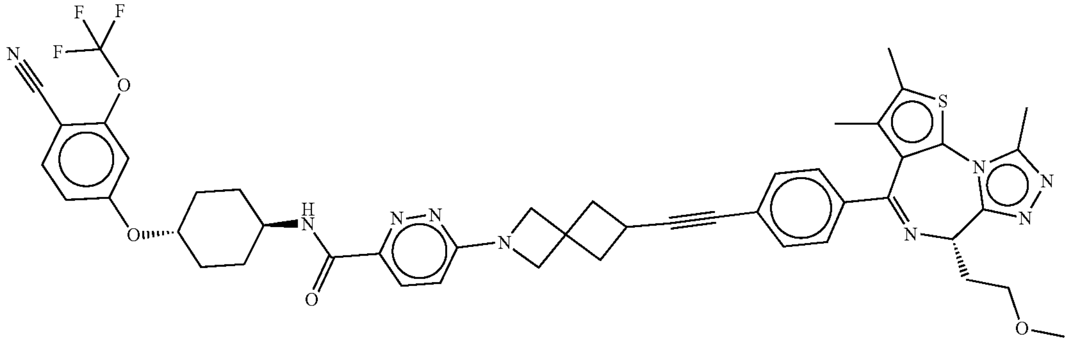 |
| I-34 | 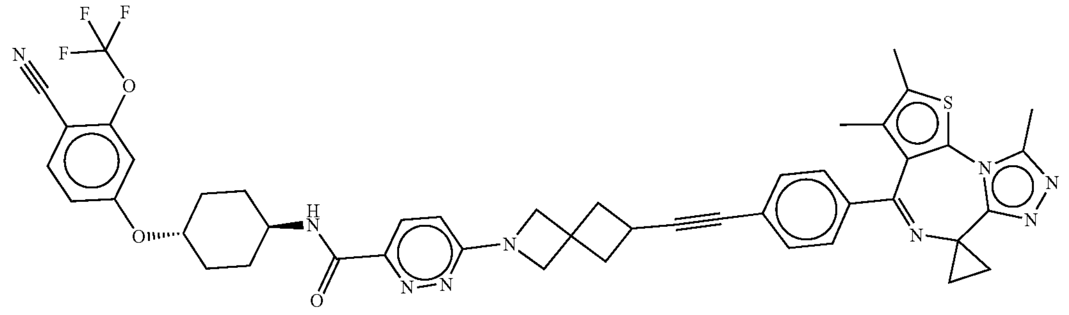 |
| I-35 | 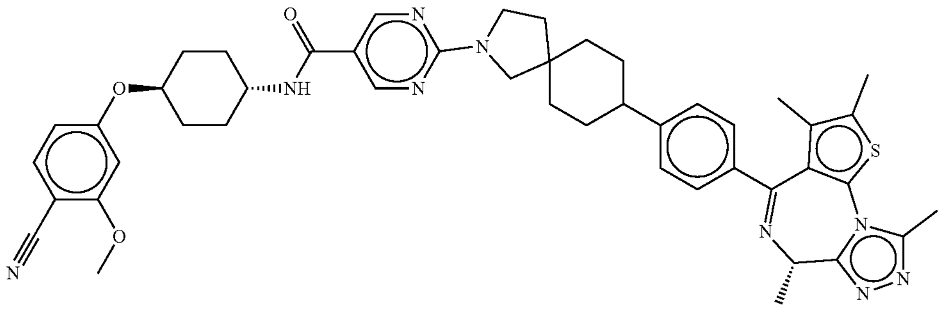 |

TABLE 1-continued
| Compound No. | Chemical Structure |
| --- | --- |
| I-36 | 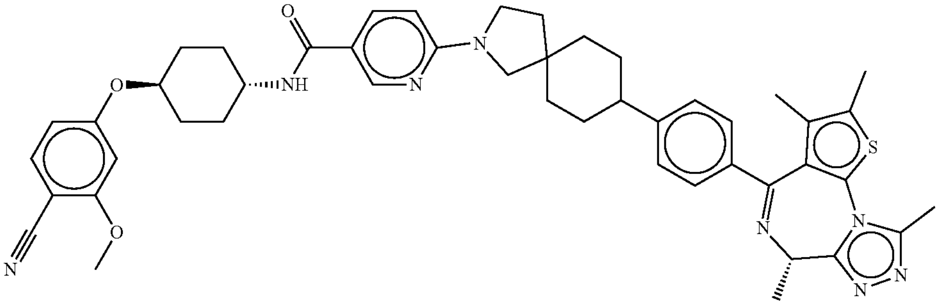 |
| I-37 | 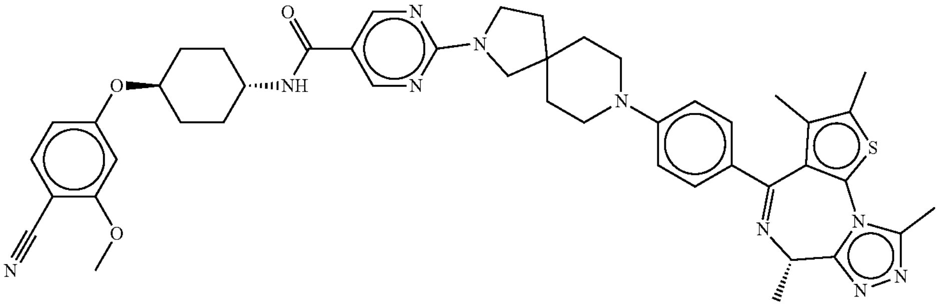 |
| I-38 | 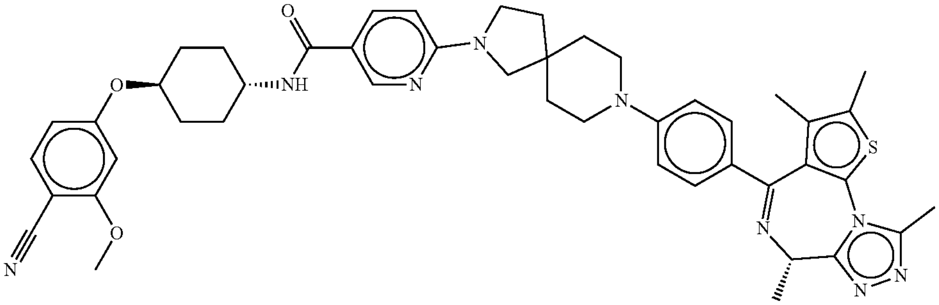 |
| I-39 | 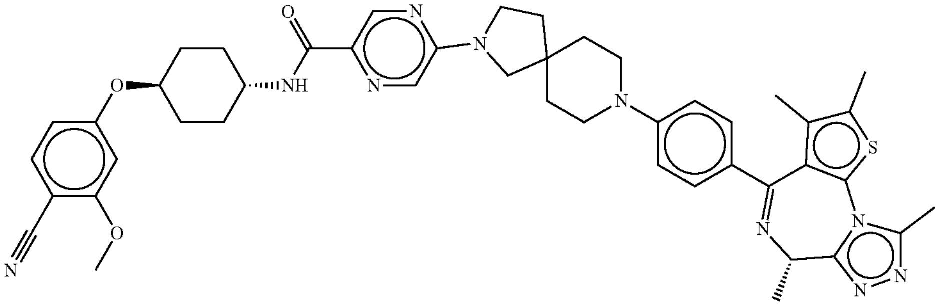 |
| I-40 | 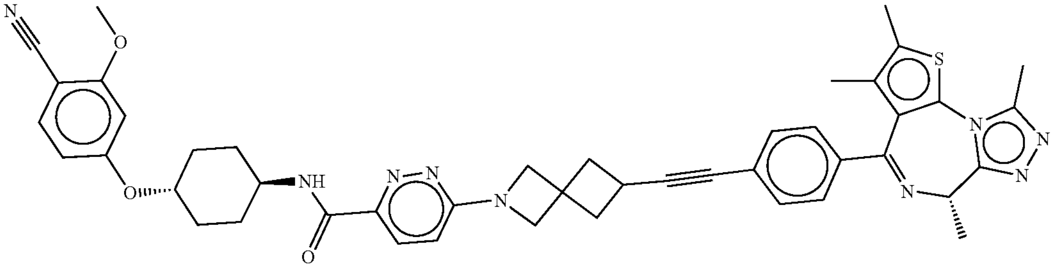 |

TABLE 1-continued
| Compound No. | Chemical Structure |
| --- | --- |
| I-41 | 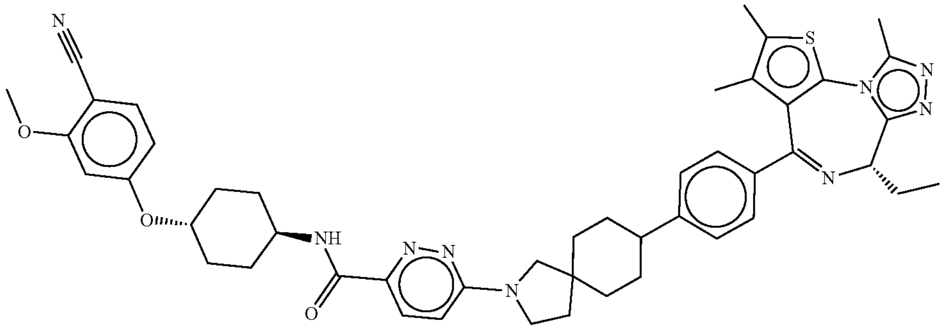 |
| I-42 | 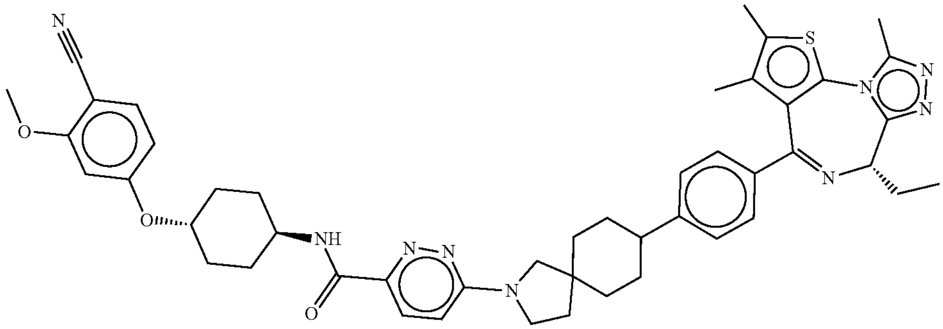 |
| I-43 | 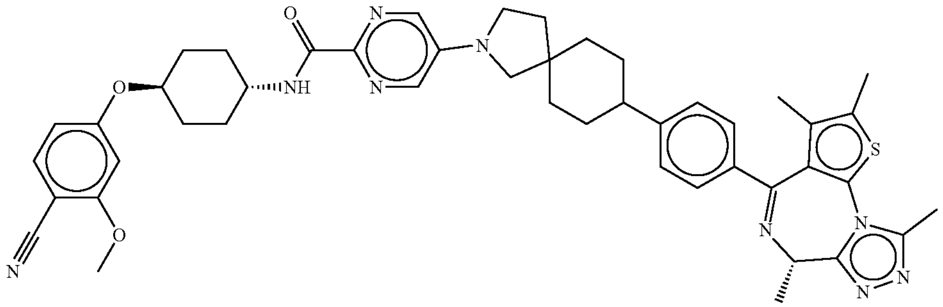 |
| I-44 | 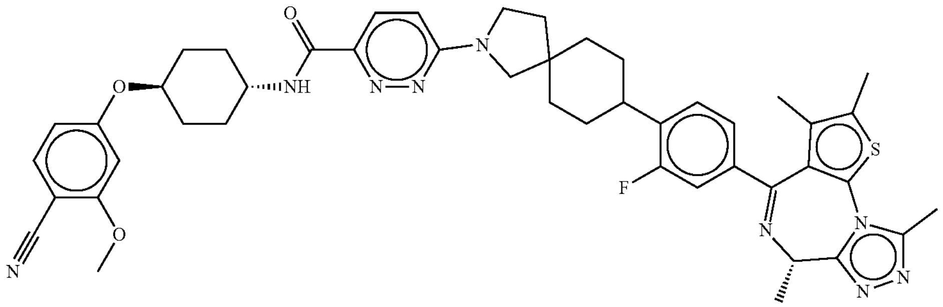 |

TABLE 1-continued
| Compound No. | Chemical Structure |
| --- | --- |
| I-45 | 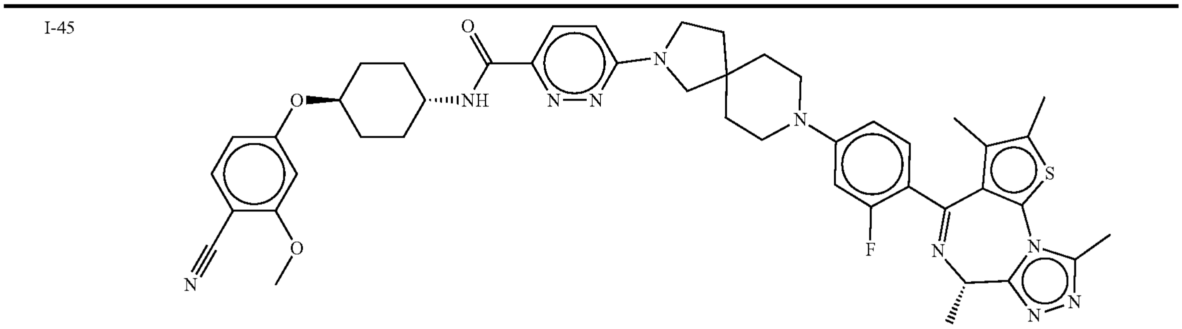 |
| I-46 | 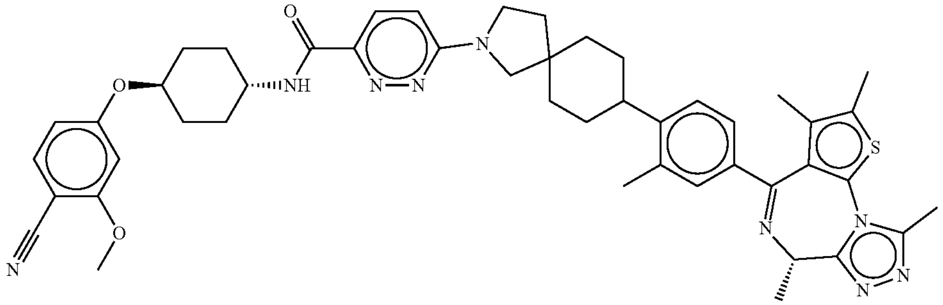 |
| I-47 | 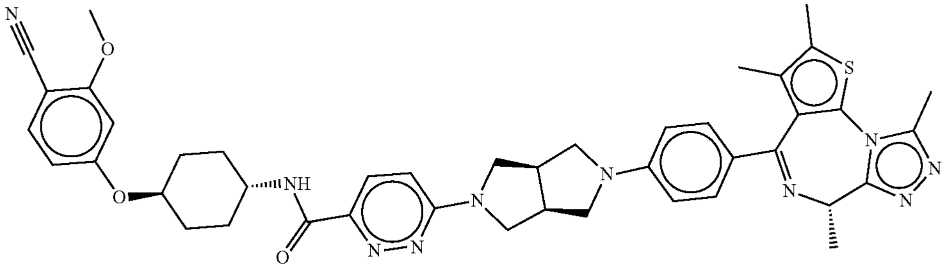 |
| I-48 | 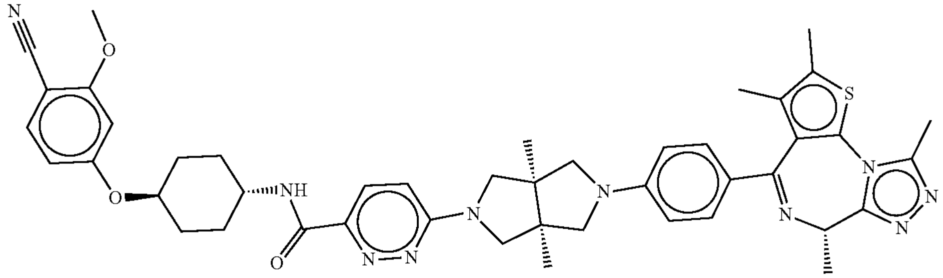 |
| I-49 | 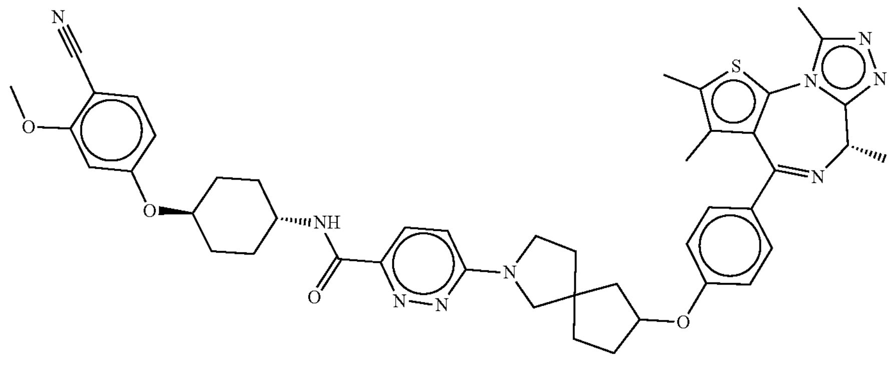 |

TABLE 1-continued
| Compound No. | Chemical Structure |
| --- | --- |
| I-50 | 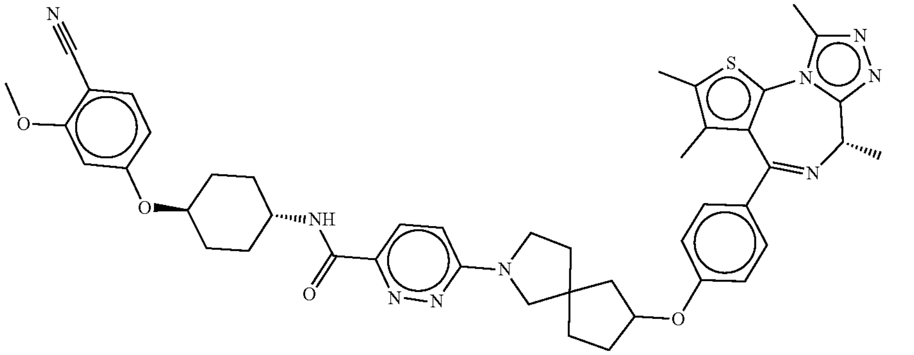 |
| I-51 | 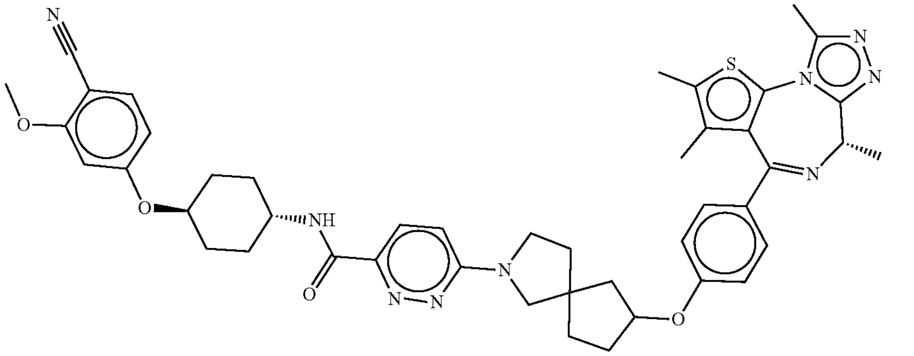 |
| I-52 | 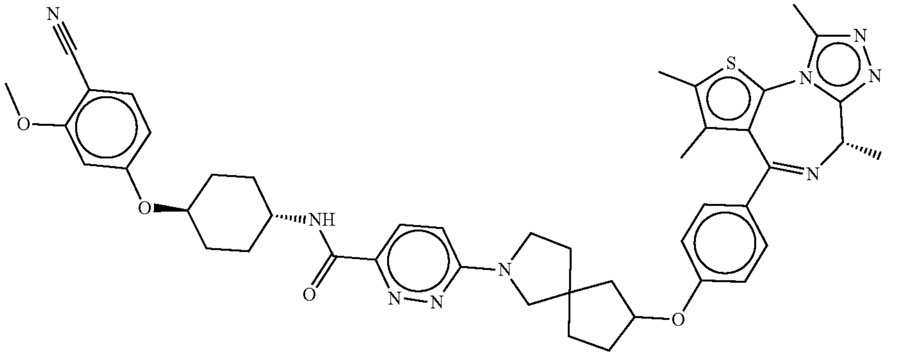 |
| I-53 | 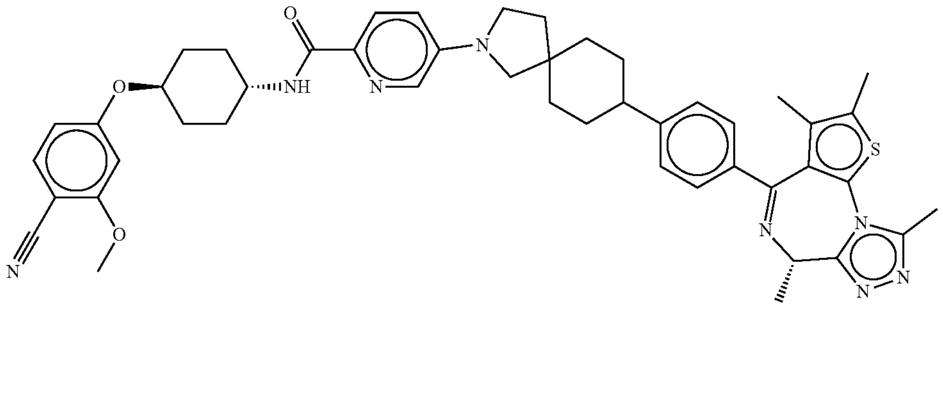 |

TABLE 1-continued
| Compound No. | Chemical Structure |
|---|---|
| I-54 | 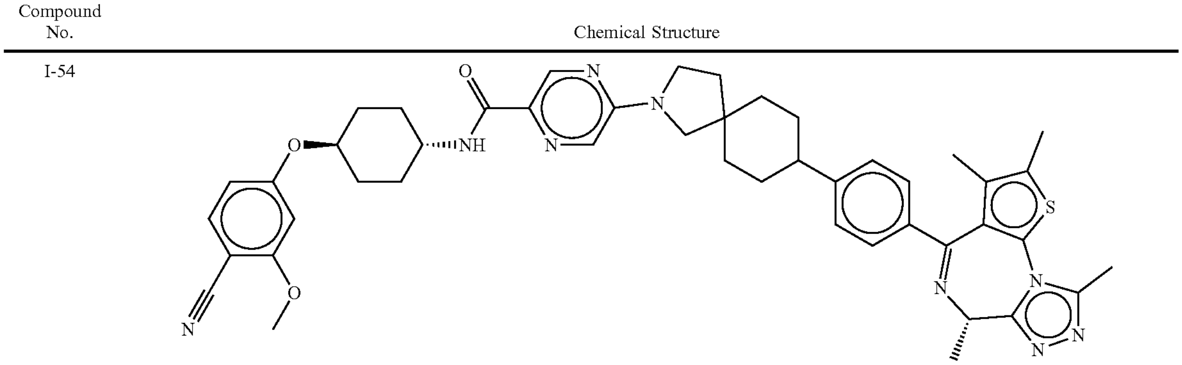 |
| I-55 | 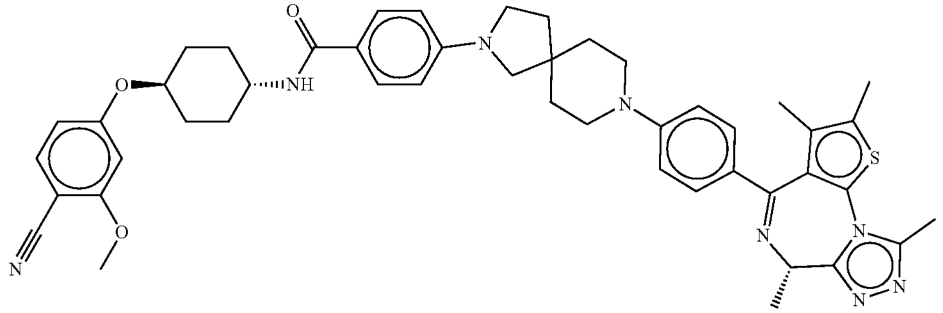 |
| I-56 | 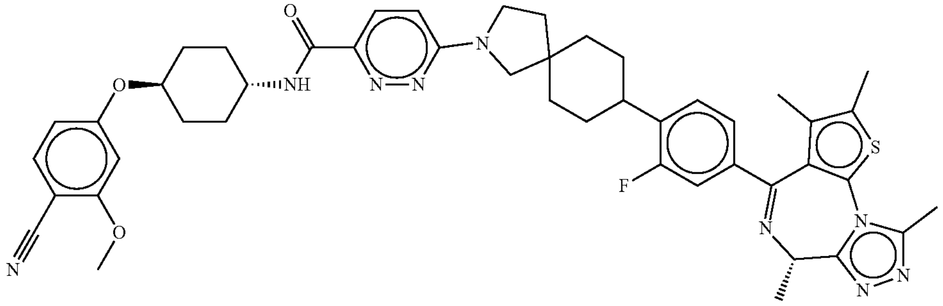 |
| I-57 | 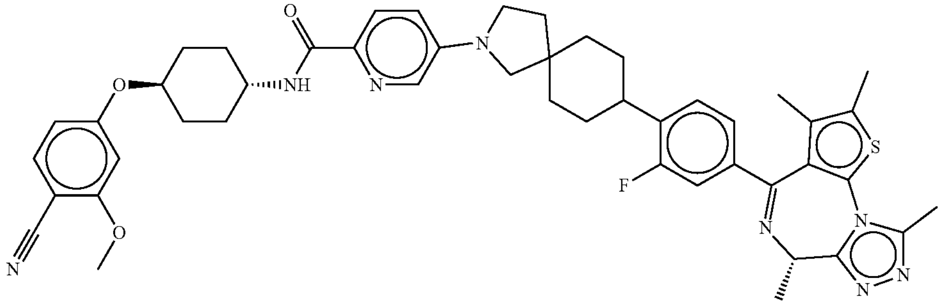 |
| I-58 | 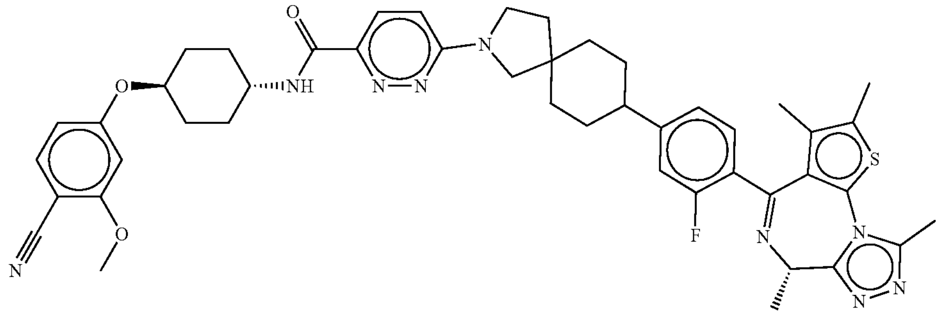 |

TABLE 1-continued
| Compound No. | Chemical Structure |
|---|---|
| I-59 | 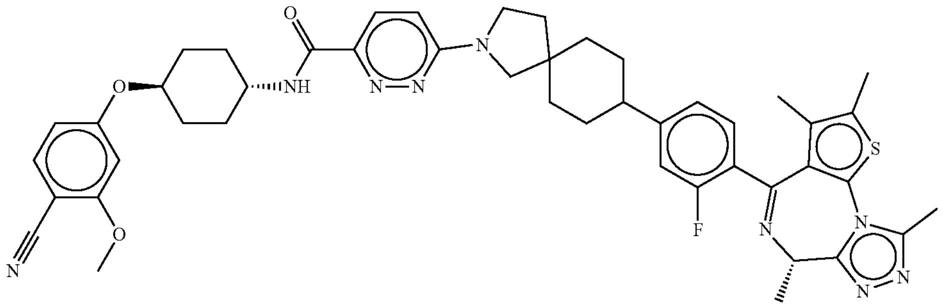 |
| I-60 | 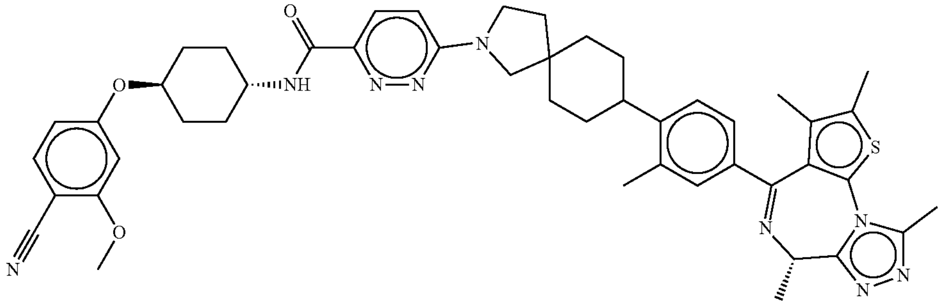 |
| I-61 | 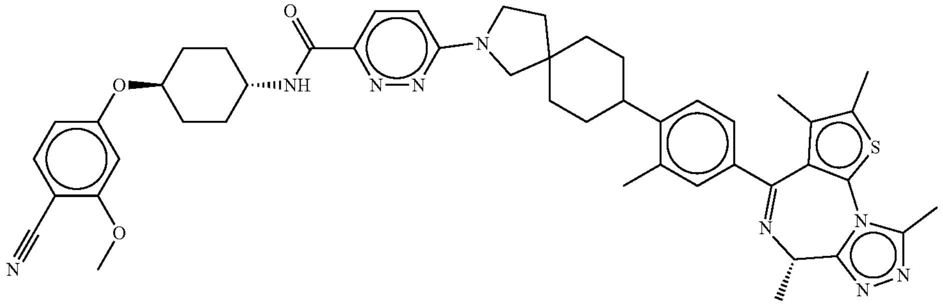 |
| I-62 | 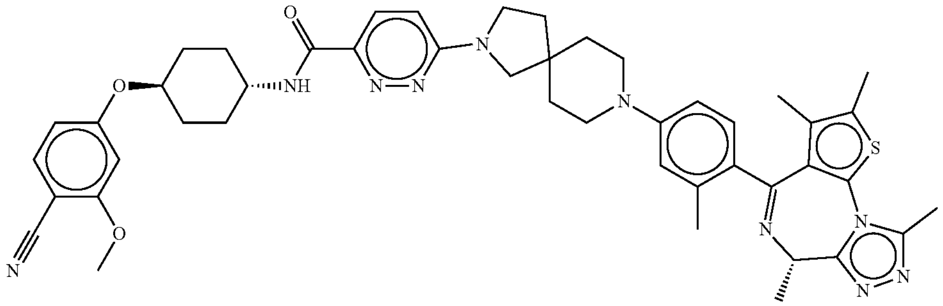 |
| I-63 | 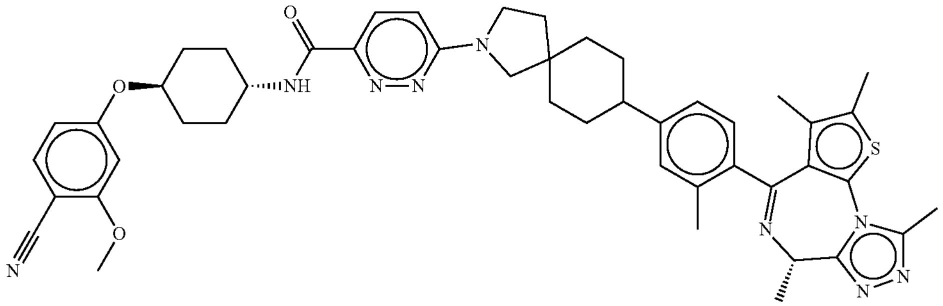 |

TABLE 1-continued
| Compound No. | Chemical Structure |
|---|---|
| I-64 | 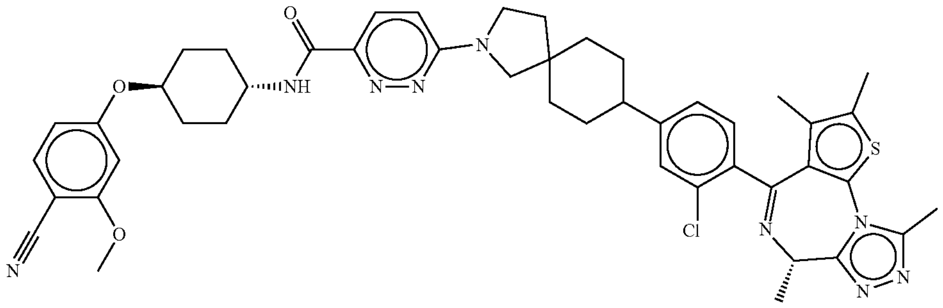 |
| I-65 | 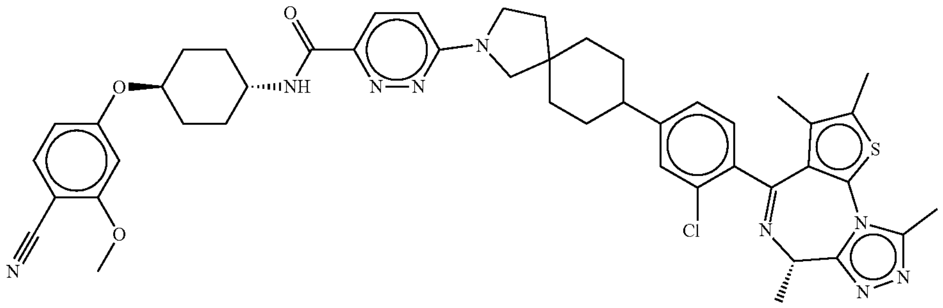 |
| I-66 | 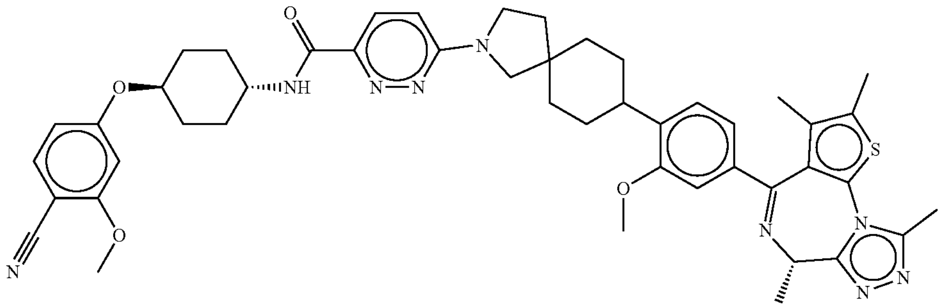 |
| I-67 | 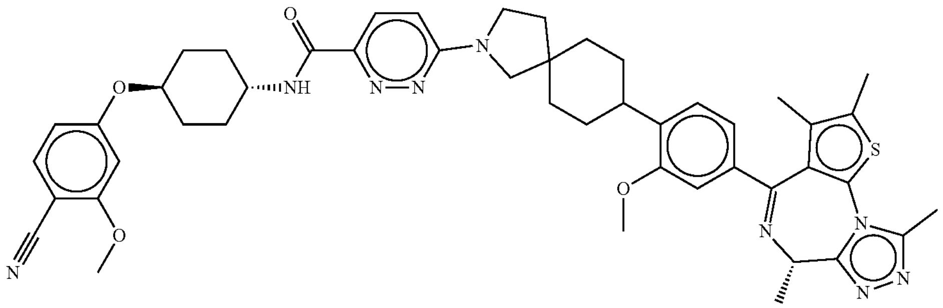 |
| I-68 | 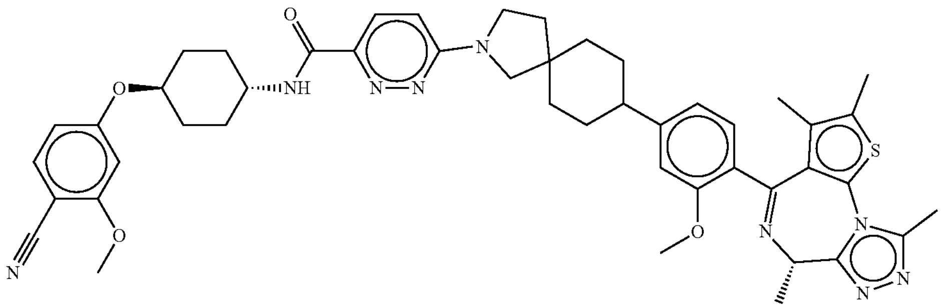 |

TABLE 1-continued
| Compound No. | Chemical Structure |
|---|---|
| I-69 | 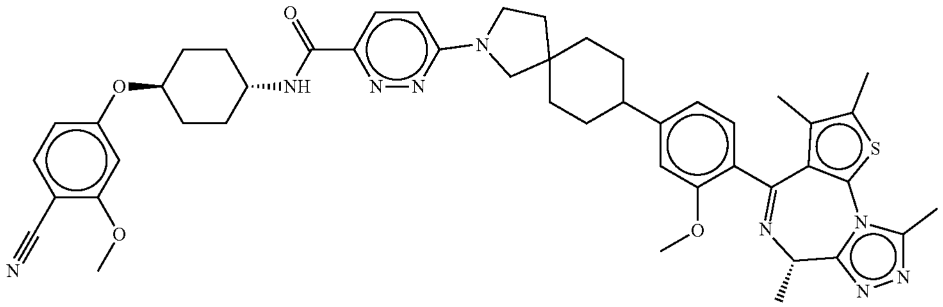 |
| I-70 | 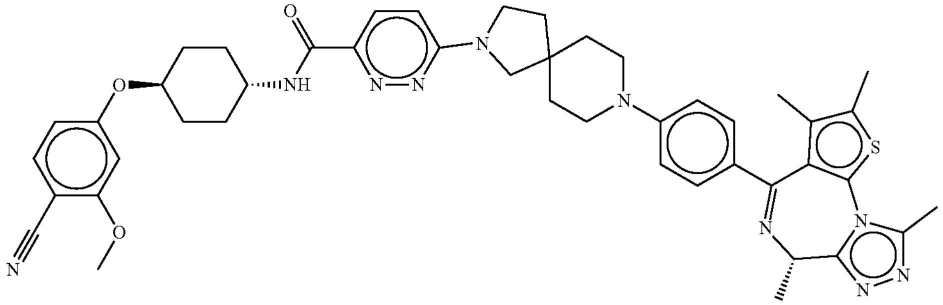 |
| I-71 | 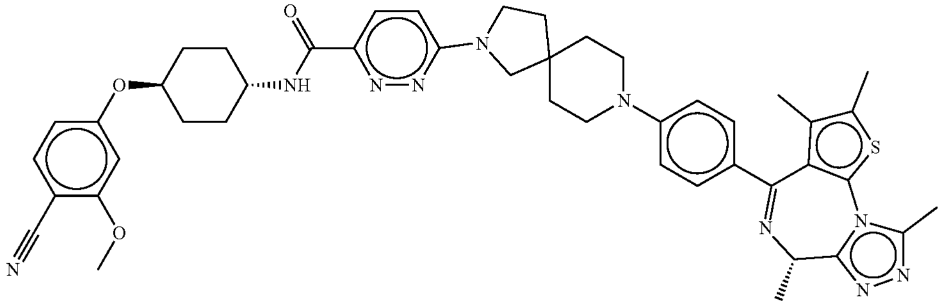 |
| I-72 | 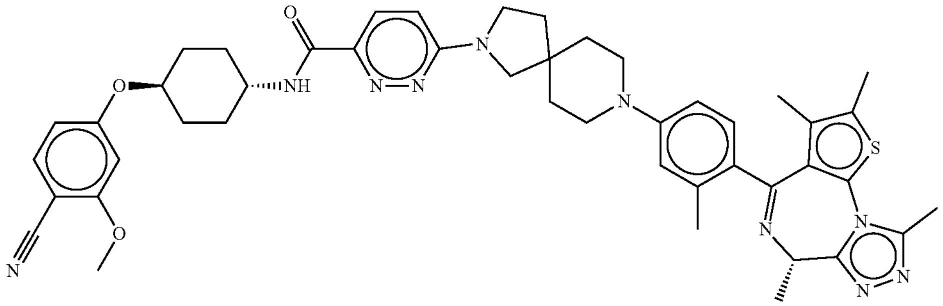 |
| I-73 | 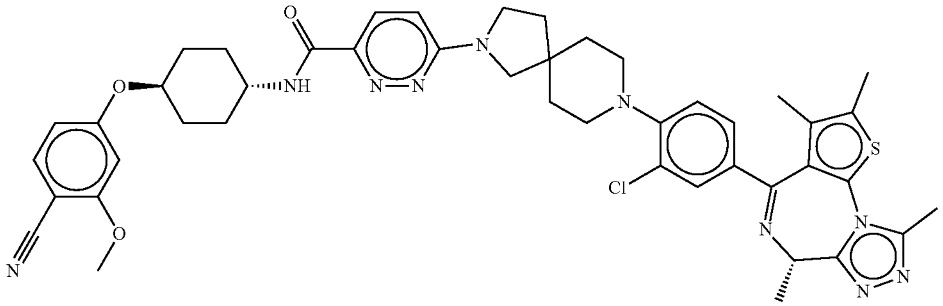 |

TABLE 1-continued
| Compound No. | Chemical Structure |
| --- | --- |
| I-74 | 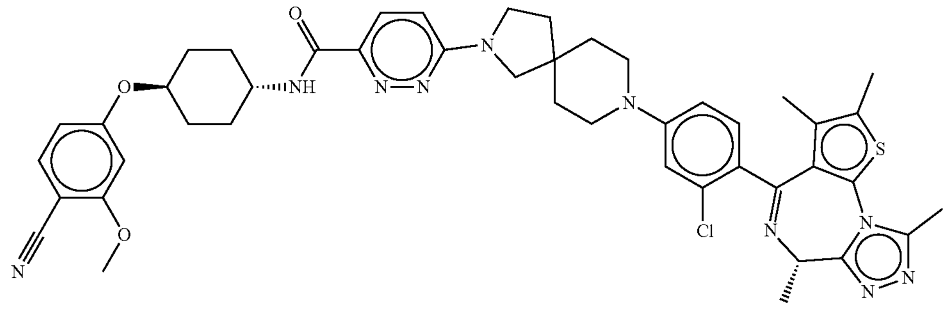 |
| I-75 | 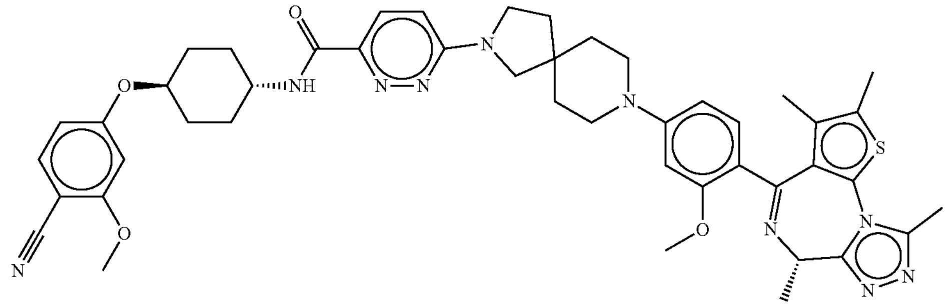 |
| I-76 | 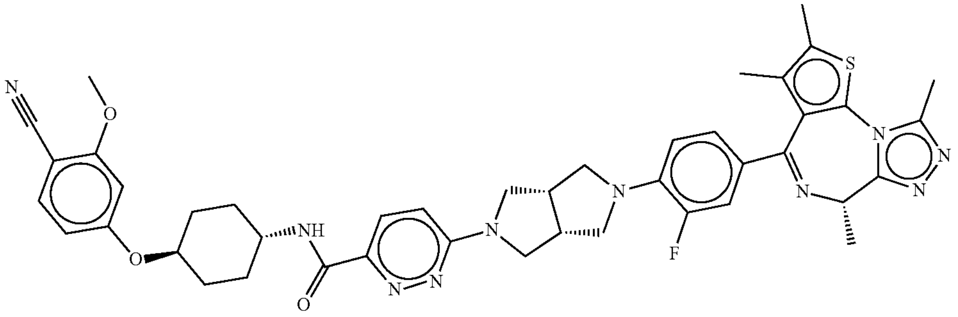 |
| I-77 | 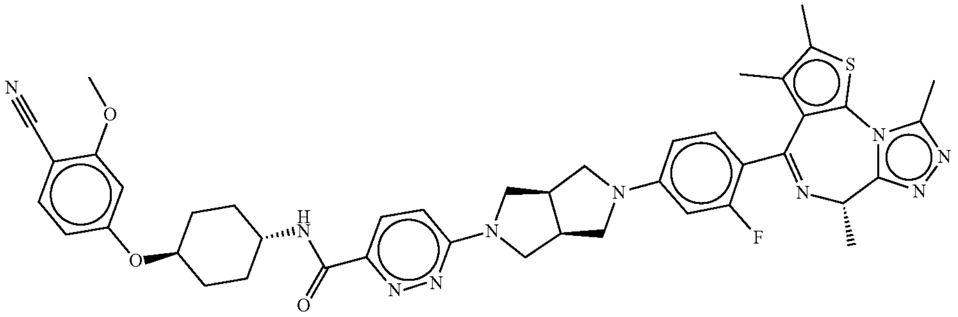 |

TABLE 1-continued
| Compound No. | Chemical Structure |
|---|---|
| I-78 | 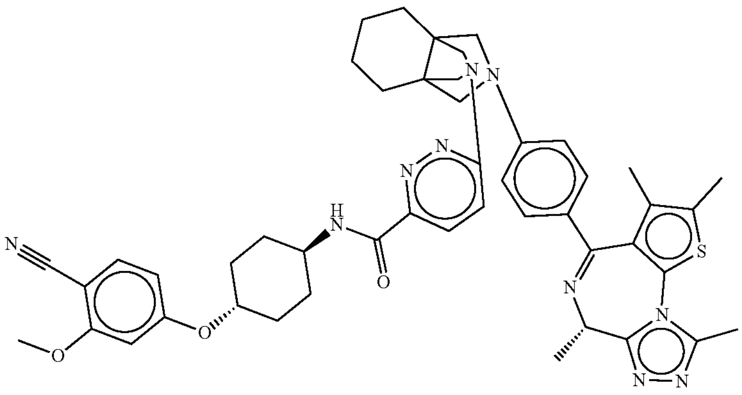 |
| I-79 | 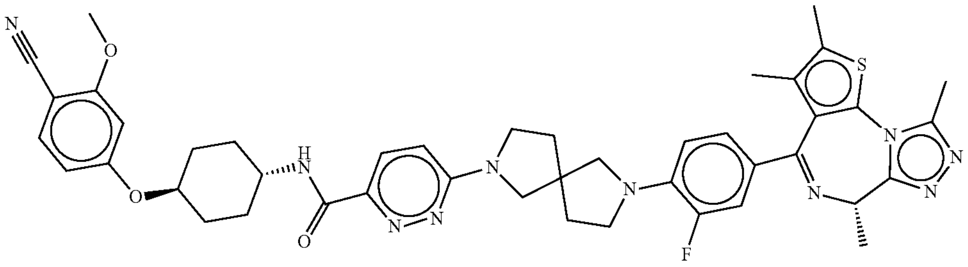 |
| I-80 | 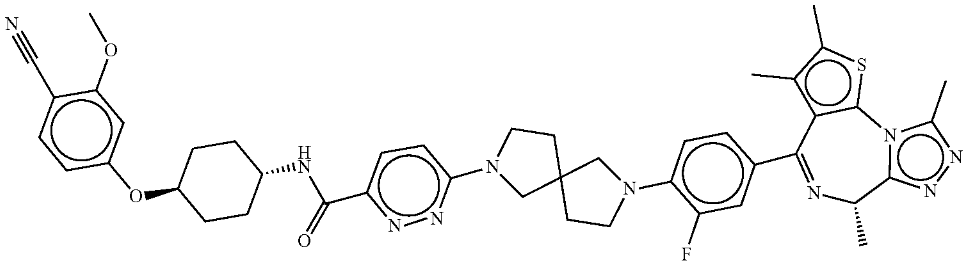 |
| I-81 | 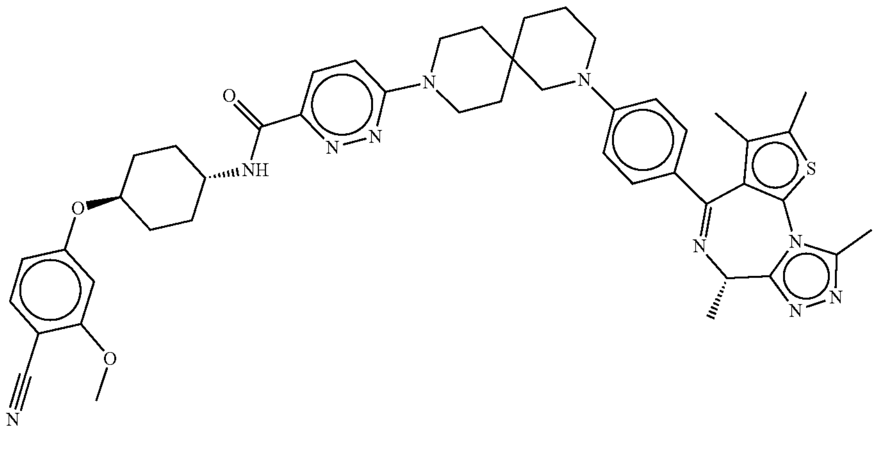 |

TABLE 1-continued
| Compound No. | Chemical Structure |
| --- | --- |
| I-82 | 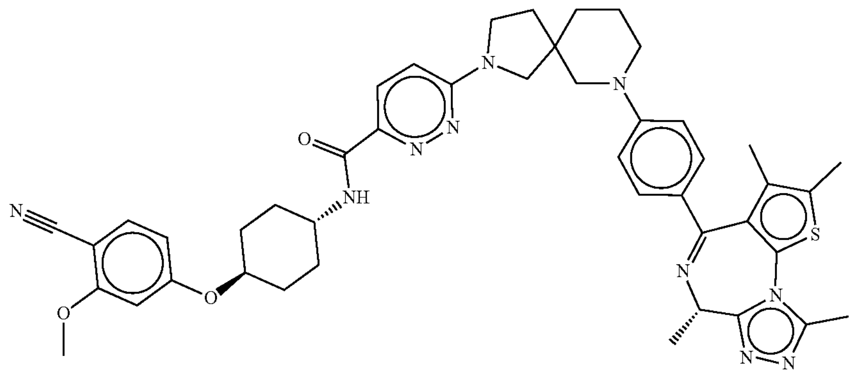 |
| I-83 | 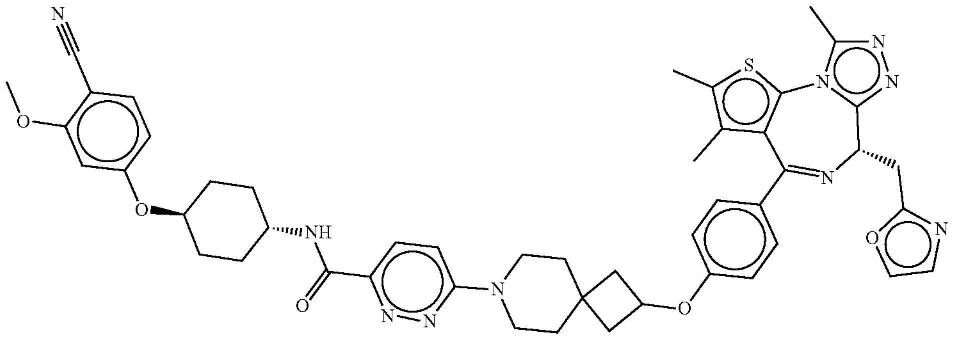 |
| I-84 | 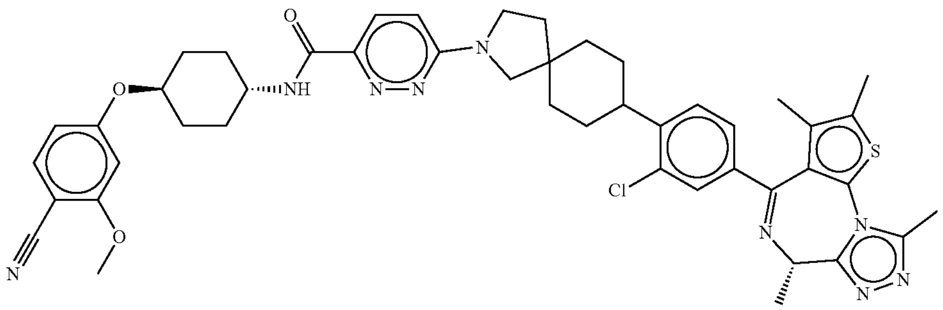 |
| I-85 | 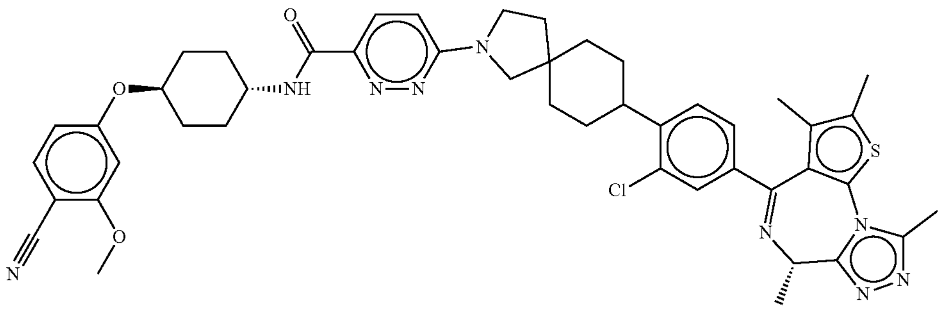 |

TABLE 1-continued
| Compound No. | Chemical Structure |
|---|---|
| I-86 | 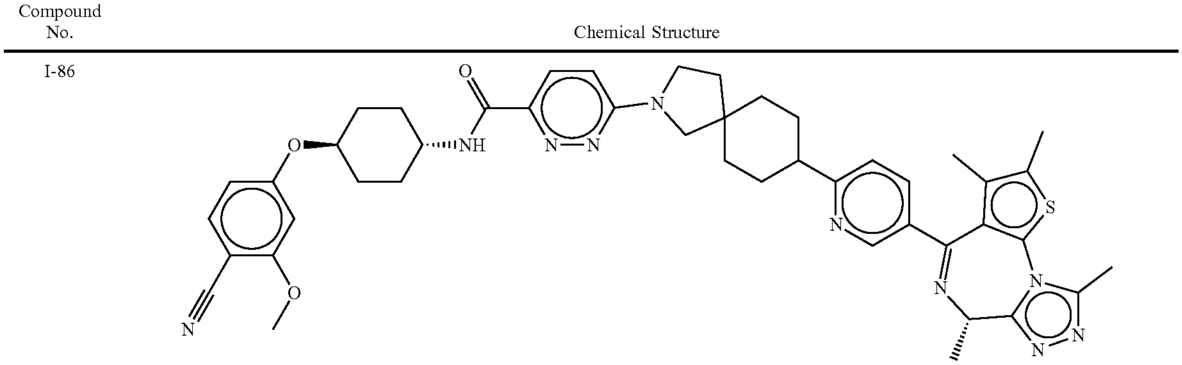 |
| I-87 | 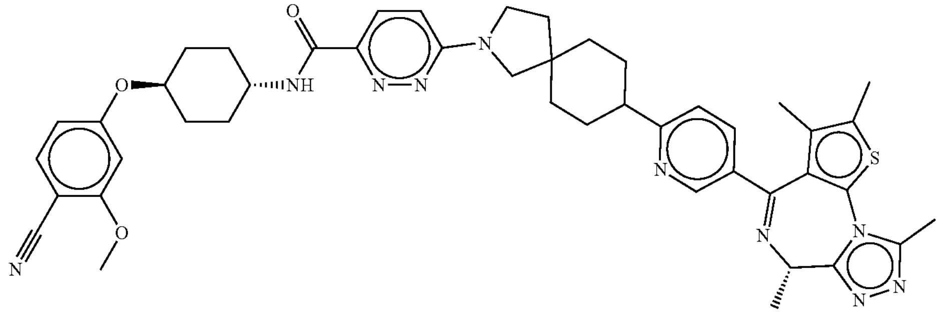 |
| I-88 | 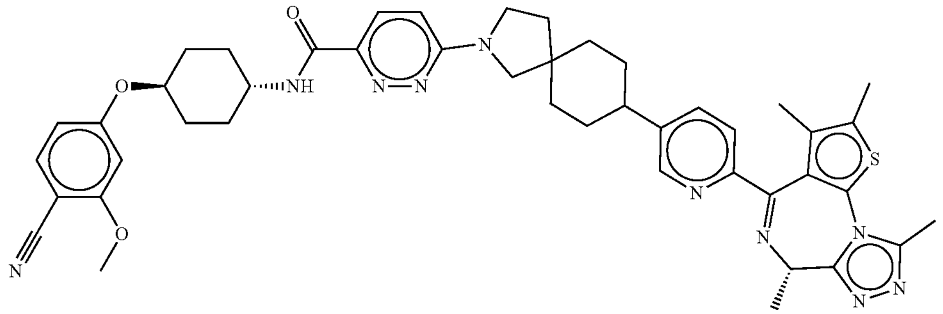 |
| I-89 | 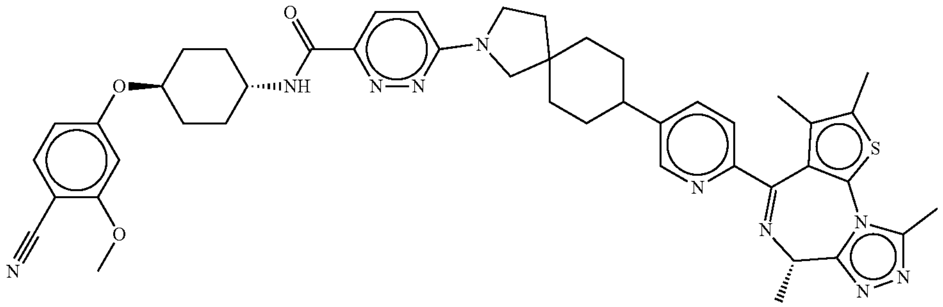 |
| I-90 | 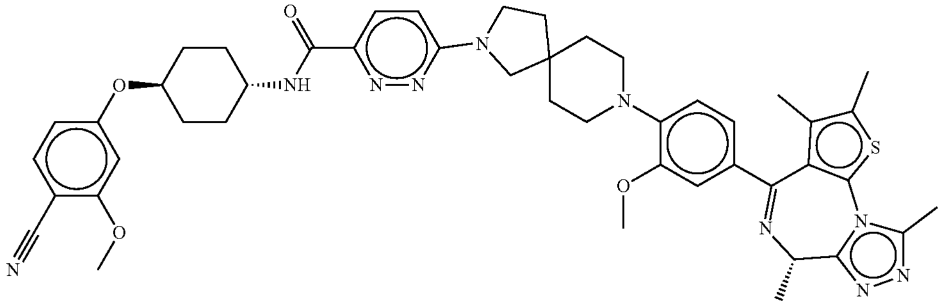 |

TABLE 1-continued
| Compound No. | Chemical Structure |
|---|---|
| I-91 | 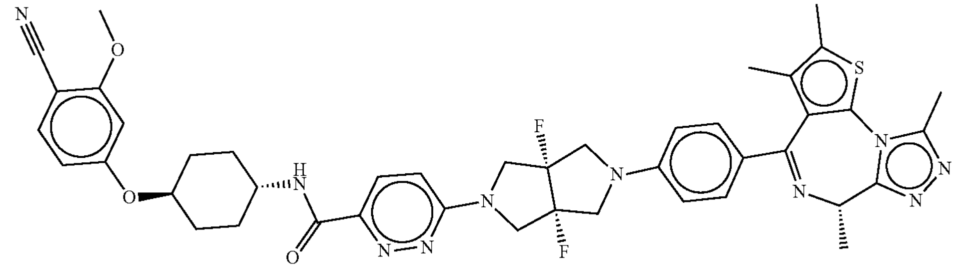 |
| I-92 | 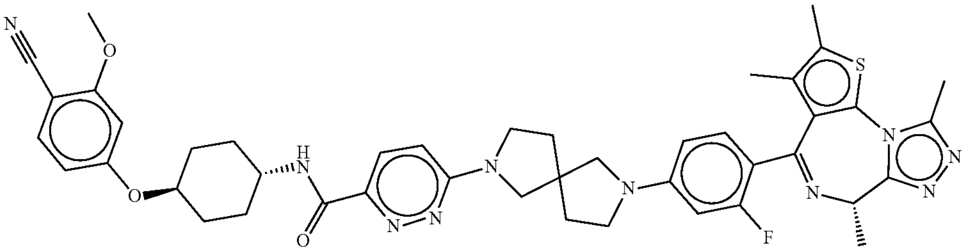 |
| I-93 | 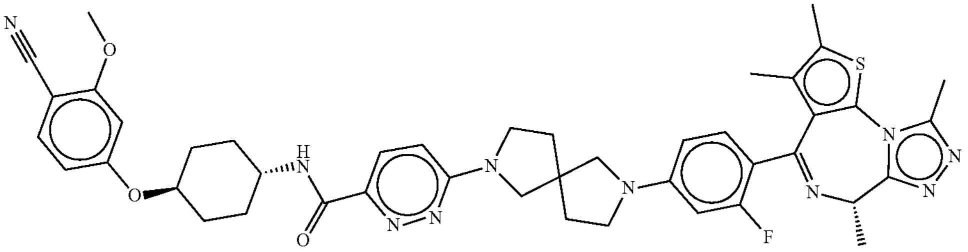 |
| I-94 | 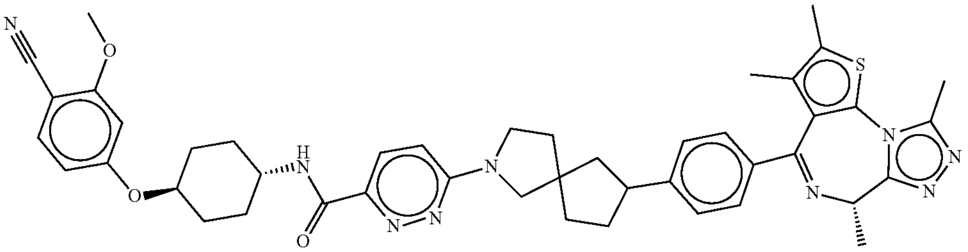 |
| I-95 | 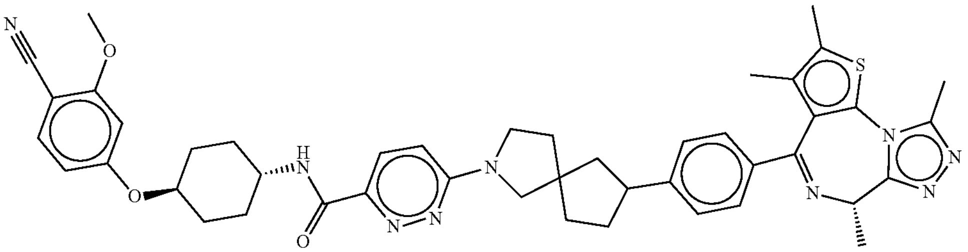 |
| I-96 | 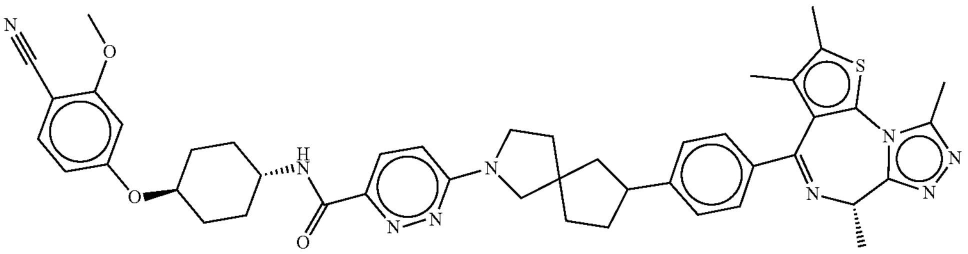 |

TABLE 1-continued
| Compound No. | Chemical Structure |
| --- | --- |
| I-97 | 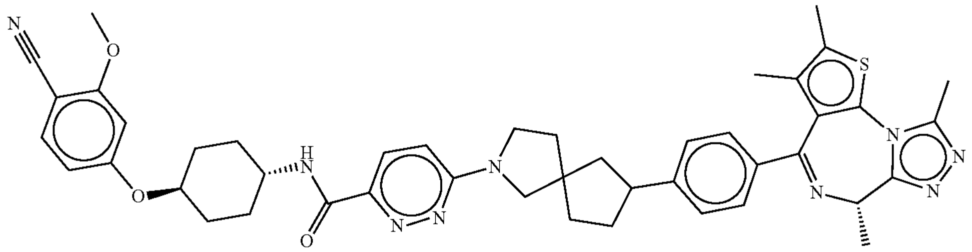 |
| I-98 | 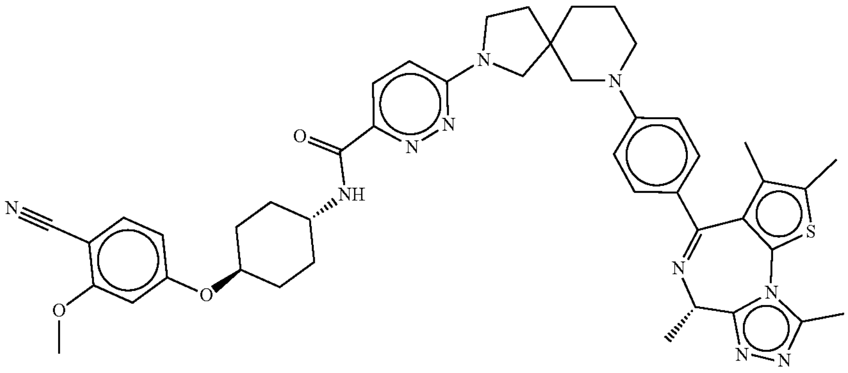 |
| I-99 | 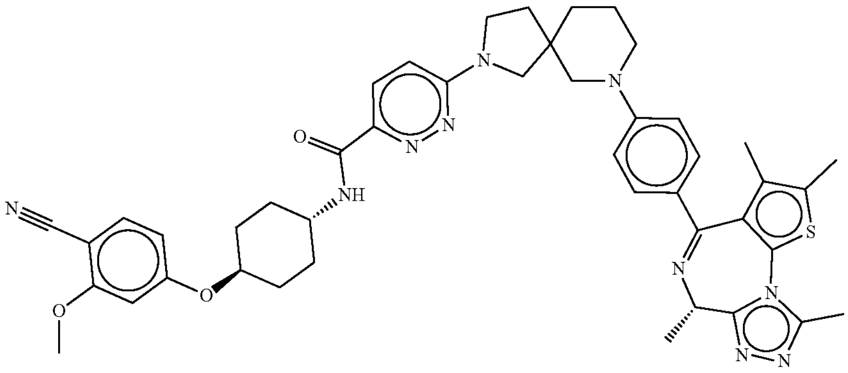 |
| I-100 | 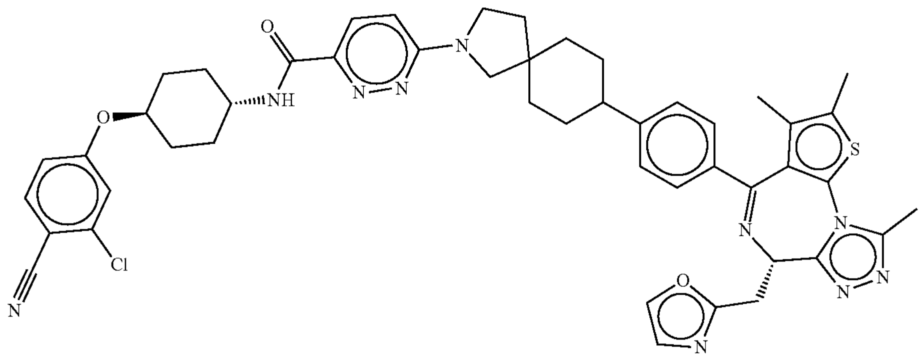 |

TABLE 1-continued
| Compound No. | Chemical Structure |
|---|---|
| I-101 | 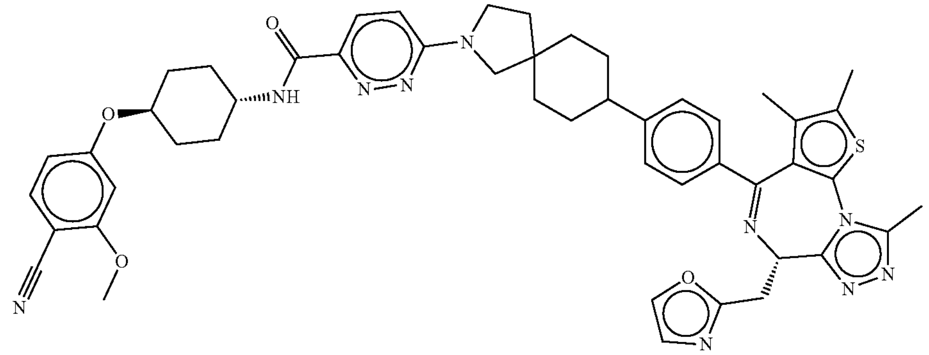 |
| I-102 | 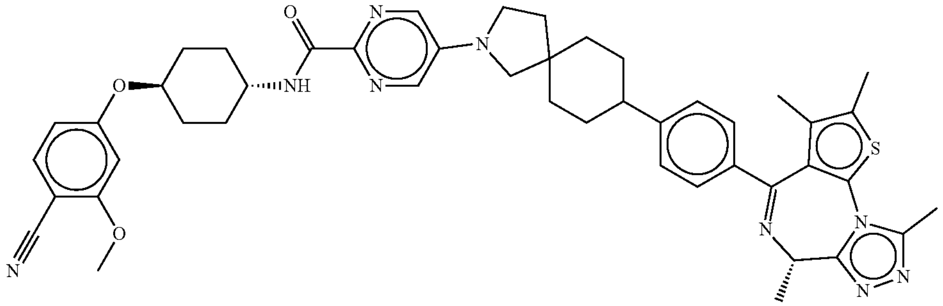 |
| I-103 | 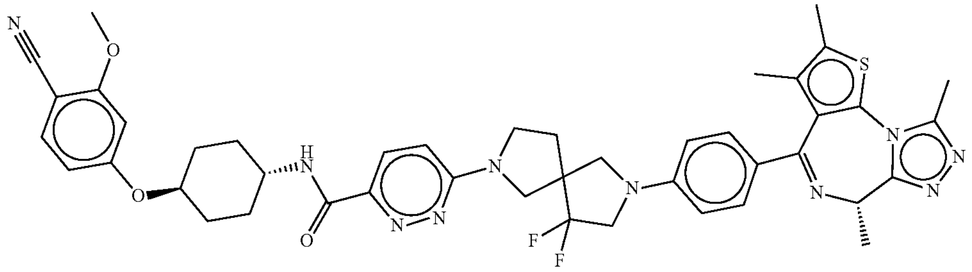 |
| I-104 | 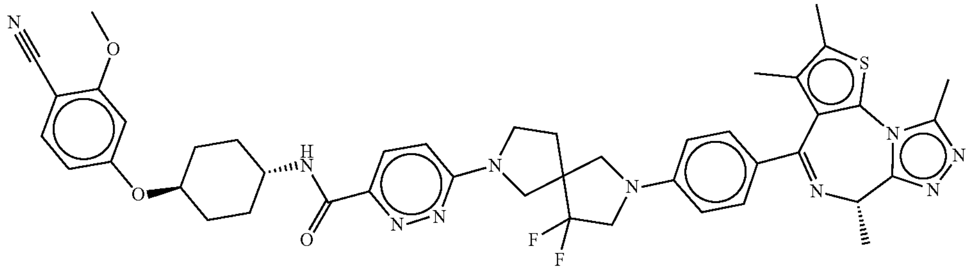 |
| I-105 | 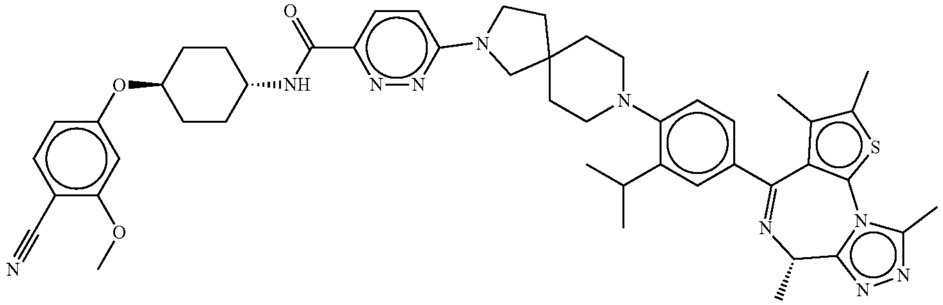 |

TABLE 1-continued
| Compound No. | Chemical Structure |
|---|---|
| I-106 | 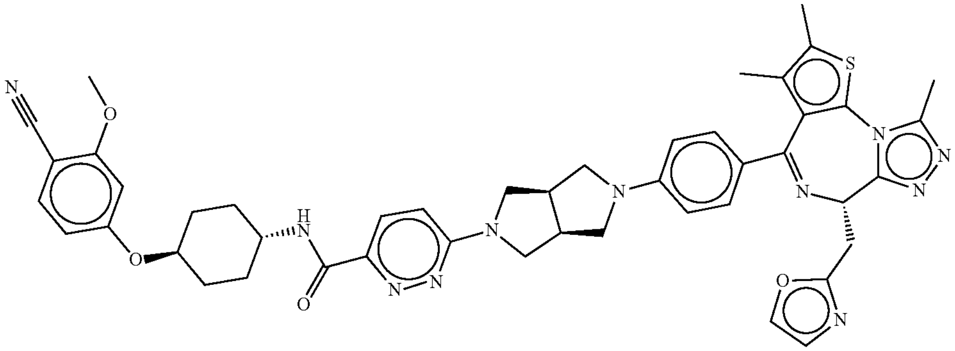 |
| I-107 | 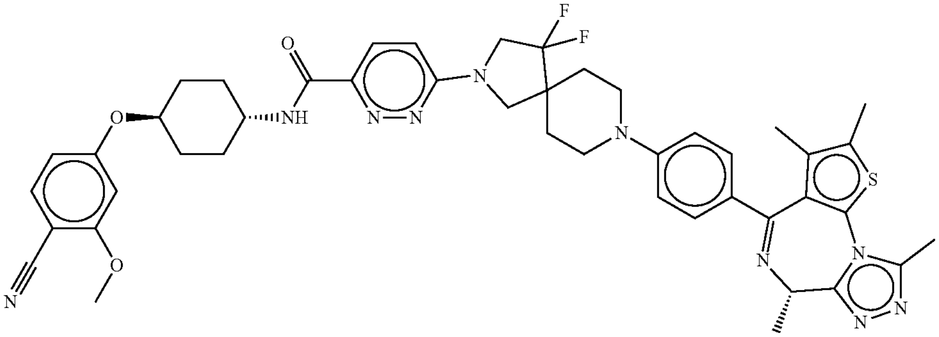 |
| I-108 | 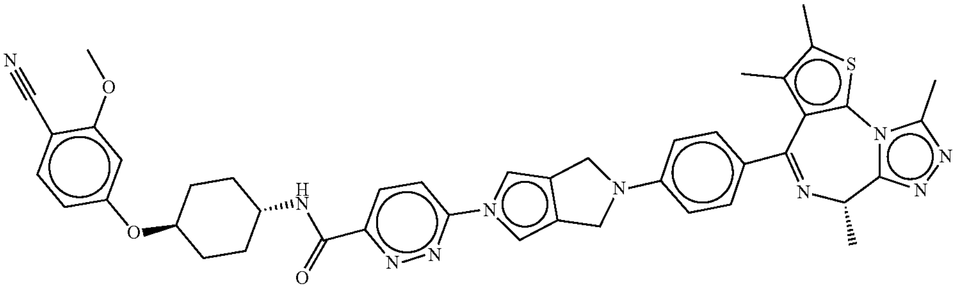 |
| I-109 | 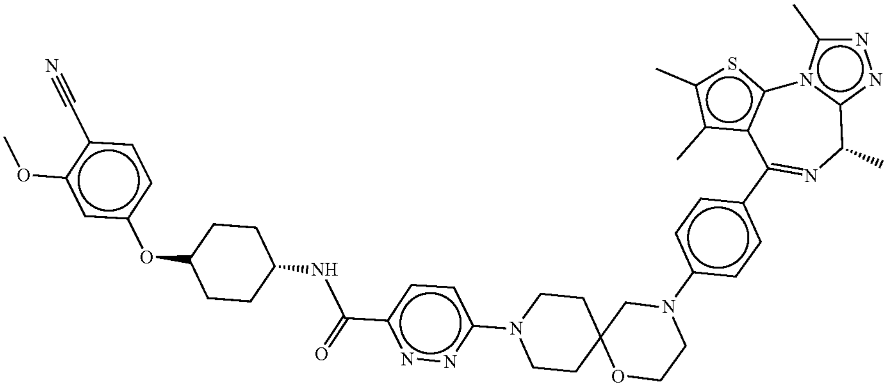 |

TABLE 1-continued
| Compound No. | Chemical Structure |
| --- | --- |
| I-110 | 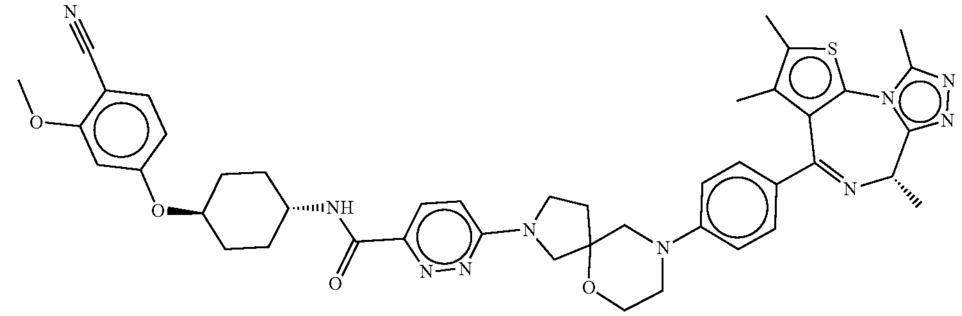 |
| I-111 | 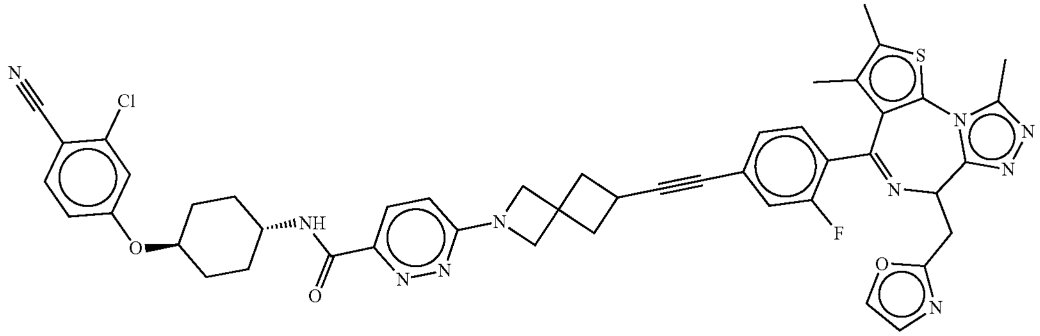 |
| I-112 | 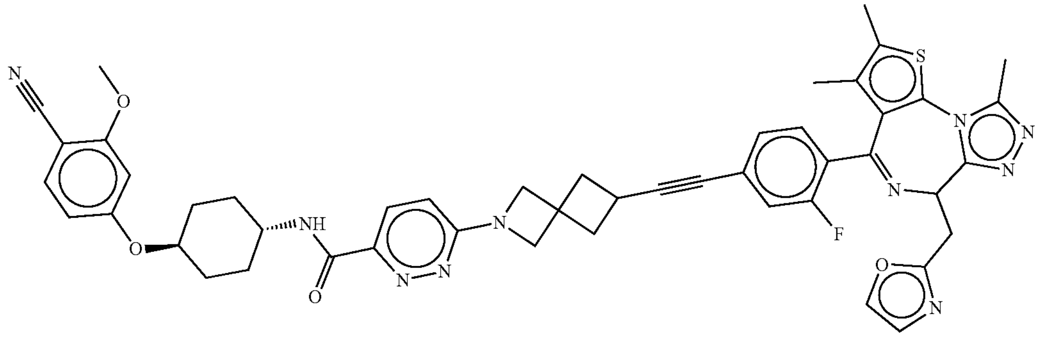 |
| I-113 | 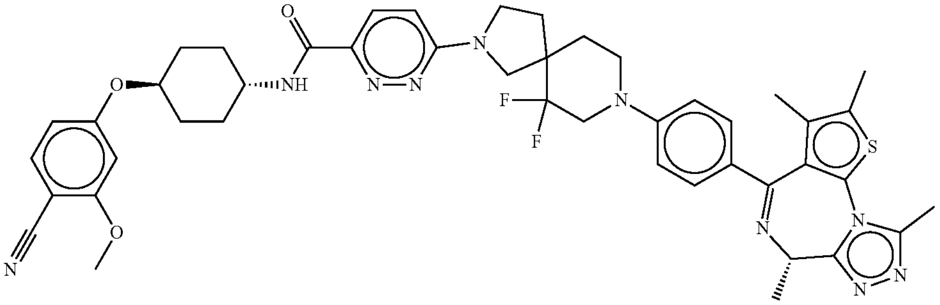 |

TABLE 1-continued
| Compound No. | Chemical Structure |
|---|---|
| I-114 | 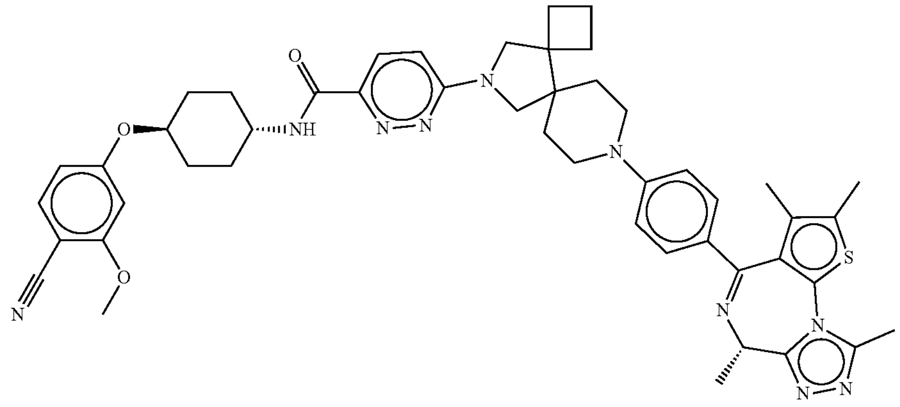 |
| I-115 | 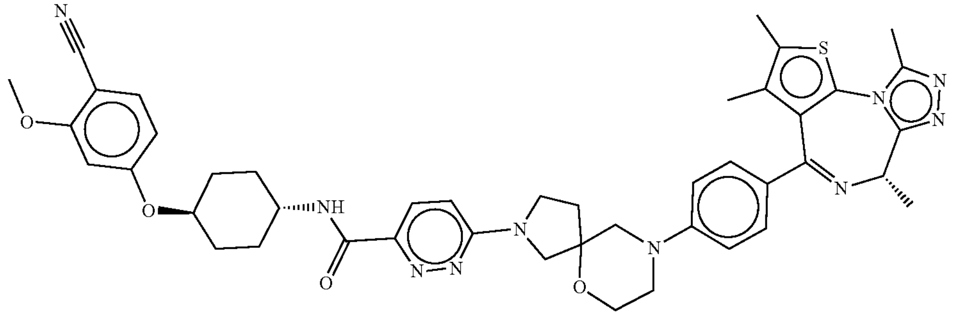 |
| I-116 | 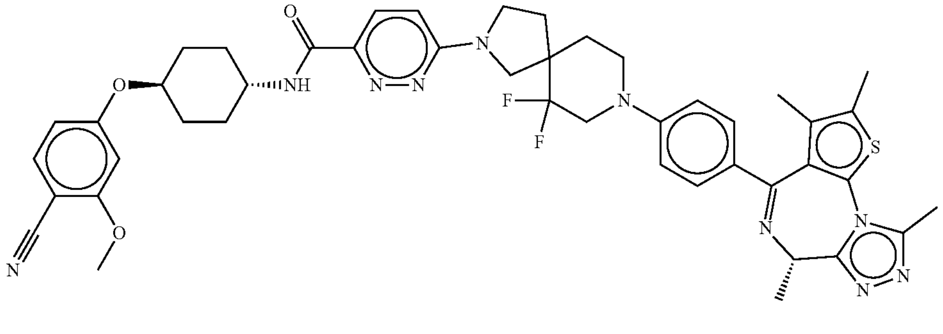 |
| I-117 | 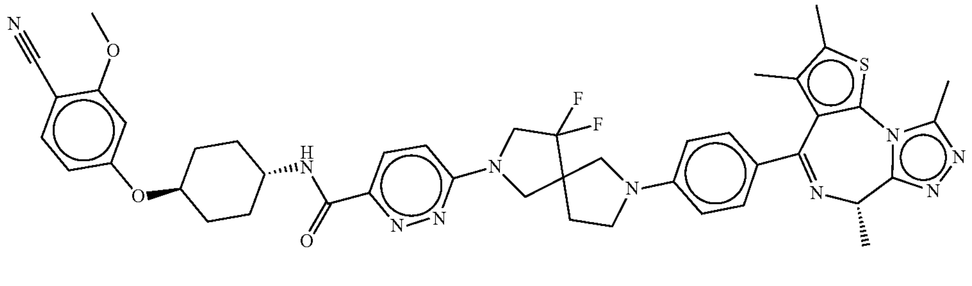 |

TABLE 1-continued
| Compound No. | Chemical Structure |
| --- | --- |
| I-118 | 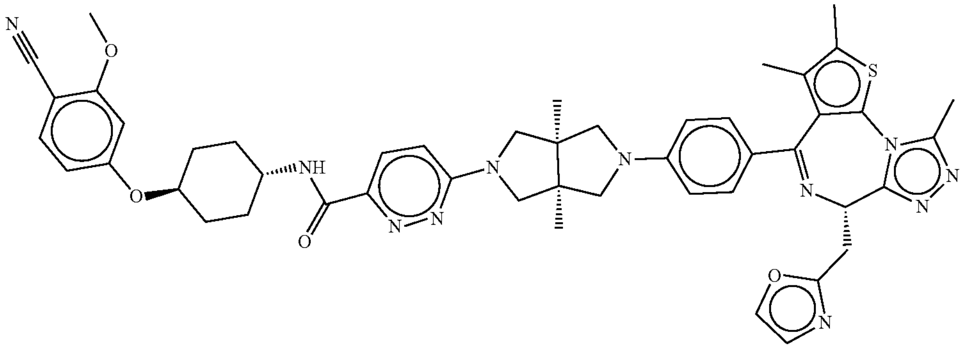 |
| I-119 | 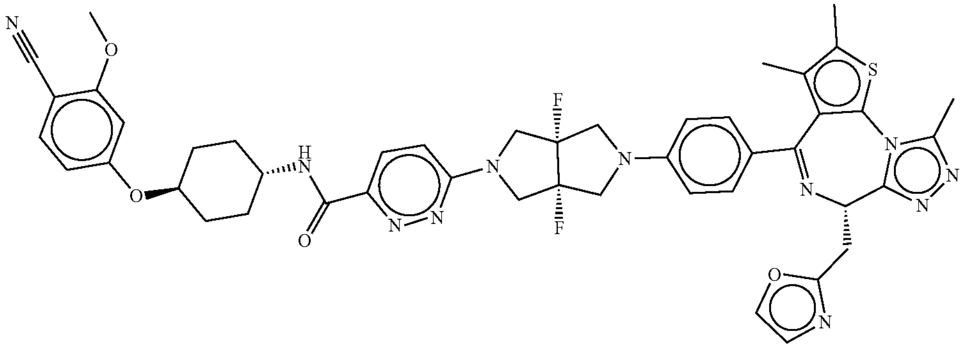 |
| I-120 | 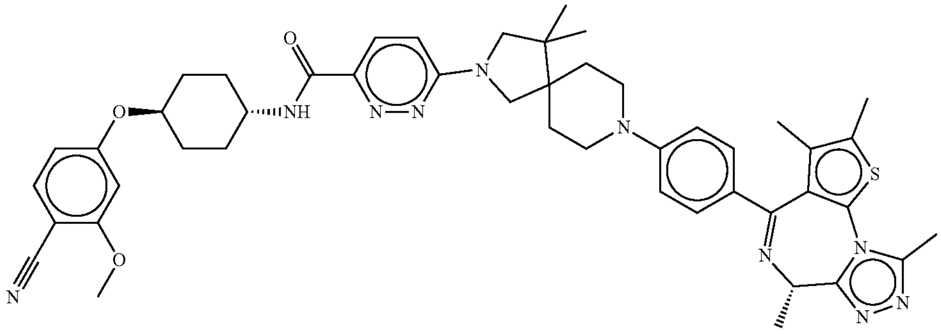 |
| I-121 | 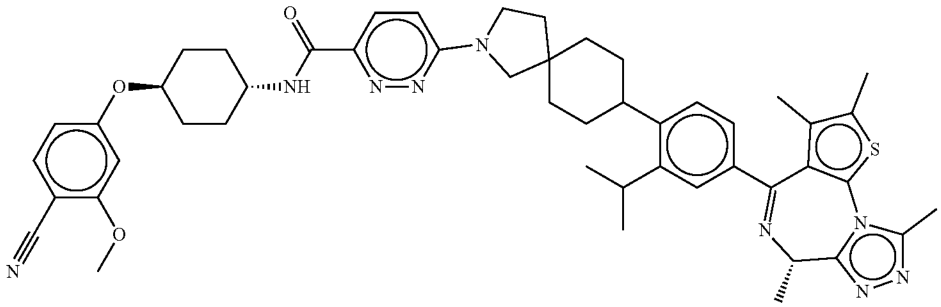 |

TABLE 1-continued
| Compound No. | Chemical Structure |
|---|---|
| I-122 | 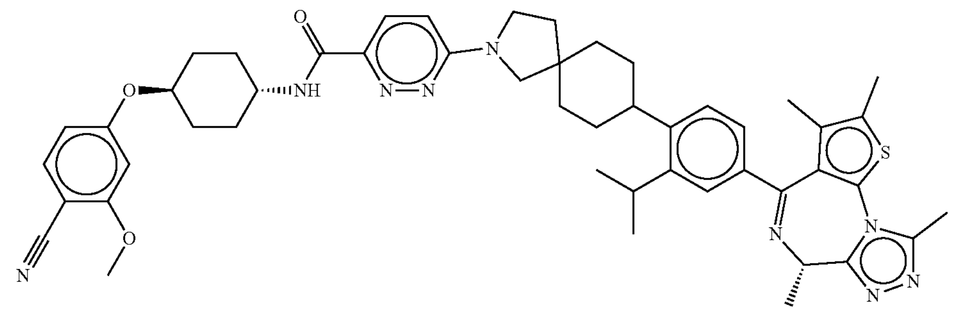 |
| I-123 | 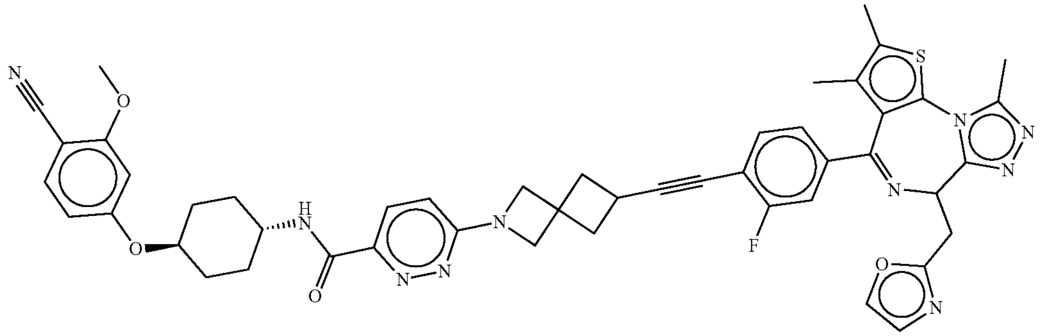 Stereoisomer I |
| I-124 | 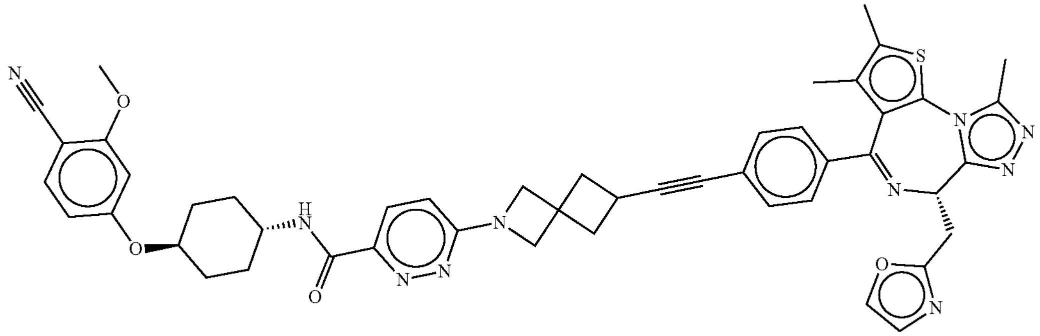 |
| I-125 | 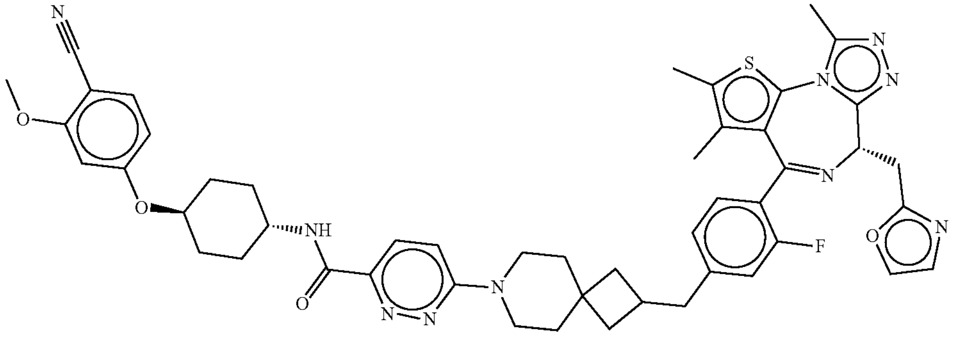 |

TABLE 1-continued
| Compound No. | Chemical Structure |
|---|---|
| I-126 | 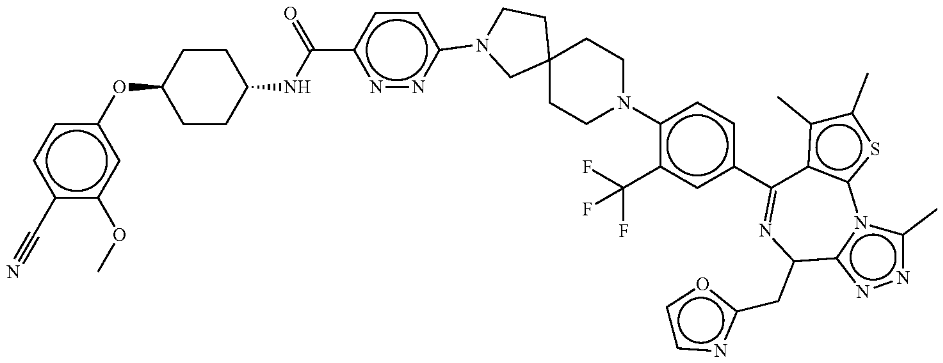 |
| I-127 | 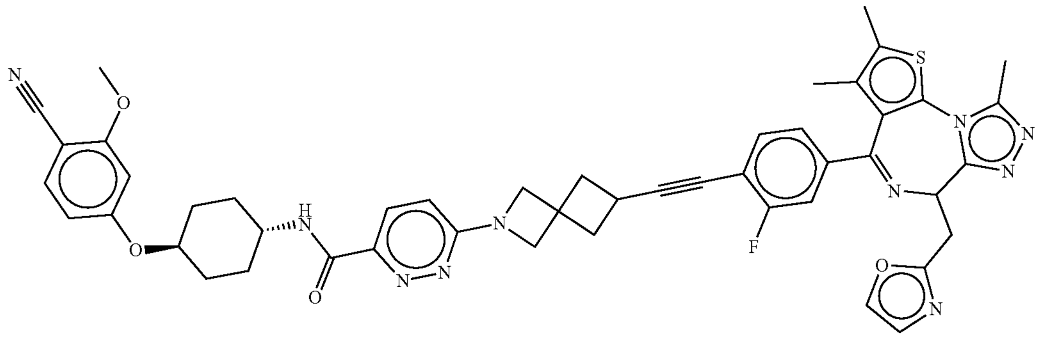 Stereoisomer II |
| I-128 | 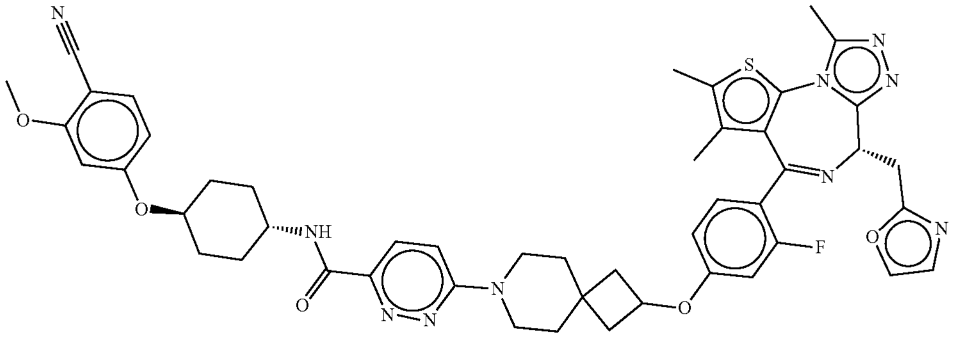 |
| I-129 | 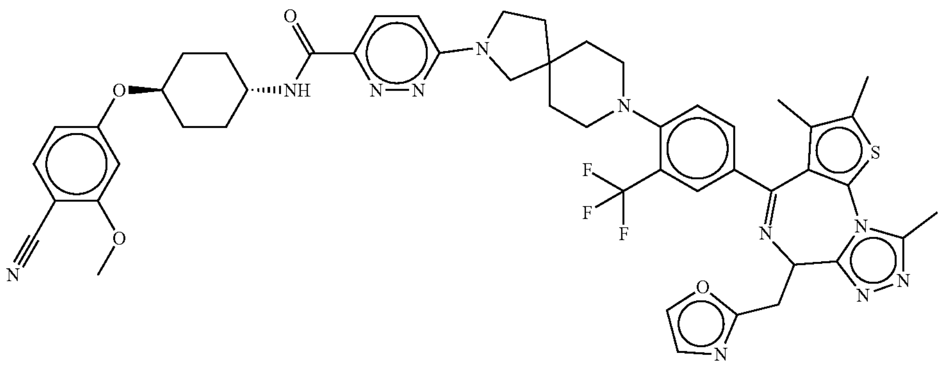 |

TABLE 1-continued
| Compound No. | Chemical Structure |
|---|---|
| I-130 | 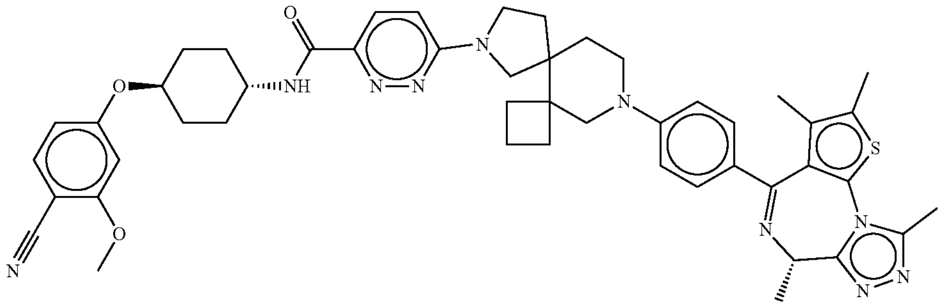 |
| I-131 | 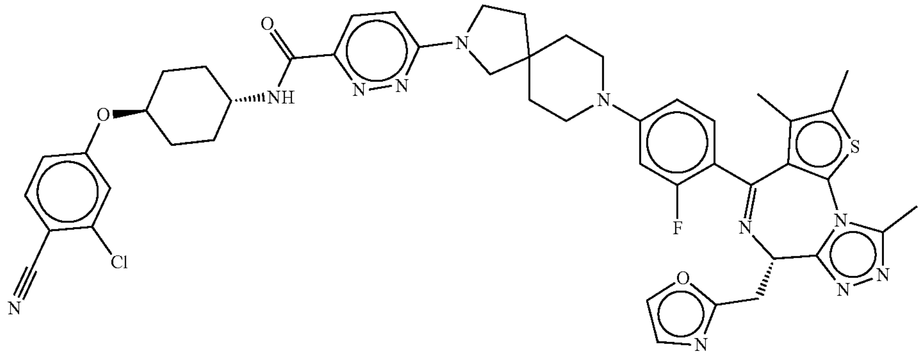 |
| I-132 | 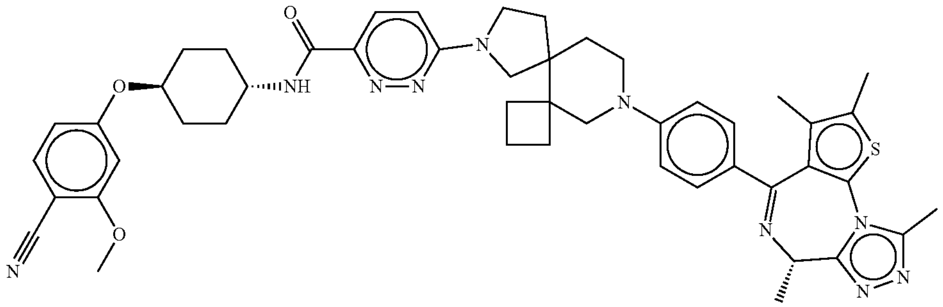 |
| I-133 | 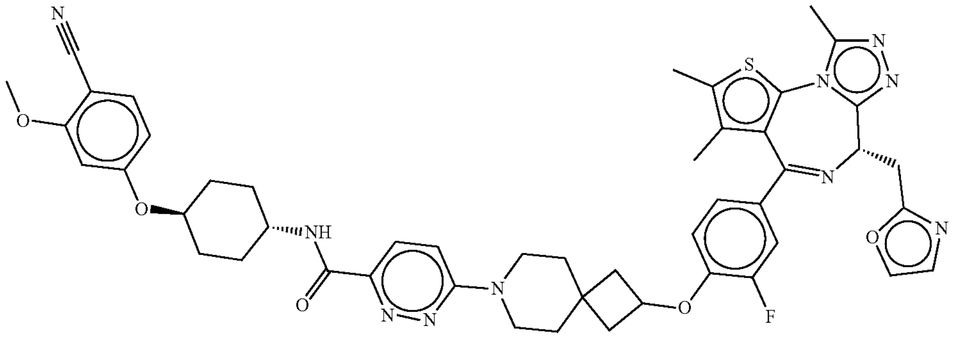 |

TABLE 1-continued
| Compound No. | Chemical Structure |
|---|---|
| I-134 | 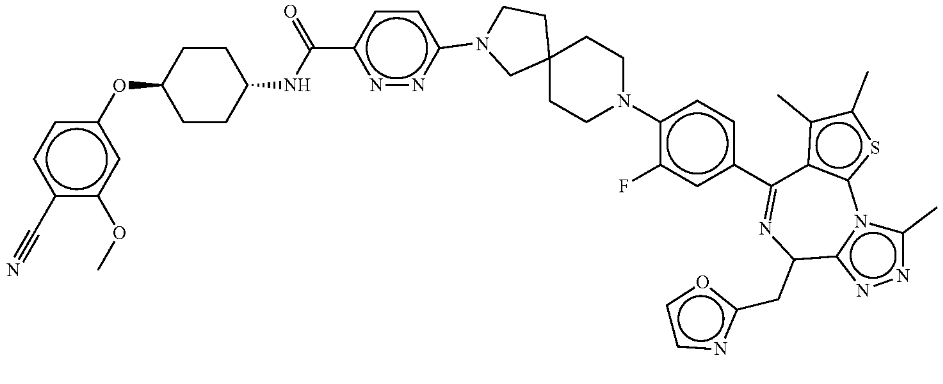<br>Stereoisomer I |
| I-135 | 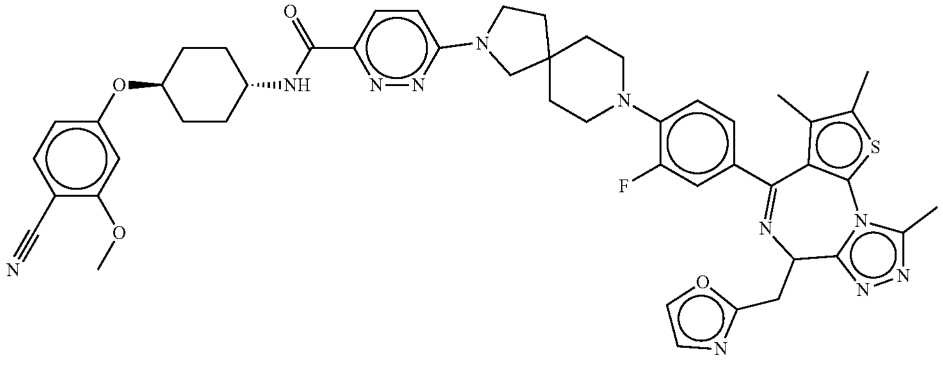<br>Stereoisomer II |
| I-136 | 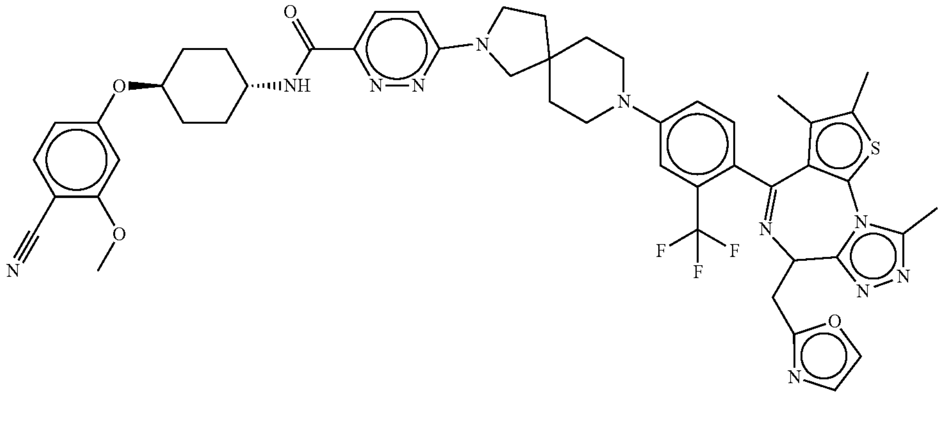 |

TABLE 1-continued
| Compound No. | Chemical Structure |
| --- | --- |
| I-137 | 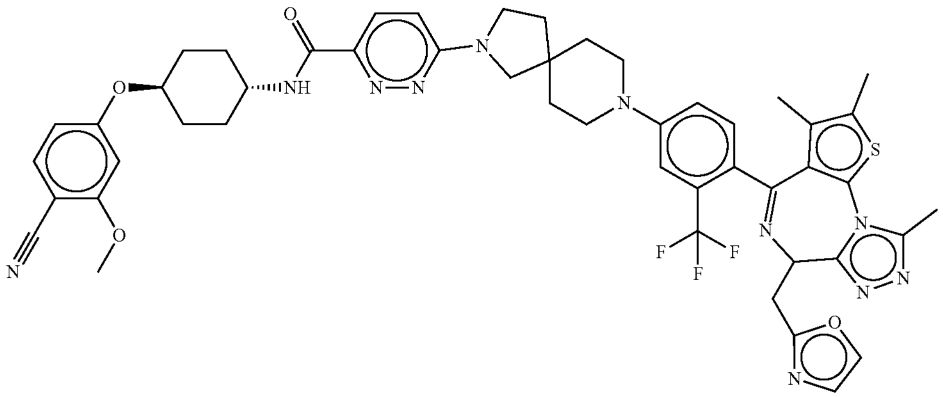 |
| I-138 | 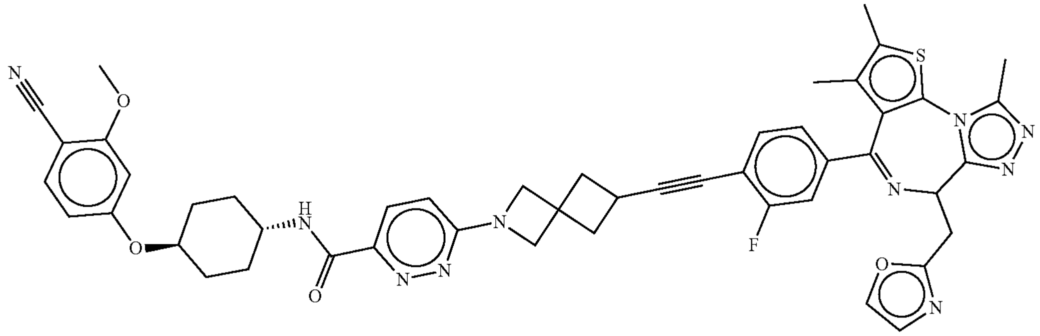 |
| I-139 | 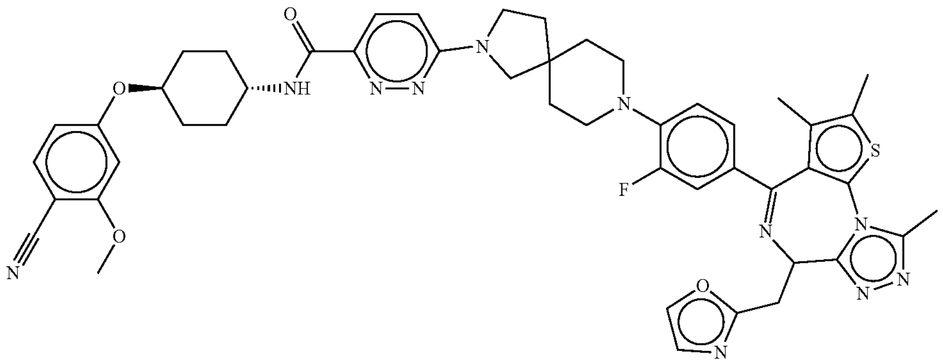 |

TABLE 2
| Compound No. | Chemical Structure |
| --- | --- |
| II-1 | 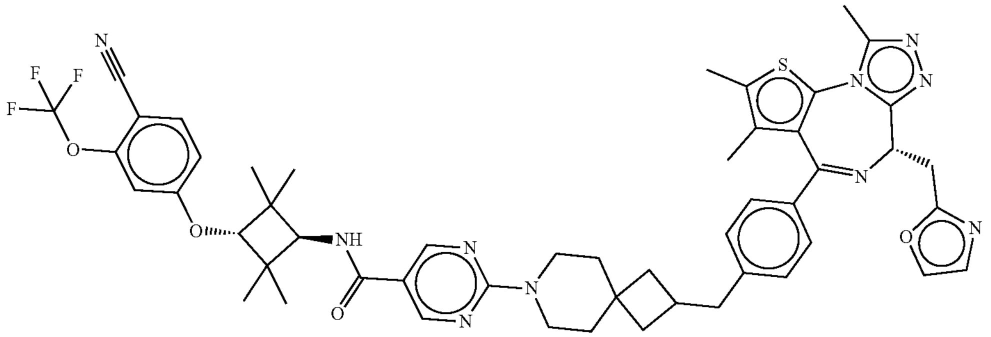 |
| II-2 | 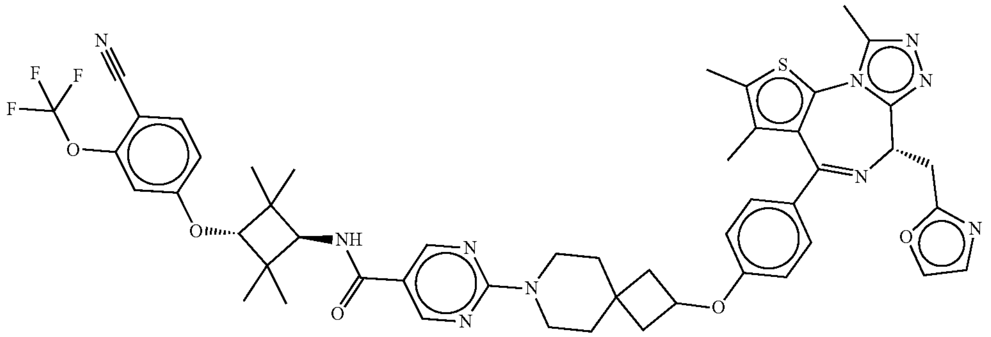 |
| II-3 | 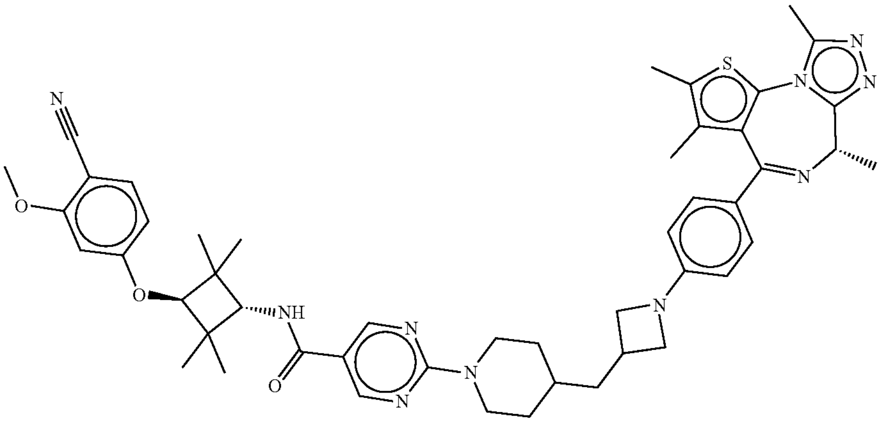 |
| II-4 | 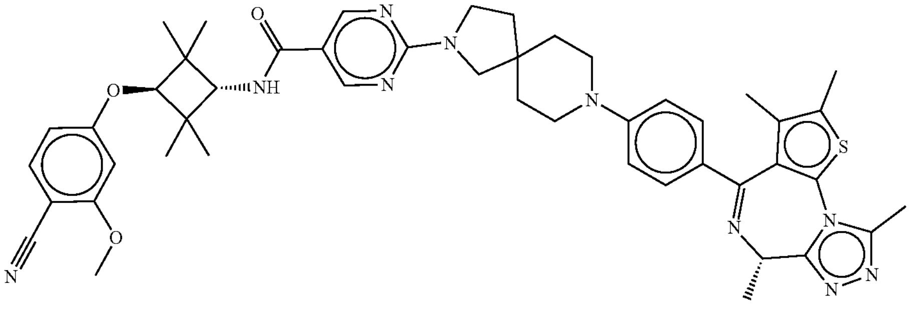 |

TABLE 2-continued
| Compound No. | Chemical Structure |
| --- | --- |
| II-5 | 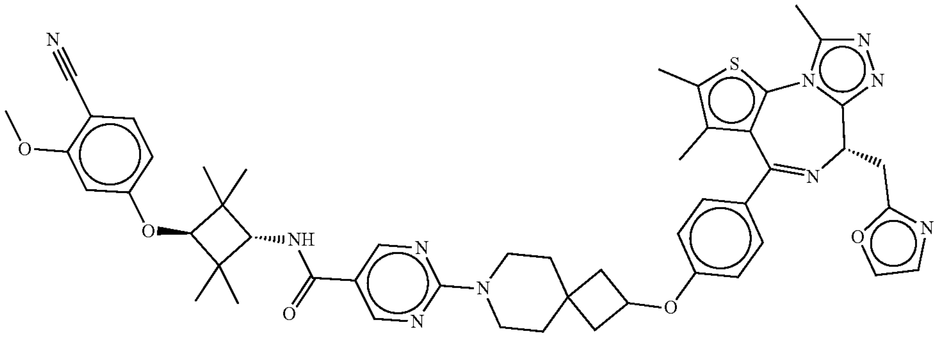 |
| II-6 | 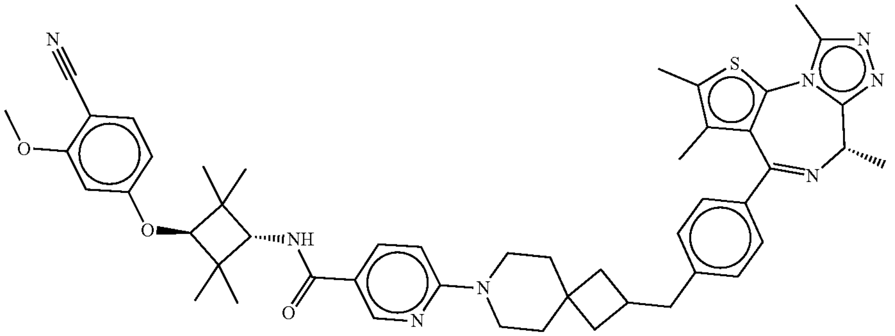 |
| II-7 | 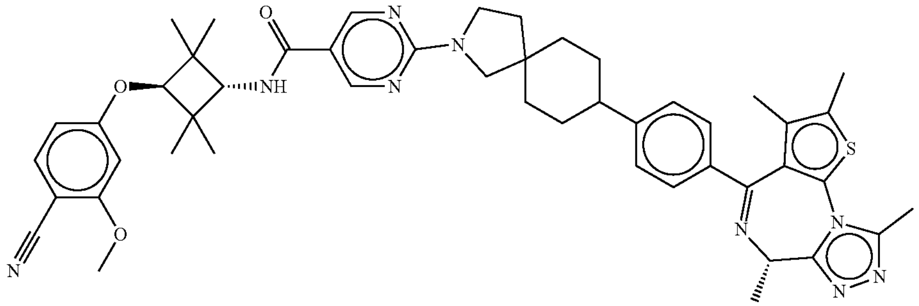 |
| II-8 | 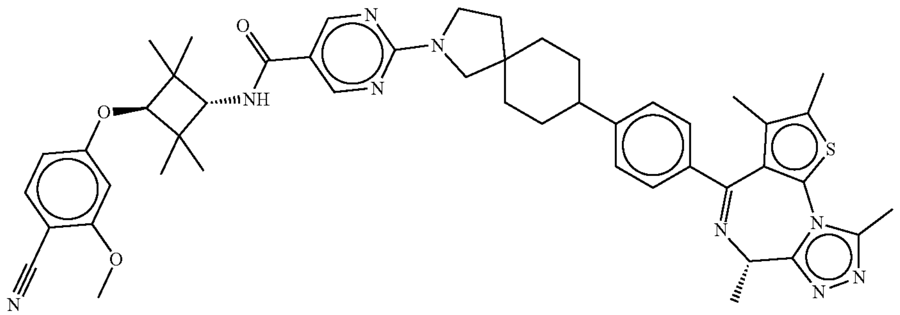 |

TABLE 2-continued
| Compound No. | Chemical Structure |
| --- | --- |
| II-9 | 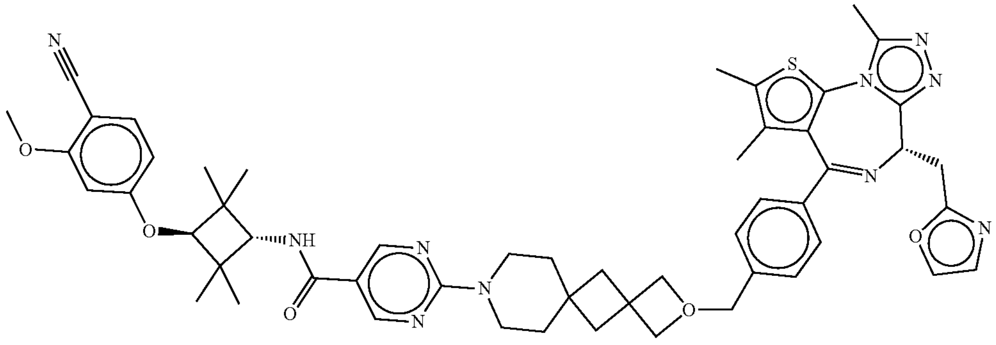 |
| II-10 | 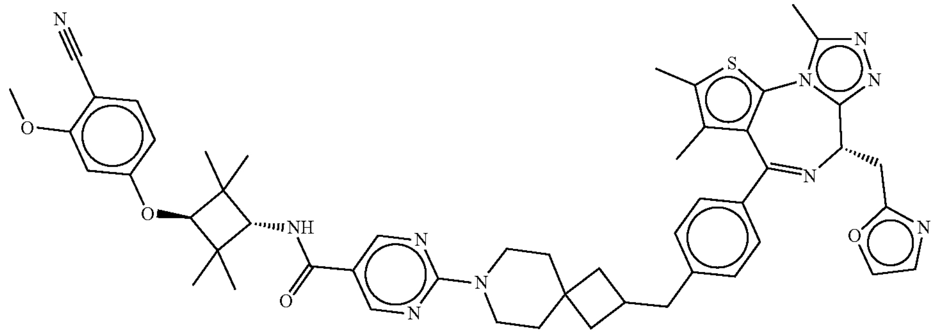 |
| II-11 | 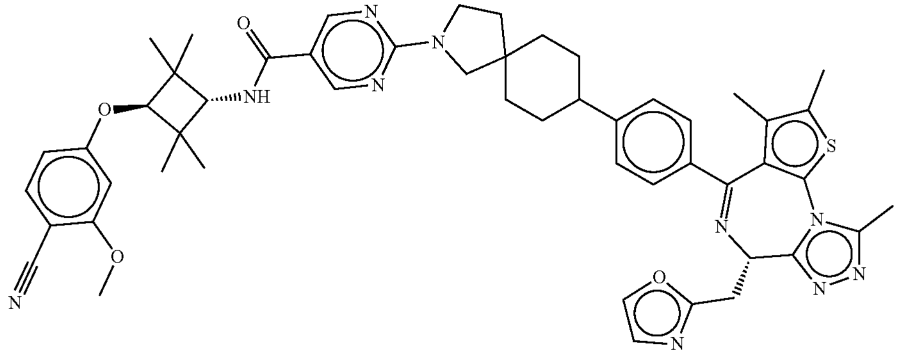 |
| II-12 | 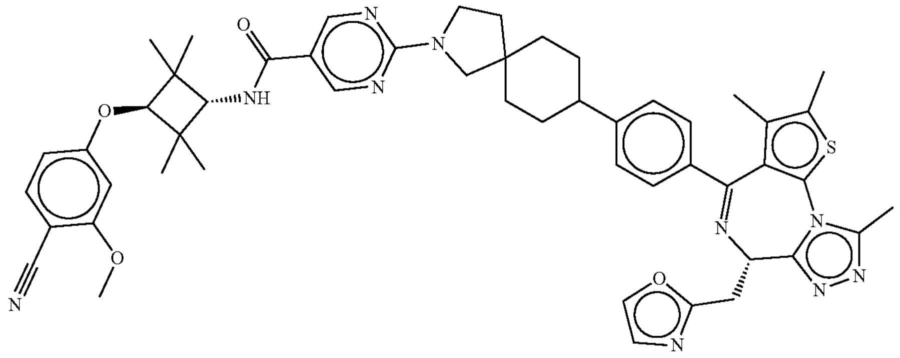 |

TABLE 2-continued
| Compound No. | Chemical Structure |
|---|---|
| II-13 | 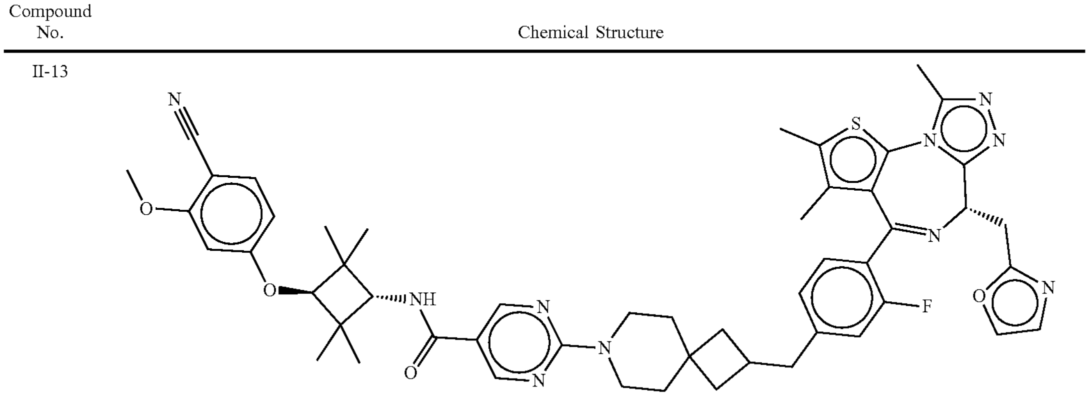 |
| II-14 | 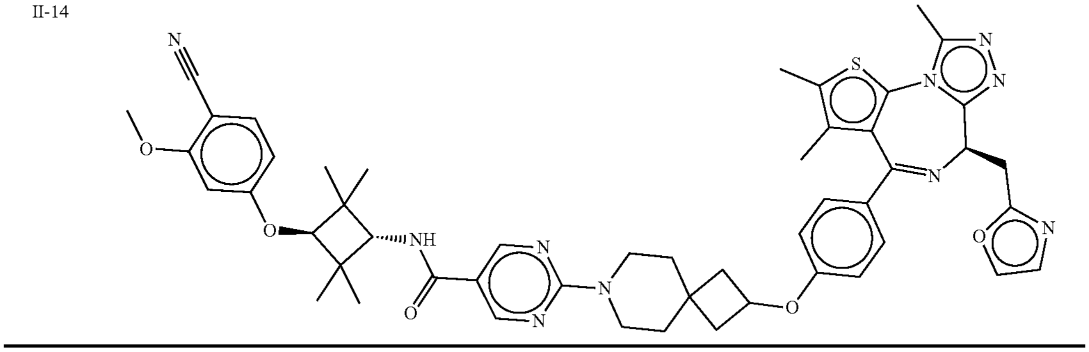 |
TABLE 3
| Compound No. | Chemical Structure |
|---|---|
| III-1 | 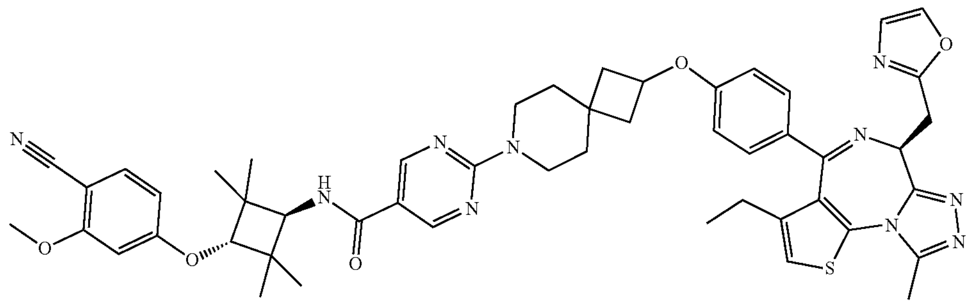 [SMILES: CCc1csc2c1C(c1ccc(OC3CC4(CCN(c5ncc(C(=O)N[C@H]6C(C)(C)[C@H](Oc7ccc(C#N)c(OC)c7)C6(C)C)cn5)CC4)C3)cc1)=N[C@@H](Cc1ncco1)c1nnc(C)n1-2] |
| III-2 | 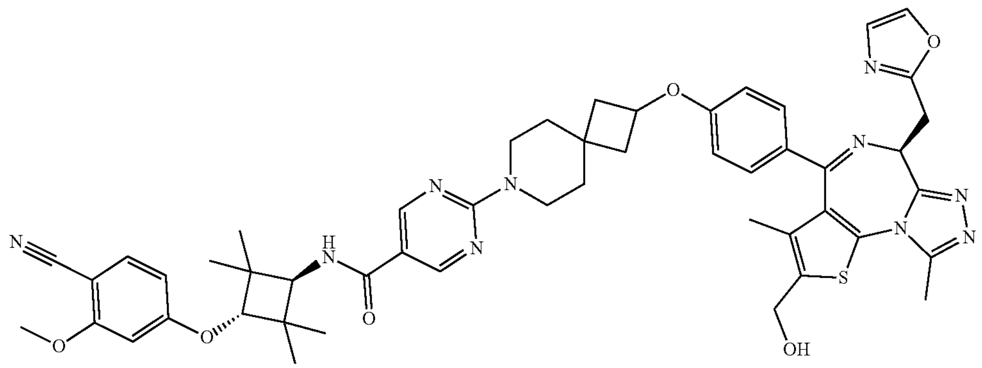 [SMILES: COc1cc(O[C@H]2C(C)(C)[C@H](NC(=O)c3cnc(N4CCC5(CC4)CC(Oc4ccc(C6=N[C@@H](Cc7ncco7)c7nnc(C)n7-c7sc(CO)c(C)c76)cc4)C5)nc3)C2(C)C)ccc1C#N] |

TABLE 3-continued

| Compound No. | Chemical Structure |
|---|---|
| III-3 | 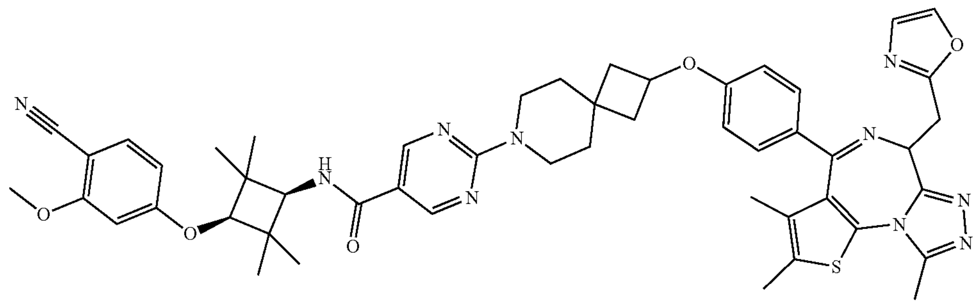 [SMILES: COc1cc(O[C@H]2C(C)(C)[C@@H](NC(=O)c3cnc(N4CCC5(CC4)CC(Oc4ccc(C6=NC(Cc7ncco7)c7nnc(C)n7-c7sc(C)c(C)c76)cc4)C5)nc3)C2(C)C)ccc1C#N] |

Synthetic Methods

Methods for preparing compounds described herein are illustrated in the following synthetic Scheme. The Scheme is given for the purpose of illustrating the invention, and is not intended to limit the scope or spirit of the invention. Starting materials shown in the Scheme can be obtained from commercial sources or can be prepared based on procedures described in the literature.

In the Scheme, it is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated (for example, use of protecting groups or alternative reactions). Protecting group chemistry and strategy is well known, such as described in, for example, "Protecting Groups in Organic Synthesis", T. W. Greene and P. G. M. Wuts, 3rd edition, John Wiley & Sons, 1999, the entire contents of which are hereby incorporated by reference.

The synthetic route illustrated in Scheme 1 is a general method for preparing compounds of Formula F. Reaction of chloride A and compound B where X is a boronic ester under palladium coupling conditions provides compound C. Removal of the protecting group (Pg) from compound C provides compound D. The Pg may be, for example, a Boc protecting group that can be removed by treating the compound with trifluoroacetic acid. Coupling of compound D with compound E (such as a nucleophilic aromatic substitution reaction when the leaving group in compound E is chloro) provides the final compound of Formula F.

SCHEME 1

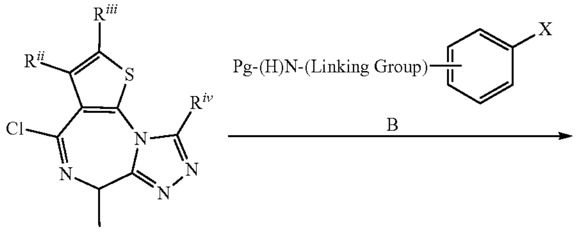

A

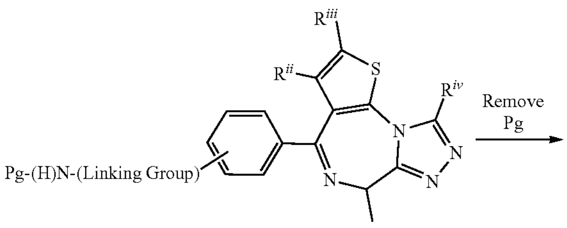

C

-continued

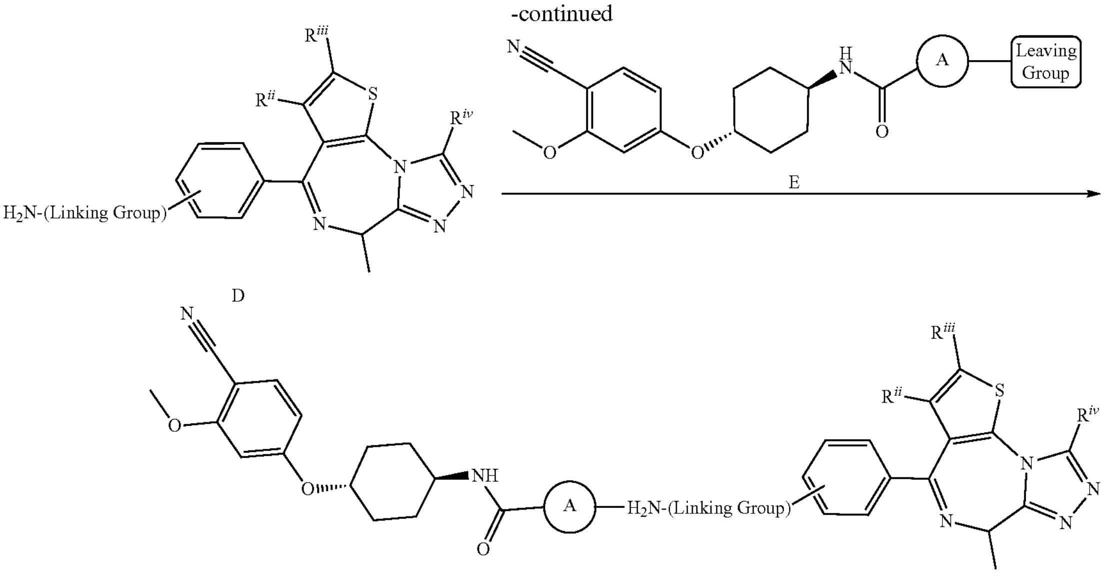

D

F

The modular synthetic route illustrated in Scheme 1 can be readily modified to provide additional compounds by conducting functional group transformations on the intermediate and/or final compounds. Such functional group transformations are well known in the art, as described in, for example, *Comprehensive Organic Synthesis* (B. M. Trost & I. Fleming, eds., 1991-1992); *Organic Synthesis, 3rd Ed.* (Michael B. Smith, Wavefunction, Inc., Irvine: 2010); *Modern Methods of Organic Synthesis, 4th Ed.* (William Carruthers and Iain Coldham, Cambridge University Press, Cambridge: 2004); *March's Advanced Organic Chemistry: Reactions, Mechanisms, and Structure, 8th Ed.*, (Michael B. Smith, John Wiley & Sons, New York: 2020); and *Comprehensive Organic Transformations: A Guide to Functional Group Preparations, 3rd Ed.* (Richard C. Larock, ed., John Wiley & Sons, New York: 2018). Protecting group strategies may be deployed as appropriate to accommodate differing functional groups in the molecules used in the synthetic route. Protecting group chemistry and strategy is described in, for example, *Protecting Groups in Organic Synthesis, 3rd Edition*, T. W. Greene and P. G. M. Wuts, John Wiley & Sons, 1999 and *Greene's Protective Groups in Organic Synthesis*, 5th *Ed.*, (Peter G. M. Wuts, John Wiley & Sons: 2014).

Part D: Crystalline Forms of the Compound of Formula II-5

Another aspect of the invention provides a crystalline compound of Formula II-5:

(II-5)

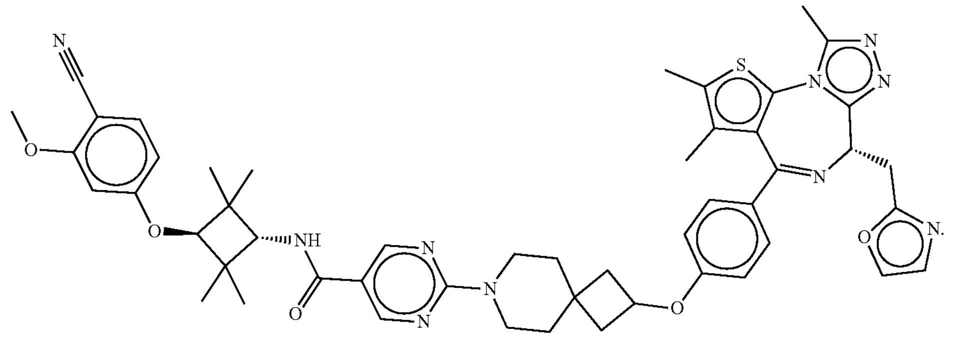

Crystalline forms of the compound of Formula II-5 can provide properties rendering the compound superior for use in manufacturing. For example, Crystal Form A of the compound of Formula II-5 having particularly good properties has been identified. One benefit of Crystal Form A is that it demonstrates superior stability relative to Crystal Form B.

Crystal Form A

One aspect of the invention provides a crystalline compound of Formula II-5 having Crystal Form A. Crystal Form A may be characterized according to X-ray powder diffraction, differential scanning calorimetry, and/or purity.

In certain embodiments, the compound exhibits an X-ray powder diffraction pattern comprising peaks at the following diffraction angles (2θ): 13.1±0.2, 17.6±0.2, 18.3±0.2, 18.7±0.2, 19.5±0.2, 23.8±0.2, and 25.6±0.2. In certain embodiments, the X-ray powder diffraction pattern further comprises a peak at the following diffraction angle (2θ): 8.1±0.2. In certain embodiments, the X-ray powder diffraction pattern further comprises a peak at the following diffraction angle (2θ): 9.9±0.2. In certain embodiments, the X-ray powder diffraction pattern further comprises a peak at the following diffraction angle (2θ): 10.5±0.2. In certain embodiments, the X-ray powder diffraction pattern further comprises a peak at the following diffraction angle (2θ): 15.8±0.2. In certain embodiments, the X-ray powder diffraction pattern further comprises a peak at the following diffraction angle (2θ): 19.8±0.2. In certain embodiments, the X-ray powder diffraction pattern further comprises a peak at the following diffraction angle (2θ): 25.3±0.2.

In certain embodiments, the compound exhibits an X-ray power diffraction pattern comprising at least one peak from the following diffraction angles (2θ): 13.1±0.2, 17.6±0.2, 18.3±0.2, 18.7±0.2, 19.5±0.2, 23.8±0.2, and 25.6±0.2. In certain embodiments, the compound exhibits an X-ray powder diffraction pattern comprising at least two, three, or four peaks from the following diffraction angles (2θ): 13.1±0.2, 17.6±0.2, 18.3±0.2, 18.7±0.2, 19.5±0.2, 23.8±0.2, and 25.6±0.2. In certain embodiments, the compound exhibits an X-ray powder diffraction pattern comprising at least five peaks from the following diffraction angles (2θ): 13.1±0.2, 17.6±0.2, 18.3±0.2, 18.7±0.2, 19.5±0.2, 23.8±0.2, and 25.6±0.2. In certain embodiments, the X-ray powder diffraction pattern further comprises a peak at the following diffraction angle (2θ): 8.1±0.2. In certain embodiments, the X-ray powder diffraction pattern further comprises a peak at the following diffraction angle (2θ): 9.9±0.2. In certain embodiments, the X-ray powder diffraction pattern further comprises a peak at the following diffraction angle (2θ): 10.5±0.2. In certain embodiments, the X-ray powder diffraction pattern further comprises a peak at the following diffraction angle (2θ): 15.8±0.2. In certain embodiments, the X-ray powder diffraction pattern further comprises a peak at the following diffraction angle (2θ): 19.8±0.2. In certain embodiments, the X-ray powder diffraction pattern further comprises a peak at the following diffraction angle (2θ): 25.3±0.2.

In certain embodiments, the relative intensity of the peak at said diffraction angles (2θ) is at least 20%. In certain embodiments, the relative intensity of the peak at said diffraction angles (2θ) is at least 30%.

In certain embodiments, the compound is characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 8.1 | 11.0 | 28 |
| 8.3 | 10.6 | 13 |
| 8.6 | 10.2 | 22 |
| 9.5 | 9.3 | 8 |
| 9.9 | 8.9 | 34 |
| 10.5 | 8.4 | 31 |
| 11.7 | 7.6 | 9 |
| 12.1 | 7.3 | 8 |
| 13.1 | 6.8 | 81 |
| 13.5 | 6.5 | 9 |
| 15.5 | 5.7 | 10 |
| 15.8 | 5.6 | 28 |
| 16.1 | 5.5 | 14 |
| 16.6 | 5.3 | 9 |
| 17.6 | 5.0 | 39 |
| 18.0 | 4.9 | 14 |
| 18.3 | 4.9 | 38 |
| 18.7 | 4.7 | 37 |
| 19.5 | 4.5 | 100 |
| 19.8 | 4.5 | 37 |

-continued

| Angle [2θ] | d-spacing [Å] | Relative Intensity [%] |
|---|---|---|
| 20.4 | 4.4 | 11 |
| 21.6 | 4.1 | 22 |
| 22.7 | 3.9 | 5 |
| 23.3 | 3.8 | 9 |
| 23.5 | 3.8 | 21 |
| 23.8 | 3.7 | 56 |
| 24.3 | 3.7 | 22 |
| 25.1 | 3.5 | 20 |
| 25.3 | 3.5 | 30 |
| 25.6 | 3.5 | 64 |
| 26.2 | 3.4 | 7 |
| 27.0 | 3.3 | 6 |
| 27.5 | 3.2 | 7 |
| 28.8 | 3.1 | 6 |
| 31.9 | 2.8 | 6 |
| 33.1 | 2.7 | 5 |
| 33.7 | 2.7 | 8 |

Figure 14:
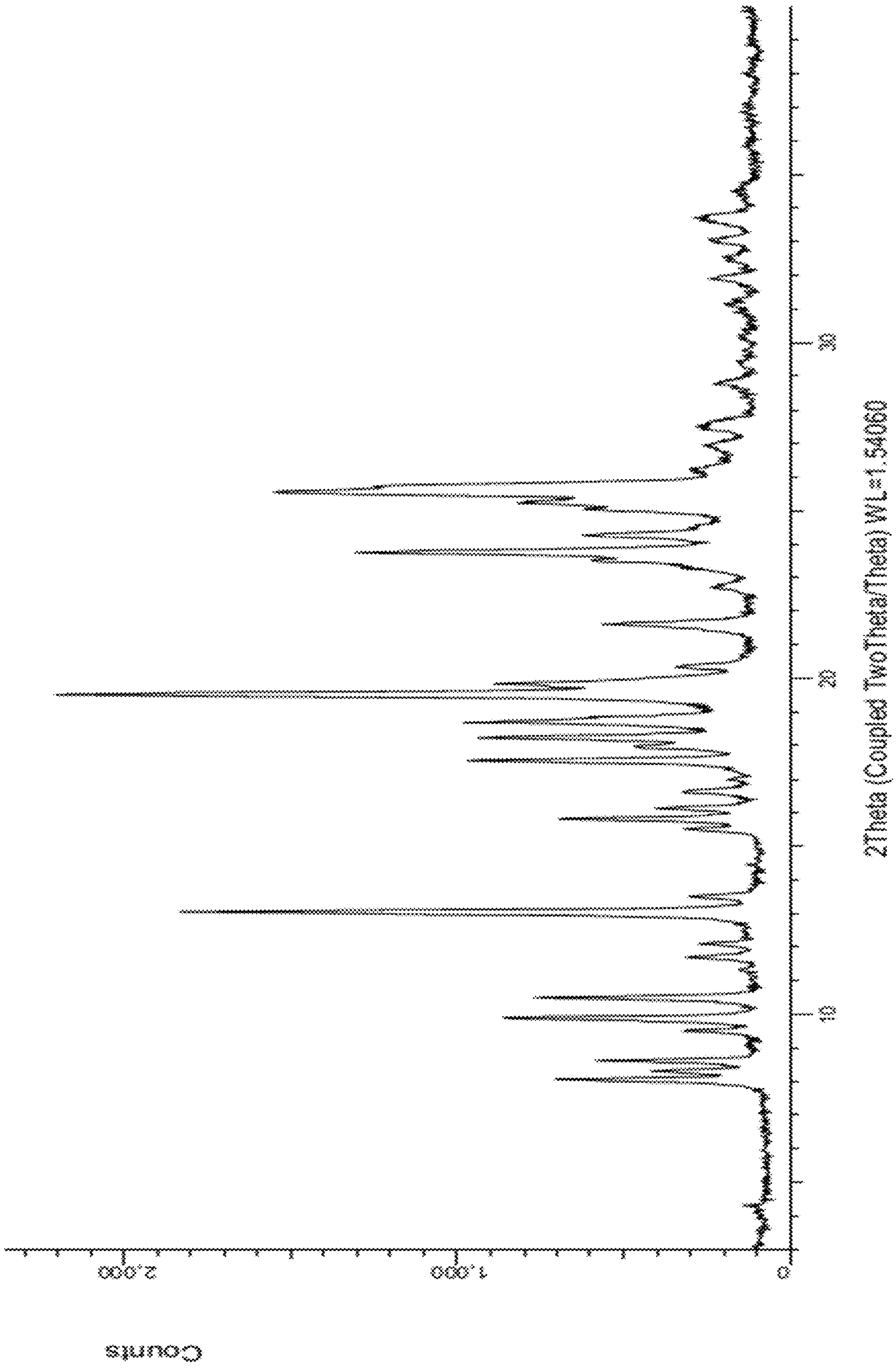
FIG. 14 depicts an X-ray powder diffractogram of Compound II-5 in Crystal Form A, as further described in Example 59.

In certain embodiments, the compound has an X-ray powder diffraction pattern substantially as shown in FIG. 14.

Figure 15:
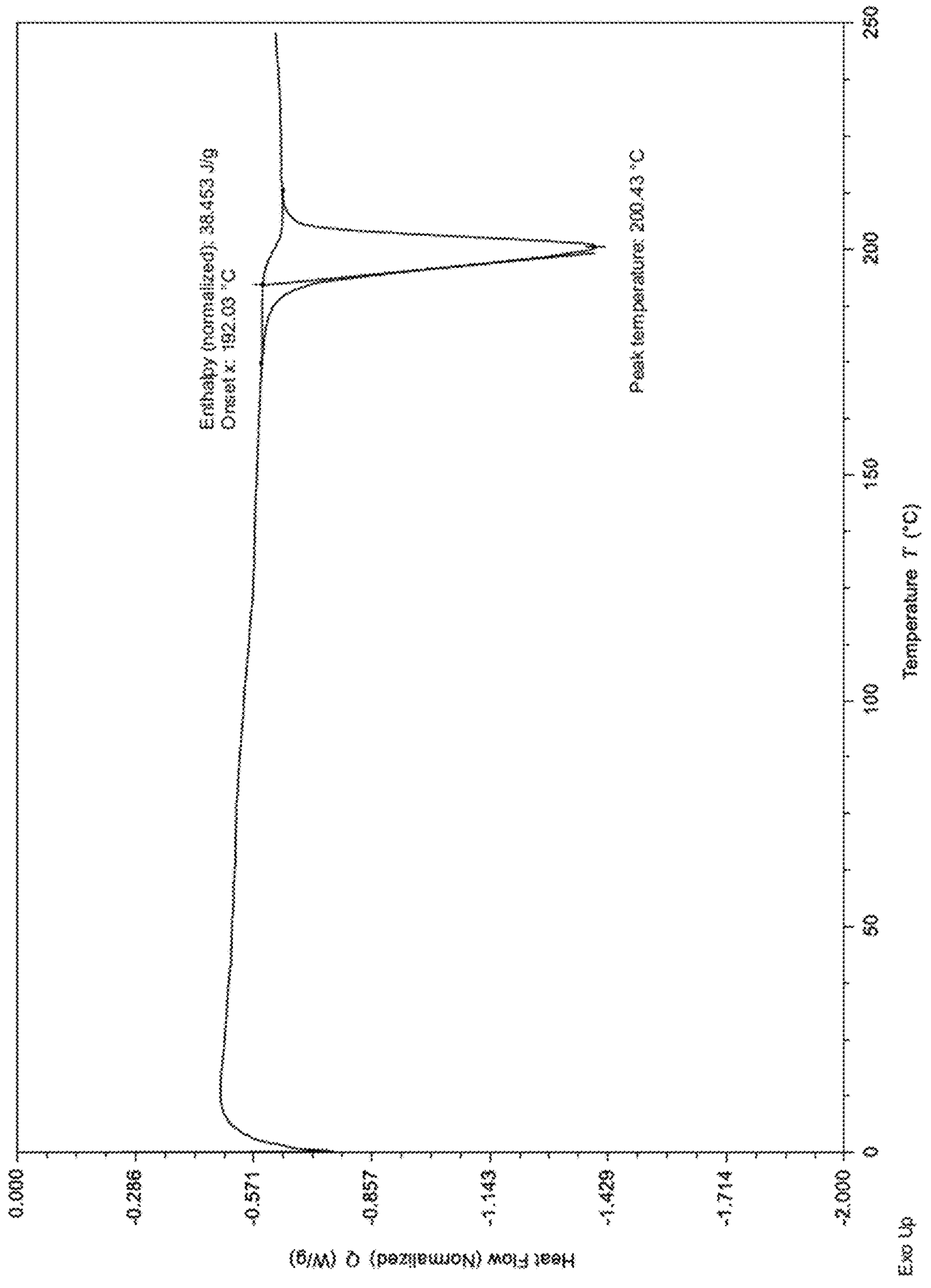
FIG. 15 depicts a differential scanning calorimetry curve of Compound II-5 in Crystal Form A, as further described in Example 59.

In certain embodiments, the compound has a melting point onset as determined by differential scanning calorimetry in the range of from about 180 degrees Celsius to about 200 degrees Celsius. In certain embodiments, the compound has a melting point onset as determined by differential scanning calorimetry at about 192 degrees Celsius. In certain embodiments, the compound has a melting point onset as determined by differential scanning calorimetry at 192 degrees Celsius. In certain embodiments, the compound has a differential scanning calorimetry curve substantially the same as shown in FIG. 15.

In certain embodiments, the compound has a purity of greater than 98% by weight. In certain embodiments, the compound has a purity of greater than 99% by weight. In certain embodiments, the compound has a purity of greater than 99.5% by weight. In certain embodiments, the purity of the compound is determined by high-performance liquid chromatography (HPLC).

Crystal Form B

Another aspect of the invention provides a crystalline compound of Formula II-5 having Crystal Form B. Crystal Form B may be characterized according to X-ray powder diffraction, differential scanning calorimetry, and/or purity.

In certain embodiments, the compound exhibits an X-ray powder diffraction pattern comprising peaks at the following diffraction angles (2θ): 9.4±0.2, 12.8±0.2, 15.4±0.2, 18.2±0.2, 18.7±0.2, 20.2±0.2, and 24.6±0.2. In certain embodiments, the X-ray powder diffraction pattern further comprises a peak at one or more of the following diffraction angles (2θ): 8.5±0.2, 11.7±0.2, 12.5±0.2, 17.6±0.2, 19.6±0.2, 21.9±0.2, and 23.5±0.2. In certain embodiments, the X-ray powder diffraction pattern further comprises a peak at the following diffraction angle (2θ): 8.5±0.2. In certain embodiments, the X-ray powder diffraction pattern further comprises a peak at the following diffraction angle (2θ): 11.7±0.2. In certain embodiments, the X-ray powder diffraction pattern further comprises a peak at the following diffraction angle (2θ): 12.5±0.2. In certain embodiments, the X-ray powder diffraction pattern further comprises a peak at the following diffraction angle (2θ): 17.6±0.2. In certain embodiments, the X-ray powder diffraction pattern further comprises a peak at the following diffraction angle (2θ): 19.6±0.2. In certain embodiments, the X-ray powder diffraction pattern further comprises a peak at the following diffraction angle (2θ): 21.9±0.2. In certain embodiments, the X-ray powder diffraction pattern further comprises a peak at the following diffraction angle (2θ): 23.5±0.2.

In certain embodiments, the compound exhibits an X-ray powder diffraction pattern comprising at least one peak from the following diffraction angles (2θ): 9.4±0.2, 12.8±0.2, 15.4±0.2, 18.2±0.2, 18.7±0.2, 20.2±0.2, and 24.6±0.2. In certain embodiments, the compound exhibits an X-ray powder diffraction pattern comprising at least two, three, or four peaks from the following diffraction angles (2θ): 9.4±0.2, 12.8±0.2, 15.4±0.2, 18.2±0.2, 18.7±0.2, 20.2±0.2, and 24.6±0.2. In certain embodiments, the compound exhibits an X-ray powder diffraction pattern comprising at least five peaks from the following diffraction angles (2θ): 9.4±0.2, 12.8±0.2, 15.4±0.2, 18.2±0.2, 18.7±0.2, 20.2±0.2, and 24.6±0.2. In certain embodiments, the X-ray powder diffraction pattern further comprises a peak at one or more of the following diffraction angles (2θ): 8.5±0.2, 11.7±0.2, 12.5±0.2, 17.6±0.2, 19.6±0.2, 21.9±0.2, and 23.5±0.2. In certain embodiments, the X-ray powder diffraction pattern further comprises a peak at the following diffraction angle (2θ): 8.5±0.2. In certain embodiments, the X-ray powder diffraction pattern further comprises a peak at the following diffraction angle (2θ): 11.7±0.2. In certain embodiments, the X-ray powder diffraction pattern further comprises a peak at the following diffraction angle (2θ): 12.5±0.2. In certain embodiments, the X-ray powder diffraction pattern further comprises a peak at the following diffraction angle (2θ): 17.6±0.2. In certain embodiments, the X-ray powder diffraction pattern further comprises a peak at the following diffraction angle (2θ): 19.6±0.2. In certain embodiments, the X-ray powder diffraction pattern further comprises a peak at the following diffraction angle (2θ): 21.9±0.2. In certain embodiments, the X-ray powder diffraction pattern further comprises a peak at the following diffraction angle (2θ): 23.5±0.2.

In certain embodiments, the relative intensity of the peak at said diffraction angles (2θ) is at least 20%. In certain embodiments, the relative intensity of the peak at said diffraction angles (2θ) is at least 30%.

In certain embodiments, the compound is characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 5.9 | 15.0 | 19 |
| 8.0 | 11.0 | 10 |
| 8.5 | 10.3 | 47 |
| 9.1 | 9.7 | 24 |
| 9.4 | 9.4 | 61 |
| 11.7 | 7.5 | 34 |
| 12.5 | 7.1 | 32 |
| 12.8 | 6.9 | 50 |
| 14.5 | 6.1 | 6 |
| 14.8 | 6.0 | 9 |
| 15.4 | 5.8 | 100 |
| 15.9 | 5.6 | 6 |
| 17.1 | 5.2 | 15 |
| 17.6 | 5.0 | 44 |
| 18.2 | 4.9 | 57 |
| 18.7 | 4.7 | 85 |
| 19.6 | 4.5 | 36 |
| 20.2 | 4.4 | 91 |
| 20.8 | 4.3 | 11 |
| 21.0 | 4.2 | 12 |
| 21.4 | 4.2 | 10 |
| 21.9 | 4.1 | 38 |
| 22.3 | 4.0 | 22 |

-continued

| Angle [2θ] | d-spacing [Å] | Relative Intensity [%] |
|---|---|---|
| 22.9 | 3.9 | 10 |
| 23.5 | 3.8 | 34 |
| 23.9 | 3.7 | 20 |
| 24.6 | 3.6 | 74 |
| 25.1 | 3.5 | 21 |
| 25.4 | 3.5 | 5 |
| 26.1 | 3.4 | 23 |
| 26.5 | 3.4 | 5 |
| 27.1 | 3.3 | 22 |
| 27.4 | 3.3 | 5 |
| 28.7 | 3.1 | 14 |
| 29.8 | 3.0 | 11 |
| 31.0 | 2.9 | 6 |
| 32.4 | 2.8 | 7 |

Figure 17:
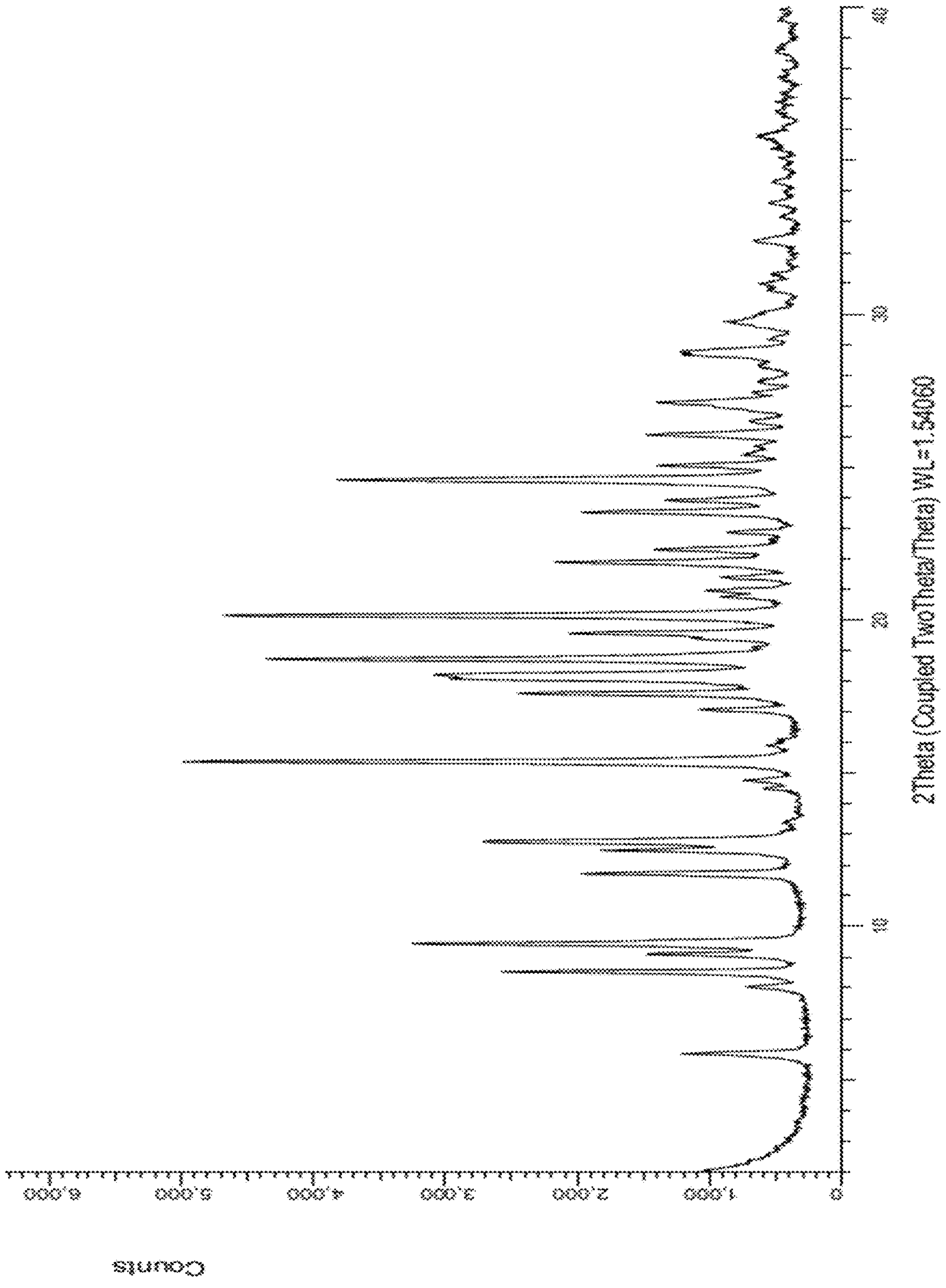
FIG. 17 depicts an X-ray powder diffractogram of Compound II-5 in Crystal Form B, as further described in Example 61.

In certain embodiments, the compound has an X-ray powder diffraction pattern substantially as shown in FIG. 17.

Figure 18:
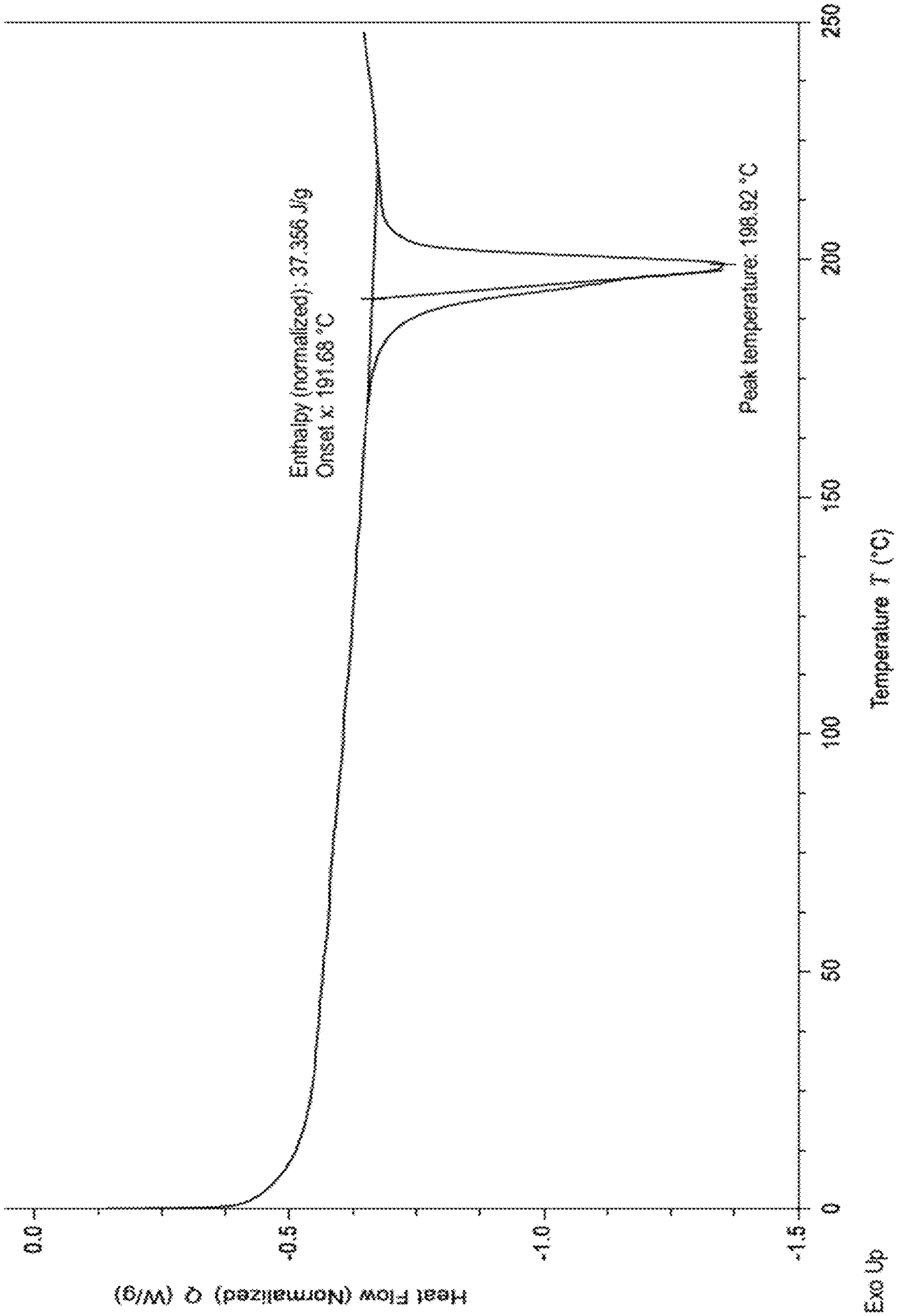
FIG. 18 depicts a differential scanning calorimetry curve of Compound II-5 in Crystal Form B, as further described in Example 61.

In certain embodiments, the compound has a melting point onset as determined by differential scanning calorimetry in the range of from about 180 degrees Celsius to about 200 degrees Celsius. In certain embodiments, the compound has a melting point onset as determined by differential scanning calorimetry at about 192 degrees Celsius. In certain embodiments, the compound has a melting point onset as determined by differential scanning calorimetry at 192 degrees Celsius. In certain embodiments, the compound has a differential scanning calorimetry curve substantially the same as shown in FIG. 18.

In certain embodiments, the compound has a purity of greater than 98% by weight. In certain embodiments, the compound has a purity of greater than 99% by weight. In certain embodiments, the compound has a purity of greater than 99.5% by weight. In certain embodiments, the purity of the compound is determined by high-performance liquid chromatography (HPLC).

The description above describes multiple embodiments related to crystalline forms of the compound of Formula II-5. The patent application specifically contemplates all combinations of the embodiments.

II. Therapeutic Applications

The heterobifunctional compounds described herein, such as a compound of Formula I, II, or other compounds in Section I, provide therapeutic benefits to patients suffering from cancer. Accordingly, one aspect of the invention provides a method of treating cancer. The method comprises administering to a patient in need thereof a therapeutically effective amount of a compound described herein, such as a compound of Formula I, II, or other compound in Section I, to treat the cancer. In certain embodiments, the compound is a compound of Formula I. In certain embodiments, the particular compound of Formula I is a compound defined by one of the embodiments described above.

Cancer

In certain embodiments, the cancer is ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct and gallbladder cancers, liver cancer, pancreatic cancer, bladder cancer, urinary tract cancer, kidney cancer, eye cancer, thyroid cancer, lymphoma, or leukemia. In certain embodiments, the cancer is prostate cancer.

In certain embodiments, the cancer is squamous cell cancer, lung cancer including small cell lung cancer, non-small cell lung cancer, vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer. In certain embodiments, the cancer is at least one selected from the group consisting of ALL, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL, Philadelphia chromosome positive CML, lymphoma, leukemia, multiple myeloma myeloproliferative diseases, large B cell lymphoma, or B cell Lymphoma.

In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

In certain embodiments, the cancer is a fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, or hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, castrate resistant prostate cancer, castrate resistant metastatic prostate cancer, papillary thyroid carcinoma, follicular thyroid carcinoma, medullary thyroid carcinoma, or leiomyoma.

In certain embodiments, the cancer is bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In certain embodiments, the cancer is hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In certain embodiments, the cancer is hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In certain embodiments, the cancer is a solid tumor, such as a sarcoma, carcinoma, or lymphoma. In certain embodiments, the cancer is kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In certain embodiments, the cancer is renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In certain embodiments, the cancer is hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In certain embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

Causing Death of Cancer Cell

Another aspect of the invention provides a method of causing death of a cancer cell. The method comprises contacting a cancer cell with an effective amount of a compound described herein, such as a compound of Formula I or II, or other compounds in Section I, to cause death of the cancer cell. In certain embodiments, the particular compound of Formula I or II is a compound defined by one of the embodiments described above.

In certain embodiments, the cancer cell is selected from ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct and gallbladder cancers, liver cancer, pancreatic cancer, bladder cancer, urinary tract cancer, kidney cancer, eye cancer, thyroid cancer, lymphoma, or leukemia. In certain embodiments, the cancer cell is one or more of the cancers recited in the section above entitled "Cancer." In certain embodiments, the cancer cell is a prostate cancer cell.

Exemplary Biological Activity Assays

Compounds described herein may be evaluated for biological activity using assays described herein.

A. Assay for Binding Affinity to Androgen Receptor

Compounds may be tested for ability to bind to the androgen receptor using the following procedure. Fractions of cell cytosol (106 cell/point) are incubated for 24 hr at 4° C. with 1 nM [$^3$H]methyltrienolone in the absence or presence of the test compound in a buffer containing 25 mM Hepes-Tris (pH 7.4), 1 mM EDTA, 10 mM $Na_2MoO_4$, 2 mM DTT, 5 μM triamcinolone acetonide, and 10% glycerol. Nonspecific binding may be determined in the presence of 1 μM testosterone. Following incubation, the samples are filtered rapidly under vacuum through glass fiber filters (GF/B, Packard) presoaked with 0.3% PEI and rinsed several times with ice-cold 50 mM Tris —HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is testosterone, which is tested in each experiment at several concentrations to obtain a competition curve from which its $IC_{50}$ is calculated.

B. Assay for Binding Affinity to BRD4-BD1

Compounds may be tested for ability to bind to BRD4-BD1 using the following experimental procedure. Compounds may be tested using a bromoKdELECT assay. T7 phage strains displaying bromodomains are grown in parallel in 24-well blocks in an *E. coli* host derived from the BL21 strain. *E. coli* are grown to log-phase and infected with T7 phage from a frozen stock (multiplicity of infection=0.4) and incubated with shaking at 32° C. until lysis (90-150 minutes). The lysates are centrifuged (5,000×g) and filtered (0.2 μm) to remove cell debris. Streptavidin-coated magnetic beads are treated with biotinylated small molecule or acetylated peptide ligands for 30 minutes at room temperature to generate affinity resins for bromodomain assays. The liganded beads are blocked with excess biotin and washed with blocking buffer (SeaBlock (Pierce), 1% BSA, 0.05% Tween 20, 1 mM DTT) to remove unbound ligand and to reduce nonspecific phage binding. Binding reactions are assembled by combining bromodomains, liganded affinity beads, and test compounds in 1× binding buffer (17%

SeaBlock, 0.33×PBS, 0.04% Tween 20, 0.02% BSA, 0.004% Sodium azide, 7.4 mM DTT). Test compounds are prepared as 1000× stocks in 100% DMSO. Kds are determined using an 11-point 3-fold compound dilution series with one DMSO control point. All compounds for Kd measurements are distributed by acoustic transfer (non-contact dispensing) in 100% DMSO. The compounds are then diluted directly into the assays such that the final concentration of DMSO was 0.09%. All reactions may be performed in polypropylene 384-well plates. Each has a final volume of 0.02 ml. The assay plates are incubated at room temperature with shaking for 1 hour and the affinity beads are washed with wash buffer (1×PBS, 0.05% Tween 20). The beads are then resuspended in elution buffer (1×PBS, 0.05% Tween 20, 2 μM non-biotinylated affinity ligand) and incubated at room temperature with shaking for 30 minutes. The bromodomain concentration in the eluates may be measured by qPCR.

C. Assay for Binding Affinity to BRD4-BD2

Compounds may be tested for ability to bind to BRD4-BD2 using the following experimental procedure. Compounds may be tested using a bromoKdELECT assay. T7 phage strains displaying bromodomains are grown in parallel in 24-well blocks in an *E. coli* host derived from the BL21 strain. *E. coli* are grown to log-phase and infected with T7 phage from a frozen stock (multiplicity of infection=0.4) and incubated with shaking at 32° C. until lysis (90-150 minutes). The lysates are centrifuged (5,000×g) and filtered (0.2 μm) to remove cell debris. Streptavidin-coated magnetic beads are treated with biotinylated small molecule or acetylated peptide ligands for 30 minutes at room temperature to generate affinity resins for bromodomain assays. The liganded beads are blocked with excess biotin and washed with blocking buffer (SeaBlock (Pierce), 1% BSA, 0.05% Tween 20, 1 mM DTT) to remove unbound ligand and to reduce nonspecific phage binding. Binding reactions are assembled by combining bromodomains, liganded affinity beads, and test compounds in 1× binding buffer (17% SeaBlock, 0.33×PBS, 0.04% Tween 20, 0.02% BSA, 0.004% Sodium azide, 7.4 mM DTT). Test compounds are prepared as 1000× stocks in 100% DMSO. Kds were determined using an 11-point 3-fold compound dilution series with one DMSO control point. All compounds for Kd measurements are distributed by acoustic transfer (non-contact dispensing) in 100% DMSO. The compounds are then diluted directly into the assays such that the final concentration of DMSO was 0.09%. Reactions may be performed in polypropylene 384-well plates. Each has a final volume of 0.02 ml. The assay plates are incubated at room temperature with shaking for 1 hour and the affinity beads are washed with wash buffer (1×PBS, 0.05% Tween 20). The beads are then resuspended in elution buffer (1×PBS, 0.05% Tween 20, 2 μM non-biotinylated affinity ligand) and incubated at room temperature with shaking for 30 minutes. The bromodomain concentration in the eluates may be measured by qPCR.

Combination Therapies

The compounds useful within the methods of the invention may be used in combination with one or more additional therapeutic agents useful for treating any disease contemplated herein. These additional therapeutic agents may comprise compounds that are commercially available or synthetically accessible to those skilled in the art. These additional therapeutic agents are known to treat, prevent, or reduce the symptoms, of a disease or disorder contemplated herein.

Accordingly, in certain embodiments, the method further comprises administering to the subject an additional therapeutic agent that treats the disease contemplated herein.

In certain embodiments, administering the compound of the invention to the subject allows for administering a lower dose of the additional therapeutic agent as compared to the dose of the additional therapeutic agent alone that is required to achieve similar results in treating the disease contemplated herein. For example, in certain embodiments, the compound of the invention enhances the therapeutic activity of the additional therapeutic compound, thereby allowing for a lower dose of the additional therapeutic compound to provide the same effect.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In certain embodiments, the compound of the invention and the therapeutic agent are co-administered to the subject. In other embodiments, the compound of the invention and the therapeutic agent are coformulated and co-administered to the subject.

In certain embodiments, the compound is administered in combination with a second therapeutic agent having activity against cancer. In certain embodiments, the second therapeutic agent is mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

In certain embodiments, the second therapeutic agent is an mTOR inhibitor, which inhibits cell proliferation, angiogenesis and glucose uptake. Approved mTOR inhibitors useful in the present invention include everolimus (Afinitor®, Novartis); temsirolimus (Torisel®, Pfizer); and sirolimus (Rapamune®, Pfizer).

In certain embodiments, the second therapeutic agent is a Poly ADP ribose polymerase (PARP) inhibitor. Approved PARP inhibitors useful in the present invention include olaparib (Lynparza®, AstraZeneca); rucaparib (Rubraca®, Clovis Oncology); and niraparib (Zejula®, Tesaro). Other PARP inhibitors being studied which may be used in the present invention include talazoparib (MDV3800/BMN 673/LT00673, Medivation/Pfizer/Biomarin); veliparib (ABT-888, Abb Vie); and BGB-290 (BeiGene, Inc.).

In certain embodiments, the second therapeutic agent is a phosphatidylinositol 3 kinase (PI3K) inhibitor. Approved PI3K inhibitors useful in the present invention include idelalisib (Zydelig®, Gilead). Other PI3K inhibitors being studied which may be used in the present invention include alpelisib (BYL719, Novartis); taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In certain embodiments, the second therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In certain embodiments, the second therapeutic agent is a histone deacetylase (HDAC) inhibitor. Approved HDAC inhibitors useful in the present invention include vorinostat (Zolinza®, Merck); romidepsin (Istodax®, Celgene); panobinostat (Farydak®, Novartis); and belinostat (Beleodaq®, Spectrum Pharmaceuticals). Other HDAC inhibitors being studied which may be used in the present invention include entinostat (SNDX-275, Syndax Pharmaceuticals) (NCT00866333); and chidamide (Epidaza®, HBI-8000, Chipscreen Biosciences, China).

In certain embodiments, the second therapeutic agent is a CDK inhibitor, such as a CDK 4/6 inhibitor. Approved CDK 4/6 inhibitors useful in the present invention include palbociclib (Ibrance®, Pfizer); and ribociclib (Kisqali®, Novartis). Other CDK 4/6 inhibitors being studied which may be used in the present invention include abemaciclib (Ly2835219, Eli Lilly); and trilaciclib (G1T28, G1 Therapeutics).

In certain embodiments, the second therapeutic agent is an indoleamine (2,3)-dioxygenase (IDO) inhibitor. IDO inhibitors being studied which may be used in the present invention include epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS: F001287 (Bristol-Myers Squibb); Phy906/KD108 (Phytoceutica); and an enzyme that breaks down kynurenine (Kynase, Kyn Therapeutics).

In certain embodiments, the second therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In certain embodiments, the second therapeutic agent is an aromatase inhibitor. Approved aromatase inhibitors which may be used in the present invention include exemestane (Aromasin®, Pfizer); anastazole (Arimidex®, AstraZeneca) and letrozole (Femara®, Novartis).

In certain embodiments, the second therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In certain embodiments, the second therapeutic agent is a folic acid inhibitor. Approved folic acid inhibitors useful in the present invention include pemetrexed (Alimta®, Eli Lilly).

In certain embodiments, the second therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In certain embodiments, the second therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In certain embodiments, the second therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In certain embodiments, the second therapeutic agent is a glutaminase inhibitor. Glutaminase inhibitors being studied which may be used in the present invention include CB-839 (Calithera Biosciences).

In certain embodiments, the second therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In certain embodiments, the second therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In certain embodiments, the second therapeutic agent is a nucleoside inhibitor, or other therapeutic that interfere with normal DNA synthesis, protein synthesis, cell replication, or will otherwise inhibit rapidly proliferating cells. Such nucleoside inhibitors or other therapeutics include trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNUR, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In certain embodiments, the second therapeutic agent is a platinum-based therapeutic, also referred to as platins. Platins cause cross-linking of DNA, such that they inhibit DNA repair and/or DNA synthesis, mostly in rapidly reproducing cells, such as cancer cells. Approved platinum-based therapeutics which may be used in the present invention include cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); and nedaplatin (Aqupla®, Shionogi). Other platinum-based therapeutics which have undergone clinical testing and may be used in the present invention include picoplatin (Poniard Pharmaceuticals); and satraplatin (JM-216, Agennix).

In certain embodiments, the second therapeutic agent is a taxane compound, which causes disruption of microtubules, which are essential for cell division. Approved taxane compounds which may be used in the present invention include paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), and cabazitaxel (Jevtana®, Sanofi-Aventis). Other taxane compounds which have undergone clinical testing and may be used in the present invention include SID530 (SK Chemicals, Co.) (NCT00931008).

In certain embodiments, the second therapeutic agent is an inhibitor of anti-apoptotic proteins, such as BCL-2. Approved anti-apoptotics which may be used in the present invention include venetoclax (Venclexta®, Abb Vie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In certain embodiments, the second therapeutic agent is a selective estrogen receptor modulator (SERM), which interferes with the synthesis or activity of estrogens. Approved SERMs useful in the present invention include raloxifene (Evista®, Eli Lilly).

In certain embodiments, the second therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In certain embodiments, the second therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA-formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In certain embodiments, the second therapeutic agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, the additional therapeutic agent is selected from an oncolytic viral therapy such as pexastimogene devacirepvec (Pexa Vec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In certain embodiments, the second therapeutic agent is an immune checkpoint inhibitor selected from a PD-1 antagonist, a PD-L1 antagonist, or a CTLA-4 antagonist. In some embodiments, a compound disclosed herein or a pharmaceutically acceptable salt thereof is administered in combination with nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); or atezolizumab (anti-PD-L1 antibody, Tecentriq®, Genentech). Other immune checkpoint inhibitors suitable for use in the present invention include REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

Another aspect of the invention provides for the use of a compound described herein (such as a compound of Formula I, Formula II, or other compounds in Section I) in the manufacture of a medicament. In certain embodiments, the medicament is for treating a disease described herein, such as cancer.

Another aspect of the invention provides for the use of a compound described herein (such as a compound of Formula I, Formula II, or other compounds in Section I) for treating a medical disease, such a disease described herein (e.g., cancer).

Another aspect of the invention provides a compound described herein (such as a compound of Formula I, Formula II, or other compounds in Section I) for use in treating a medical disorder, such as a medical disorder described herein, such as cancer.

Evaluation of Cellular Growth Inhibition of HEK293 cells and HeLa cells

Compounds can be evaluated for ability to inhibit the proliferation of HEK293 cells or HeLa cells according to the following procedure. HEK293 and HeLa cells are cultured in DMEM medium supplemented with 10% fetal bovine serum and 1% Penn/Strep. Cells are seeded in white 384-well plates at 500 cells/well in 25 μL complete medium. Following seeding, plates are spun at 300×g for three minutes and cultured at 37° C. with 5% $CO_2$ in a humidified tissue culture incubator. After 24 hours, compounds are titrated in 100% DMSO and diluted in complete cell culture medium. A 25 μL aliquot of compound/media mixture is added to cells to bring total volume in well to 50 μL. DMSO alone is used as a negative control. Plates are then spun at 300×g for three minutes and stored at 37° C. with 5% $CO_2$ for three days. On Day 0 and Day 3 of compound treatment, cell viability is quantified with CellTiter-Glo 2.0 reagent (Promega). After equilibrating microplates at room temperature for 30 minutes, 25 μL CellTiter-Glo 2.0 reagent is dispensed into each well to bring total volume to 75 L. Plates are mixed on shaker for 2 minutes at 500 rpm, followed by a 10-minute incubation at room temperature. Following a quick spin, luminescence readings are measured with an En Vision Plate Reader. Data is normalized to DMSO treated Day 0 and Day 3 readings. A four-parameter non-linear regression curve fit is applied to dose-response data in GraphPad Prism data analysis software to determine the half maximal growth inhibitory concentration ($GI_{50}$) for each compound.

III. Pharmaceutical Compositions and Dosing Considerations

As indicated above, the invention provides pharmaceutical compositions, which comprise a therapeutically effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In certain embodiments, the invention provides a pharmaceutical composition comprising a compound described herein (e.g., a compound of Formula I) and a pharmaceutically acceptable carrier.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a heterobifunctional substituted phenylpyrimidinone or related compound described herein in a therapeutically effective amount for the treatment of a medical disorder described herein.

IV. Medical Kits

Another aspect of this invention is a kit comprising (i) a compound described herein, such as a compound of Formula I, Formula II, or other compounds in Section I, and (ii) instructions for use, such as treating cancer.

EXAMPLES

The invention now being generally described, will be more readily understood by reference to the following examples, which are included merely for purposes of illustration of certain aspects and embodiments of the present invention, and are not intended to limit the invention.

General Methods

All reactions were carried out under an atmosphere of dry nitrogen or argon. Glassware was oven-dried prior to use. Unless otherwise indicated, common reagents or materials were obtained from commercial sources and used without further purification. Anhydrous N,N-Diisopropylethylamine (DIPEA) was obtained by distillation over potassium hydroxide. Tetrahydrofuran (THF), dichloromethane ($CH_2Cl_2$), and dimethylformamide (DMF) were dried by a PureSolv™ solvent drying system. PTLC refers to preparatory thin layer chromatographic separation. Abbreviations: HFIP (hexafluoroisopropanol), HEPES (4-(2-hydroxyethyl)-1-piperazineethanesulfonic acid. Flash column chromatography was performed using silica gel 60 (230-400 mesh). Analytical thin layer chromatography (TLC) was carried out on Merck silica gel plates with QF-254 indicator and visualized by UV or $KMnO_4$.

$^1H$ and $^{13}C$ NMR spectra were recorded on an Agilent $DD_2$ 500 (500 MHz 1H; 125 MHz $^{13}C$) or Agilent $DD_2$ 600 (600 MHz 1H; 150 MHz $^{13}C$) or Agilent $DD_2$ 400 (400 MHz 1H; 100 MHz $^{13}C$) spectrometer at room temperature. Chemical shifts were reported in ppm relative to residual $CDCl_3$ (δ 7.26 ppm $^1H$; δ 77.0 ppm $^{13}C$), $CD_3OD$ (δ 3.31 ppm 1H; δ 49.00 ppm $^{13}C$), or $d_6$-DMSO (δ 2.50 ppm $^1H$; δ 39.52 ppm $^{13}C$). NMR chemical shifts were expressed in ppm relative to internal solvent peaks, and coupling constants were measured in Hz. (bs=broad signal). In most cases, only peaks of the major rotamer are reported.

Mass spectra were obtained using Agilent 1100 series LC/MSD spectrometers. Analytical HPLC analyses were carried out on a 250×4.6 mm C-18 column using gradient conditions (10-100% B, flow rate=1.0 mL/min, 20 min), or as described in the LC-MS Method tables.

Unless indicated otherwise, preparative HPLC was carried out on a 250×21.2 mm C-18 column using gradient conditions (10-100% B, flow rate=10.0 mL/min, 20 min). The eluents used were: solvent A ($H_2O$ with 0.1% TFA) and solvent B ($CH_3CN$ with 0.1% TFA). Final products were typically purified via reversed-phase HPLC, PTLC, or flash column chromatography.

LC-MS Method 01

| | | | | |
|---|---|---|---|---|
| Instrument | | Agilent 1100 LC & Agilent G1956A | | |
| Software | | Agilent Chemstation Rev. B. 04.03[54] | | |
| HPLC | Column | Agilent ZORBAX 5 μm SB-Aq, 2.1*50 mm | | |
| | Mobile Phase | A: 0.0375% TFA in water (v/v)<br>B: 0.01875% TFA in Acetonitrile (v/v) | | |
| | Gradient | Time (min) | B (%) | Flow (mL/min) |
| | | 0.00 | 1 | 0.8 |
| | | 0.40 | 1 | 0.8 |
| | | 3.40 | 90 | 0.8 |
| | | 3.90 | 100 | 0.8 |
| | | 3.91 | 1 | 0.8 |
| | | 4.00 | 1 | 1.0 |
| | | 4.50 | 1 | 1.0 |
| | Post time (min) | 0 | | |
| | Column Temp | 50° C. | | |
| | Detector | DAD | | |

-continued

| LC-MS Method 01 | | |
|---|---|---|
| MS | Ionization source | ESI |
| | Drying Gas | $N_2$ |
| | Drying Gas Flow | 10 (L/min) |
| | Nebulizer Pressure | 40 (psi) |
| | Drying Gas Temperature | 350° C. |
| | Capillary Voltage | 2500 (V) |
| | MS Polarity | Positive |

| LC-MS Method 5-95 | | | | |
|---|---|---|---|---|
| Instrument | | SHIMADZU LCMS-2020 | | |
| Software | | LabSolution Version 5.93 | | |
| HPLC | Column | Kinetex EVO C18 2.1 × 30 mm, 5 um | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.0 | 5 | 1.5 |
| | | 0.80 | 95 | 1.5 |
| | | 1.20 | 95 | 1.5 |
| | | 1.21 | 5 | 1.5 |
| | | 1.55 | 5 | 1.5 |
| | Column Temp | 50° C. | | |
| | Detector | PDA (220 nm&254 nm) | | |
| MS | Ionization source | ESI | | |
| | Drying Gas Flow | 15(L/min) | | |
| | DL Voltage | 120(v) | | |
| | Qarray DC Voltage | 20(V) | | |
| | MS Polarity | Positive | | |
| | MS Mode | Scan | | |
| | Mass range | 100-1000 | | |

| LC-MS Method 10 | | | | |
|---|---|---|---|---|
| Instrument | | Agilent 1100 LC & Agilent G1956A | | |
| Software | | Agilent Chemstation Rev. B. 04.03[54] | | |
| HPLC | Column | Agilent ZORBAX 5 μm SB-Aq, 2.1*50 mm | | |
| | Mobile Phase | A: 0.0375% TFA in water (v/v) | | |
| | | B: 0.01875% TFA in Acetonitrile (v/v) | | |
| | Gradient | Time (min) | B (%) | Flow (mL/min) |
| | | 0.00 | 10 | 0.8 |
| | | 0.40 | 10 | 0.8 |
| | | 3.40 | 100 | 0.8 |
| | | 3.90 | 100 | 0.8 |
| | | 3.91 | 10 | 0.8 |
| | | 4.00 | 10 | 1.0 |
| | | 4.50 | 10 | 1.0 |
| | Post time (min) | 0 | | |
| | Column Temp | 50° C. | | |
| | Detector | DAD | | |
| MS | Ionization source | ESI | | |
| | Drying Gas | $N_2$ | | |
| | Drying Gas Flow | 10 (L/min) | | |
| | Nebulizer Pressure | 40 (psi) | | |
| | Drying Gas Temperature | 350° C. | | |
| | Capillary Voltage | 2500 (V) | | |
| | MS Polarity | Positive | | |
| | MS Mode | Scan | | |
| | Mass Range | 100-1500 | | |

| LC-MS Method 25 | | | | |
|---|---|---|---|---|
| Instrument | | Agilent 1100 LC & Agilent G1956A | | |
| Software | | Agilent Chemstation Rev. B. 04.03[54] | | |
| HPLC | Column | Agilent ZORBAX 5 μm SB-Aq, 2.1*50 mm | | |
| | Mobile Phase | A: 0.0375% TFA in water (v/v) | | |
| | | B: 0.01875% TFA in Acetonitrile (v/v) | | |
| | Gradient | Time (min) | B (%) | Flow (mL/min) |
| | | 0.00 | 25 | 0.8 |
| | | 0.40 | 25 | 0.8 |
| | | 3.40 | 100 | 0.8 |
| | | 3.90 | 100 | 0.8 |
| | | 3.91 | 25 | 0.8 |
| | | 4.00 | 25 | 1.0 |
| | | 4.50 | 25 | 1.0 |
| | Post time (min) | 0 | | |
| | Column Temp | 50° C. | | |
| | Detector | DAD | | |
| MS | Ionization source | ESI | | |
| | Drying Gas | $N_2$ | | |
| | Drying Gas Flow | 10 (L/min) | | |
| | Nebulizer Pressure | 40 (psi) | | |
| | Drying Gas Temperature | 350° C. | | |
| | Capillary Voltage | 2500 (V) Positive | | |
| | MS Polarity | Positive | | |
| | MS Mode | Scan | | |

| LC-MS METHOD 40 | | | | |
|---|---|---|---|---|
| Instrument | | Agilent 1100 LC & Agilent G1956A | | |
| Software | | Agilent Chemstation Rev. B. 04.03[16] | | |
| HPLC | Column | Agilent ZORBAX 5 μm SB-Aq, 2.1*50 mm | | |
| | Mobile Phase | A: 0.0375% TFA in water (v/v) | | |
| | | B: 0.01875% TFA in Acetonitrile (v/v) | | |
| | Gradient | Time (min) | B (%) | Flow (mL/min) |
| | | 0.00 | 40 | 0.8 |
| | | 0.40 | 40 | 0.8 |
| | | 3.40 | 100 | 0.8 |
| | | 3.90 | 100 | 0.8 |
| | | 3.91 | 40 | 0.8 |
| | | 4.00 | 40 | 1.0 |
| | | 4.50 | 40 | 1.0 |
| | Post time (min) | 0 | | |
| | Column Temp | 50° C. | | |
| | Detector | DAD(Agilent 1100)/ELSD(Agilent 1260 Infinity) | | |
| MS | Ionization source | ESI | | |
| | Drying Gas | $N_2$ | | |
| | Drying Gas Flow | 10 (L/min) | | |
| | Nebulizer Pressure | 2070 (Torr) | | |
| | Drying Gas Temperature | 350° C. | | |
| | Capillary Voltage | 2500 (V) Positive | | |

The following abbreviations are used herein: ACN or MeCN: acetonitrile; AcO: acetate; AcOH: acetic acid; $B_2pin_2$: bis(pinacolato)diboron; BINAP: 2,2'-bis(diphenylphosphino)-1,1'-binaphthyl; Bn: benzyl; Boc: tert-butoxycarbonyl; BPD: bis(pinacolato) diboron; BrettPhos Pd G3: [(2-di-cyclohexylphosphino-3,6-dimethoxy-2',4',6'-triisopropyl-1,1'-biphenyl)-2-(2'-amino-1,1'-biphenyl)]palladium (II) methanesulfonate methanesulfonate; DavePhos Pd G3: [2-(dicyclohexyl-phosphino)-2-(N,N-dimethylamino)-1,1-biphenyl]-2-(2-amino-1,1-biphenyl)]palladium (II) methanesulfonate; DCM: dichloromethane; DIAD: diisopropyl azodicarboxylate; DIEA: diisopropylethylamine; DMAC:

dimethylacetamide; DMAP: 4-dimethylaminopyridine; DMF: dimethylformamide; DMSO: dimethylsulfoxide; EtOH: ethanol; EA or EtOAc: ethyl acetate; equiv or eq: molar equivalents; FA: formic acid; Fmoc: fluorenylmethoxycarbonyl; h: hour or hours; HATU: 1-[bis(dimethylamino)methylene]-1H-1,2,3-triazolo[4,5-b]pyridinium 3-oxide hexafluoro-phosphate; HPLC: high-pressure liquid chromatography; IPA or i-PrOH: isopropyl alcohol; JQ1: 2-[(9S)-7-(4-chlorophenyl)-4,5,13-trimethyl-3-thia-1,8,11,12-tetrazatricyclo[8.3.0.0$^{2,6}$]trideca-2 (6), 4,7,10,12-pentaen-9-yl]acetic acid; LCMS or LC-MS: liquid chromatography-mass spectrometry; MeOH: methanol; min: minute or minutes; MS: mass spectrometry; n-BuLi: n-butyl lithium; NMM: N-methylmorpholine; NMP: N-methylpyrrolidone; NMR: nuclear magnetic resonance; $PCy_3$: tricyclohexylphospine; $Pd(dba)_2$: Palladium(0) bis(dibenzylidene-acetone); $Pd_2(dba)_3$: tris(dibenzylideneacetone) dipalladium (0); $Pd(dppf)Cl_2$: [1,1'-bis(diphenylphosphino) ferrocene] dichloro palladium (II); PE: petroleum ether; PPA: polyphosphoric acid; psi: pounds-per-square-inch; rt: room temperature; SFC: supercritical fluid chromatography; SPhos Pd G3: (2-dicyclohexylphosphino-2',6'-dimethoxybiphenyl) [2-(2'-amino-1,1'-biphenyl)]palladium (II) methanesulfonate; tBuXPhos Pd G3: methanesulfonato (2-di-t-butylphosphino-2',4',6'-tri-i-propyl-1,1'-biphenyl) (2'-amino-1,1'-biphenyl-2-yl) palladium (II); tert-BuO: tert-butoxide; tert-BuOH: tert-butanol; TEA: triethylamine; TFA: trifluoroacetic acid; THF: tetrahydrofuran; TMP: tetramethylpiperidine; TMS: trimethylsilyl; Tos or Ts: p-toluenesulfonyl; T4P: 3-{2,6,8-trioxo-9-[(2R,3R,4R)-2,3,4,5-tetrahydroxypentyl]-1,2,3,6,8,9-hexahydro-7H-purin-7-yl}propyl dihydrogen phosphate; XANTPHOS: (9,9-dimethyl-9H-xanthene-4,5-diyl) bis(diphenylphosphane); and XPhos: dicyclohexyl[2',4',6'-tris(propan-2-yl) [1,1'-biphenyl]-2-yl] phosphane.

Example 1—Synthesis of N-[4-[4-cyano-3-(trifluoromethoxy)phenoxy]cyclohexyl]-6-[6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-6)

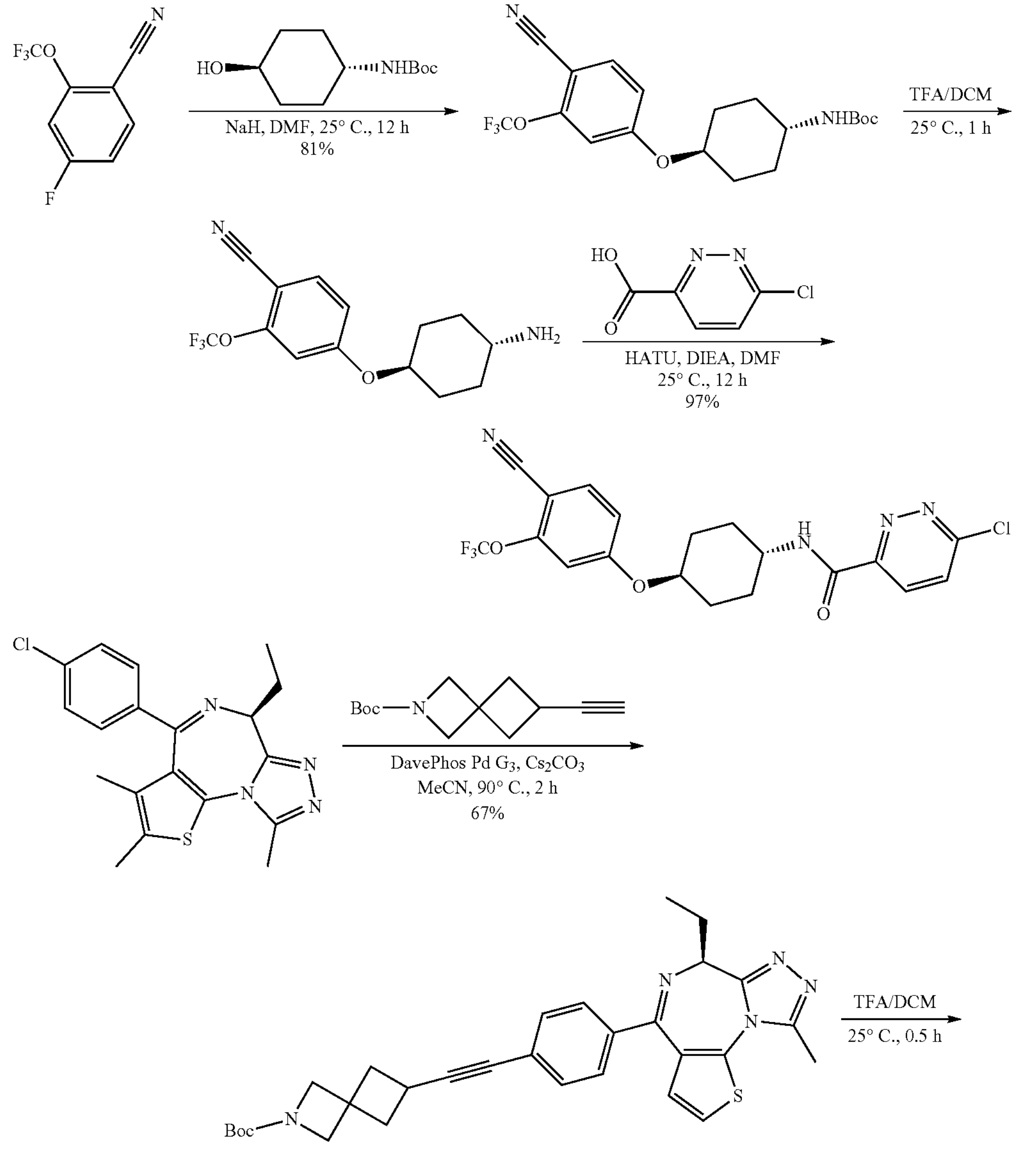

-continued

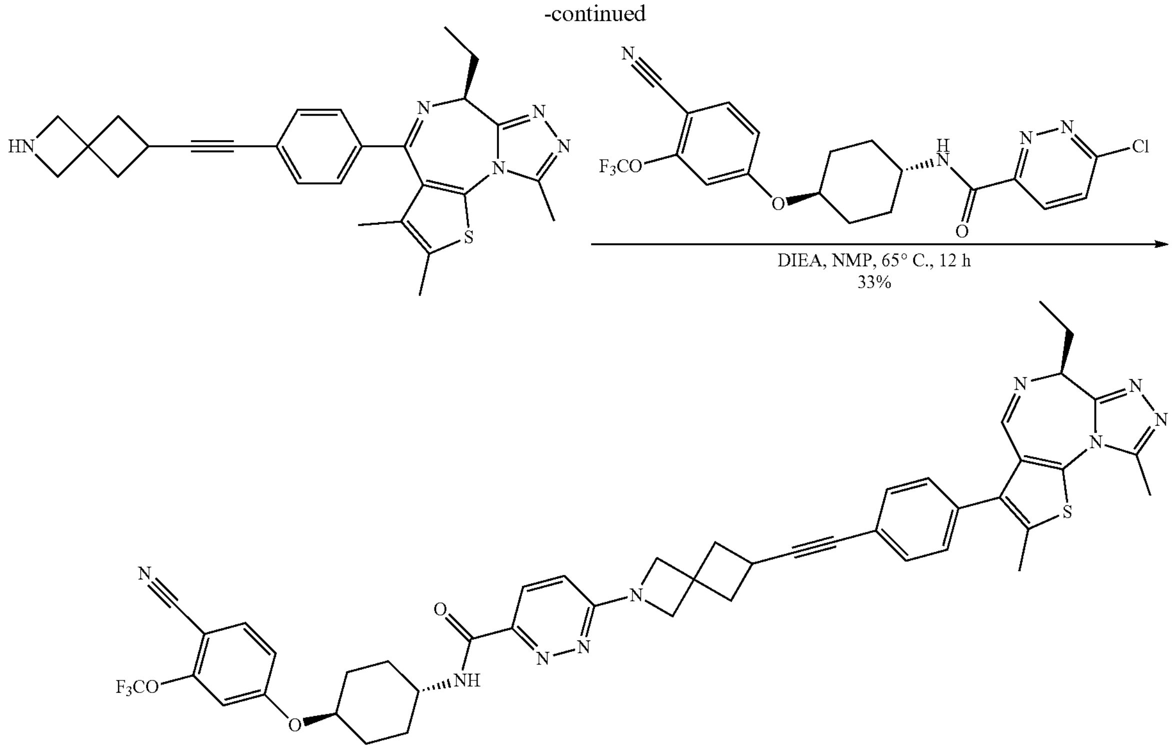

I-6

Step 1: Preparation of tert-butyl ((1r,4r)-4-(4-cyano-3-(trifluoromethoxy) phenoxy)cyclohexyl) carbamate. To a solution of tert-butyl ((1r,4r)-4-hydroxycyclohexyl) carbamate (3.15 g, 14.63 mmol, 1.5 equiv) in DMF (20 mL) and THF (20 mL) was added NaH (585 mg, 14.63 mmol, 60% purity, 1.5 equiv) at 0° C. The mixture was stirred at 25° C. for 0.5 hour. Then, 4-fluoro-2-(trifluoromethoxy) benzonitrile (2 g, 9.75 mmol, 1.0 equiv) was added. The mixture was stirred at 25° C. for 12 hours. The reaction mixture was quenched with $NH_4Cl$ (20 mL) at 0° C., and then extracted with EtOAc (50 mL×3). The combined organic layers were washed with $H_2O$ (100 mL×3), dried over anhydrous $Na_2SO_4$, filtered, and concentrated under reduced pressure to give a residue. The residue was purified by column chromatography ($SiO_2$, petroleum ether/ethyl acetate=20/1 to 5/1). Tert-butyl ((1r,4r)-4-(4-cyano-3-(trifluoromethoxy) phenoxy)cyclohexyl) carbamate (3.15 g, 7.87 mmol, 81% yield) was obtained as a white solid.

Step 2: Preparation of 4-(((1r,4r)-4-aminocyclohexyl) oxy)-2-(trifluoromethoxy) benzonitrile. A solution of tert-butyl ((1r,4r)-4-(4-cyano-3-(trifluoromethoxy)phenoxy) cyclohexyl) carbamate (3.14 g, 7.84 mmol, 1.0 equiv) in DCM (20 mL) and TFA (10 mL) was stirred at 25° C. for 1 hour. The reaction mixture was concentrated to afford 4-(((1r,4r)-4-aminocyclohexyl)oxy)-2-(trifluoromethoxy) benzonitrile (3.25 g, 7.84 mmol, TFA salt) as a colorless oil.

Step 3: Preparation of 6-chloro-N-[4-[4-cyano-3-(trifluoromethoxy)phenoxy]cyclohexyl]pyridazine-3-carboxamide. To a solution of 4-(((1r,4r)-4-aminocyclohexyl)oxy)-2-(trifluoromethoxy) benzonitrile (3.25 g, 7.84 mmol, 1.0 equiv, TFA salt) and 6-chloropyridazine-3-carboxylic acid (1.24 g, 7.84 mmol, 1.0 equiv) in DMF (20 mL) was added DIEA (3.04 g, 23.53 mmol, 4.10 mL, 3.0 equiv) and HATU (4.47 g, 11.77 mmol, 1.5 equiv). The mixture was stirred at 25° C. for 0.5 hour. The reaction mixture was added to ice water (200 mL) and filtered to afford 6-chloro-N-[4-[4-cyano-3-(trifluoromethoxy)phenoxy]cyclohexyl]pyridazine-3-carboxamide (3.34 g, 7.58 mmol, 97% yield) as a white solid.

Step 4: Preparation of tert-butyl 6-[2-[4-[(9S)-9-ethyl-4,5,13-trimethyl-3-thia-1,8,11,12-tetrazatricyclo[8.3.0.$0^{2,6}$] trideca-2 (6),4,7,10,12-pentaen-7-yl]phenyl]ethynyl]-2-azaspiro[3.3]heptane-2-carboxylate. To a solution of (9S)-7-(4-chlorophenyl)-9-ethyl-4,5,13-trimethyl-3-thia-1,8,11,12-tetrazatricyclo[8.3.0.$0^{2,6}$]trideca-2 (6),4,7,10,12-pentaene (400 mg, 1.08 mmol, 1.0 equiv), tert-butyl 6-ethynyl-2-azaspiro[3.3]heptane-2-carboxylate (597 mg, 2.70 mmol, 2.5 equiv), and $Cs_2CO_3$ (597 mg, 2.70 mmol, 2.5 equiv) in MeCN (8 mL) was added DavePhos Pd G3 (82 mg, 0.11 mmol, 0.1 equiv). The mixture was stirred at 90° C. for 2 hours under $N_2$ atmosphere. The reaction mixture was filtered, and the filtrate was concentrated to afford crude product. The residue was purified by prep-HPLC (column: Phenomenex luna C18 150 mm×25 mm×10 μm; mobile phase: [water (FA)-ACN]; gradient: 70%-90% B over 10 min) to give tert-butyl 6-[2-[4-[(9S)-9-ethyl-4,5,13-trimethyl-3-thia-1,8,11,12-tetrazatricyclo[8.3.0.$0^{2,6}$]trideca-2 (6),4,7,10,12-pentaen-7-yl]phenyl]ethynyl]-2-azaspiro[3.3] heptane-2-carboxylate (400 mg, $Z^{20}$ μmol, 67% yield) as a white solid.

Step 5: Preparation of (9S)-7-[4-[2-(2-azaspiro[3.3]heptan-6-yl)ethynyl]phenyl]-9-ethyl-4,5,13-trimethyl-3-thia-1,8,11,12-tetrazatricyclo[8.3.0.$0^{2,6}$]trideca-2 (6),4,7,10,12-pentaene. To a solution of tert-butyl 6-[2-[4-[(9S)-9-ethyl-4,5,13-trimethyl-3-thia-1,8,11,12-tetrazatricyclo[8.3.0.$0^{2,6}$] trideca-2 (6),4,7,10,12-pentaen-7-yl]phenyl]ethynyl]-2-azaspiro[3.3]heptane-2-carboxylate (100 mg, 180 μmol, 1.0 equiv) in DCM (1 mL) was added TFA (0.5 mL). The mixture was stirred at 25° C. for 0.5 hour. The reaction mixture was concentrated and basified with saturated $NaHCO_3$ at 0° C. The mixture were extracted with DCM/

MeOH (10:1, 20 mL×2), dried over $Na_2SO_4$, filtered, and concentrated to give (9S)-7-[4-[2-(2-azaspiro[3.3]heptan-6-yl)ethynyl]phenyl]-9-ethyl-4,5,13-trimethyl-3-thia-1,8,11,12-tetrazatricyclo[8.3.0.0$^{2,6}$]trideca-2 (6),4,7,10,12-pentaene (82 mg) as a yellow oil.

Step 6: Preparation of N-[4-[4-cyano-3-(trifluoromethoxy)phenoxy]cyclohexyl]-6-[6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-6). To a solution of (9S)-7-[4-[2-(2-azaspiro[3.3]heptan-6-yl)ethynyl]phenyl]-9-ethyl-4,5,13-trimethyl-3-thia-1,8,11,12-tetrazatricyclo[8.3.0.0$^{2,6}$]trideca-2 (6),4,7,10,12-pentaene (82 mg, 0.18 mmol, 1.0 equiv) and 6-chloro-N-[4-[4-cyano-3-(trifluoromethoxy)phenoxy]cyclohexyl]pyridazine-3-carboxamide (95 mg, 0.22 mmol, 1.2 equiv) in NMP (0.5 mL) was added DIEA (70 mg, 0.54 mmol, 3.0 equiv). The mixture was stirred at 65° C. for 12 hours. The residue was purified by prep-HPLC (column: Phenomenex luna C18 150×25 mm×10 μm; mobile phase: [water (FA)-ACN]; gradient: 70%-90% B over 10 min) to give N-[4-[4-cyano-3-(trifluoromethoxy)phenoxy]cyclohexyl]-6-[6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (53 mg, 60 μmol, 33% yield) as a white solid. $^1$H NMR (400 MHz, $CD_3OD$) 7.91 (d, J=9.4 Hz, 1H), 7.76 (d, J=8.6 Hz, 1H), 7.47-7.40 (m, 4H), 7.13 (d, J=8.6 Hz, 1H), 7.06 (s, 1H), 6.87 (d, J=9.2 Hz, 1H), 4.61-4.44 (m, 1H), 4.25 (d, J=6.0 Hz, 4H), 4.03-3.91 (m, 2H), 3.25 (t, J=7.8 Hz, 1H), 2.77-2.68 (m, 5H), 2.52-2.43 (m, 7H), 2.21 (s, 2H), 2.09 (d, J=3.6 Hz, 2H), 1.70 (s, 3H), 1.65 (t, J=9.8 Hz, 4H), 1.23 (t, J=7.4 Hz, 3H). LC-MS: MS (ES$^+$): RT=2.416 min, m/z=860.5 [M+H]$^+$.

Example 2—Synthesis of N-[4-[4-cyano-3-(trifluoromethoxy)phenoxy]cyclohexyl]-6-[6-[2-[4-(4,5,13-trimethylspiro[3-thia-1,8,11,12-tetrazatricyclo[8.3.0.0$^{2,6}$]trideca-2 (6),4,7,10,12-pentaene-9,1'-cyclopropane]-7-yl)phenyl]ethynyl]-2-azaspiro[3.3]heptan-2-yl]pyridazine-3-carboxamide (I-7)

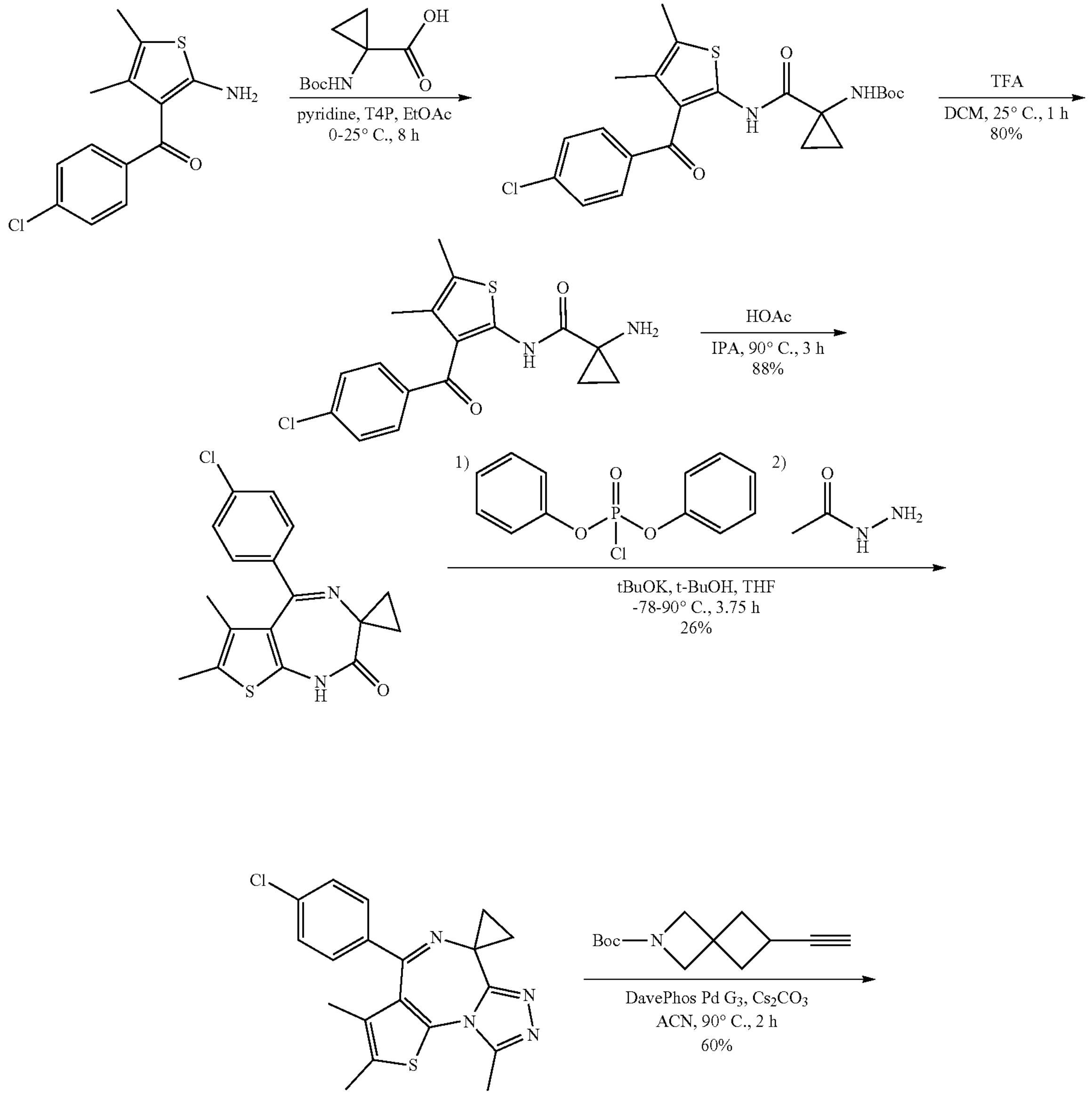

-continued

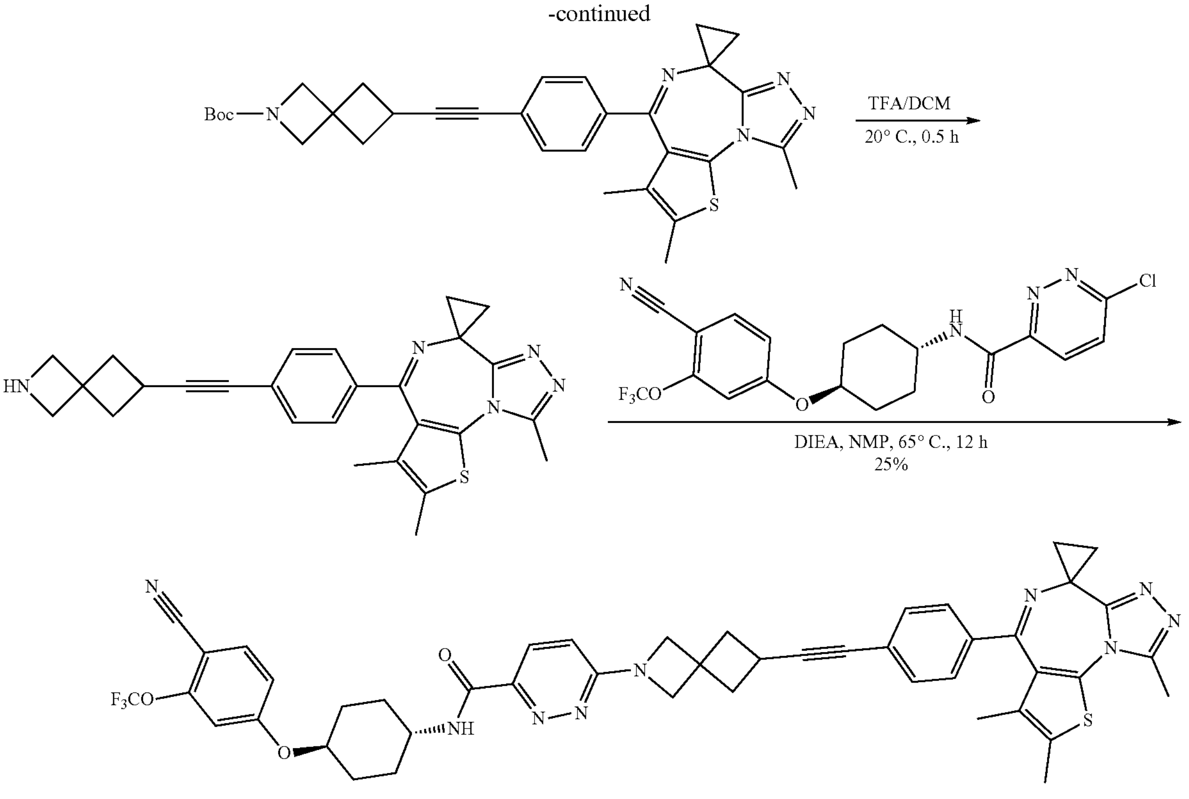

I-7

Step 1: Preparation of tert-butyl N-[1-[[3-(4-chlorobenzoyl)-4,5-dimethyl-2-thienyl]carbamoyl]cyclopropyl]carbamate. To a solution of (2-amino-4,5-dimethyl-3-thienyl)-(4-chlorophenyl) methanone (26 g, 97.8 mmol, 1.0 equiv), 1-(tert-butoxycarbonylamino) cyclopropanecarboxylic acid (59 g, 293.5 mmol, 3.0 equiv), and pyridine (38.7 g, 489 mmol, 39.5 mL, 5.0 equiv) in EtOAc (50 mL) was added T4P (211.5 g, 293.5 mmol, 50% purity, 3.0 equiv) at 0° C. The mixture was stirred at 25° C. for 8 hours. The reaction mixture was concentrated under reduced pressure to remove solvent. The residue was diluted with $NaHCO_3$ (100 mL) and extracted with ethyl acetate (250 mL×2). The combined organic layers were washed with brine (200 mL), dried over $Na_2SO_4$, filtered, and concentrated under reduced pressure to give a residue. The residue was triturated with petroleum ether/ethyl acetate (3:1, 200 mL) to give tert-butyl N-[1-[[3-(4-chlorobenzoyl)-4,5-dimethyl-2-thienyl]carbamoyl]cyclopropyl]carbamate (48 g, crude) as a yellow solid.

Step 2: Preparation of 1-amino-N-[3-(4-chlorobenzoyl)-4,5-dimethyl-2-thienyl]cyclopropanecarboxamide. To a solution of tert-butyl N-[1-[[3-(4-chlorobenzoyl)-4,5-dimethyl-2-thienyl]carbamoyl]cyclopropyl]carbamate (43 g, 95.8 mmol, 1.0 equiv) in DCM (140 mL) was added TFA (218 g, 1.9 mol, 142 mL, 20.0 equiv). The mixture was stirred at 25° C. for 1 hour. The reaction mixture was concentrated under reduced pressure to remove solvent. The residue was diluted with $NaHCO_3$ (200 mL) and extracted with ethyl acetate (250 mL×2). The combined organic layers were washed with brine (100 mL), dried over $Na_2SO_4$, filtered, and concentrated under reduced pressure to give 1-amino-N-[3-(4-chlorobenzoyl)-4,5-dimethyl-2-thienyl]cyclopropanecarboxamide (27 g, 80% yield) as a yellow solid.

Step 3: Preparation of 5-(4-chlorophenyl)-6,7-dimethyl-spiro[1H-thieno[2,3-e][1,4]diazepine-3,1'-cyclopropane]-2-one. To a solution of 1-amino-N-[3-(4-chlorobenzoyl)-4,5-dimethyl-2-thienyl]cyclopropanecarboxamide (27 g, 77.4 mmol, 1.0 equiv) in IPA (270 mL) was added AcOH (23.2 g, 387 mmol, 22 mL, 5.0 equiv). The mixture was stirred at 90° C. for 1 hour. The reaction mixture was concentrated under reduced pressure to remove solvent. The residue was triturated with ethyl acetate (200 mL) to give 5-(4-chlorophenyl)-6,7-dimethyl-spiro[1H-thieno[2,3-e][1,4]diazepine-3,1'-cyclopropane]-2-one (22.6 g, 88% yield) as a yellow solid.

Step 4: Preparation of 7-(4-chlorophenyl)-4,5,13-trimethyl-spiro[3-thia-1,8,11,12-tetrazatricyclo[8.3.0.$0^{2,6}$]trideca-2 (6),4,7,10,12-pentaene-9,1'-cyclopropane]. Tert-BuOK (1 M, 6.7 mL, 1.1 equiv) was added to a solution of 5-(4-chlorophenyl)-6,7-dimethyl-spiro[1H-thieno[2,3-e][1,4]diazepine-3, 1'-cyclopropane]-2-one (2 g, 6 mmol, 1.0 equiv) in THF (25 mL) at −78° C. The reaction mixture was warmed to −10° C. over 0.5 hour and stirred at 25° C. for 0.5 hour. The reaction mixture was cooled to −78° C. [Chloro (phenoxy) phosphoryl]oxybenzene (1.95 g, 7.3 mmol, 1.5 mL, 1.2 equiv) was added to reaction mixture. The resulting mixture was warmed to −10° C. over 0.75 hour. Then, acetohydrazide (672 mg, 9 mmol, 1.5 equiv) was added to the reaction mixture. The reaction mixture was stirred at 25° C. After 1 hour, tert-BuOH (30 mL) was added to the reaction mixture, and the mixture was heated at 90° C. for 1 hour. The mixture was poured into water (100 mL) and extracted with DCM (200 mL×2). The combined organic layer was washed with brine (200 mL) and dried over $Na_2SO_4$. The mixture was concentrated to give a residue, which was purified by prep-HPLC (column: Phenomenex luna C18 150×40 mm×15 μm; mobile phase: [water (FA)-ACN]; gradient: 37%-67% B over 15 min) to give 7-(4-chlorophenyl)-4,5,13-trimethyl-spiro[3-thia-1,8,11,12-tetrazatricyclo[8.3.0.0$^{2,6}$]trideca-2 (6),4,7,10,12-pentaene-9,1'-cyclopropane] (600 mg, 26% yield) as a white solid.

Step 5: Preparation of tert-butyl 6-[2-[4-(4,5,13-trimethylspiro[3-thia-1,8,11,12-tetrazatricyclo[8.3.0.0$^{2,6}$]trideca-2 (6),4,7,10,12-pentaene-9,1'-cyclopropane]-7-yl)phenyl] ethynyl]-2-azaspiro[3.3]heptane-2-carboxylate. To a solution of 7-(4-chlorophenyl)-4,5,13-trimethyl-spiro[3-thia-1,8,11,12-tetrazatricyclo[8.3.0.0$^{2,6}$]trideca-2 (6),4,7,10,12-pentaene-9,1'-cyclopropane] (400 mg, 1.08 mmol, 1.0 equiv) and tert-butyl 6-ethynyl-2-azaspiro[3.3]heptane-2-carboxylate (599 mg, 2.71 mmol, 2.5 equiv) in ACN (8 mL) was added DavePhos Pd G3 (82.7 mg, 108 μmol, 0.1 equiv) and $Cs_2CO_3$ (706 mg, 2.17 mmol, 2.0 equiv). The mixture was stirred at 90° C. for 2 hours. The reaction mixture was filtered and concentrated to afford crude product. The residue was purified by prep-HPLC (column: Phenomenex luna C18 150×40 mm×15 μm; mobile phase: [water (FA)-ACN]; gradient: 55%-85% B over 15 min) to give tert-butyl 6-[2-[4-(4,5,13-trimethylspiro[3-thia-1,8,11,12-tetrazatricyclo [8.3.0.0$^{2,6}$]trideca-2 (6),4,7,10,12-pentaene-9,1'-cyclopropane]-7-yl)phenyl]ethynyl]-2-azaspiro[3.3]heptane-2-carboxylate (360 mg, 650 μmol, 60% yield) as a yellow solid.

Step 6: Preparation of 7-[4-[2-(2-azaspiro[3.3]heptan-6-yl)ethynyl]phenyl]-4,5,13-trimethyl-spiro[3-thia-1,8,11,12-tetrazatricyclo[8.3.0.0$^{2,6}$]trideca-2 (6),4,7,10,12-pentaene-9,1'-cyclopropane]. To a solution of tert-butyl 6-[2-[4-(4,5,13-trimethylspiro[3-thia-1,8,11,12-tetrazatricyclo[8.3.0.0$^{2,6}$] trideca-2 (6),4,7,10,12-pentaene-9,1'-cyclopropane]-7-yl) phenyl]ethynyl]-2-azaspiro[3.3]heptane-2-carboxylate (180 mg, 325 μmol, 1.0 equiv) in DCM (2 mL) was added TFA (1 mL). The mixture was stirred at 20° C. for 0.5 hour. The reaction mixture was concentrated, basified with aqueous $NaHCO_3$ and extracted with DCM/MeOH (10:1, 30 mL×2). The combined organic phase was washed with brine (10 mL×2), dried over anhydrous $Na_2SO_4$, filtered, and concentrated to afford 7-[4-[2-(2-azaspiro[3.3]heptan-6-yl)ethynyl] phenyl]-4,5,13-trimethyl-spiro[3-thia-1,8,11,12-tetrazatricyclo[8.3.0.0$^{2,6}$]trideca-2 (6),4,7,10,12-pentaene-9,1'-cyclopropane] (146 mg, 321 μmol, crude) as a yellow oil, which was used directly in the next step without purification.

Step 7: Preparation of N-[4-[4-cyano-3-(trifluoromethoxy)phenoxy]cyclohexyl]-6-[6-[2-[4-(4,5,13-trimethylspiro[3-thia-1,8,11,12-tetrazatricyclo[8.3.0.0$^{2,6}$]trideca-2(6),4,7,10,12-pentaene-9,1'-cyclopropane]-7-yl) phenyl]ethynyl]-2-azaspiro[3.3]heptan-2-yl]pyridazine-3-carboxamide (I-7). To a solution of 7-[4-[2-(2-azaspiro[3.3] heptan-6-yl)ethynyl]phenyl]-4,5,13-trimethyl-spiro[3-thia-1,8,11,12-tetrazatricyclo[8.3.0.0$^{2,6}$]trideca-2 (6),4,7,10,12-pentaene-9,1'-cyclopropane] (73.0 mg, 160 μmol, 1.0 equiv) in NMP (1 mL) was added DIEA (62.4 mg, 482 μmol, 84.1 μL, 3.0 equiv) and 6-chloro-N-[4-[4-cyano-3-(trifluoromethoxy)phenoxy]cyclohexyl]pyridazine-3-carboxamide (70.9 mg, 160 μmol, 1.0 equiv). The mixture was stirred at 65° C. for 12 hours. The residue was purified by prep-HPLC (column: Waters xbridge 150×25 mm 10 μm; mobile phase: [water ($NH_4HCO_3$)-ACN]; gradient: 60%-80% B over 8 min) to afford N-[4-[4-cyano-3-(trifluoromethoxy)phenoxy] cyclohexyl]-6-[6-[2-[4-(4,5,13-trimethyl-spiro[3-thia-1,8,11,12-tetrazatricyclo[8.3.0.0$^{2,6}$]trideca-2 (6),4,7,10,12-pentaene-9,1'-cyclopropane]-7-yl)phenyl]ethynyl]-2-azaspiro [3.3]heptan-2-yl]pyridazine-3-carboxamide (34.4 mg, 40.1 μmol, 25% yield) as a white solid. $^1$H NMR (400 MHz, $CD_3OD$) δ 7.91 (d, J=9.3 Hz, 1H), 7.76 (d, J=8.8 Hz, 1H), 7.47-7.40 (m, 4H), 7.13 (dd, J=2.3, 8.8 Hz, 1H), 7.06 (s, 1H), 6.85 (d, J=9.4 Hz, 1H), 4.56-4.51 (m, 1H), 4.24 (d, J=5.9 Hz, 4H), 4.02-3.92 (m, 1H), 3.25 (t, J=8.0 Hz, 1H), 2.79-2.68 (m, 5H), 2.51-2.42 (m, 5H), 2.22 (br d, J=4.2 Hz, 2H), 2.10 (br s, 2H), 1.96-1.86 (m, 1H), 1.70-1.60 (m, 7H), 1.54 (dt, J=6.5, 8.5 Hz, 1H), 0.90 (br t, J=8.7 Hz, 2H). LC-MS: MS ($ES^+$): RT=2.376 min, m/z=858.5 $[M+H]^+$.

Example 3—Synthesis of N-[4-[4-cyano-3-(trifluoromethoxy)phenoxy]cyclohexyl]-6-[6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-8)

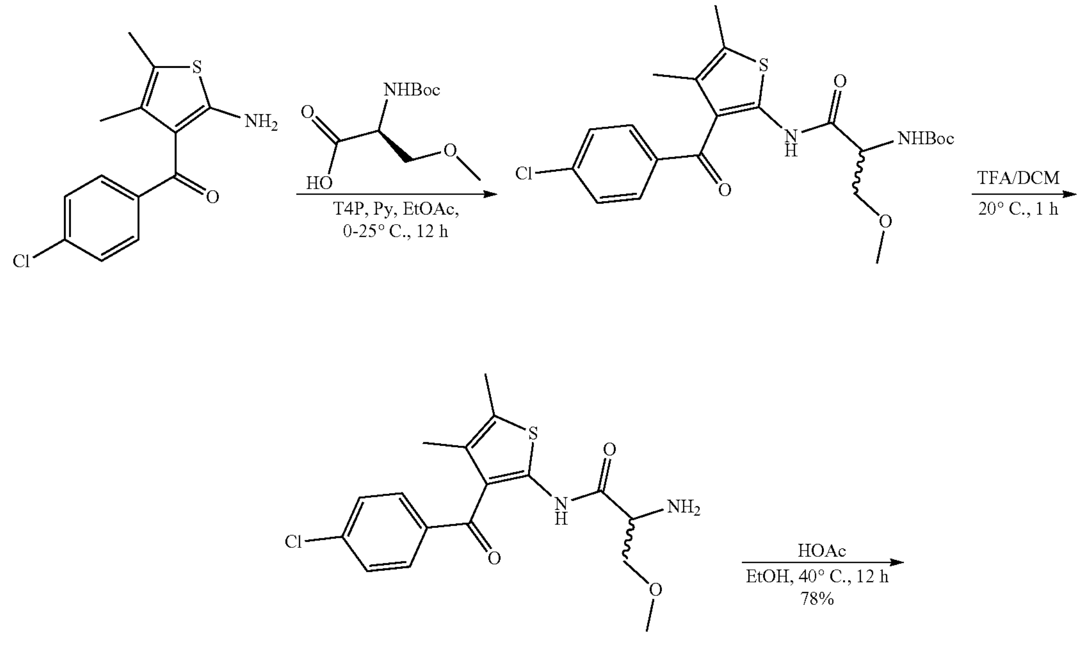

-continued
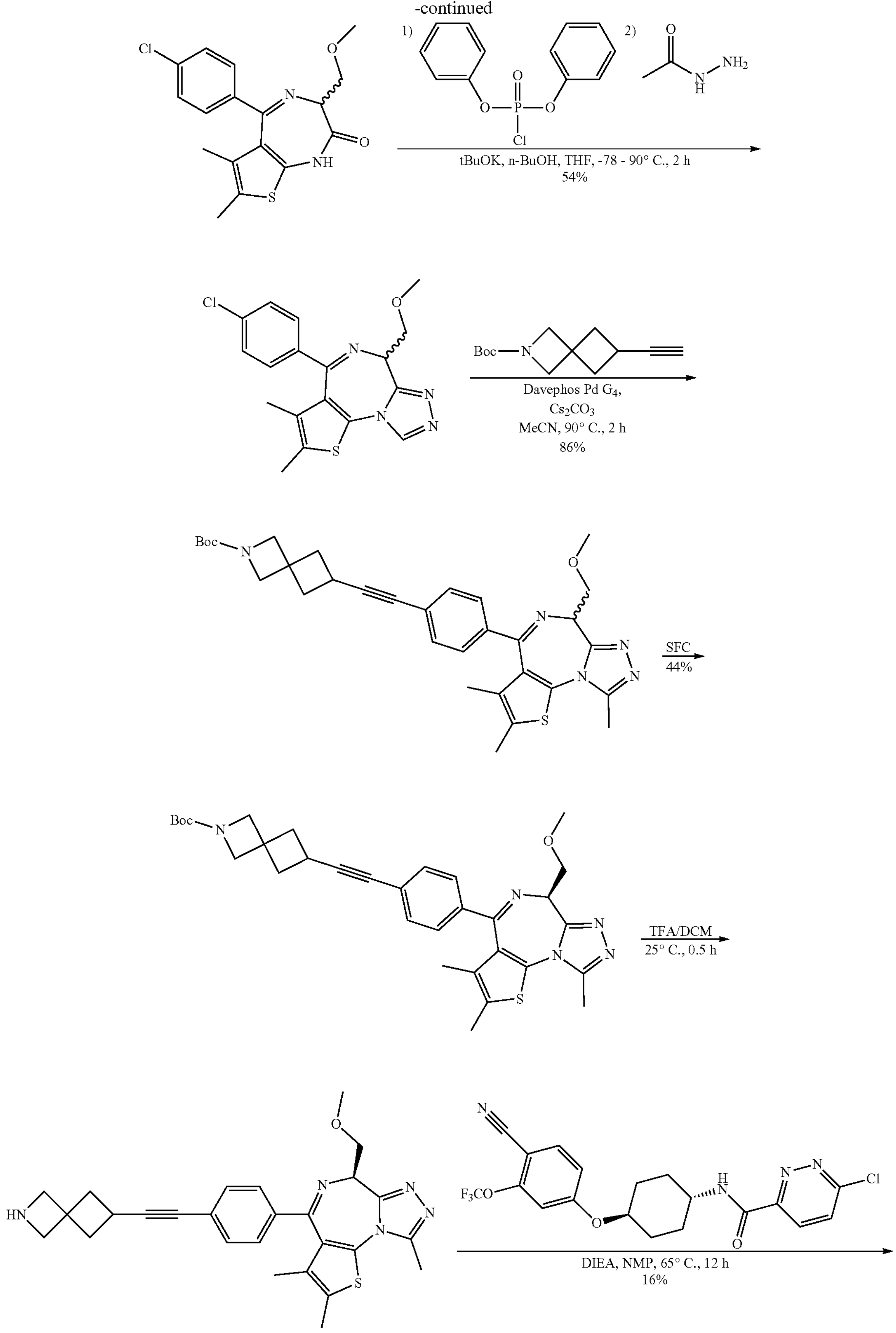

-continued

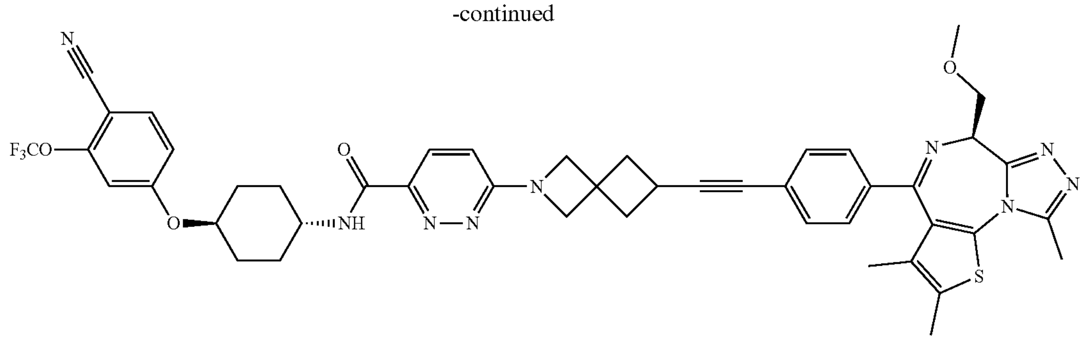

I-8

Step 1: Preparation of tert-butyl (1-((3-(4-chlorobenzoyl)-4,5-dimethylthiophen-2-yl)amino)-3-methoxy-1-oxopropan-2-yl) carbamate. To a solution of (2-amino-4,5-dimethylthiophen-3-yl) (4-chlorophenyl) methanone (10.0 g, 37.6 mmol, 1.0 equiv) and N-(tert-butoxycarbonyl)-O-methyl-L-serine (16.5 g, 75.26 mmol, 2.0 equiv) in e (25 mL) was added pyridine (17.8 g, 225.7 mmol, 18.2 mL, 6.0 equiv) and T4P (81.3 g, 112.8 mmol, 50% purity, 3.0 equiv). The mixture was stirred at 25° C. for 12 hours. To the reaction mixture was added ice water (200 mL) and the mixture was extracted with ethyl acetate (2×200 mL). The combined organic phase was washed with 0.5 M HCl (100 mL), dried over anhydrous $Na_2SO_4$, filtered, and concentrated in vacuo to give tert-butyl (1-((3-(4-chlorobenzoyl)-4,5-dimethylthiophen-2-yl) amino)-3-methoxy-1-oxopropan-2-yl) carbamate (17.0 g, crude) as a yellow solid.

Step 2: Preparation of 2-amino-N-(3-(4-chlorobenzoyl)-4,5-dimethylthiophen-2-yl)-3-methoxypropanamide. To a solution of tert-butyl (1-((3-(4-chlorobenzoyl)-4,5-dimethylthiophen-2-yl)amino)-3-methoxy-1-oxopropan-2-yl) carbamate (17.0 g, 36.4 mmol, 1.0 equiv) in DCM (20 mL) was added TFA (20 mL). The mixture was stirred at 20° C. for 1 hour. The reaction mixture was concentrated under reduced pressure to give a residue. To the residue was added DCM (100 mL), and pH was adjusted to 7 with the addition of $NaHCO_3$ (250 mL). The mixture was extracted with dichloromethane:methanol (10:1, 3×750 mL). The combined organic phase was washed with brine (250 mL), dried over anhydrous $Na_2SO_4$, filtered, and concentrated in vacuo to give crude 2-amino-N-(3-(4-chlorobenzoyl)-4,5-dimethylthiophen-2-yl)-3-methoxypropanamide (13 g, crude), which was used directly in the next step without purification.

Step 3: Preparation of 5-(4-chlorophenyl)-3-(methoxymethyl)-6,7-dimethyl-1,3-dihydro-2H-thieno[2,3-e][1,4]diazepin-2-one. To a solution of 2-amino-N-(3-(4-chlorobenzoyl)-4,5-dimethylthiophen-2-yl)-3-methoxypropanamide (12.0 g, 32.7 mmol, 1.0 equiv) in EtOH (60 mL) was added AcOH (10.4 g, 174.6 mmol, 10 mL, 5.3 equiv). The mixture was stirred at 40° C. for 12 hours. To the reaction mixture was added water (250 mL), and the mixture was extracted with dichloromethane:methanol (10:1, 200 mL). The organic phase was washed with brine (250 mL), dried over anhydrous $Na_2SO_4$, filtered, and concentrated in vacuo. The residue was purified by column chromatography ($SiO_2$, petroleum ether/ethyl acetate=10/1 to 3/1). 5-(4-Chlorophenyl)-3-(methoxymethyl)-6,7-dimethyl-1,3-dihydro-2H-thieno[2,3-e][1,4]diazepin-2-one (9.0 g, 25.8 mmol, 78% yield) was obtained as a yellow solid.

Step 4: Preparation of (9R)-7-(4-chlorophenyl)-9-(methoxymethyl)-4,5,13-trimethyl-3-thia-1,8,11,12-tetrazatricyclo[8.3.0.0$^{2,6}$]trideca-2 (6),4,7,10,12-pentaene. Potassium tert-butoxide (1.0 M, 15.7 mL, 1.1 equiv) was added to a solution of 5-(4-chlorophenyl)-3-(methoxymethyl)-6,7-dimethyl-1,3-dihydro-2H-thieno[2,3-e][1,4]diazepin-2-one (5.0 g, 14.3 mmol, 1.0 equiv) in THF (50 mL) at −78° C. The reaction mixture was warmed to 25° C. and stirred at 25° C. for 30 minutes. The reaction mixture was cooled to −78° C. Diphenyl phosphorochloridate (4.6 g, 17.2 mmol, 3.5 mL, 1.2 equiv) was added to the reaction mixture. The resulting mixture was warmed to 25° C. for 30 minutes. Acetohydrazide (1.59 g, 21.5 mmol, 1.5 eq) was added to the reaction mixture at 25° C. n-Butanol (50 mL) was then added to the reaction mixture immediately with stirring, and the mixture was heated to 90° C. for 1 hour. The reaction mixture was quenched with $H_2O$ (100 mL) at 0° C. and then extracted with EtOAc (2×100 mL). The combined organic layers were washed with $H_2O$ (100 mL), dried over $Na_2SO_4$, filtered, and concentrated under reduced pressure to give a residue. The residue was purified by prep-HPLC (column: Phenomenex luna C18 250×80 mm×10 μm; mobile phase: [water (TFA)-ACN]; gradient: 45%-75% B over 20 min) to give (9R)-7-(4-chlorophenyl)-9-(methoxymethyl)-4,5,13-trimethyl-3-thia-1,8,11,12-tetrazatricyclo[8.3.0.0$^{2,6}$]trideca-2 (6),4,7,10,12-pentaene (8.0 g, 7.75 mmol, 54% yield) as a yellow solid.

Step 5: Preparation of tert-butyl 6-[2-[4-[9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. To a solution of (9R)-7-(4-chlorophenyl)-9-(methoxy-methyl)-4,5,13-trimethyl-3-thia-1,8,11,12-tetrazatricyclo[8.3.0.0$^{2,6}$]trideca-2 (6),4,7,10,12-pentaene (400 mg, 1.03 mmol, 1.0 equiv) and tert-butyl 6-ethynyl-2-azaspiro[3.3]heptane-2-carboxylate (572 mg, 2.58 mmol, 2.5 equiv) in MeCN (5 mL) was added DavePhos Pd G3 (79 mg, 103 μmol, 0.1 equiv) and $Cs_2CO_3$ (674 mg, 2.07 mmol, 2.0 equiv). The mixture was stirred at 90° C. for 2 hours. The mixture was filtered and concentrated. The residue was purified by prep-HPLC (column: Phenomenex luna C18 150×25 mm×10 μm; mobile phase: [water (FA)-ACN]; gradient: 56%-86% B over 10 min) to give tert-butyl 6-[2-[4-[9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (450 mg, 787 μmol, 76% yield) as a colorless oil.

Step 6: Preparation of tert-butyl-6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. Tert-butyl 6-[2-[4-[9-(methoxymethyl)-4,5,13-trimethyl-3-thia- 1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate was purified by prep-SFC (column: DAICEL CHIRALPAK AS (250 mm×30 mm, 10 μm); mobile phase: [$CO_2$-EtOH]; B %: 40%, isocratic elution mode) and prep-HPLC (column: Phenomenex luna C18 150×25 mm×10 μm; mobile phase: [water (FA)-ACN]; gradient: 58%-88% B over 10 min) to afford tert-butyl-6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (200 mg, 350 μmol, 44% yield) as a colorless oil.

Step 7: Preparation of (9R)-7-[4-[2-(2-azaspiro[3.3]heptan-6-yl)ethynyl]phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene. To a solution of tert-butyl 6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (190 mg, 332 μmol, 1.0 equiv) in DCM (2 mL) was added TFA (1 mL). The mixture was stirred at 25° C. for 0.5 hour. The reaction mixture was concentrated and basified with saturated $NaHCO_3$ at 0° C. The mixture were extracted with DCM/MeOH (10:1, 50 mL×2), dried over $Na_2SO_4$, filtered, and concentrated to afford (9R)-7-[4-[2-(2-azaspiro[3.3]heptan-6-yl)ethynyl]phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene (157 mg, crude) as a colorless oil.

Step 8: Preparation of N-[4-[4-cyano-3-(trifluoromethoxy)phenoxy]cyclohexyl]-6-[6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-8). To a solution of (9R)-7-[4-[2-(2-azaspiro[3.3]heptan-6-yl)ethynyl]phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene (78 mg, 165 μmol, 1.0 equiv) and 6-chloro-N-[4-[4-cyano-3-(trifluoromethoxy)phenoxy]cyclohexyl]pyridazine-3-carboxamide (80 mg, 182 μmol, 1.1 equiv) in NMP (1 mL) was added DIEA (64 mg, 496 μmol, 86 μL, 3.0 equiv). The mixture was stirred at 65° C. for 12 hours. The residue was purified by prep-HPLC (column: Phenomenex luna C18 150×25 mm×10 μm; mobile phase: [water (FA)-ACN]; gradient: 58%-88% B over 10 min) to afford compound N-[4-[4-cyano-3-(trifluoromethoxy)phenoxy]cyclohexyl]-6-[6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (23 mg, 26 μmol, 16% yield) as a white solid. $^1$H NMR (400 MHz, $CD_3OD$) 7.93 (s, 1H), 7.80-7.77 (m, 1H), 7.50-7.42 (m, 4H), 7.17-7.14 (m, 1H), 7.08 (s, 1H), 6.93-6.88 (m, 1H), 4.60-4.49 (m, 1H), 4.48-4.42 (m, 1H), 4.42-4.37 (m, 2H), 4.31-4.26 (m, 4H), 4.05-3.93 (m, 1H), 3.57 (s, 3H), 3.25 (s, 1H), 2.81-2.73 (m, 2H), 2.72 (s, 3H), 2.53-2.48 (m, 2H), 2.47 (s, 3H), 2.27-2.18 (m, 2H), 2.16-2.05 (m, 2H), 1.72 (s, 3H), 1.70-1.63 (m, 4H), −2.51-2.53 (m, 1H). LC-MS: MS ($ES^+$): RT=2.341 min, m/z=876.5 $[M+H]^+$; LCMS method: 25.

Example 4—Synthesis of N-[4-[4-cyano-3-(trifluoromethoxy)phenoxy]cyclohexyl]-6-[6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-9)

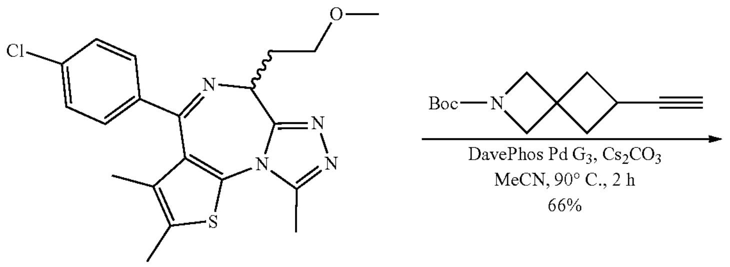

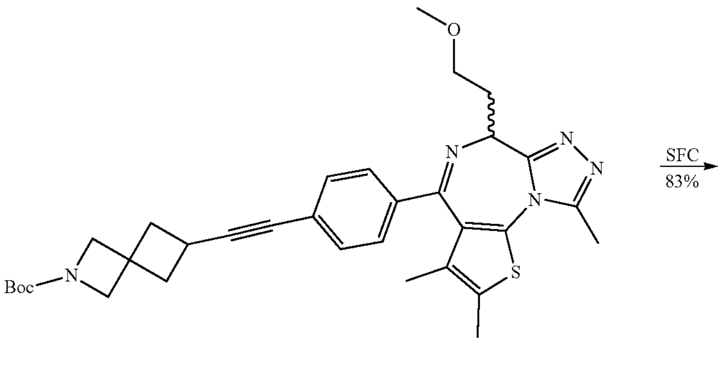

-continued

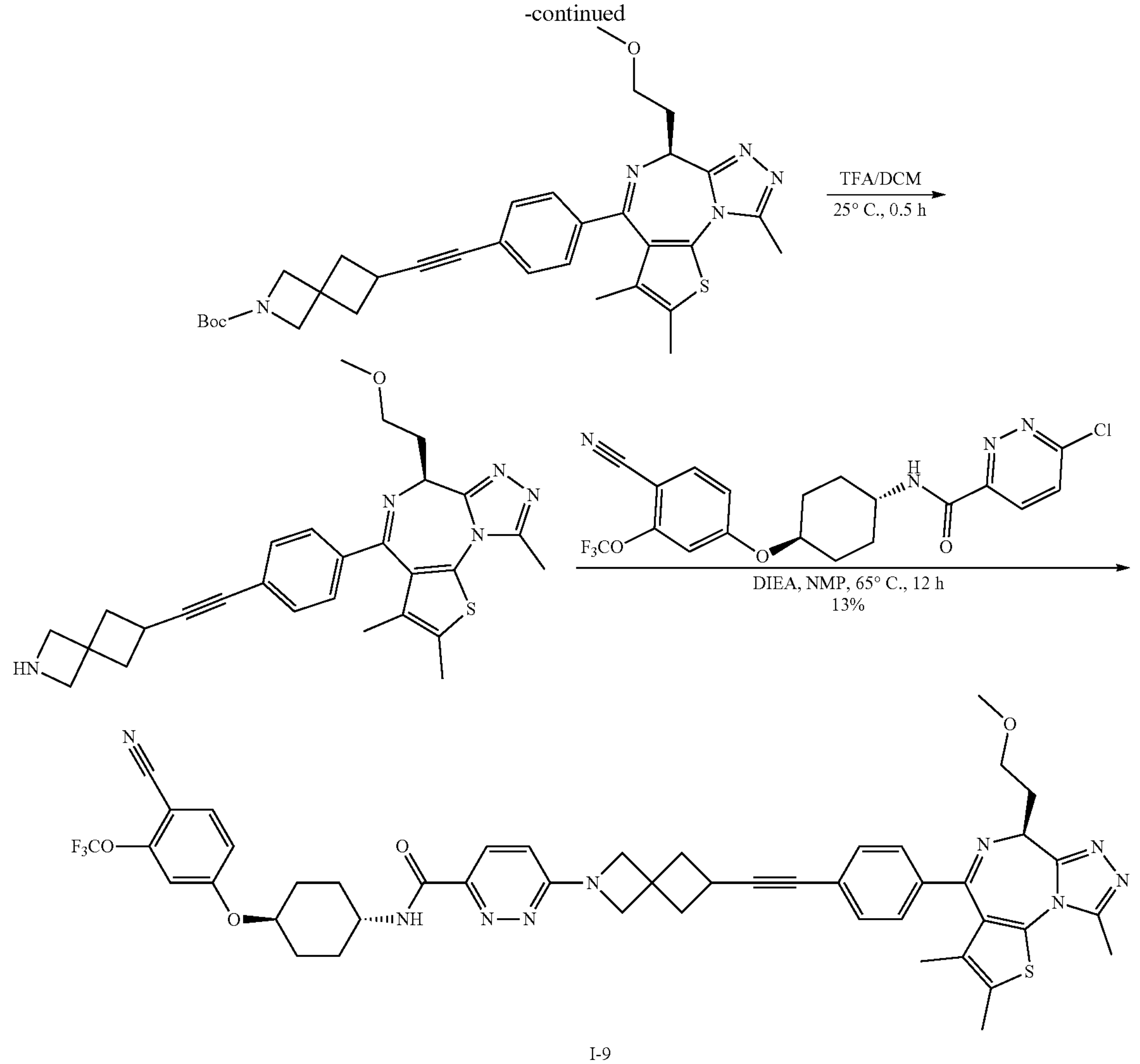

I-9

Step 1: Preparation of tert-butyl 6-[2-[4-[9-(2-methoxyethyl)-4,5,13-trimethyl-3-thia-1,8,11,12-tetrazatricyclo [8.3.0.0$^{2,6}$]trideca-2 (6),4,7,10,12-pentaen-7-yl]phenyl] ethynyl]-2-azaspiro[3.3]heptane-2-carboxylate. To a solution of (9S)-7-(4-chlorophenyl)-9-(2-methoxyethyl)-4,5,13-trimethyl-3-thia-1,8,11,12-tetrazatricyclo[8.3.0.0$^{2,6}$] trideca-2 (6),4,7,10,12-pentaene (250 mg, 624 μmol, 1.0 equiv), tert-butyl 6-ethynyl-2-azaspiro[3.3]heptane-2-carboxylate (345 mg, 1.56 mmol, 2.5 equiv), and $Cs_2CO_3$ (406 mg, 1.25 mmol, 2.0 equiv) in MeCN (5 mL) was added DavePhos Pd G3 (47 mg, 62 μmol, 0.1 equiv). The mixture was stirred at 90° C. for 2 hours under $N_2$ atmosphere. The reaction mixture was filtered, and the filtrate was concentrated to afford crude product. The residue was purified by prep-HPLC (column: Phenomenex luna C18 150×25 mm×10 μm; mobile phase: [water (FA)-ACN]; gradient: 68%-88% B over 10 min) to afford tert-butyl 6-[2-[4-[9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (240 mg, 410 μmol, 66% yield) as a white solid.

Step 2: Preparation of tert-butyl 6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. Tert-butyl 6-[2-[4-[9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate was purified by prep-SFC (column: DAICEL CHIRALPAK AD (250 mm×30 mm, 10 μm); mobile phase: [$CO_2$-ACN/i-PrOH (0.1% $NH_3$·$H_2O$)]; B %: 45%, isocratic elution mode) to afford tert-butyl 6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (200 mg, 341 μmol, 83% yield) as a white solid.

Step 3: Preparation of (9S)-7-[4-[2-(2-azaspiro[3.3]heptan-6-yl)ethynyl]phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene. To a solution of tert-butyl 6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (100 mg, 171 μmol, 1.0 equiv) in DCM (1 mL) was added TFA (0.5 mL). The mixture was stirred at 25° C. for 0.5 hour. The reaction mixture was concentrated and basified with saturated $NaHCO_3$ at 0° C. The mixture were extracted with DCM/MeOH (10:1, 2×20 mL), dried over $Na_2SO_4$, filtered, and concentrated to give (9S)-7-[4-[2-(2-azaspiro[3.3]heptan-6-yl)ethynyl]phenyl]-9-(2-methoxyethyl)-4,5,13-trimethyl-3-thia-1,8,11,12-tetrazatricyclo [8.3.0.0$^{2,6}$]trideca-2 (6),4,7,10,12-pentaene (83 mg) as a yellow oil.

Step 4: Preparation of N-[4-[4-cyano-3-(trifluoromethoxy)phenoxy]cyclohexyl]-6-[6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-9). To a solution of (9S)-7-[4-[2-(2-azaspiro[3.3]heptan-6-yl)ethynyl]phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene (83 mg, 0.17 mmol, 1.0 equiv) and 6-chloro-N-[4-[4-cyano-3-(trifluoromethoxy)phenoxy]cyclohexyl]pyridazine-3-carboxamide (90 mg, 0.21 mmol, 1.2 equiv) in NMP (0.5 mL) was added DIEA (66 mg, 0.51 mmol, 3.0 equiv). The mixture was stirred at 65° C. for 12 hours. The residue was purified by prep-HPLC (column: Phenomenex luna C18 150×25 mm×10 μm; mobile phase: [water (FA)-ACN]; gradient: 66%-86% B over 10 min) to afford N-[4-[4-cyano-3-(trifluoromethoxy)phenoxy]cyclohexyl]-6-[6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (20 mg, 22 μmol, 13% yield) as a white solid. $^1$H NMR (400 MHz, $CD_3OD$) 7.93 (d, J=9.2 Hz, 1H), 7.76 (d, J=8.8 Hz, 1H), 7.47-7.40 (m, 4H), 7.13 (d, J=8.8 Hz, 1H), 7.05 (s, 1H), 6.89 (d, J=9.4 Hz, 1H), 4.60-4.48 (m, 1H), 4.29-4.23 (m, 5H), 4.03-3.92 (m, 1H), 3.87-3.73 (m, 2H), 3.35 (s, 3H), 3.28-3.23 (m, 1H), 2.77-2.69 (m, 7H), 2.51-2.44 (m, 5H), 2.21 (d, J=6.4 Hz, 2H), 2.10 (d, J=3.8 Hz, 2H), 1.70 (s, 3H), 1.68-1.61 (m, 4H).

Example 5—Synthesis of N-[4-[4-cyano-3-(trifluoromethoxy)phenoxy]cyclohexyl]-6-[6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-12)

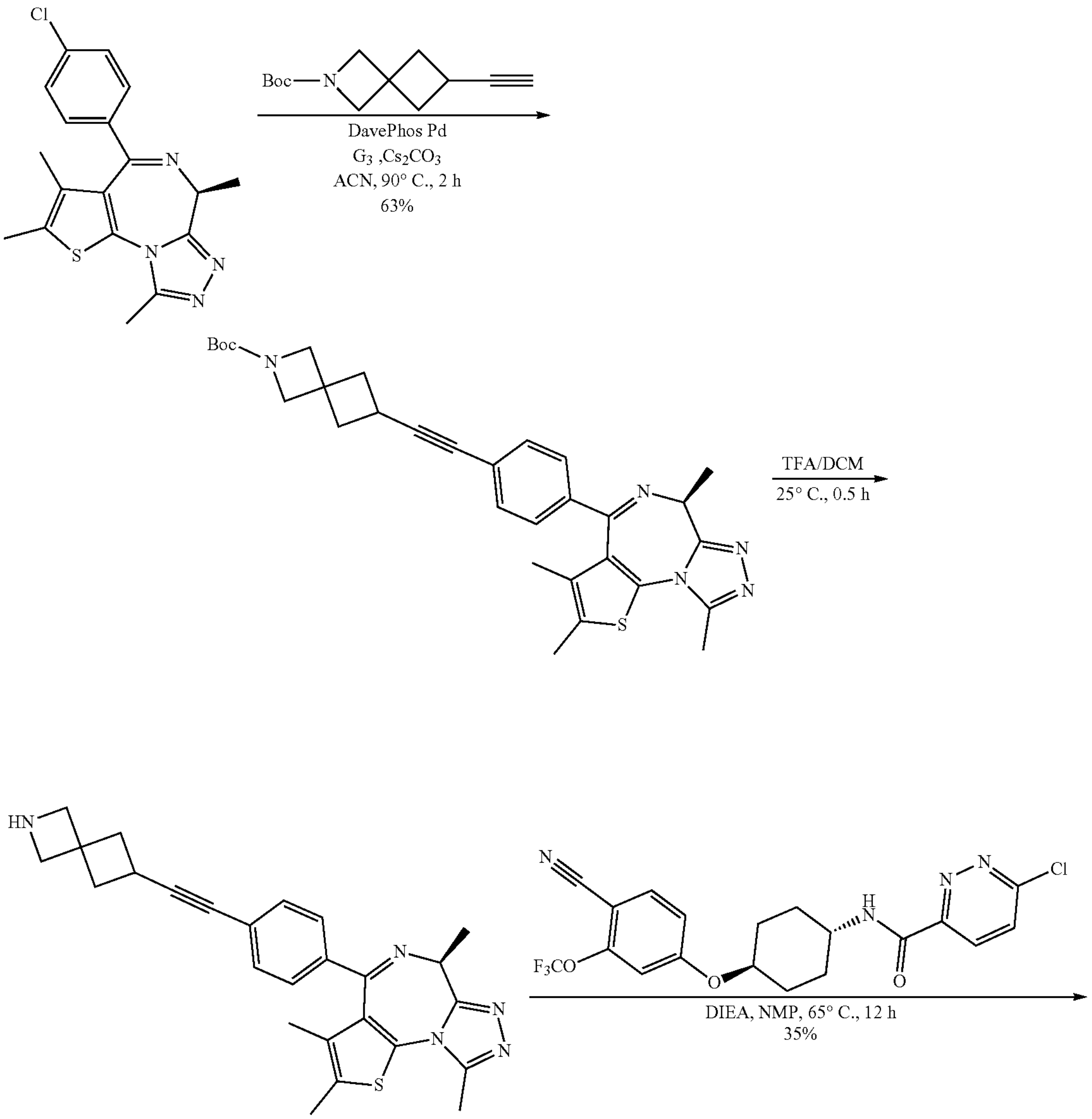

-continued

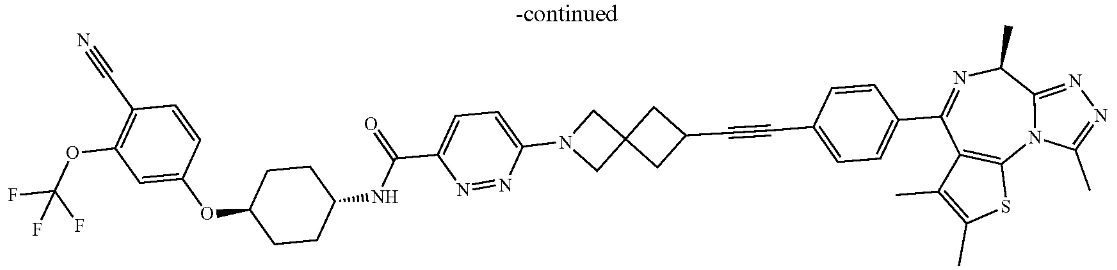

I-12

Step 1: Preparation of tert-butyl 6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. To a solution of (9S)-7-(4-chlorophenyl)-4,5,9,13-tetramethyl-3-thia-1,8,11,12-tetrazatricyclo[8.3.0.0$^{2,6}$]trideca-2 (6),4,7,10,12-pentaene (400 mg, 1.12 mmol, 1.0 equiv) and tert-butyl 6-ethynyl-2-azaspiro[3.3]heptane-2-carboxylate (620 mg, 2.80 mmol, 2.5 equiv) in ACN (5.0 mL) was added DavePhos Pd G3 (86.0 mg, 112 μmol, 0.1 equiv) and $Cs_2CO_3$ (730 mg, 2.24 mmol, 2.0 equiv) under $N_2$. The suspension was degassed under vacuum and purged with $N_2$ 3 times. The mixture was stirred under $N_2$ at 90° C. for 2 hours. The reaction mixture was filtered and concentrated to give a residue. The residue was purified by prep-HPLC (column: Phenomenex luna C18 150×40 mm×15 μm; mobile phase: [water (FA)-ACN]; gradient: 57%-87% B over 15 min). Compound tert-butyl 6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (380 mg, 701 μmol, 63% yield) was obtained as a brown oil.

Step 2: Preparation of (9S)-7-[4-[2-(2-azaspiro[3.3]heptan-6-yl)ethynyl]phenyl]-4,5,9,13-tetramethyl-3-thia-1,8,11,12-tetrazatricyclo[8.3.0.0$^{2,6}$]trideca-2 (6),4,7,10,12-pentaene. To a solution of tert-butyl 6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (100 mg, 185 μmol, 1.0 equiv) in DCM (2.0 mL) was added TFA (1.0 mL). The reaction mixture was stirred at 25° C. for 0.5 hour. The reaction mixture was concentrated and basified with aqueous $NaHCO_3$ and extracted with DCM/MeOH (10:1, 20 mL×2) dried over $Na_2SO_4$, filtered, and concentrated under reduced pressure to afford (9S)-7-[4-[2-(2-azaspiro[3.3]heptan-6-yl)ethynyl]phenyl]-4,5,9,13-tetramethyl-3-thia-1,8,11,12-tetrazatricyclo[8.3.0.0$^{2,6}$]trideca-2 (6),4,7,10,12-pentaene (82.0 mg, 185 μmol, 100% yield) as a colorless oil.

Step 3: Preparation of N-[4-[4-cyano-3-(trifluoromethoxy)phenoxy]cyclohexyl]-6-[6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-12). To a solution of 6-chloro-N-[4-(3-chloro-4-cyano-phenoxy)cyclohexyl]pyridazine-3-carboxamide (83.0 mg, 212 μmol, 1.3 equiv) in NMP (0.5 mL) was added DIEA (63.0 mg, 490 μmol, 85 μL, 3.0 equiv) and 6-chloro-N-[4-[4-cyano-3-(trifluoromethoxy) phenoxy]cyclohexyl]pyridazine-3-carboxamide (89.0 mg, 203 μmol, 1.1 equiv). The mixture was stirred at 65° C. for 12 hours. The residue was purified by prep-HPLC (column: Waters Xbridge 150×25 mm×5 μm; mobile phase: [water ($NH_4HCO_3$)-ACN]; gradient: 53%-73% B over min) to afford N-[4-[4-cyano-3-(trifluoromethoxy)phenoxy]cyclohexyl]-6-[6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (54.68 mg, 64.64 μmol, 35% yield) as an off-white solid. $^1H$ NMR (400 MHz, $CD_3OD$) δ 7.91 (d, J=9.3 Hz, 1H), 7.76 (d, J=8.8 Hz, 1H), 7.46-7.40 (m, 4H), 7.15-7.11 (m, 1H), 7.05 (s, 1H), 6.86 (d, J=9.4 Hz, 1H), 4.53 (br s, 1H), 4.33-4.22 (m, 5H), 3.98 (br d, J=3.5 Hz, 1H), 3.64-3.58 (m, 1H), 3.29-3.21 (m, 1H), 2.76-2.72 (m, 1H), 2.70 (s, 3H), 2.49 (br d, J=7.8 Hz, 2H), 2.44 (s, 3H), 2.21 (br s, 2H), 2.09 (br s, 2H), 2.0 (d, J=6.7 Hz, 3H), 1.71-1.62 (m, 6H). LC-MS: MS ($ES^+$): RT=2.416 min, m/z=860.5 $[M+H]^+$; LCMS method: 25.

Example 6—Synthesis of N-((1r,4r)-4-(4-cyano-3-(trifluoromethoxy)phenoxy) cyclohexyl)-6-(8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]decan-2-yl) pyridazine-3-carboxamide (I-13)

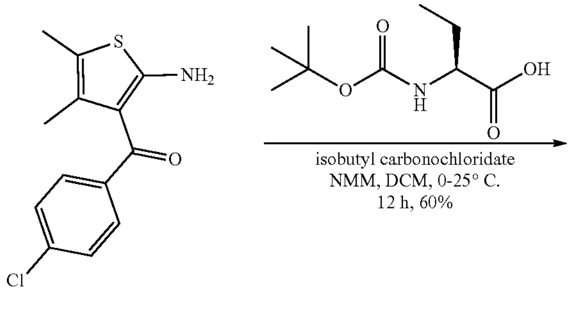

-continued
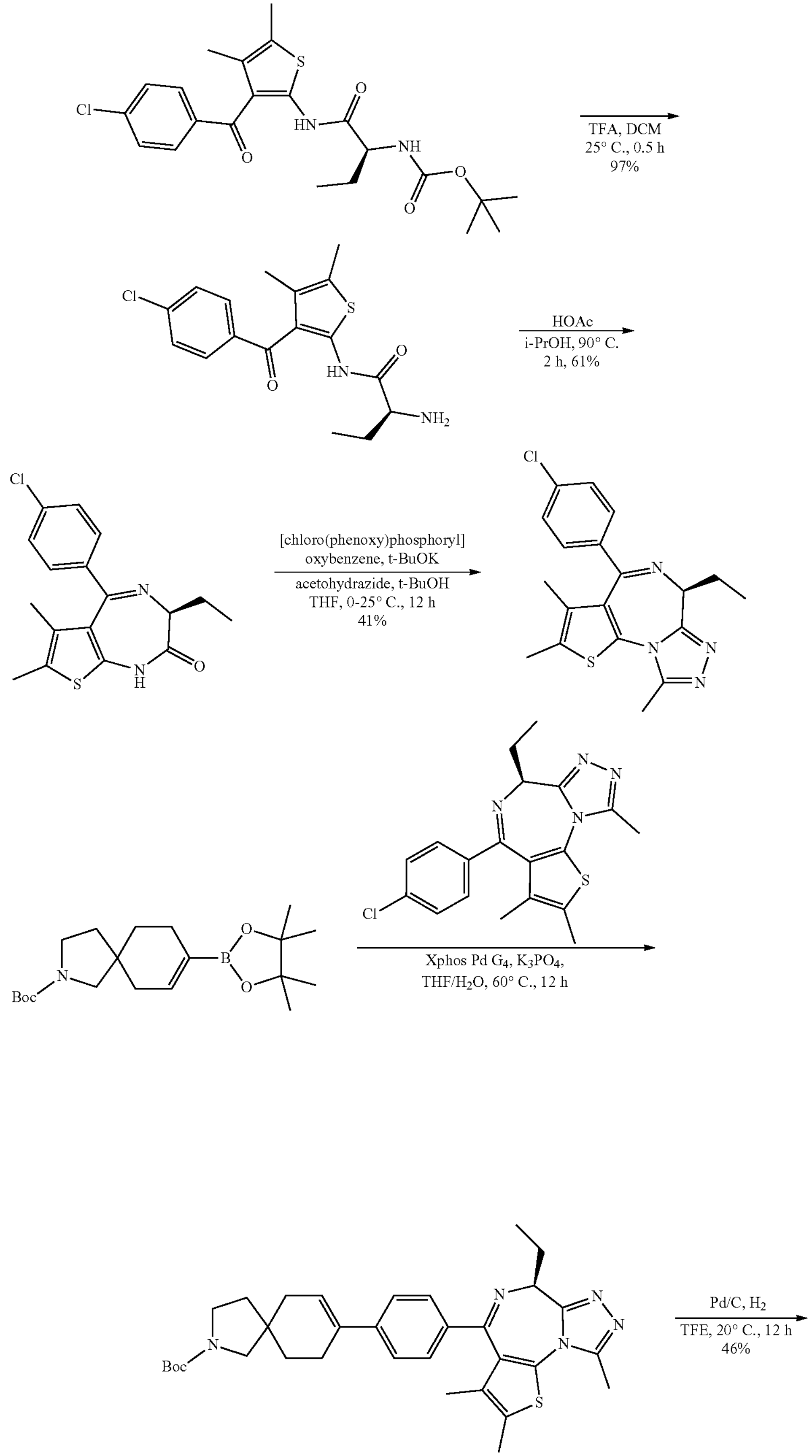

-continued

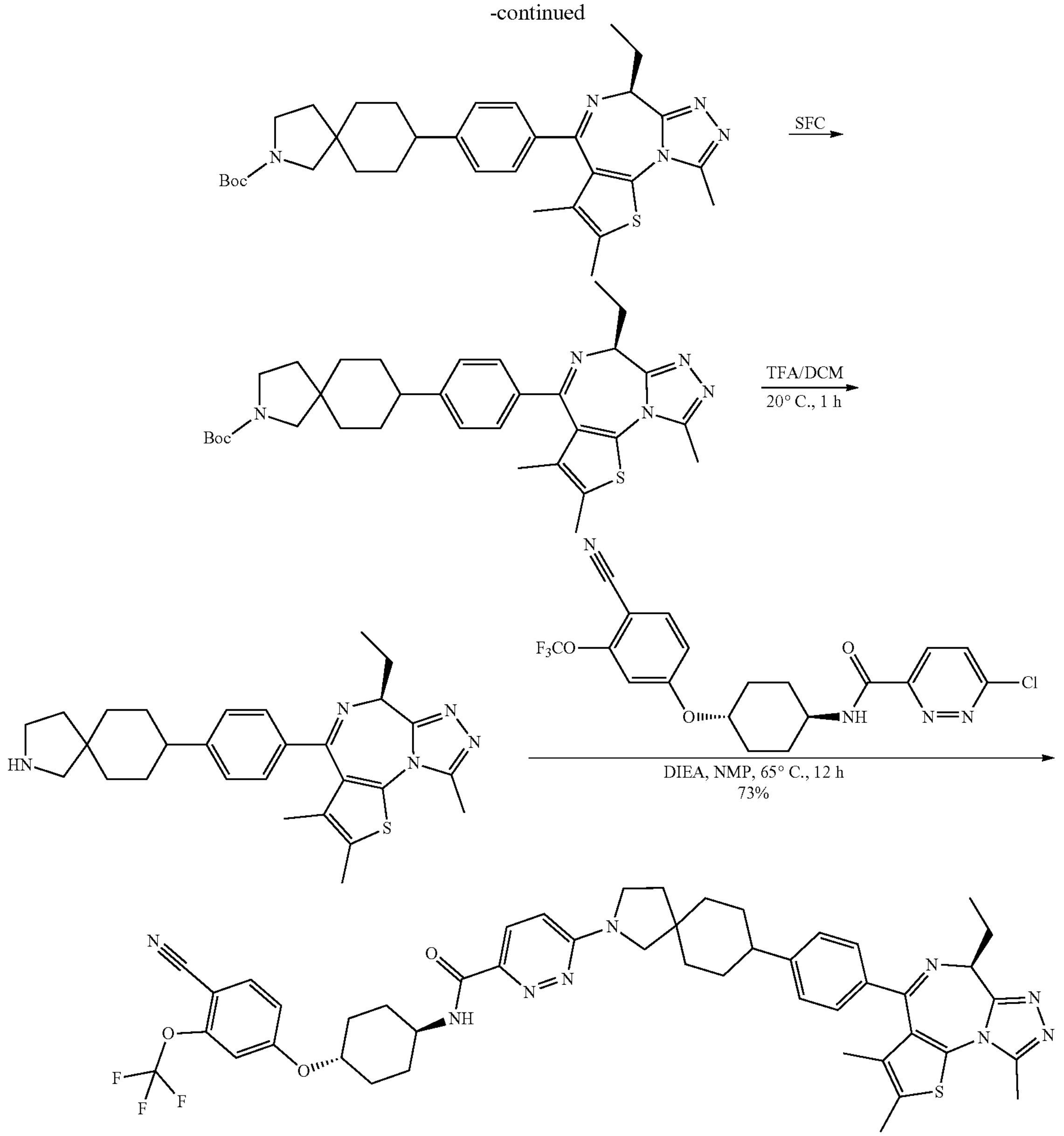

I-13

Step 1: Preparation of tert-butyl N-[(1S)-1-[[3-(4-chlorobenzoyl)-4,5-dimethyl-2-thienyl]carbamoyl]propyl]carbamate. To a solution of (2S)-2-(tert-butoxycarbonylamino) butanoic acid (4.6 g, 22.6 mmol, 3.0 equiv) in DCM (30 mL) was added NMM (4.6 g, 45 mmol, 5.0 mL, 6.0 equiv) and isobutyl carbonochloridate (4.6 g, 33 mmol, 4.4 mL, 4.5 equiv) at 0° C. The mixture was stirred at 25° C. for 1 hour. Next, (2-amino-4,5-dimethyl-3-thienyl)-(4-chlorophenyl) methanone (2 g, 7.5 mmol, 1.0 equiv) was added, and the mixture was stirred at 25° C. for an additional 11 hours. The reaction mixture was filtered, and the filtrate was concentrated. The residue was purified by prep-HPLC (column: Phenomenex luna C18 150×40 mm×15 μm; mobile phase: [water (FA)-ACN]; gradient: 62%-92% B over 15 min) to give tert-butyl N-[(1S)-1-[[3-(4-chlorobenzoyl)-4,5-dimethyl-2-thienyl]carbamoyl]propyl]carbamate (1 g, 29% yield).

Step 2: Preparation of (2S)-2-amino-N-[3-(4-chlorobenzoyl)-4,5-dimethyl-2-thienyl]butanamide. To a solution of tert-butyl N-[(1S)-1-[[3-(4-chlorobenzoyl)-4,5-dimethyl-2-thienyl]carbamoyl]propyl]carbamate (500 mg, 1.1 mmol, 1.0 equiv) in DCM (5 mL) was added TFA (1.3 g, 11.1 mmol, 823 μL, 10.0 equiv). The mixture was stirred at 25° C. for 0.5 hour. The reaction mixture was filtered, and the filtrate was concentrated. The product, (2S)-2-amino-N-[3-(4-chlorobenzoyl)-4,5-dimethyl-2-thienyl]butanamide, was used directly in the next step without purification.

Step 3: Preparation of (3S)-5-(4-chlorophenyl)-3-ethyl-6,7-dimethyl-1,3-dihydrothieno[2,3-e][1,4]diazepin-2-one. To a solution of (2S)-2-amino-N-[3-(4-chlorobenzoyl)-4,5-dimethyl-2-thienyl]butanamide (380 mg, 1.1 mmol, 1.0 equiv) in i-PrOH (5 mL) was added AcOH (325 mg, 5.4 mmol, 310 μL, 5.0 equiv). The mixture was stirred at 90° C. for 2 hours. The reaction mixture was filtered, and the filtrate was concentrated. The residue was purified by column chromatography ($SiO_2$, petroleum ether/ethyl acetate=10/1 to 3/1) to give (3S)-5-(4-chlorophenyl)-3-ethyl-6,7-dimethyl-1,3-dihydrothieno[2,3-e][1,4]diazepin-2-one (220 mg, 61% yield).

Step 4: Preparation of (9S)-7-(4-chlorophenyl)-9-ethyl-4,5,13-trimethyl-3-thia-1,8,11,12-tetrazatricyclo[8.3.0.0$^{2,6}$]trideca-2 (6),4,7,10,12-pentaene. Potassium tert-butoxide (1 M, 859 μL, 1.3 equiv) was added to (3S)-5-(4-chlorophenyl)-3-ethyl-6,7-dimethyl-1,3-dihydrothieno[2,3-e][1,4]diazepin-2-one (220 mg, 660 μmol, 1.0 equiv) in THF (5 mL) at −78° C. The reaction mixture was warmed to −10° C. over 0.5 hour and stirred at 25° C. for an additional 0.5 hour. The reaction mixture was cooled to −78° C. [Chloro(phenoxy)phosphoryl]oxybenzene (230 mg, 859 μmol, 178 μL, 1.3 equiv) was added to the reaction mixture. The resulting mixture was warmed to −10° C. over 0.75 hour. Then, acetohydrazide (73 mg, 991 μmol, 1.5 equiv) was added to the reaction mixture. The reaction mixture was stirred at 25° C. After 1 hour, tert-BuOH (5 mL) was added to the reaction mixture, and the mixture was heated to 90° C. for 1 hour. The reaction mixture was concentrated. The residue was purified by prep-HPLC (column: Phenomenex Luna C18 150×25 mm×10 μm; mobile phase: [water (FA)-ACN]; gradient: 47%-77% B over 10 min) to give (9S)-7-(4-chlorophenyl)-9-ethyl-4,5,13-trimethyl-3-thia-1,8,11,12-tetrazatricyclo[8.3.0.0$^{2,6}$]trideca-2 (6),4,7,10,12-pentaene (100 mg, 41% yield).

Step 5: Preparation of tert-butyl 8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]dec-7-ene-2-carboxylate. A mixture of tert-butyl 8-(4,4,5,5-tetramethyl-1,3,2-dioxaborolan-2-yl)-2-azaspiro[4.5]dec-7-ene-2-carboxylate (636 mg, 1.75 mmol, 1.0 equiv), (9S)-7-(4-chlorophenyl)-9-ethyl-4,5,13-trimethyl-3-thia-1,8,11,12-tetrazatricyclo[8.3.0.0$^{2,6}$]trideca-2 (6),4,7,10,12-pentaene (650 mg, 1.75 mmol, 1.0 equiv), Xphos Pd G4 (150 mg, 175 μmol, 0.1 equiv), and $K_3PO_4$ (1.12 g, 5.26 mmol, 3.0 equiv) in $H_2O$ (1 mL) and THF (4 mL) was stirred at 60° C. for 12 hours under $N_2$ atmosphere. The reaction mixture was concentrated under reduced pressure to afford a residue. The residue was purified by column chromatography ($SiO_2$, petroleum ether/ethyl acetate=1:1 to 0:1) to afford tert-butyl 8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]dec-7-ene-2-carboxylate (1.3 g, crude) as a yellow solid.

Step 6: Preparation of tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate. To a solution of tert-butyl 8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]dec-7-ene-2-carboxylate (1.3 mg, 2.3 mmol, 1.0 equiv) in TFE (4 mL) was added Pd/C (940 mg, 10% purity). The mixture was stirred at 20° C. for 12 hours. The reaction mixture was filtered and concentrated under reduced pressure to afford a residue. The residue was purified by prep-HPLC (column: Phenomenex luna C18 150×40 mm×15 μm; mobile phase: [water (TFA)-ACN]; gradient: 45%-75% B over 10 min) to afford tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate (600 mg, 1.05 mmol, 46% yield) as a yellow solid.

Step 7: Preparation of tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate. Tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate (600 mg, 1.05 mmol) was separated by SFC (column: DAICEL CHIRALPAK AD (250 mm×30 mm, 10 μm); mobile phase: [$CO_2$-EtOH (0.1% $NH_3 \cdot H_2O$)]; B %: 50%, isocratic elution mode) to afford tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate (350 mg, 609 μmol).

Step 8: Preparation of(S)-4-(4-(2-azaspiro[4.5]decan-8-yl)phenyl)-6-ethyl-2,3,9-trimethyl-6H-thieno[3,2-f][1,2,4]triazolo[4,3-a][1,4]diazepine. To a solution of tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate (300 mg, 575 μmol, 1.0 equiv) in DCM (2 mL) was added TFA (1 mL). The mixture was stirred at 20° C. for 1 hour. The reaction mixture was concentrated and basified by aqueous $NaHCO_3$. After extraction with DCM/MeOH (10:1, 10 mL×2), the organic phase was concentrated to afford crude product, (S)-4-(4-(2-azaspiro[4.5]decan-8-yl)phenyl)-6-ethyl-2,3,9-trimethyl-6H-thieno[3,2-f][1,2,4]triazolo[4,3-a][1,4]diazepine (270 mg, crude), which was used directly in the next step without purification.

Step 9: Preparation of N-((1r,4r)-4-(4-cyano-3-(trifluoromethoxy)phenoxy) cyclohexyl)-6-(8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]decan-2-yl) pyridazine-3-carboxamide (I-13). To a solution of(S)-4-(4-(2-azaspiro[4.5]decan-8-yl)phenyl)-6-ethyl-2,3,9-trimethyl-6H-thieno[3,2-f][1,2,4]triazolo[4,3-a][1,4]diazepine (130 mg, 274 μmol, 1.0 equiv) in NMP (0.5 mL) was added DIEA (106 mg, 823 μmol, 143 μL, 3.0 equiv) and 6-chloro-N-((1r,4r)-4-(4-cyano-3-(trifluoromethoxy)phenoxy)cyclohexyl) pyridazine-3-carboxamide (157 mg, 356 μmol, 1.3 equiv). The mixture was stirred at 65° C. for 12 hours. The residue was purified by prep-HPLC (column: Phenomenex luna C18 150×50 mm×10 μm; mobile phase: [water ($NH_4HCO_3$)-ACN]; gradient: 60%-90% B over 10 min) to afford N-((1r,4r)-4-(4-cyano-3-(trifluoromethoxy) phenoxy)cyclohexyl)-6-(8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]decan-2-yl) pyridazine-3-carboxamide (177 mg, 199 μmol, 73% yield) as a white solid. $^1$H NMR (400 MHz, $CD_3OD$): δ 7.92 (d, J=9.5 Hz, 1H), 7.76 (d, J=8.8 Hz, 1H), 7.45-7.38 (m, 2H), 7.37-7.29 (m, 2H), 7.14 (dd, J=2.3, 8.8 Hz, 1H), 7.09-7.01 (m, 2H), 4.57-4.47 (m, 1H), 4.05-3.90 (m, 2H), 3.77-3.50 (m, 4H), 2.70 (s, 3H), 2.68-2.59 (m, 1H), 2.57-2.46 (m, 2H), 2.44 (s, 3H), 2.29-2.18 (m, 2H), 2.15-2.04 (m, 2H), 1.96 (br t, J=7.0 Hz, 2H), 1.91-1.76 (m, 4H), 1.74-1.56 (m, 11H), 1.23 (t, J=7.3 Hz, 3H). LC-MS: MS ($ES^+$): RT=2.306 min, m/z=878.6 $[M+H]^+$; LCMS method: 25.

Example 7—Synthesis of N-[(1r,4r)-4-(4-cyano-3-methoxy-phenoxy)cyclohexyl]-6-[8-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-2-azaspiro[4.5]decan-2-yl]pyridazine-3-carboxamide (I-19)
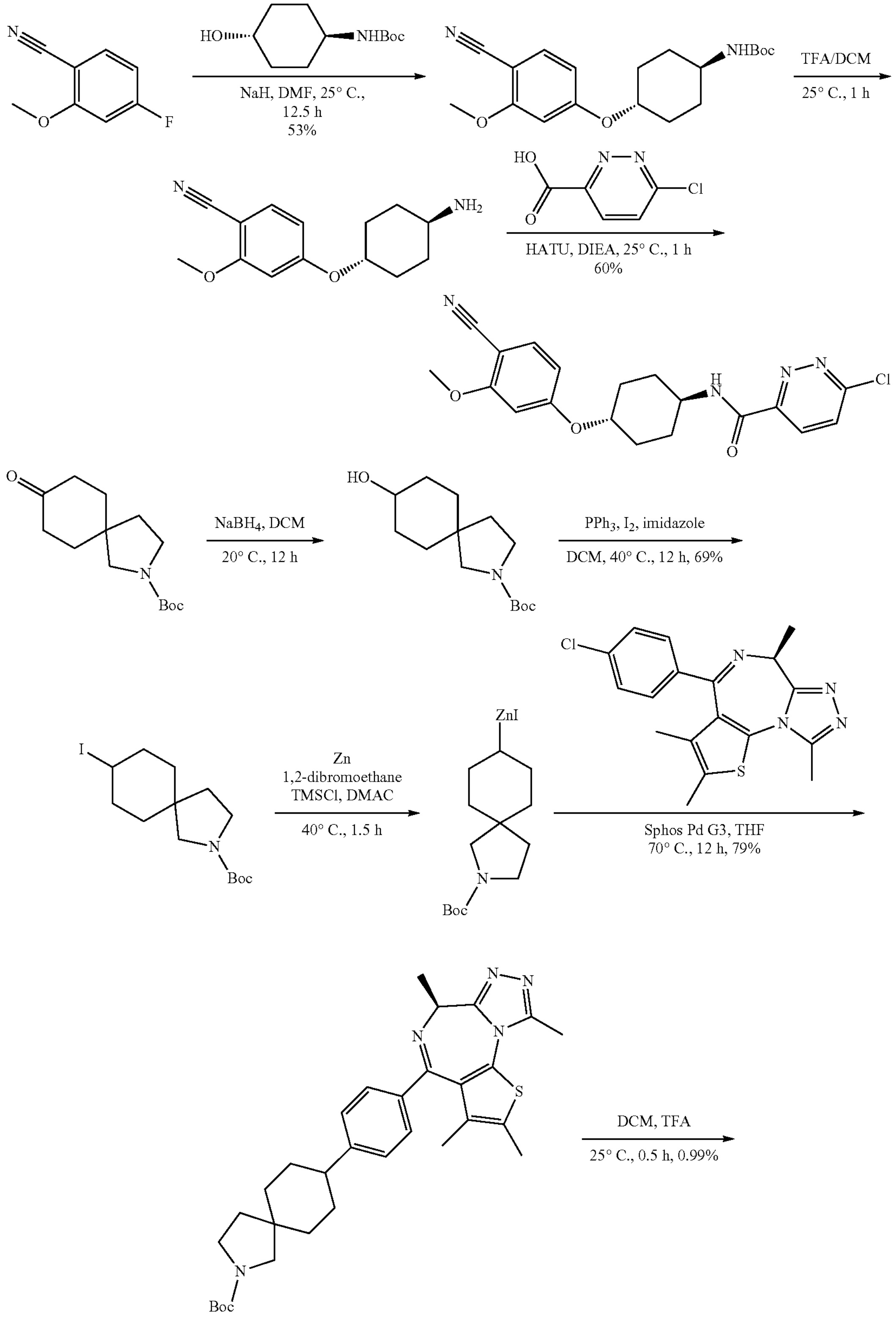

-continued

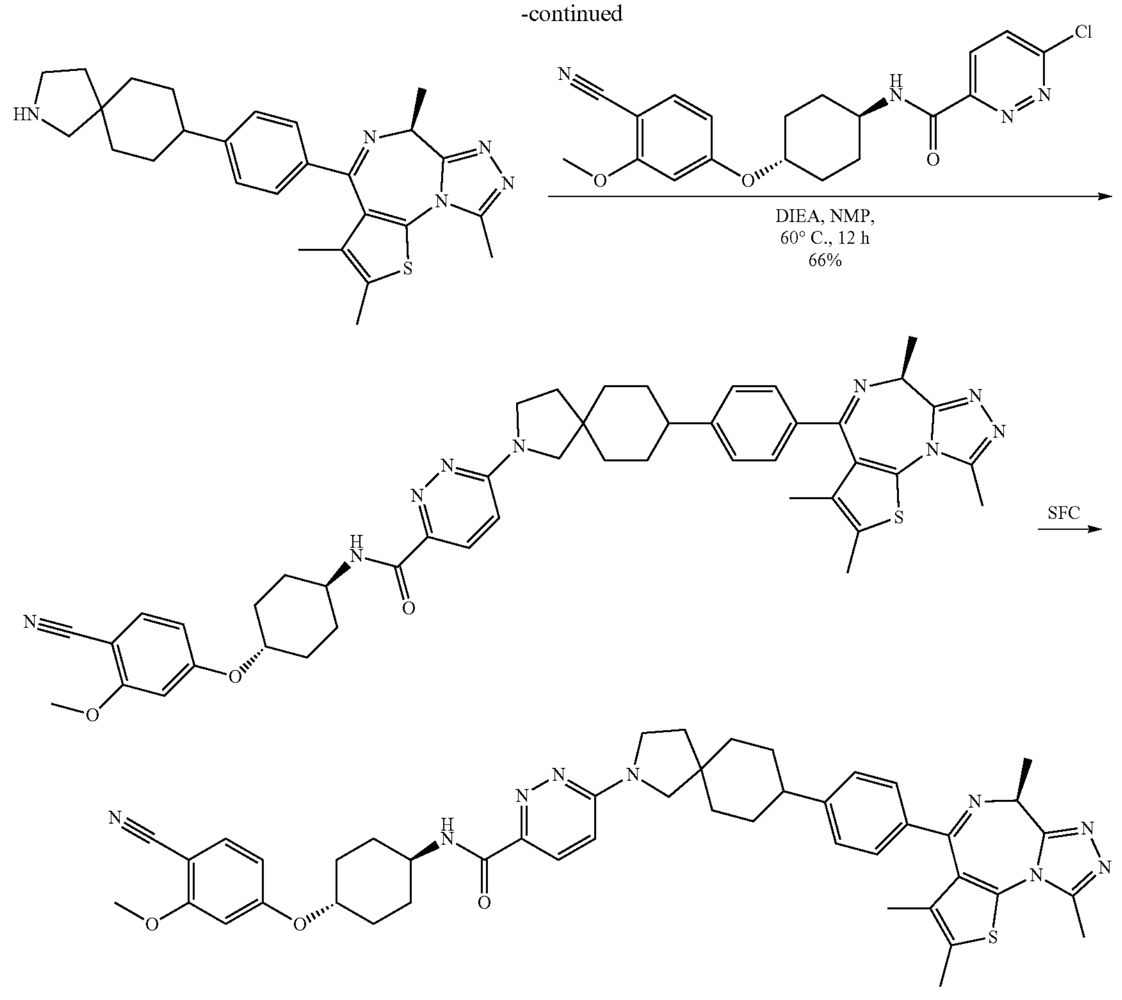

I-19

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxycyclohexyl) carbamate (5.6 g, 26.01 mmol, 1.0 equiv). After 30 minutes, 4-fluoro-2-methoxy-benzonitrile (3.93 g, 26.01 mmol, 1.0 equiv) was added. The reaction mixture was slowly allowed to warm to 25° C. and stirred for 12 hours. The reaction mixture was quenched with saturated aqueous $NH_4Cl$ (100 mL) solution at 0° C. The resulting mixture was extracted with ethyl acetate (100 mL×3). The combined organic layers were dried over anhydrous $Na_2SO_4$, filtered, and concentrated in vacuo. The residue was purified by column chromatography ($SiO_2$, petroleum ether:ethyl acetate=0:1 to 3:1) to afford tert-butyl ((1r,4r)-4-(4-cyano-3-methoxyphenoxy) cyclohexyl) carbamate (4.8 g, 13.86 mmol, 53% yield) as a white solid.

Step 2: Preparation of 4-(((1r,4r)-4-aminocyclohexyl) oxy)-2-methoxy-benzonitrile. To a solution of tert-butyl ((1r,4r)-4-(4-cyano-3-methoxyphenoxy) cyclohexyl) carbamate (0.5 g, 1.44 mmol, 1.0 equiv) in DCM (2 mL) was added TFA (1 mL). The mixture was stirred at 25° C. for 1 hour. The reaction mixture was concentrated under reduced pressure to remove solvent to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-[(1r,4r)-4-(4-cyano-3-methoxy-phenoxy) cyclohexyl]pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 μL, 3.0 equiv). The mixture was stirred at 25° C. for 1 hour. The reaction mixture was concentrated under reduced pressure to remove solvent. The residue was purified by prep-HPLC (column: Waters xbridge 150×25 mm×10 μm; mobile phase: [water ($NH_4HCO_3$)-ACN]; gradient: 49%-69% B over 8 min) to afford 6-chloro-N-[(1r,4r)-4-(4-cyano-3-methoxy-phenoxy)cyclohexyl]pyridazine-3-carboxamide (337 mg, 871 μmol, 60% yield) as a white solid.

Step 4: Preparation of tert-butyl 8-hydroxy-2-azaspiro[4.5]decane-2-carboxylate. To a solution of tert-butyl 8-oxo-2-azaspiro[4.5]decane-2-carboxylate (2 g, 7.8 mmol, 1 equiv) in DCM (20 mL) was added $NaBH_4$ (400 mg, 10 mmol, 1.3 equiv). The mixture was stirred at 20° C. for 12 hours. The reaction mixture was filtered, and the filtrate was concentrated to afford crude tert-butyl 8-hydroxy-2-azaspiro[4.5]decane-2-carboxylate, which was used directly in the next step without purification.

Step 5: Preparation of tert-butyl 8-iodo-2-azaspiro[4.5]decane-2-carboxylate. To a solution of tert-butyl 8-hydroxy-2-azaspiro[4.5]decane-2-carboxylate (2 g, 7.8 mmol, 1 equiv) in DCM (20 mL) was added $PPh_3$ (2.8 g, 10 mmol, 1.4 equiv), imidazole (1.6 g, 23 mmol, 3 equiv), and $I_2$ (2.9 g, 11 mmol, 2 mL, 1.5 equiv). The mixture was stirred at 40° C. for 12 hours. The reaction mixture was filtered and concentrated under reduced pressure to give a residue. The residue was purified by prep-TLC ($SiO_2$, EA:PE=5:1) to afford tert-butyl 8-iodo-2-azaspiro[4.5]decane-2-carboxylate (2 g, 69% yield) as a white oil.

Step 6: Preparation of (2-tert-butoxycarbonyl-2-azaspiro[4.5]decan-8-yl)-iodo-zinc. To a stirred solution of Zn (830 mg, 12 mmol, 5.8 equiv) in DMAC (2 mL) was added TMSCl (88 mg, 810 μmol, 102 μL, 0.37 equiv) and 1,2-dibromoethane (152 mg, 810 μmol, 61 μL, 0.37 equiv) in DMAC (1 mL) at 40° C. After 30 minutes of stirring, tert-butyl 8-iodo-2-azaspiro[4.5]decane-2-carboxylate (800 mg, 2 mmol, 1 equiv) was added. The mixture was stirred at 40° C. for an additional 1 hour and filtered. After filtration, the filtrate was concentrated to afford crude (2-tert-butoxycarbonyl-2-azaspiro[4.5]decan-8-yl)-iodo-zinc, which was used directly in the next step without purification.

Step 7: Preparation of tert-butyl 8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate. To a solution of (2-tert-butoxycarbonyl-2-azaspiro[4.5]decan-8-yl)-iodo-zinc (940 mg, 2 mmol, 3.8 equiv) and (9S)-7-(4-chlorophenyl)-4,5,9,13-tetramethyl-3-thia-1,8,11,12-tetrazatricyclo[8.3.0.$0^{2,6}$]trideca-2 (6),4,7,10,12-pentaene (200 mg, 560 μmol, 1 equiv) in THF (1 mL) was added dicyclohexyl-[2-(2,6-dimethoxyphenyl)phenyl]phosphane; methanesulfonate; (2-phenylanilino) palladium (1+) (87 mg, 112 μmol, 0.2 equiv). The mixture was stirred at 70° C. for 12 hours. The residue was purified by prep-HPLC (column: Phenomenex Luna C18 150×25 mm×10 μm; mobile phase: [water (FA)-ACN]; gradient: 65%-95% B over 9 min) to afford tert-butyl 8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (250 mg, 79% yield) as a yellow solid.

Step 8: Preparation of (9S)-7-[4-(2-azaspiro[4.5]decan-8-yl)phenyl]-4,5,9,13-tetramethyl-3-thia-1,8,11,12-tetrazatricyclo[8.3.0.$0^{2,6}$]trideca-2 (6),4,7,10,12-pentaene. To a solution of tert-butyl 8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (830 mg, 1 mmol, 1 equiv) in DCM (3 mL) was added TFA (1 g, 13 mmol, 1 mL, 9 equiv). The mixture was stirred at 25° C. for 0.5 hour. The reaction mixture was filtered, diluted with $H_2O$ (20 mL), and extracted with ethyl acetate (30 mL). The combined organic layers were washed with brine (50 mL), filtered, and concentrated under reduced pressure to give (9S)-7-[4-(2-azaspiro[4.5]decan-8-yl)phenyl]-4,5,9,13-tetramethyl-3-thia-1,8,11,12-tetrazatricyclo[8.3.0.$0^{2,6}$]trideca-2 (6),4,7,10,12-pentaene. The residue was used directly in the next step without purification.

Step 9: Preparation of N-[(1r,4r)-4-(4-cyano-3-methoxy-phenoxy)cyclohexyl]-6-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide. To a solution of (9S)-7-[4-(2-azaspiro[4.5]decan-8-yl)phenyl]-4,5,9,13-tetramethyl-3-thia-1,8,11,12-tetrazatricyclo[8.3.0.$0^{2,6}$]trideca-2 (6),4,7,10,12-pentaene (0.15 g, 326 μmol, 1 equiv) in NMP (1 mL) was added DIEA (371 mg, 2 mmol, 0.5 mL, 8 equiv) and 6-chloro-N-[(1r,4r)-4-(4-cyano-3-methoxy-phenoxy)cyclohexyl]pyridazine-3-carboxamide (138 mg, 358 μmol, 1.1 equiv). The mixture was stirred at 60° C. for 12 hours. The reaction mixture was filtered, diluted with $H_2O$ (20 mL), and extracted with ethyl acetate (30 mL). The combined organic layers were washed with brine (50 mL), filtered, and concentrated under reduced pressure to give a residue. The residue was purified by column chromatography ($SiO_2$, dichloromethane:methanol=10:1) to give N-[(1r,4r)-4-(4-cyano-3-methoxy-phenoxy)cyclohexyl]-6-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide (0.17 g, 195 μmol, 59% yield, 93% purity) as a white solid.

Step 10: Preparation of N-[(1r,4r)-4-(4-cyano-3-methoxy-phenoxy)cyclohexyl]-6-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide (I-19). N-[(1r,4r)-4-(4-Cyano-3-methoxy-phenoxy)cyclohexyl]-6-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide (170 mg) was purified by prep-SFC (column: DAICEL CHIRALCEL OD (250 mm×30 mm×10 μm); mobile phase: [$CO_2$-ACN/MeOH (0.1% $NH_3 \cdot H_2O$)]; B %: 65%, isocratic elution mode) to give N-[(1r,4r)-4-(4-cyano-3-methoxy-phenoxy)cyclohexyl]-6-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide (53 mg, 33%) as a white solid. $^1$H NMR: (400 MHz, MeOD) δ=7.94 (d, J=9.5 Hz, 1H), 7.52 (d, J=9.4 Hz, 1H), 7.46-7.40 (m, 2H), 7.38-7.32 (m, 2H), 7.06 (d, J=9.5 Hz, 1H), 6.72-6.64 (m, 2H), 4.58 (s, 1H), 4.55-4.46 (m, 1H), 4.34-4.24 (m, 1H), 4.05-3.96 (m, 1H), 3.94 (s, 3H), 3.74-3.52 (m, 4H), 2.72 (s, 3H), 2.44 (s, 3H), 2.24 (s, 2H), 2.16-2.08 (m, 2H), 2.04-1.94 (m, 5H), 1.92-1.82 (m, 4H), 1.72-1.62 (m, 10H). QCMS: MS ($ES^+$): RT=1.977 min, m/z=810 [M+1]; LCMS Method: 25.

Example 8—Synthesis of N-[4-(4-cyano-3-methoxy-phenoxy)cyclohexyl]-6-[2-[[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl]pyridazine-3-carboxamide (I-25)
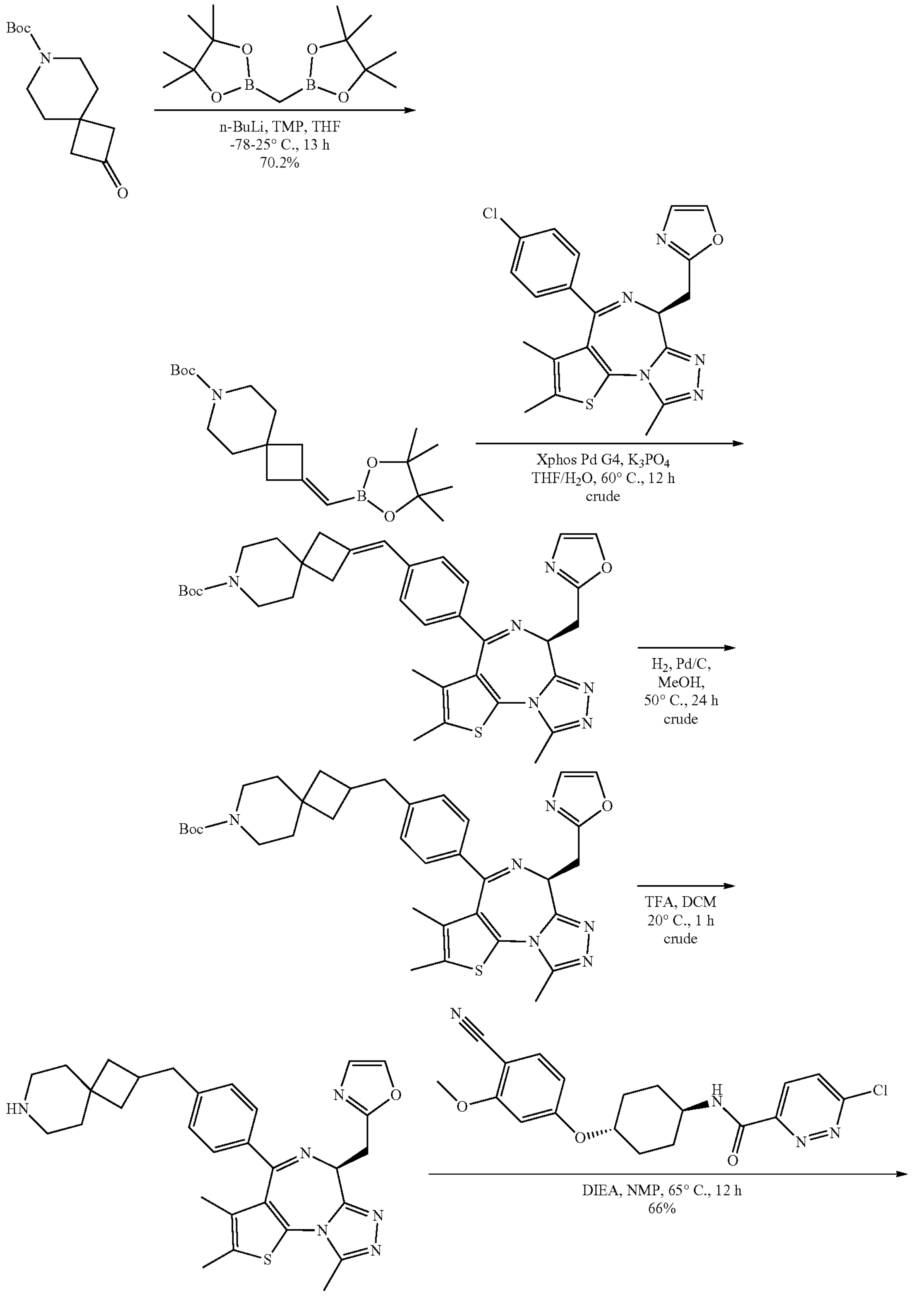

-continued

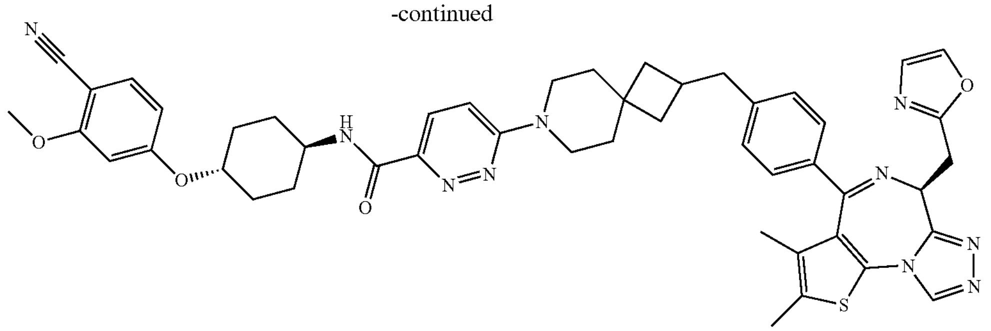

I-25

Step 1: Preparation of tert-butyl 2-[(4,4,5,5-tetramethyl-1,3,2-dioxaborolan-2-yl)methylene]-7-azaspiro[3.5]nonane-7-carboxylate. To a solution of TMP (18.50 g, 131.00 mmol, 22.24 mL, 2.09 eq) in THF (150 mL) was added dropwise n-BuLi (2.5 M, 52.40 mL, 2.09 eq) at −30° C. After addition, the mixture was stirred at −30° C. for 1 hour, and then 4,4,5,5-tetramethyl-2-[(4,4,5,5-tetramethyl-1,3,2-dioxaborolan-2-yl)methyl]-1,3,2-dioxaborolane (25.53 g, 95.27 mmol, 1.52 eq) in THF (40 mL) was added dropwise at −78° C. The resulting mixture was stirred at −78° C. for 1 hour. Next, tert-butyl 2-oxo-7-azaspiro[3.5]nonane-7-carboxylate (15 g, 62.68 mmol, 1 eq) in THF (40 mL) was added at −78° C. The mixture was stirred at −78° C. for 1 hour and then stirred at 25° C. for an additional 10 hours. The reaction mixture was quenched with aqueous $NH_4Cl$ (150 mL). The aqueous phase was extracted with EtOAc (100 mL×3). The combined organic layers were dried with anhydrous $Na_2SO_4$, filtered, and concentrated to give a residue. The residue was purified by flash silica gel chromatography (ISCO®; 80 g SepaFlash® Silica Flash Column, eluent of 0~10% ethyl acetate/petroleum ether gradient at 100 mL/min). Compound tert-butyl 2-[(4,4,5,5-tetramethyl-1,3,2-dioxaborolan-2-yl)methylene]-7-azaspiro[3.5]nonane-7-carboxylate (16 g, 44.04 mmol, 70.26% yield) was obtained as a yellow oil.

Step 2: Preparation of tert-butyl 2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methylene]-7-azaspiro[3.5]nonane-7-carboxylate. A mixture of tert-butyl 2-[(4,4,5,5-tetramethyl-1,3,2-dioxaborolan-2-yl)methylene]-7-azaspiro[3.5]nonane-7-carboxylate (1.29 g, 3.55 mmol, 1.51 eq), 2-[[(9S)-7-(4-chlorophenyl)-4,5,13-trimethyl-3-thia-1,8,11,12-tetrazatricyclo[8.3.0.$0^{2,6}$]trideca-2 (6),4,7,10,12-pentaen-9-yl]methyl]oxazole (1 g, 2.36 mmol, 1 eq), Xphos Pd G4 (203 mg, 235.92 μmol, 0.1 eq), and $K_3PO_4$ (1.00 g, 4.72 mmol, 2 eq) in THF (10 mL) and $H_2O$ (1 mL) was degassed and purged with $N_2$ 3 times. The mixture was stirred at 60° C. for 12 hours under $N_2$ atmosphere. The reaction mixture was filtered and concentrated under reduced pressure to give a residue. The residue was purified by flash silica gel chromatography (ISCO®; 40 g SepaFlash® Silica Flash Column, eluent of 0~9% DCM/MeOH at 30 mL/min). Compound tert-butyl 2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methylene]-7-azaspiro[3.5]nonane-7-carboxylate (1.85 g, crude) was obtained as a yellow solid.

Step 3: Preparation of tert-butyl 2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methyl]-7-azaspiro[3.5]nonane-7-carboxylate. To a solution of tert-butyl 2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methylene]-7-azaspiro[3.5]nonane-7-carboxylate (850 mg, 1.36 mmol, 1 eq) in MeOH (10 mL) was added Pd/C (300 mg, 281.90 μmol, 10% purity, $2.07\times10^{-1}$ eq) under $N_2$ atmosphere. The suspension was degassed and purged with $H_2$ 3 times. The mixture was stirred under $H_2$ (50 psi) at 50° C. for 24 hours. The reaction mixture was filtered and concentrated under reduced pressure to give a residue. Compound tert-butyl 2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methyl]-7-azaspiro[3.5]nonane-7-carboxylate ($Z^{20}$ mg, crude) was obtained as a yellow solid.

Step 4: Preparation of 2-[[(9S)-7-[4-(7-azaspiro[3.5]nonan-2-ylmethyl)phenyl]-4,5,13-trimethyl-3-thia-1,8,11,12-tetrazatricyclo[8.3.0.$0^{2,6}$]trideca-2 (6),4,7,10,12-pentaen-9-yl]methyl]oxazole. To a solution of tert-butyl 2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methyl]-7-azaspiro[3.5]nonane-7-carboxylate (720 mg, 1.15 mmol, 1 eq) in DCM (8 mL) was added TFA (2.30 g, 20.19 mmol, 1.5 mL, 17.58 eq). The mixture was stirred at 20° C. for 1 hour. The reaction mixture was concentrated under reduced pressure to remove solvent. The residue was diluted with aqueous $NaHCO_3$ (20 mL) and extracted with DCM (20 mL×3). The combined organic layers were dried over $Na_2SO_4$, filtered, and concentrated under reduced pressure to give a residue. Compound 2-[[(9S)-7-[4-(7-azaspiro[3.5]nonan-2-ylmethyl)phenyl]-4,5,13-trimethyl-3-thia-1,8,11,12-tetrazatricyclo[8.3.0.$0^{2,6}$]trideca-2 (6),4,7,10,12-pentaen-9-yl]methyl]oxazole (540 mg, crude) was obtained as an off-white solid.

Step 5: Preparation of N-[4-(4-cyano-3-methoxy-phenoxy)cyclohexyl]-6-[2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methyl]-7-azaspiro[3.5]nonan-7-yl]pyridazine-3-carboxamide (I-25). To a solution of 2-[[(9S)-7-[4-(7-azaspiro[3.5]nonan-2-ylmethyl)phenyl]-4,5,13-trimethyl-3-thia-1,8,11,12-tetrazatricyclo[8.3.0.$0^{2,6}$]trideca-2 (6),4,7,10,12-pentaen-9-yl]methyl]oxazole (160 mg, 304 μmol, 1.0 equiv) in NMP (0.5 mL) was added DIEA (118 mg, 911 μmol, 159 μL, 3.0 equiv) and 6-chloro-N-[4-(4-cyano-3-methoxy-phenoxy)cyclohexyl]pyridazine-3-carboxamide (153 mg, 395 μmol, 1.3 equiv). The mixture was stirred at 65° C. for 12 hours. The residue was purified by prep-HPLC (column: Phenomenex luna C18 150×25 mm×10 μm; mobile phase: [water (FA)-ACN]; gradient: 64%-94% B over 10 min) to afford compound N-[4-(4-cyano-3-methoxy-phenoxy)cyclohexyl]-6-[2-[[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl] pyridazine-3-carboxamide (178 mg, 200 μmol, 66% yield) as an off-white solid. $^1$H NMR (400 MHz, $CD_3OD$) 7.93-7.79 (m, 2H), 7.49 (d, J=9.3 Hz, 1H), 7.35-7.24 (m, 3H), 7.22-7.15 (m, 2H), 7.14-7.08 (m, 1H), 6.71-6.57 (m, 2H), 4.82-4.69 (m, 1H), 4.58-4.34 (m, 1H), 3.93 (br s, 3H), 3.92-3.88 (m, 3H), 3.73-3.57 (m, 4H), 2.84-2.72 (m, 2H), 2.71-2.66 (m, 3H), 2.63-2.51 (m, 1H), 2.47-2.35 (m, 3H), 2.25-2.04 (m, 4H), 2.02-1.93 (m, 2H), 1.76-1.49 (m, 13H). LC-MS: MS ($ES^+$): RT=2.426 min, m/z=877.4 $[M+H]^+$; LCMS method: 25.

Example 9—Synthesis of N-[4-(4-cyano-3-methoxy-phenoxy)cyclohexyl]-6-[8-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl] pyridazine-3-carboxamide (I-27)

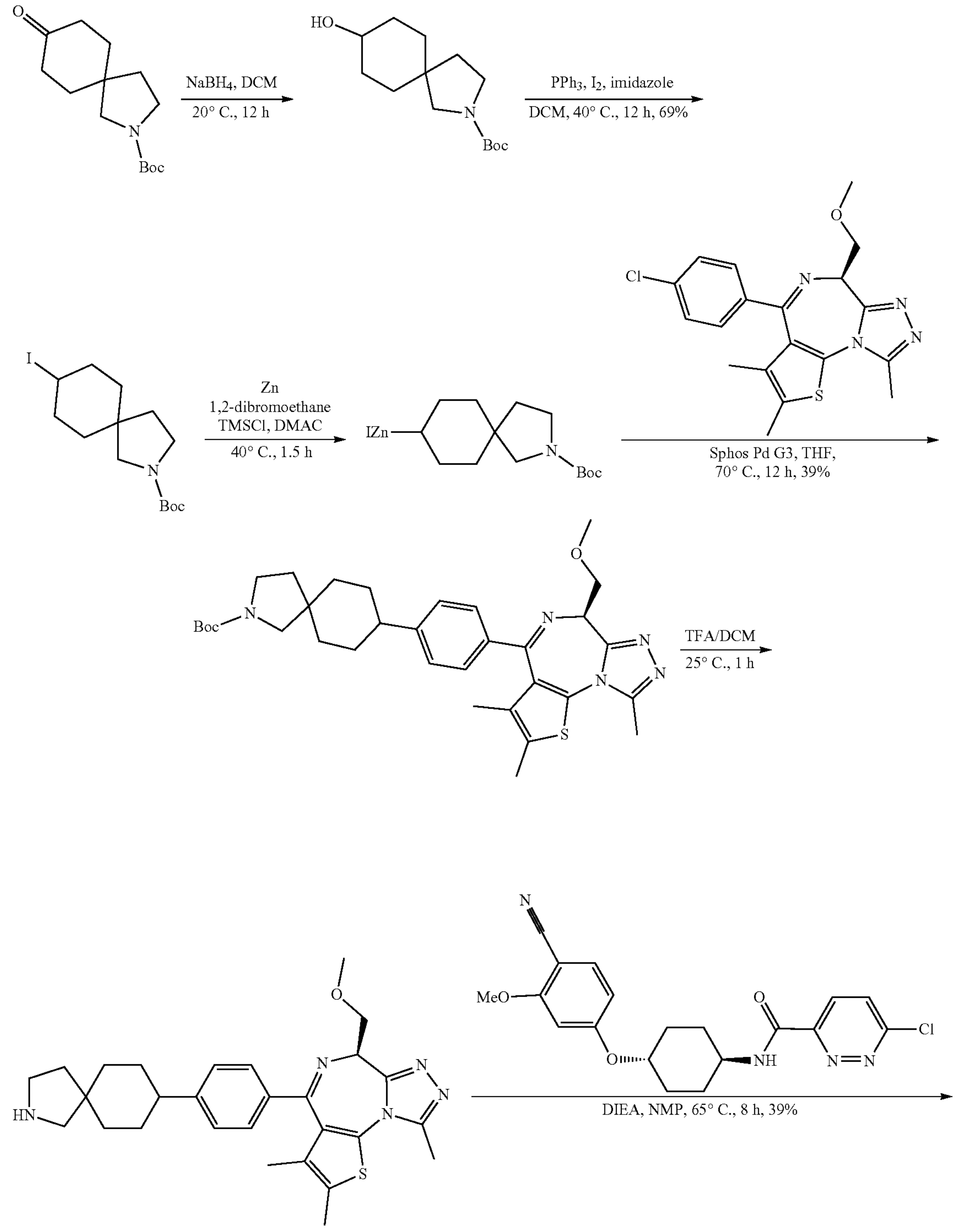

-continued

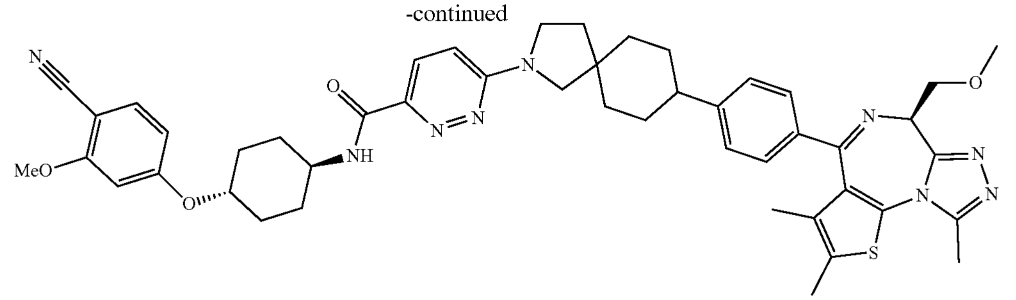

I-27

Step 1: Preparation of tert-butyl 8-hydroxy-2-azaspiro[4.5]decane-2-carboxylate. To a solution of tert-butyl 8-oxo-2-azaspiro[4.5]decane-2-carboxylate (2 g, 7.8 mmol, 1 equiv) in DCM (20 mL) was added $NaBH_4$ (400 mg, 10 mmol, 1.3 equiv). The mixture was stirred at 20° C. for 12 hours. The reaction mixture was filtered and concentrated under reduced pressure to afford crude tert-butyl 8-hydroxy-2-azaspiro[4.5]decane-2-carboxylate, which was used directly in the next step without purification.

Step 2: Preparation of tert-butyl 8-iodo-2-azaspiro[4.5]decane-2-carboxylate. To a solution of tert-butyl 8-hydroxy-2-azaspiro[4.5]decane-2-carboxylate (2 g, 7.8 mmol, 1 equiv) in DCM (20 mL) was added $PPh_3$ (2.8 g, 10 mmol, 1.4 equiv), imidazole (1.6 g, 23 mmol, 3 equiv), and $I_2$ (2.9 g, 11 mmol, 2 mL, 1.5 equiv). The mixture was stirred at 40° C. for 12 hours. The reaction mixture was filtered and concentrated under reduced pressure to give a residue, which was purified by prep-TLC ($SiO_2$, ethyl acetate:petroleum ether=5:1) to afford tert-butyl 8-iodo-2-azaspiro[4.5]decane-2-carboxylate (2 g, 69% yield) as a white oil.

Step 3: Preparation of (2-tert-butoxycarbonyl-2-azaspiro[4.5]decan-8-yl)-iodo-zinc. To a stirred solution of Zn (830 mg, 12 mmol, 5.8 equiv) in DMAC (2 mL) was added TMSCl (88 mg, 810 μmol, 102 μL, 0.37 equiv) and 1,2-dibromoethane (152 mg, 810 μmol, 61 μL, 0.37 equiv) in DMAC (1 mL) at 40° C. After stirring for 30 minutes, tert-butyl 8-iodo-2-azaspiro[4.5]decane-2-carboxylate (800 mg, 2 mmol, 1 equiv) was added. The mixture was stirred at 40° C. for an additional 1 hour and then filtered. The filtrate was concentrated to afford crude product (2-tert-butoxycarbonyl-2-azaspiro[4.5]decan-8-yl)-iodo-zinc.

Step 4: Preparation of tert-butyl 8-[4-[(9R)-9-(methoxymethyl)-4,5,13-trimethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate. To a solution of (9R)-7-(4-chlorophenyl)-9-(methoxymethyl)-4,5,13-trimethyl-3-thia-1,8,11,12-tetrazatricyclo[8.3.0.$0^{2,6}$]trideca-2 (6),4,7,10,12-pentaene (202 mg, 522 μmol, 1 equiv) and (2-tert-butoxycarbonyl-2-azaspiro[4.5]decan-8-yl)-iodo-zinc (900 mg, 2.09 mmol, 4 equiv) in THF (2 mL) was added Sphos Pd G3 (81 mg, 104 μmol, 0.2 equiv). The mixture was stirred at 70° C. for 12 hours. The reaction mixture was diluted with water (80 mL) and extracted with EtOAc (80 mL×3). The combined organic layers were washed with brine (300 mL), dried over $Na_2SO_4$, filtered, and concentrated under reduced pressure to give a residue. The residue was purified by prep-HPLC (FA condition; column: Phenomenex luna C18 150×25 mm×10 μm; mobile phase: [water (FA)-ACN]; gradient: 66%-96% B over 10 min) to give tert-butyl 8-[4-[(9R)-9-(methoxymethyl)-4,5,13-trimethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (120 mg, 39% yield).

Step 5: Preparation of (9R)-7-[4-(2-azaspiro[4.5]decan-8-yl)phenyl]-9-(methoxymethyl)-4,5,13-trimethyl-3-thia-1,8,11,12-tetrazatricyclo[8.3.0.$0^{2,6}$]trideca-2 (6),4,7,10,12-pentaene. To a solution of tert-butyl 8-[4-[(9R)-9-(methoxymethyl)-4,5,13-trimethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (70 mg, 118 μmol, 1.0 equiv) in DCM (1 mL) was added TFA (0.5 mL). The mixture was stirred at 25° C. for 1 hour. The reaction mixture was concentrated, basified with aqueous $NaHCO_3$ and extracted with DCM/MeOH (10:1, 10 mL×3). The combined organic phase was dried over anhydrous $Na_2SO_4$, filtered, and concentrated to give (9R)-7-[4-(2-azaspiro[4.5]decan-8-yl)phenyl]-9-(methoxymethyl)-4,5,13-trimethyl-3-thia-1,8,11,12-tetrazatricyclo[8.3.0.$0^{2,6}$]trideca-2 (6),4,7,10,12-pentaene (110 mg, 224 μmol) as a yellow solid.

Step 6: Preparation of N-[4-(4-cyano-3-methoxy-phenoxy)cyclohexyl]-6-[8-[4-[(9R)-9-(methoxymethyl)-4,5,13-trimethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide (I-27). To a solution of (9R)-7-[4-(2-azaspiro[4.5]decan-8-yl)phenyl]-9-(methoxymethyl)-4,5,13-trimethyl-3-thia-1,8,11,12-tetrazatricyclo[8.3.0.$0^{2,6}$]trideca-2 (6),4,7,10,12-pentaene (55 mg, 112 μmol, 1.0 equiv) and 6-chloro-N-[4-(4-cyano-3-methoxy-phenoxy)cyclohexyl]pyridazine-3-carboxamide (56 mg, 146 μmol, 1.3 equiv) in NMP (0.5 mL) was added DIEA (45 mg, 336 μmol, 0.1 mL, 3.0 equiv). The mixture was stirred at 65° C. for 8 hours. The residue was purified by prep-HPLC (column: Waters xbridge 150×25 mm 10 μm; mobile phase: [water ($NH_4HCO_3$)-ACN]; gradient: 60%-80% B over 8 minutes) to afford N-[4-(4-cyano-3-methoxy-phenoxy)cyclohexyl]-6-[8-[4-[(9R)-9-(methoxymethyl)-4,5,13-trimethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide (38.17 mg, 44.31 μmol, 39.45% yield, 97.51% purity) as a white solid. $^1$H NMR (400 MHz, $CD_3OD$) δ 7.94 (d, J=9.4 Hz, 1H), 7.53 (d, J=9.0 Hz, 1H), 7.48-7.41 (m, 2H), 7.35 (d, J=8.3 Hz, 2H), 7.07 (br d, J=9.1 Hz, 1H), 6.72-6.62 (m, 2H), 4.47-4.32 (m, 3H), 4.05-3.96 (m, 1H), 3.94 (s, 3H), 3.74-3.53 (m, 7H), 2.77-2.61 (m, 4H), 2.46 (s, 3H), 2.29-2.18 (m, 2H), 2.13 (br d, J=4.0 Hz, 2H), 1.98 (t, J=7.1 Hz, 2H), 1.86-1.86 (m, 1H), 1.92-1.80 (m, 4H), 1.74-1.59 (m, 11H). LC-MS: MS ($ES^+$): RT=2.115 min, m/z=840.1 $[M+H]^+$; LCMS method: 25.

Example 10—Synthesis of N-[4-(4-cyano-3-methoxy-phenoxy)cyclohexyl]-6-[8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl] pyridazine-3-carboxamide (I-29)
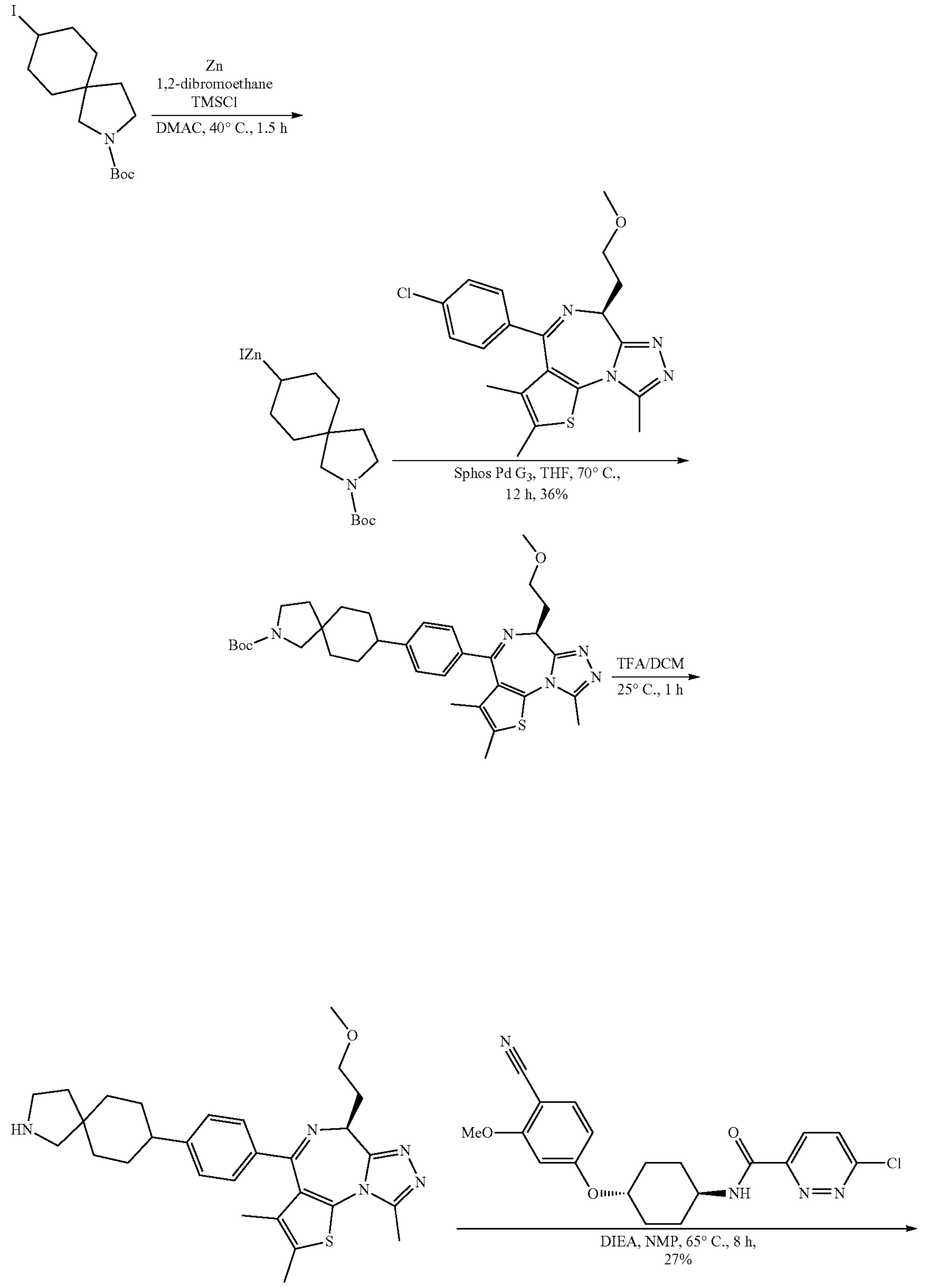

-continued

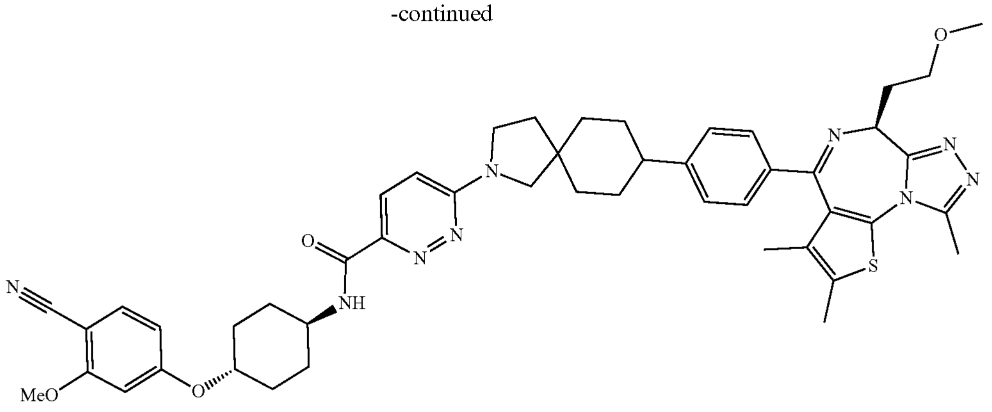

I-29

Step 1: Preparation of (2-tert-butoxycarbonyl-2-azaspiro[4.5]decan-8-yl)-iodo-zinc. To a stirred solution of Zn (1.4 g, 22 mmol, 10 equiv) in DMAC (2 mL) was added TMSCl (88 mg, 810 μmol, 102 L, 0.37 equiv) and 1,2-dibromoethane (152 mg, 810 μmol, 61 μL, 0.37 equiv) in DMAC (1 mL) at 40° C. After stirring for 30 minutes, tert-butyl 8-iodo-2-azaspiro[4.5]decane-2-carboxylate (800 mg, 2 mmol, 1 equiv) was added. The mixture was stirred at 40° C. for an additional 1 hour and filtered. The filtrate was concentrated to afford crude (2-tert-butoxy-carbonyl-2-azaspiro[4.5]decan-8-yl)-iodo-zinc, which was used directly in the next step without purification.

Step 2: Preparation of tert-butyl 8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate. To a solution of (2-tert-butoxycarbonyl-2-azaspiro[4.5]decan-8-yl)-iodo-zinc (940 mg, 2 mmol, 4 equiv) and (9S)-7-(4-chlorophenyl)-9-(2-methoxyethyl)-4,5,13-trimethyl-3-thia-1,8,11,12-tetrazatricyclo[8.3.0.0$^{2,6}$]trideca-2 (6),4,7,10,12-pentaene (200 mg, 498 μmol, 1 equiv) in THF (1 mL) was added Sphos Pd G3 (77 mg, 99 μmol, 0.2 equiv). The mixture was stirred at 70° C. for 12 hours. The residue was purified by prep-HPLC (column: Phenomenex luna C18 150×25 mm×10 μm; mobile phase: [water (FA)-ACN]; gradient: 68%-98% B over 10 min) to afford tert-butyl 8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (110 mg, 182 μmol, 36% yield) as a white solid.

Step 3: Preparation of (9S)-7-[4-(2-azaspiro[4.5]decan-8-yl)phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene. To a solution of tert-butyl 8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (75 mg, 124 μmol, 1.0 equiv) in DCM (1 mL) was added TFA (0.5 mL). The mixture was stirred at 25° C. for 1 hour. The reaction mixture was concentrated, basified with aqueous $NaHCO_3$, and extracted with DCM/MeOH (10:1, 10 mL×3). The combined organic phase was dried over $Na_2SO_4$, filtered, and concentrated to afford (9S)-7-[4-(2-azaspiro[4.5]decan-8-yl)phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene (120 mg, 238 μmol) as a yellow solid.

Step 4: Preparation of N-[4-(4-cyano-3-methoxy-phenoxy)cyclohexyl]-6-[8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-29). To a solution of (9S)-7-[4-(2-azaspiro[4.5]decan-8-yl)phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene (60 mg, 120 μmol, 1.0 equiv) and 6-chloro-N-[4-(4-cyano-3-methoxy-phenoxy)cyclohexyl]pyridazine-3-carboxamide (60 mg, 155 μmol, 1.3 equiv) in NMP (0.5 mL) was added DIEA (50 mg, 357 μmol, 0.1 mL, 3.0 equiv). The mixture was stirred at 65° C. for 8 hours. The residue was purified by prep-HPLC (column: Waters xbridge 150×25 mm 10 μm; mobile phase: [water ($NH_4HCO_3$)-ACN]; gradient: 60%-80% B over 8 min) to give N-[4-(4-cyano-3-methoxy-phenoxy)cyclohexyl]-6-[8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (28.66 mg, 32.78 μmol, 27.51% yield, 97.67% purity) as a white solid. $^1$H NMR (400 MHz, $CD_3OD$) δ 7.94 (d, J=9.5 Hz, 1H), 7.56-7.49 (m, 1H), 7.47-7.40 (m, 2H), 7.38-7.32 (m, 2H), 7.07 (br d, J=9.6 Hz, 1H), 6.71-6.65 (m, 2H), 4.27 (t, J=7.2 Hz, 1H), 4.05-3.96 (m, 1H), 3.94 (s, 3H), 3.88-3.82 (m, 1H), 3.82-3.75 (m, 1H), 3.72-3.58 (m, 4H), 3.37 (s, 3H), 2.73-2.72 (m, 1H), 2.77-2.71 (m, 5H), 2.69-2.61 (m, 1H), 2.46 (s, 3H), 2.28-2.20 (m, 2H), 2.16-2.08 (m, 2H), 1.98 (t, J=7.1 Hz, 2H), 1.92-1.83 (m, 4H), 1.70-1.63 (m, 11H). LC-MS: MS ($ES^+$): RT=2.145 min, m/z=854.1 [$M+H^+$]; LCMS method: 25.

Example 11—Synthesis of N-[4-(4-cyano-3-methoxy-phenoxy)cyclohexyl]-6-[6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-31)

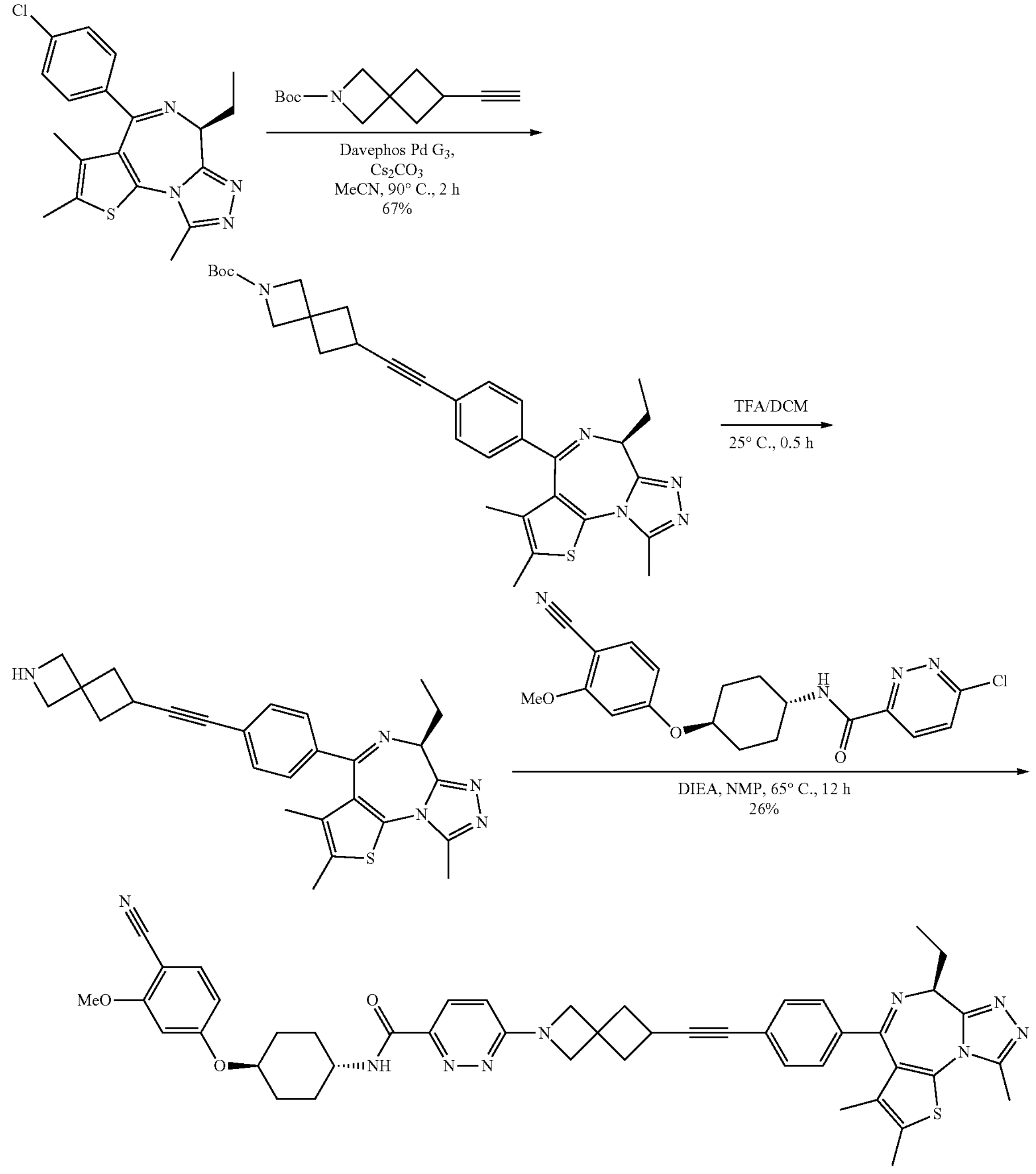

I-31

Step 1: Preparation of tert-butyl 6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. To a solution of (9S)-7-(4-chlorophenyl)-9-ethyl-4,5,13-trimethyl-3-thia-1,8,11,12-tetrazatricyclo[8.3.0.0$^{2,6}$]trideca-2 (6),4,7,10,12-pentaene (400 mg, 1.08 mmol, 1.0 equiv), tert-butyl 6-ethynyl-2-azaspiro[3.3]heptane-2-carboxylate (597 mg, 2.70 mmol, 2.5 equiv), and $Cs_2CO_3$ (597 mg, 2.70 mmol, 2.5 equiv) in MeCN (8 mL) was added DavePhos Pd G3 (82 mg, 0.11 mmol, 0.1 equiv). The mixture was stirred at 90° C. for 2 hours under $N_2$ atmosphere. The reaction mixture was filtered, and the filtrate was concentrated to afford crude product. The residue was purified by prep-HPLC (column:

Phenomenex luna C18 150×25 mm×10 μm; mobile phase: [water (FA)-ACN]; gradient: 70%-90% B over 10 min) to give tert-butyl 6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (400 mg, $Z^{20}$ μmol, 67% yield) as a white solid.

Step 2: Preparation of (9S)-7-[4-[2-(2-azaspiro[3.3]heptan-6-yl)ethynyl]phenyl]-9-ethyl-4,5,13-trimethyl-3-thia-1,8,11,12-tetrazatricyclo[8.3.0.0$^{2,6}$]trideca-2 (6),4,7,10,12-pentaene. To a solution of tert-butyl 6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (100 mg, 180 μmol, 1.0 equiv) in DCM (1 mL) was added TFA (0.5 mL). The mixture was stirred at 25° C. for 0.5 hour. The reaction mixture was concentrated and basified with saturated $NaHCO_3$ at 0° C. The mixture were extracted with DCM/MeOH (10:1, 20 mL×2), dried over $Na_2SO_4$, filtered, and concentrated to give (9S)-7-[4-[2-(2-azaspiro[3.3]heptan-6-yl)ethynyl]phenyl]-9-ethyl-4,5,13-trimethyl-3-thia-1,8,11,12-tetrazatricyclo[8.3.0.0$^{2,6}$]trideca-2 (6),4,7,10,12-pentaene (82 mg) as a yellow oil.

Step 3: Preparation of N-[4-(4-cyano-3-methoxy-phenoxy)cyclohexyl]-6-[6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-31). To a solution of (9S)-7-[4-[2-(2-azaspiro[3.3]heptan-6-yl)ethynyl]phenyl]-9-ethyl-4,5,13-trimethyl-3-thia-1,8,11,12-tetrazatricyclo[8.3.0.0$^{2,6}$]trideca-2 (6),4,7,10,12-pentaene (82 mg, 0.18 mmol, 1.0 equiv) and 6-chloro-N-[4-(4-cyano-3-methoxy-phenoxy)cyclohexyl]pyridazine-3-carboxamide (84 mg, 0.22 mmol, 1.2 equiv) in NMP (0.5 mL) was added DIEA (70 mg, 0.54 mmol, 3.0 equiv). The mixture was stirred at 65° C. for 12 hours. To the reaction mixture was added water (10 mL), and the mixture was extracted with EtOAc (10 mL). The combined organic phase was washed with brine (3×10 mL), dried over anhydrous $Na_2SO_4$, filtered, and concentrated in vacuo. The residue was purified by prep-HPLC (column: column: Phenomenex luna C18 150×25 mm×10 μm; mobile phase: [water (FA)-ACN]; gradient: 62%-82% B over 10 min) to give N-[4-(4-cyano-3-methoxy-phenoxy)cyclohexyl]-6-[6-[2-[4-[(9S)-9-ethyl-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (38 mg, 47 μmol, 26% yield) as a gray solid. $^1H$ NMR (400 MHz, $CD_3OD$) 7.91 (d, J=9.4 Hz, 1H), 7.50 (d, J=8.8 Hz, 1H), 7.47-7.39 (m, 4H), 6.85 (d, J=9.4 Hz, 1H), 6.70-6.62 (m, 2H), 4.53-4.42 (m, 1H), 4.24 (d, J=6.2 Hz, 4H), 4.02-3.94 (m, 2H), 3.92 (s, 3H), 3.25 (t, J=8.2 Hz, 1H), 2.77-2.67 (m, 5H), 2.51 (s, 7H), 2.21 (d, J=5.0 Hz, 2H), 2.14-2.03 (m, 2H), 1.70 (s, 3H), 1.63 (t, J=9.6 Hz, 4H), 1.23 (t, J=7.4 Hz, 3H). LC-MS: MS ($ES^+$): RT=2.237 min, m/z=806.5 $[M+H]^+$.

Example 12—Synthesis of N-[4-(4-cyano-3-methoxy-phenoxy)cyclohexyl]-6-[6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-32)

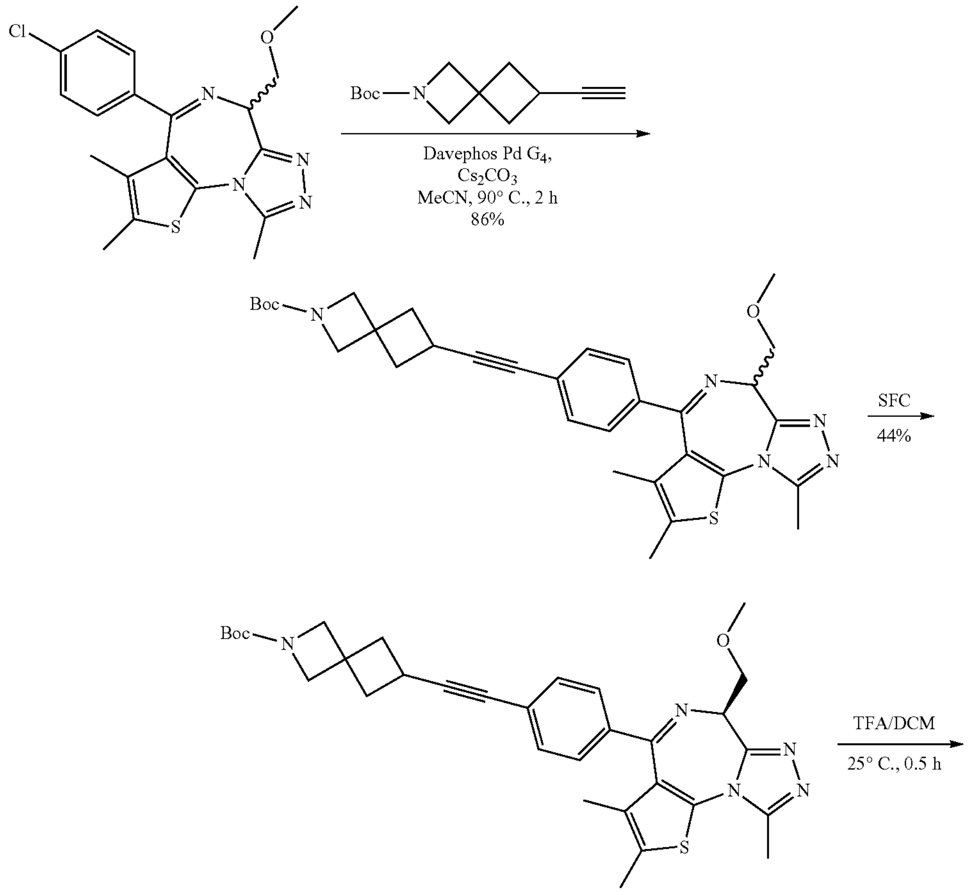

-continued

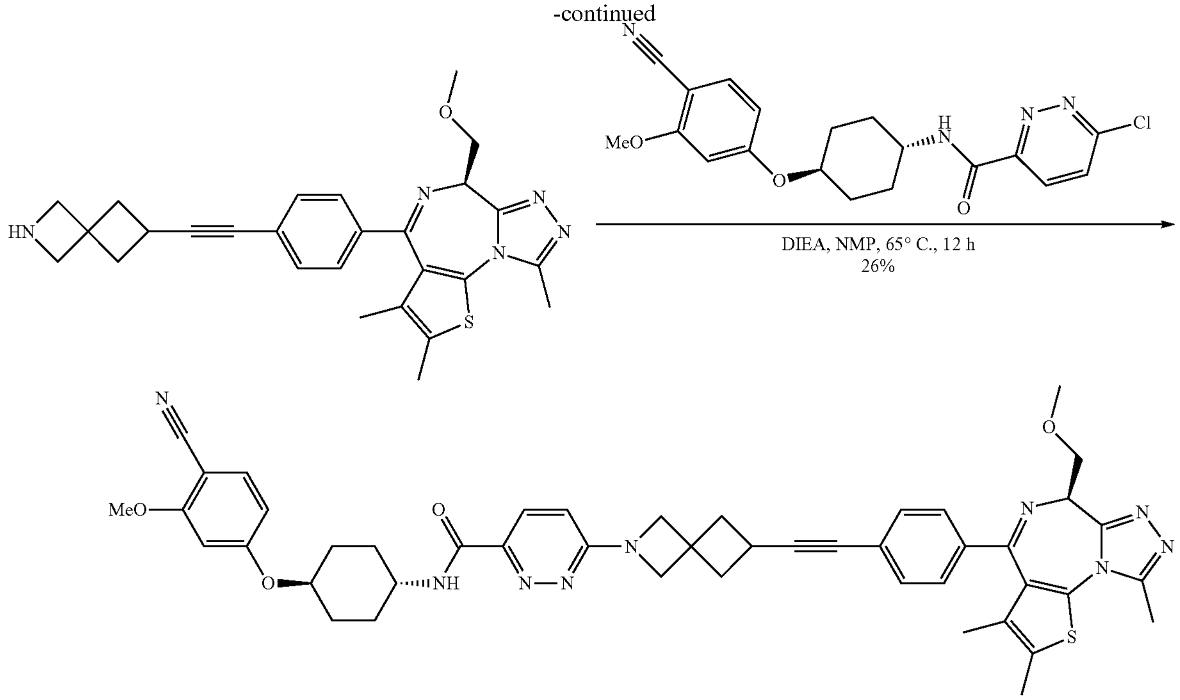

I-32

Step 1: Preparation of tert-butyl 6-[2-[4-[9-(methoxymethyl)-4,5,13-trimethyl-3-thia-1,8,11,12-tetrazatricyclo [8.3.0.0$^{2,6}$]trideca-2 (6),4,7,10,12-pentaen-7-yl]phenyl] ethynyl]-2-azaspiro[3.3]heptane-2-carboxylate. To a solution of (9R)-7-(4-chlorophenyl)-9-(methoxymethyl)-4,5,13-trimethyl-3-thia-1,8,11,12-tetrazatricyclo[8.3.0.0$^{2,6}$] trideca-2 (6),4,7,10,12-pentaene (400 mg, 1.03 mmol, 1.0 equiv) and tert-butyl 6-ethynyl-2-azaspiro[3.3]heptane-2-carboxylate (572 mg, 2.58 mmol, 2.5 equiv) in MeCN (5 mL) was added DavePhos Pd G3 (79 mg, 103 μmol, 0.1 equiv) and $Cs_2CO_3$ (674 mg, 2.07 mmol, 2.0 equiv). The mixture was stirred at 90° C. for 2 hours. The mixture was filtered and concentrated. The residue was purified by prep-HPLC (column: Phenomenex luna C18 150×25 mm×10 μm; mobile phase: [water (FA)-ACN]; gradient: 56%-86% B over 10 min) to give tert-butyl 6-[2-[4-[9-(methoxymethyl)-4,5,13-trimethyl-3-thia-1,8,11,12-tetrazatricyclo[8.3.0.0$^{2,6}$] trideca-2 (6),4,7,10,12-pentaen-7-yl]phenyl]ethynyl]-2-azaspiro[3.3]heptane-2-carboxylate (450 mg, 787 μmol, 76% yield) as a colorless oil.

Step 2: Preparation of tert-butyl-6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. Tert-butyl 6-[2-[4-[9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate was purified by prep-SFC (column: DAICEL CHIRALPAK AS (250 mm×30 mm, 10 μm); mobile phase: [$CO_2$-EtOH]; B %: 40%, isocratic elution mode) and prep-HPLC (column: Phenomenex luna C18 150×25 mm×10 μm; mobile phase: [water (FA)-ACN]; gradient: 58%-88% B over 10 min) to afford tert-butyl-6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (200 mg, 350 μmol, 44% yield) as a colorless oil.

Step 3: Preparation of (9R)-7-[4-[2-(2-azaspiro[3.3]heptan-6-yl)ethynyl]phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene. To a solution of tert-butyl 6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (190 mg, 332 μmol, 1.0 equiv) in DCM (2 mL) was added TFA (1 mL). The mixture was stirred at 25° C. for 0.5 hour. The reaction mixture was concentrated and basified with saturated $NaHCO_3$ at 0° C. The mixture was extracted with DCM/MeOH (10:1, 50 mL×2), dried over $Na_2SO_4$, filtered, and concentrated to afford (9R)-7-[4-[2-(2-azaspiro[3.3]heptan-6-yl)ethynyl]phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene (157 mg, crude) as a colorless oil.

Step 4: Preparation of N-[4-(4-cyano-3-methoxy-phenoxy)cyclohexyl]-6-[6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-32). To a solution of (9R)-7-[4-[2-(2-azaspiro[3.3]heptan-6-yl) ethynyl]phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene (78 mg, 165 μmol, 1.0 equiv) and 6-chloro-N-[4-(4-cyano-3-methoxy-phenoxy)cyclohexyl]pyridazine-3-carboxamide (71 mg, 182 μmol, 1.1 equiv) in NMP (1 mL) was added DIEA (64 mg, 496 μmol, 86 μL, 3.0 equiv). The mixture was stirred at 65° C. for 12 hours. The residue was purified by prep-HPLC (column: Phenomenex luna C18 150×25 mm×10 μm; mobile phase: [water (FA)-ACN]; gradient: 52%-82% B over 10 min) to afford N-[4-(4-cyano-3-methoxy-phenoxy)cyclohexyl]-6-[6-[2-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]

phenyl]ethynyl]-2-azaspiro[3.3]heptan-2-yl]pyridazine-3-carboxamide (35 mg, 42 μmol, 26% yield) as a white solid. $^1$H NMR (400 MHz, $CD_3OD$) 7.93 (d, J=9.2 Hz, 1H), 7.54-7.42 (m, 5H), 6.87 (d, J=9.2 Hz, 1H), 6.67 (s, 2H), 4.54-4.42 (m, 2H), 4.41-4.34 (m, 2H), 4.26 (d, J=6.4 Hz, 4H), 4.03-3.96 (m, 1H), 3.94 (s, 3H), 3.57 (s, 3H), 3.27 (t, J=7.6 Hz, 1H), 2.79-2.73 (m, 2H), 2.72 (s, 3H), 2.54-2.47 (m, 2H), 2.47 (s, 3H), 2.23 (s, 2H), 2.16-2.07 (m, 2H), 1.72 (s, 3H), 1.65 (t, J=9.8 Hz, 4H). LC-MS: MS ($ES^+$): RT=2.47 min, m/z=822.4 $[M+H]^+$; LCMS method: 10.

Example 13—Synthesis of N-[4-(4-cyano-3-methoxy-phenoxy)cyclohexyl]-6-[6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-30)

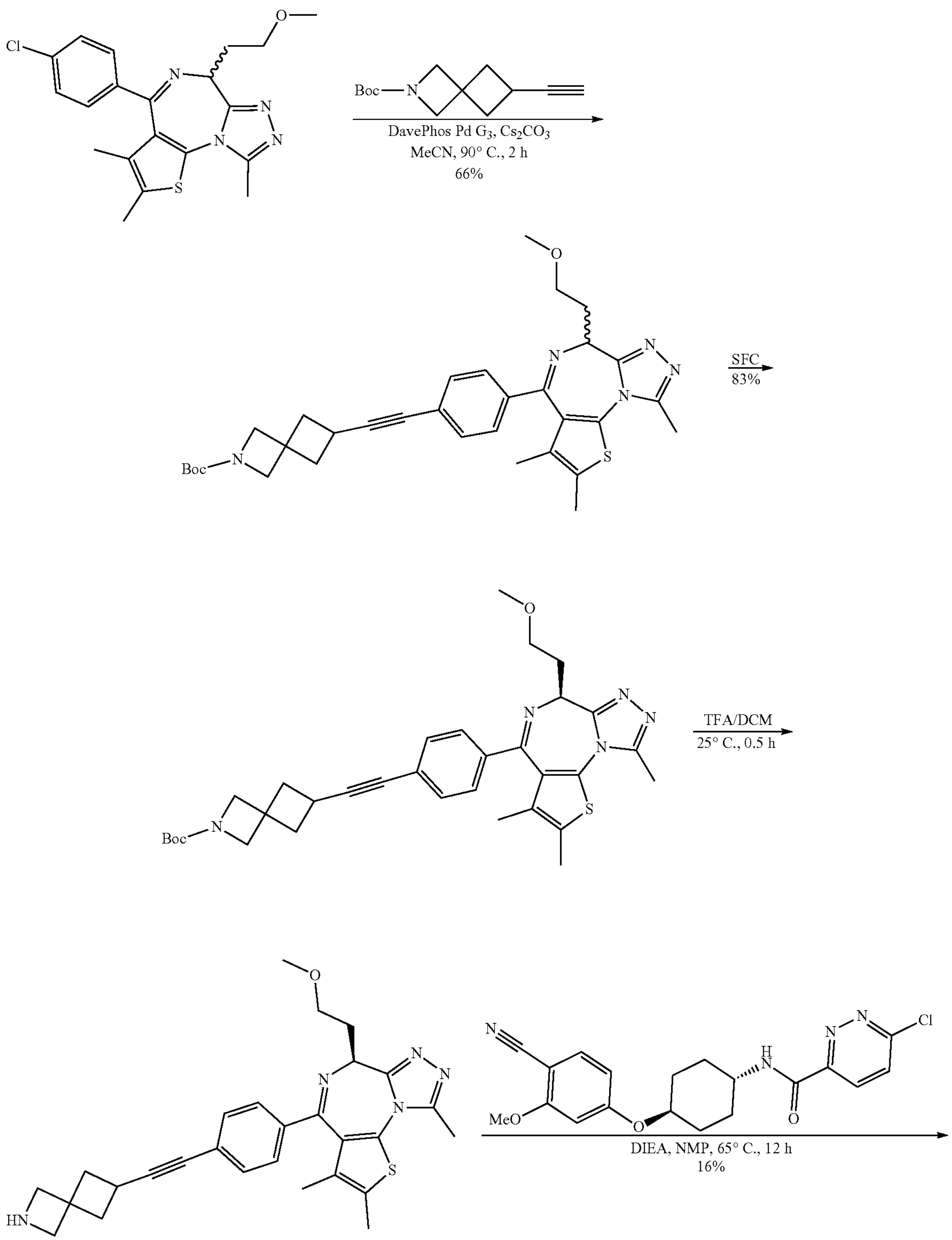

-continued

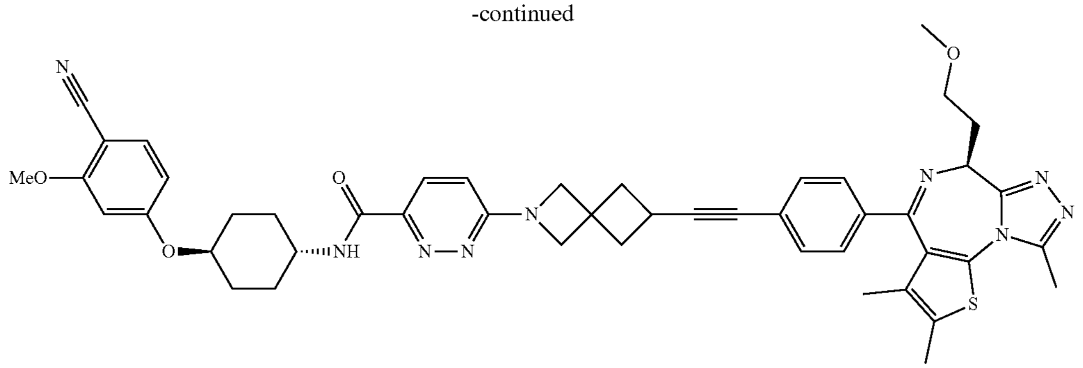

I-30

Step 1: Preparation of tert-butyl 6-[2-[4-[9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. To a solution of (9S)-7-(4-chlorophenyl)-9-(2-methoxyethyl)-4,5,13-trimethyl-3-thia-1,8,11,12-tetrazatricyclo[8.3.0.0$^{2,6}$]trideca-2 (6),4,7,10,12-pentaene (250 mg, 624 μmol, 1.0 equiv), tert-butyl 6-ethynyl-2-azaspiro[3.3]heptane-2-carboxylate (345 mg, 1.56 mmol, 2.5 equiv), and $Cs_2CO_3$ (406 mg, 1.25 mmol, 2.0 equiv) in MeCN (5 mL) was added DavePhos Pd G3 (47 mg, 62 μmol, 0.1 equiv). The mixture was stirred at 90° C. for 2 hours under $N_2$ atmosphere. The reaction mixture was filtered, and the filtrate was concentrated to afford crude product. The residue was purified by prep-HPLC (column: Phenomenex luna C18 150×25 mm×10 μm; mobile phase: [water (FA)-ACN]; gradient: 68%-88% B over 10 min) to afford tert-butyl 6-[2-[4-[9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (240 mg, 410 μmol, 66% yield) as a white solid.

Step 2: Preparation of tert-butyl 6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. Tert-butyl 6-[2-[4-[9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate was purified by prep-SFC (column: DAICEL CHIRALPAK AD (250 mm×30 mm, 10 μm); mobile phase: [$CO_2$-ACN/i-PrOH (0.1% $NH_3 \cdot H_2O$)]; B %: 45%, isocratic elution mode) to afford tert-butyl 6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (200 mg, 341 μmol, 83% yield) was obtained as a white solid.

Step 3: Preparation of (9S)-7-[4-[2-(2-azaspiro[3.3]heptan-6-yl)ethynyl]phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene. To a solution of tert-butyl 6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (100 mg, 171 μmol, 1.0 equiv) in DCM (1 mL) was added TFA (0.5 mL). The mixture was stirred at 25° C. for 0.5 hour. The reaction mixture was concentrated and basified with saturated $NaHCO_3$ at 0° C. The mixture were extracted with DCM/MeOH (10:1, 2×20 mL), dried over $Na_2SO_4$, filtered, and concentrated to give (9S)-7-[4-[2-(2-azaspiro[3.3]heptan-6-yl)ethynyl]phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene (83 mg) as a yellow oil.

Step 4: Preparation of N-[4-(4-cyano-3-methoxy-phenoxy)cyclohexyl]-6-[6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-30). To a solution of (9S)-7-[4-[2-(2-azaspiro[3.3]heptan-6-yl)ethynyl]phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene (83 mg, 0.17 mmol, 1.0 equiv) and 6-chloro-N-[4-(4-cyano-3-methoxy-phenoxy)cyclohexyl]pyridazine-3-carboxamide (80 mg, 0.21 mmol, 1.2 equiv) in NMP (0.5 mL) was added DIEA (66 mg, 0.51 mmol, 3.0 equiv). The residue was purified by prep-HPLC (column: Phenomenex luna C18 150×25 mm×10 μm; mobile phase: [water (FA)-ACN]; gradient: 57%-77% B over 10 min) to afford N-[4-(4-cyano-3-methoxy-phenoxy)cyclohexyl]-6-[6-[2-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (24 mg, 28 μmol, 16% yield) as a white solid. $^1H$ NMR (400 MHz, $CD_3OD$) 7.91 (d, J=9.4 Hz, 1H), 7.50 (d, J=9.0 Hz, 1H), 7.47-7.40 (m, 4H), 6.85 (d, J=9.4 Hz, 1H), 6.69-6.64 (m, 2H), 4.53-4.45 (m, 1H), 4.29-4.21 (m, 5H), 4.02-3.94 (m, 1H), 3.92 (s, 3H), 3.87-3.73 (m, 2H), 3.35 (s, 3H), 3.28-3.23 (m, 1H), 2.76-2.67 (m, 7H), 2.51-2.43 (m, 5H), 2.27-2.16 (m, 2H), 2.09 (s, 2H), 1.70 (s, 3H), 1.63 (t, J=9.8 Hz, 4H).

Example 14—Synthesis of N-((1r,4r)-4-(4-cyano-3-methoxyphenoxy)cyclohexyl)-2-(8-(4-((S)-2,3,6,9-tetramethyl-6H-thieno[3,2-f][1,2,4]triazolo[4,3-a][1,4]diazepin-4-yl)phenyl)-2,8-diazaspiro[4.5]decan-2-yl)pyrimidine-5-carboxamide (I-37)

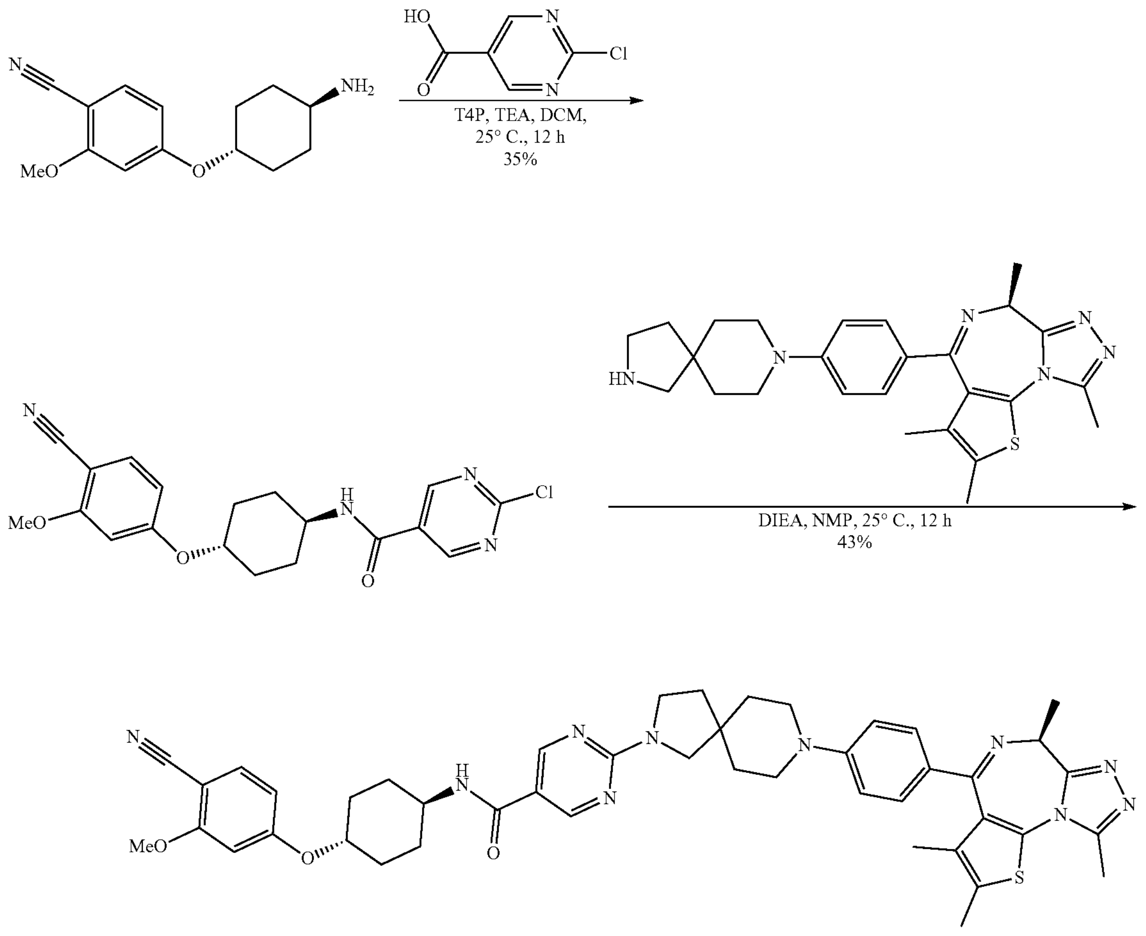

I-37

Step 1: Preparation of 2-chloro-N-((1r,4r)-4-(4-cyano-3-methoxyphenoxy) cyclohexyl) pyrimidine-5-carboxamide. To a solution of 4-(((1r,4r)-4-aminocyclohexyl)oxy)-2-methoxybenzonitrile (500 mg, 1.39 mmol, 1.0 equiv, TFA salt) and 2-chloropyrimidine-5-carboxylic acid (286 mg, 1.80 mmol, 1.3 equiv) in DCM (2 mL) was added T4P (1.69 g, 2.35 mmol, 50% purity, 1.7 equiv) and TEA (421 mg, 4.16 mmol, 579 μL, 3.0 equiv). The mixture was stirred at 25° C. for 12 hours. The reaction mixture was concentrated under reduced pressure to afford crude product. The residue was purified by prep-HPLC (column: Waters Xbridge C18 150 mm×50 mm×10 μm; mobile phase: [water ($NH_4HCO_3$)-ACN]; gradient: 30%-60% B over 10 min) to afford 2-chloro-N-((1r,4r)-4-(4-cyano-3-methoxyphenoxy)cyclohexyl) pyrimidine-5-carboxamide (190 mg, 491 μmol, 35% yield) as a white solid.

Step 2: Preparation of N-((1r,4r)-4-(4-cyano-3-methoxyphenoxy)cyclohexyl)-2-(8-(4-((S)-2,3,6,9-tetramethyl-6H-thieno[3,2-f][1,2,4]triazolo[4,3-a][1,4]diazepin-4-yl)phenyl)-2,8-diazaspiro[4.5]decan-2-yl)pyrimidine-5-carboxamide (1-37). To a solution of (S)-4-(4-(2,8-diazaspiro[4.5]decan-8-yl)phenyl)-2,3,6,9-tetramethyl-6H-thieno[3,2-f][1,2,4]triazolo[4,3-a][1,4]diazepine (75 mg, 163 μmol, 1.0 equiv) and 2-chloro-N-((1r,4r)-4-(4-cyano-3-methoxyphenoxy)cyclohexyl) pyrimidine-5-carboxamide (69 mg, 179 μmol, 1.1 equiv)) in NMP (0.5 mL) was added DIEA (63 mg, 488 μmol, 85 μL, 3.0 equiv). The mixture was stirred at 25° C. for 12 hours. The residue was purified by prep-HPLC (column: Waters xbridge 150 mm×25 mm×10 μm; mobile phase: [water ($NH_4HCO_3$)-ACN]; gradient: 46%-66% B over 8 min) to give N-((1r,4r)-4-(4-cyano-3-methoxyphenoxy)cyclohexyl)-2-(8-(4-((S)-2,3,6,9-tetramethyl-6H-thieno[3,2-f][1,2,4]triazolo[4,3-a][1,4]diazepin-4-yl)phenyl)-2,8-diazaspiro[4.5]decan-2-yl) pyrimidine-5-carboxamide (59 mg, 69 μmol, 43% yield, 95% purity) as a yellow solid. $^1$H NMR (400 MHz, $CD_3OD$) δ 8.75 (s, 2H), 7.50 (d, J=9.0 Hz, 1H), 7.34 (d, J=8.8 Hz, 2H), 6.97 (d, J=9.0 Hz, 2H), 6.69-6.57 (m, 2H), 4.58 (br s, 3H), 4.48-4.38 (m, 1H), 4.23 (q, J=6.7 Hz, 1H), 3.91 (s, 4H), 3.71 (t, J=7.1 Hz, 2H), 3.55 (s, 2H), 3.49-3.39 (m, 2H), 2.69 (s, 3H), 2.44 (s, 3H), 2.28-2.16 (m, 2H), 2.07 (br d, J=7.9 Hz, 2H), 2.02-1.93 (m, 5H), 1.82-1.69 (m, 7H), 1.65-1.49 (m, 4H). LC-MS: MS ($ES^+$): RT=1.825 min, m/z=811.6 $[M+H]^+$; LCMS method: 25.

Example 15—Synthesis of N-((1r,4r)-4-(4-cyano-3-methoxyphenoxy)cyclohexyl)-5-(8-(4-((S)-2,3,6,9-tetramethyl-6H-thieno[3,2-f][1,2,4]triazolo[4,3-a][1,4]diazepin-4-yl)phenyl)-2,8-diazaspiro[4.5]decan-2-yl) pyrazine-2-carboxamide (I-39)

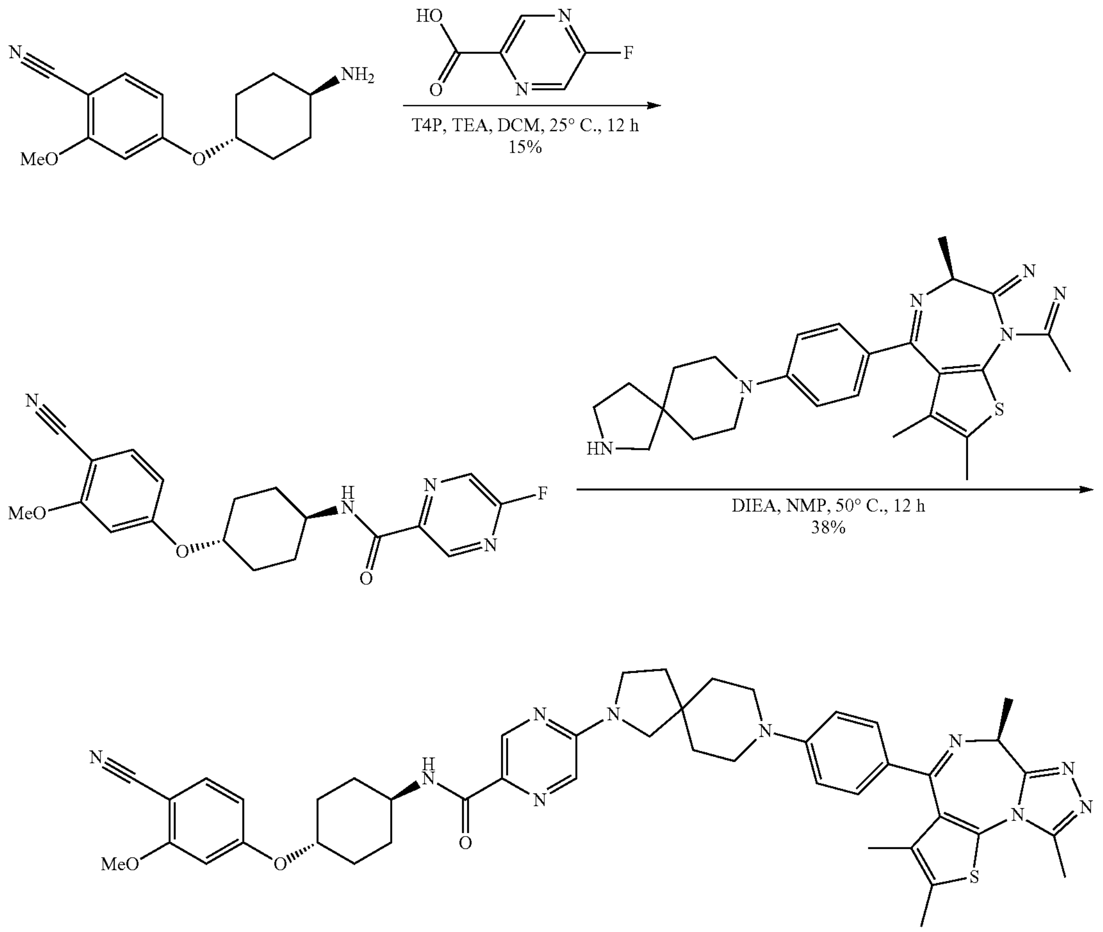

I-39

Step 1: Preparation of N-((1r,4r)-4-(4-cyano-3-methoxyphenoxy)cyclohexyl)-5-fluoropyrazine-2-carboxamide. To a solution of 4-(((1r,4r)-4-aminocyclohexyl)oxy)-2-methoxybenzonitrile (500 mg, 1.39 mmol, 1.0 equiv, TFA salt) and 5-fluoropyrazine-2-carboxylic acid (286 mg, 1.80 mmol, 1.3 equiv) in DCM (4 mL) was added T4P (1.69 g, 2.35 mmol, 50% purity, 1.7 equiv) and TEA (421 mg, 4.16 mmol, 579 μL, 3.0 equiv). The mixture was stirred at 25° C. for 12 hours. The reaction mixture was concentrated under reduced pressure to afford crude product. The residue was purified by prep-HPLC (column: Waters Xbridge C18 150×50 mm×10 μm; mobile phase: [water ($NH_4HCO_3$)-ACN]; gradient: 33%-63% B over 10 min) to give compound N-((1r,4r)-4-(4-cyano-3-methoxyphenoxy)cyclohexyl)-5-fluoropyrazine-2-carboxamide (80 mg, 207 μmol, 15% yield) as a white solid.

Step 2: Preparation of N-((1r,4r)-4-(4-cyano-3-methoxyphenoxy)cyclohexyl)-5-(8-(4-((S)-2,3,6,9-tetramethyl-6H-thieno[3,2-f][1,2,4]triazolo[4,3-a][1,4]diazepin-4-yl)phenyl)-2,8-diazaspiro[4.5]decan-2-yl) pyrazine-2-carboxamide (1-39). To a solution of (S)-4-(4-(2,8-diazaspiro[4.5]decan-8-yl)phenyl)-2,3,6,9-tetramethyl-6H-thieno[3,2-f][1,2,4]triazolo[4,3-a][1,4]diazepine (76 mg, 196 μmol, 1.1 equiv) and N-((1r,4r)-4-(4-cyano-3-methoxyphenoxy)cyclohexyl)-5-fluoropyrazine-2-carboxamide (82 mg, 178 μmol, 1.0 equiv) in NMP (0.5 mL) was added DIEA (69 mg, 534 μmol, 93 μL, 3.0 equiv). The mixture was stirred at 50° C. for 12 hours. The residue was purified by prep-HPLC (column: Waters xbridge 150 mm×25 mm×10 μm; mobile phase: [water ($NH_4HCO_3$)-ACN]; gradient: 53%-73% B over 8 min) to give compound N-((1r,4r)-4-(4-cyano-3-methoxyphenoxy)cyclohexyl)-5-(8-(4-((S)-2,3,6,9-tetramethyl-6H-thieno[3,2-f][1,2,4]triazolo[4,3-a][1,4]diazepin-4-yl)phenyl)-2,8-diazaspiro[4.5]decan-2-yl) pyrazine-2-carboxamide (57 mg, 67 μmol, 38% yield, 95% purity) as a yellow solid. $^1$H NMR (400 MHz, $CD_3OD$) δ 8.65 (d, J=1.3 Hz, 1H), 7.93 (d, J=1.3 Hz, 1H), 7.55-7.44 (m, 1H), 7.34 (d, J=8.8 Hz, 2H), 6.96 (d, J=9.1 Hz, 2H), 6.70-6.60 (m, 2H), 4.58 (br s, 3H), 4.51-4.42 (m, 1H), 4.22 (q, J=6.8 Hz, 1H), 4.00-3.86 (m, 4H), 3.70-3.65 (m, 2H), 3.51 (s, 2H), 3.47-3.38 (m, 2H), 2.69 (s, 3H), 2.44 (s, 3H), 2.19 (br d, J=2.6 Hz, 2H), 2.11-1.93 (m, 8H), 1.82-1.74 (m, 4H), 1.73 (s, 3H), 1.66-1.57 (m, 4H). LC-MS: MS ($ES^+$): RT=1.912 min, m/z=811.6 $[M+H]^+$; LCMS method: 25.

Example 16—Synthesis of N-[4-(4-cyano-3-methoxy-phenoxy)cyclohexyl]-6-[6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-40)

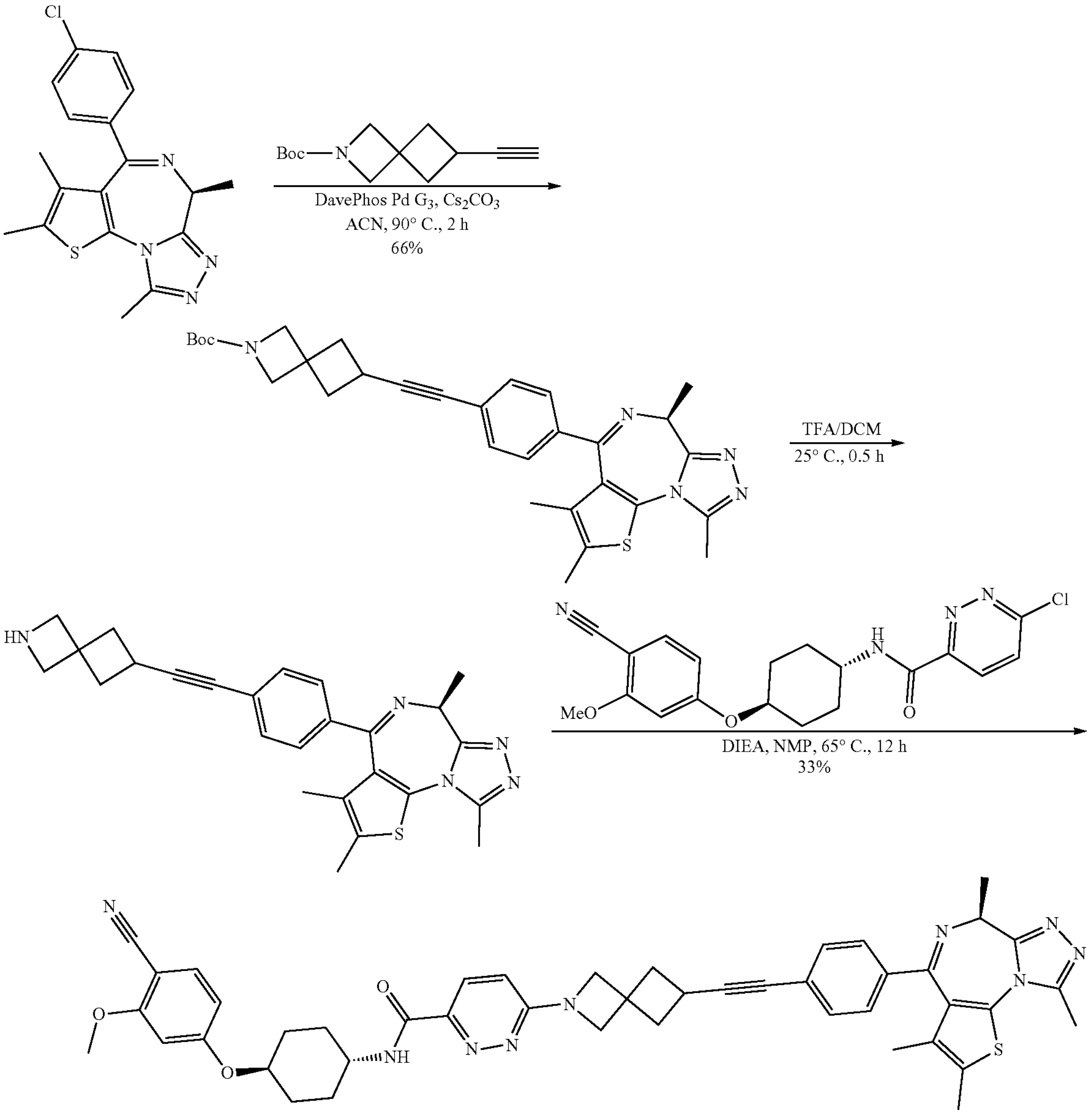

I-40

Step 1: Preparation of tert-butyl 6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. To a solution of (9S)-7-(4-chlorophenyl)-4,5,9,13-tetramethyl-3-thia-1,8,11,12-tetrazatricyclo[8.3.0.0$^{2,6}$]trideca-2 (6),4,7,10,12-pentaene (400 mg, 1.12 mmol, 1.0 equiv) and tert-butyl 6-ethynyl-2-azaspiro[3.3]heptane-2-carboxylate (620 mg, 2.80 mmol, 2.5 equiv) in ACN (5.0 mL) was added DavePhos Pd G3 (86.0 mg, 112 μmol, 0.1 equiv) and $Cs_2CO_3$ (730 mg, 2.24 mmol, 2.0 equiv) under $N_2$. The suspension was degassed under vacuum and purged with $N_2$ 3 times. The mixture was stirred under $N_2$ at 90° C. for 2 hours. The reaction mixture was filtered and concentrated to give a residue. The residue was purified by prep-HPLC (column: Phenomenex luna C18 150×40 mm×15 μm; mobile phase: [water (FA)-ACN]; gradient: 57%-87% B over 15 min). Compound tert-butyl 6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (380 mg, 701 μmol, 63% yield) was obtained as a brown oil.

Step 2: Preparation of (9S)-7-[4-[2-(2-azaspiro[3.3]heptan-6-yl)ethynyl]phenyl]-4,5,9,13-tetramethyl-3-thia-1,8,11,12-tetrazatricyclo[8.3.0.0$^{2,6}$]trideca-2 (6),4,7,10,12-pentaene. To a solution of tert-butyl 6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (100 mg, 185 μmol, 1.0 equiv) in DCM (2.0 mL) was added TFA (1.0 mL). The reaction mixture was stirred at 25° C. for 0.5 hour. The reaction mixture was concentrated and basified with aqueous $NaHCO_3$, extracted with DCM/MeOH (10:1, 20 mL×2) dried over $Na_2SO_4$, filtered, and concentrated under reduced pressure to afford (9S)-7-[4-[2-(2-azaspiro[3.3]heptan-6-yl)ethynyl]phenyl]-4,5,9,13-tetramethyl-3-thia-1,8,11,12-tetrazatricyclo[8.3.0.0$^{2,6}$]trideca-2 (6),4,7,10,12-pentaene (82.0 mg, 185 μmol, 100% yield) as a colorless oil.

Step 3: Preparation of N-[4-(4-cyano-3-methoxy-phenoxy)cyclohexyl]-6-[6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-40). To a solution of (9S)-7-[4-[2-(2-azaspiro[3.3]heptan-6-yl)ethynyl]phenyl]-4,5,9,13-tetramethyl-3-thia-1,8,11,12-tetrazatricyclo[8.3.0.0$^{2,6}$]trideca-2 (6),4,7,10,12-pentaene (82 mg, 185 μmol, 1.0 equiv) and 6-chloro-N-[4-(4-cyano-3-methoxy-phenoxy)cyclohexyl]pyridazine-3-carboxamide (79 mg, 203 μmol, 1.1 equiv) in NMP (0.5 mL) was added DIEA (119 mg, 923 μmol, 161 μL, 5.0 equiv). The reaction mixture was stirred at 65° C. for 12 hours. The residue was purified by prep-HPLC (column: Phenomenex luna C18 150×25 mm×10 μm; mobile phase: [water (FA)-ACN]; gradient: 62%-82% B over 10 min). Compound N-[4-(4-cyano-3-methoxy-phenoxy)cyclohexyl]-6-[6-[2-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (49 mg, 62 μmol, 33% yield) was obtained as a yellow solid. $^1H$ NMR (400 MHz, $CD_3OD$) δ 7.97 (d, J=9.4 Hz, 1H), 7.50 (d, J=8.9 Hz, 1H), 7.46-7.40 (m, 4H), 6.98 (d, J=9.4 Hz, 1H), 6.65 (s, 1H), 6.66 (d, J=8.2 Hz, 1H), 4.99-4.90 (m, 1H), 4.47 (br d, J=4.4 Hz, 1H), 4.35-4.27 (m, 5H), 3.95 (br d, J=4.8 Hz, 1H), 3.91 (s, 3H), 3.63-3.58 (m, 1H), 3.29-3.22 (m, 1H), 2.77-2.66 (m, 5H), 2.51-2.45 (m, 2H), 2.44 (s, 3H), 2.21 (br s, 2H), 2.11-1.97 (m, 5H), 1.69 (s, 3H), 1.67-1.58 (m, 4H). LC-MS: MS ($ES^+$): RT=2.148 min, m/z=792.5 $[M+H]^+$; LCMS method: 25.

Example 17—Synthesis of N-((1r,4r)-4-(4-cyano-3-methoxyphenoxy)cyclohexyl)-6-(8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]decan-2-yl) pyridazine-3-carboxamide (I-41)

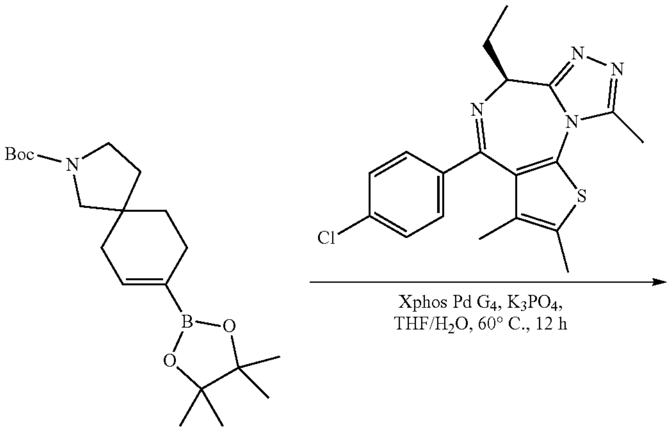

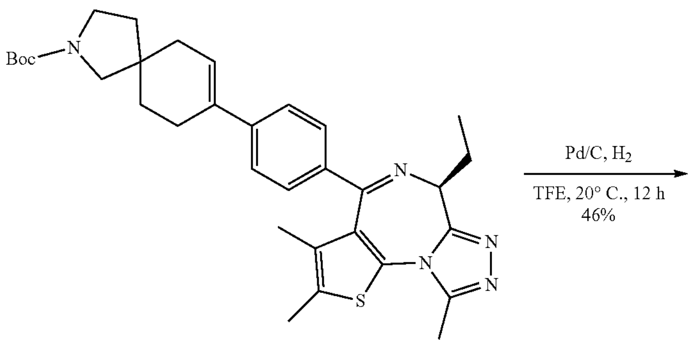

-continued
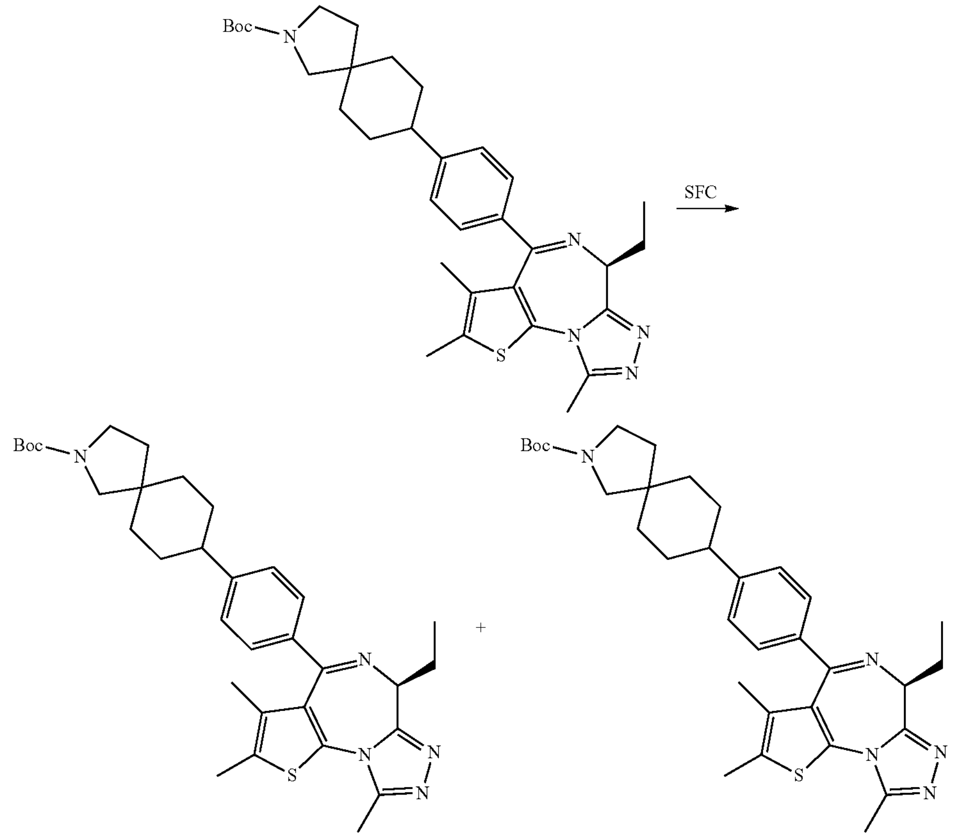
Stereoisomer 1 Stereoisomer 2
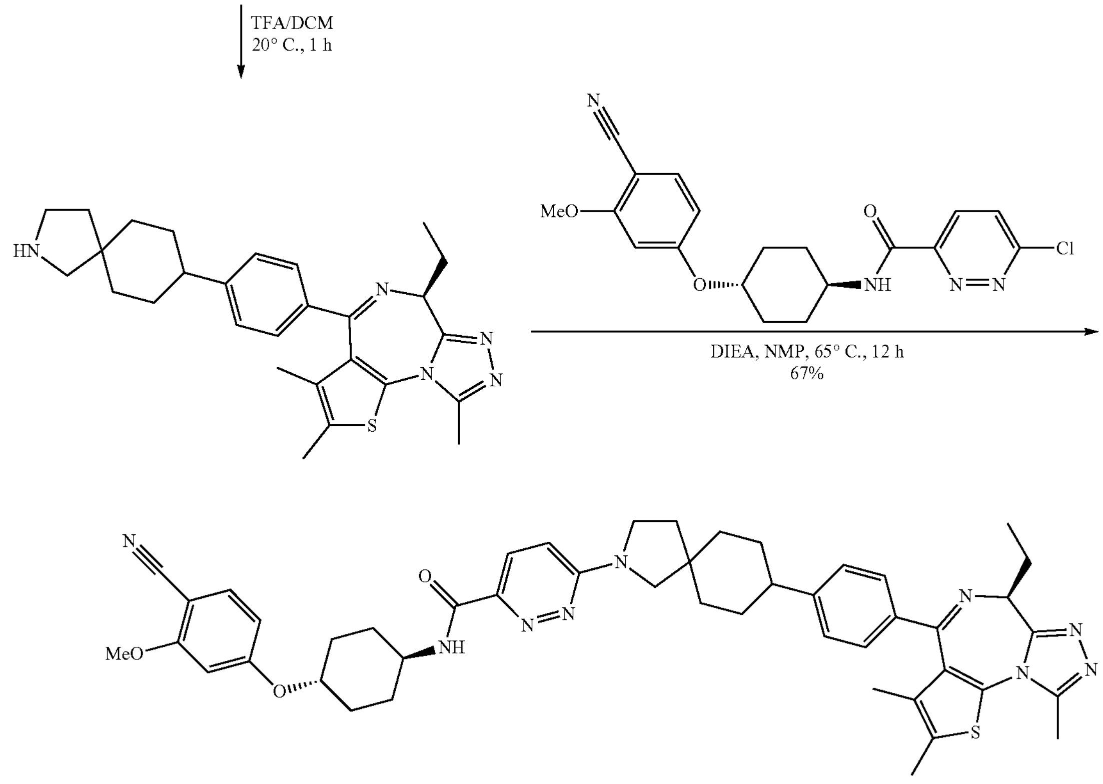
I-41

Step 1: Preparation of tert-butyl 8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]dec-7-ene-2-carboxylate. A mixture of tert-butyl 8-(4,4,5,5-tetramethyl-1,3,2-dioxaborolan-2-yl)-2-azaspiro[4.5]dec-7-ene-2-carboxylate (636 mg, 1.75 mmol, 1.0 equiv), (9S)-7-(4-chlorophenyl)-9-ethyl-4,5,13-trimethyl-3-thia-1,8,11,12-tetrazatricyclo [8.3.0.0$^{2,6}$]trideca-2 (6),4,7,10,12-pentaene (650 mg, 1.75 mmol, 1.0 equiv), Xphos Pd G4 (150 mg, 175 μmol, 0.1 equiv), and $K_3PO_4$ (1.12 g, 5.26 mmol, 3.0 equiv) in $H_2O$ (1 mL) and THF (4 mL) was stirred at 60° C. for 12 hours under $N_2$ atmosphere. The reaction mixture was concentrated under reduced pressure to afford a residue. The residue was purified by column chromatography ($SiO_2$, petroleum ether: ethyl acetate=1:1 to 0:1) to afford tert-butyl 8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]dec-7-ene-2-carboxylate (1.3 g, crude) as a yellow solid.

Step 2: Preparation of tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate. To a solution of tert-butyl 8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]dec-7-ene-2-carboxylate (1.3 mg, 2.3 mmol, 1.0 equiv) in TFE (4 mL) was added Pd/C (940 mg, 10% purity). The reaction mixture was stirred under $H_2$ at 20° C. (15 psi) for 12 hours. The reaction mixture was filtered and concentrated under reduced pressure to afford a residue. The residue was purified by prep-HPLC (column: Phenomenex luna C18 150 mm×40 mm×15 μm; mobile phase: [water (TFA)-ACN]; gradient: 45%-75% B over 10 min) to afford tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate (600 mg, 1.05 mmol, 46% yield) as a yellow solid.

Step 3: Preparation of tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate. Tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate (600 mg, 1.05 mmol) was separated by SFC (column: DAICEL CHIRALPAK AD (250 mm×30 mm, 10 μm); mobile phase: [$CO_2$-EtOH (0.1% $NH_3 \cdot H_2O$)]; B %: 50%, isocratic elution mode) to afford stereoisomer 1 (350 mg, 609 μmol) and stereosiomer 2 (230 mg, 400 μmol) that differ by the stereochemistry at the spiro-center adjacent to the pyrrolidine.

Step 4: Preparation of(S)-4-(4-(2-azaspiro[4.5]decan-8-yl)phenyl)-6-ethyl-2,3,9-trimethyl-6H-thieno[3,2-f][1,2,4]triazolo[4,3-a][1,4]diazepine. To a solution of tert-butyl(S)-8-(4-(6-ethyl-2,3,9-trimethyl-6H-thieno[3,2-f][1,2,4]triazolo[4,3-a][1,4]diazepin-4-yl)phenyl)-2-azaspiro[4.5]decane-2-carboxylate (300 mg, 575 μmol, 1.0 equiv) in DCM (2 mL) was added TFA (1 mL). The mixture was stirred at 20° C. for 1 hour. The reaction mixture was concentrated and basified by aqueous $NaHCO_3$. After extraction with DCM/MeOH (10:1, 10 mL×2), the organic phase was concentrated to afford crude product(S)-4-(4-(2-azaspiro[4.5]decan-8-yl)phenyl)-6-ethyl-2,3,9-trimethyl-6H-thieno[3,2-f][1,2,4]triazolo[4,3-a][1,4]diazepine (270 mg, crude) and used directly in the next step without purification.

Step 5: Preparation of N-((1r,4r)-4-(4-cyano-3-methoxyphenoxy)cyclohexyl)-6-(8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]decan-2-yl) pyridazine-3-carboxamide (I-41). To a solution of(S)-4-(4-(2-azaspiro[4.5]decan-8-yl)phenyl)-6-ethyl-2,3,9-trimethyl-6H-thieno[3,2-f][1,2,4]triazolo[4,3-a][1,4]diazepine (130 mg, 274 μmol, 1.0 equiv) in NMP (0.5 mL) was added DIEA (106 mg, 822 μmol, 143 μL, 3.0 equiv) and 6-chloro-N-((1r,4r)-4-(4-cyano-3-methoxyphenoxy) cyclohexyl) pyridazine-3-carboxamide (138 mg, 356 μmol, 1.3 equiv). The mixture was stirred at 65° C. for 12 hours. The residue was purified by prep-HPLC (column: Phenomenex luna C18 150 mm×50 mm×10 μm; mobile phase: [water ($NH_4HCO_3$)-ACN]; gradient: 57%-87% B over 10 min) to afford N-((1r,4r)-4-(4-cyano-3-methoxyphenoxy)cyclohexyl)-6-(8-(4-((S)-6-ethyl-2,3,9-trimethyl-6H-thieno[3,2-f][1,2,4]triazolo[4,3-a][1,4]diazepin-4-yl)phenyl)-2-azaspiro[4.5]decan-2-yl) pyridazine-3-carboxamide (155 mg, 184 μmol, 67% yield) as a yellow solid. $^1$H NMR (400 MHz, $CD_3OD$): δ 7.92 (d, J=9.4 Hz, 1H), 7.54-7.47 (m, 1H), 7.46-7.38 (m, 2H), 7.37-7.28 (m, 2H), 7.05 (brd, J=9.2 Hz, 1H), 6.70-6.63 (m, 2H), 4.54-4.43 (m, 1H), 3.97 (dd, J=6.5, 7.9 Hz, 2H), 3.92 (s, 3H), 3.79-3.50 (m, 4H), 2.75-2.69 (m, 3H), 2.68-2.58 (m, 1H), 2.55-2.46 (m, 2H), 2.44 (s, 3H), 2.27-2.17 (m, 2H), 2.15-2.05 (m, 2H), 1.95 (t, J=7.0 Hz, 2H), 1.90-1.77 (m, 4H), 1.74-1.54 (m, 12H), 1.22 (t, J=7.3 Hz, 3H). LC-MS: MS ($ES^+$): RT=2.124 min, m/z=824.7 $[M+H]^+$; LCMS method: 25.

Example 18—Synthesis of N-[4-(4-cyano-3-methoxy-phenoxy)cyclohexyl]-6-[8-[2-fluoro-4-[(9S)-4,5,9,13-tetramethyl-3-thia1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (I-44)

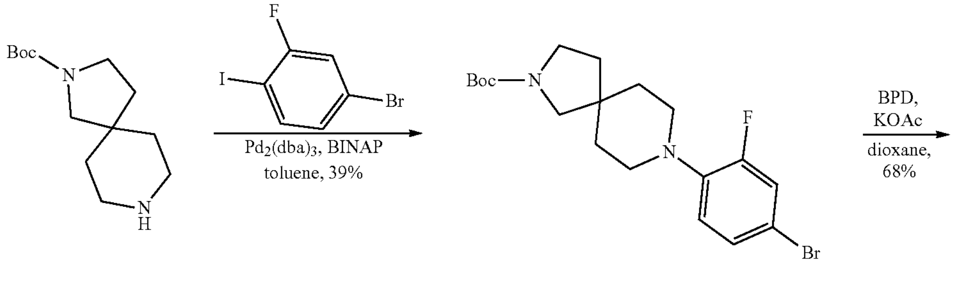

-continued

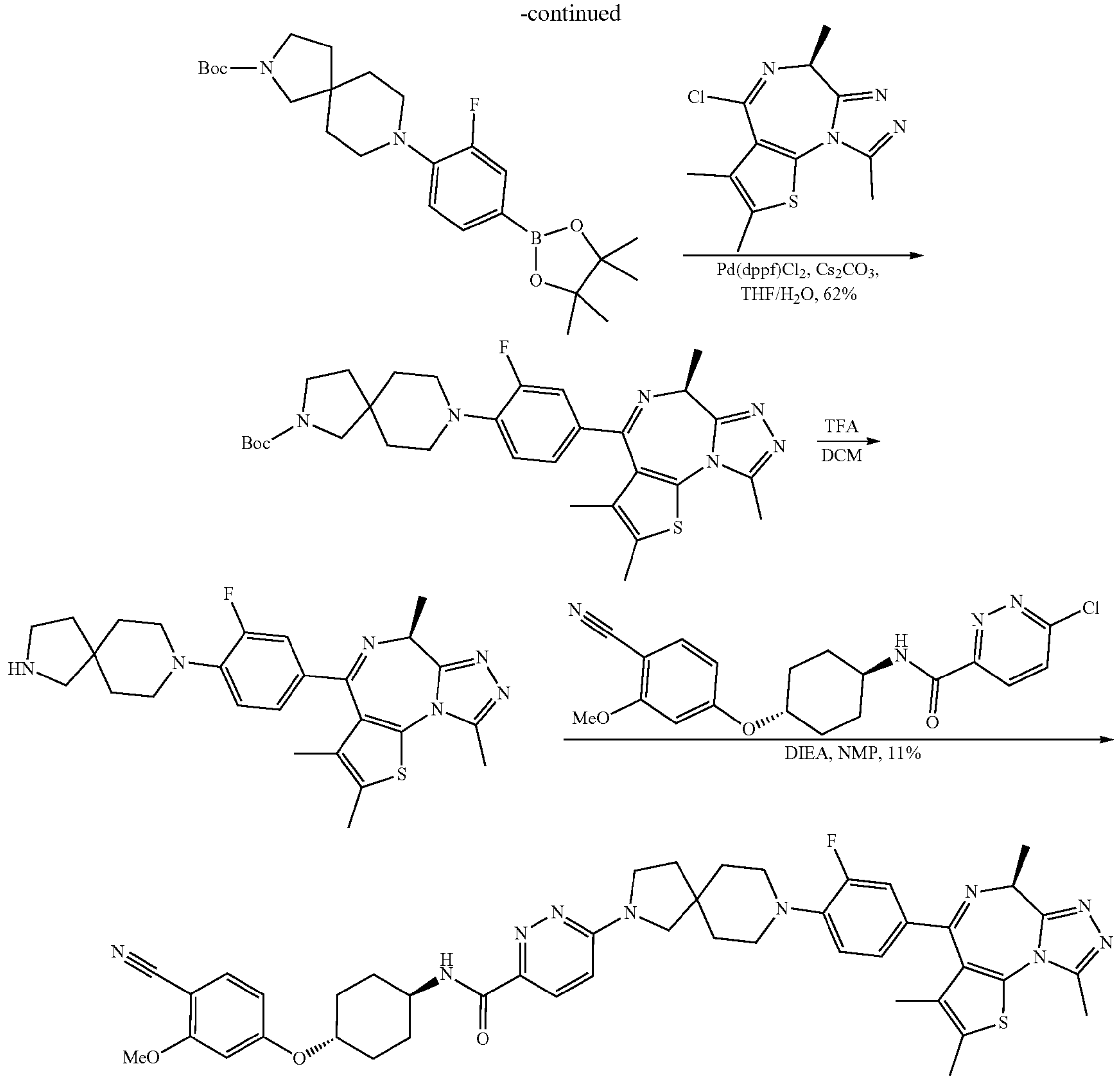

I-44

Step 1: Preparation of tert-butyl 8-(4-bromo-2-fluoro-phenyl)-2,8-diazaspiro[4.5]decane-2-carboxylate. To a solution of tert-butyl 2,8-diazaspiro[4.5]decane-2-carboxylate (1.0 g, 4.16 mmol, 1 eq) and 4-bromo-2-fluoro-1-iodo-benzene (1.25 g, 4.16 mmol, 1 eq) in toluene (20 mL) was added $Cs_2CO_3$ (3.39 g, 10.40 mmol, 2.5 eq), $Pd_2(dba)_3$ (381.01 mg, 416.08 μmol, 0.03 eq), and Xantphos (240.75 mg, 416.08 μmol, 0.1 eq). The mixture was stirred at 100° C. for 12 hours. The reaction mixture was concentrated under reduced pressure to remove toluene. The residue was diluted with $H_2O$ (50 mL) and extracted with EtOAc (50 mL×3). The combined organic layers were washed with brine (150 mL×1), dried over $Na_2SO_4$, filtered, and concentrated under reduced pressure to give a residue. The residue was purified by column chromatography ($SiO_2$, petroleum ether:ethyl acetate=1:0 to 9:1). Compound tert-butyl 8-(4-bromo-2-fluoro-phenyl)-2,8-diazaspiro[4.5]decane-2-carboxylate (673 mg, 1.61 mmol, 38.74% yield, 99.0% purity) was obtained as a yellow solid, which was confirmed by LCMS.

Step 2: Preparation of tert-butyl 8-[2-fluoro-4-(4,4,5,5-tetramethyl-1,3,2-dioxaborolan-2-yl)phenyl]-2,8-diazaspiro[4.5]decane-2-carboxylate. To a solution of tert-butyl 8-(4-bromo-2-fluoro-phenyl)-2,8-diazaspiro[4.5]decane-2-carboxylate (370 mg, 895.18 μmol, 1 eq) in dioxane (15 mL) was added BPD (272.79 mg, 1.07 mmol, 1.2 eq), Pd(dppf) $Cl_2{\cdot}CH_2Cl_2$ (73.10 mg, 89.52 μmol, 0.1 eq), and KOAc (263.57 mg, 2.69 mmol, 3 eq). The mixture was stirred at 100° C. for 12 hours. The reaction mixture was filtered and concentrated under reduced pressure to give a residue. The residue was purified by column chromatography ($SiO_2$, petroleum ether:ethyl acetate=1:0 to 9:1). Compound tert-butyl 8-[2-fluoro-4-(4,4,5,5-tetramethyl-1,3,2-dioxaborolan-2-yl)phenyl]-2,8-diazaspiro[4.5]decane-2-carboxylate (280 mg, 608.18 μmol, 67.94% yield) was obtained as a light-yellow solid.

Step 3: Preparation of tert-butyl 8-[2-fluoro-4-[(9S)-4,5,9,13-tetramethyl-3-thia-1,8,11,12-tetrazatricyclo[8.3.0.0$^{2,6}$]trideca2 (6),4,7,10,12-pentaen-7-yl]phenyl]-2,8-diazaspiro[4.5]decane-2-carboxylate. To a solution of tert-butyl 8-[2-fluoro-4-(4,4,5,5-tetramethyl-1,3,2-dioxaborolan-2-yl) phenyl]-2,8-diazaspiro[4.5]decane-2-carboxylate (327.94 mg, 712.31 μmol, 1.0 eq) and (9S)-7-chloro-4,5,9,13-tetramethyl-3-thia1,8,11,12-tetrazatricyclo[8.3.0.0$^{2,6}$]trideca-2 (6), 4,7,10,12-pentaene (200 mg, 712.31 μmol, 1.0 eq) in THF (9 mL) and $H_2O$ (3 mL) was added $Cs_2CO_3$ (580.21 mg, 1.78 mmol, 2.5 eq) and $Pd(dppf)Cl_2 \cdot CH_2Cl_2$ (116.34 mg, 142.46 μmol, 0.2 eq). The mixture was stirred at 50° C. for 12 hours. The reaction mixture was concentrated under reduced pressure to remove THF. The residue was diluted with $H_2O$ (50 mL) and extracted with DCM (50 mL×3). The combined organic layers were washed with brine (150 mL×2), dried over $Na_2SO_4$, filtered, and concentrated under reduced pressure to give a residue. The residue was purified by prep-TLC ($SiO_2$, DCM:MeOH=10:1). Compound tert-butyl 8-[2-fluoro-4-[(9S)-4,5,9,13-tetramethyl-3-thia-1,8,11,12-tetrazatricyclo[8.3.0.0$^{2,6}$]trideca2 (6),4,7,10,12-pentaen-7-yl]phenyl]-2,8-diazaspiro[4.5]decane-2-carboxylate (290 mg, 444.96 μmol, 62.47% yield, 88.8% purity) was obtained as a yellow solid, which was confirmed by LCMS and $^1$H NMR.

Step 4: Preparation of (9S)-7-[4-(2,8-diazaspiro[4.5]decan-8-yl)-3-fluoro-phenyl]-4,5,9,13-tetramethyl-3-thia-1,8,11,12-tetrazatricyclo[8.3.0.0$^{2,6}$]trideca-2 (6),4,7,10,12-pentaene. To a solution of tert-butyl 8-[2-fluoro-4-[(9S)-4,5,9,13-tetramethyl-3-thia-1,8,11,12-tetrazatricyclo[8.3.0.0$^{2,6}$]trideca2 (6),4,7,10,12-pentaen-7-yl]phenyl]-2,8-diazaspiro[4.5]decane-2-carboxylate (170 mg, 260.84 μmol, 1 eq) in DCM (6 mL) as added TFA (11.92 g, 104.54 mmol, 7.77 mL, 400.80 eq) at 25° C. The mixture was stirred at 25° C. for 30 minutes. The reaction mixture was concentrated under vacuum to give a residue. Compound (9S)-7-[4-(2,8-diazaspiro[4.5]decan-8-yl)-3-fluoro-phenyl]-4,5,9,13-tetramethyl-3-thia-1,8,11,12-tetrazatricyclo[8.3.0.0$^{2,6}$]trideca-2 (6),4,7,10,12-pentaene (120 mg, crude) was obtained as a brown oil.

Step 5: Preparation of N-[4-(4-cyano-3-methoxy-phenoxy)cyclohexyl]-6-[8-[2-fluoro-4-[(9S)-4,5,9,13-tetramethyl-3-thia1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (I-44). To a solution of (9S)-7-[4-(2,8-diazaspiro[4.5]decan-8-yl)-3-fluoro-phenyl]-4,5,9,13-tetramethyl-3-thia-1,8,11,12-tetrazatricyclo[8.3.0.0$^{2,6}$]trideca-2 (6),4,7,10,12-pentaene (120 mg, 250.72 μmol, 1 eq) and 6-chloro-N-[4-(4-cyano-3-methoxy-phenoxy)cyclohexyl]pyridazine-3-carboxamide (96.99 mg, 250.72 μmol, 1 eq) in NMP (2 mL) was added DIEA (324.03 mg, 2.51 mmol, 436.69 μL, 10 eq). The mixture was stirred at 70° C. for 12 hours. The reaction mixture was concentrated under reduced pressure to give a residue. The residue was purified by prep-HPLC (column: Phenomenex luna C18 150×25 mm×10 μm; mobile phase: [water (FA)-ACN]; gradient: 45%-75% B over 1 min). Compound N-[4-(4-cyano-3-methoxy-phenoxy)cyclohexyl]-6-[8-[2-fluoro-4-[(9S)-4,5,9,13-tetramethyl-3-thia1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (24.04 mg, 28.19 μmol, 11.24% yield, 97.20% purity) was obtained as a white solid, which was confirmed by SFC, QC LCMS, and $^1$H NMR). $^1$H NMR (400 MHz, DMSO): δ 8.50 (d, J=8.4 Hz, 1H), 7.82 (d, J=9.2 Hz, 1H), 7.63-7.56 (m, 1H), 7.21 (d, J=14.0 Hz, 1H), 7.17-7.10 (m, 1H), 7.09-7.02 (m, 1H), 6.97 (d, J=9.6 Hz, 1H), 6.75-6.68 (m, 2H), 4.56-4.42 (m, 1H), 4.21-4.14 (m, 1H), 3.95-3.80 (m, 4H), 3.70-3.53 (m, 2H), 3.52-3.40 (m, 2H), 3.18-3.05 (m, 4H), 2.59 (s, 3H), 2.41 (s, 3H), 2.16-2.07 (m, 2H), 1.99-1.84 (m, 7H), 1.76-1.49 (m, 11H). LC-MS: MS (ES$^+$): Rt=0.513 min, m/z=829.3 [M+H]$^+$; LCMS method: 5-95.

Example 19—Synthesis of N-[4-(4-cyano-3-methoxy-phenoxy)cyclohexyl]-6-[8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (I-45)

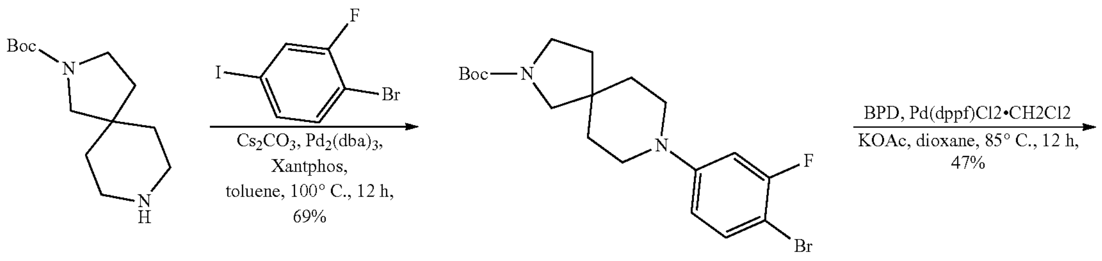

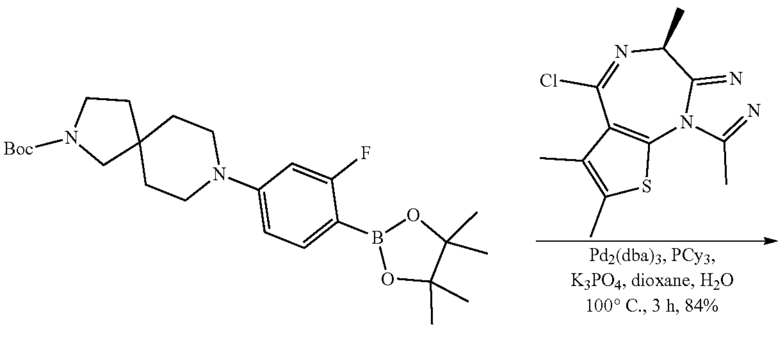

-continued

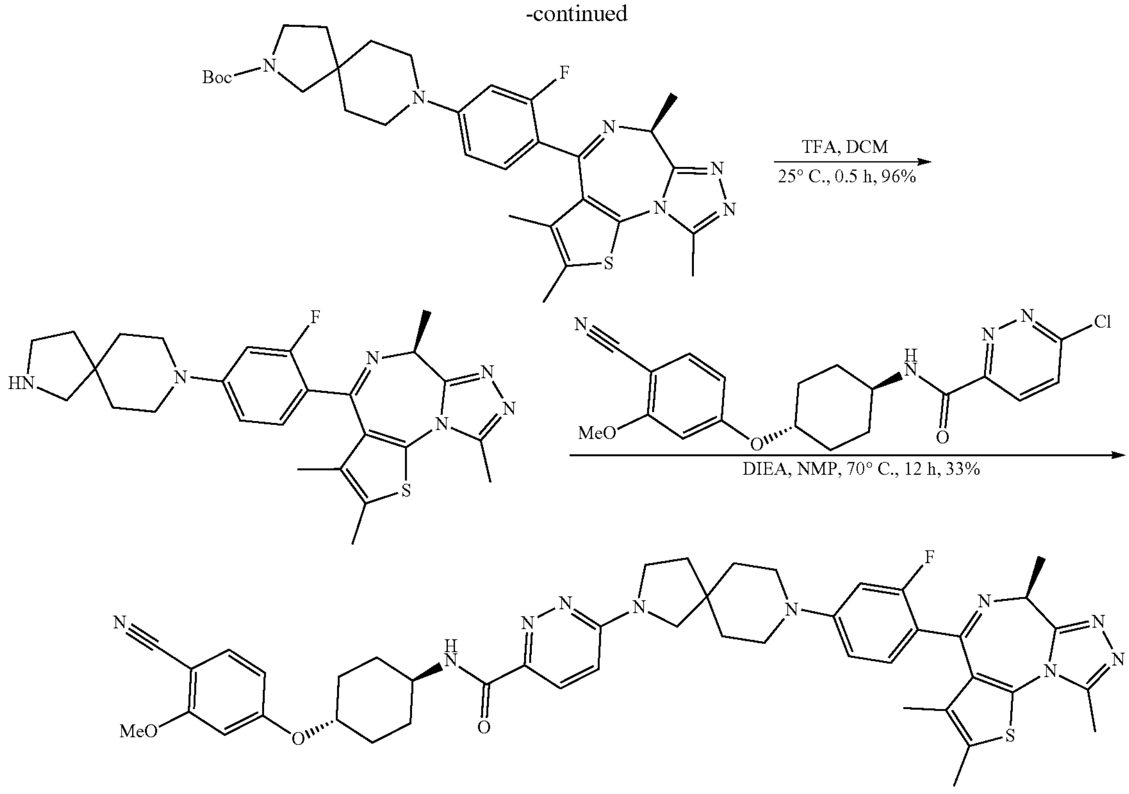

I-45

Step 1: Preparation of tert-butyl 8-(4-bromo-3-fluoro-phenyl)-2,8-diazaspiro[4.5]decane-2-carboxylate. To a solution of tert-butyl 2,8-diazaspiro[4.5]decane-2-carboxylate (1 g, 4.16 mmol, 1 eq) and 1-bromo-2-fluoro-4-iodo-benzene (1.25 g, 4.16 mmol, 1 eq) in toluene (20 mL) was added $Cs_2CO_3$ (3.39 g, 10.40 mmol, 2.5 eq), $Pd_2(dba)_3$ (114.30 mg, 124.82 μmol, 0.03 eq), and Xantphos (240.75 mg, 416.08 μmol, 0.1 eq). The mixture was stirred at 100° C. for 12 hours. To the reaction mixture was added water (80 mL), and the mixture was extracted with ethyl acetate (100 mLx3). The combined organic phase was washed with brine (100 mLx3), dried over anhydrous $Na_2SO_4$, filtered, and concentrated in vacuo. The crude product was purified by flash silica gel chromatography (ISCO®; 12 g SepaFlash® Silica Flash Column, eluent of 0~8% ethyl acetate/petroleum ether gradient at 80 mL/min). Compound tert-butyl 8-(4-bromo-3-fluoro-phenyl)-2,8-diazaspiro[4.5]decane-2-carboxylate (1.2 g, 2.90 mmol, 69.78% yield) was obtained as a yellow oil.

Step 2: Preparation of tert-butyl 8-[3-fluoro-4-(4,4,5,5-tetramethyl-1,3,2-dioxaborolan-2-yl)phenyl]-2,8-diazaspiro[4.5]decane-2-carboxylate. To a solution of tert-butyl 8-(4-bromo-3-fluoro-phenyl)-2,8-diazaspiro[4.5]decane-2-carboxylate (600 mg, 1.45 mmol, 1 eq) in dioxane (10 mL) was added BPD (442.36 mg, 1.74 mmol, 1.2 eq), Pd(dppf) $Cl_2 \cdot CH_2Cl_2$ (118.55 mg, 145.16 μmol, 0.1 eq), and KOAc (427.40 mg, 4.35 mmol, 3 eq). The mixture was stirred at 85° C. for 12 hours. To the reaction mixture was added water (80 mL), and the mixture was extracted with ethyl acetate (100 mLx3). The combined organic phase was washed with brine (100 mLx3), dried over anhydrous $Na_2SO_4$, filtered, and concentrated in vacuo. The crude product was purified by flash silica gel chromatography (ISCO®; 20 g SepaFlash® Silica Flash Column, eluent of 0~10% ethyl acetate/petroleum ether gradient at 70 mL/min). Compound tert-butyl 8-[3-fluoro-4-(4,4,5,5-tetramethyl-1,3,2-dioxaborolan-2-yl)phenyl]-2,8-diazaspiro[4.5]decane-2-carboxylate (320 mg, 695.07 μmol, 47.88% yield) was obtained as a yellow solid.

Step 3: Preparation of tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate. To a solution of tert-butyl 8-[3-fluoro-4-(4,4,5,5-tetramethyl-1,3,2-dioxaborolan-2-yl)phenyl]-2,8-diazaspiro[4.5]decane-2-carboxylate (426.32 mg, 926.01 μmol, 1.3 eq) and (9S)-7-chloro-4,5,9,13-tetramethyl-3-thia-1,8,11,12-tetrazatricyclo[8.3.0.0$^{2,6}$]trideca-2 (6),4,7,10,12-pentaene (200 mg, 712.31 μmol, 1 eq) in $H_2O$ (1.2 mL) was added $Pd_2(dba)_3$ (65.23 mg, 71.23 μmol, 0.1 eq), $Pcy_3$ (39.95 mg, 142.46 μmol, 46.19 μL, 0.2 eq), and $K_3PO_4$ (453.60 mg, 2.14 mmol, 3 eq) in dioxane (6 mL). The suspension was degassed and purged with $N_2$ 3 times. The mixture was stirred under $N_2$ at 100° C. for 3 hours. To the reaction mixture was added water (80 mL), and the mixture was extracted with ethyl acetate (100 mLx3). The combined organic phase was washed with brine (100 mLx3), dried over anhydrous $Na_2SO_4$, filtered, and concentrated in vacuo. The residue was purified by prep-TLC ($SiO_2$, DCM: MeOH=10:1). Compound tert-butyl 8-[3-fluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-2,8-diazaspiro[4.5]decane-2-carboxylate (350 mg, 604.76 μmol, 84.90% yield) was obtained as a yellow solid.

Step 4: Preparation of (9S)-7-[4-(2,8-diazaspiro[4.5]decan-8-yl)-2-fluoro-phenyl]-4,5,9,13-tetramethyl-3-thia-1,8,11,12-tetrazatricyclo[8.3.0.0$^{2,6}$]trideca-2 (6),4,7,10,12-pentaene. To a solution of tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (100 mg, 172.79 μmol, 1 eq) in DCM (5 mL) was added TFA (19.70 mg, 172.79 μmol, 12.83 μL, 1 eq). The mixture was stirred at 25° C. for 0.5 hour. The reaction mixture was concentrated under reduced pressure to give a residue. The crude product was purified by prep-HPLC (column: YMC-Actus Triart C18 150 mm×30 mm×7 μm; mobile phase: [water (FA)-ACN]; gradient: 8%-38% B over 10 min). Compound (9S)-7-[4-(2,8-diazaspiro[4.5]decan-8-yl)-2-fluoro-phenyl]-4,5,9,13-tetramethyl-3-thia-1,8,11,12-tetrazatricyclo[8.3.0.0$^{2,6}$]trideca-2 (6),4,7,10,12-pentaene (80 mg, 167.14 μmol, 96.73% yield) was obtained as a yellow solid.

Step 5: Preparation of N-[4-(4-cyano-3-methoxy-phenoxy)cyclohexyl]-6-[8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (I-45). A mixture of (9S)-7-[4-(2,8-diazaspiro[4.5]decan-8-yl)-2-fluoro-phenyl]-4,5,9,13-tetramethyl-3-thia-1,8,11,12-tetrazatricyclo[8.3.0.0$^{2,6}$]trideca-2 (6),4,7,10,12-pentaene (110 mg, 229.82 μmol, 1 eq), DIEA (594.06 mg, 4.60 mmol, 800.62 μL, 20 eq), and 6-chloro-N-[4-(4-cyano-3-methoxy-phenoxy)cyclohexyl]pyridazine-3-carboxamide (88.90 mg, 229.82 μmol, 1 eq) in NMP (5 mL) was degassed and purged with $N_2$ 3 times. The mixture was stirred at 70° C. for 12 hours under $N_2$ atmosphere. To the reaction mixture was added water (20 mL), and the mixture was extracted with ethyl acetate (30 mL×3). The combined organic phase was washed with brine (20 mL×3), dried over anhydrous $Na_2SO_4$, filtered, and concentrated in vacuo. The crude product was purified by prep-HPLC (column: YMC-Actus Triart C18 150 mm×30 mm×7 μm; mobile phase: [water (FA)-ACN]; gradient: 40%-70% B over 10 min). Compound N-[4-(4-cyano-3-methoxy-phenoxy)cyclohexyl]-6-[8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (67.95 mg, 76.83 μmol, 33.43% yield, 93.73% purity) was obtained as a yellow solid. $^1H$ NMR (400 MHz, DMSO-$d_6$) δ: 8.51 (d, J=8.4 Hz, 1H), 7.83 (d, J=9.6 Hz, 1H), 7.62 (d, J=9.2 Hz, 1H), 7.32 (br t, J=8.8 Hz, 1H), 6.98 (d, J=9.6 Hz, 1H), 6.83 (dd, J=2.0, 8.8 Hz, 1H), 6.76-6.66 (m, 3H), 4.58-4.43 (m, 1H), 4.21-4.11 (m, 1H), 3.92-3.81 (m, 4H), 3.64 (br d, J=5.2 Hz, 2H), 3.52-3.36 (m, 5H), 2.58 (s, 3H), 2.38 (s, 3H), 2.16-2.08 (m, 2H), 1.99-1.89 (m, 4H), 1.86 (d, J=6.8 Hz, 3H), 1.71-1.58 (m, 9H), 1.57-1.48 (m, 2H), 1.24 (br s, 1H). LC-MS: MS ($ES^+$): RT=0.480 min, m/z=829.4 [M+1]; LCMS Method: 5-95.

Example 20—Synthesis of N-[4-(4-cyano-3-methoxy-phenoxy)cyclohexyl]-6-[8-[2-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (I-46)

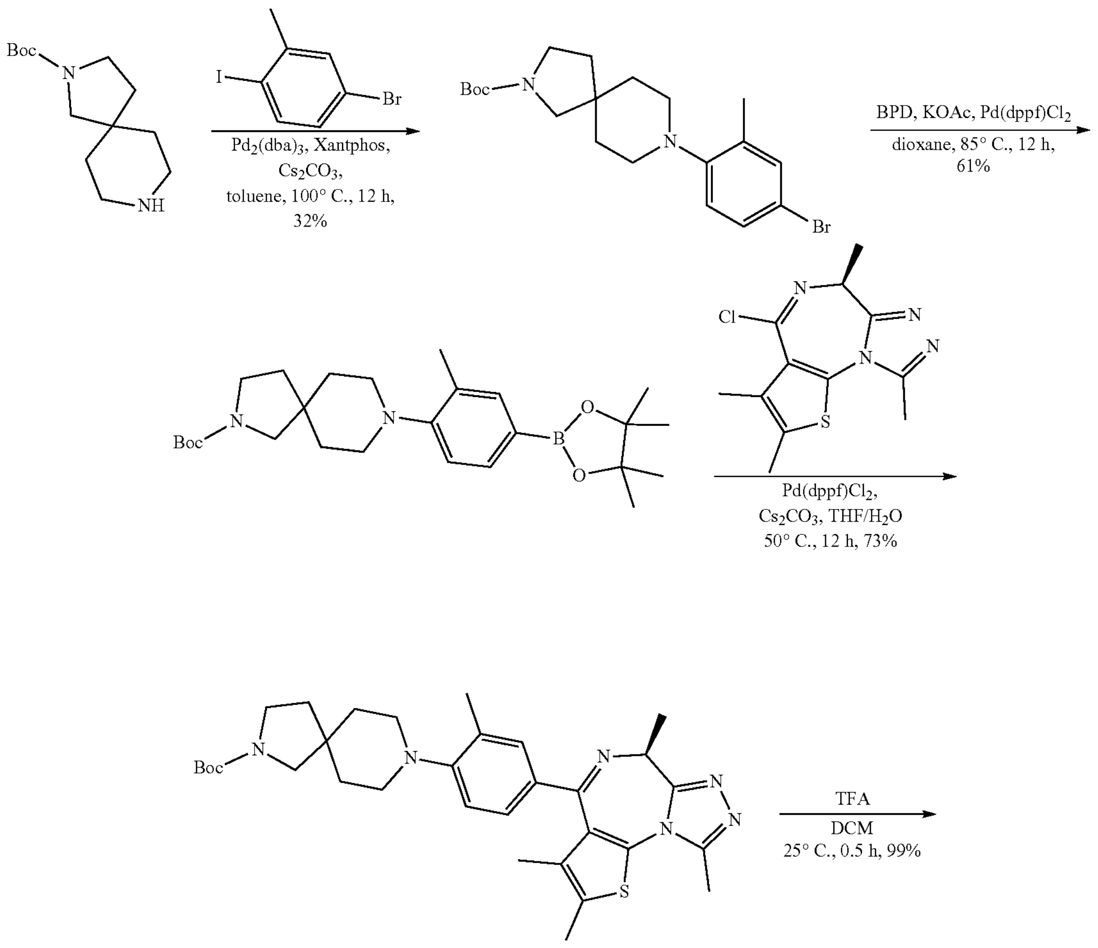

-continued

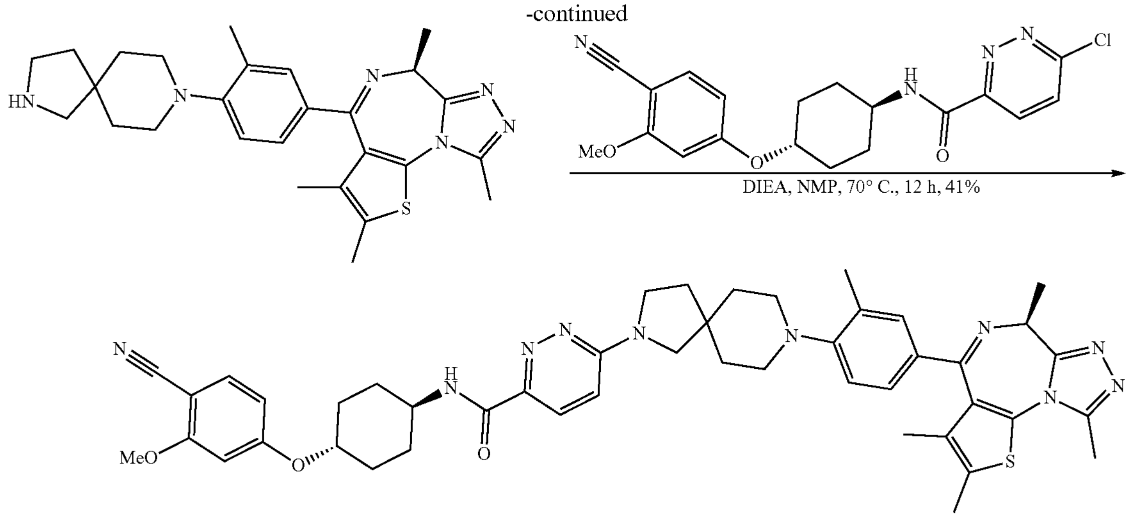

I-46

Step 1: Preparation of tert-butyl 8-(4-bromo-2-methyl-phenyl)-2,8-diazaspiro[4.5]decane-2-carboxylate. To a solution of tert-butyl 2,8-diazaspiro[4.5]decane-2-carboxylate (500 mg, 2.08 mmol, 1.0 equiv) in toluene (10 mL) was added $Cs_2CO_3$ (1.69 g, 5.20 mmol, 2.5 equiv), $Pd_2(dba)_3$ (57 mg, 62 μmol, 0.03 equiv), 4-bromo-1-iodo-2-methyl-benzene (926 mg, 3.12 mmol, 1.5 equiv), and Xantphos (120 mg, 208 μmol, 0.1 equiv). The mixture was stirred at 100° C. for 12 hours. The residue was purified by column chromatography ($SiO_2$, petroleum ether:ethyl acetate=20:1 to 5:1) to give tert-butyl 8-(4-bromo-2-methyl-phenyl)-2,8-diazaspiro[4.5]decane-2-carboxylate (270 mg, 32% yield).

Step 2: Preparation of tert-butyl 8-[2-methyl-4-(4,4,5,5-tetramethyl-1,3,2-dioxaborolan-2-yl)phenyl]-2,8-diazaspiro[4.5]decane-2-carboxylate. To a solution of tert-butyl 8-(4-bromo-2-methyl-phenyl)-2,8-diazaspiro[4.5]decane-2-carboxylate (440 mg, 1.07 mmol, 1.0 equiv) in dioxane (5 mL) was added BPD (818.84 mg, 3.22 mmol, 3.0 equiv), $Pd(dppf)Cl_2$ (157 mg, 215 μmol, 0.2 equiv), and KOAc (421.94 mg, 4.30 mmol, 4.0 equiv). The mixture was stirred at 85° C. for 12 hours. The residue was purified by prep-TLC ($SiO_2$, ethyl acetate: MeOH=20:1) to give tert-butyl 8-[2-methyl-4-(4,4,5,5-tetramethyl-1,3,2-dioxaborolan-2-yl)phenyl]-2,8-diazaspiro[4.5]decane-2-carboxylate (300 mg, 61% yield).

Step 3: Preparation of tert-butyl 8-[2-methyl-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decane-2-carboxylate. To a solution of tert-butyl 8-[2-methyl-4-(4,4,5,5-tetramethyl-1,3,2-dioxaborolan-2-yl)phenyl]-2,8-diazaspiro[4.5]decane-2-carboxylate (243 mg, 534 μmol, 1.5 equiv) in THF (4 mL) and $H_2O$ (2 mL) was added $Pd(dppf)Cl_2$ (52 mg, 71 μmol, 0.2 equiv), $Cs_2CO_3$ (348 mg, 1.07 mmol, 3.0 equiv), and (9S)-7-chloro-4,5,9,13-tetramethyl-3-thia-1,8,11,12-tetrazatricyclo[8.3.0.$0^{2,6}$]trideca-2 (6),4,7,10,12-pentaene (100 mg, 356 μmol, 1.0 equiv). The mixture was stirred at 50° C. for 12 hours. The residue was purified by prep-TLC ($SiO_2$, ethyl acetate: MeOH=30:1) to give tert-butyl 8-[2-methyl-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decane-2-carboxylate (150 mg, 73% yield).

Step 4: Preparation of (9S)-7-[4-(2,8-diazaspiro[4.5]decan-8-yl)-3-methyl-phenyl]-4,5,9,13-tetramethyl-3-thia-1,8,11,12-tetrazatricyclo[8.3.0.$0^{2,6}$]trideca-2 (6),4,7,10,12-pentaene. To a solution of tert-butyl 8-[2-methyl-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decane-2-carboxylate (150 mg, 261 μmol, 1.0 equiv) in DCM (1 mL) was added TFA (0.3 mL). The mixture was stirred at 25° C. for 0.5 hour to give (9S)-7-[4-(2,8-diazaspiro[4.5]decan-8-yl)-3-methyl-phenyl]-4,5,9,13-tetramethyl-3-thia-1,8,11,12-tetrazatricyclo[8.3.0.$0^{2,6}$]trideca-2 (6),4,7,10,12-pentaene (123.8 mg, 99% yield) as a residue, which was used directly in the next step.

Step 5: Preparation of N-[4-(4-cyano-3-methoxy-phenoxy)cyclohexyl]-6-[8-[2-methyl-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decan-2-yl]pyridazine-3-carboxamide (I-46). To a solution of (9S)-7-[4-(2,8-diazaspiro[4.5]decan-8-yl)-3-methyl-phenyl]-4,5,9,13-tetramethyl-3-thia-1,8,11,12-tetrazatricyclo[8.3.0.$0^{2,6}$]trideca-2 (6),4,7,10,12-pentaene (123 mg, 259 μmol, 1.0 equiv) in NMP (1 mL) was added DIEA (67 mg, 518 μmol, 2.0 equiv) and 6-chloro-N-[4-(4-cyano-3-methoxy-phenoxy)cyclohexyl]pyridazine-3-carboxamide (100 mg, 259 μmol, 1.0 equiv). The mixture was stirred at 70° C. for 12 hours and purified by prep-HPLC (column: Phenomenex luna C18 150 mm×25 mm×10 μm; mobile phase: [water (TFA)-ACN]; gradient: 30%-60% B over 10 min) to give N-[4-(4-cyano-3-methoxy-phenoxy) cyclohexyl]-6-[8-[2-methyl-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decan-2-yl] pyridazine-3-carboxamide (92 mg, 41% yield). $^1H$ NMR (400 MHz, $CDCl_3$): δ 8.14 (d, J=9.6 Hz, 1H), 7.84 (d, J=8.0 Hz, 1H), 7.57-7.42 (m, 2H), 7.27 (s, 1H), 6.99 (s, 2H), 6.59-6.37 (m, 2H), 4.45-4.25 (m, 2H), 4.14-3.98 (m, 1H), 3.91 (s, 3H), 3.84-3.57 (m, 4H), 3.26-2.86 (m, 5H), 2.79 (s, 3H), 2.48 (s, 3H), 2.33 (s, 3H), 2.23-2.15 (m, 7H), 2.10 (s, 2H), 1.86 (s, 3H), 1.75 (s, 3H), 1.72-1.61 (m, 2H), 1.58-1.46 (m, 2H). LC-MS: MS ($ES^+$): RT=1.796 min, m/z=825.6 $[M+H]^+$; LCMS method: 25.

Example 21—Synthesis of N-[4-(4-cyano-3-methoxy-phenoxy)cyclohexyl]-5-[8-[4-[(9S)-pentaen-7-yl]phenyl]-2-azaspiro[4.5]decan-2-yl]pyrazine-2-carboxamide (I-54)
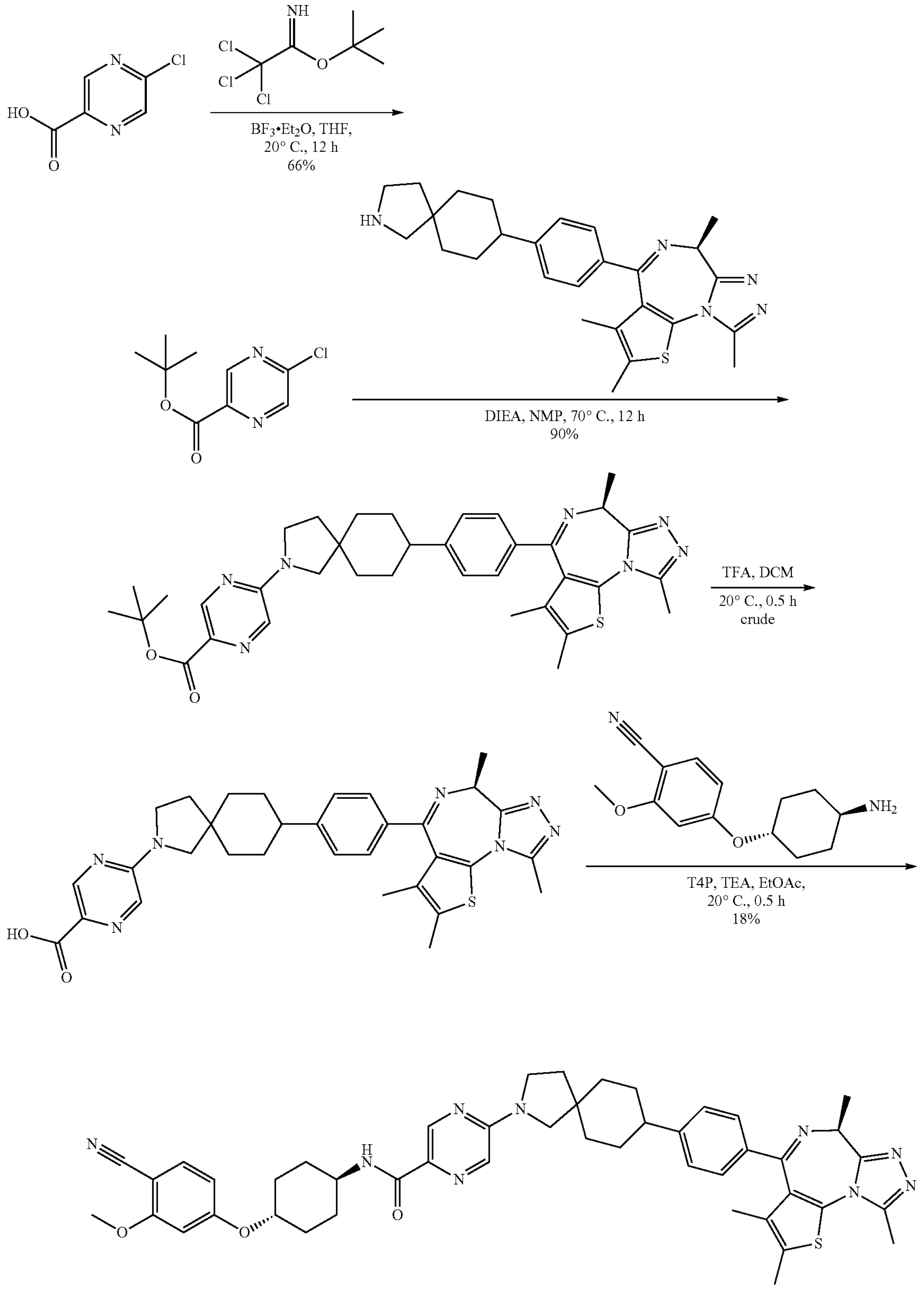
I-54

Step 1: Preparation of tert-butyl 5-chloropyrazine-2-carboxylate. To a solution of 5-chloropyrazine-2-carboxylic acid (1.12 g, 7.04 mmol, 1 equiv) in THF (20 mL) was added boron trifluoride etherate (400 mg, 2.82 mmol, 0.4 equiv) and tert-butyl 2,2,2-trichloroethanimidate (3.08 g, 14.08 mmol, 2 equiv). The mixture was stirred at 20° C. for 12 hours. The residue was purified by column chromatography ($SiO_2$, petroleum ether:ethyl acetate=100:1 to 10:1) to give tert-butyl 5-chloropyrazine-2-carboxylate (1 g, 66% yield) as a white solid.

Step 2: Preparation of tert-butyl 5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxylate. To a solution of tert-butyl 5-chloropyrazine-2-carboxylate (224 mg, 1.04 mmol, 3 equiv) in NMP (1 mL) was added DIEA (135 mg, 1.04 mmol, 3 equiv) and (9S)-7-[4-(2-azaspiro[4.5]decan-8-yl)phenyl]-4,5,9,13-tetramethyl-3-thia-1,8,11,12-tetrazatricyclo[8.3.0.$0^{2,6}$]trideca-2 (6),4,7,10,12-pentaene (160 mg, 348 μmol, 1 equiv). The mixture was stirred at 70° C. for 12 hours. The residue was purified by prep-TLC ($SiO_2$, DCM: MeOH=10:1) to give tert-butyl 5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxylate (200 mg, 90% yield) as a yellow oil.

Step 3: Preparation of 5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxylic acid. To a solution of tert-butyl 5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxylate (200 mg, 313 μmol, 1 equiv) in DCM (2 mL) was added TFA (1 mL). The mixture was stirred at 20° C. for 0.5h. The reaction mixture was filtered and concentrated under reduced pressure to give 5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxylic acid (180 mg) as a yellow oil.

Step 4: Preparation of N-[4-(4-cyano-3-methoxy-phenoxy)cyclohexyl]-5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxamide (I-54). To a solution of 4-(4-aminocyclohexoxy)-2-methoxy-benzonitrile (64 mg, 178 μmol, 1.4 equiv, TFA salt) in EtOAc (1 mL) was added T4P (134 mg, 186 μmol, 50% purity, 1.5 equiv), 5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxylic acid (72 mg, 124 μmol, 1 equiv), and TEA (63 mg, 620 μmol, 5 equiv). The mixture was stirred at 20° C. for 0.5 hour. The reaction mixture was concentrated under reduced pressure to remove solvent. The residue was purified by prep-HPLC (column: Phenomenex luna C18 150 mm×25 mm×10 μm; mobile phase: [water (FA)-ACN]; gradient: 63%-93% B over 10 min) to give N-[4-(4-cyano-3-methoxy-phenoxy) cyclohexyl]-5-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyrazine-2-carboxamide (18 mg, 18% yield) as a white solid. $^1H$ NMR (400 MHz, $CDCl_3$) δ ppm 8.87 (d, J=0.76 Hz, 1H), 7.73 (s, 1H), 7.37-7.50 (m, 4H), 7.21 (d, J=8.12 Hz, 2H), 6.42-6.55 (m, 2H), 4.27-4.38 (m, 1H), 4.16-4.21 (m, 1H), 4.00-4.10 (m, 1H), 3.90 (s, 3H), 3.43-3.72 (m, 4H), 2.63-2.72 (m, 3H), 2.50-2.61 (m, 1H), 2.42 (s, 3H), 2.16-2.25 (m, 4H), 2.10 (d, J=6.76 Hz, 3H), 1.77-1.96 (m, 8H), 1.40-1.66 (m, 9H). LC-MS: MS ($ES^+$): RT=2.461 min, m/z=810.5 $[M+H]^+$; LCMS method: 25.

Example 22—Synthesis of N-[4-(4-cyano-3-methoxy-phenoxy)cyclohexyl]-6-[8-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-?-yl]pyridazine-3-carboxamide (1-56)

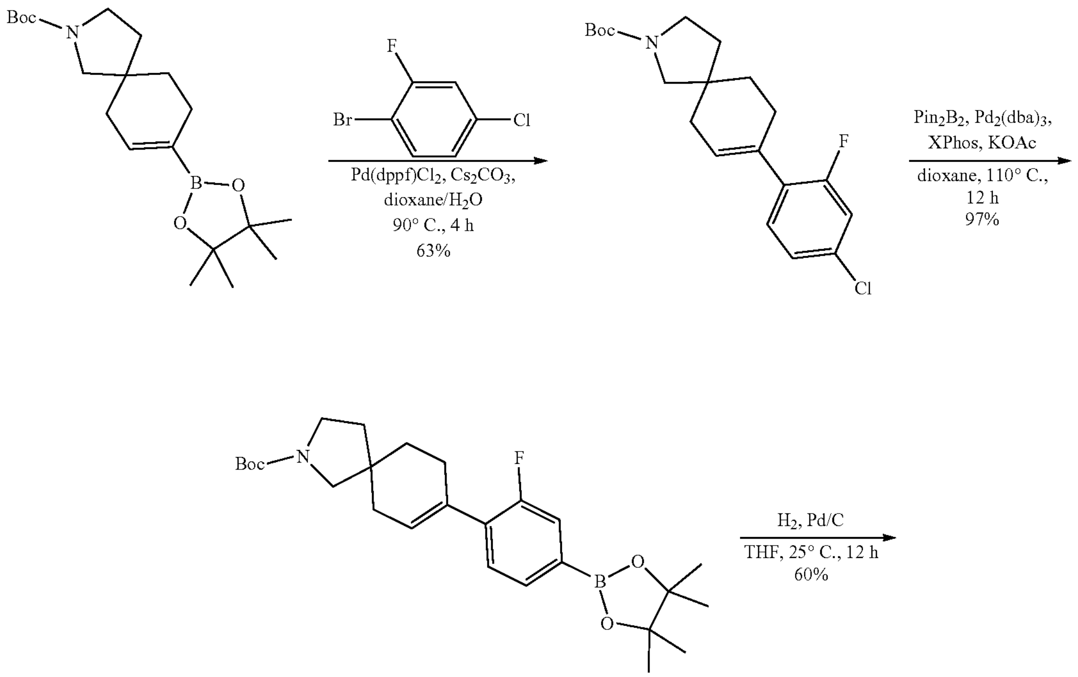

-continued
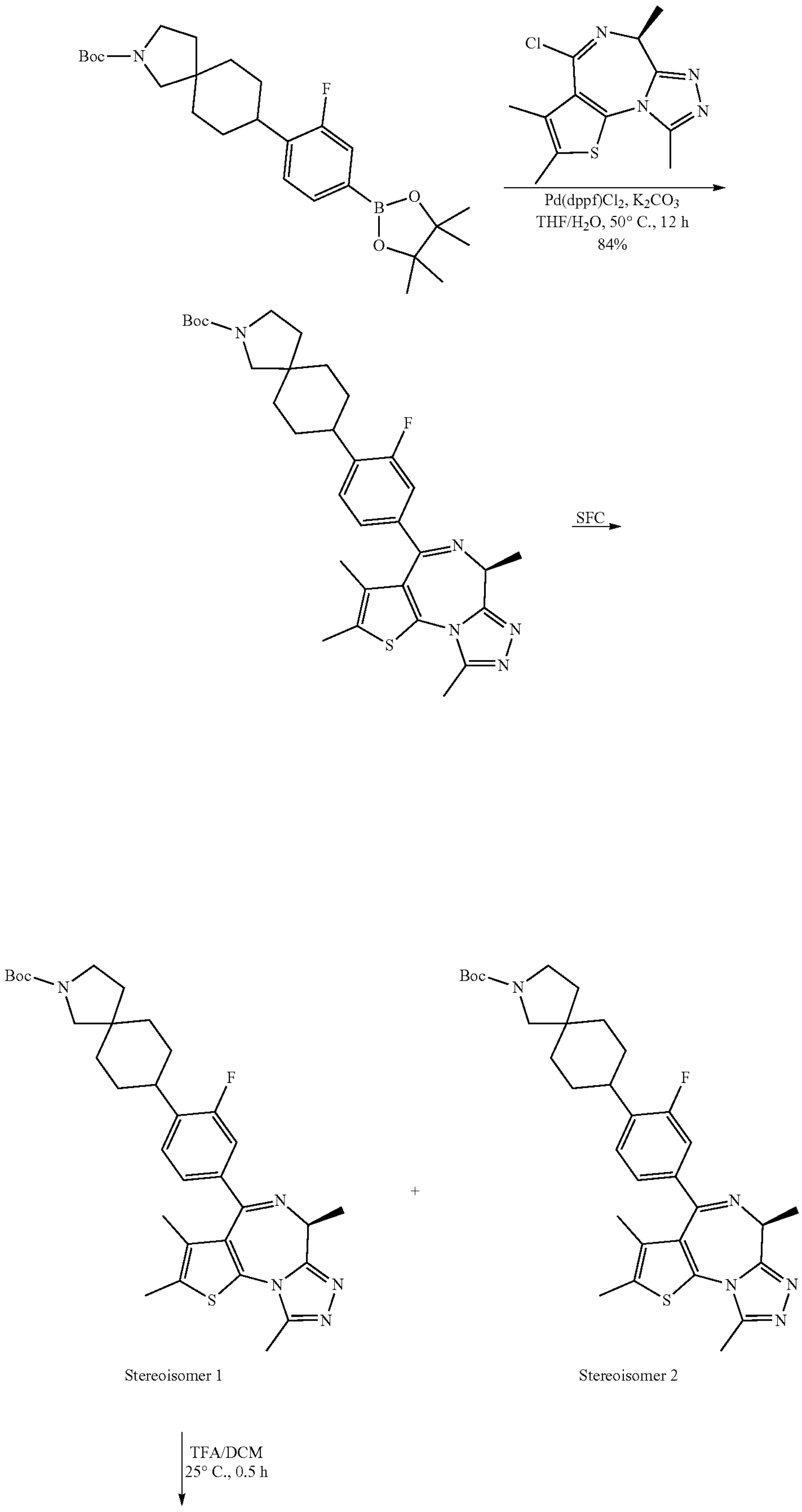

-continued

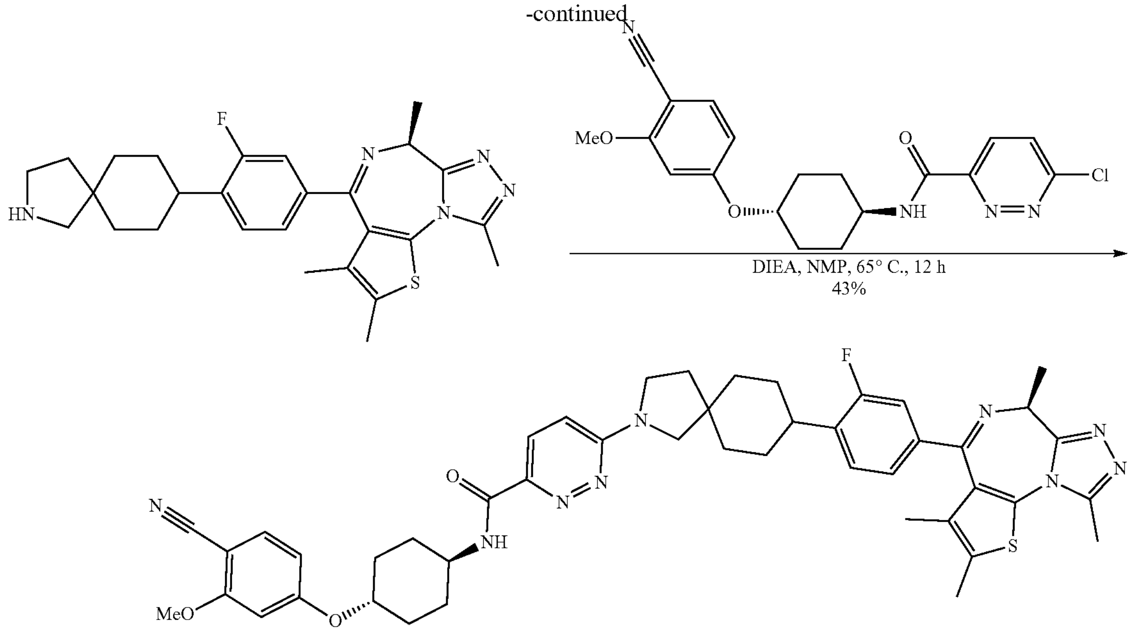

I-56

Step 1: Preparation of tert-butyl 8-(4-chloro-2-fluoro-phenyl)-2-azaspiro[4.5]dec-7-ene-2-carboxylate. To a solution of tert-butyl 8-(4,4,5,5-tetramethyl-1,3,2-dioxaborolan-2-yl)-2-azaspiro[4.5]dec-7-ene-2-carboxylate (400 mg, 1.10 mmol, 1.1 equiv) and 1-bromo-4-chloro-2-fluoro-benzene (201 mg, 1.00 mmol, 1.0 equiv) in dioxane (10 mL) and $H_2O$ (2 mL) was added $Cs_2CO_3$ (978 mg, 3.00 mmol, 3.0 equiv) and Pd(dppf)$Cl_2$ (146 mg, 200 μmol, 0.2 equiv) under $N_2$. The reaction mixture was stirred at 90° C. for 4 hours. The reaction mixture was diluted with water (50 mL) and extracted with ethyl acetate (30 mL×3). The organic layers were combined, dried over $Na_2SO_4$, filtered, and concentrated to afford crude product. The residue was purified by column chromatography ($SiO_2$, petroleum ether:ethyl acetate=10:1 to 5:1). Compound tert-butyl 8-(4-chloro-2-fluoro-phenyl)-2-azaspiro[4.5]dec-7-ene-2-carboxylate (230 mg, 629 μmol, 63% yield) was obtained as a colorless oil.

Step 2: Preparation of tert-butyl 8-[2-fluoro-4-(4,4,5,5-tetramethyl-1,3,2-dioxaborolan-2-yl)phenyl]-2-azaspiro[4.5]dec-7-ene-2-carboxylate. To a solution of tert-butyl 8-(4-chloro-2-fluoro-phenyl)-2-azaspiro[4.5]dec-7-ene-2-carboxylate (230 mg, 629 μmol, 1.0 equiv) and 4,4,5,5-tetramethyl-2-(4,4,5,5-tetramethyl-1,3,2-dioxaborolan-2-yl)-1,3,2-dioxaborolane (239 mg, 943 μmol, 1.5 equiv) in dioxane (5 mL) was added $Pd_2(dba)_3$ (17.3 mg, 18.9 μmol, 0.03 equiv), XPhos (36.0 mg, 75.4 μmol, 0.12 equiv), and KOAc (185 mg, 1.89 mmol, 3.0 equiv) under $N_2$. The reaction was stirred at 110° C. for 12 hours. The reaction mixture was diluted with water (50 mL) and extracted with ethyl acetate (30 mL×3). The organic layers were combined, dried over $Na_2SO_4$, filtered, and concentrated to afford crude product. Compound tert-butyl 8-[2-fluoro-4-(4,4,5,5-tetramethyl-1,3,2-dioxaborolan-2-yl)phenyl]-2-azaspiro[4.5]dec-7-ene-2-carboxylate (280 mg, 612 μmol, 97.38% yield) was obtained as a colorless oil.

Step 3: Preparation of tert-butyl 8-[2-fluoro-4-(4,4,5,5-tetramethyl-1,3,2-dioxaborolan-2-yl)phenyl]-2-azaspiro[4.5]decane-2-carboxylate. To a solution of tert-butyl 8-[2-fluoro-4-(4,4,5,5-tetramethyl-1,3,2-dioxaborolan-2-yl)phenyl]-2-azaspiro[4.5]dec-7-ene-2-carboxylate (300 mg, 656 μmol, 1.0 equiv) in THF (10 mL) was added Pd/C (69.8 mg, 10% purity, wet) under $N_2$. The suspension was purged with $H_2$ and then stirred under $H_2$ at 25° C. (15 psi) for 12 hours. The reaction mixture was filtered and concentrated to afford crude product. The residue was purified by prep-TLC (petroleum ether:ethyl acetate=2:1). Compound tert-butyl 8-[2-fluoro-4-(4,4,5,5-tetramethyl-1,3,2-dioxaborolan-2-yl)phenyl]-2-azaspiro[4.5]decane-2-carboxylate (180 mg, 392 μmol, 60% yield) was obtained as a colorless oil.

Step 4: Preparation of tert-butyl 8-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate. To a solution of tert-butyl 8-[2-fluoro-4-(4,4,5,5-tetramethyl-1,3,2-dioxaborolan-2-yl)phenyl]-2-azaspiro[4.5]decane-2-carboxylate (170 mg, 370 μmol, 1.0 equiv) and (9S)-7-chloro-4,5,9,13-tetramethyl-3-thia-1,8,11,12-tetrazatricyclo[8.3.0.$0^{2,6}$]trideca-2 (6),4,7,10,12-pentaene (125 mg, 444 μmol, 1.2 equiv) in THF (2 mL) and $H_2O$ (0.4 mL) was added Pd(dppf)$Cl_2$ (27.1 mg, 37.0 μmol, 0.1 equiv) and $K_2CO_3$ (153 mg, 1.11 mmol, 3.0 equiv) under $N_2$. The reaction mixture was stirred at 50° C. for 12 hours. The reaction mixture was filtered and concentrated to afford crude product. The residue was purified by prep-HPLC (column: Phenomenex luna C18 150 mm×25 mm×10 μm; mobile phase: [water (FA)-ACN]; gradient: 75%-95% B over 10 min). Compound tert-butyl 8-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (180 mg, 312 μmol, 84% yield) was obtained as a colorless oil.

Step 5: Preparation of tert-butyl 8-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate. The mixture was purified by prep-SFC (column: DAICEL CHIRALPAK AD (250 mm×30 mm, 10 μm); mobile phase: [$CO_2$-ACN/i-PrOH (0.1% $NH_3 \cdot H_2O$)]; B %: 55%, isocratic elution mode) to afford a first stereoisomer of tert-butyl 8-[2-fluoro-4-[(9S)-

4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (30 mg, 51.93 μmol, 16.67% yield) and a second stereoisomer of tert-butyl 8-[2-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (26 mg, 45.00 μmol, 14.44% yield) as a colorless oil. The two stereoisomers differ by the stereochemistry at the spiro-center adjacent to the pyrrolidine.

Step 6: Preparation of (9S)-7-[4-(2-azaspiro[4.5]decan-8-yl)-3-fluoro-phenyl]-pentaene. To a solution of tert-butyl 8-[2-fluoro-4-[(9S)-4,9,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (30.0 mg, 53.2 μmol, 1.0 equiv) in DCM (2 mL) was added TFA (1.0 mL). The reaction was stirred at 25° C. for 0.5 hour. The reaction mixture was concentrated and basified with saturated $NaHCO_3$ at 0° C. The mixture was extracted with DCM/MeOH (10:1, 20 mL×2), dried over $Na_2SO_4$, filtered, and concentrated to afford crude product. Compound (9S)-7-[4-(2-azaspiro[4.5]decan-8-yl)-3-fluoro-phenyl]-4,5,9,13-tetramethyl-3-thia-1,8,11,12-tetrazatricyclo[8.3.0.0$^{2,6}$]trideca-2 (6),4,7,10,12-pentaene (25.4 mg, 53.2 μmol, 100.00% yield) was obtained as a yellow oil and used directly in the next step without purification.

Step 7: Preparation of N-[4-(4-cyano-3-methoxy-phenoxy)cyclohexyl]-6-[8-[2-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-56). To a solution of (9S)-7-[4-(2-azaspiro[4.5]decan-8-yl)-3-fluoro-phenyl]-4,5,9,13-tetramethyl-3-thia-1,8,11,12-tetrazatricyclo[8.3.0.0$^{2,6}$]trideca-2 (6),4,7,10,12-pentaene (25.4 mg, 53.2 μmol, 1.0 equiv) and 6-chloro-N-[4-(4-cyano-3-methoxy-phenoxy)cyclohexyl]pyridazine-3-carboxamide (20.6 mg, 53.2 μmol, 1.0 equiv) in NMP (0.5 mL) was added DIEA (34.4 mg, 266 μmol, 46.4 μL, 5.0 equiv). The reaction mixture was stirred at 65° C. for 12 hours. The residue was purified by prep-HPLC (column: Waters Xbridge 150 mm×25 mm×5 μm; mobile phase: [water ($NH_4HCO_3$)-ACN]; gradient: 55%-75% B over 53 min). Compound N-[4-(4-cyano-3-methoxy-phenoxy)cyclohexyl]-6-[8-[2-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (18.8 mg, 22.7 μmol, 43% yield) was obtained as a white solid. $^1$HNMR (400 MHz, $CD_3OD$) δ 7.92 (d, J=9.5 Hz, 1H), 7.50 (d, J=8.9 Hz, 1H), 7.40 (t, J=7.6 Hz, 1H), 7.22 (d, J=9.5 Hz, 2H), 7.04 (br d, J=9.5 Hz, 1H), 6.65 (s, 1H), 6.67 (d, J=8.2 Hz, 2H), 5.17 (s, 1H), 4.58 (s, 7H), 4.28 (d, J=6.7 Hz, 1H), 3.92 (s, 3H), 3.61 (br s, 3H), 2.70 (s, 3H), 2.44 (s, 3H), 2.22 (br s, 2H), 2.10 (br s, 2H), 2.04-1.93 (m, 5H), 1.85 (br d, J=9.5 Hz, 4H), 1.76-1.57 (m, 12H), 1.37 (d, J=6.6 Hz, 1H). LC-MS: MS ($ES^+$): RT=2.278 min, m/z=828.6 $[M+H]^+$; LCMS method: 25.

Example 23—Synthesis of N-[4-(4-cyano-3-methoxy-phenoxy)cyclohexyl]-6-[8-[3-fluoro-4-[(9S)-4,5,9,13-tetramethyl-3-thia-1,8,11,12-tetraza-tricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-58)

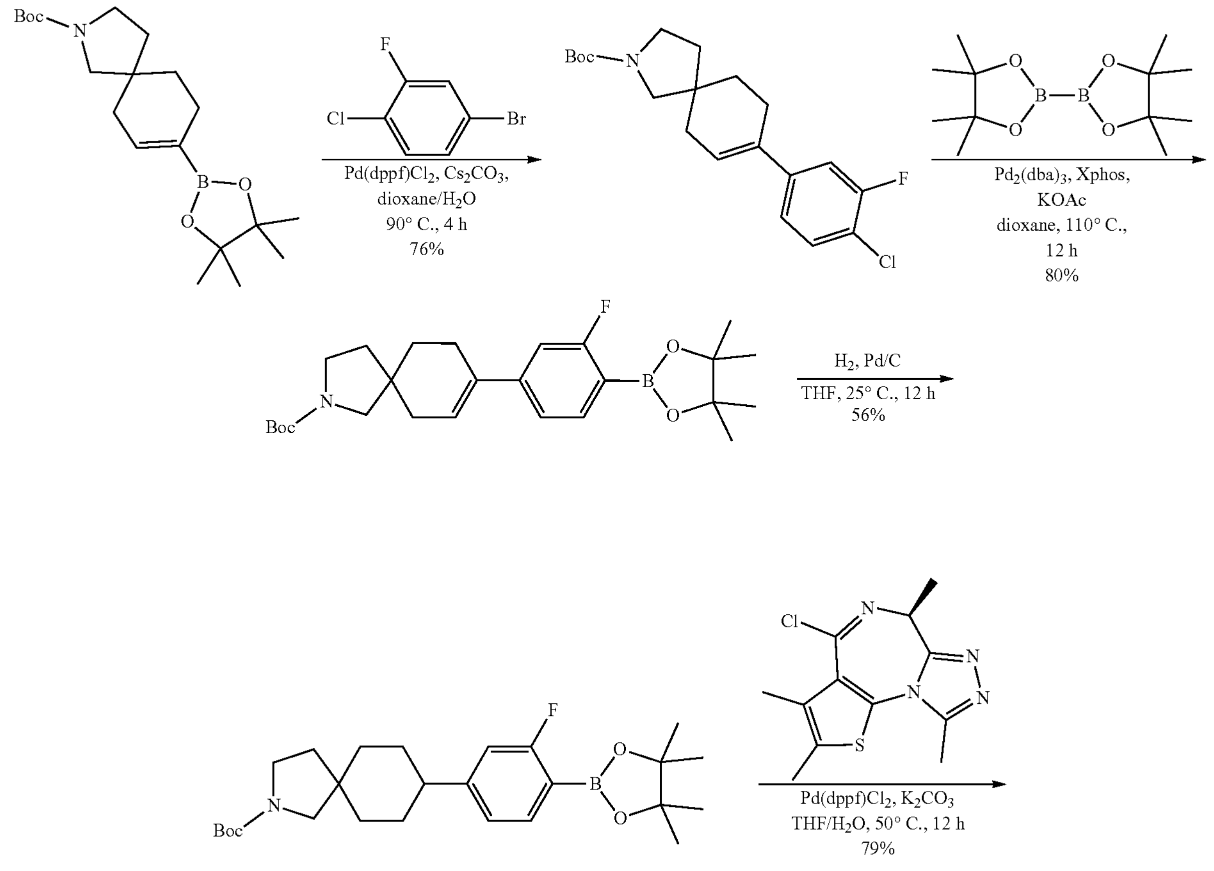

-continued

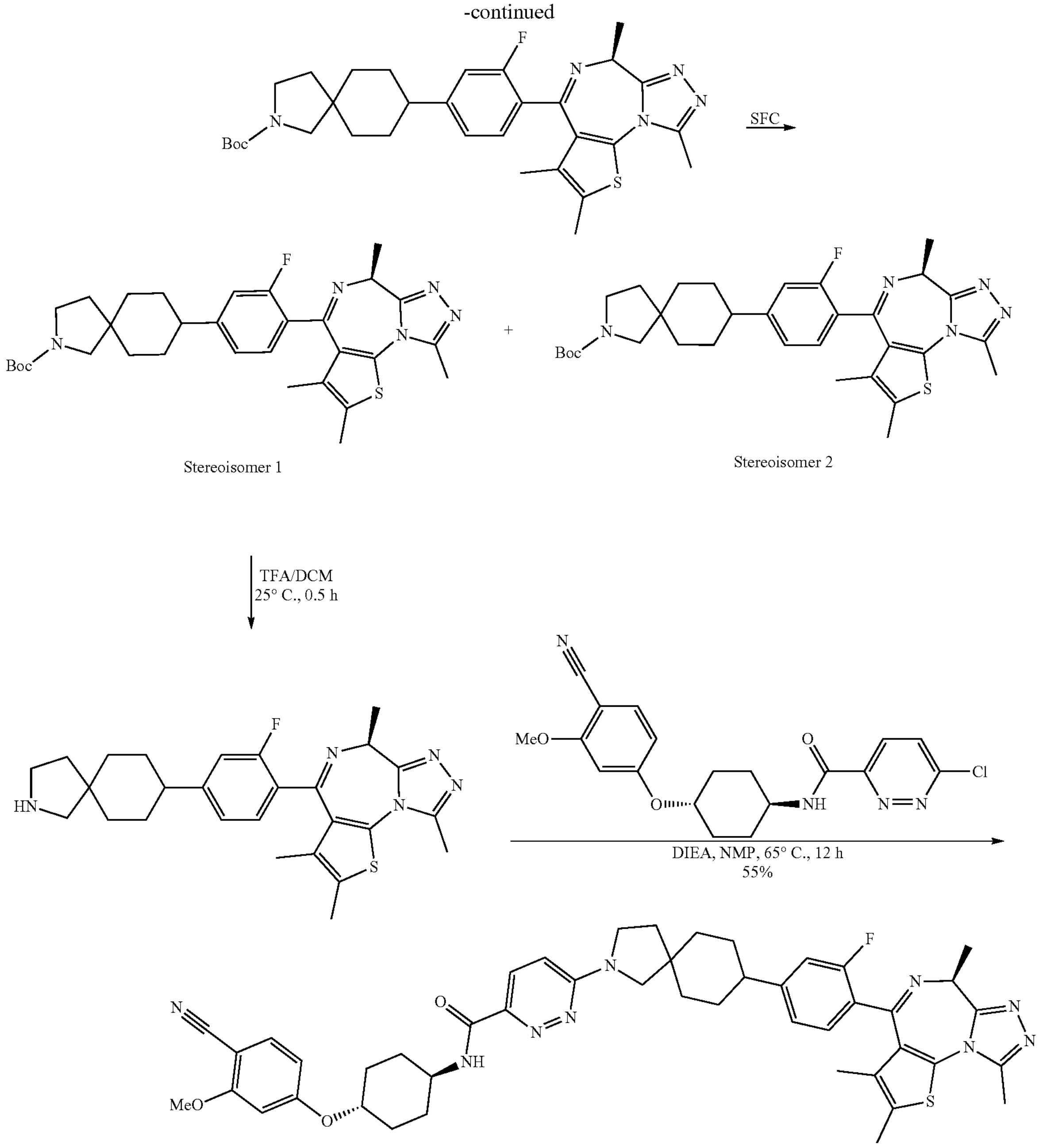

Stereoisomer 1

Stereoisomer 2

I-58

Step 1: Preparation of tert-butyl 8-(4-chloro-3-fluoro-phenyl)-2-azaspiro[4.5]dec-7-ene-2-carboxylate. To a solution of tert-butyl 8-(4,4,5,5-tetramethyl-1,3,2-dioxaborolan-2-yl)-2-azaspiro[4.5]dec-7-ene-2-carboxylate (400 mg, 1.10 mmol, 1.1 equiv) and 4-bromo-1-chloro-2-fluoro-benzene (210 mg, 1.00 mmol, 1.0 equiv) in dioxane (10 mL) and water (2 mL) was added Pd(dppf)$Cl_2$ (146 mg, 200 μmol, 0.2 equiv) and $Cs_2CO_3$ (978 mg, 3.00 mmol, 3.0 equiv). The mixture was stirred at 90° C. for 4 hours. The reaction mixture was diluted with water (50 mL) and extracted with EtOAc (20 mL×3). The combined organic layers were washed with brine (15 mL×3), dried over $Na_2SO_4$, filtered, and concentrated under reduced pressure to give a residue. The residue was purified by column chromatography ($SiO_2$, petroleum ether: ethyl acetate=50:1 to 5:1) to give tert-butyl 8-(4-chloro-3-fluoro-phenyl)-2-azaspiro[4.5]dec-7-ene-2-carboxylate (280 mg, 765 μmol, 76% yield) as a white solid.

Step 2: Preparation of tert-butyl 8-[3-fluoro-4-(4,4,5,5-tetramethyl-1,3,2-dioxaborolan-2-yl)phenyl]-2-azaspiro[4.5]dec-7-ene-2-carboxylate. To a solution of tert-butyl 8-(4-chloro-3-fluoro-phenyl)-2-azaspiro[4.5]dec-7-ene-2-carboxylate (250 mg, 683 μmol, 1.0 equiv) and 4,4,5,5-tetramethyl-2-(4,4,5,5-tetramethyl-1,3,2-dioxaborolan-2-yl)-1,3,2-dioxaborolane (260 mg, 1.02 mmol, 1.5 equiv) in dioxane (1 mL) was added $Pd_2(dba)_3$ (63 mg, 68 μmol, 0.1 equiv), KOAc (201 mg, 2.05 mmol, 3.0 equiv), and Xphos (65 mg, 137 μmol, 0.2 equiv). The mixture was stirred at 110° C. for 12 hours. The reaction mixture was diluted with water (20 mL) and extracted with EtOAc (15 mL×3). The combined organic layers were washed with brine (15 mL×3), dried over $Na_2SO_4$, filtered, and concentrated under reduced pressure to give a residue. The residue was purified by column chromatography ($SiO_2$, petroleum ether:ethyl acetate=20:1 to 0:1) to afford tert-butyl 8-[3-fluoro-4-(4,4,5,5-tetramethyl-1,3,2-dioxaborolan-2-yl)phenyl]-2-azaspiro[4.5]dec-7-ene-2-carboxylate (250 mg, 546 μmol, 80% yield) as a white solid.

Step 3: Preparation of tert-butyl 8-[3-fluoro-4-(4,4,5,5-tetramethyl-1,3,2-dioxaborolan-2-yl)phenyl]-2-azaspiro[4.5]decane-2-carboxylate. To a solution of tert-butyl 8-[3-fluoro-4-(4,4,5,5-tetramethyl-1,3,2-dioxaborolan-2-yl)phenyl]-2-azaspiro[4.5]dec-7-ene-2-carboxylate (250 mg, 546 μmol, 1.0 equiv) in THF (5 mL) was added Pd/C (60 mg, 55 μmol, 10% purity, 0.1 equiv) under $N_2$ atmosphere. The suspension was degassed and purged with $H_2$ 3 times. The mixture was stirred under $H_2$ (15 psi) at 25° C. for 12 hours. The reaction mixture was filtered, and the filtrate was concentrated. The residue was purified by prep-TLC ($SiO_2$, petroleum ether:ethyl acetate=5:1) to afford tert-butyl 8-[3-fluoro-4-(4,4,5,5-tetramethyl-1,3,2-dioxaborolan-2-yl)phenyl]-2-azaspiro[4.5]decane-2-carboxylate (140 mg, 305 μmol, 56% yield) as a colorless oil.

Step 4: Preparation of tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate. To a solution of tert-butyl 8-[3-fluoro-4-(4,4,5,5-tetramethyl-1,3,2-dioxaborolan-2-yl)phenyl]-2-azaspiro[4.5]decane-2-carboxylate (131 mg, 284 μmol, 1.0 equiv) and (9S)-7-chloro-4,5,9,13-tetramethyl-3-thia-1,8,11,12-tetrazatricyclo[8.3.0.0$^{2,6}$]trideca-2 (6),4,7,10,12-pentaene (96 mg, 341 μmol, 1.2 equiv) in THF (1 mL) and $H_2O$ (0.2 mL) was added $K_2CO_3$ (118 mg, 853 μmol, 3.0 equiv) and Pd(dppf)$Cl_2$ (21 mg, 28 μmol, 0.1 equiv). The mixture was stirred at 50° C. for 12 hours. The reaction mixture was filtered and concentrated to afford crude product. The residue was purified by prep-HPLC (column: Phenomenex luna C18 150 mm×25 mm×10 μm; mobile phase: [water (FA)-ACN]; gradient: 62%-92% B over 10 min) to afford tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (130 mg, 225 μmol, 79% yield) as a colorless oil.

Step 5: Preparation of tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate. Tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate was purified by prep-SFC (column: DAICEL CHIRALPAK AD (250 mm×30 mm, 10 μm); mobile phase: [$CO_2$-ACN/i-PrOH (0.1% $NH_3 \cdot H_2O$)]; B %: 60%, isocratic elution mode) to afford a first stereoisomer of tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (60 mg, 104 μmol, 46% yield) and a second stereoisomer of tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (40 mg, 69 μmol, 31% yield) as a white solid. The two stereoisomers differ by the stereochemistry at the spiro-center adjacent to the pyrrolidine.

Step 6: Preparation of (9S)-7-[4-(2-azaspiro[4.5]decan-8-yl)-2-fluoro-phenyl]-pentaene. To a solution of tert-butyl 8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (60 mg, 104 μmol, 1.0 equiv) in DCM (1 mL) was added TFA (0.5 mL). The mixture was stirred at 25° C. for 0.5 hour. The reaction mixture was concentrated and basified with saturated $NaHCO_3$ at 0° C. The mixture were extracted with DCM/MeOH (10:1, 20 mL×2), dried over $Na_2SO_4$, filtered, and concentrated to give compound (9S)-7-[4-(2-azaspiro[4.5]decan-8-yl)-2-fluoro-phenyl]-4,5,9,13-tetramethyl-3-thia-1,8,11,12-tetrazatricyclo[8.3.0.0$^{2,6}$]trideca-2 (6),4,7,10,12-pentaene (49 mg, 104 μmol, 100% yield) as a colorless oil.

Step 7: Preparation of N-[4-(4-cyano-3-methoxy-phenoxy)cyclohexyl]-6-[8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-58). To a solution of (9S)-7-[4-(2-azaspiro[4.5]decan-8-yl)-2-fluoro-phenyl]-4,5,9,13-tetramethyl-3-thia-1,8,11,12-tetrazatricyclo[8.3.0.0$^{2,6}$]trideca-2 (6),4,7,10,12-pentaene (50 mg, 104 μmol, 1.0 equiv) and 6-chloro-N-[4-(4-cyano-3-methoxy-phenoxy)cyclohexyl]pyridazine-3-carboxamide (40 mg, 104 μmol, 1.0 equiv) in NMP (1 mL) was added DIEA (40 mg, 312 μmol, 54 μL, 3.0 equiv). The mixture was stirred at 65° C. for 12 hours. The residue was purified by prep-HPLC (column: Waters xbridge 150 mm×25 mm×10 μm; mobile phase: [water ($NH_4HCO_3$)-ACN]; gradient: 60%-80% B over 8 min) to afford N-[4-(4-cyano-3-methoxy-phenoxy)cyclohexyl]-6-[8-[3-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (49 mg, 57 μmol, 55% yield, 96% purity) d as a white solid. $^1$H NMR (400 MHz, $CD_3OD$) δ 7.94 (d, J=9.6 Hz, 1H), 7.60-7.40 (m, 2H), 7.22 (d, J=8.0 Hz, 1H), 7.14-7.03 (m, 2H), 6.73-6.64 (m, 2H), 4.55-4.48 (m, 1H), 4.34 (d, J=6.8 Hz, 1H), 4.06-3.96 (m, 1H), 3.94 (s, 3H), 3.65 (s, 2H), 2.72 (s, 4H), 2.43 (s, 3H), 2.27-2.08 (m, 4H), 2.02 (d, J=6.8 Hz, 3H), 1.98 (t, J=7.2 Hz, 2H), 1.94-1.83 (m, 4H), 1.74-1.67 (m, 6H), 1.67-1.60 (m, 5H). LC-MS: MS ($ES^+$): RT=2.216 min, m/z=828.5 $[M+H]^+$; LCMS method: 25.

Example 24—Synthesis of N-[4-(4-cyano-3-methoxy-phenoxy)cyclohexyl]-6-[8-[3-methyl-4-[(9S)-4,5,9,13-tetramethyl-3-thia-1,8,11,12-tetraza-tricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-62)
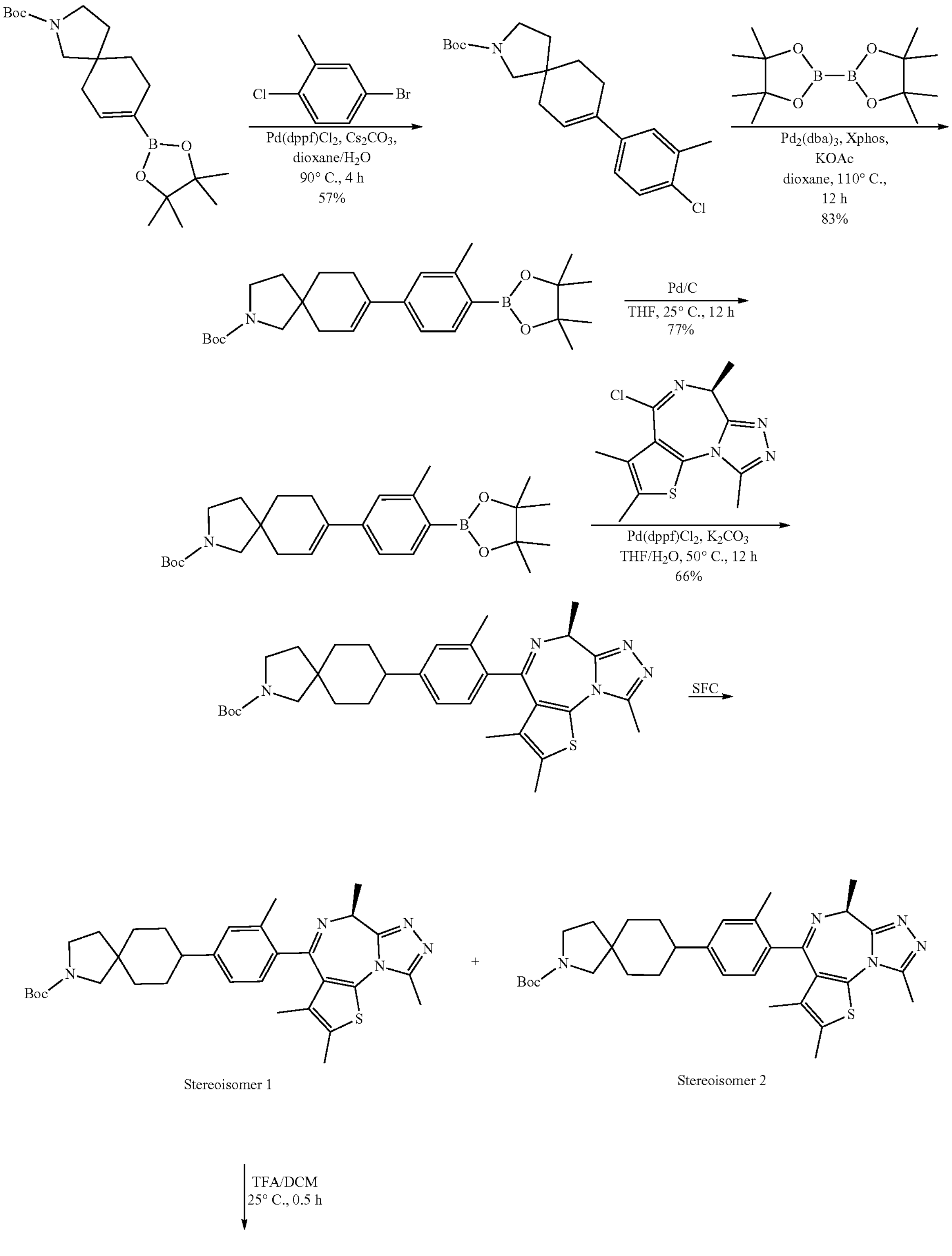

-continued

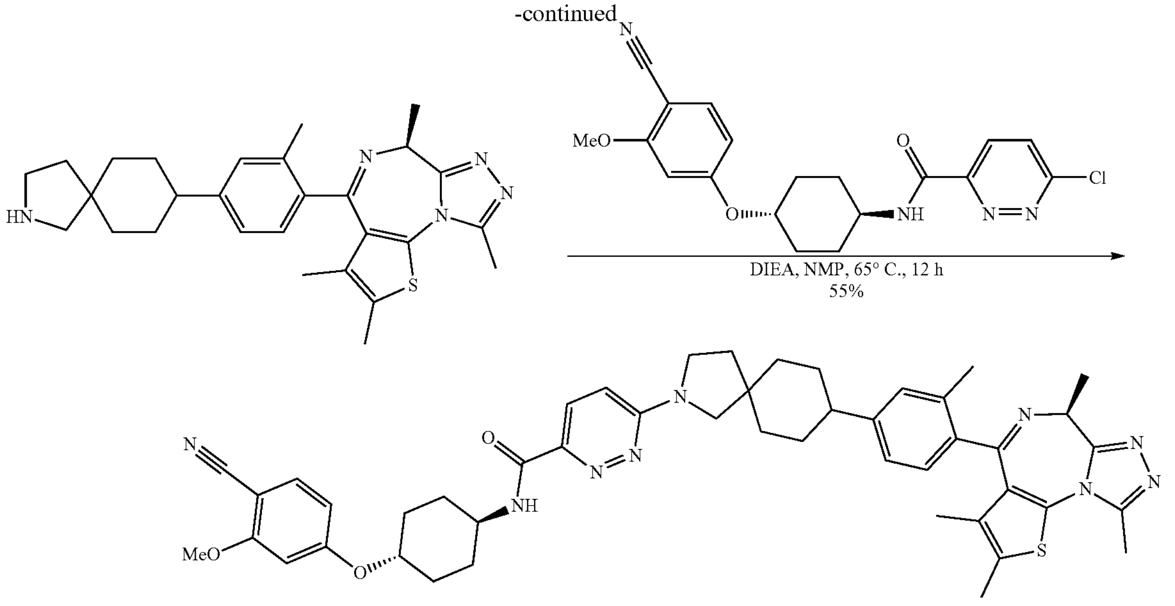

I-62

Step 1: Preparation of tert-butyl 8-(4-chloro-3-methyl-phenyl)-2-azaspiro[4.5]dec-7-ene-2-carboxylate. To a solution of tert-butyl 8-(4,4,5,5-tetramethyl-1,3,2-dioxaborolan-2-yl)-2-azaspiro[4.5]dec-7-ene-2-carboxylate (500 mg, 1.38 mmol, 1.1 equiv) and 4-bromo-1-chloro-2-methyl-benzene (257 mg, 1.25 mmol, 1.0 equiv) in dioxane (10 mL) and water (2 mL) was added Pd(dppf)$Cl_2$ (183 mg, 250 μmol, 0.2 equiv) and $Cs_2CO_3$ (1.22 g, 3.75 mmol, 3.0 equiv). The mixture was stirred at 90° C. for 4 hours. The reaction mixture was diluted with water (20 mL) and extracted with EtOAc (20 mL×3). The combined organic layers were washed with brine (15 mL×3), dried over $Na_2SO_4$, filtered, and concentrated under reduced pressure to afford crude product. The residue was purified by column chromatography ($SiO_2$, petroleum ether:ethyl acetate=50:1 to 5:1) to give tert-butyl 8-(4-chloro-3-methyl-phenyl)-2-azaspiro[4.5]dec-7-ene-2-carboxylate (260 mg, 718 μmol, 57% yield) as a colorless oil.

Step 2: Preparation of tert-butyl 8-[3-methyl-4-(4,4,5,5-tetramethyl-1,3,2-dioxaborolan-2-yl)phenyl]-2-azaspiro[4.5]dec-7-ene-2-carboxylate. To a solution of tert-butyl 8-(4-chloro-3-methyl-phenyl)-2-azaspiro[4.5]dec-7-ene-2-carboxylate (250 mg, 691 μmol, 1.0 equiv) and 4,4,5,5-tetramethyl-2-(4,4,5,5-tetramethyl-1,3,2-dioxaborolan-2-yl)-1,3,2-dioxaborolane (263 mg, 1.04 mmol, 1.5 equiv) in dioxane (1 mL) was added $Pd_2(dba)_3$ (63 mg, 69 μmol, 0.1 equiv), KOAc (203 mg, 2.07 mmol, 3.0 equiv), and XPhos (66 mg, 138 μmol, 0.2 equiv). The mixture was stirred at 110° C. for 12 hours. The reaction mixture was diluted with water (20 mL) and extracted with EtOAc (15 mL×3). The combined organic layers were washed with brine (15 mL×3), dried over $Na_2SO_4$, filtered, and concentrated to afford crude product. The residue was purified by column chromatography ($SiO_2$, petroleum ether: ethyl acetate=20:1 to 0:1) to afford tert-butyl 8-[3-methyl-4-(4,4,5,5-tetramethyl-1,3,2-dioxaborolan-2-yl)phenyl]-2-azaspiro[4.5]dec-7-ene-2-carboxylate (260 mg, 573 μmol, 83% yield) as a white solid.

Step 3: Preparation of tert-butyl 8-[3-methyl-4-(4,4,5,5-tetramethyl-1,3,2-dioxaborolan-2-yl)phenyl]-2-azaspiro[4.5]decane-2-carboxylate. To a solution of tert-butyl 8-[3-methyl-4-(4,4,5,5-tetramethyl-1,3,2-dioxaborolan-2-yl) phenyl]-2-azaspiro[4.5]dec-7-ene-2-carboxylate (260 mg, 573 μmol, 1.0 equiv) in THF (5 mL) was added Pd/C (61 mg, 10% purity) under $N_2$ atmosphere. The suspension was degassed and purged with $H_2$ 3 times. The mixture was stirred under $H_2$ (15 psi) at 25° C. for 1 hour. The reaction mixture was filtered, and the filtrate was concentrated. The residue was purified by prep-TLC ($SiO_2$, petroleum ether: ethyl acetate=5:1) to give tert-butyl 8-[3-methyl-4-(4,4,5,5-tetramethyl-1,3,2-dioxaborolan-2-yl)phenyl]-2-azaspiro[4.5]decane-2-carboxylate (200 mg, 439 μmol, 77% yield) as a colorless oil.

Step 4: Preparation of tert-butyl 8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate. To a solution of tert-butyl 8-[3-methyl-4-(4,4,5,5-tetramethyl-1,3,2-dioxaborolan-2-yl) phenyl]-2-azaspiro[4.5]decane-2-carboxylate (190 mg, 419 μmol, 1.0 equiv) and (9S)-7-chloro-4,5,9,13-tetramethyl-3-thia-1,8,11,12-tetrazatricyclo[8.3.0.0$^{2,6}$]trideca-2 (6), 4,7,10,12-pentaene (141 mg, 503 μmol, 1.2 equiv) in THF (1 mL) and $H_2O$ (0.2 mL) was added $K_2CO_3$ (174 mg, 1.26 mmol, 3.0 equiv) and Pd(dppf)$Cl_2$ (31 mg, 42 μmol, 0.1 equiv). The mixture was stirred at 50° C. for 12 hours. The reaction mixture was diluted with water (20 mL) and extracted with EtOAc (20 mL×3). The combined organic layers were washed with brine (20 mL×3), dried over $Na_2SO_4$, filtered, and concentrated under reduced pressure to give a residue. The residue was purified by prep-HPLC (column: Phenomenex luna C18 150 mm×25 mm×10 μm; mobile phase: [water (FA)-ACN]; gradient: 62%-92% B over 10 min) to give tert-butyl 8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (160 mg, 279 μmol, 66% yield) as a colorless oil.

Step 5: Preparation of tert-butyl 8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro

[4.5]decane-2-carboxylate. Tert-butyl 8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate was purified by prep-SFC (column: DAICEL CHIRALPAK AD (250 mm×30 mm, 10 μm); mobile phase: [$CO_2$-ACN/i-PrOH (0.1% $NH_3 \cdot H_2O$)]; B %: 55%, isocratic elution mode) to give a first stereoisomer of tert-butyl 8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (60 mg, 104 μmol, 46% yield) and a second stereoisomer of tert-butyl 8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (40 mg, 69 μmol, 31% yield) as a white solid. The two stereoisomers differ by the stereochemistry at the spiro-center adjacent to the pyrrolidine.

Step 6: Preparation of (9S)-7-[4-(2-azaspiro[4.5]decan-8-yl)-2-methyl-phenyl]-pentaene. To a solution of tert-butyl 8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (60 mg, 104.57 μmol, 1.0 equiv) in DCM (1 mL) was added TFA (0.5 mL). The mixture was stirred at 25° C. for 0.5 hour. The reaction mixture was concentrated and basified with saturated $NaHCO_3$ at 0° C. The mixture were extracted with DCM/MeOH (10:1, 20 mL×2), dried over $Na_2SO_4$, filtered, and concentrated to give (9S)-7-[4-(2-azaspiro[4.5]decan-8-yl)-2-methyl-phenyl]-4,5,9,13-tetramethyl-3-thia-1,8,11,12-tetrazatricyclo[8.3.0.0$^{2,6}$]trideca-2 (6), 4,7,10,12-pentaene (49 mg, 104 μmol, 100% yield) as a colorless oil.

Step 7: Preparation of N-[4-(4-cyano-3-methoxy-phenoxy)cyclohexyl]-6-[8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-62). To a solution of (9S)-7-[4-(2-azaspiro[4.5]decan-8-yl)-2-methyl-phenyl]-4,5,9,13-tetramethyl-3-thia-1,8,11,12-tetrazatricyclo[8.3.0.0$^{2,6}$]trideca-2 (6),4,7,10,12-pentaene (49 mg, 105 μmol, 1.0 equiv) and 6-chloro-N-[4-(4-cyano-3-methoxy-phenoxy)cyclohexyl]pyridazine-3-carboxamide (40 mg, 105 μmol, 1.0 equiv) in NMP (1 mL) was added DIEA (40 mg, 313 μmol, 54 μL, 3.0 equiv). The mixture was stirred at 65° C. for 12 hours. The residue was purified by prep-HPLC (column: Waters xbridge 150 mm×25 mm×10 μm; mobile phase: [water ($NH_4HCO_3$)-ACN]; gradient: 64%-84% B over 8 min) to give N-[4-(4-cyano-3-methoxy-phenoxy)cyclohexyl]-6-[8-[3-methyl-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (50 mg, 58 μmol, 55% yield, 96.08% purity) as a white solid. 1H NMR (400 MHz, $CD_3OD$) δ 8.49 (d, J=8.0 Hz, 1H), 8.02-7.89 (m, 1H), 7.53 (d, J=9.2 Hz, 1H), 7.21-7.02 (m, 4H), 6.77-6.63 (m, 2H), 4.44-4.30 (m, 1H), 4.05-3.97 (m, 1H), 3.94 (s, 3H), 3.79-3.65 (m, 2H), 3.36 (s, 2H), 2.73 (s, 3H), 2.66-2.58 (m, 1H), 2.41 (s, 3H), 2.28-2.20 (m, 2H), 2.12 (s, 4H), 2.01 (d, J=6.8 Hz, 3H), 1.98 (t, J=7.2 Hz, 2H), 1.86 (d, J=9.4 Hz, 4H), 1.73-1.61 (m, 8H), 1.56 (s, 3H). LC-MS: MS ($ES^+$): RT=2.058 min, m/z=824.6 [M+H]; LCMS method: 25.

Example 25—Synthesis of 6-[8-[2-chloro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]-N-[4-(4-cyano-3-methoxy-phenoxy)cyclohexyl]pyridazine-3-carboxamide (I-73)

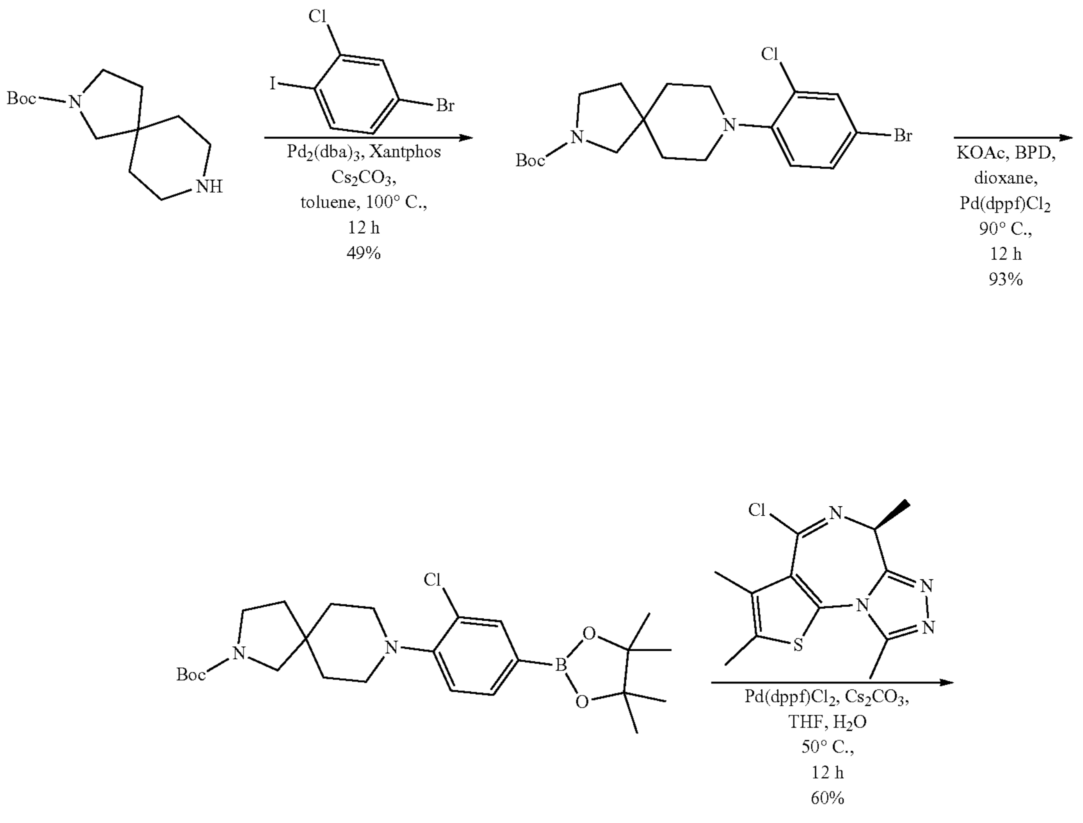

-continued

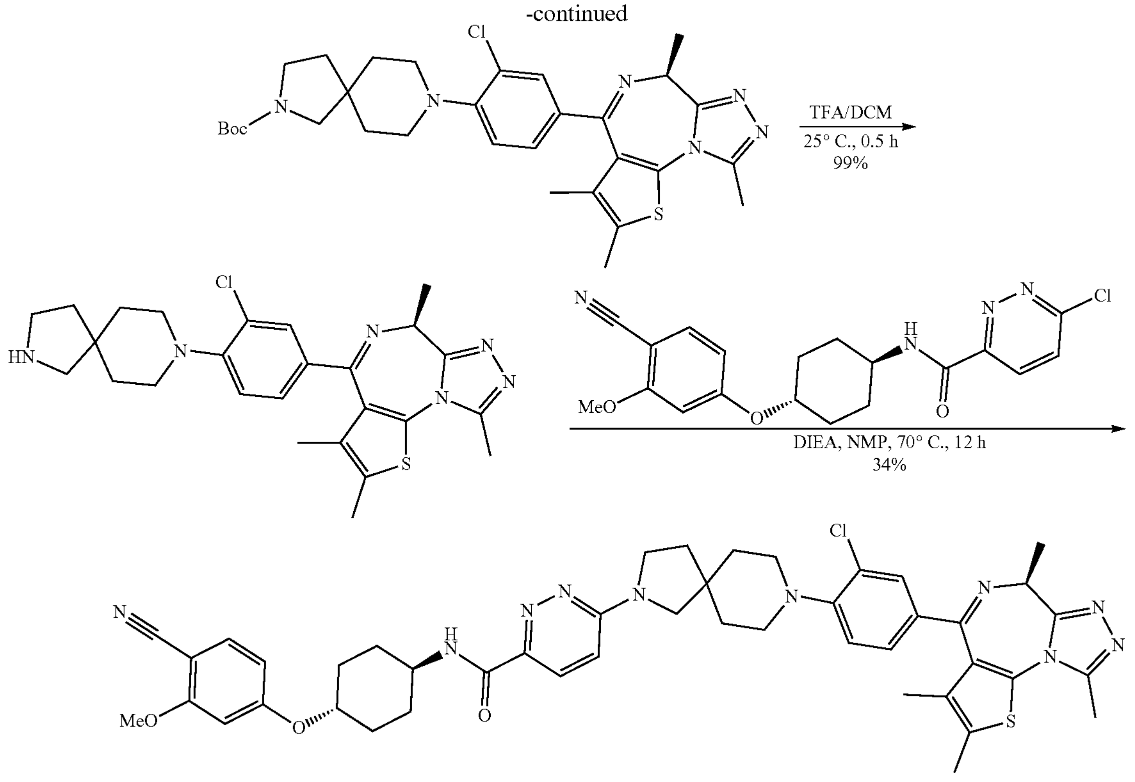

I-73

Step 1: Preparation of tert-butyl 8-(4-bromo-2-chloro-phenyl)-2,8-diazaspiro[4.5]decane-2-carboxylate. To a solution of tert-butyl 2,8-diazaspiro[4.5]decane-2-carboxylate (1 g, 4.16 mmol, 1.0 equiv) in toluene (20 mL) was added 4-bromo-2-chloro-1-iodo-benzene (1.98 g, 6.24 mmol, 1.5 equiv), $Pd_2(dba)_3$ (190 mg, 208 µmol, 0.05 equiv), Xantphos (240 mg, 416 µmol, 0.1 equiv), and $Cs_2CO_3$ (3.39 g, 10.40 mmol, 2.5 equiv). The mixture was stirred at 100° C. for 12 hours. The reaction mixture was diluted with $H_2O$ (20 mL) and extracted with ethyl acetate (10 mL×3). The combined organic layers were washed with brine (10 mL×2), dried over $Na_2SO_4$, filtered, and concentrated under reduced pressure to give a residue. The residue was purified by prep-TLC ($SiO_2$, ethyl acetate:petroleum ether=1:0) to give tert-butyl 8-(4-bromo-2-chloro-phenyl)-2,8-diazaspiro[4.5]decane-2-carboxylate (880 mg, 49% yield).

Step 2: Preparation of tert-butyl 8-[2-chloro-4-(4,4,5,5-tetramethyl-1,3,2-dioxaborolan-2-yl)phenyl]-2,8-diazaspiro[4.5]decane-2-carboxylate. To a solution of tert-butyl 8-(4-bromo-2-chloro-phenyl)-2,8-diazaspiro[4.5]decane-2-carboxylate (780 mg, 1.81 mmol, 1.0 equiv) in dioxane (28 mL) was added $Pd(dppf)Cl_2$ (265 mg, 363 µmol, 0.2 equiv), BPD (691 mg, 2.72 mmol, 1.5 equiv), and KOAc (534 mg, 5.44 mmol, 3.0 equiv). The mixture was stirred at 90° C. for 12 hours. The mixture was diluted with $H_2O$ (20 mL) and extracted with ethyl acetate (10 mL×3). The combined organic layers were washed with brine (10 mL×2), dried over $Na_2SO_4$, filtered, and concentrated. The residue was purified by prep-TLC ($SiO_2$, ethyl acetate:petroleum ether=1:0) to give tert-butyl 8-[2-chloro-4-(4,4,5,5-tetramethyl-1,3,2-dioxaborolan-2-yl)phenyl]-2,8-diazaspiro[4.5]decane-2-carboxylate (800 mg, 93% yield).

Step 3: Preparation of tert-butyl 8-[2-chloro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate. To a solution of tert-butyl 8-[2-chloro-4-(4,4,5,5-tetramethyl-1,3,2-dioxaborolan-2-yl)phenyl]-2,8-diazaspiro[4.5]decane-2-carboxylate (382 mg, 802 µmol, 1.5 equiv) in THF (9 mL) and $H_2O$ (4.5 mL) was added (9S)-7-chloro-4,5,9,13-tetramethyl-3-thia-1,8,11,12-tetrazatricyclo[8.3.0.0$^{2,6}$]trideca-2 (6),4,7,10,12-pentaene (150 mg, 535 µmol, 1.0 equiv), $Pd(dppf)Cl_2$ (78 mg, 107 µmol, 0.2 equiv), and $Cs_2CO_3$ (522 mg, 1.60 mmol, 3.0 equiv). The mixture was stirred at 50° C. for 12 hours. The reaction mixture was diluted with $H_2O$ (20 mL) and extracted with ethyl acetate (10 mL×3). The combined organic layers were washed with brine (10 mL×2), dried over $Na_2SO_4$, filtered, and concentrated under reduced pressure to give a residue. The residue was purified by prep-TLC ($SiO_2$, ethyl acetate:petroleum ether=1:0) to give tert-butyl 8-[2-chloro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (320 mg, 60 yield).

Step 4: Preparation of (9S)-7-[3-chloro-4-(2,8-diazaspiro[4.5]decan-8-yl)phenyl]-pentaene. To a solution of tert-butyl 8-[2-chloro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (150 mg, 152 µmol, 1.0 equiv) in DCM (3 mL) was added TFA (1.0 mL). The mixture was stirred at 25° C. for 0.5 hour. The residue was diluted with $NaHCO_3$ (20 mL) and extracted with DCM (10 mL×3). The combined organic layers were washed with saturated brine (30 mL), dried over anhydrous sodium sulfate, filtered, and concentrated to give (9S)-7-[3-chloro-4-(2,8-diazaspiro[4.5]decan-8-yl)phenyl]-4,5,9,13-tetramethyl-3-thia-1,8,11,12-tetrazatricyclo[8.3.0.0$^{2,6}$]trideca-2 (6),4,7,10,12-pentaene (124 mg, 99% yield).

Step 5: Preparation of 6-[8-[2-chloro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]-N-[4-(4-cyano-3-methoxy-phenoxy)cyclohexyl]pyridazine-3-carboxamide (I-73). To a solution of (9S)-7-[3-chloro-4-(2,8-diazaspiro[4.5]decan-8-yl)phenyl]-4,5,9,13-tetramethyl-3-thia-1,8,11,12-tetrazatricyclo[8.3.0.0$^{2,6}$]trideca-2 (6),4,7,10,12-pentaene (124 mg, 151 μmol, 1.0 equiv) in NMP (0.4 mL) was added DIEA (58 mg, 450 μmol, 3.0 equiv) and 6-chloro-N-[4-(4-cyano-3-methoxy-phenoxy)cyclohexyl]pyridazine-3-carboxamide (69 mg, 180 μmol, 1.2 equiv). The mixture was stirred at 70° C. for 12 hours. The reaction mixture was washed with $H_2O$ (20 mL), extracted with ethyl acetate (10 mL×3), filtered, and concentrated. The residue was purified by prep-HPLC (column: Phenomenex luna C18 150 mm×25 mm×10 μm; mobile phase: [water (FA)-ACN]; gradient: 58%-88% B over 10 min) to give 6-[8-[2-chloro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]-N-[4-(4-cyano-3-methoxy-phenoxy)cyclohexyl]pyridazine-3-carboxamide (47.04 mg, 34% yield). $^1$H NMR (400 MHz, $CDCl_3$): δ 8.00 (d, J=9.4 Hz, 1H), 7.89 (d, J=8.1 Hz, 1H), 7.56 (d, J=1.6 Hz, 1H), 7.47 (d, J=8.6 Hz, 1H), 7.39-7.31 (m, 1H), 7.00 (d, J=8.4 Hz, 1H), 6.73 (d, J=9.4 Hz, 1H), 6.55-6.49 (m, 1H), 6.47 (d, J=2.0 Hz, 1H), 4.38-4.30 (m, 1H), 4.11-4.00 (m, 1H), 3.90 (s, 3H), 3.78-3.54 (m, 3H), 3.30-2.92 (m, 4H), 2.69 (s, 3H), 2.43 (s, 3H), 2.25-2.13 (m, 4H), 2.11-2.00 (m, 5H), 1.90-1.83 (m, 4H), 1.74-1.62 (m, 7H), 1.53-1.40 (m, 2H). LC-MS: MS (ES$^+$): RT=2.084 min, m/z=845.5 [M+H]$^+$; LCMS Method: 25.

Example 26—Synthesis of N-[4-(4-cyano-3-methoxy-phenoxy)cyclohexyl]-6-[7-[2-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,7-diazaspiro[4.4]nonan-2-yl]pyridazine-3-carboxamide (I-79)

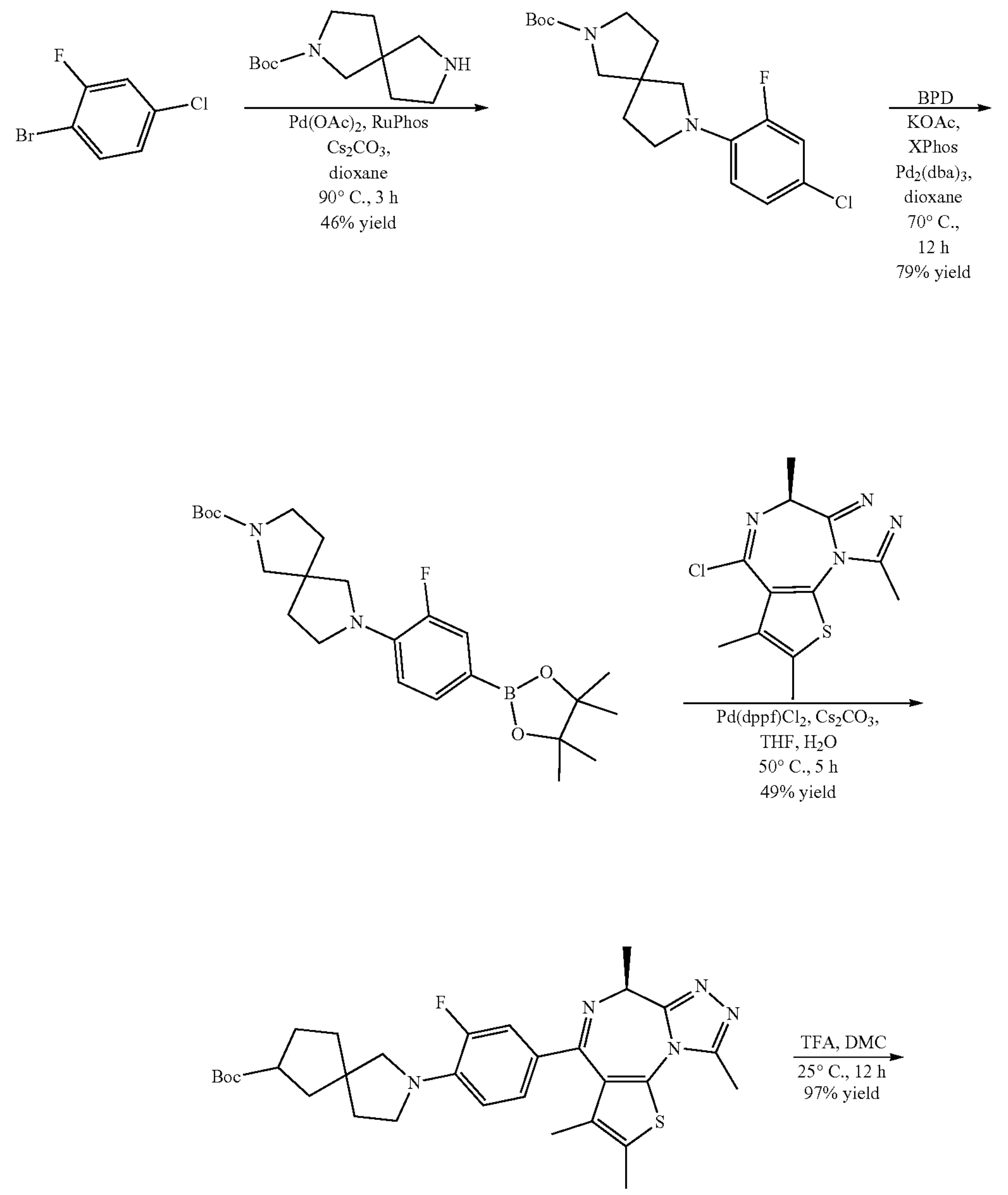

-continued

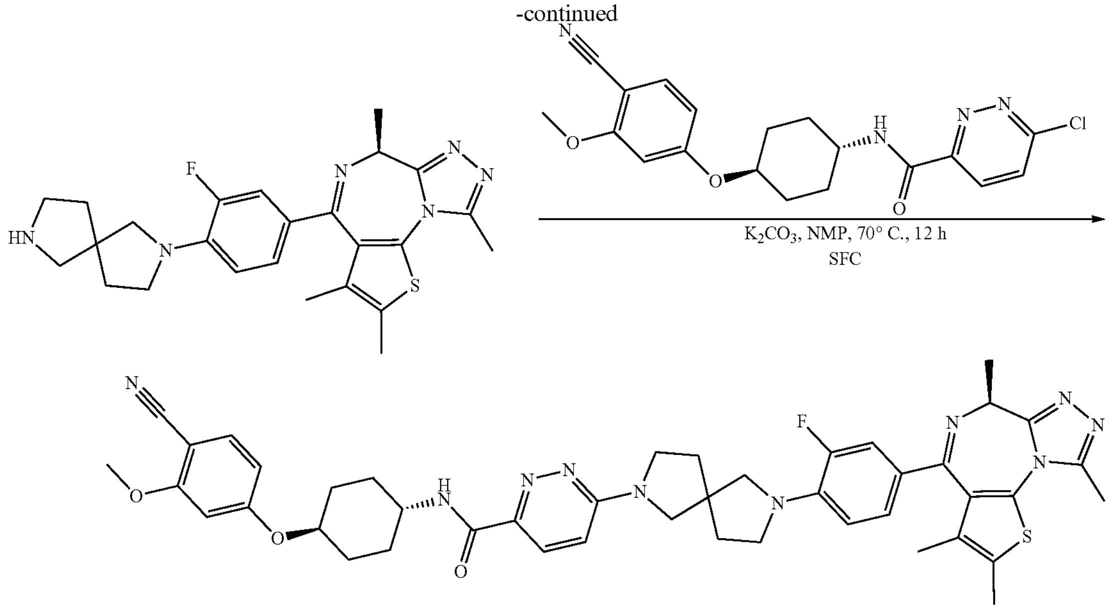

I-79

Step 1: Preparation of tert-butyl 7-(4-chloro-2-fluoro-phenyl)-2,7-diazaspiro[4.4]nonane-2-carboxylate. To a solution of tert-butyl 2,7-diazaspiro[4.4]nonane-2-carboxylate (1.5 g, 6.6 mmol, 1.0 equiv) and 1-bromo-4-chloro-2-fluoro-benzene (2 g, 9.9 mmol, 1.24 mL, 1.5 equiv) in dioxane (15 mL) was added Pd(OAc) 2 (149 mg, 663 μmol, 0.1 equiv), $Cs_2CO_3$ (6.5 g, 19.9 mmol, 3.0 equiv), and RuPhos (619 mg, 1.3 mmol, 0.2 equiv). The mixture was stirred at 90° C. for 3 hours under $N_2$ atmosphere. The mixture was diluted with water (10 mL) and extracted with ethyl acetate (3x20 mL). The combined organic layers were dried over sodium sulfate, filtered, and concentrated. The residue was purified by column chromatography ($SiO_2$, petroleum ether:ethyl acetate=20:1 to 10:1) to give tert-butyl 7-(4-chloro-2-fluoro-phenyl)-2,7-diazaspiro[4.4]nonane-2-carboxylate (1.1 g, 46% yield).

Step 2: Preparation of tert-butyl 7-[2-fluoro-4-(4,4,5,5-tetramethyl-1,3,2-dioxaborolan-2-yl)phenyl]-2,7-diazaspiro[4.4]nonane-2-carboxylate. A mixture of tert-butyl 7-(4-chloro-2-fluoro-phenyl)-2,7-diazaspiro[4.4]nonane-2-carboxylate (500 mg, 1.4 mmol, 1.0 equiv), 4,4,5,5-tetramethyl-2-(4,4,5,5-tetramethyl-1,3,2-dioxaborolan-2-yl)-1,3,2-dioxaborolane (716 mg, 2.8 mmol, 2.0 equiv), KOAc (553 mg, 5.6 mmol, 4.0 equiv), XPhos (100 mg, 211 μmol, 0.15 equiv), and $Pd_2(dba)_3$ (65 mg, 70 μmol, 0.05 equiv) in dioxane (10 mL) was degassed and purged with $N_2$ 3 times. Then, the mixture was stirred at 70° C. for 12 hours under $N_2$ atmosphere. The mixture was diluted with water (10 mL) and extracted with ethyl acetate (3x20 mL). The combined organic layers were dried over sodium sulfate, filtered, and concentrated. The residue was purified by column chromatography ($SiO_2$, petroleum ether:ethyl acetate=50:1 to 10:1) to give tert-butyl 7-[2-fluoro-4-(4,4,5,5-tetramethyl-1,3,2-dioxaborolan-2-yl)phenyl]-2,7-diazaspiro[4.4]nonane-2-carboxylate (500 mg, 79% yield) as a yellow solid.

Step 3: Preparation of tert-butyl 7-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,7-diazaspiro[4.4]nonane-2-carboxylate. To a solution of (9S)-7-chloro-4,5,9,13-tetramethyl-3-thia-1,8,11,12-tetrazatricyclo[8.3.0.$0^{2,6}$]trideca-2 (6),4,7,10,12-pentaene (200 mg, 712 μmol, 1.0 equiv) and tert-butyl 7-[2-fluoro-4-(4,4,5,5-tetramethyl-1,3,2-dioxaborolan-2-yl)phenyl]-2,7-diazaspiro[4.4]nonane-2-carboxylate (540 mg, 1.2 mmol, 1.7 eq) in THF (8 mL) and $H_2O$ (4 mL) was added $Pd(dppf)Cl_2$ (104 mg, 142 μmol, 0.2 equiv) and $Cs_2CO_3$ (696 mg, 2.1 mmol, 3.0 equiv). The mixture was stirred at 50° C. for 12 hours under $N_2$ atmosphere. The mixture was diluted with water (5 mL) and extracted with ethyl acetate (3x10 mL). The combined organic layers were dried over sodium sulfate, filtered, and concentrated. The residue was purified by prep-TLC ($SiO_2$, petroleum ether:ethyl acetate=0:1) to give tert-butyl 7-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,7-diazaspiro[4.4]nonane-2-carboxylate (200 mg, 49% yield).

Step 4: Preparation of (9S)-7-[4-(2,7-diazaspiro[4.4]nonan-2-yl)-3-fluoro-phenyl]-4,5,9,13-tetramethyl-3-thia-1,8,11,12-tetrazatricyclo[8.3.0.$0^{2,6}$]trideca-2 (6),4,7,10,12-pentaene. To a solution of tert-butyl 7-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,7-diazaspiro[4.4]nonane-2-carboxylate (200 mg, 354 μmol, 1.0 equiv) in DCM (3 mL) was added TFA (1 mL). The mixture was stirred at 25° C. for 0.5 hour. The reaction mixture was concentrated under reduced pressure to remove solvent. The residue was diluted with $NaHCO_3$ (10 mL) and extracted with ethyl acetate (20 mLx3). The combined organic layers were washed with brine (30 mL), dried over $Na_2SO_4$, filtered, and concentrated to give (9S)-7-[4-(2,7-diazaspiro[4.4]nonan-2-yl)-3-fluoro-phenyl]-4,5,9,13-tetramethyl-3-thia-1,8,11,12-tetrazatricyclo[8.3.0.$0^{2,6}$]trideca-2 (6),4,7,10,12-pentaene (160 mg, 97% yield).

Step 5: Preparation of N-[4-(4-cyano-3-methoxy-phenoxy)cyclohexyl]-6-[7-[2-fluoro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,7-diazaspiro[4.4]nonan-2-yl]pyridazine-3-carboxamide (I-79). To a solution of (9S)-7-[4-(2,7-diazaspiro[4.4]nonan-2-yl)-3-fluoro-phenyl]-4,5,9,13-tetramethyl-3-thia-1,8,11,12-tetrazatricyclo [8.3.0.0$^{2,6}$]trideca-2 (6),4,7,10,12-pentaene (160 mg, 344 μmol, 1.0 equiv) in NMP (0.5 mL) was added DIEA (89 mg, 688 μmol, 2.0 equiv) and 6-chloro-N-[4-(3-chloro-4-methoxy-phenoxy)cyclohexyl]pyridazine-3-carboxamide (122 mg, 310 μmol, 0.9 equiv). The mixture was stirred at 70° C. for 12 hours and concentrated. The residue was purified by prep-HPLC (column: Phenomenex luna C18 150 mmx25 mmx10 μm; mobile phase: [water (TFA)-ACN]; gradient: 29%-59% B over 10 min) and SFC (column: DAICEL CHIRALPAK AS (250 mmx30 mm, 10 μm); mobile phase: [$CO_2$-MeOH/ACN]; B %: 65%, isocratic elution mode) to give N-[4-(4-cyano-3-methoxy-phenoxy) cyclohexyl]-6-[7-[2-fluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,7-diazaspiro[4.4]nonan-2-yl] pyridazine-3-carboxamide (37 mg, 12% yield). $^1$H NMR (400 MHz, $CDCl_3$) δ 8.04-7.97 (m, 1H), 7.92-7.84 (m, 1H), 7.50-7.43 (m, 1H), 7.25-7.09 (m, 2H), 6.76-6.69 (m, 1H), 6.57-6.44 (m, 3H), 4.39-4.29 (m, 1H), 4.19-4.00 (m, 2H), 3.90 (s, 3H), 3.84-3.56 (m, 6H), 3.55-3.47 (m, 2H), 2.67 (s, 3H), 2.42 (s, 3H), 2.26-2.12 (m, 6H), 2.12-2.00 (m, 5H), 1.80 (s, 3H), 1.76-1.71 (m, 2H), 1.53-1.39 (m, 2H). LC-MS: MS ($ES^+$): RT=1.665 min, m/z=815.5 $[M+H]^+$; LCMS Method: 25.

Example 27—Synthesis of N-((1r,4r)-4-(4-cyano-3-methoxyphenoxy)cyclohexyl)-6-(2-(4-((S)-2,3,6,9-tetramethyl-6H-thieno[3,2-f][1,2,4]triazolo[4,3-a][1,4]diazepin-4-yl)phenyl)-2,9-diazaspiro[5.5]undecan-9-yl) pyridazine-3-carboxamide (I-81)

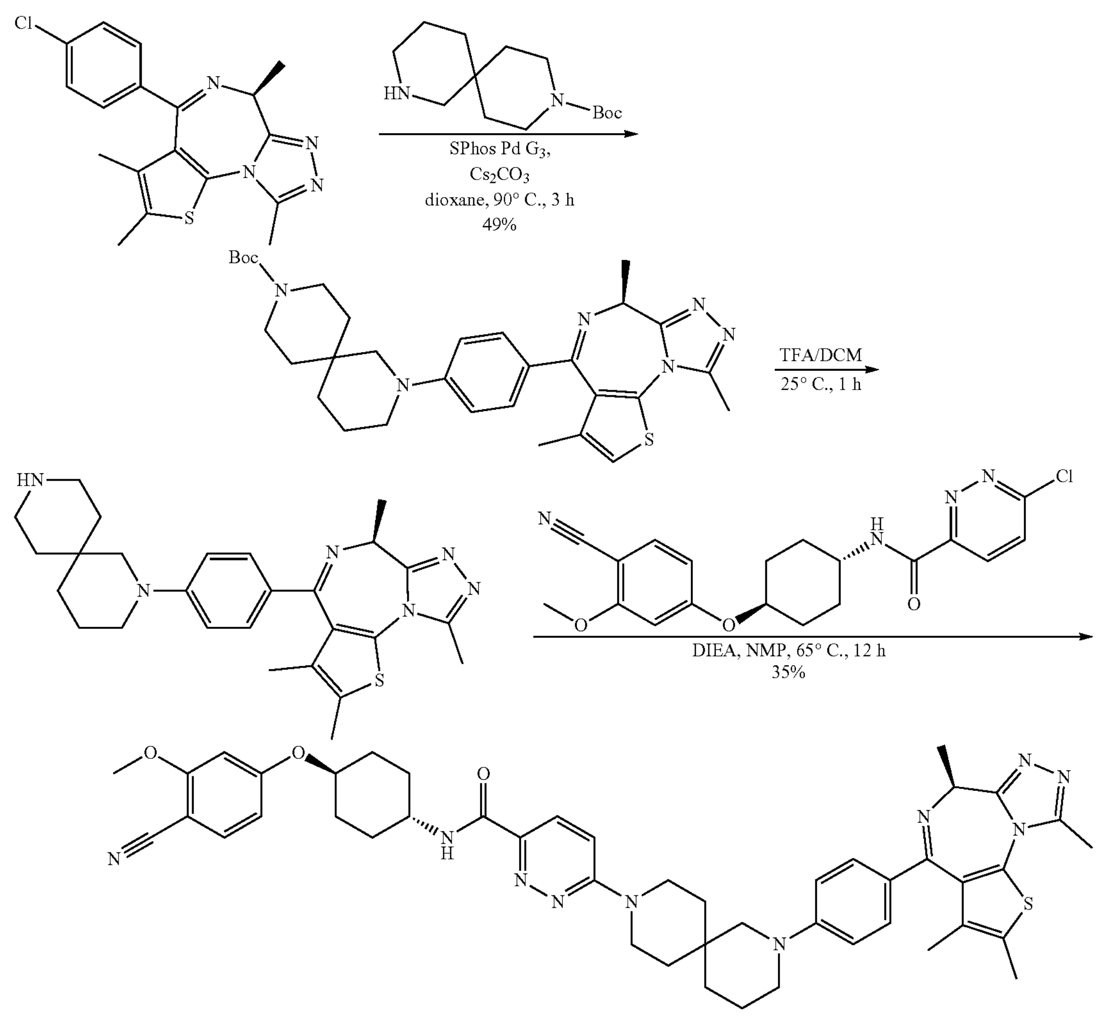

I-81

Step 1: Preparation of tert-butyl(S)-2-(4-(2,3,6,9-tetramethyl-6H-thieno[3,2-f][1,2,4]triazolo[4,3-a][1,4]diazepin-4-yl)phenyl)-2,9-diazaspiro[5.5]undecane-9-carboxylate. To a solution of(S)-4-(4-chlorophenyl)-2,3,6,9-tetramethyl-6H-thieno[3,2-f][1,2,4]triazolo[4,3-a][1,4]diazepine (215 mg, 602 μmol, 1.0 equiv) and tert-butyl 2,9-diazaspiro[5.5]undecane-9-carboxylate (230 mg, 904 μmol, 1.5 equiv) in dioxane (4 mL) was added SPhos Pd G3 (47 mg, 60 μmol, 0.1 equiv) and $Cs_2CO_3$ (393 mg, 1.2 mmol, 2.0 equiv). The mixture was stirred at 90° C. for 3 hours. The reaction mixture was concentrated under reduced pressure to remove solvent. The residue was purified by prep-HPLC (column: Phenomenex luna C18 150 mmx25 mmx10 μm; mobile phase: [water (FA)-ACN]; gradient: 28%-58% B over 10 min) to give compound tert-butyl(S)-2-(4-(2,3,6,9-tetramethyl-6H-thieno[3,2-f][1,2,4]triazolo[4,3-a][1,4]diazepin-4- yl)phenyl)-2,9-diazaspiro[5.5]undecane-9-carboxylate (170 mg, 296 μmol, 49% yield) as a yellow solid.

Step 2: Preparation of(S)-4-(4-(2,9-diazaspiro[5.5]undecan-2-yl)phenyl)-2,3,6,9-tetramethyl-6H-thieno[3,2-f][1,2,4]triazolo[4,3-a][1,4]diazepine. To a solution of tert-butyl (S)-2-(4-(2,3,6,9-tetramethyl-6H-thieno[3,2-f][1,2,4]triazolo[4,3-a][1,4]diazepin-4-yl)phenyl)-2,9-diazaspiro[5.5]undecane-9-carboxylate (170 mg, 296 μmol, 1.0 equiv) in DCM (2 mL) was added TFA (1 mL). The mixture was stirred at 25° C. for 1 hour. The reaction mixture was concentrated and basified with saturated $NaHCO_3$ at 0° C. The mixture was extracted with DCM/MeOH (10:1, 2×20 mL), dried over $Na_2SO_4$, filtered, and concentrated to give (S)-4-(4-(2,9-diazaspiro[5.5]undecan-2-yl)phenyl)-2,3,6,9-tetramethyl-6H-thieno[3,2-f][1,2,4]triazolo[4,3-a][1,4]diazepine (140 mg, 295 μmol, 99% yield) as a yellow oil.

Step 3: Preparation of N-((1r,4r)-4-(4-cyano-3-methoxyphenoxy)cyclohexyl)-6-(2-(4-((S)-2,3,6,9-tetramethyl-6H-thieno[3,2-f][1,2,4]triazolo[4,3-a][1,4]diazepin-4-yl)phenyl)-2,9-diazaspiro[5.5]undecan-9-yl) pyridazine-3-carboxamide (I-81). To a solution of(S)-4-(4-(2,9-diazaspiro[5.5]undecan-2-yl)phenyl)-2,3,6,9-tetramethyl-6H-thieno[3,2-f][1,2,4]triazolo[4,3-a][1,4]diazepine (70 mg, 147 μmol, 1 equiv) and 6-chloro-N-((1r,4r)-4-(4-cyano-3-methoxyphenoxy)cyclohexyl) pyridazine-3-carboxamide (74 mg, 192 μmol, 1.3 equiv) in NMP (0.5 mL) was added DIEA (57 mg, 442 μmol, 77 μL, 3.0 equiv). The mixture was stirred at 65° C. for 12 hours. The residue was purified by prep-HPLC (column: Waters xbridge 150 mm×25 mm×10 μm; mobile phase: [water ($NH_4HCO_3$)-ACN]; gradient: 60%-80% B over 8 min) to afford compound N-((1r,4r)-4-(4-cyano-3-methoxyphenoxy)cyclohexyl)-6-(2-(4-((S)-2,3,6,9-tetramethyl-6H-thieno[3,2-f][1,2,4]triazolo[4,3-a][1,4]diazepin-4-yl)phenyl)-2,9-diazaspiro[5.5]undecan-9-yl) pyridazine-3-carboxamide (45 mg, 52 μmol, 35.00% yield, 95% purity) as a white solid. $^1H$ NMR (400 MHz, $CD_3OD$) δ 7.88 (d, J=9.7 Hz, 1H), 7.49 (d, J=9.3 Hz, 1H), 7.31 (d, J=8.6 Hz, 2H), 7.24 (d, J=9.7 Hz, 1H), 6.93 (d, J=9.0 Hz, 2H), 6.67-6.62 (m, 2H), 4.63-4.37 (m, 2H), 4.23 (q, J=6.7 Hz, 1H), 4.01-3.86 (m, 4H), 3.75 (br t, J=5.6 Hz, 4H), 3.30-3.26 (m, 2H), 3.23 (s, 2H), 2.68 (s, 3H), 2.43 (s, 3H), 2.19 (br s, 2H), 2.12-2.01 (m, 2H), 1.96 (d, J=6.7 Hz, 3H), 1.78-1.69 (m, 5H), 1.69-1.54 (m, 10H). LC-MS: MS ($ES^+$): RT=1.817 min, m/z=825.6 $[M+H]^+$; LCMS method: 25.

Example 28—Synthesis of N-((1r,4r)-4-(4-cyano-3-methoxyphenoxy)cyclohexyl)-6-(7-(4-((S)-2,3,6,9-tetramethyl-6H-thieno[3,2-f][1,2,4]triazolo[4,3-a][1,4]diazepin-4-yl)phenyl)-2,7-diazaspiro[4.5]decan-2-yl) pyridazine-3-carboxamide (I-82)

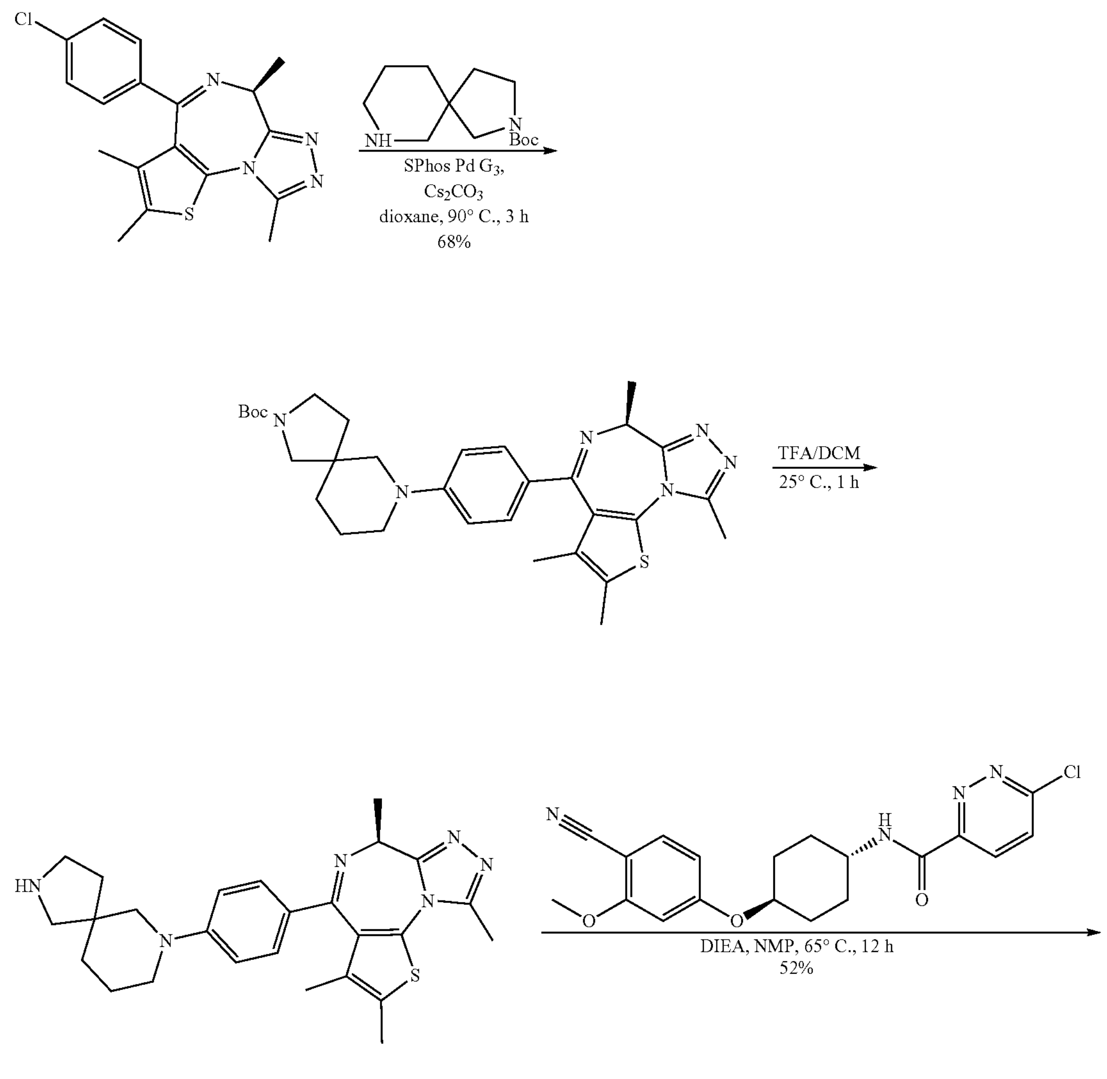

-continued

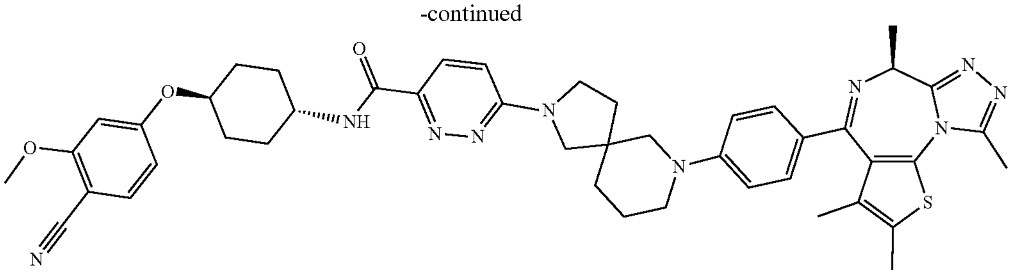

I-82

Step 1: Preparation of tert-butyl 7-(4-((S)-2,3,6,9-tetramethyl-6H-thieno[3,2-f][1,2,4]triazolo[4,3-a][1,4]diazepin-4-yl)phenyl)-2,7-diazaspiro[4.5]decane-2-carboxylate. To a solution of(S)-4-(4-chlorophenyl)-2,3,6,9-tetramethyl-6H-thieno[3,2-f][1,2,4]triazolo[4,3-a][1,4]diazepine (215 mg, 602 μmol, 1.0 equiv) and tert-butyl 2,7-diazaspiro[4.5]decane-2-carboxylate (217 mg, 904 μmol, 1.5 equiv) in dioxane (4 mL) was added SPhos Pd G3 (47 mg, 60 μmol, 0.1 equiv) and $Cs_2CO_3$ (393 mg, 1.2 mmol, 2.0 equiv). The mixture was stirred at 90° C. for 3 hours. The reaction mixture was concentrated under reduced pressure to remove solvent. The residue was purified by prep-HPLC (column: Phenomenex luna C18 150 mm×25 mm×10 μm; mobile phase: [water (FA)-ACN]; gradient: 26%-56% B over 10 min) to give compound tert-butyl 7-(4-((S)-2,3,6,9-tetramethyl-6H-thieno[3,2-f][1,2,4]triazolo[4,3-a][1,4]diazepin-4-yl)phenyl)-2,7-diazaspiro[4.5]decane-2-carboxylate (230 mg, 410 μmol, 68% yield) as a yellow solid.

Step 2: Preparation of (6S)-4-(4-(2,7-diazaspiro[4.5]decan-7-yl)phenyl)-2,3,6,9-tetramethyl-6H-thieno[3,2-f][1,2,4]triazolo[4,3-a][1,4]diazepine. To a solution of tert-butyl 7-(4-((S)-2,3,6,9-tetramethyl-6H-thieno[3,2-f][1,2,4]triazolo[4,3-a][1,4]diazepin-4-yl)phenyl)-2,7-diazaspiro[4.5]decane-2-carboxylate (230 mg, 410 μmol, 1.0 equiv) in DCM (2 mL) was added TFA (1 mL). The mixture was stirred at 25° C. for 1 hour. The reaction mixture was concentrated, basified with aqueous $NaHCO_3$, and extracted with DCM/MeOH (10:1, 10 mL×2). The combined organic phase was washed with brine (10 mL×3), dried over anhydrous $Na_2SO_4$, filtered, and concentrated to afford (6S)-4-(4-(2,7-diazaspiro[4.5]decan-7-yl)phenyl)-2,3,6,9-tetramethyl-6H-thieno[3,2-f][1,2,4]triazolo[4,3-a][1,4]diazepine (188 mg, 408 μmol, 99% yield) as a yellow oil.

Step 3: Preparation of N-((1r,4r)-4-(4-cyano-3-methoxyphenoxy)cyclohexyl)-6-(7-(4-((S)-2,3,6,9-tetramethyl-6H-thieno[3,2-f][1,2,4]triazolo[4,3-a][1,4]diazepin-4-yl)phenyl)-2,7-diazaspiro[4.5]decan-2-yl) pyridazine-3-carboxamide (1-82). To a solution of (6S)-4-(4-(2,7-diazaspiro[4.5]decan-7-yl)phenyl)-2,3,6,9-tetramethyl-6H-thieno[3,2-f][1,2,4]triazolo[4,3-a][1,4]diazepine (94 mg, 204 μmol, 1.0 equiv) and 6-chloro-N-((1r,4r)-4-(4-cyano-3-methoxyphenoxy)cyclohexyl) pyridazine-3-carboxamide (103 mg, 265 μmol, 1.3 equiv) in NMP (0.5 mL) was added DIEA (79 mg, 612 μmol, 107 μL, 3.0 equiv). The mixture was stirred at 65° C. for 12 hours. The residue was purified by prep-HPLC (column: Waters xbridge 150 mm×25 mm×10 μm; mobile phase: [water ($NH_4HCO_3$)-ACN]; gradient: 55%-75% B over 8 min) to afford compound N-((1r,4r)-4-(4-cyano-3-methoxyphenoxy)cyclohexyl)-6-(7-(4-((S)-2,3,6,9-tetramethyl-6H-thieno[3,2-f][1,2,4]triazolo[4,3-a][1,4]diazepin-4-yl)phenyl)-2,7-diazaspiro[4.5]decan-2-yl) pyridazine-3-carboxamide (90 mg, 106 μmol, 52% yield, 95% purity) as a white solid. $^1H$ NMR (400 MHz, $CD_3OD$) δ 7.95-7.83 (m, 1H), 7.50 (d, J=8.8 Hz, 1H), 7.29 (br d, J=8.4 Hz, 2H), 6.99 (d, J=9.5 Hz, 1H), 6.90 (d, J=8.7 Hz, 2H), 6.70-6.60 (m, 2H), 4.54-4.44 (m, 2H), 4.29-4.17 (m, 1H), 4.03-3.84 (m, 4H), 3.80-3.65 (m, 3H), 3.55-3.34 (m, 3H), 3.22-3.08 (m, 2H), 2.68 (s, 3H), 2.47-2.37 (m, 3H), 2.29-2.17 (m, 2H), 2.16-2.05 (m, 3H), 2.00-1.91 (m, 4H), 1.89-1.76 (m, 3H), 1.74-1.67 (m, 4H), 1.67-1.59 (m, 4H). LC-MS: MS ($ES^+$): RT=1.642 min, m/z=811.5 $[M+H]^+$; LCMS method: 25.

Example 29—Synthesis of N-[4-(4-cyano-3-methoxy-phenoxy)cyclohexyl]-6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl] pyridazine-3-carboxamide (I-83)

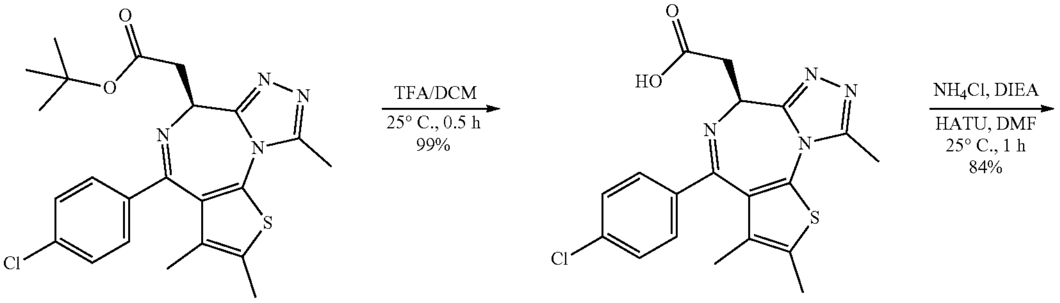

-continued

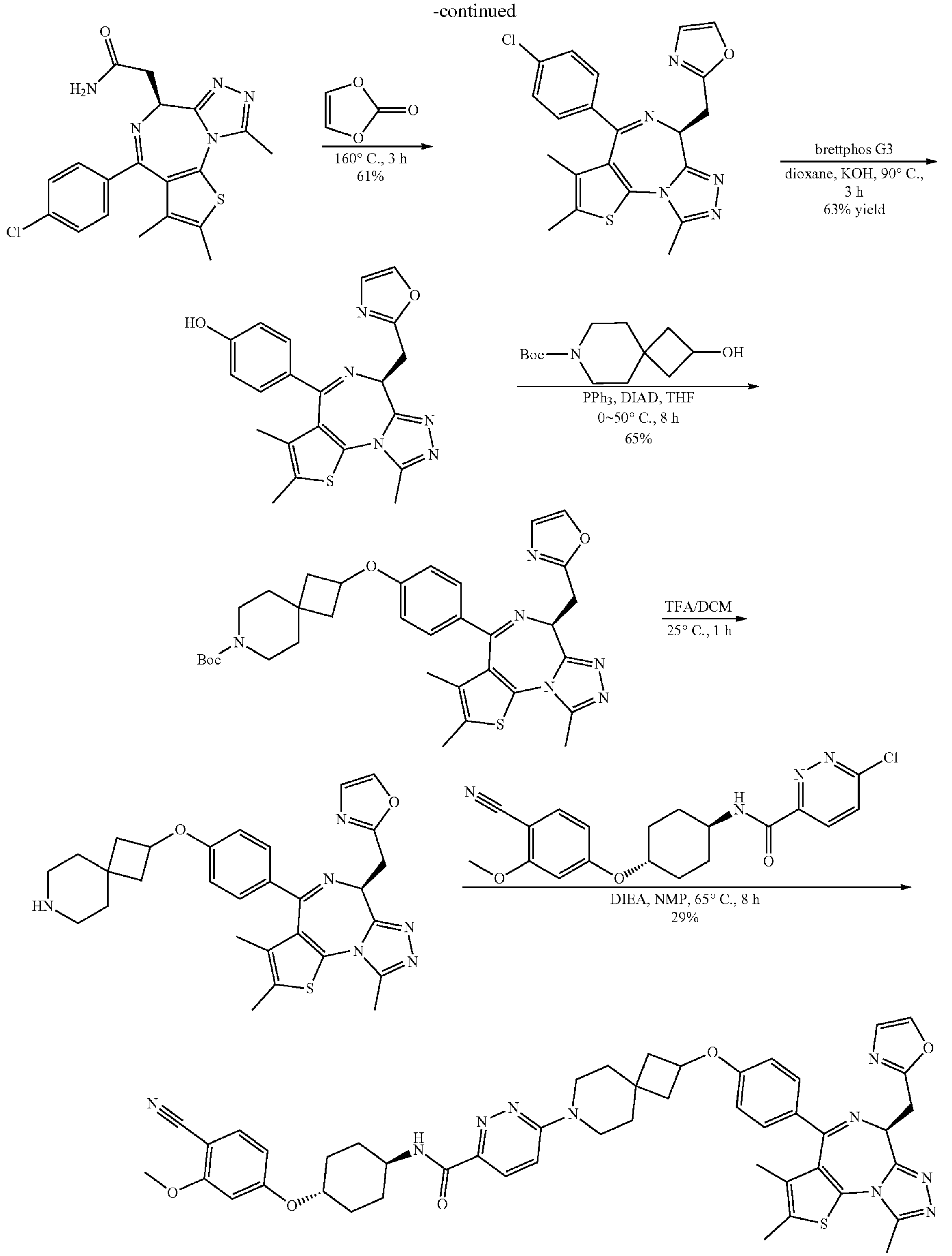

I-83

Step 1: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid. To a solution of commercially available tert-butyl 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetate (CAS Registry No. 1268524-70-4; 1.0 g, 2.1 mmol, 1.0 equiv) in DCM (10 mL) was added TFA (7.7 g, 67 mmol, 5.0 mL, 30 equiv). The mixture was stirred at 25° C. for 0.5 hour. The reaction mixture was filtered and concentrated under reduced pressure to give a residue. The residue, 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 99% yield), was used directly in the next step without purification.

Step 2: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide. To a solution of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 2.19 mmol, 1.0 equiv) and $NH_4Cl$ (351 mg, 6.56 mmol, 3.0 equiv) in DMF (8 mL) was added HATU (915 mg, 2.41 mmol, 1.1 equiv) and DIEA (848 mg, 6.56 mmol, 3.0 equiv). The mixture was stirred at 25° C. for 1 hour. The mixture was filtered and concentrated. The residue was purified by prep-HPLC (column: Waters Xbridge C18 150 mm×50 mm×10 μm; mobile phase: [water ($NH_4HCO_3$)-ACN]; B %: 24%-54%, 10 min) to give 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (740 mg, 84% yield).

Step 3: Preparation of 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of 1,3-dioxol-2-one (103 mg, 1.20 mmol, 1.2 equiv) and 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (400 mg, 1.00 mmol, 1.0 equiv) in PPA (4 mL). The mixture was stirred at 160° C. for 3 hours. The mixture was quenched with $H_2O$ (50 mL) at 0° C. and then diluted with ethyl acetate (200 mL). The mixture was washed with $H_2O$ (15 mL×2) and then further washed with $H_2O$ (10 mL×3) again to remove PPA. The combined organic layers were washed with $H_2O$ (10 mL×3), dried over $Na_2SO_4$, filtered, and concentrated. The residue was purified by column chromatography ($SiO_2$, petroleum ether:ethyl acetate=2:1 to 0:1) to give 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (260 mg, 61% yield).

Step 4: Preparation of 4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenol. A mixture of 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (5.8 g, 13.7 mmol, 1.0 equiv), BrettPhos Pd G3 (1.2 g, 1.4 mmol, 0.1 equiv), and KOH (3.8 g, 68.4 mmol, 5.0 equiv) in dioxane (58 mL) and $H_2O$ (11.6 mL) was degassed and purged with $N_2$ 3 times. Then, the mixture was stirred at 90° C. for 3 hours under $N_2$ atmosphere. The reaction mixture was partitioned between ethyl acetate (2000 mL) and water (500 mL). The organic phase was separated, washed with brine (500 mL×2), dried over $Na_2SO_4$, filtered, and concentrated under reduced pressure to give a residue. The residue was purified by column chromatography ($SiO_2$, dichloromethane:methanol=40:1) to give 4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenol (3.5 g, 8.6 mmol, 63% yield) as a yellow solid.

Step 5: Preparation of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate. To a solution of $PPh_3$ (485 mg, 1.85 mmol, 2.5 equiv) in THF (3 mL) was added DIAD (300 mg, 1.48 mmol, 0.3 mL, 2.0 equiv) at 0° C. for 30 minutes. Next, 4-[(9S)-4,5,13-trimethyl-9-(oxazol-2-ylmethyl)-3-thia-1,8,11,12-tetraza-tricyclo[8.3.0.0$^{2,6}$]trideca-2 (6),4,7,10,12-pentaen-7-yl]phenol (300 mg, 740 μmol, 1.0 equiv) and tert-butyl 2-hydroxy-7-azaspiro[3.5]nonane-7-carboxylate (357 mg, 1.48 mmol, 2.0 equiv) in THF (3 mL) was added. The mixture was stirred at 0-50° C. for 8 hours. The reaction mixture was filtered and concentrated under reduced pressure to give a residue. The residue was purified by column chromatography ($SiO_2$, petroleum ether:ethyl acetate to dichloromethane:methanol=1:1 to 10:1) to give tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (300 mg, 477 μmol, 65% yield) as a colorless oil.

Step 6: Preparation of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (200 mg, 318 μmol, 1.0 equiv) in DCM (2 mL) was added TFA (1 mL). The mixture was stirred at 25° C. for 1 hour. The reaction mixture was concentrated and quenched with $NaHCO_3$ (30 mL) at 0° C. The combined organic layers were washed with DCM/MeOH (10:1, 20 mL×3), dried over $Na_2SO_4$, filtered, and concentrated under reduced pressure to give 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (160 mg, 302 μmol) as a yellow solid.

Step 7: Preparation of N-[4-(4-cyano-3-methoxy-phenoxy)cyclohexyl]-6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyridazine-3-carboxamide (I-83). To a solution of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (100 mg, 190 μmol, 1.0 equiv) and 6-chloro-N-[4-(4-cyano-3-methoxy-phenoxy)cyclohexyl]pyridazine-3-carboxamide (88 mg, 227 μmol, 1.2 equiv) in NMP (0.5 mL) was added DIEA (75 mg, 567 μmol, 0.1 mL, 3.0 equiv). The mixture was stirred at 65° C. for 8 hours. The residue was purified by prep-HPLC (column: Phenomenex luna C18 150 mm×25 mm×10 μm; mobile phase: [water (FA)-ACN]; gradient: 60%-90% B over 10 min) to give N-[4-(4-cyano-3-methoxy-phenoxy)cyclohexyl]-6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyridazine-3-carboxamide (49.42 mg, 56.01 μmol, 29% yield, 99.63% purity) as an off-white solid. $^1$H NMR (400 MHz, $CD_3OD$) δ 7.91 (t, J=4.8 Hz, 2H), 7.55-7.50 (m, 1H), 7.38-7.29 (m, 3H), 7.14 (s, 1H), 6.86 (d, J=8.9 Hz, 2H), 6.71-6.65 (m, 2H), 4.76 (dd, J=6.4, 8.3 Hz, 1H), 4.51 (br s, 1H), 4.04-3.95 (m, 3H), 3.93 (s, 3H), 3.83-3.76 (m, 2H), 3.75-3.68 (m, 2H), 2.72 (s, 3H), 2.60-2.51 (m, 2H), 2.47 (s, 3H), 2.29-2.19 (m, 2H), 2.16-2.07 (m, 2H), 2.00 (br dd, J=6.1, 13.1 Hz, 2H), 1.78 (td, J=5.5, 15.8 Hz, 4H), 1.72 (s, 3H), 1.65 (br t, J=9.6 Hz, 4H). LC-MS: MS ($ES^+$): RT=2.346 min, m/z=879.1 [M+H]; LCMS method: 25.

Example 30—Synthesis of N-[3-(4-cyano-3-methoxy-phenoxy)-2,2,4,4-tetramethyl-cyclobutyl]-2-[8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyrimidine-5-carboxamide (II-4)
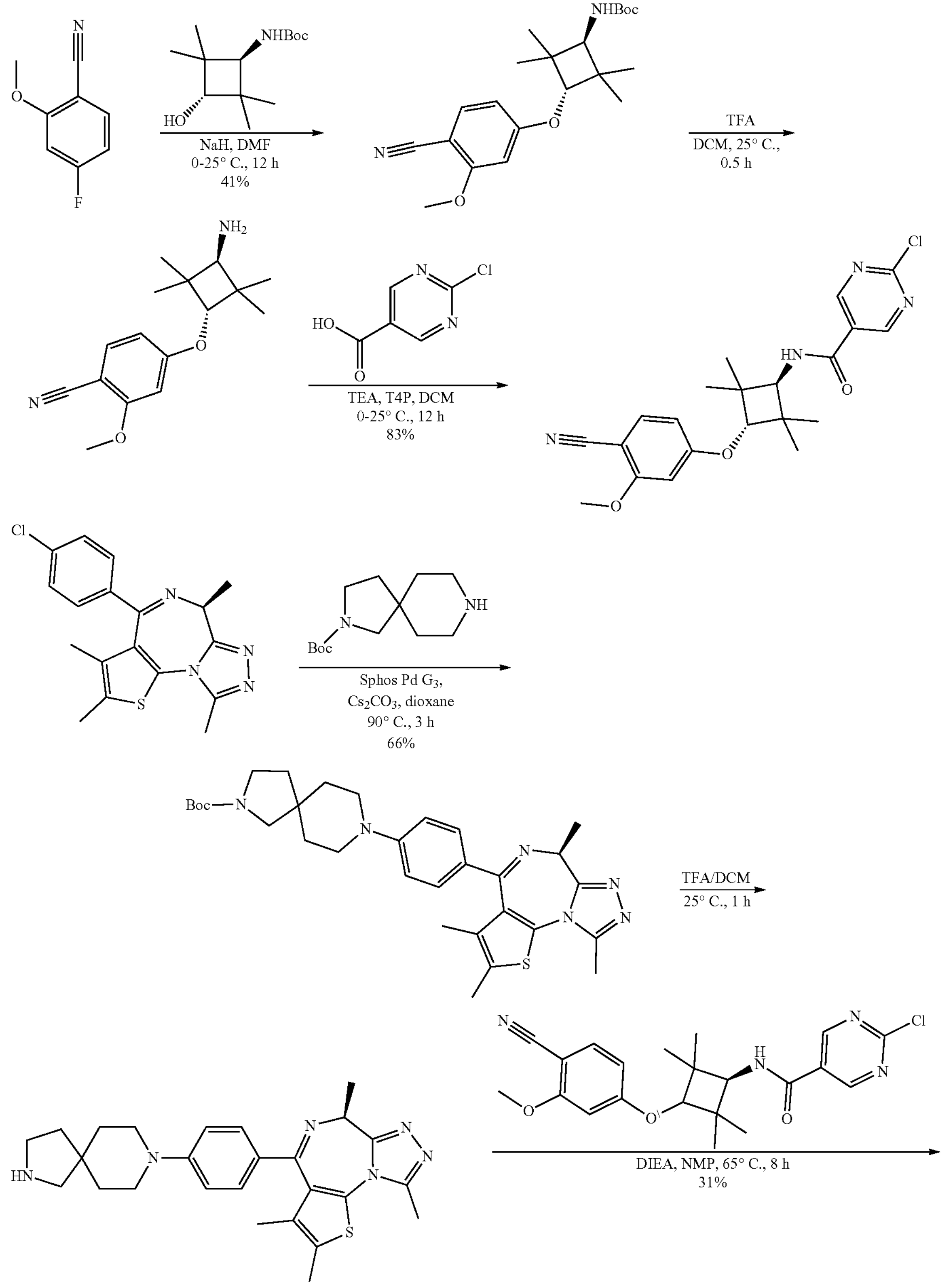

-continued

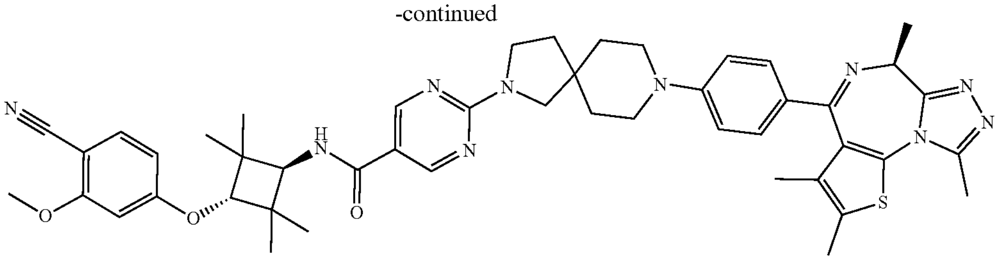

II-4

Step 1: Preparation of tert-butyl N-[3-(4-cyano-3-methoxy-phenoxy)-2,2,4,4-tetramethyl-cyclobutyl]carbamate. To a solution of tert-butyl N-(3-hydroxy-2,2,4,4-tetramethyl-cyclobutyl) carbamate (7.0 g, 28 mmol, 1.0 equiv) in THF (130 mL) was added NaH (1.38 g, 34.5 mmol, 60% purity, 1.2 equiv) at 0° C. After stirring at 25° C. for 0.5 hour, 4-fluoro-2-methoxy-benzonitrile (5.22 g, 34.5 mmol, 1.2 equiv) was added at 0° C. The mixture was stirred at 25° C. for 12 hours. The reaction mixture was slowly added to cold water (500 mL) and extracted with DCM (300 mL×3). The organic phase was washed with water (500 mL×3). The organic phase was dried and concentrated. The crude product was triturated with ethyl acetate (200 mL) at 0° C. for 10 minutes. The mixture was filtered to get a cake. The cake was washed with ethyl acetate (50 mL×3) and dried. Tert-butyl N-[3-(4-cyano-3-methoxy-phenoxy)-2,2,4,4-tetramethyl-cyclobutyl]carbamate (15 g, 35 mmol, 41% yield, 89% purity) was obtained as a white solid.

Step 2: Preparation of 4-(3-amino-2,2,4,4-tetramethyl-cyclobutoxy)-2-methoxy-benzonitrile. To a solution of tert-butyl N-[3-(4-cyano-3-methoxy-phenoxy)-2,2,4,4-tetramethyl-cyclobutyl]carbamate (14 g, 37 mmol, 1.0 equiv) in DCM (20 mL) was added TFA (10 mL). The reaction mixture was stirred at 25° C. for 0.5 hour and then concentrated to give crude 4-(3-Amino-2,2,4,4-tetramethyl-cyclobutoxy)-2-methoxy-benzonitrile (14.52 g, 37.39 mmol, TFA) as a colorless oil.

Step 3: Preparation of 2-chloro-N-[3-(4-cyano-3-methoxy-phenoxy)-2,2,4,4-tetramethyl-cyclobutyl]pyrimidine-5-carboxamide. To a solution of 4-(3-amino-2,2,4,4-tetramethyl-cyclobutoxy)-2-methoxy-benzonitrile (14.52 g, 37.39 mmol, 1.0 equiv, TFA) in DCM (100 mL) was added TEA (18.92 g, 186.9 mmol, 26 mL, 5.0 equiv), 2-chloropyrimidine-5-carboxylic acid (5.93 g, 37.3 mmol, 1.0 equiv), and T4P (26.94 g, 37.39 mmol, 50% purity, 1.0 equiv) at 0° C. The reaction mixture was stirred at 25° C. for 12 hours. The reaction mixture was diluted with DCM (400 mL) and washed with 1 M HCl (200 mL). The organic phase was washed with saturated $NaHCO_3$ (200 mL), dried, and concentrated. The crude product was triturated with petroleum ether/ethyl acetate (1:1, 200 mL) at 25° C. for 5 minutes. The mixture was filtered to give a cake that was washed with petroleum ether/ethyl acetate (1:1, 50 mL×3) and dried. The product, 2-chloro-N-[3-(4-cyano-3-methoxy-phenoxy)-2,2,4,4-tetramethyl-cyclobutyl]pyrimidine-5-carboxamide (13 g, 31 mmol, 83% yield), was obtained as a white solid.

Step 4: Preparation of tert-butyl 8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decane-2-carboxylate. A mixture of (9S)-7-(4-chlorophenyl)-4,5,9,13-tetramethyl-3-thia-1,8,11,12-tetrazatricyclo[8.3.0.$0^{2,6}$]trideca-2 (6),4,7,10,12-pentaene (200 mg, 560 μmol, 1.0 equiv), tert-butyl 2,8-diazaspiro[4.5]decane-2-carboxylate (202 mg, 840 μmol, 1.5 equiv), SPhos Pd G3 (88 mg, 112 μmol, 0.2 equiv), and $Cs_2CO_3$ (548 mg, 1.68 mmol, 3.0 equiv) in dioxane (3 mL) was degassed and purged with $N_2$ 3 times. The mixture was stirred at 90° C. for 3 hours under $N_2$ atmosphere. The reaction mixture was filtered and concentrated under reduced pressure to give a residue. The residue was purified by prep-HPLC (column: Phenomenex luna C18 150 mm×25 mm×10 μm; mobile phase: [water (FA)-ACN]; gradient: 28%-58% B over 25 min) to give tert-butyl 8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decane-2-carboxylate (210 mg, 374 μmol, 66% yield) as a yellow solid.

Step 5: Preparation of (9S)-7-[4-(2,8-diazaspiro[4.5]decan-8-yl)phenyl]-4,5,9,13-tetramethyl-3-thia-1,8,11,12-tetrazatricyclo[8.3.0.$0^{2,6}$]trideca-2 (6),4,7,10,12-pentaene. To a solution of tert-butyl 8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decane-2-carboxylate (210 mg, 374 μmol, 1.0 equiv) in DCM (2 mL) was added TFA (1 mL). The mixture was stirred at 25° C. for 1 hour and then concentrated to give a residue. The residue was basified by aqueous $NaHCO_3$ and then extracted with DCM:MeOH (10:1, 20 mL×3). The combined organic phase was washed with brine (40 mL), dried over anhydrous $Na_2SO_4$, filtered, and concentrated to give (9S)-7-[4-(2,8-diazaspiro[4.5]decan-8-yl)phenyl]-4,5,9,13-tetramethyl-3-thia-1,8,11,12-tetrazatricyclo[8.3.0.$0^{2,6}$]trideca-2 (6),4,7,10,12-pentaene (170 mg, 369 μmol) as a yellow solid.

Step 6: Preparation of N-[3-(4-cyano-3-methoxy-phenoxy)-2,2,4,4-tetramethyl-cyclobutyl]-2-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decan-2-yl]pyrimidine-5-carboxamide (II-4). To a solution of (9S)-7-[4-(2,8-diazaspiro[4.5]decan-8-yl)phenyl]-4,5,9,13-tetramethyl-3-thia-1,8,11,12-tetrazatricyclo[8.3.0.$0^{2,6}$]trideca-2 (6),4,7,10,12-pentaene (100 mg, 217 μmol, 1.0 equiv) and 2-chloro-N-[3-(4-cyano-3-methoxy-phenoxy)-2,2,4,4-tetramethyl-cyclobutyl]pyrimidine-5-carboxamide (117 mg, 282 μmol, 1.3 equiv) in NMP (1 mL) was added DIEA (85 mg, 651 μmol, 0.1 mL, 3.0 equiv). The mixture was stirred at 65° C. for 8 hours. The residue was purified by prep-HPLC (column: Waters xbridge 150 mm×25 mm×10 μm; mobile phase: [water ($NH_4HCO_3$)-ACN]; gradient: 80%-100% B over 10 min) to afford N-[3-(4-cyano-3-methoxy-phenoxy)-2,2,4,4-tetramethyl-cyclobutyl]-2-[8-[4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decan-2-yl]pyrimidine-5-carboxamide (61.05 mg, 67.16 μmol, 31% yield, 92.3% purity) as a white solid. $^1H$ NMR (400 MHz, $CD_3OD$) δ 8.77 (s, 2H), 7.54 (d, J=8.6 Hz, 1H), 7.37 (d, J=8.8 Hz, 2H), 6.99 (d, J=9.1 Hz, 2H), 6.64 (d, J=2.1 Hz, 1H), 6.57 (dd, J=2.1, 8.6 Hz, 1H), 4.31-4.23 (m, 2H), 4.15 (s, 1H), 3.95 (s, 3H), 3.74 (t, J=7.1 Hz, 2H), 3.59 (s, 2H), 3.45 (br s, 2H), 3.34 (br s, 2H), 3.31 (br s, 1H), 2.71 (s, 3H), 2.46 (s, 3H), 2.06-1.97 (m, 5H), 1.79 (br s, 3H), 1.76 (s, 3H), 1.31 (s, 6H), 1.24 (s, 6H). LC-MS: MS ($ES^+$): RT=1.943 min, m/z=839.4 $[M+H]^+$.

Example 31—Synthesis of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (II-5)
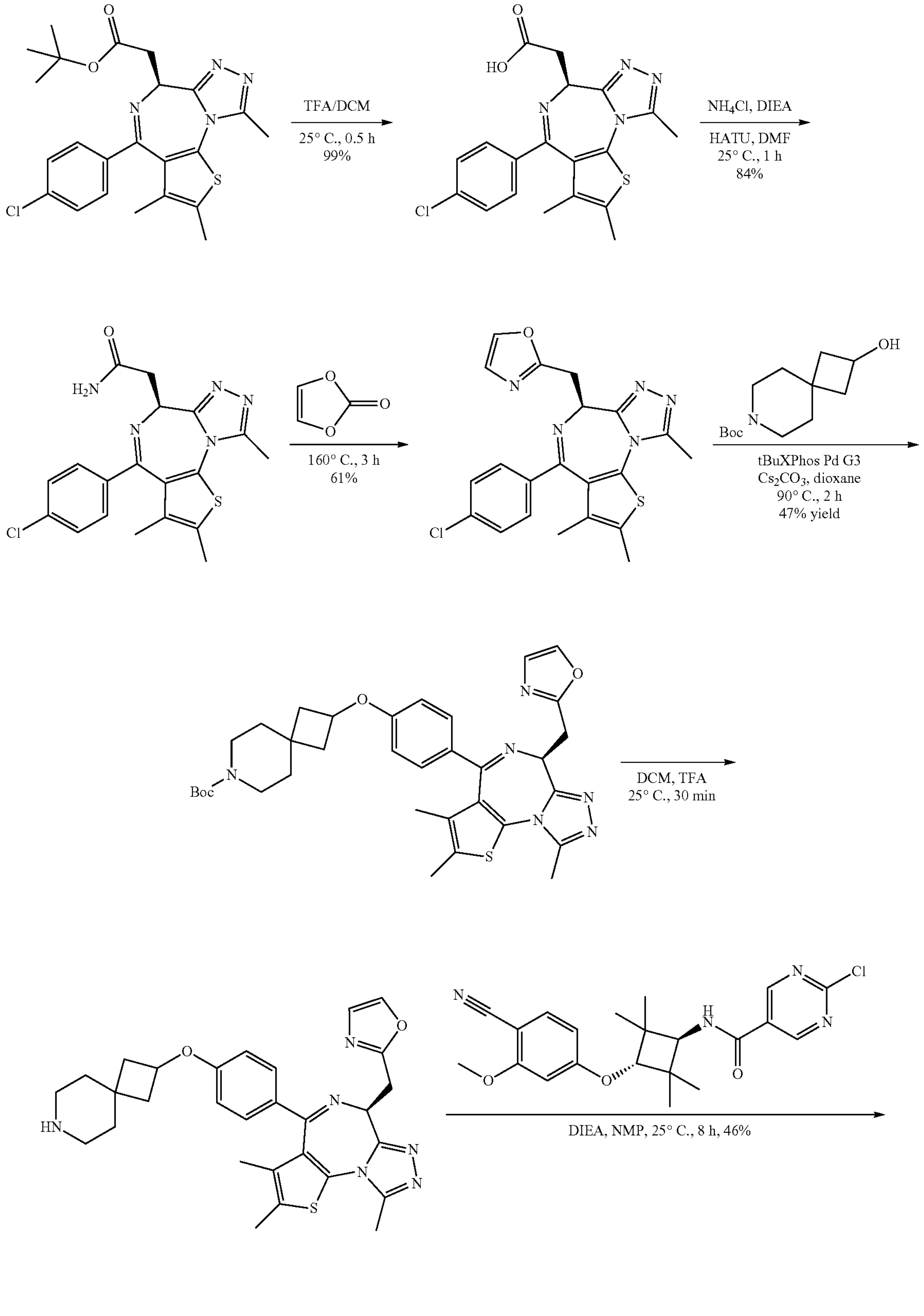

-continued

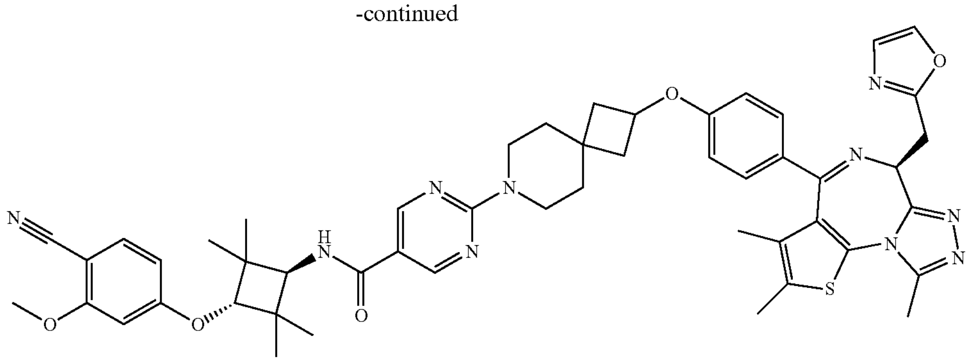

II-5

Step 1: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid. To a solution of tert-butyl 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetate (1.0 g, 2.1 mmol, 1.0 equiv) in DCM (10 mL) was added TFA (7.7 g, 67 mmol, 5.0 mL, 30 equiv). The mixture was stirred at 25° C. for 0.5 hour. The reaction mixture was filtered and concentrated under reduced pressure to give a residue. The residue, 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 99% yield), was used directly in the next step without purification.

Step 2: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide. To a solution of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 2.19 mmol, 1.0 equiv) and $NH_4Cl$ (351 mg, 6.56 mmol, 3.0 equiv) in DMF (8 mL) was added HATU (915 mg, 2.41 mmol, 1.1 equiv) and DIEA (848 mg, 6.56 mmol, 3.0 equiv). The mixture was stirred at 25° C. for 1 hour. The mixture was filtered and concentrated. The residue was purified by prep-HPLC (column: Waters Xbridge C18 150 mm×50 mm×10 μm; mobile phase: [water ($NH_4HCO_3$)-ACN]; B %: 24%-54%, 10 min) to give 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (740 mg, 84% yield).

Step 3: Preparation of 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole. A solution of 1,3-dioxol-2-one (103 mg, 1.20 mmol, 1.2 equiv) and 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (400 mg, 1.00 mmol, 1.0 equiv) in PPA (4 mL) was stirred at 160° C. for 3 hours. The mixture was quenched with $H_2O$ (50 mL) at 0° C. and then diluted with ethyl acetate (200 mL). The mixture was washed with $H_2O$ (15 mL×2) and then further washed with $H_2O$ (10 mL×3) again to remove PPA. The combined organic layers were washed with $H_2O$ (10 mL×3), dried over $Na_2SO_4$, filtered, and concentrated. The residue was purified by column chromatography ($SiO_2$, petroleum ether:ethyl acetate=2:1 to 0:1) to give 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (260 mg, 61% yield).

Step 4: Preparation of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate. To a solution of 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (300 mg, 707 μmol, 1.0 equiv) and tert-butyl 2-hydroxy-7-azaspiro[3.5]nonane-7-carboxylate (853 mg, 3.54 mmol, 5.0 equiv) in dioxane (5 mL) was added tBuXPhos Pd G3 (112 mg, 141 μmol, 0.2 equiv) and $Cs_2CO_3$ (1.1 g, 3.5 mmol, 5.0 equiv). The mixture was degassed and purged with $N_2$ 3 times, and then the mixture was stirred at 90° C. for 2 hours under $N_2$ atmosphere. The reaction mixture was filtered and concentrated under reduced pressure to give a residue. The residue was purified by flash silica gel chromatography (ISCO®; 2 g SepaFlash® Silica Flash Column, eluent of 0~3% methanol/dichloromethane gradient at 18 mL/min) to give tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (210 mg, 333 μmol, 47% yield) as a yellow solid.

Step 5: Preparation of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. A mixture of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (210 mg, 333 μmol, 1.0 equiv) in DCM (2 mL) and TFA (0.6 mL) was degassed and purged with $N_2$ 3 times. The mixture was stirred at 25° C. for 30 minutes under $N_2$ atmosphere. The mixture was concentrated to give a residue, 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (214 mg, 332 μmol, 99% yield, TFA), as a brown oil, which was used directly in the next step without purification.

Step 6: Preparation of N-[(1r,3r)-3-(4-cyano-3-methoxyphenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (II-5). To a solution of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (80 mg, 151 μmol, 1.0 equiv) and 2-chloro-N-[(1r,3r)-3-(4-cyano-3-methoxy-phenoxy)-2,2,4,4-tetramethyl-cyclobutyl]pyrimidine-5-carboxamide (94 mg, 227 μmol, 1.5 equiv) in NMP (0.5 mL) was added DIEA (60 mg, 460 μmol, 0.1 mL, 3.0 equiv). The mixture was stirred at 25° C. for 8 hours. The reaction mixture was filtered and concentrated to give a residue. The residue was purified by prep-HPLC (column: Waters Xbridge C18 150 mm×50 mm×10 μm; mobile phase: [water ($NH_4HCO_3$)-ACN]; gradient: 54%-84% B over 10 min) to give N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (63.7 mg, 70.13 μmol, 46% yield, 99.86% purity) as a white solid. $^1$H NMR (400 MHz, $CD_3OD$) δ 8.74 (s, 2H), 7.91 (d, J=0.8 Hz, 1H), 7.54 (d, J=8.6 Hz, 1H), 7.34 (d, J=8.8 Hz, 2H), 7.14 (d, J=0.8 Hz, 1H), 6.85 (d, J=8.9 Hz, 2H), 6.64 (d, J=2.1 Hz, 1H), 6.57 (dd, J=2.1, 8.6 Hz, 1H), 4.79-4.71 (m, 2H), 4.27-4.25 (m, 1H), 4.16-4.12 (m, 1H), 3.95 (s, 7H), 3.90-3.83 (m, 2H), 2.72 (s, 3H), 2.61-2.50 (m, 2H), 2.48 (s, 3H), 2.03-1.92 (m, 2H), 1.72 (s, 7H), 1.30 (s, 6H), 1.24 (s, 6H). LC-MS: MS (ES$^+$): RT=2.698 min, m/z=907.4 [M+H]$^+$.

Example 32—Synthesis of N-[3-(4-cyano-3-methoxy-phenoxy)-2,2,4,4-tetramethyl-cyclobutyl]-2-[2-[[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl]pyrimidine-5-carboxamide (II-10)

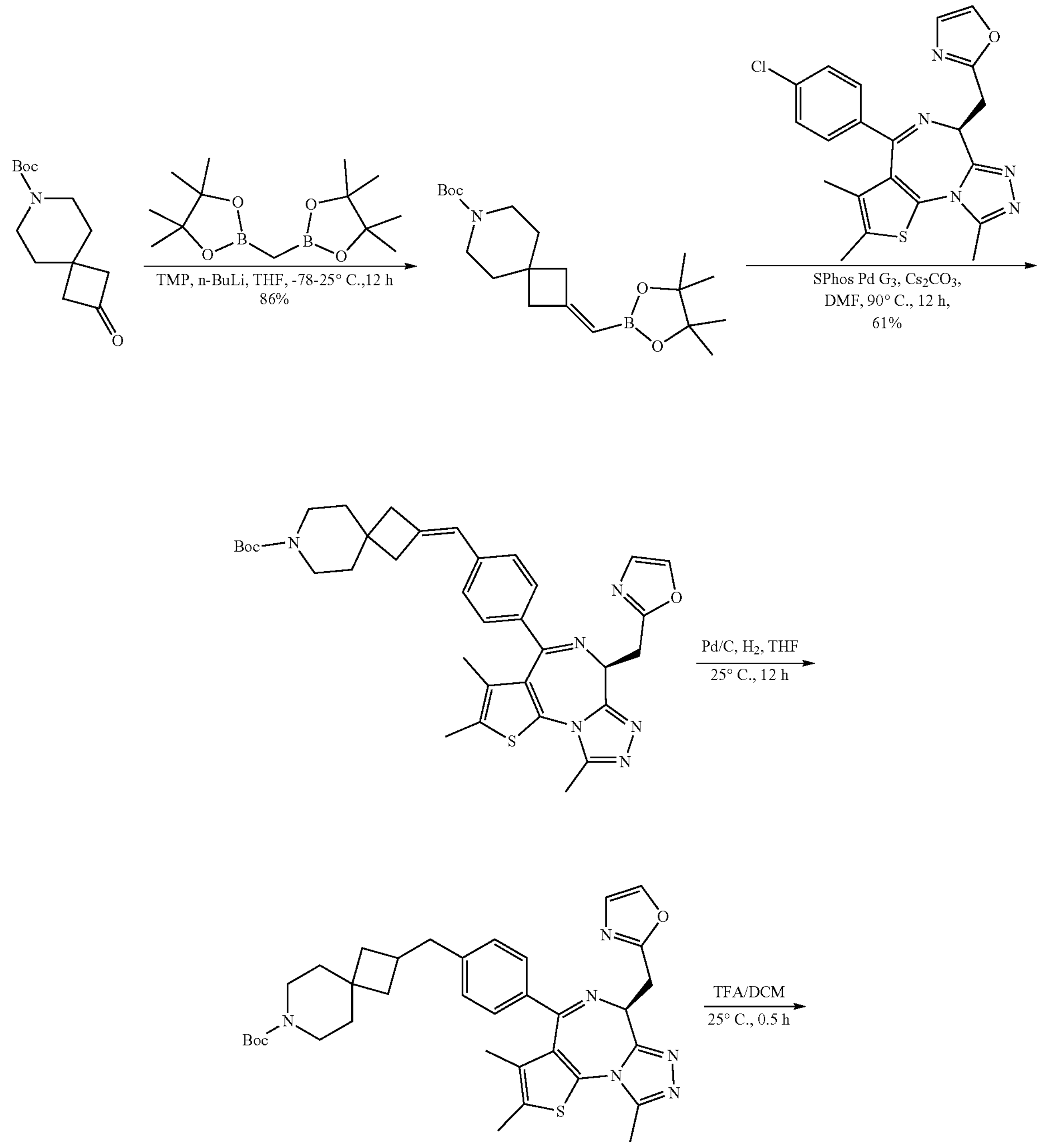

-continued

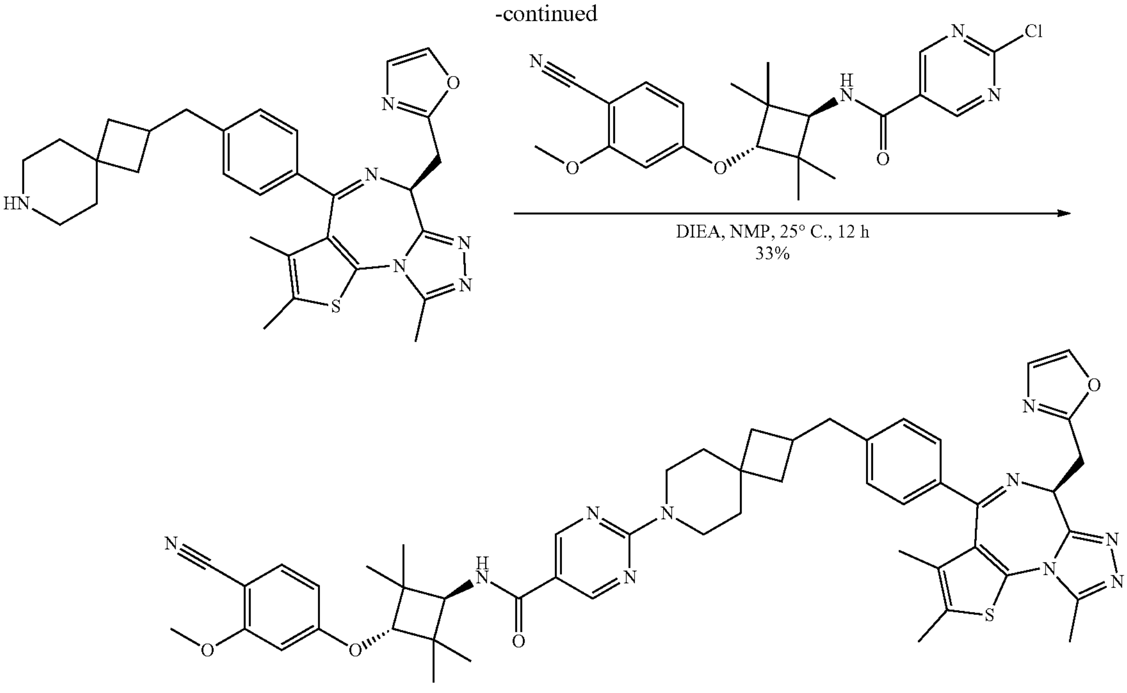

II-10

Step 1: Preparation of tert-butyl 2-[(4,4,5,5-tetramethyl-1,3,2-dioxaborolan-2-yl)methylene]-7-azaspiro[3.5]nonane-7-carboxylate. To a solution of TMP (885 mg, 6.2 mmol, 1.0 mL, 1.5 equiv) in THF (4 mL) was added n-BuLi (2.5 M, 2.5 mL, 1.5 equiv) at −30° C. under $N_2$ atmosphere. After addition, the mixture was stirred at −30° C. for 30 minutes. Next, 4,4,5,5-tetramethyl-2-[(4,4,5,5-tetramethyl-1,3,2-dioxaborolan-2-yl)methyl]-1,3,2-dioxaborolane (1.4 g, 5.0 mmol, 1.2 equiv) in THF (3 mL) was added dropwise at −78° C. After addition, the mixture was stirred at −78° C. for 30 minutes. Next, tert-butyl 2-oxo-7-azaspiro[3.5]nonane-7-carboxylate (1.0 g, 4.18 mmol, 1.0 equiv) in THF (3 mL) was added dropwise at −78° C. The resulting mixture was stirred at 25° C. for 12 hours. The resultant mixture was then cooled to 0° C., and saturated aqueous $NH_4Cl$ (15 mL) was added dropwise. After stirring for an additional 1 hour, the resulting mixture was filtered, and the solvent was removed in vacuo. Water (20 mL) was added to the resultant residue, and the aqueous layer was extracted with EtOAc (20 mL×3). The combined organic phase was washed with brine (20 mL), dried over anhydrous $Na_2SO_4$ and concentrated under vacuum to give tert-butyl 2-[(4,4,5,5-tetramethyl-1,3,2-dioxaborolan-2-yl)methylene]-7-azaspiro[3.5]nonane-7-carboxylate (1.3 g, 86% yield) as a colorless oil.

Step 2: Preparation of tert-butyl 2-[[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methylene]-7-azaspiro[3.5]nonane-7-carboxylate. To a solution of 2-[[7-(4-chlorophenyl)-4,5,13-trimethyl-3-thia-1,8,11,12-tetrazatricyclo[8.3.0.02,6]trideca-2 (6),4,7,10,12-pentaen-9-yl]methyl]oxazole (400 mg, 943.8 μmol, 1.0 equiv) and tert-butyl 2-[(4,4,5,5-tetramethyl-1,3,2-dioxaborolan-2-yl)methylene]-7-azaspiro[3.5]nonane-7-carboxylate (530 mg, 1.6 mmol, 1.5 equiv) in DMF (6 mL) was added SPhos Pd G3 (73 mg, 94 μmol, 0.1 equiv) and $Cs_2CO_3$ (307 mg, 943 μmol, 1.0 equiv). The mixture was stirred at 90° C. for 12 hours. The reaction mixture was filtered and concentrated under reduced pressure to give a residue. The residue was purified by prep-HPLC (column: Phenomenex Luna C18 150 mm×25 mm×10 μm; mobile phase: [water (FA)-ACN]; B %: 62%-92%, 10 min) to give tert-butyl 2-[[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methylene]-7-azaspiro[3.5]nonane-7-carboxylate (400 mg, 61% yield) as a yellow solid.

Step 3: Preparation of tert-butyl 2-[[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonane-7-carboxylate. To a solution of tert-butyl 2-[[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methylene]-7-azaspiro[3.5]nonane-7-carboxylate (0.4 g, 642 μmol, 1.0 equiv) in THF (8 mL) was added Pd/C (0.45 g, 10% purity) under $H_2$ (15 psi). The mixture was stirred at 25° C. for 12 hours under $H_2$ (15 psi). The reaction mixture was filtered and concentrated under reduced pressure to give tert-butyl 2-[[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonane-7-carboxylate (0.4 g, 99% yield) as a white solid.

Step 4: Preparation of 2-[[7-[4-(7-azaspiro[3.5]nonan-2-ylmethyl)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 2-[[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonane-7-carboxylate (0.4 g, 638 μmol, 1.0 equiv) in DCM (1 mL) was added TFA (1.2 g, 10.7 mmol, 800 μL, 16.8 equiv). The mixture was stirred at 25° C. for 0.5 hour. The reaction mixture was filtered and concentrated under reduced pressure to give 2-[[7-[4-(7-azaspiro[3.5]nonan-2-ylmethyl)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (0.407 g, 99% yield) as a colorless oil.

Step 5: Preparation of N-[3-(4-cyano-3-methoxy-phenoxy)-2,2,4,4-tetramethyl-cyclobutyl]-2-[2-[[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl]pyrimidine-5- carboxamide (II-10). To a solution of 2-[[(9S)-7-[4-(7-azaspiro[3.5]nonan-2-ylmethyl)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (100 mg, 189 μmol, 1.0 equiv) and 2-chloro-N-[3-(4-cyano-3-methoxy-phenoxy)-2,2,4,4-tetramethyl-cyclobutyl]pyrimidine-5-carboxamide (102 mg, 246 μmol, 1.3 equiv) in NMP (0.5 mL) was added DIEA (74.2 mg, 574 μmol, 100 μL, 3.0 equiv). The mixture was stirred at 25° C. for 12 hours. The residue was purified by prep-HPLC (column: Waters Xbridge 150 mm×25 mm×5 μm; mobile phase: [water ($NH_4HCO_3$)-ACN]; gradient: 70%-100% B over 10 min) to afford N-[3-(4-cyano-3-methoxy-phenoxy)-2,2,4,4-tetramethyl-cyclobutyl]-2-[2-[[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl]pyrimidine-5-carboxamide (58 mg, 33% yield) as a white solid. 1H NMR (400 MHz, $CD_3OD$): δ 8.70 (s, 2H), 7.90 (s, 1H), 7.51 (d, J=8.56 Hz, 1H), 7.29 (d, J=8.07 Hz, 2H), 7.18 (d, J=8.07 Hz, 2H), 7.12 (s, 1H), 6.62 (d, J=1.83 Hz, 1H), 6.54 (dd, J=8.56, 1.96 Hz, 1H), 4.74-4.79 (m, 1H), 4.23 (s, 1H), 4.11 (s, 1H), 3.90-4.04 (m, 5H), 3.79-3.87 (m, 2H), 3.72-3.78 (m, 2H), 2.76 (d, J=7.34 Hz, 2H), 2.70 (s, 3H), 2.54-2.63 (m, 1H), 2.45 (s, 3H), 1.92-2.02 (m, 2H), 1.49-1.67 (m, 9H), 1.27 (s, 6H), 1.21 (s, 6H). LC-MS: MS ($ES^+$): RT=2.936 min, m/z=905.6 $[M+H]^+$; LCMS method: 25.

Example 33—Synthesis of N-[4-(4-cyano-3-methoxy-phenoxy)cyclohexyl]-6-[8-[4-[(9S)-pentaen-7-yl]phenyl]-2,8-diazaspiro[4.5]decan-2-yl]pyridazine-3-carboxamide (I-17)

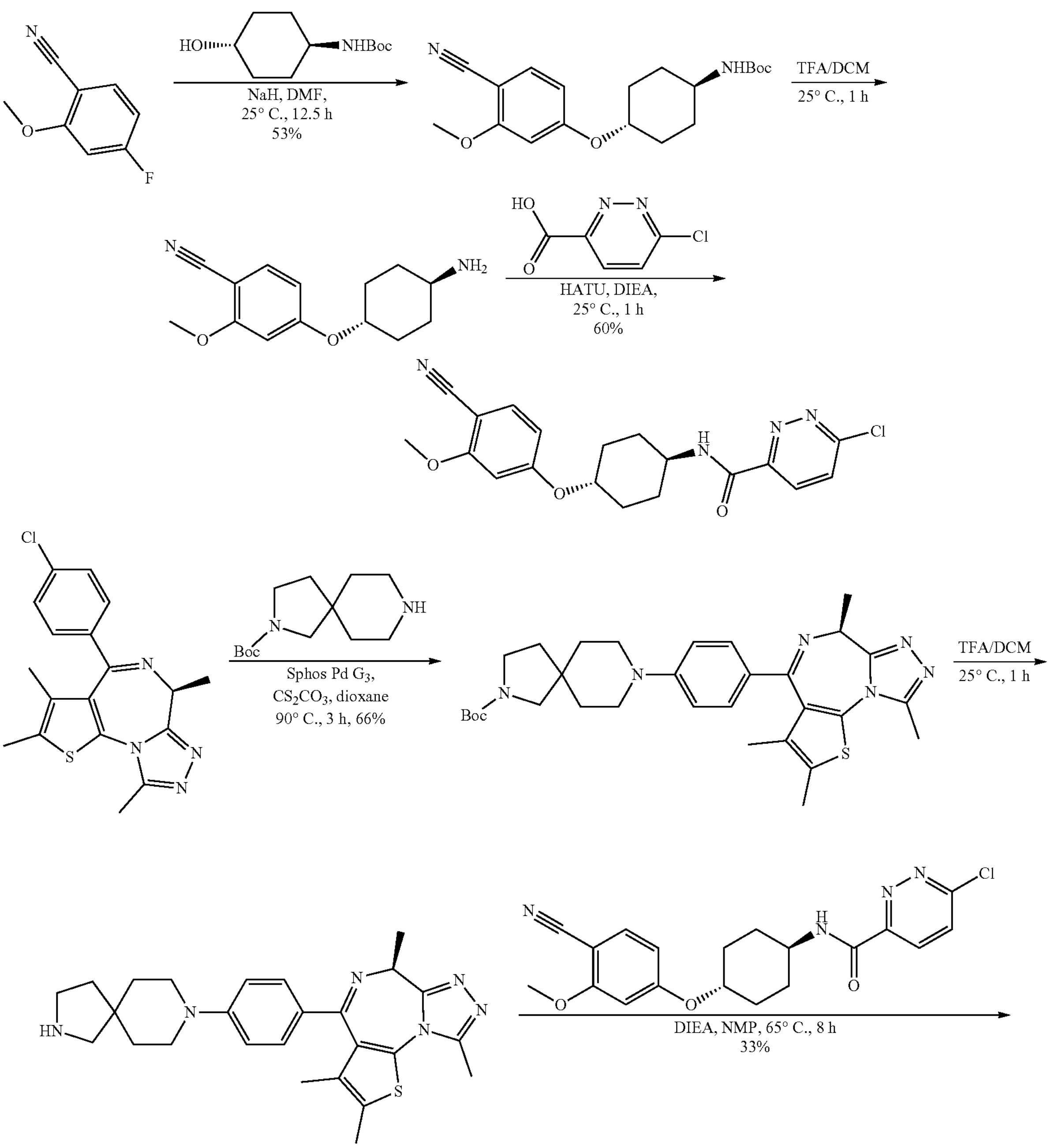

-continued

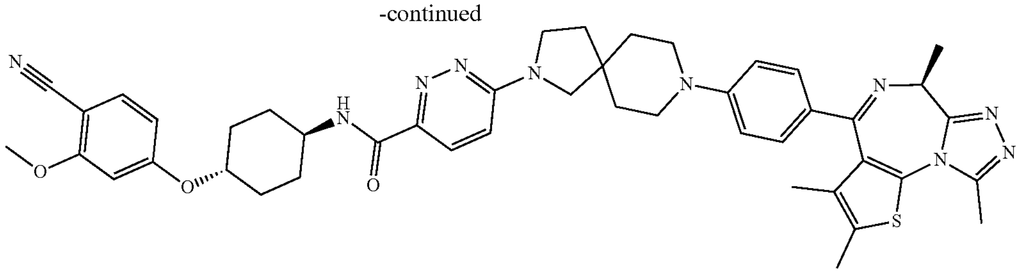

I-17

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxycyclohexyl) carbamate (5.6 g, 26.01 mmol, 1.0 equiv). After 30 minutes 4-fluoro-2-methoxybenzonitrile (3.93 g, 26.01 mmol, 1.0 equiv) was added. The reaction mixture was slowly allowed to reach 25° C. and stirred for 12 hours. The reaction mixture was quenched with saturated aqueous $NH_4Cl$ (100 mL) at 0° C. The resulting mixture was extracted with ethyl acetate (100 mL×3). The combined organic layers were dried over anhydrous $Na_2SO_4$, filtered, and concentrated in vacuo. The residue was purified by column chromatography ($SiO_2$, petroleum ether:ethyl acetate=0:1 to 3:1) to afford tert-butyl ((1r,4r)-4-(4-cyano-3-methoxyphenoxy)cyclohexyl) carbamate (4.8 g, 13.86 mmol, 53% yield) as a white solid.

Step 2: Preparation of 4-(((1r,4r)-4-aminocyclohexyl) oxy)-2-methoxybenzonitrile. To a solution of tert-butyl ((1r, 4r)-4-(4-cyano-3-methoxyphenoxy)cyclohexyl) carbamate (0.5 g, 1.44 mmol, 1.0 equiv) in DCM (2 mL) was added TFA (1 mL). The mixture was stirred at 25° C. for 1 hour. The reaction mixture was concentrated under reduced pressure to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-[4-(4-cyano-3-methoxy-phenoxy)cyclohexyl]pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 μL, 3.0 equiv). The mixture was stirred at 25° C. for 1 hour. The reaction mixture was concentrated under reduced pressure to provide a residue. The residue was purified by prep-HPLC (column: Waters xbridge 150 mm×25 mm×10 μm; mobile phase: [water ($NH_4HCO_3$)-ACN]; gradient: 49%-69% B over 8 min) to afford 6-chloro-N-[4-(4-cyano-3-methoxy-phenoxy)cyclohexyl]pyridazine-3-carboxamide (337 mg, 871 μmol, 60% yield) as a white solid.

Step 4: Preparation of tert-butyl 8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro [4.5]decane-2-carboxylate. A mixture of (9S)-7-(4-chlorophenyl)-4,5,9,13-tetramethyl-3-thia-1,8,11,12-tetrazatricyclo[8.3.0.0$^{2,6}$]trideca-2 (6),4,7,10,12-pentaene (200 mg, 560 μmol, 1.0 equiv), tert-butyl 2,8-diazaspiro[4.5] decane-2-carboxylate (202 mg, 840 μmol, 1.5 equiv), SPhos Pd G3 (88 mg, 112 μmol, 0.2 equiv), and $Cs_2CO_3$ (548 mg, 1.68 mmol, 3.0 equiv) in dioxane (3 mL) was degassed and purged with $N_2$ 3 times. The mixture was stirred at 90° C. for 3 hours under $N_2$ atmosphere. The reaction mixture was filtered and concentrated under reduced pressure to give a residue. The residue was purified by prep-HPLC (column: Phenomenex luna C18 150 mm×25 mm×10 μm; mobile phase: [water (FA)-ACN]; gradient: 28%-58% B over 25 min) to give tert-butyl 8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (210 mg, 374 μmol, 66% yield) as a yellow solid.

Step 5: Preparation of (9S)-7-[4-(2,8-diazaspiro[4.5]decan-8-yl)phenyl]-4,5,9,13-tetramethyl-3-thia-1,8,11,12-tetrazatricyclo[8.3.0.0$^{2,6}$]trideca-2 (6),4,7,10,12-pentaene. To a solution of tert-butyl 8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (210 mg, 374 μmol, 1.0 equiv) in DCM (2 mL) was added TFA (1 mL). The mixture was stirred at 25° C. for 1 hour and then concentrated in vacuo. The residue was basified by aqueous $NaHCO_3$ and then extracted with DCM: MeOH (10:1, 20 mL×3). The combined organic phase was washed with brine (40 mL), dried over anhydrous $Na_2SO_4$, filtered, and concentrated to give (9S)-7-[4-(2,8-diazaspiro [4.5]decan-8-yl)phenyl]-4,5,9,13-tetramethyl-3-thia-1,8,11,12-tetrazatricyclo[8.3.0.0$^{2,6}$]trideca-2 (6),4,7,10,12-pentaene (170 mg, 369 μmol) as a yellow solid.

Step 6: Preparation of N-[4-(4-cyano-3-methoxy-phenoxy)cyclohexyl]-6-[8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl] pyridazine-3-carboxamide (I-17). To a solution of (9S)-7-[4-(2,8-diazaspiro[4.5]decan-8-yl)phenyl]-4,5,9,13-tetramethyl-3-thia-1,8,11,12-tetrazatricyclo[8.3.0.0$^{2,6}$] trideca-2 (6),4,7,10,12-pentaene (100 mg, 217 μmol, 1.0 equiv) and 6-chloro-N-[4-(4-cyano-3-methoxy-phenoxy)cyclohexyl]pyridazine-3-carboxamide (109 mg, 282 μmol, 1.3 equiv) in NMP (1 mL) was added DIEA (85 mg, 651 μmol, 0.1 mL, 3.0 equiv). The mixture was stirred at 65° C. for 8 hours. The reaction mixture was filtered and concentrated under reduced pressure to give a residue. The residue was purified by prep-HPLC (column: Waters Xbridge C18 150 mm×50 mm×10 μm; mobile phase: [water ($NH_4HCO_3$)-ACN]; gradient: 45%-75% B over 10 min) to give N-[4-(4-cyano-3-methoxy-phenoxy) cyclohexyl]-6-[8-[4-[(9S)-4,5,9,13-tetramethyl-3-thia-1,8,11,12-tetrazatricyclo[8.3.0.0$^{2,6}$] trideca-2 (6),4,7,10,12-pentaen-7-yl]phenyl]-2,8-diazaspiro [4.5]decan-2-yl]pyridazine-3-carboxamide (58.59 mg, 71.79 μmol, 33% yield, 99.37% purity) as a yellow solid. $^1H$ NMR (400 MHz, $CD_3OD$) δ 7.94 (d, J=9.5 Hz, 1H), 7.52 (d, J=9.3 Hz, 1H), 7.36 (d, J=8.8 Hz, 2H), 7.01 (dd, J=9.3, 18.0 Hz, 3H), 6.73-6.63 (m, 2H), 4.56-4.43 (m, 1H), 4.30-4.20 (m, 1H), 4.04-3.96 (m, 1H), 3.93 (s, 3H), 3.71 (br d, J=3.4 Hz, 2H), 3.61-3.41 (m, 4H), 3.38-3.34 (m, 2H), 2.71 (s, 3H), 2.46 (s, 3H), 2.28-2.18 (m, 2H), 2.16-2.03 (m, 4H), 1.99 (d, J=6.8 Hz, 3H), 1.86-1.78 (m, 4H), 1.75 (s, 3H), 1.65 (br t, J=9.6 Hz, 4H). LC-MS: MS ($ES^+$): RT=1.597 min, m/z=811.4 $[M+H]^+$.

Example 34—Synthesis of N-[4-[4-cyano-3-(trifluoromethoxy)phenoxy]cyclohexyl]-6-[8-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-2)
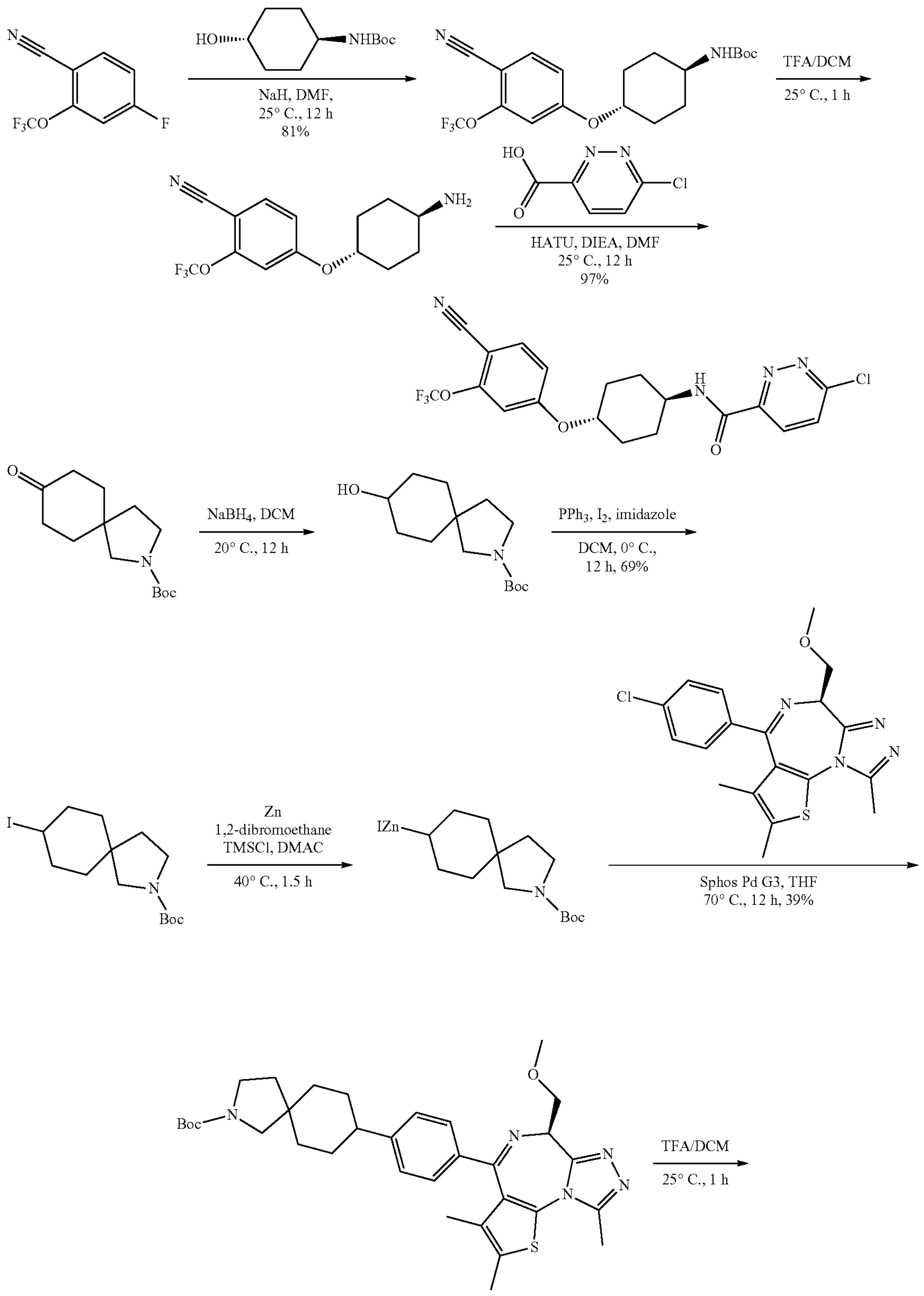

-continued

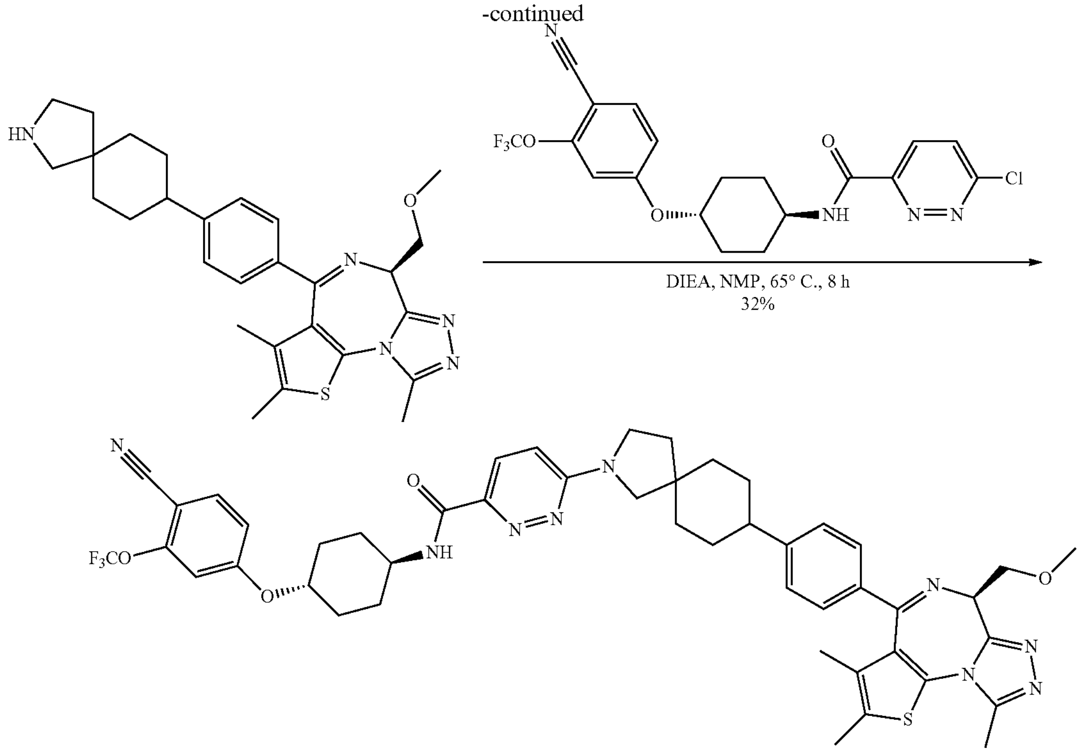

I-2

Step 1: Preparation of tert-butyl ((1r,4r)-4-(4-cyano-3-(trifluoromethoxy) phenoxy)cyclohexyl) carbamate. To a solution of tert-butyl ((1r,4r)-4-hydroxycyclohexyl) carbamate (3.15 g, 14.63 mmol, 1.5 equiv) in DMF (20 mL) and THF (20 mL) was added NaH (585 mg, 14.63 mmol, 60% purity, 1.5 equiv) at 0° C. The mixture was stirred at 25° C. for 0.5 hour. Next, 4-fluoro-2-(trifluoromethoxy) benzonitrile (2 g, 9.75 mmol, 1.0 equiv) was added. The mixture was stirred at 25° C. for 12 hours. The reaction mixture was quenched with saturated aqueous $NH_4Cl$ (20 mL) at 0° C. and then extracted with EtOAc (50 mL×3). The combined organic layers were washed with $H_2O$ (100 mL×3), dried over anhydrous $Na_2SO_4$, filtered, and concentrated under reduced pressure to give a residue. The residue was purified by column chromatography ($SiO_2$, petroleum ether:ethyl acetate=20:1 to 5:1). Compound tert-butyl ((1r,4r)-4-(4-cyano-3-(trifluoromethoxy)phenoxy)cyclohexyl) carbamate (3.15 g, 7.87 mmol, 81% yield) was obtained as a white solid.

Step 2: Preparation of 4-(((1r,4r)-4-aminocyclohexyl) oxy)-2-(trifluoromethoxy) benzonitrile. To a solution of tert-butyl ((1r,4r)-4-(4-cyano-3-(trifluoromethoxy)phenoxy) cyclohexyl) carbamate (3.14 g, 7.84 mmol, 1.0 equiv) in DCM (20 mL) was added TFA (10 mL). The mixture was stirred at 25° C. for 1 hour. The reaction mixture was concentrated to afford 4-(((1r,4r)-4-aminocyclohexyl)oxy)-2-(trifluoromethoxy) benzonitrile (3.25 g, 7.84 mmol, TFA salt) as a colorless oil.

Step 3: Preparation of 6-chloro-N-((1r,4r)-4-(4-cyano-3-(trifluoromethoxy) phenoxy)cyclohexyl) pyridazine-3-carboxamide. To a solution of 4-(((1r,4r)-4-amino-cyclohexyl) oxy)-2-(trifluoromethoxy) benzonitrile (3.25 g, 7.84 mmol, 1.0 equiv, TFA salt) and 6-chloropyridazine-3-carboxylic acid (1.24 g, 7.84 mmol, 1.0 equiv) in DMF (20 mL) was added DIEA (3.04 g, 23.53 mmol, 4.10 mL, 3.0 equiv) and HATU (4.47 g, 11.77 mmol, 1.5 equiv). The mixture was stirred at 25° C. for 0.5 hour. The reaction mixture was added to ice water (200 mL) and filtered to afford 6-chloro-N-((1r,4r)-4-(4-cyano-3-(trifluoromethoxy)phenoxy)cyclohexyl) pyridazine-3-carboxamide (3.34 g, 7.58 mmol, 97% yield) as a white solid.

Step 4: Preparation of tert-butyl 8-hydroxy-2-azaspiro[4.5]decane-2-carboxylate. To a solution of tert-butyl 8-oxo-2-azaspiro[4.5]decane-2-carboxylate (2 g, 7.8 mmol, 1 equiv) in DCM (20 mL) was added $NaBH_4$ (400 mg, 10 mmol, 1.3 equiv). The mixture was stirred at 20° C. for 12 hours. The reaction mixture was filtered, and the filtrate was concentrated under reduced pressure to give crude product tert-butyl 8-hydroxy-2-azaspiro[4.5]decane-2-carboxylate as a residue.

Step 5: Preparation of tert-butyl 8-iodo-2-azaspiro[4.5] decane-2-carboxylate. To a solution of tert-butyl 8-hydroxy-2-azaspiro[4.5]decane-2-carboxylate (2 g, 7.8 mmol, 1 equiv) in DCM (20 mL) was added $PPh_3$ (2.8 g, 10 mmol, 1.4 equiv), imidazole (1.6 g, 23 mmol, 3 equiv), and $I_2$ (2.9 g, 11 mmol, 2 mL, 1.5 equiv). The mixture was stirred at 40° C. for 12 hours. The reaction mixture was filtered and concentrated under reduced pressure to give a residue. The residue was purified by prep-TLC ($SiO_2$, ethyl acetate: petroleum ether=5:1) to afford tert-butyl 8-iodo-2-azaspiro[4.5]decane-2-carboxylate (2 g, 69% yield) as a white oil.

Step 6: Preparation of (2-tert-butoxycarbonyl-2-azaspiro[4.5]decan-8-yl)-iodo-zinc. To a stirred solution of Zn (830 mg, 12 mmol, 5.8 equiv) in DMAC (2 mL) was added TMSCl (88 mg, 810 μmol, 102 μL, 0.37 equiv) and 1,2-dibromoethane (152 mg, 810 μmol, 61 μL, 0.37 equiv) in DMAC (1 mL) at 40° C. After stirring for 30 minutes, tert-butyl 8-iodo-2-azaspiro[4.5]decane-2-carboxylate (800 mg, 2 mmol, 1 equiv) was added. The mixture was stirred at 40° C. for an additional 1 hour and filtered. The filtrate was concentrated to afford crude (2-tert-butoxycarbonyl-2-azaspiro[4.5]decan-8-yl)-iodo-zinc.

Step 7: Preparation of tert-butyl 8-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate. To a solution of (9R)-7-(4-chlorophenyl)-9-(methoxymethyl)-4,5,13-trimethyl-3-thia-1,8,11,12-tetrazatricyclo[8.3.0.0$^{2,6}$]trideca-2 (6),4,7,10,12-pentaene (202 mg, 522 μmol, 1 equiv) and (2-tert-butoxycarbonyl-2-azaspiro[4.5]decan-8-yl)-iodo-zinc (900 mg, 2.09 mmol, 4 equiv) in THF (2 mL) was added SPhos Pd G3 (81 mg, 104 μmol, 0.2 equiv). The mixture was stirred at 70° C. for 12 hours. The reaction mixture was diluted with water (80 mL) and extracted with EtOAc (80 mL×3). The combined organic layers were washed with brine (300 mL), dried over $Na_2SO_4$, filtered, and concentrated under reduced pressure to give a residue. The residue was purified by prep-HPLC (FA condition; column: Phenomenex luna C18 150 mm×25 mm×10 μm; mobile phase: [water (FA)-ACN]; gradient: 66%-96% B over 10 min) to give tert-butyl 8-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (120 mg, 39% yield).

Step 8: Preparation of (9R)-7-[4-(2-azaspiro[4.5]decan-8-yl)phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene. To a solution of tert-butyl 8-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (70 mg, 118 μmol, 1.0 equiv) in DCM (1 mL) was added TFA (0.5 mL). The mixture was stirred at 25° C. for 1 hour. The reaction mixture was concentrated, basified with aqueous $NaHCO_3$ and extracted with DCM/MeOH (10:1, 10 mL×3). The organic phase was combined, dried over anhydrous $Na_2SO_4$, filtered, and concentrated to give (9R)-7-[4-(2-azaspiro[4.5]decan-8-yl)phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene (110 mg, 224 μmol) as a yellow solid.

Step 9: Preparation of N-[4-[4-cyano-3-(trifluoromethoxy)phenoxy]cyclohexyl]-6-[8-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (1-2). To a solution of (9R)-7-[4-(2-azaspiro[4.5]decan-8-yl) phenyl]-9-(methoxymethyl)-4,5,13-trimethyl-3-thia-1,8,11,12-tetrazatricyclo[8.3.0.0$^{2,6}$]trideca-2 (6),4,7,10,12-pentaene (55 mg, 112 μmol, 1.0 equiv) and 6-chloro-N-[4-[4-cyano-3-(trifluoromethoxy)phenoxy]cyclohexyl]pyridazine-3-carboxamide (65 mg, 146 μmol, 1.3 equiv) in NMP (0.5 mL) was added DIEA (45 mg, 336 μmol, 0.1 mL, 3.0 equiv). The mixture was stirred at 65° C. for 8 hours. The residue was purified by prep-HPLC (column: Waters xbridge 150 mm×25 mm×10 μm; mobile phase: [water ($NH_4HCO_3$)-ACN]; gradient: 65%-85% B over 8 min) to give N-[4-[4-cyano-3-(trifluoromethoxy)phenoxy]cyclohexyl]-6-[8-[4-[(9R)-9-(methoxymethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (32.72 mg, 36.05 μmol, 32.09% yield, 98.49% purity) as a white solid. $^1$H NMR (400 MHz, $CD_3OD$) δ 7.94 (d, J=9.5 Hz, 1H), 7.78 (d, J=8.8 Hz, 1H), 7.49-7.42 (m, 2H), 7.35 (d, J=8.3 Hz, 2H), 7.16 (dd, J=2.3, 8.7 Hz, 1H), 7.08 (s, 2H), 4.38 (br d, J=11.9 Hz, 3H), 4.05-3.94 (m, 1H), 3.57 (s, 7H), 2.72 (s, 3H), 2.70-2.61 (m, 1H), 2.46 (s, 3H), 2.24 (br s, 2H), 2.16-2.08 (m, 2H), 1.98 (t, J=7.1 Hz, 2H), 1.93-1.81 (m, 4H), 1.74-1.62 (m, 11H). LC-MS: MS ($ES^+$): RT=2.305 min, m/z=894.6 $[M+H]^+$; LCMS method: 25.

Example 35—Synthesis of N-[4-[4-cyano-3-(trifluoromethoxy)phenoxy]cyclohexyl]-6-[8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-4)

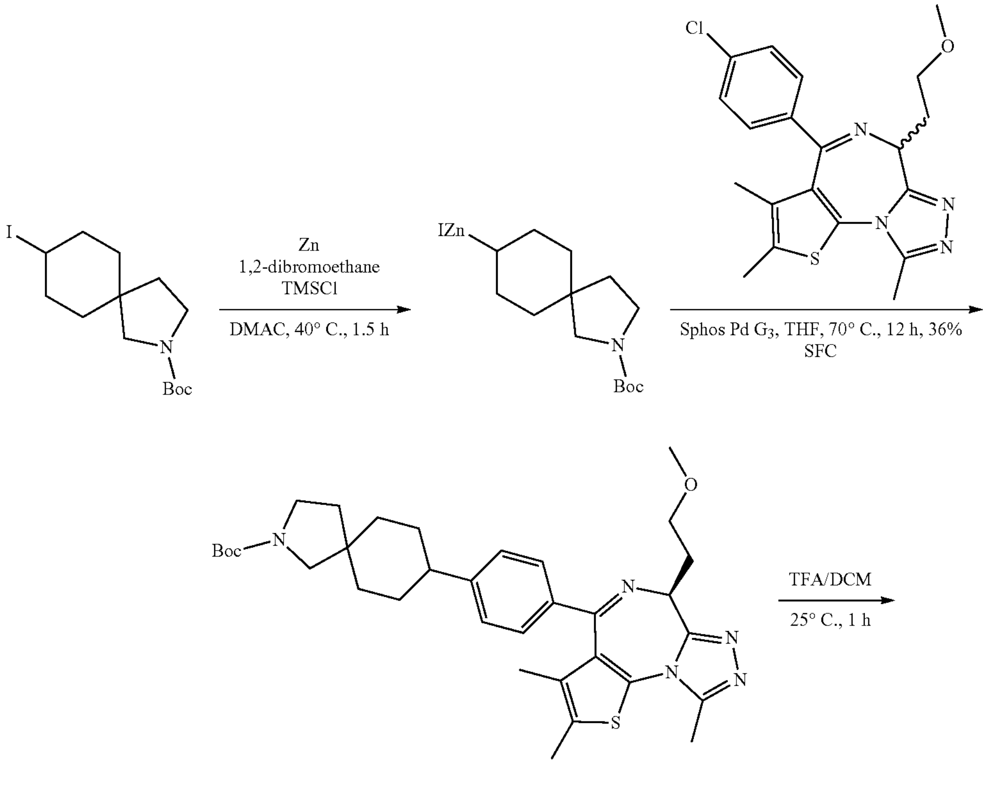

-continued

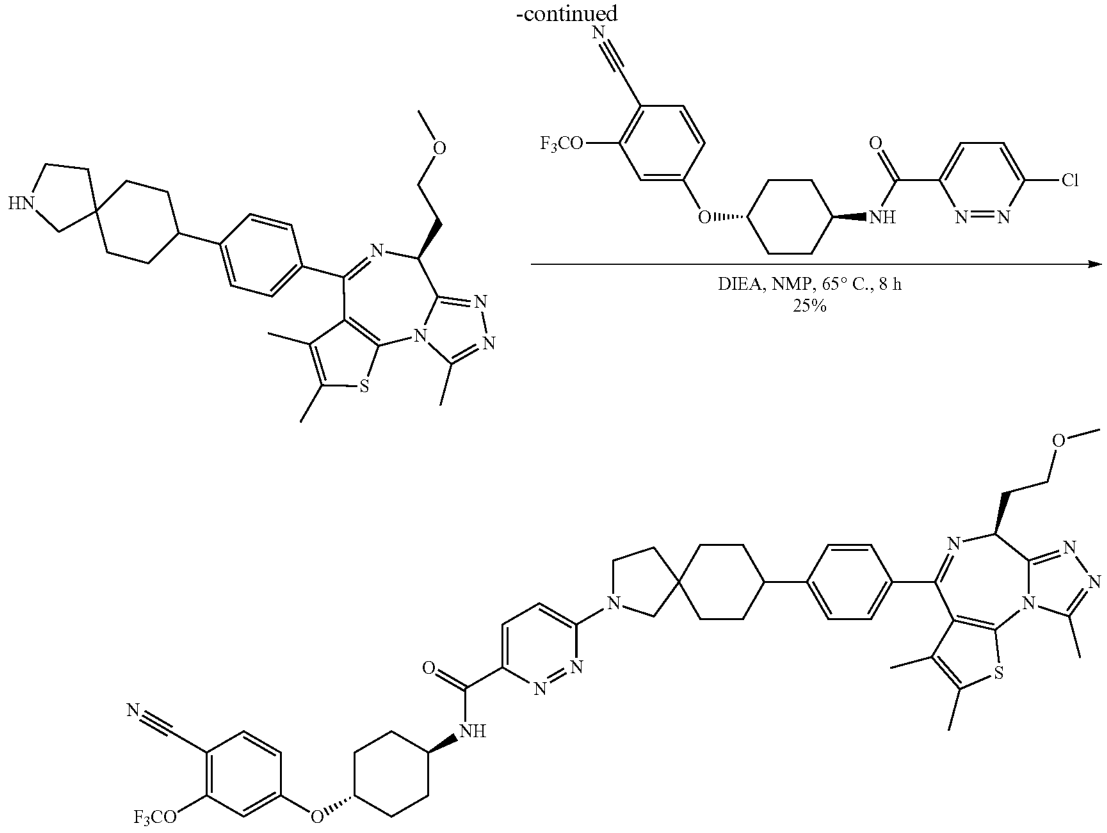

I-4

Step 1: Preparation of (2-tert-butoxycarbonyl-2-azaspiro[4.5]decan-8-yl)-iodo-zinc. To a stirred solution of Zn (1.4 g, 22 mmol, 10 equiv) in DMAC (2 mL) was added TMSCl (88 mg, 810 μmol, 102 μL, 0.37 equiv) and 1,2-dibromoethane (152 mg, 810 μmol, 61 μL, 0.37 equiv) in DMAC (1 mL) at 40° C. After stirring for 30 minutes, tert-butyl 8-iodo-2-azaspiro[4.5]decane-2-carboxylate (800 mg, 2 mmol, 1 equiv) was added. The mixture was stirred at 40° C. for an additional 1 hour and then filtered. After filtration, the filtrate was concentrated to afford crude (2-tert-butoxycarbonyl-2-azaspiro[4.5]decan-8-yl)-iodo-zinc.

Step 2: Preparation of tert-butyl 8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate. To a solution of (2-tert-butoxycarbonyl-2-azaspiro[4.5]decan-8-yl)-iodo-zinc (940 mg, 2 mmol, 4 equiv) and (9S)-7-(4-chlorophenyl)-9-(2-methoxyethyl)-4,5,13-trimethyl-3-thia-1,8,11,12-tetrazatricyclo[8.3.0.0$^{2,6}$]trideca-2 (6), 4,7,10,12-pentaene (200 mg, 498 μmol, 1 equiv) in THF (1 mL) was added SPhos Pd G3 (77 mg, 99 μmol, 0.2 equiv). The mixture was stirred at 70° C. for 12 hours. The residue was purified by prep-HPLC (column: Phenomenex luna C18 150 mm×25 mm×10 μm; mobile phase: [water (FA)-ACN]; gradient: 68%-98% B over 10 min) to afford tert-butyl 8-[4-[(9S)-9-(2-methoxyethyl)-4,5,13-trimethyl-3-thia-1,8,11,12-tetrazatricyclo[8.3.0.0$^{2,6}$]trideca-2 (6), 4,7,10,12-pentaen-7-yl]phenyl]-2-azaspiro[4.5]decane-2-carboxylate (110 mg, 182 μmol, 36% yield) as a white solid. The residue (110 mg, 182 μmol) was separated by chiral SFC (column: DAICEL CHIRALPAK IK (250 mm×50 mm, 10 μm); mobile phase: [$CO_2$-ACN/i-PrOH (0.1% $NH_3 \cdot H_2O$)]; B %: 60%, isocratic elution mode) and then further purified by chiral SFC (column: DAICEL CHIRALPAK IK (250 mm×30 mm, 10 μm); mobile phase: [$CO_2$-ACN/i-PrOH (0.1% $NH_3 \cdot H_2O$)]; B %: 50%, isocratic elution mode) to give desired enantiopure product (47 mg, 76 μmol, 42% yield) as a white solid.

Step 3: Preparation of (9S)-7-[4-(2-azaspiro[4.5]decan-8-yl)phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene. To a solution of tert-butyl 8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decane-2-carboxylate (75 mg, 124 μmol, 1.0 equiv) in DCM (1 mL) was added TFA (0.5 mL). The mixture was stirred at 25° C. for 1 hour. The reaction mixture was concentrated, basified with aqueous $NaHCO_3$, and extracted with DCM/MeOH (10:1, 10 mL×3). The organic phase was combined, dried over $Na_2SO_4$, filtered, and concentrated to afford (9S)-7-[4-(2-azaspiro[4.5]decan-8-yl)phenyl]-9-(2-methoxyethyl)-4,5,13-trimethyl-3-thia-1,8,11,12-tetrazatricyclo[8.3.0.0$^{2,6}$]trideca-2 (6),4,7,10,12-pentaene (120 mg, 238 μmol) as a yellow solid.

Step 4: Preparation of N-[4-[4-cyano-3-(trifluoromethoxy)phenoxy]cyclohexyl]-6-[8-[4-[(9S)-9-(2-methoxyethyl)-4,5,13-trimethyl-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyridazine-3-carboxamide (I-4). To a solution of (9S)-7-[4-(2-azaspiro[4.5]decan-8-yl)phenyl]-9-(2-methoxyethyl)-4,5,13-trimethyl-3-thia-1,8,11,12-tetrazatricyclo[8.3.0.0$^{2,6}$]trideca-2 (6), 4,7,10,12-pentaene (60 mg, 120 μmol, 1.0 equiv) and 6-chloro-N-[4-[4-cyano-3-(trifluoromethoxy)phenoxy]cyclohexyl]pyridazine-3-carboxamide (68 mg, 155 μmol, 1.3 equiv) in NMP (0.5 mL) was added DIEA (50 mg, 357 μmol, 0.1 mL, 3.0 equiv). The mixture was stirred at 65° C. for 8 hours. The reaction mixture was filtered and concentrated to give a residue. The residue was purified by prep-HPLC (column: Waters xbridge 150 mm×25 mm×10 μm; mobile phase: [water ($NH_4HCO_3$)-ACN]; gradient: 67%-87% B over 8 min) to afford N-[4-[4-cyano-3-(trifluoromethoxy)phenoxy]cyclohexyl]-6-[8-[4-[(9S)-9-(2-methoxyethyl)-4,5,13-trimethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]pyridazine-3-carboxamide (28.26 mg, 30.80 μmol, 25.86% yield, 98.96% purity) as a white solid. $^1$H NMR (400 MHz, $CD_3OD$) δ 7.94 (d, J=9.5 Hz, 1H), 7.78 (d, J=8.8 Hz, 1H), 7.47-7.40 (m, 2H), 7.39-7.31 (m, 2H), 7.16 (dd, J=2.3, 8.8 Hz, 1H), 7.08 (s, 2H), 4.27 (t, J=7.2 Hz, 1H), 4.05-3.96 (m, 1H), 3.88-3.83 (m, 1H), 3.81-3.76 (m, 1H), 3.73-3.58 (m, 3H), 3.37 (s, 3H), 2.76-2.70 (m, 5H), 2.69-2.63 (m, 1H), 2.46 (s, 3H), 2.28-2.20 (m, 2H), 2.18-2.09 (m, 2H), 2.01-1.94 (m, 2H), 1.93-1.82 (m, 4H), 1.69 (s, 11H). LC-MS: MS ($ES^+$): RT=2.331 min, m/z=908.1 $[M+H]^+$; LCMS Method: 25.

Example 36—Synthesis of N-[4-(4-cyano-3-methoxy-phenoxy)cyclohexyl]-6-[6-[2-[4-(4,5,13-trimethylspiro[3-thia-1,8,11,12-tetrazatricyclo[8.3.0.$0^{2,6}$]trideca-2 (6),4,7,10,12-pentaene-9,1'-cyclopropane]-7-yl)phenyl]ethynyl]-2-azaspiro[3.3]heptan-2-yl]pyridazine-3-carboxamide (I-34)

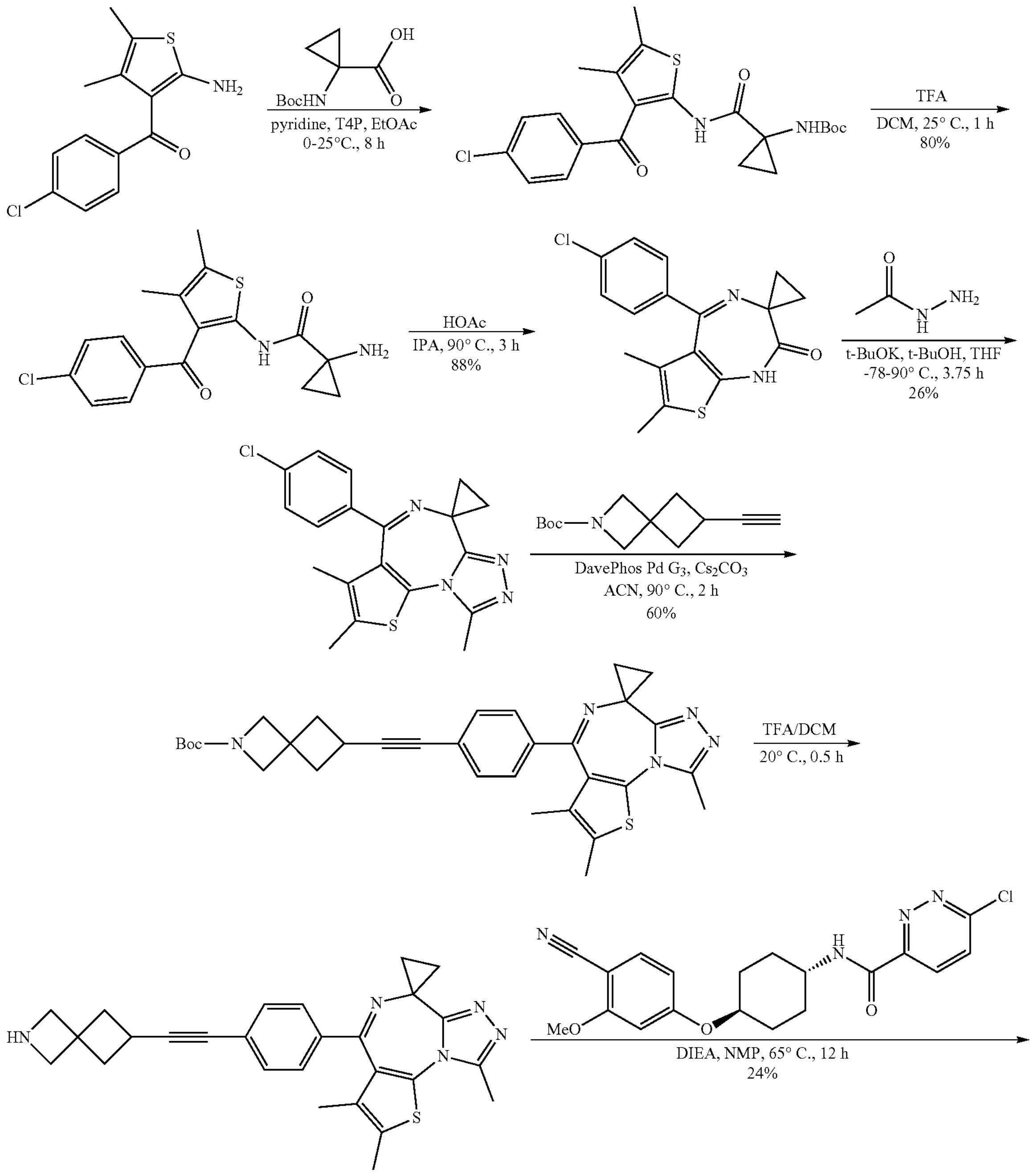

-continued

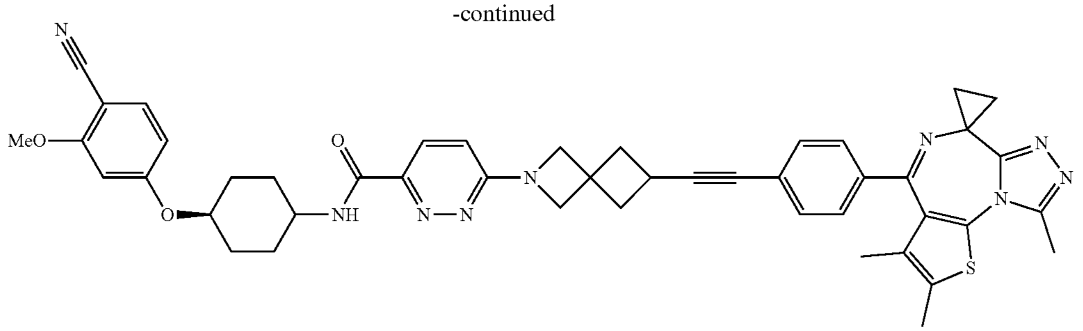

I-34

Step 1: Preparation of tert-butyl N-[1-[[3-(4-chlorobenzoyl)-4,5-dimethyl-2-thienyl]carbamoyl]cyclopropyl]carbamate. To a solution of (2-amino-4,5-dimethyl-3-thienyl)-(4-chlorophenyl) methanone (26 g, 97.8 mmol, 1.0 equiv), 1-(tert-butoxycarbonylamino) cyclopropanecarboxylic acid (59 g, 293.5 mmol, 3.0 equiv), and pyridine (38.7 g, 489 mmol, 39.5 mL, 5.0 equiv) in EtOAc (50 mL) was added T4P (211.5 g, 293.5 mmol, 50% purity, 3.0 equiv) at 0° C. The mixture was stirred at 25° C. for 8 hours. The reaction mixture was concentrated under reduced pressure to remove solvent. The residue was diluted with saturated aqueous $NaHCO_3$ (100 mL) and extracted with ethyl acetate 500 mL (250 mL×2). The combined organic layers were washed with brine (200 mL), dried over $Na_2SO_4$, filtered, and concentrated under reduced pressure to give a residue. The residue was triturated with petroleum ether:ethyl acetate (3:1, 200 mL) to give tert-butyl N-[1-[[3-(4-chlorobenzoyl)-4,5-dimethyl-2-thienyl]carbamoyl]cyclopropyl]carbamate (48 g, crude) as a yellow solid.

Step 2: Preparation of 1-amino-N-[3-(4-chlorobenzoyl)-4,5-dimethyl-2-thienyl]cyclopropane carboxamide. To a solution of tert-butyl N-[1-[[3-(4-chlorobenzoyl)-4,5-dimethyl-2-thienyl]carbamoyl]cyclopropyl]carbamate (43 g, 95.8 mmol, 1.0 equiv) in DCM (140 mL) was added TFA (218 g, 1.9 mol, 142 mL, 20.0 equiv). The mixture was stirred at 25° C. for 1 hour. The reaction mixture was concentrated under reduced pressure to remove solvent. The residue was diluted with saturated aqueous $NaHCO_3$ (200 mL) and extracted with ethyl acetate 500 mL (250 mL×2). The combined organic layers were washed with brine (100 mL), dried over $Na_2SO_4$, filtered, and concentrated under reduced pressure to give 1-amino-N-[3-(4-chlorobenzoyl)-4,5-dimethyl-2-thienyl]cyclopropane carboxamide (27 g, 80% yield) as a yellow solid.

Step 3: Preparation of 5-(4-chlorophenyl)-6,7-dimethyl-spiro[1H-thieno[2,3-e][1,4]diazepine-3,1'-cyclopropane]-2-one. To a solution of 1-amino-N-[3-(4-chlorobenzoyl)-4,5-dimethyl-2-thienyl]cyclopropane carboxamide (27 g, 77.4 mmol, 1.0 equiv) in IPA (270 mL) was added AcOH (23.2 g, 387 mmol, 22 mL, 5.0 equiv). The mixture was stirred at 90° C. for 1 hour. The reaction mixture was concentrated under reduced pressure to remove solvent. The residue was triturated with ethyl acetate (200 mL) to give 5-(4-chlorophenyl)-6,7-dimethyl-spiro[1H-thieno[2,3-e][1,4]diazepine-3,1'-cyclopropane]-2-one (22.6 g, 88% yield) as a yellow solid.

Step 4: Preparation of 7-(4-chlorophenyl)-4,5,13-trimethyl-spiro[3-thia-1,8,11,12-tetrazatricyclo[8.3.0.0$^{2,6}$]trideca-2 (6),4,7,10,12-pentaene-9,1'-cyclopropane]. Potassium tert-butoxide (1 M, 6.7 mL, 1.1 equiv) was added to a solution of 5-(4-chlorophenyl)-6,7-dimethyl-spiro[1H-thieno[2,3-e][1,4]diazepine-3,1'-cyclopropane]-2-one (2 g, 6 mmol, 1.0 equiv) in THF (25 mL) at −78° C. The reaction mixture was warmed to −10° C. over 0.5 hour and stirred at 25° C. for 0.5 hour. The reaction mixture was cooled to −78° C. [Chloro(phenoxy) phosphoryl]oxybenzene (1.95 g, 7.3 mmol, 1.5 mL, 1.2 equiv) was added to the reaction mixture. The resulting mixture was warmed to −10° C. over 0.75 hour. Next, acetohydrazide (672 mg, 9 mmol, 1.5 equiv) was added to the reaction mixture. The reaction mixture was stirred at 25° C. After 1 hour, tert-BuOH (30 mL) was added, and the reaction mixture was heated to 90° C. for 1 hour. The mixture was poured into water (100 mL) and extracted with DCM (200 mL×2). The combined organic layer was washed with brine (200 mL) and dried over $Na_2SO_4$. The mixture was concentrated to give a residue. The residue was purified by prep-HPLC (column: Phenomenex luna C18 150 mm×40 mm×15 μm; mobile phase: [water (FA)-ACN]; gradient: 37%-67% B over 15 min) to give 7-(4-chlorophenyl)-4,5,13-trimethyl-spiro[3-thia-1,8,11,12-tetrazatricyclo[8.3.0.0$^{2,6}$]trideca-2 (6),4,7,10,12-pentaene-9, l'-cyclopropane] (600 mg, 26% yield) as a white solid.

Step 5: Preparation of tert-butyl 6-[2-[4-(4,5,13-trimethylspiro[3-thia-1,8,11,12-tetrazatricyclo[8.3.0.0$^{2,6}$]trideca-2 (6),4,7,10,12-pentaene-9,1'-cyclopropane]-7-yl)phenyl]ethynyl]-2-azaspiro[3.3]heptane-2-carboxylate. To a solution of 7-(4-chlorophenyl)-4,5,13-trimethyl-spiro[3-thia-1,8,11,12-tetrazatricyclo[8.3.0.0$^{2,6}$]trideca-2 (6),4,7,10,12-pentaene-9,1'-cyclopropane] (400 mg, 1.08 mmol, 1.0 equiv) and tert-butyl 6-ethynyl-2-azaspiro[3.3]heptane-2-carboxylate (599 mg, 2.71 mmol, 2.5 equiv) in ACN (8 mL) was added DavePhos Pd G3 (82.7 mg, 108 μmol, 0.1 equiv) and $Cs_2CO_3$ (706 mg, 2.17 mmol, 2.0 equiv). The mixture was stirred at 90° C. for 2 hours. The reaction mixture was filtered, and the filtrate was concentrated to afford a residue. The residue was purified by prep-HPLC (column: Phenomenex luna C18 150 mm×40 mm×15 μm; mobile phase: [water (FA)-ACN]; gradient: 55%-85% B over 15 min) to give tert-butyl 6-[2-[4-(4,5,13-trimethylspiro[3-thia-1,8,11,12-tetrazatricyclo[8.3.0.0$^{2,6}$]trideca-2 (6),4,7,10,12-pentaene-9,1'-cyclopropane]-7-yl)phenyl]ethynyl]-2-azaspiro[3.3]heptane-2-carboxylate (360 mg, 650 μmol, 60% yield) as a yellow solid.

Step 6: Preparation of 7-[4-[2-(2-azaspiro[3.3]heptan-6-yl)ethynyl]phenyl]-4,5,13-trimethyl-spiro[3-thia-1,8,11,12-tetrazatricyclo[8.3.0.0$^{2,6}$]trideca-2 (6),4,7,10,12-pentaene-9, 1'-cyclopropane]. To a solution of tert-butyl 6-[2-[4-(4,5,13-trimethylspiro[3-thia-1,8,11,12-tetrazatricyclo[8.3.0.0$^{2,6}$]trideca-2 (6),4,7,10,12-pentaene-9,1'-cyclopropane]-7-yl)phenyl]ethynyl]-2-azaspiro[3.3]heptane-2-carboxylate (180 mg, 325 μmol, 1.0 equiv) in DCM (2 mL) was added TFA (1 mL). The mixture was stirred at 20° C. for 0.5 hour. The reaction mixture was concentrated, basified with aqueous $NaHCO_3$, and extracted with DCM/MeOH (10:1, 30 mL×2). The combined organic phase was washed with brine (10 mL×2), dried over anhydrous $Na_2SO_4$, filtered, and concentrated to afford 7-[4-[2-(2-azaspiro[3.3]heptan-6-yl)ethynyl]phenyl]-4,5,13-trimethyl-spiro[3-thia-1,8,11,12-tetrazatricyclo[8.3.0.$0^{2,6}$]trideca-2 (6),4,7,10,12-pentaene-9,1'-cyclopropane] (146 mg, 321 μmol, crude) as a yellow oil, which was used directly in the next step without purification.

Step 7: Preparation of N-[4-(4-cyano-3-methoxy-phenoxy)cyclohexyl]-6-[6-[2-[4-(4,5,13-trimethylspiro[3-thia-1,8,11,12-tetrazatricyclo[8.3.0.$0^{2,6}$]trideca-2 (6),4,7,10,12-pentaene-9,1'-cyclopropane]-7-yl)phenyl]ethynyl]-2-azaspiro[3.3]heptan-2-yl]pyridazine-3-carboxamide (I-34). To a solution of 7-[4-[2-(2-azaspiro[3.3]heptan-6-yl)ethynyl]phenyl]-4,5,13-trimethyl-spiro[3-thia-1,8,11,12-tetrazatricyclo[8.3.0.$0^{2,6}$]trideca-2 (6),4,7,10,12-pentaene-9,1'-cyclopropane] (73.0 mg, 160 μmol, 1.0 equiv) in NMP (1 mL) was added DIEA (62.4 mg, 482 μmol, 84.1 μL, 3.0 equiv) and 6-chloro-N-[4-(4-cyano-3-methoxy-phenoxy)cyclohexyl]pyridazine-3-carboxamide (62.2 mg, 160 μmol, 1.0 equiv). The mixture was stirred at 65° C. for 12 hours. The residue was purified by prep-HPLC (column: Waters xbridge 150 mm×25 mm×10 μm; mobile phase: [water ($NH_4HCO_3$)-ACN]; gradient: 52%-72% B over 8 min) to afford N-[4-(4-cyano-3-methoxy-phenoxy)cyclohexyl]-6-[6-[2-[4-(4,5,13-trimethylspiro[3-thia-1,8,11,12-tetrazatricyclo[8.3.0.$0^{2,6}$]trideca-2 (6),4,7,10,12-pentaene-9,1'-cyclopropane]-7-yl)phenyl]ethynyl]-2-azaspiro[3.3]heptan-2-yl]pyridazine-3-carboxamide (31.5 mg, 39.1 μmol, 24% yield) as a white solid. $^1$H NMR (400 MHz, $CD_3OD$) δ 7.91 (d, J=9.4 Hz, 1H), 7.50 (d, J=8.9 Hz, 1H), 7.45-7.40 (m, 4H), 6.85 (d, J=9.3 Hz, 1H), 6.70-6.63 (m, 2H), 4.53-4.44 (m, 1H), 4.24 (d, J=6.1 Hz, 4H), 3.99-3.90 (m, 4H), 3.25 (t, J=8.0 Hz, 1H), 2.77-2.68 (m, 5H), 2.51-2.42 (m, 5H), 2.25-2.17 (m, 2H), 2.09 (br d, J=1.7 Hz, 2H), 1.90 (dt, J=5.4, 8.7 Hz, 1H), 1.68-1.59 (m, 7H), 1.58-1.50 (m, 1H), 0.94-0.86 (m, 2H). LC-MS: MS ($ES^+$): RT=2.191 min, m/z=804.6 $[M+H]^+$.

Example 37—Synthesis of N-[4-(4-cyano-3-methoxy-phenoxy)cyclohexyl]-6-[8-[4-[(9S)-pentaen-7-yl]phenoxy]-2-azaspiro[4.4]nonan-2-yl]pyridazine-3-carboxamide (I-49)

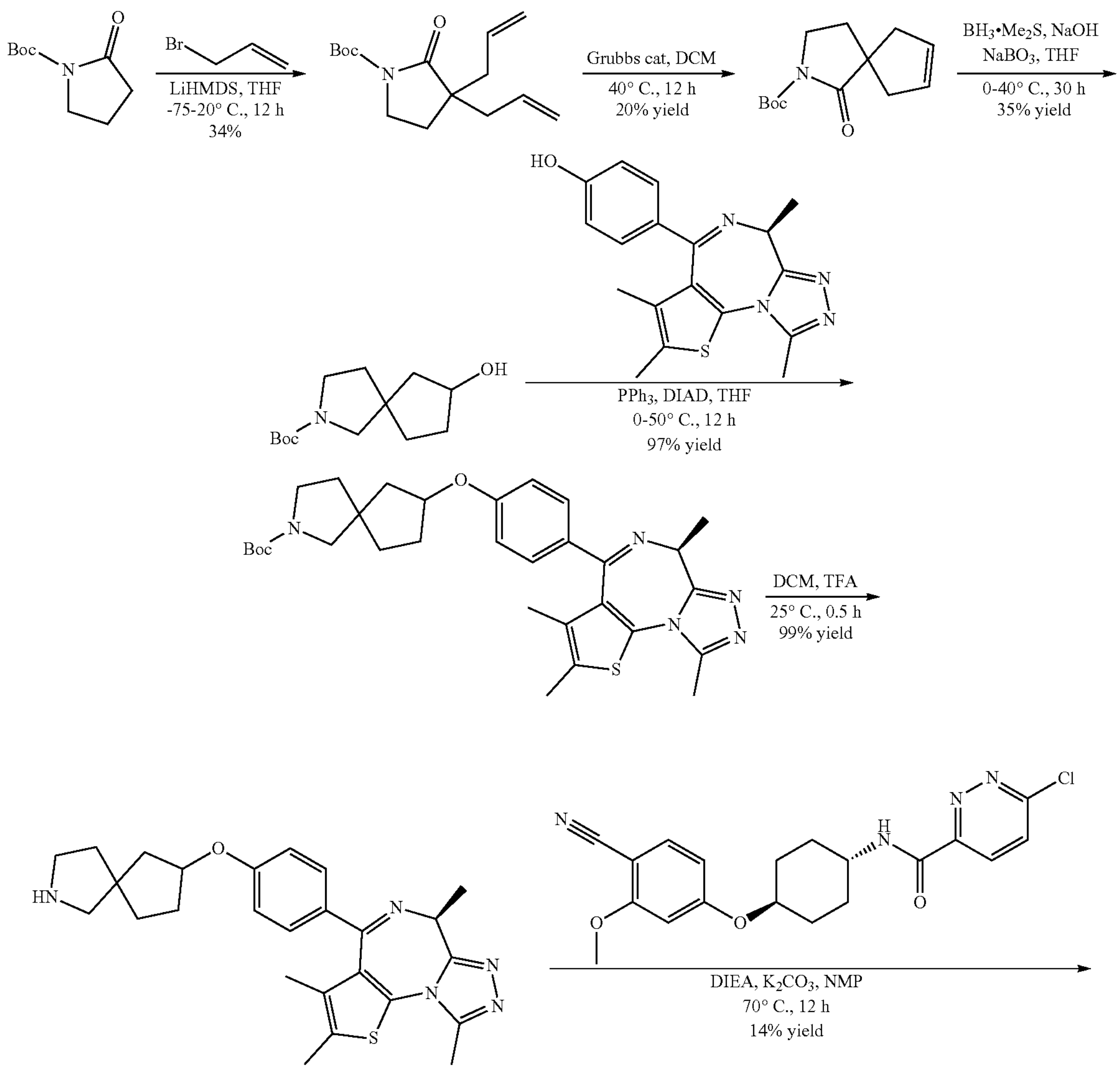

-continued

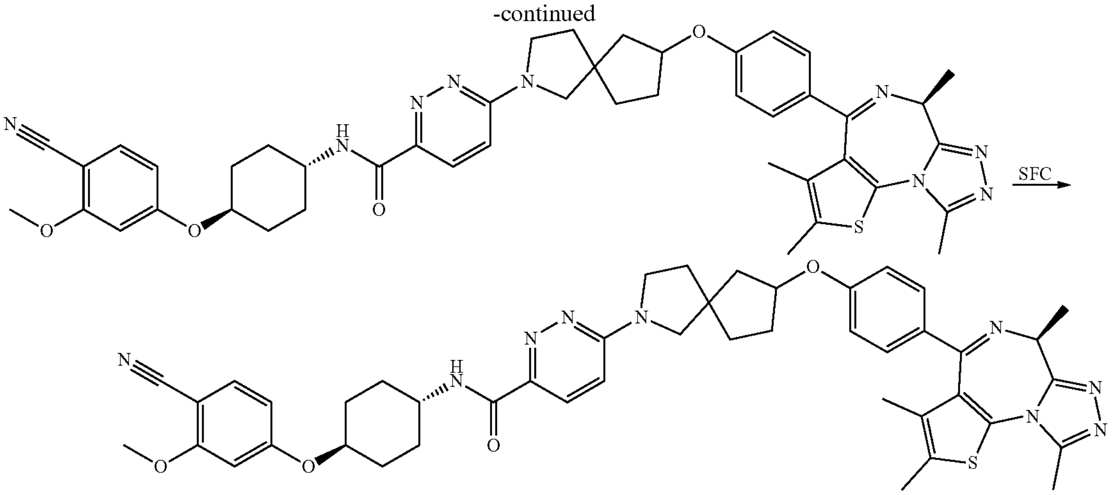

I-49

Step 1: Preparation of tert-butyl 3,3-diallyl-2-oxo-pyrrolidine-1-carboxylate. To a solution of tert-butyl 2-oxopyrrolidine-1-carboxylate (20.0 g, 107.9 mmol, 18.4 mL, 1.0 equiv) in THF (200 mL) was added dropwise LiHMDS (1 M, 269.9 mL, 2.5 equiv) at −75° C. After addition, the mixture was stirred at −75° C. for 0.5 hour. Next, 3-bromoprop-1-ene (39.2 g, 323.9 mmol, 3.0 equiv) was added dropwise at −78° C. The resulting mixture was stirred at 20° C. for 12 hours. The residue was diluted with EtOAc (1000 mL) and washed with $H_2O$ (1000 mL). The combined organic layers were washed with brine (1000 mL×2), dried over $Na_2SO_4$, filtered, and concentrated under reduced pressure to give a residue. The residue was purified by column chromatography ($SiO_2$, petroleum ether:ethyl acetate=1:0 to 20:1) to give tert-butyl 3,3-diallyl-2-oxo-pyrrolidine-1-carboxylate (10.0 g, 37.7 mmol, 34% yield) as a yellow oil.

Step 2: Preparation of tert-butyl 1-oxo-2-azaspiro[4.4]non-7-ene-2-carboxylate. A mixture of tert-butyl 3,3-diallyl-2-oxo-pyrrolidine-1-carboxylate (5.5 g, 20.7 mmol, 1.0 equiv), benzylidene-[1,3-bis(2,4,6-trimethylphenyl) imidazolidin-2-ylidene]-dichloro-ruthenium; tricyclohexylphosphane (352 mg, 415 μmol, 0.1 equiv) in DCM (500 mL) was degassed and purged with $N_2$ 3 times. The mixture was stirred at 40° C. for 12 hours under $N_2$ atmosphere. The mixture was concentrated to give a residue, which was purified by column chromatography ($SiO_2$, petroleum ether: ethyl acetate=1:0 to 40:1) to give tert-butyl 1-oxo-2-azaspiro[4.4]non-7-ene-2-carboxylate (1.0 g, 4.2 mmol, 20% yield) as a yellow oil.

Step 3: Preparation of tert-butyl 8-hydroxy-2-azaspiro[4.4]nonane-2-carboxylate. To a solution of tert-butyl 1-oxo-2-azaspiro[4.4]non-7-ene-2-carboxylate (1.0 g, 4.2 mmol, 1.0 equiv) in THF (10 mL) was added $BH_3$-$Me_2S$ (10 M, 2.1 mL, 5.0 equiv) at 0° C. The mixture was stirred at 40° C. for 12 hours. Then, to the mixture was added NaOH (5 M, 2.9 mL, 3.5 equiv) and sodium; 3-oxidodioxaborirane; tetrahydrate (2.6 g, 16.9 mmol, 3.3 mL, 4.0 equiv) at 0° C. The mixture was stirred at 25° C. for 12 hours. The residue was quenched with NaOH (40 mL), extracted with EtOAc (200 mL×3), and washed with $H_2O$ (300 mL). The organic phase was concentrated to afford a residue, which was purified by column chromatography ($SiO_2$, petroleum ether:ethyl acetate=6:1 to 2:1) to give tert-butyl 8-hydroxy-2-azaspiro[4.4]nonane-2-carboxylate (360 mg, 1.5 mmol, 35% yield) as a yellow oil.

Step 4: Preparation of tert-butyl 8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenoxy]-2-azaspiro[4.4]nonane-2-carboxylate. To a mixture of $PPh_3$ (0.5 M, 21.7 mL, 22.0 equiv) in THF (3 mL) was added DIAD (1.8 g, 8.9 mmol, 1.7 mL, 20.0 equiv) at 0° C. for 0.5 hour. Then, the solution was added to a mixture of tert-butyl 8-hydroxy-2-azaspiro[4.4]nonane-2-carboxylate (214 mg, 886 μmol, 2.0 equiv) and 4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenol (150 mg, 443 μmol, 1.0 equiv) in THF (0.6 mL). After addition, the mixture was degassed, purged with $N_2$ 3 times, and stirred at 50° C. for 12 hours under $N_2$ atmosphere. The residue was purified by column chromatography ($SiO_2$, petroleum ether:ethyl acetate=3:1 to 0:1) to give tert-butyl 8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenoxy]-2-azaspiro[4.4]nonane-2-carboxylate (270 mg, 433 μmol, 97% yield) as a yellow solid.

Step 5: Preparation of (9S)-7-[4-(2-azaspiro[4.4]nonan-8-yloxy)phenyl]-4,5,9,13-tetramethyl-3-thia-1,8,11,12-tetrazatricyclo[8.3.0.0$^{2,6}$]trideca-2 (6),4,7,10,12-pentaene. A mixture of tert-butyl 8-[4-[(9S)-4,5,9,13-tetramethyl-3-thia-1,8,11,12-tetrazatricyclo[8.3.0.0$^{2,6}$]trideca-2 (6), 4,7,10,12-pentaen-7-yl]phenoxy]-2-azaspiro[4.4]nonane-2-carboxylate (270 mg, 481 μmol, 1.0 equiv) in DCM (3 mL) and TFA (1 mL) was degassed and purged with $N_2$ 3 times. The mixture was stirred at 25° C. for 0.5 hour under $N_2$ atmosphere. The reaction mixture was concentrated under reduced pressure to remove solvent. The crude product, (9S)-7-[4-(2-azaspiro[4.4]nonan-8-yloxy)phenyl]-4,5,9,13-tetramethyl-3-thia-1,8,11,12-tetrazatricyclo[8.3.0.0$^{2,6}$]trideca-2 (6),4,7,10,12-pentaene (220 mg, 476 μmol, 99% yield), was used directly in the next step without purification.

Step 6: Preparation of N-[4-(4-cyano-3-methoxy-phenoxy)cyclohexyl]-6-[8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenoxy]-2-azaspiro[4.4]nonan-2-yl]pyridazine-3-carboxamide. A mixture of (9S)-7-[4-(2-azaspiro[4.4]nonan-8-yloxy)phenyl]-4,5,9,13-tetramethyl-3-thia-1,8,11,12-tetrazatricyclo[8.3.0.0$^{2,6}$]trideca-2 (6),4,7,10,12-pentaene (95 mg, 206 μmol, 1.0 equiv), 6-chloro-N-[4-(4-cyano-3-methoxy-phenoxy)cyclohexyl]pyridazine-3-carboxamide (80 mg, 206 μmol, 1.0 equiv), DIEA (27 mg, 206 μmol, 36 μL, 1.0 equiv), and $K_2CO_3$ (142 mg, 1.1 mmol, 5.0 equiv) in NMP (2 mL) was degassed and purged with $N_2$ 3 times. The mixture was stirred at 70° C. for 12 hours under $N_2$ atmosphere. The residue was purified by prep-TLC ($SiO_2$, dichloromethane:methanol=15:1) to give the product as a white solid.

Step 7: Preparation of N-[4-(4-cyano-3-methoxy-phenoxy)cyclohexyl]-6-[8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenoxy]-2-azaspiro[4.4]nonan-2-yl] pyridazine-3-carboxamide (I-49). The residue was separated by SFC (column: DAICEL CHIRALPAK AS (250 mm×30 mm, 10 μm); mobile phase: [$CO_2$-MeOH/ACN]; B %: 50%, isocratic elution mode) to give N-[4-(4-cyano-3-methoxy-phenoxy)cyclohexyl]-6-[8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenoxy]-2-azaspiro[4.4]nonan-2-yl] pyridazine-3-carboxamide (14 mg, 16 μmol, 7% yield) obtained as an off-white solid. 1H NMR: (400 MHz, MeOD-d4) δ=8.00 (d, J=9.6 Hz, 1H), 7.54-7.42 (m, 3H), 7.18 (d, J=9.6 Hz, 1H), 7.01 (d, J=9.2 Hz, 2H), 6.71-6.61 (m, 2H), 5.07-5.01 (m, 1H), 4.52-4.42 (m, 2H), 4.03-3.93 (m, 1H), 3.74-3.51 (m, 4H), 2.73 (s, 3H), 2.46 (s, 3H), 2.32-2.20 (m, 4H), 2.20-2.05 (m, 5H), 2.05-1.91 (m, 6H), 1.88-1.77 (m, 1H), 1.71 (s, 3H), 1.64 (d, J=9.6 Hz, 4H), 1.36-1.26 (m, 2H). LC-MS: MS ($ES^+$): RT=1.792 min, m/z=812.5 $[M+H]^+$.

Example 38—Synthesis of N-[4-[4-cyano-3-(trifluoromethoxy)phenoxy]cyclohexyl]-6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl] pyridazine-3-carboxamide (I-16)

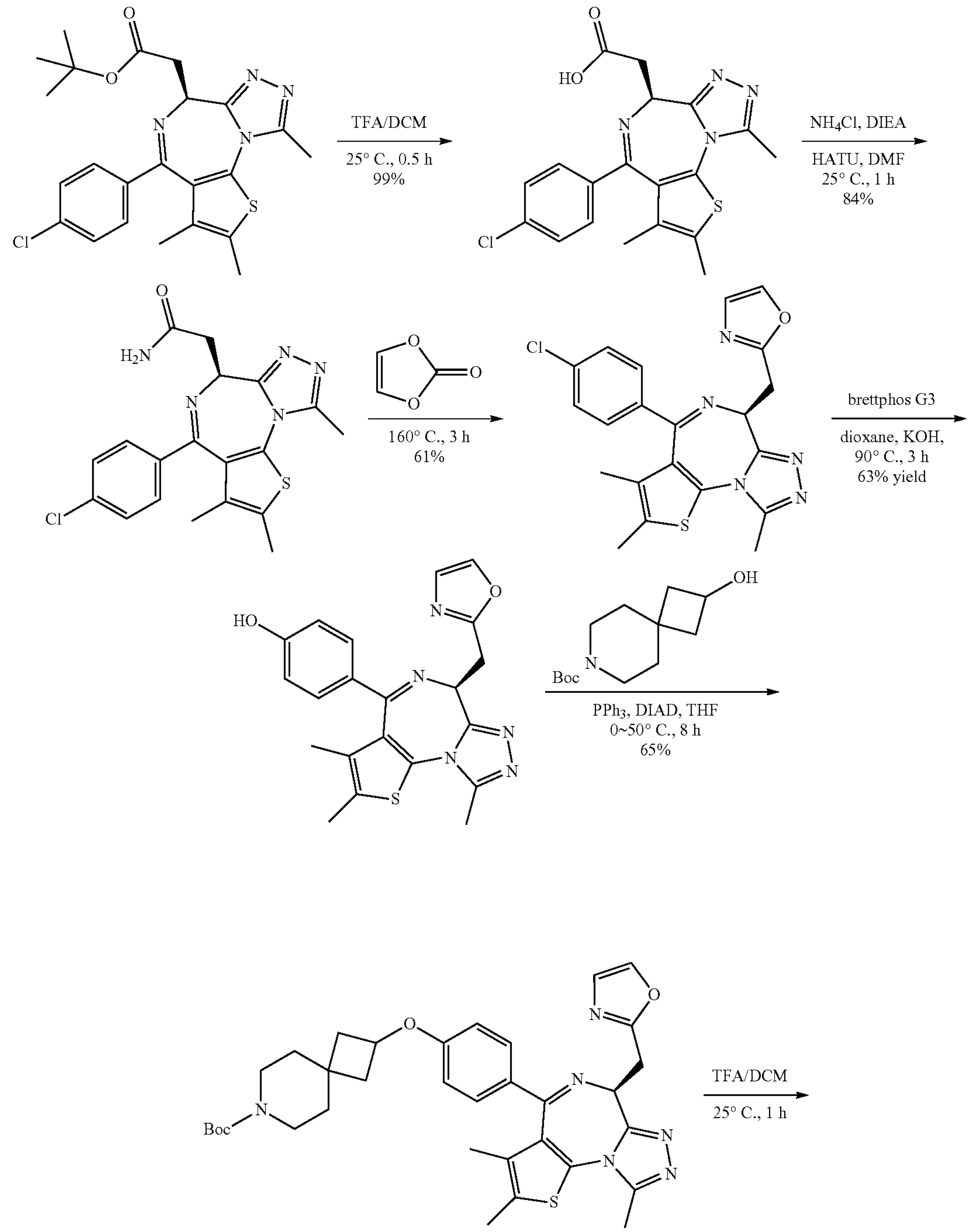

-continued

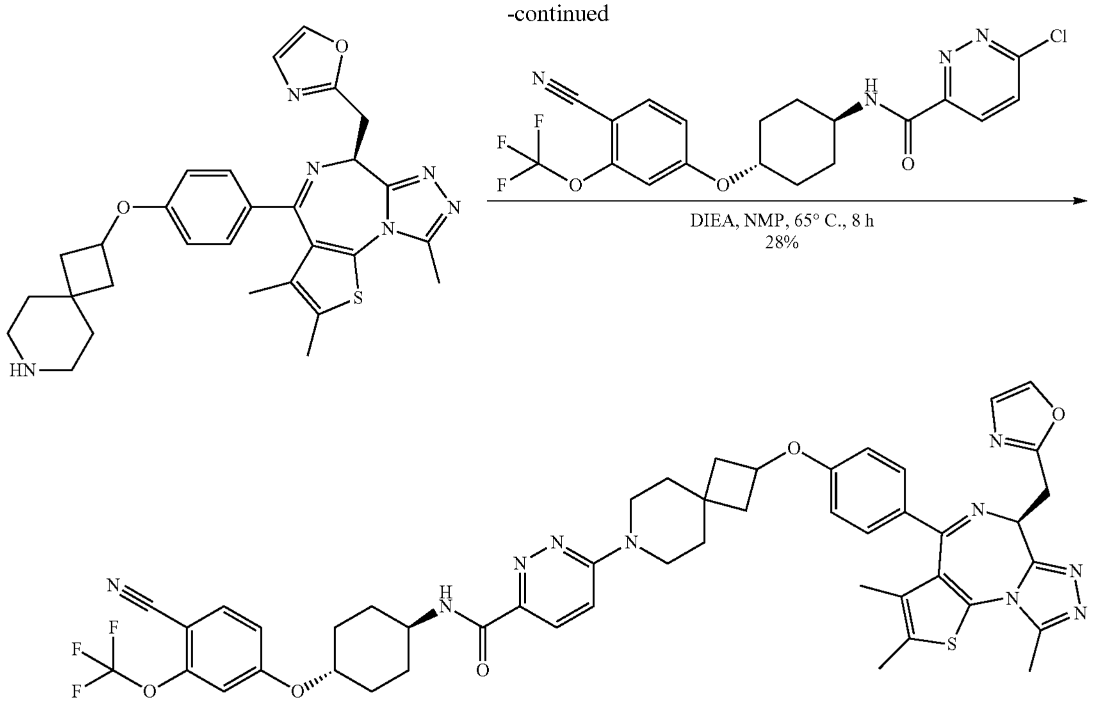

I-16

Step 1: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid. To a solution of tert-butyl 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetate (1.0 g, 2.1 mmol, 1.0 equiv) in DCM (10 mL) was added TFA (7.7 g, 67 mmol, 5.0 mL, 30 equiv). The mixture was stirred at 25° C. for 0.5 hour. The reaction mixture was filtered and concentrated under reduced pressure to give 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 99% yield) as a residue, which was used directly in the next step without purification.

Step 2: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide. To a solution of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 2.19 mmol, 1.0 equiv) and $NH_4Cl$ (351 mg, 6.56 mmol, 3.0 equiv) in DMF (8 mL) was added HATU (915 mg, 2.41 mmol, 1.1 equiv) and DIEA (848 mg, 6.56 mmol, 3.0 equiv). The mixture was stirred at 25° C. for 1 hour. The mixture was filtered and concentrated under reduced pressure. The residue was purified by prep-HPLC (column: Waters Xbridge C18 150 mm×50 mm×10 µm; mobile phase: [water ($NH_4HCO_3$)-ACN]; B %: 24%-54%, 10 min) to give 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (740 mg, 84% yield).

Step 3: Preparation of 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole. A solution of 1,3-dioxol-2-one (103 mg, 1.20 mmol, 1.2 equiv) and 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (400 mg, 1.00 mmol, 1.0 equiv) in PPA (4 mL) was stirred at 160° C. for 3 hours. The mixture was quenched with $H_2O$ (50 mL) at 0° C. and then diluted with ethyl acetate (200 mL). The mixture was washed with $H_2O$ (15 mL×2) and then further washed with $H_2O$ (10 mL×3) again to remove PPA. The combined organic layers were washed with $H_2O$ (10 mL×3), dried over $Na_2SO_4$, filtered, and concentrated. The residue was purified by column chromatography ($SiO_2$, petroleum ether:ethyl acetate=2:1 to 0:1) to give 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (260 mg, 61% yield).

Step 4: Preparation of 4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenol. A mixture of 2-[[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]methyl]oxazole (5.8 g, 13.7 mmol, 1.0 equiv), BrettPhos Pd G3 (1.2 g, 1.4 mmol, 0.1 equiv), and KOH (3.8 g, 68.4 mmol, 5.0 equiv) in dioxane (58 mL) and $H_2O$ (11.6 mL) was degassed and purged with $N_2$ 3 times. The mixture was stirred at 90° C. for 3 hours under $N_2$ atmosphere. The reaction mixture was partitioned between ethyl acetate (2000 mL) and water (500 mL). The organic phase was separated, washed with brine (500 mL×2), dried over $Na_2SO_4$, filtered, and concentrated under reduced pressure to give a residue. The residue was purified by column chromatography ($SiO_2$, dichloromethane:methanol=40:1) to give 4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenol (3.5 g, 8.6 mmol, 63% yield) as a yellow solid.

Step 5: Preparation of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7- azaspiro[3.5]nonane-7-carboxylate. To a solution of $PPh_3$ (485 mg, 1.85 mmol, 2.5 equiv) in THF (3 mL) was added DIAD (300 mg, 1.48 mmol, 0.3 mL, 2.0 equiv) at 0° C. for 30 minutes. Next, 4-[(9S)-4,5,13-trimethyl-9-(oxazol-2-yl-methyl)-3-thia-1,8,11,12-tetrazatricyclo[8.3.0.0$^{2,6}$]trideca-2 (6),4,7,10,12-pentaen-7-yl]phenol (300 mg, 740 μmol, 1.0 equiv) and tert-butyl 2-hydroxy-7-azaspiro[3.5]nonane-7-carboxylate (357 mg, 1.48 mmol, 2.0 equiv) in THF (3 mL) was added. The mixture was stirred at 0-50° C. for 8 hours. The reaction mixture was filtered, and the filtrate was concentrated under reduced pressure to give a residue. The residue was purified by column chromatography ($SiO_2$, petroleum ether:ethyl acetate to dichloromethane:methanol=1:1 to 10:1) to give tert-butyl 2-[4-[(9S)-4,5,13-trimethyl-9-(oxazol-2-ylmethyl)-3-thia-1,8,11,12-tetrazatricyclo [8.3.0.0$^{2,6}$]trideca-2 (6),4,7,10,12-pentaen-7-yl]phenoxy]-7-azaspiro[3.5]nonane-7-carboxylate (300 mg, 477 μmol, 65% yield) as a colorless oil.

Step 6: Preparation of 2-[[(9S)-7-[4-(7-azaspiro[3.5] nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (200 mg, 318 μmol, 1.0 equiv) in DCM (2 mL) was added TFA (1 mL). The mixture was stirred at 25° C. for 1 hour. The reaction mixture was concentrated and quenched with saturated aqueous $NaHCO_3$ (30 mL) at 0° C. The combined organic layer was washed with DCM/MeOH (10:1, 20 mL×3), dried over $Na_2SO_4$, filtered, and concentrated under reduced pressure to give 2-[[(9S)-7-[4-(7-azaspiro[3.5] nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (160 mg, 302 μmol) as a yellow solid.

Step 7: Preparation of N-[4-[4-cyano-3-(trifluoromethoxy)phenoxy]cyclohexyl]-6-[2-[4-[(9S)-4,5,13-trimethyl-9-(oxazol-2-ylmethyl)-3-thia-1,8,11,12-tetrazatricyclo [8.3.0.0$^{2,6}$]trideca-2 (6),4,7,10,12-pentaen-7-yl]phenoxy]-7-azaspiro[3.5]nonan-7-yl]pyridazine-3-carboxamide (1-16). To a solution of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6), 4,7,10,12-pentaen-9-yl] methyl]oxazole (100 mg, 190 μmol, 1.0 equiv) and 6-chloro-N-[4-[4-cyano-3-(trifluoromethoxy)phenoxy]cyclohexyl] pyridazine-3-carboxamide (100 mg, 227 μmol, 1.2 equiv) in NMP (0.5 mL) was added DIEA (75 mg, 567 μmol, 0.1 mL, 3.0 equiv). The mixture was stirred at 65° C. for 8 hours. The residue was purified by prep-HPLC (column: Phenomenex luna C18 150 mm×25 mm×10 μm; mobile phase: [water (FA)-ACN]; gradient: 70%-100% B over 10 min) to give N-[4-[4-cyano-3-(trifluoromethoxy)phenoxy]cyclohexyl]-6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl] pyridazine-3-carboxamide (49.7 mg, 52.5 μmol, 28% yield, 98% purity) as an off-white solid. $^1$H NMR (400 MHz, $CD_3OD$) δ 7.95-7.88 (m, 2H), 7.78 (d, J=8.8 Hz, 1H), 7.39-7.30 (m, 3H), 7.19-7.12 (m, 2H), 7.08 (s, 1H), 6.86 (d, J=8.9 Hz, 2H), 4.75 (dd, J=6.4, 8.4 Hz, 2H), 4.61-4.51 (m, 1H), 4.04-3.93 (m, 3H), 3.84-3.77 (m, 2H), 3.76-3.69 (m, 2H), 2.72 (s, 3H), 2.56 (br dd, J=7.3, 12.8 Hz, 2H), 2.48 (s, 3H), 2.23 (br d, J=2.8 Hz, 2H), 2.16-2.08 (m, 2H), 2.04-1.97 (m, 2H), 1.78 (td, J=5.3, 16.0 Hz, 4H), 1.72 (s, 3H), 1.67 (br t, J=10.2 Hz, 4H). LC-MS: MS ($ES^+$): RT=2.533 min, m/z=933.6 $[M+H]^+$; LCMS method: 25.

Example 39—Synthesis of 6-[8-[3-chloro-4-[(9S)-4,5,9,13-tetramethyl-3-thia-1,8,11,12-tetrazatricyclo [8.3.0.0$^{2,6}$]trideca-2 (6),4,7,10,12-pentaen-7-yl]phenyl]-2-azaspiro[4.5]decan-2-yl]-N-[4-(4-cyano-3-methoxy-phenoxy)cyclohexyl]pyridazine-3-carboxamide (I-64)

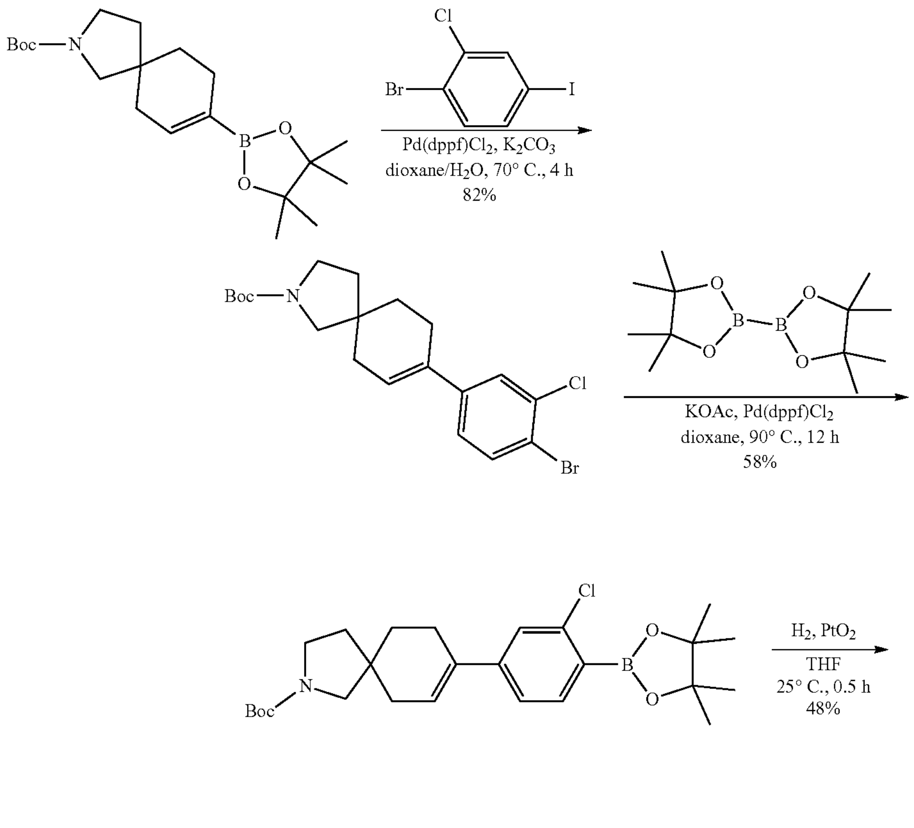

-continued
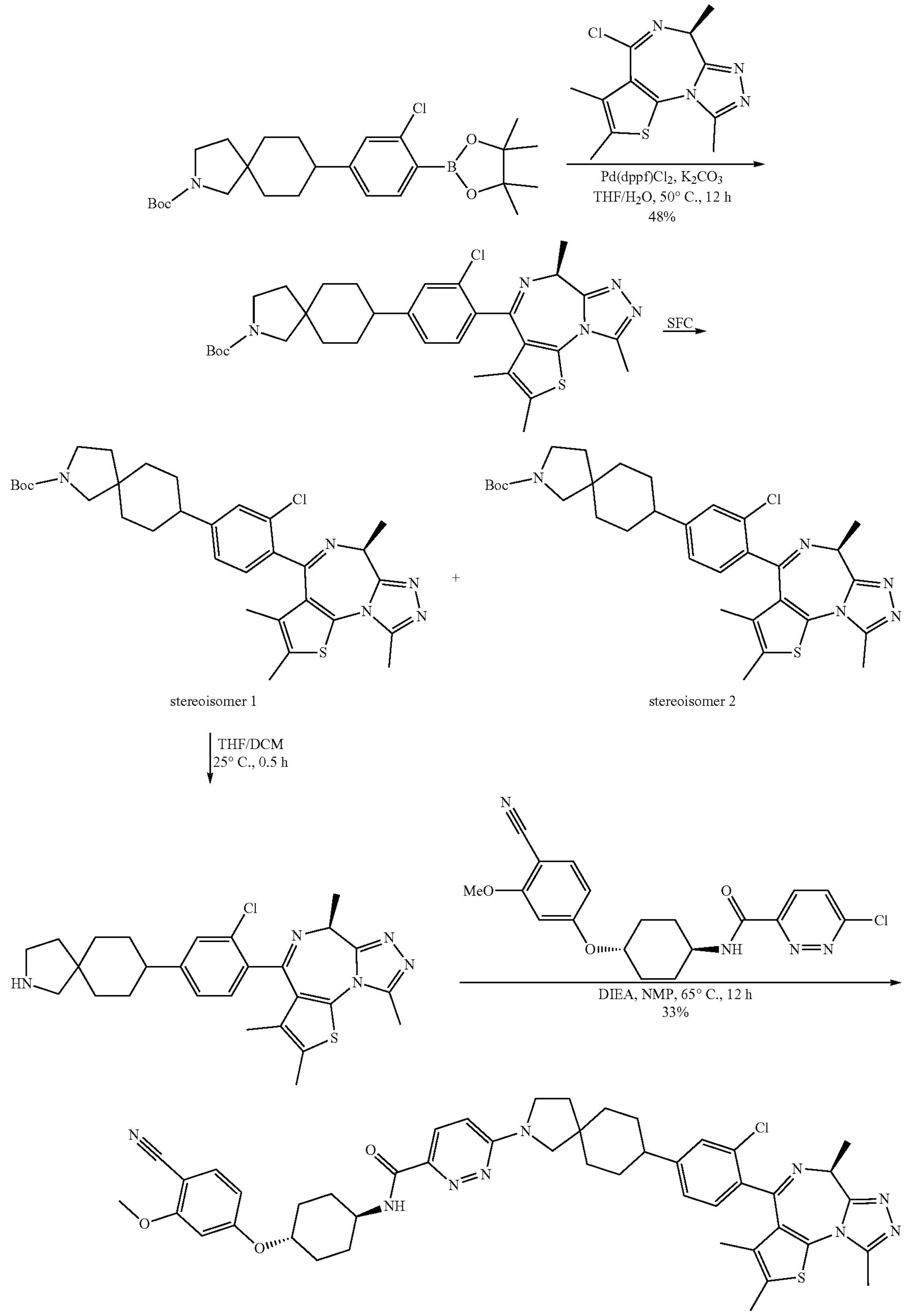
I-64

Step 1: Preparation of tert-butyl 8-(4-bromo-3-chloro-phenyl)-2-azaspiro[4.5]dec-7-ene-2-carboxylate. To a solution of commercially available tert-butyl 8-(4,4,5,5-tetramethyl-1,3,2-dioxaborolan-2-yl)-2-azaspiro[4.5]dec-7-ene-2-carboxylate (CAS Registry No. 2411223-24-8; 440 mg, 1.21 mmol, 1.1 equiv) and 1-bromo-2-chloro-4-iodo-benzene (350 mg, 1.10 mmol, 1.0 equiv) in dioxane (1 mL) and $H_2O$ (0.2 mL) was added Pd(dppf)$Cl_2$ (161 mg, 220 μmol, 0.2 equiv) and $K_2CO_3$ (457 mg, 3.31 mmol, 3.0 equiv). The mixture was stirred at 70° C. for 4 hours. The reaction mixture was filtered and concentrated under reduced pressure to give a residue. The residue was purified by column chromatography ($SiO_2$, petroleum ether: ethyl acetate=100:1 to 10:1) to afford compound tert-butyl 8-(4-bromo-3-chloro-phenyl)-2-azaspiro[4.5]dec-7-ene-2-carboxylate (385 mg, 1.21 mmol, 82% yield) as a white solid.

Step 2: Preparation of tert-butyl 8-[3-chloro-4-(4,4,5,5-tetramethyl-1,3,2-dioxaborolan-2-yl)phenyl]-2-azaspiro[4.5]dec-7-ene-2-carboxylate. A mixture of tert-butyl 8-(4-bromo-3-chloro-phenyl)-2-azaspiro[4.5]dec-7-ene-2-carboxylate (385 mg, 902 μmol, 1.0 equiv), 4,4,5,5-tetramethyl-2-(4,4,5,5-tetramethyl-1,3,2-dioxaborolan-2-yl)-1,3,2-dioxaborolane (343 mg, 1.35 mmol, 1.5 equiv), Pd(dppf)$Cl_2$ (66.0 mg, 90.2 μmol, 0.1 equiv), and KOAc (265 mg, 2.71 mmol, 3.0 equiv) in dioxane (4 mL) was stirred at 90° C. for 12 hours. The reaction mixture was filtered, and the filtrate was concentrated under reduced pressure to give a residue. The residue was purified by column chromatography ($SiO_2$, petroleum ether:ethyl acetate=60:1 to 10:1) to afford tert-butyl 8-[3-chloro-4-(4,4,5,5-tetramethyl-1,3,2-dioxaborolan-2-yl)phenyl]-2-azaspiro[4.5]dec-7-ene-2-carboxylate (250 mg, 902 μmol, 58% yield) as a white solid.

Step 3: Preparation of tert-butyl 8-[3-chloro-4-(4,4,5,5-tetramethyl-1,3,2-dioxaborolan-2-yl)phenyl]-2-azaspiro[4.5]decane-2-carboxylate. To a solution of tert-butyl 8-[3-chloro-4-(4,4,5,5-tetramethyl-1,3,2-dioxaborolan-2-yl)phenyl]-2-azaspiro[4.5]dec-7-ene-2-carboxylate (250 mg, 527 μmol, 1.0 equiv) in THF (4 mL) was added $PtO_2$ (62.5 mg). The suspension was degassed under vacuum and purged with $H_2$ several times, and then the reaction mixture was stirred under $H_2$ (15 PSI) at 25° C. for 0.5 hours. Next, the reaction mixture was filtered, and the filtrate was concentrated under reduced pressure to give a residue. The residue was purified by prep-TLC ($SiO_2$, petroleum ether: ethyl acetate=10:1) to afford tert-butyl 8-[3-chloro-4-(4,4,5,5-tetramethyl-1,3,2-dioxaborolan-2-yl)phenyl]-2-azaspiro[4.5]decane-2-carboxylate (120 mg, 527 μmol, 48% yield) as a white solid.

Step 4: Preparation of tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate. To a solution of tert-butyl 8-[3-chloro-4-(4,4,5,5-tetramethyl-1,3,2-dioxaborolan-2-yl)phenyl]-2-azaspiro[4.5]decane-2-carboxylate (100 mg, 210 μmol, 1.0 equiv) and (9S)-7-chloro-4,5,9,13-tetramethyl-3-thia-1,8,11,12-tetrazatricyclo[8.3.0.$0^{2,6}$]trideca-2 (6),4,7,10,12-pentaene (88.5 mg, 315 μmol, 1.5 equiv) in THF (2 mL) and $H_2O$ (0.4 mL) was added Pd(dppf)$Cl_2$ (30.7 mg, 42.0 μmol, 0.2 equiv) and $K_2CO_3$ (87.1 mg, 630 μmol, 3.0 equiv). The mixture was stirred at 50° C. for 12 hours. The reaction mixture was filtered, and the filtrate was concentrated under reduced pressure to give a residue. The residue was purified by prep-HPLC (column: Phenomenex luna C18 150 mm×25 mm×10 μm; mobile phase: [water (FA)-ACN]; gradient: 67%-97% B over 10 min) to afford tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (60 mg, 48% yield) as a white solid.

Step 5: Preparation of stereoisomer 1 of tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate and stereoisomer 2 of tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate. Compound tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (60 mg, 1.0 equiv) was purified by prep-SFC (column: DAICEL CHIRALCEL OD-H (250 mm×30 mm, 5 μm); mobile phase: [$CO_2$-MeOH (0.1% $NH_3 \cdot H_2O$)]; B %: 30%, isocratic elution mode) to afford stereoisomer 1 of tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (30 mg, 50% yield) as a white solid and stereoisomer 2 of tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (11 mg, 18% yield) as a white solid. The two stereoisomers differ by the stereochemistry at the spiro-center adjacent to the pyrrolidine.

Step 6: Preparation of (9S)-7-[4-(2-azaspiro[4.5]decan-8-yl)-2-chloro-phenyl]-4,5,9,13-tetramethyl-3-thia-1,8,11,12-tetrazatricyclo[8.3.0.$0^{2,6}$]trideca-2 (6),4,7,10,12-pentaene. To a solution of tert-butyl 8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decane-2-carboxylate (30.0 mg, 50.5 μmol, 1.0 equiv) in DCM (1 mL) was added TFA (0.5 mL). The mixture was stirred at 25° C. for 0.5 hour. The reaction mixture was concentrated and basified with saturated aqueous $NaHCO_3$ at 0° C. The mixture were extracted with DCM/MeOH (10:1, 20 mL×2), dried over $Na_2SO_4$, filtered, and concentrated to afford (9S)-7-[4-(2-azaspiro[4.5]decan-8-yl)-2-chloro-phenyl]-4,5,9,13-tetramethyl-3-thia-1,8,11,12-tetrazatricyclo[8.3.0.$0^{2,6}$]trideca-2 (6),4,7,10,12-pentaene (24.5 mg) as a yellow oil.

Step 7: Preparation of 6-[8-[3-chloro-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2-azaspiro[4.5]decan-2-yl]-N-[4-(4-cyano-3-methoxy-phenoxy)cyclohexyl]pyridazine-3-carboxamide (I-64). To a solution of (9S)-7-[4-(2-azaspiro[4.5]decan-8-yl)-2-chloro-phenyl]-4,5,9,13-tetramethyl-3-thia-1,8,11,12-tetrazatricyclo[8.3.0.$0^{2,6}$]trideca-2 (6),4,7,10,12-pentaene (24.0 mg, 48.5 μmol, 1.0 equiv) and 6-chloro-N-[4-(4-cyano-3-methoxy-phenoxy)cyclohexyl]pyridazine-3-carboxamide (28.2 mg, 72.8 μmol, 1.5 equiv; prepared as described above in Example 7) in NMP (0.5 mL) was added DIEA (71.4 mg, 552 μmol, 100 μL, 11.3 equiv). The mixture was stirred at 65° C. for 12 hours. The reaction mixture was filtered and concentrated under reduced pressure to give a residue. The residue was purified by prep-HPLC (column: Phenomenex luna C18 150 mm×25 mm×10 μm; mobile phase: [water (FA)-ACN]; gradient: 58%-88% B over 10 min) to afford 6-[8-[3-chloro-4-[(9S)-4,5,9,13-tetramethyl-3-thia-1,8,11,12-tetrazatricyclo[8.3.0.$0^{2,6}$]trideca-2 (6), 4,7,10,12-pentaen-7-yl]phenyl]-2-azaspiro[4.5]decan-2-yl]-N-[4-(4-cyano-3-methoxy-phenoxy)cyclohexyl]pyridazine-3-carboxamide (13.5 mg, 48.5 μmol, 33% yield) as a white solid. $^1H$ NMR (400 MHz, $CD_3OD$) δ 7.92 (d, J=9.54 Hz, 1H), 7.44-7.54 (m, 2H), 7.31-7.37 (m, 2H), 7.06 (d, J=10.27 Hz, 1H), 6.61-6.71 (m, 2H), 4.58 (s, 2H), 4.47-4.53 (m, 1H), 4.35-4.40 (m, 1H), 3.91-4.01 (m, 4H), 3.53-3.70 (m, 4H), 2.69 (s, 4H), 2.39 (s, 3H), 2.22 (d, J=3.42 Hz, 2H), 2.07-2.16 (m, 2H), 2.01 (d, J=6.72 Hz, 3H), 1.94-1.97 (m, 2H), 1.82-1.91 (m, 4H), 1.61-1.67 (m, 7H), 1.59 (s, 2H). LC-MS: MS ($ES^+$): RT=2.244 min, m/z=884.5 $[M+H]^+$; LCMS method: 25.

Example 40—Synthesis of N-((1r,4r)-4-(4-cyano-3-methoxyphenoxy)cyclohexyl)-6-(8-(2-methoxy-4-((S)-2,3,6,9-tetramethyl-6H-thieno[3,2-f][1,2,4]triazolo[4,3-a][1,4]diazepin-4-yl)phenyl)-2-azaspiro[4.5]decan-2-yl) pyridazine-3-carboxamide (I-66)
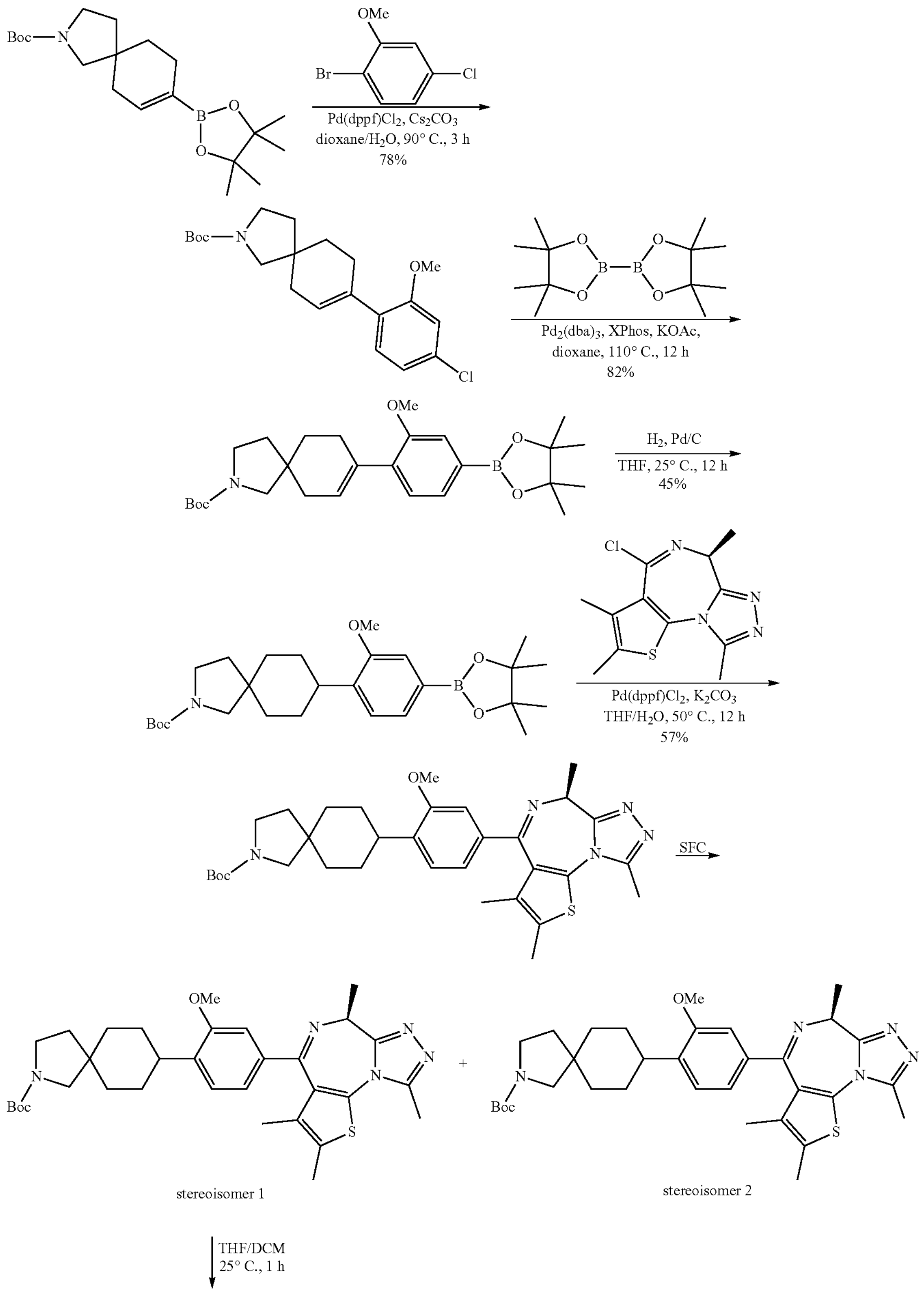

-continued

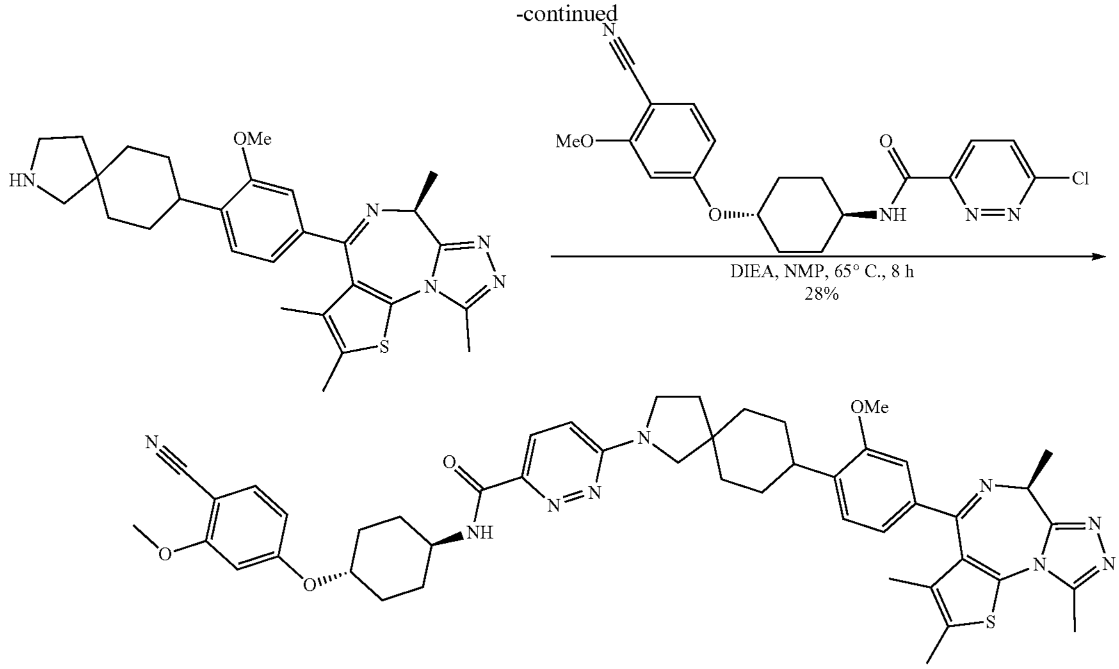

I-66

Step 1: Preparation of tert-butyl 8-(4-chloro-2-methoxyphenyl)-2-azaspiro[4.5]dec-7-ene-2-carboxylate. To a solution of commercially available tert-butyl 8-(4,4,5,5-tetramethyl-1,3,2-dioxaborolan-2-yl)-2-azaspiro[4.5]dec-7-ene-2-carboxylate (500 mg, 1.38 mmol, 1.1 equiv) and 1-bromo-4-chloro-2-methoxybenzene (277 mg, 1.25 mmol, 1.0 equiv) in dioxane (5 mL) was added Pd(dppf)$Cl_2$ (183 mg, 250 μmol, 0.2 equiv) and $Cs_2CO_3$ (1.22 g, 3.75 mmol, 3.0 equiv) in $H_2O$ (1 mL). The mixture was stirred at 90° C. for 4 hours. The reaction mixture was diluted with $H_2O$ (10 mL) and extracted with ethyl acetate (10 mLx2). The combined organic layers were dried over $Na_2SO_4$, filtered, and concentrated under reduced pressure to give a residue. The residue was purified by column chromatography ($SiO_2$, petroleum ether:ethyl acetate=20:1 to 5:1) to give tert-butyl 8-(4-chloro-2-methoxyphenyl)-2-azaspiro[4.5]dec-7-ene-2-carboxylate (370 mg, 980 μmol, 78% yield) as a yellow oil.

Step 2: Preparation of tert-butyl 8-(2-methoxy-4-(4,4,5,5-tetramethyl-1,3,2-dioxaborolan-2-yl)phenyl)-2-azaspiro[4.5]dec-7-ene-2-carboxylate. To a solution of tert-butyl 8-(4-chloro-2-methoxyphenyl)-2-azaspiro[4.5]dec-7-ene-2-carboxylate (370 mg, 980 μmol, 1.0 equiv) and 4,4,5,5-tetramethyl-2-(4,4,5,5-tetramethyl-1,3,2-dioxaborolan-2-yl)-1,3,2-dioxaborolane (372 mg, 1.47 mmol, 1.5 equiv) in dioxane (5 mL) was added $Pd_2(dba)_3$ (45 mg, 50 μmol, 0.05 equiv), XPhos (70.0 mg, 146 μmol, 0.15 equiv), and KOAc (288 mg, 2.94 mmol, 3.0 equiv). The mixture was stirred at 110° C. for 12 hours. The residue was purified by column chromatography ($SiO_2$, petroleum ether:ethylacetate=30:1 to 3:1) to give tert-butyl 8-(2-methoxy-4-(4,4,5,5-tetramethyl-1,3,2-dioxaborolan-2-yl)phenyl)-2-azaspiro[4.5]dec-7-ene-2-carboxylate (380 mg, 810 μmol, 82% yield) as a yellow oil.

Step 3: Preparation of tert-butyl 8-(2-methoxy-4-(4,4,5,5-tetramethyl-1,3,2-dioxaborolan-2-yl)phenyl)-2-azaspiro[4.5]decane-2-carboxylate. To a solution of tert-butyl 8-(2-methoxy-4-(4,4,5,5-tetramethyl-1,3,2-dioxaborolan-2-yl)phenyl)-2-azaspiro[4.5]dec-7-ene-2-carboxylate (350 mg, 745 μmol, 1.0 equiv) in THF (5 mL) was added Pd/C (200 mg, 10% purity) under $N_2$ atmosphere. The mixture was stirred under $H_2$ (15 psi) at 25° C. for 12 hours. The residue was purified by prep-TLC ($SiO_2$, petroleum ether:ethyl acetate=5:1) to give tert-butyl 8-(2-methoxy-4-(4,4,5,5-tetramethyl-1,3,2-dioxaborolan-2-yl)phenyl)-2-azaspiro[4.5]decane-2-carboxylate (160 mg, 340 μmol, 45% yield) as a white solid.

Step 4: Preparation of tert-butyl(S)-8-(2-methoxy-4-(2,3,6,9-tetramethyl-6H-thieno[3,2-f][1,2,4]triazolo[4,3-a][1,4]diazepin-4-yl)phenyl)-2-azaspiro[4.5]decane-2-carboxylate. To a solution of tert-butyl 8-(2-methoxy-4-(4,4,5,5-tetramethyl-1,3,2-dioxaborolan-2-yl)phenyl)-2-azaspiro[4.5]decane-2-carboxylate (140 mg, 300 μmol, 1.0 equiv) and(S)-4-chloro-2,3,6,9-tetramethyl-6H-thieno[3,2-f][1,2,4]triazolo[4,3-a][1,4]diazepine (100 mg, 356 μmol, 1.2 equiv) in THF (2 mL) was added Pd(dppf)$Cl_2$ (22 mg, 30 μmol, 0.1 equiv) and $K_2CO_3$ (123 mg, 890 μmol, 3.0 equiv) in $H_2O$ (0.4 mL). The mixture was stirred at 50° C. for 12 hours. The reaction mixture was diluted with $H_2O$ (10 mL) and extracted with ethyl acetate (15 mLx2). The combined organic layers were dried over $Na_2SO_4$, filtered, and concentrated under reduced pressure to give a residue. The residue was purified by prep-HPLC (column: Phenomenex luna C18 150 mmx25 mmx10 μm; mobile phase: [water (FA)-ACN]; gradient: 65%-95% B over 10 min) to give tert-butyl(S)-8-(2-methoxy-4-(2,3,6,9-tetramethyl-6H-thieno[3,2-f][1,2,4]triazolo[4,3-a][1,4]diazepin-4-yl)phenyl)-2-azaspiro[4.5]decane-2-carboxylate (100 mg, 170 μmol, 57% yield) as an off-white solid.

Step 5: Preparation of tert-butyl(S)-8-(2-methoxy-4-(2,3,6,9-tetramethyl-6H-thieno[3,2-f][1,2,4]triazolo[4,3-a][1,4]diazepin-4-yl)phenyl)-2-azaspiro[4.5]decane-2-carboxylate. Tert-butyl(S)-8-(2-methoxy-4-(2,3,6,9-tetramethyl-6H-thieno[3,2-f][1,2,4]triazolo[4,3-a][1,4]diazepin-4-yl)phenyl)-2-azaspiro[4.5]decane-2-carboxylate was separated by prep-SFC (column: DAICEL CHIRALPAK AS (250 mm×30 mm, 10 μm); mobile phase: [$CO_2$-ACN/i-PrOH (0.1% $NH_3 \cdot H_2O$)]; B %: 50%, isocratic elution mode) to give stereoisomer 1 of tert-butyl(S)-8-(2-methoxy-4-(2,3,6,9-tetramethyl-6H-thieno[3,2-f][1,2,4]triazolo[4,3-a][1,4]diazepin-4-yl)phenyl)-2-azaspiro[4.5]decane-2-carboxylate (60 mg, 101 μmol, 60% yield) as a yellow solid and stereoisomer 2 of tert-butyl(S)-8-(2-methoxy-4-(2,3,6,9-tetramethyl-6H-thieno[3,2-f][1,2,4]triazolo[4,3-a][1,4]diazepin-4-yl)phenyl)-2-azaspiro[4.5]decane-2-carboxylate (30 mg, 50 μmol, 30% yield) as a yellow solid.

Step 6: Preparation of(S)-4-(3-methoxy-4-(2-azaspiro[4.5]decan-8-yl)phenyl)-2,3,6,9-tetramethyl-6H-thieno[3,2-f][1,2,4]triazolo[4,3-a][1,4]diazepine. To a solution of tert-butyl(S)-8-(2-methoxy-4-(2,3,6,9-tetramethyl-6H-thieno[3,2-f][1,2,4]triazolo[4,3-a][1,4]diazepin-4-yl)phenyl)-2-azaspiro[4.5]decane-2-carboxylate (60 mg, 101 μmol, 1.0 equiv) in DCM (1 mL) was added TFA (0.5 mL). The mixture was stirred at 25° C. for 1 hour. The reaction mixture was concentrated and basified with saturated aqueous $NaHCO_3$ at 0° C. The mixture were extracted with DCM/MeOH (10:1, 20 mL×2), dried over $Na_2SO_4$, filtered, and concentrated to give(S)-4-(3-methoxy-4-(2-azaspiro[4.5]decan-8-yl)phenyl)-2,3,6,9-tetramethyl-6H-thieno[3,2-f][1,2,4]triazolo[4,3-a][1,4]diazepine (49 mg, 100 μmol, crude) as a yellow solid.

Step 7: Preparation of N-((1r,4r)-4-(4-cyano-3-methoxyphenoxy)cyclohexyl)-6-(8-(2-methoxy-4-((S)-2,3,6,9-tetramethyl-6H-thieno[3,2-f][1,2,4]triazolo[4,3-a][1,4]diazepin-4-yl)phenyl)-2-azaspiro[4.5]decan-2-yl) pyridazine-3-carboxamide (I-66). To a solution of (S)-4-(3-methoxy-4-(2-azaspiro[4.5]decan-8-yl)phenyl)-2,3,6,9-tetramethyl-6H-thieno[3,2-f][1,2,4]triazolo[4,3-a][1,4]diazepine (49 mg, 100 μmol, 1.0 equiv) and 6-chloro-N-((1r,4r)-4-(4-cyano-3-methoxyphenoxy)cyclohexyl) pyridazine-3-carboxamide (46 mg, 120 μmol, 1.2 equiv, prepared as described above in Example 7) in NMP (0.5 mL) was added DIEA (40 mg, 300 μmol, 0.1 mL, 3.0 equiv). The mixture was stirred at 65° C. for 8 hours. The residue was purified by prep-HPLC (column: Phenomenex luna C18 150 mm×25 mm×10 μm; mobile phase: [water (FA)-ACN]; gradient: 58%-88% B over 10 min) to give N-((1r,4r)-4-(4-cyano-3-methoxyphenoxy)cyclohexyl)-6-(8-(2-methoxy-4-((S)-2,3,6,9-tetramethyl-6H-thieno[3,2-f][1,2,4]triazolo[4,3-a][1,4]diazepin-4-yl)phenyl)-2-azaspiro[4.5]decan-2-yl) pyridazine-3-carboxamide (25.62 mg, 28.62 μmol, 28% yield, 93.84% purity) as an off-white solid. $^1H$ NMR (400 MHz, $CD_3OD$) δ 7.94 (d, J=9.4 Hz, 1H), 7.52 (d, J=9.0 Hz, 1H), 7.26 (d, J=7.9 Hz, 1H), 7.20 (s, 1H), 7.08 (br d, J=9.4 Hz, 1H), 6.90 (br d, J=7.7 Hz, 1H), 6.73-6.63 (m, 2H), 4.31 (d, J=6.8 Hz, 1H), 3.98 (br d, J=3.8 Hz, 1H), 3.93 (s, 3H), 3.88 (s, 3H), 3.74-3.53 (m, 4H), 3.12-3.00 (m, 1H), 2.73 (s, 3H), 2.47-2.47 (m, 1H), 2.46 (s, 3H), 2.22 (br d, J=3.9 Hz, 2H), 2.11 (br s, 2H), 2.02 (d, J=6.7 Hz, 3H), 1.96 (br t, J=7.0 Hz, 2H), 1.84 (br d, J=8.6 Hz, 4H), 1.74-1.53 (m, 12H). LC-MS: MS ($ES^+$): RT=2.081 min, m/z=840.6 $[M+H]^+$; LCMS method: 25.

Example 41—Synthesis of N-[3-[4-cyano-3-(trifluoromethoxy)phenoxy]-2,2,4,4-tetramethyl-cyclobutyl]-2-[2-[[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl] methyl]-7-azaspiro[3.5]nonan-7-yl]pyrimidine-5-carboxamide (II-1)

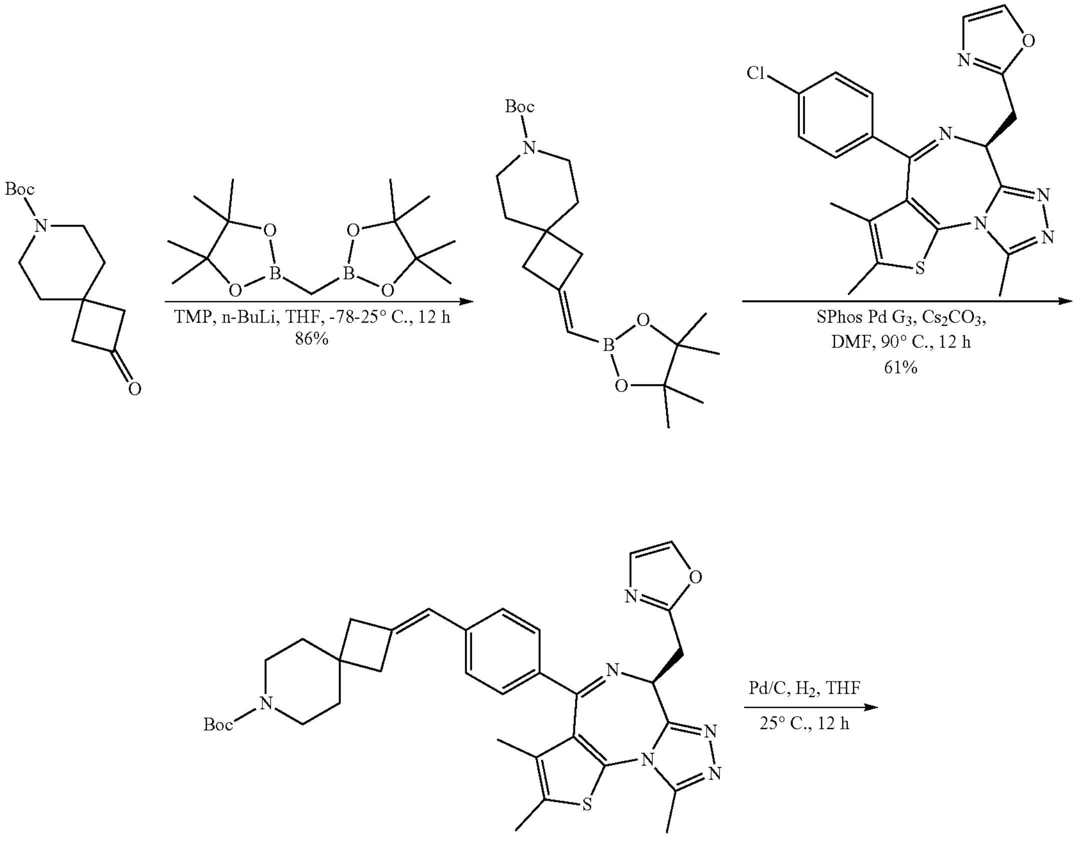

-continued

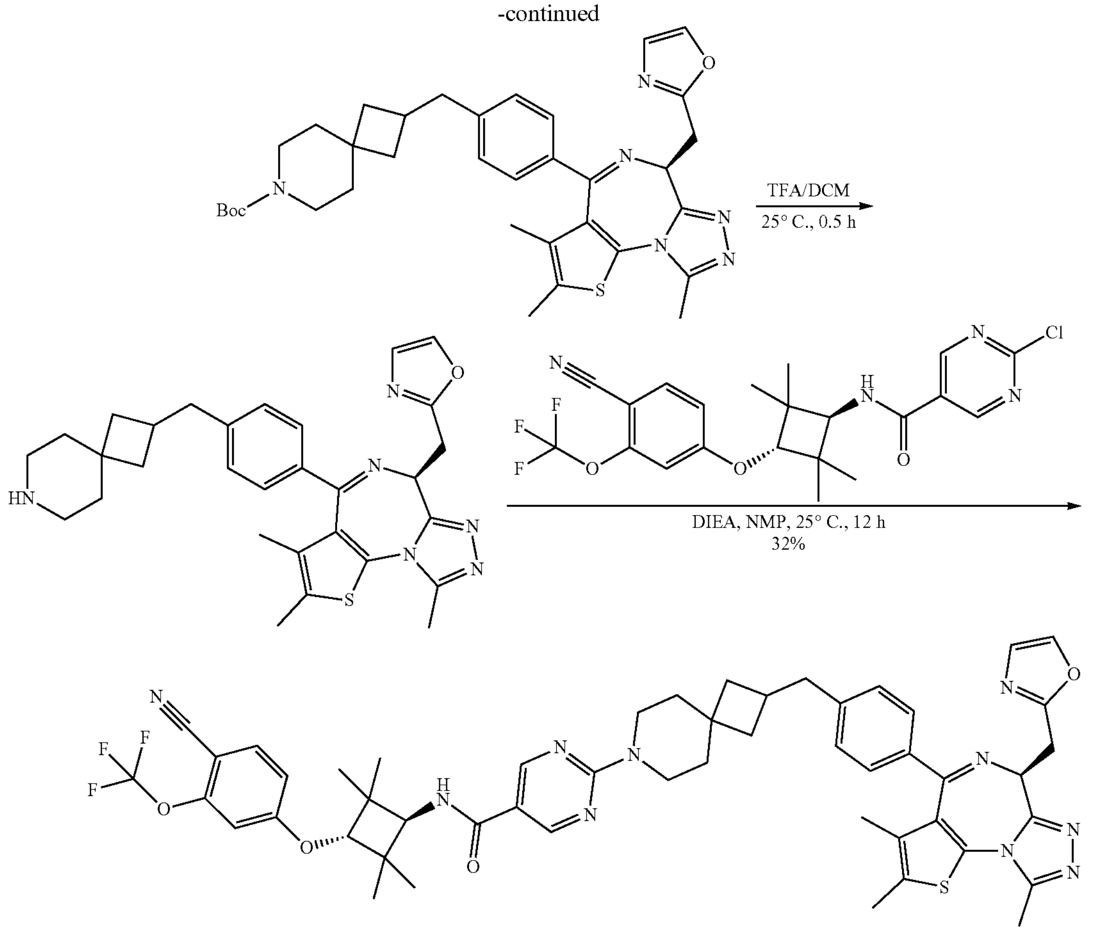

II-1

Step 1: Preparation of tert-butyl 2-[(4,4,5,5-tetramethyl-1,3,2-dioxaborolan-2-yl)methylene]-7-azaspiro[3.5]nonane-7-carboxylate. To a solution of TMP (885 mg, 6.2 mmol, 1.0 mL, 1.5 equiv) in THF (4 mL) was added n-BuLi (2.5 M, 2.5 mL, 1.5 equiv) at −30° C. under $N_2$ atmosphere. After addition, the mixture was stirred at −30° C. for 30 minutes. Next, 4,4,5,5-tetramethyl-2-[(4,4,5,5-tetramethyl-1,3,2-dioxaborolan-2-yl)methyl]-1,3,2-dioxaborolane (1.4 g, 5.0 mmol, 1.2 equiv) in THF (3 mL) was added dropwise at −78° C. After addition, the mixture was stirred at −78° C. for 30 minutes, and then tert-butyl 2-oxo-7-azaspiro[3.5]nonane-7-carboxylate (1.0 g, 4.18 mmol, 1.0 equiv) in THF (3 mL) was added dropwise at −78° C. The resulting mixture was stirred at 25° C. for 12 hours. The resultant mixture was then cooled to 0° C., and saturated aqueous $NH_4Cl$ (15 mL) was added dropwise. After stirring for an additional 1 hour, the resultant mixture was filtered, and the filtrate was concentrated in vacuo. Water (20 mL) was added to the resultant residue, and the aqueous layer was extracted with EtOAc (20 mL×3). The combined organic phase was washed with brine (20 mL), dried over anhydrous $Na_2SO_4$, and concentrated under vacuum to give tert-butyl 2-[(4,4,5,5-tetramethyl-1,3,2-dioxaborolan-2-yl)methylene]-7-azaspiro[3.5]nonane-7-carboxylate (1.3 g, 86% yield) as a colorless oil.

Step 2: Preparation of tert-butyl 2-[[4-[4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methylene]-7-azaspiro[3.5]nonane-7-carboxylate. To a solution of 2-[[7-(4-chlorophenyl)-4,5,13-trimethyl-3-thia-1,8,11,12-tetrazatricyclo[8.3.0.02,6]trideca-2 (6),4,7,10,12-pentaen-9-yl]methyl]oxazole (400 mg, 943.8 μmol, 1.0 equiv) and tert-butyl 2-[(4,4,5,5-tetramethyl-1,3,2-dioxaborolan-2-yl)methylene]-7-azaspiro[3.5]nonane-7-carboxylate (530 mg, 1.6 mmol, 1.5 equiv) in DMF (6 mL) was added SPhos Pd G3 (73 mg, 94 μmol, 0.1 equiv) and $Cs_2CO_3$ (307 mg, 943 μmol, 1.0 equiv). The mixture was stirred at 90° C. for 12 hours. The reaction mixture was filtered and concentrated under reduced pressure to give a residue. The residue was purified by prep-HPLC (column: Phenomenex Luna C18 150 mm×25 mm×10 μm; mobile phase: [water (FA)-ACN]; B %: 62%-92%, 10 min) to give tert-butyl 2-[[4-[4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methylene]-7-azaspiro[3.5]nonane-7-carboxylate (400 mg, 61% yield) as a yellow solid.

Step 3: Preparation of tert-butyl 2-[[4-[4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methyl]-7-azaspiro[3.5]nonane-7-carboxylate. To a solution of tert-butyl 2-[[4-[4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methylene]-7-azaspiro[3.5]nonane-7-carboxylate (0.4 g, 642 μmol, 1.0 equiv) in THF (8 mL) was added Pd/C (0.45 g, 10% purity) under $H_2$ (15 psi). The mixture was stirred at 25° C. for 12 hours under $H_2$ (15 psi). The reaction mixture was filtered and the filtrate was concentrated under reduced pressure to give tert-butyl 2-[[4-[4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]methyl]-7-azaspiro[3.5]nonane-7-carboxylate (0.4 g, 99% yield) as a white solid.

Step 4: Preparation of 2-[[7-[4-(7-azaspiro[3.5]nonan-2-ylmethyl)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 2-[[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonane-7-carboxylate (0.4 g, 638 μmol, 1.0 equiv) in DCM (1 mL) was added TFA (1.2 g, 10.7 mmol, 800 μL, 16.8 equiv). The mixture was stirred at 25° C. for 0.5 hour. The reaction mixture was filtered, and the filtrate was concentrated under reduced pressure to give 2-[[7-[4-(7-azaspiro[3.5]nonan-2-ylmethyl)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (0.407 g, 99% yield) as a colourless oil.

Step 5: Preparation of N-[3-[4-cyano-3-(trifluoromethoxy)phenoxy]-2,2,4,4-tetramethyl-cyclobutyl]-2-[2-[[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl]pyrimidine-5-carboxamide (II-1). To a solution of 2-[[(9S)-7-[4-(7-azaspiro[3.5]nonan-2-ylmethyl)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (100 mg, 189 μmol, 1.0 equiv) and 2-chloro-N-[3-[4-cyano-3-(trifluoromethoxy)phenoxy]-2,2,4,4-tetramethyl-cyclobutyl]pyrimidine-5-carboxamide (115 mg, 246 μmol, 1.3 equiv; prepared as described above in Example 30) in NMP (0.5 mL) was added DIEA (24.5 mg, 189 μmol, 33.0 μL, 1.0 equiv). The mixture was stirred at 25° C. for 12 hours. The reaction mixture was filtered, and the filtrate was concentrated under reduced pressure to give a residue. The residue was purified by prep-HPLC (column: Waters Xbridge 150 mm×25 mm×5 μm; mobile phase: [water ($NH_4HCO_3$)-ACN]; gradient: 76%-100% B over 10 min) to afford N-[3-[4-cyano-3-(trifluoromethoxy)phenoxy]-2,2,4,4-tetramethyl-cyclobutyl]-2-[2-[[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl]pyrimidine-5-carboxamide (60 mg, 60 μmol 32% yield) as a white solid. $^1$H NMR (400 MHz, $CD_3OD$): δ 8.70 (s, 2H), 7.90 (s, 1H), 7.78 (d, J=8.80 Hz, 1H), 7.29 (d, J=8.07 Hz, 2H), 7.20 (d, J=8.19 Hz, 2H), 7.13 (s, 1H), 7.04 (dd, J=8.80, 2.20 Hz, 1H), 6.99 (s, 1H), 4.27 (s, 1H), 4.13 (s, 1H), 3.90-4.02 (m, 2H), 3.82-3.87 (m, 2H), 3.75-3.80 (m, 2H), 2.78 (d, J=7.34 Hz, 2H), 2.71 (s, 3H), 2.60 (d, J=7.09 Hz, 1H), 2.45 (s, 3H), 1.93-2.04 (m, 2H), 1.50-1.69 (m, 10H), 1.27 (s, 6H), 1.21 (s, 6H). LC-MS: MS ($ES^+$): RT=3.093 min, m/z=959.6 $[M+H]^+$; LCMS method: 25.

Example 42—Synthesis of N-[4-(4-cyano-3-methoxy-phenoxy)cyclohexyl]-6-[8-[5-[(9S)-pentaen-7-yl]-2-pyridyl]-2-azaspiro[4.5]decan-2-yl]pyridazine-3-carboxamide (I-86)

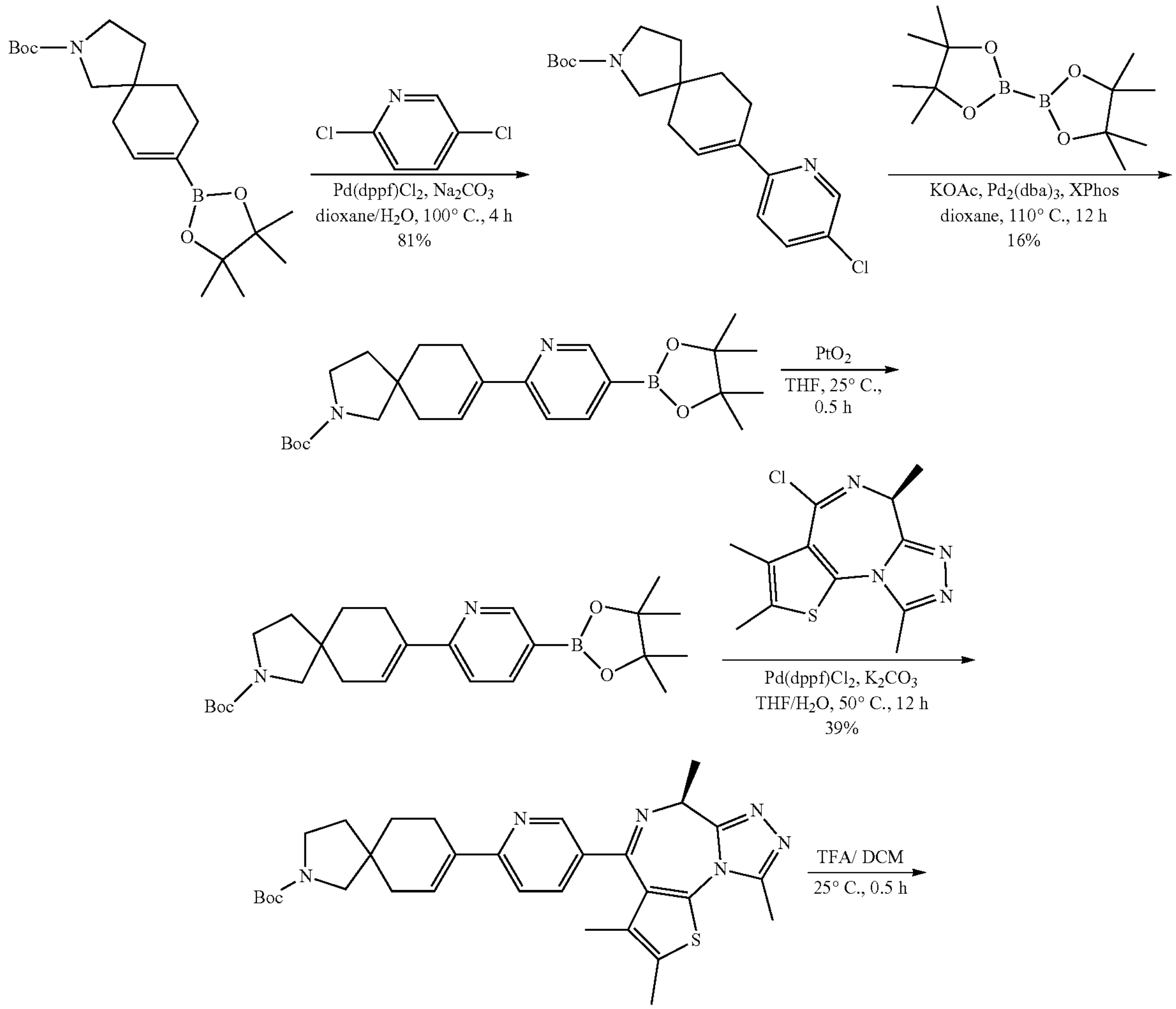

-continued

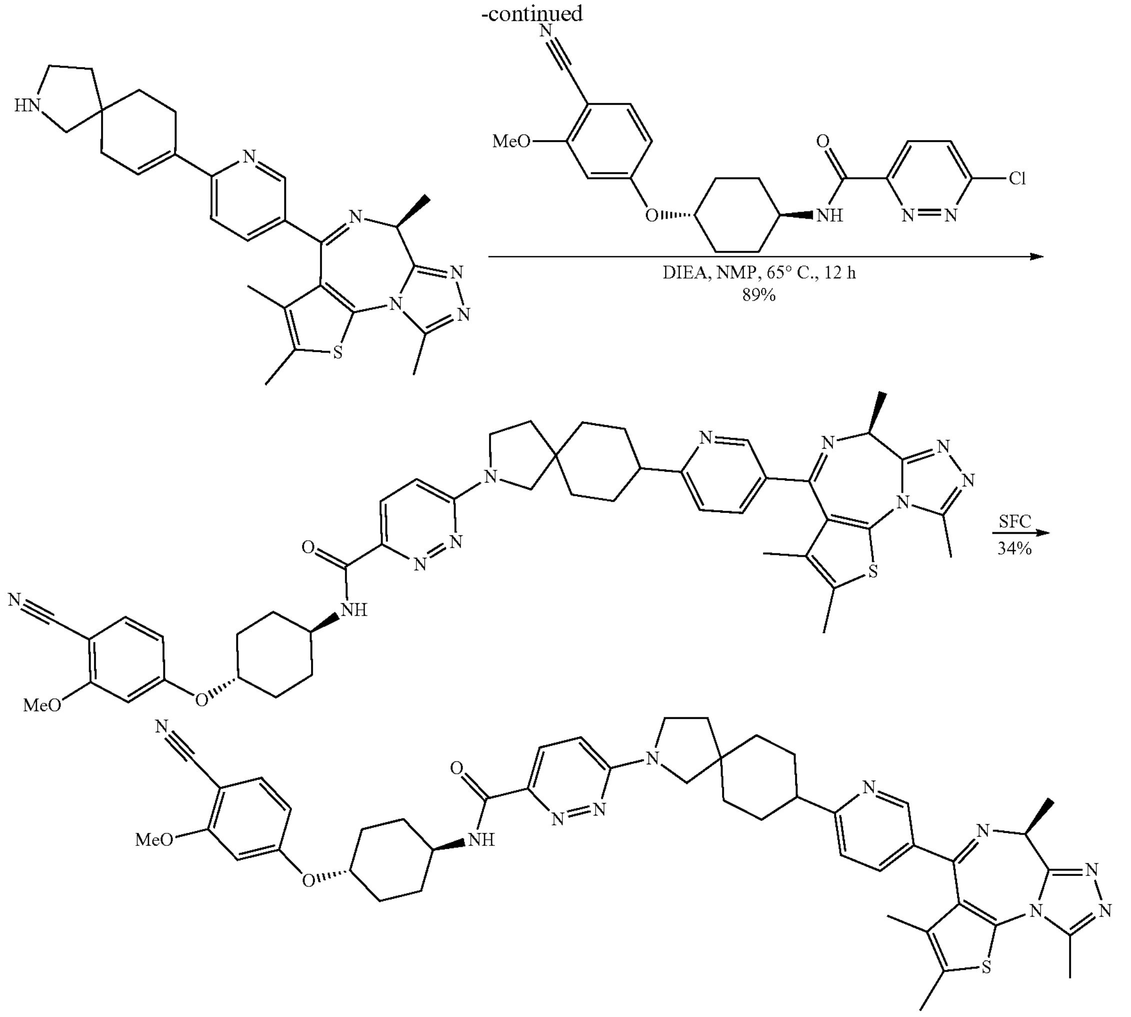

I-86

Step 1: Preparation of tert-butyl 8-(5-chloro-2-pyridyl)-2-azaspiro[4.5]dec-7-ene-2-carboxylate. To a solution of tert-butyl 8-(4,4,5,5-tetramethyl-1,3,2-dioxaborolan-2-yl)-2-azaspiro[4.5]dec-7-ene-2-carboxylate (567 mg, 1.56 mmol, 1.1 equiv) and 2,5-dichloropyridine (210 mg, 1.42 mmol, 1.0 equiv) in dioxane (3 mL) and $H_2O$ (0.6 mL) was added Pd(dppf)$Cl_2$ (207 mg, 283 μmol, 0.2 equiv) and $Na_2CO_3$ (451 mg, 4.26 mmol, 3.0 equiv). The mixture was stirred at 100° C. for 4 hours. The reaction mixture was filtered, and the filtrate was concentrated under reduced pressure to give a residue. The residue was purified by column chromatography ($SiO_2$, petroleum ether:ethyl acetate=60:1 to 35:1) to afford tert-butyl 8-(5-chloro-2-pyridyl)-2-azaspiro[4.5]dec-7-ene-2-carboxylate (400 mg, 1.26 mmol, 81% yield) as a white solid.

Step 2: Preparation of tert-butyl 8-[5-(4,4,5,5-tetramethyl-1,3,2-dioxaborolan-2-yl)-2-pyridyl]-2-azaspiro[4.5]dec-7-ene-2-carboxylate. A mixture of tert-butyl 8-(5-chloro-2-pyridyl)-2-azaspiro[4.5]dec-7-ene-2-carboxylate (400 mg, 1.15 mmol, 1.0 equiv), 4,4,5,5-tetramethyl-2-(4,4,5,5-tetramethyl-1,3,2-dioxaborolan-2-yl)-1,3,2-dioxaborolane (436 mg, 1.72 mmol, 1.5 equiv), $Pd_2(dba)_3$ (42.0 mg, 45.8 μmol, 0.1 equiv), Xphos (87.4 mg, 183 μmol, 0.4 equiv), and KOAc (337 mg, 3.44 mmol, 3.0 equiv) in dioxane (5 mL) was stirred at 110° C. for 12 hours. The reaction mixture was filtered, and the filtrate was concentrated under reduced pressure to give a residue. The residue was purified by prep-HPLC (column: Waters Xbridge 150 mm×25 mm×5 μm; mobile phase: [water ($NH_4HCO_3$)-ACN]; gradient: 32%-62% B over 10 min) to afford tert-butyl 8-[5-(4,4,5,5-tetramethyl-1,3,2-dioxaborolan-2-yl)-2-pyridyl]-2-azaspiro[4.5]dec-7-ene-2-carboxylate (80 mg, 0.18 mmol, 16% yield) as a white solid.

Step 3: Preparation of tert-butyl 8-[5-(4,4,5,5-tetramethyl-1,3,2-dioxaborolan-2-yl)-2-pyridyl]-2-azaspiro[4.5]decane-2-carboxylate. To a solution of tert-butyl 8-[5-(4,4,5,5-tetramethyl-1,3,2-dioxaborolan-2-yl)-2-pyridyl]-2-azaspiro[4.5]dec-7-ene-2-carboxylate (80.0 mg, 181 mol, 1.0 equiv) in THF (2 mL) was added $PtO_2$ (21.8 mg). The mixture was stirred at 25° C. for 0.5 hour. The reaction mixture was filtered, and the filtrate was concentrated under reduced pressure to afford tert-butyl 8-[5-(4,4,5,5-tetramethyl-1,3,2-dioxaborolan-2-yl)-2-pyridyl]-2-azaspiro[4.5]decane-2-carboxylate (80 mg) as a white solid.

Step 4: Preparation of tert-butyl 8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decane-2-carboxylate. To a solution of tert-butyl 8-[5-(4,4,5,5-tetramethyl-1,3,2-dioxaborolan-2-yl)-2-pyridyl]-2-azaspiro[4.5]decane-2-carboxylate (80.0 mg, 180 μmol, 1.0 equiv) and (9S)-7-chloro-4,5,9,13-tetramethyl-3-thia-1,8,11,12-tetrazatricyclo[8.3.0.$0^{2,6}$]trideca-2 (6),4,7,10,12-pentaene (76.1 mg, 271 μmol, 1.5 equiv) in THF (2 mL) and $H_2O$ (0.4 mL) was added Pd(dppf)$Cl_2$ (26.5 mg, 36.2 μmol, 0.2 equiv) and $K_2CO_3$ (74.9 mg, 542 μmol, 3.0 equiv). The mixture was stirred at 50° C. for 12 hours. The reaction mixture was filtered, and the filtrate was concentrated under reduced pressure to give a residue. The residue was purified by prep-TLC ($SiO_2$, DCM:MeOH=10:1) to afford tert-butyl 8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decane-2-carboxylate (40 mg, 70 mmol, 39% yield) as a white solid.

Step 5: Preparation of (9S)-7-[6-(2-azaspiro[4.5]decan-8-yl)-3-pyridyl]-4,5,9,13-tetramethyl-3-thia-1,8,11,12 tetrazatricyclo[8.3.0.$0^{2,6}$]trideca-2 (6),4,7,10,12-pentaene. To a solution of tert-butyl 8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decane-2-carboxylate (40.0 mg, 71.3 μmol, 1.0 equiv) in DCM (1 mL) was added TFA (0.5 ml). The mixture was stirred at 25° C. for 0.5 hour. The reaction mixture was concentrated and basified with saturated aqueous $NaHCO_3$ at 0° C. The mixture were extracted with DCM/MeOH (10:1, 20 mL×2), dried over $Na_2SO_4$, filtered, and concentrated to afford (9S)-7-[6-(2-azaspiro[4.5]decan-8-yl)-3-pyridyl]-4,5,9,13-tetramethyl-3-thia-1,8,11,12 tetrazatricyclo[8.3.0.$0^{2,6}$]trideca-2 (6),4,7,10,12-pentaene (32 mg, crude) as a yellow solid.

Step 6: Preparation of N-[4-(4-cyano-3-methoxy-phenoxy)cyclohexyl]-6-[8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decan-2-yl] pyridazine-3-carboxamide. To a solution of (9S)-7-[6-(2-azaspiro[4.5]decan-8-yl)-3-pyridyl]-4,5,9,13-tetramethyl-3-thia-1,8,11,12-tetrazatricyclo[8.3.0.$0^{2,6}$]trideca-2 (6),4,7,10,12-pentaene (32.0 mg, 69.4 μmol, 1.0 equiv) and 6-chloro-N-[4-(4-cyano-3-methoxy-phenoxy)cyclohexyl]pyridazine-3-carboxamide (34.9 mg, 90.3 μmol, 1.3 equiv; prepared as described above in Example 7) in NMP (0.5 mL) was added DIEA (72.3 mg, 560 μmol, 97.5 μL, 8.0 equiv). The mixture was stirred at 65° C. for 12 hours. The residue was diluted with $H_2O$ (20 mL) and extracted with DCM/MeOH (10:1, 20 mL×2). The combined organic layers were filtered and concentrated under reduced pressure to give a residue. The residue was purified by column chromatography ($SiO_2$, petroleum ether: ethyl acetate=1:1 to 0:1) to afford N-[4-(4-cyano-3-methoxy-phenoxy)cyclohexyl]-6-[8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decan-2-yl]pyridazine-3-carboxamide (50 mg, 61.7 μmol, 89% yield) as a white solid.

Step 7: Preparation of N-[4-(4-cyano-3-methoxy-phenoxy)cyclohexyl]-6-[8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decan-2-yl] pyridazine-3-carboxamide (1-86). The compound N-[4-(4-cyano-3-methoxy-phenoxy)cyclohexyl]-6-[8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decan-2-yl]pyridazine-3-carboxamide (50 mg, 1.0 equiv) was purified by prep-SFC (column: DAICEL CHIRALCEL OD (250 mm×30 mm, 10 μm); mobile phase: [$CO_2$-ACN/EtOH (0.1% $NH_3$·$H_2O$)]; B %: 50%, isocratic elution mode) to afford N-[4-(4-cyano-3-methoxy-phenoxy)cyclohexyl]-6-[8-[5-[(9S)-4,5,9,13-tetramethyl-3-thia-1,8,11,12-tetrazatricyclo[8.3.0.$0^{2,6}$]trideca-2 (6),4,7,10,12-pentaen-7-yl]-2-pyridyl]-2-azaspiro[4.5]decan-2-yl]pyridazine-3-carboxamide (17.5 mg, 34% yield) as a white solid. $^1H$ NMR (400 MHz, $CD_3OD$) δ 8.55 (d, J=1.96 Hz, 1H), 7.91-7.98 (m, 1H), 7.80-7.91 (m, 1H), 7.51 (d, J=9.05 Hz, 1H), 7.42 (d, J=8.19 Hz, 1H), 7.04 (d, J=9.41 Hz, 1H), 6.60-6.70 (m, 2H), 4.46-4.54 (m, 1H), 4.30-4.35 (m, 1H), 3.90-4.01 (m, 4H), 3.58-3.69 (m, 3H), 2.80-2.89 (m, 1H), 2.71 (s, 3H), 2.45 (s, 3H), 2.18-2.27 (m, 2H), 2.06-2.14 (m, 2H), 1.85-2.03 (m, 10H), 1.76 (s, 1H), 1.61-1.71 (m, 10H). LC-MS: MS ($ES^+$): RT=1.804 min, m/z=811.6 $[M+H]^+$; LCMS method: 25.

Example 43—Synthesis of N-((1r,4r)-4-(4-cyano-3-methoxyphenoxy)cyclohexyl)-6-(8-(4-((S)-2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decan-2-yl) pyridazine-3-carboxamide (I-100)

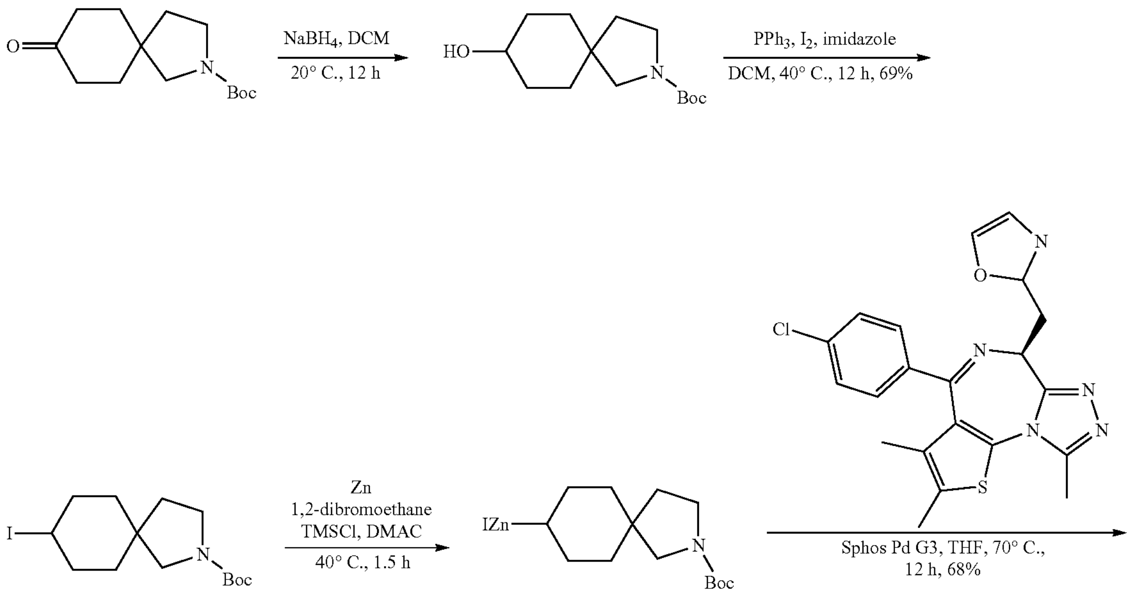

-continued

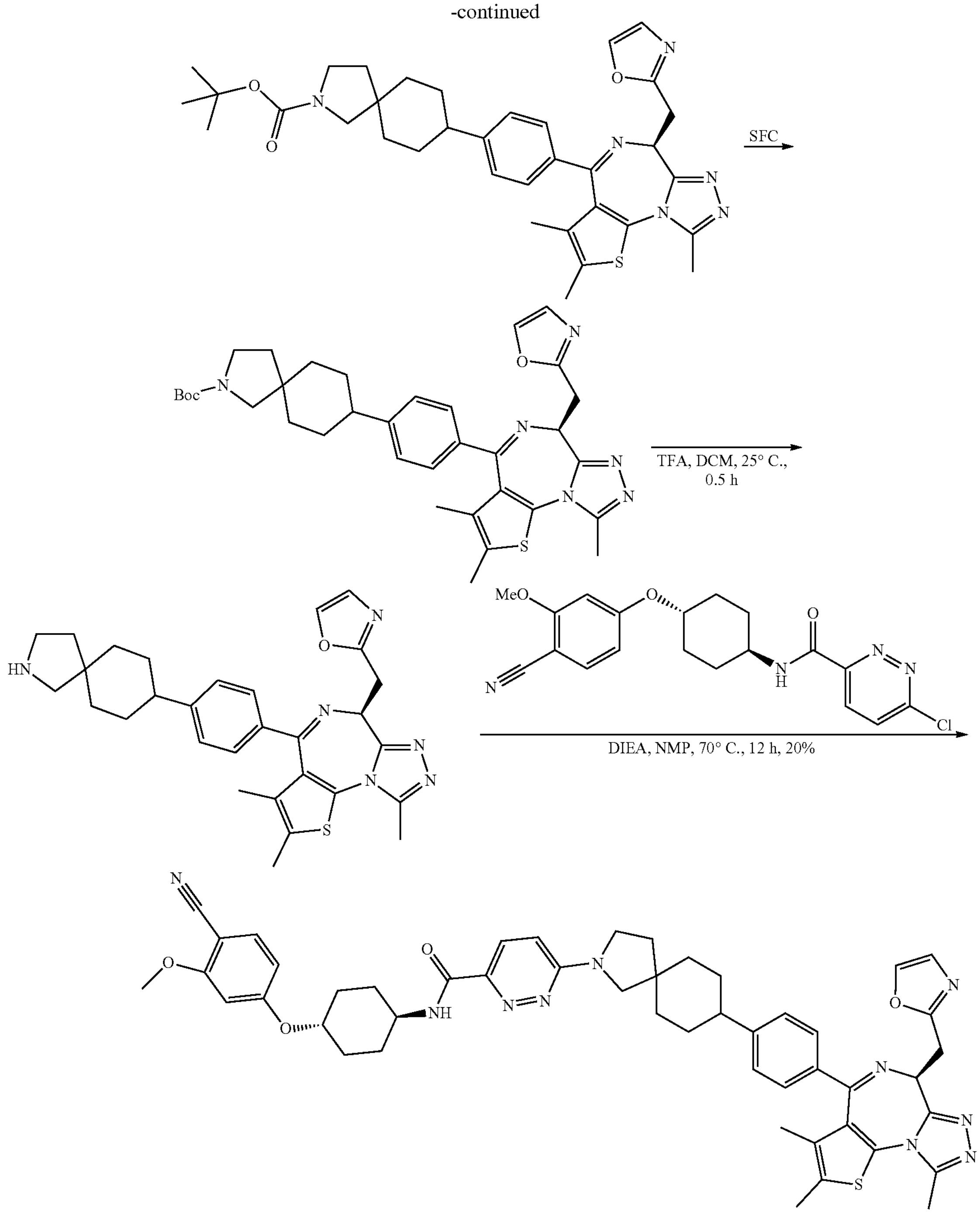

I-100

Step 1: Preparation of tert-butyl 8-hydroxy-2-azaspiro[4.5]decane-2-carboxylate. To a solution of tert-butyl 8-oxo-2-azaspiro[4.5]decane-2-carboxylate (2 g, 7.8 mmol, 1 equiv) in DCM (20 mL) was added $NaBH_4$ (400 mg, 10 mmol, 1.3 equiv). The mixture was stirred at 20° C. for 12 hours. The reaction mixture was filtered, and the filtrate was concentrated under reduced pressure to give a residue.

Step 2: Preparation of tert-butyl 8-iodo-2-azaspiro[4.5]decane-2-carboxylate. To a solution of tert-butyl 8-hydroxy-2-azaspiro[4.5]decane-2-carboxylate (2 g, 7.8 mmol, 1 equiv) in DCM (20 mL) was added $PPh_3$ (2.8 g, 10 mmol, 1.4 equiv), imidazole (1.6 g, 23 mmol, 3 equiv), and $I_2$ (2.9 g, 11 mmol, 2 mL, 1.5 equiv). The mixture was stirred at 40° C. for 12 hours. The reaction mixture was filtered and concentrated under reduced pressure to give a residue, which was purified by prep-TLC ($SiO_2$, ethyl acetate:petroleum ether=5:1) to afford tert-butyl 8-iodo-2-azaspiro[4.5]decane-2-carboxylate (2 g, 69% yield) as a white oil.

Step 3: Preparation of (2-tert-butoxycarbonyl-2-azaspiro[4.5]decan-8-yl)-iodo-zinc. To a stirred solution of Zn (830 mg, 12 mmol, 5.8 equiv) in DMAC (2 mL) was added TMSCl (88 mg, 810 μmol, 102 μL, 0.37 equiv) and 1,2- dibromoethane (152 mg, 810 μmol, 61 μL, 0.37 equiv) in DMAC (1 mL) at 40° C. After stirring for 30 minutes, tert-butyl 8-iodo-2-azaspiro[4.5]decane-2-carboxylate (800 mg, 2 mmol, 1 equiv) was added. The mixture was stirred at 40° C. for an additional 1 hour and filtered. The filtrate was concentrated to afford crude product.

Step 4: Preparation of tert-butyl(S)-8-(4-(2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decane-2-carboxylate. To a solution of (2-(tert-butoxycarbonyl)-2-azaspiro[4.5]decan-8-yl) zinc (II) iodide (3.50 g, 8 mmol, 3.5 equiv) and(S)-2-((4-(4-chlorophenyl)-3,9-dimethyl-6H-thieno[3,2-f][1,2,4]triazolo[4,3-a][1,4]diazepin-6-yl) methyl)oxazole (984 mg, 2 mmol, 1 equiv) in THF (10 mL) was added dicyclohexyl-[2-(2,6-dimethoxyphenyl)phenyl] phosphane; methanesulfonate; (2-phenylanilino) palladium (1+) (362 mg, 464 μmol, 0.2 equiv). The mixture was stirred at 70° C. for 3 hours. The reaction mixture was partitioned with ethyl acetate (20 mL). The organic phase was separated, washed with $H_2O$ (5 mL×3), dried over $Na_2SO_4$, filtered, and concentrated under reduced pressure to give a residue. The residue was purified by prep-HPLC (FA condition; column: Phenomenex luna C18 150 mm×25 mm×10 μm; mobile phase: [water (FA)-ACN]; gradient: 63%-93% B over 10 min) to give tert-butyl(S)-8-(4-(2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decane-2-carboxylate (1 g, 68.70% yield).

Step 5: Preparation of tert-butyl(S)-8-(4-(2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decane-2-carboxylate. Tert-butyl(S)-8-(4-(2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decane-2-carboxylate was purified by SFC (column: DAICEL CHIRALPAK IK (250 mm×30 mm, 10 μm); mobile phase: [$CO_2$-ACN/EtOH (0.1% $NH_3$·$H_2O$)]; B %: 55%, isocratic elution mode) and further purified by SFC (column: DAICEL CHIRALPAK AD (250 mm×30 mm, 10 μm); mobile phase: [$CO_2$-ACN/i-PrOH (0.1% $NH_3$·$H_2O$)]; B %: 60%, isocratic elution mode) to give tert-butyl(S)-8-(4-(2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decane-2-carboxylate (400 mg, 36% yield).

Step 6: Preparation of(S)-2-((4-(4-(2-azaspiro[4.5]decan-8-yl)phenyl)-2,3,9-trimethyl-6H-thieno[3,2-f][1,2,4]triazolo[4,3-a][1,4]diazepin-6-yl)methyl)oxazole. To a solution of tert-butyl(S)-8-(4-(2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decane-2-carboxylate (180 mg, 287 μmol, 1 equiv) in DCM (2 mL) was added TFA (98 mg, 861 μmol, 63 μL, 3 equiv). The mixture was stirred at 25° C. for 0.5 hour. The reaction mixture was filtered, and the filtrate was concentrated under reduced pressure to give a residue. Crude(S)-2-((4-(4-(2-azaspiro[4.5]decan-8-yl)phenyl)-2,3,9-trimethyl-6H-thieno[3,2-f][1,2,4]triazolo[4,3-a][1,4]diazepin-6-yl)methyl) oxazole (150 mg) was used directly in the next step without purification.

Step 7: Preparation of N-((1r,4r)-4-(4-cyano-3-methoxyphenoxy)cyclohexyl)-6-(8-(4-((S)-2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decan-2-yl) pyridazine-3-carboxamide (I-100). To a solution of(S)-2-((4-(4-(2-azaspiro[4.5]decan-8-yl)phenyl)-2,3,9-trimethyl-6H-thieno[3,2-f][1,2,4]triazolo[4,3-a][1,4]diazepin-6-yl) methyl)oxazole (60 mg, 113 μmol, 1 equiv) and 6-chloro-N-((1r,4r)-4-(4-cyano-3-methoxyphenoxy)cyclohexyl) pyridazine-3-carboxamide (46 mg, 119 μmol, 1.05 equiv; prepared as described above in Example 7) in NMP (1 mL) was added DIEA (44 mg, 341 μmol, 59 μL, 3 equiv). The mixture was stirred at 70° C. for 12 hours. The reaction mixture was filtered and concentrated under reduced pressure to give a residue. The residue was purified by prep-HPLC (FA condition; column: Phenomenex luna C18 150 mm×25 mm×10 μm; mobile phase: [water (FA)-ACN]; gradient: 60%-90% B over 10 min) to give N-((1r,4r)-4-(4-cyano-3-methoxyphenoxy)cyclohexyl)-6-(8-(4-((S)-2,3,9-trimethyl-6-(oxazol-2-ylmethyl)-6H-thieno[3,2-f][1,2,4]triazolo[4,3-a][1,4]diazepin-4-yl)phenyl)-2-azaspiro[4.5]decan-2-yl) pyridazine-3-carboxamide (21 mg, 20% yield). $^1$H NMR: (400 MHz, METHANOL-$d_4$) δ ppm 1.68-1.60 (m, 9H) 1.82 (m, J=9.72 Hz, 4H) 1.94 (m, 2H) 2.10 (m, 2H) 2.22 (m, 2H) 2.46 (s, 3H) 2.62 (m, 1H) 2.72 (s, 3H) 3.34-3.32 (m, 2H) 3.76-3.49 (m, 4H) 3.92 (s, 3H) 4.09-3.94 (m, 3H) 4.54-4.45 (m, 1H) 4.77 (m, 1H) 6.71-6.60 (m, 2H) 7.05 (m, 1H) 7.15 (s, 1H) 7.39-7.25 (m, 4H) 7.51 (d, J=9.12 Hz, 1H) 7.99-7.88 (m, 2H). QC-LCMS: MS ($ES^+$): RT=2.184 min, m/z=877.6 $[M+H]^+$, LCMS method: 25.

Example 44—Synthesis of N-[(1r,3r)-3-(4-cyano-3-methoxy-phenoxy)-2,2,4,4-tetramethyl-cyclobutyl]-2-[8-[4-[(9S)-4,5,13-trimethyl-9-(oxazol-2-ylmethyl)-3-thia-1,8,11,12-tetrazatricyclo[8.3.0.0$^{2,6}$] trideca-2 (6),4,7,10,12-pentaen-7-yl]phenyl]-2-azaspiro[4.5]decan-2-yl]pyrimidine-5-carboxamide (II-11)

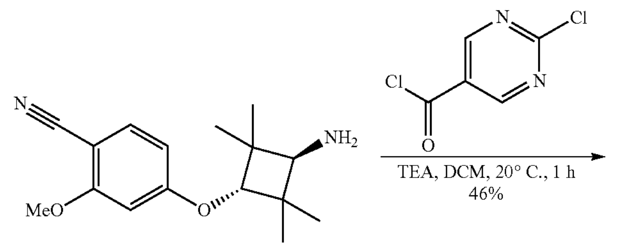

-continued

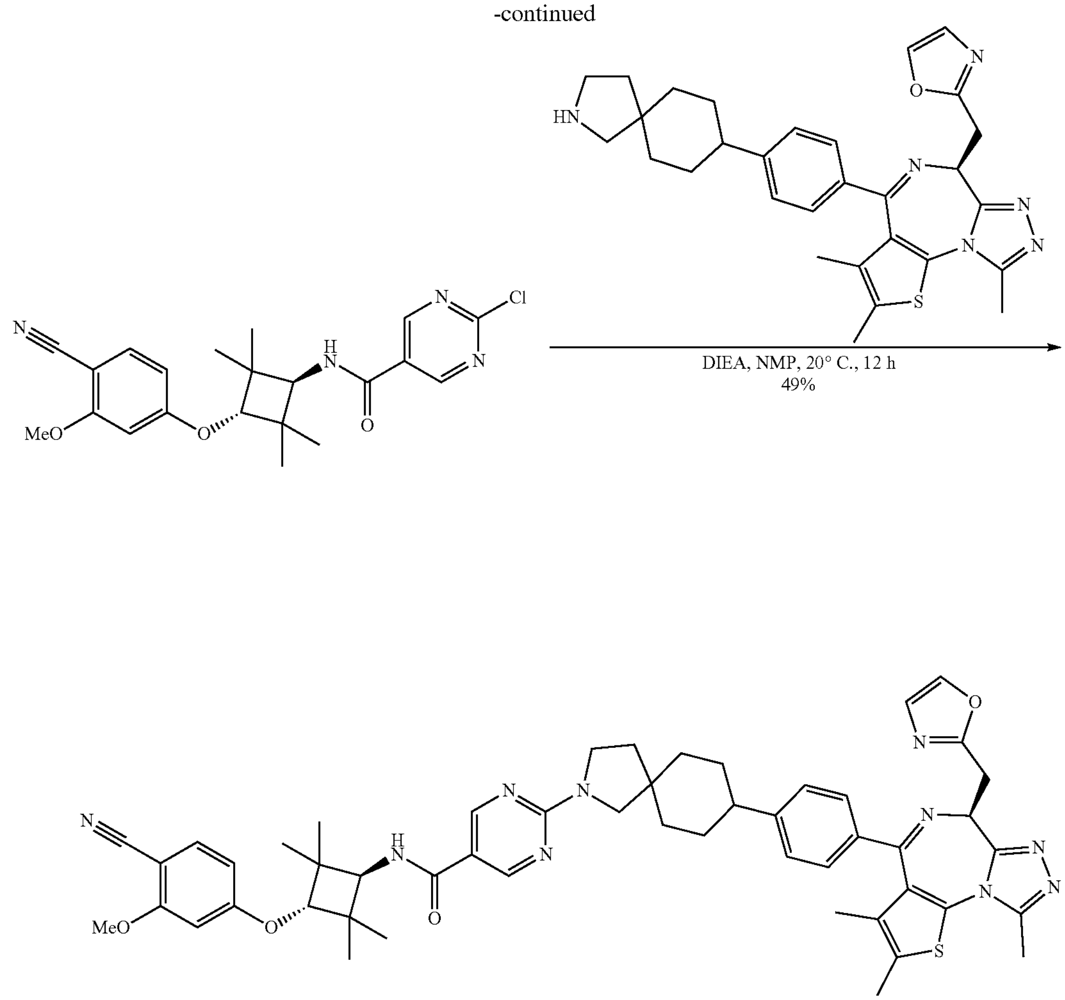

II-11

Step 1: Preparation of 2-chloro-N-[(1r,3r)-3-(4-cyano-3-methoxy-phenoxy)-2,2,4,4-tetramethyl-cyclobutyl]pyrimidine-5-carboxamide. To a solution of 2-chloropyrimidine-5-carbonyl chloride (273 mg, 1.54 mmol, 2 equiv) in DCM (3 mL) was added TEA (390 mg, 3.86 mmol, 537 μL, 5 equiv) and 4-((1r,3r)-3-amino-2,2,4,4-tetramethyl-cyclobutoxy)-2-methoxy-benzonitrile (300 mg, 772 μmol, 1 equiv, TFA). The mixture was stirred at 20° C. for 1 hour. The reaction mixture was partitioned between dichloromethane (100 mL) and water (50 mL). The organic layer was filtered, and concentrated under reduced pressure to give a residue. The residue was purified by column chromatography on silica gel (petroleum ether:ethyl acetate from 1:0 to 1:1) to give 2-chloro-N-[(1r,3r)-3-(4-cyano-3-methoxy-phenoxy)-2,2,4,4-tetramethyl-cyclobutyl]pyrimidine-5-carboxamide (150 mg, 46% yield) as a white solid.

Step 2: Preparation of N-[(1r,3r)-3-(4-cyano-3-methoxy-phenoxy)-2,2,4,4-tetramethyl-cyclobutyl]-2-[8-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyrimidine-5-carboxamide. To a solution of 2-chloro-N-[(1r,3r)-3-(4-cyano-3-methoxy-phenoxy)-2,2,4,4-tetramethyl-cyclobutyl]pyrimidine-5-carboxamide (60 mg, 146 μmol, 1.1 equiv) in NMP (0.5 mL) was added DIEA (51 mg, 398 μmol, 69 μL, 3 equiv) and 2-[(9S)-7-[4-(2-azaspiro[4.5]decan-8-yl) phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (70 mg, 132 μmol, 1 equiv; prepared as described above in Example 43). The mixture was stirred at 20° C. for 12 hours. The reaction mixture was filtered, and the filtrate was concentrated under reduced pressure to give a residue. The residue was purified by prep-HPLC (column: Phenomenex luna C18 150 mm×25 mm×10 μm; mobile phase: [water (FA)-ACN]; gradient: 68%-98% B over 10 min) to give N-[(1r,3r)-3-(4-cyano-3-methoxy-phenoxy)-2,2,4,4-tetramethyl-cyclobutyl]-2-[8-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2-azaspiro[4.5]decan-2-yl]pyrimidine-5-carboxamide (59 mg, 49% yield) as a yellow solid. $^1$H NMR (400 MHz, MeOD) δ=8.78 (s, 2H), 7.92 (s, 1H), 7.81 (d, J=9.0 Hz, 1H), 7.55 (d, J=8.8 Hz, 1H), 7.38-7.27 (m, 4H), 7.15 (s, 1H), 6.65 (d, J=2.0 Hz, 1H), 6.57 (dd, J=2.2, 8.8 Hz, 1H), 4.78 (s, 1H), 4.27 (s, 1H), 4.18-4.13 (m, 1H), 4.08-3.97 (m, 2H), 3.95 (s, 3H), 3.71 (t, J=7.2 Hz, 2H), 3.66 (s, 2H), 2.73 (s, 3H), 2.68-2.59 (m, 1H), 2.47 (s, 3H), 1.97-1.78 (m, 6H), 1.68 (s, 3H), 1.66-1.53 (m, 4H), 1.31 (s, 6H), 1.25 (s, 6H). LC-MS: MS (ES$^+$): RT=2.772 min, m/z=905.7 [M+H]$^+$; LCMS method: 25.

Example 45—Synthesis of N-[4-(4-cyano-3-methoxy-phenoxy)cyclohexyl]-6-[8-[2-isopropyl-4-[(9S)-4,5,9,13-tetramethyl-3-thia1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (I-105)

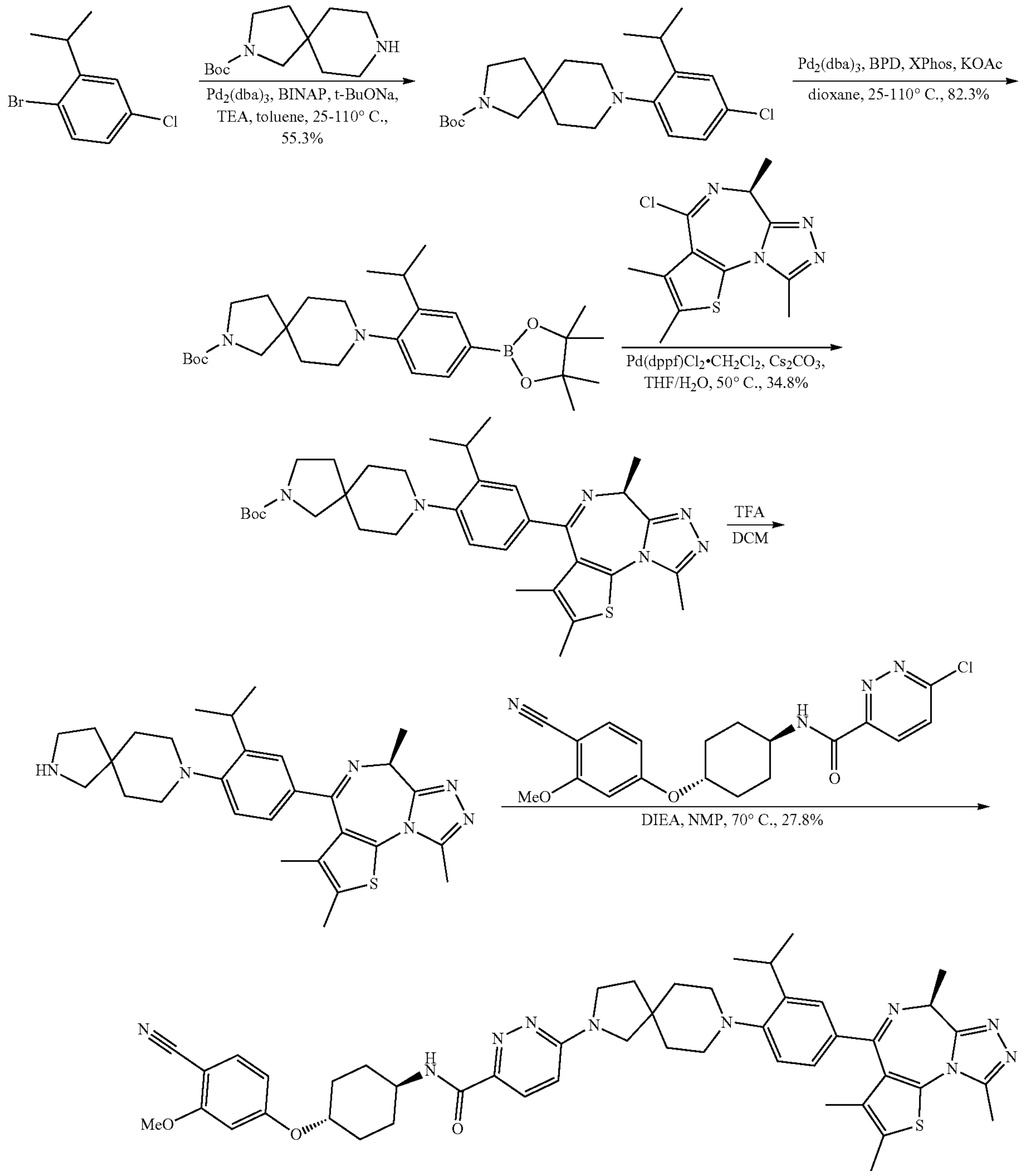

I-105

Step 1: Preparation of tert-butyl 8-(4-chloro-2-isopropyl-phenyl)-2,8-diazaspiro[4.5]decane-2-carboxylate. To a solution of 1-bromo-4-chloro-2-isopropyl-benzene (1.0 g, 4.28 mmol, 1 eq) and tert-butyl 2,8-diazaspiro[4.5]decane-2-carboxylate (1.03 g, 4.28 mmol, 1 eq) in toluene (40 mL) was added $Pd_2(dba)_3$ (117.63 mg, 128.46 μmol, 0.03 eq), BINAP (266.63 mg, 428.21 μmol, 0.1 eq), TEA (476.63 mg, 4.71 mmol, 655.61 μL, 1.1 eq), and sodium tert-butoxide (1.36 g, 14.13 mmol, 3.3 eq) at 25° C. under $N_2$ atmosphere. The mixture was stirred at 110° C. for 12 hours under $N_2$ atmosphere. The reaction mixture was filtered, and the filtrate was concentrated under reduced pressure to give a residue. The residue was purified by column chromatography ($SiO_2$, petroleum ether:ethyl acetate=1:0 to 5:1). Compound tert-butyl 8-(4-chloro-2-isopropyl-phenyl)-2,8-diazaspiro[4.5]decane-2-carboxylate (1.02 g, 2.37 mmol, 55.28% yield, 91.2% purity) was obtained as a yellow oil.

Step 2: Preparation of tert-butyl 8-[2-isopropyl-4-(4,4,5,5-tetramethyl-1,3,2-dioxaborolan-2-yl)phenyl]-2,8-diazaspiro[4.5]decane-2-carboxylate. To a solution of tert-butyl 8-(4-chloro-2-isopropyl-phenyl)-2,8-diazaspiro[4.5]decane-2-carboxylate (350 mg, 812.29 µmol, 1 eq) and BPD (309.41 mg, 1.22 mmol, 1.5 eq) in dioxane (7 mL) was added $Pd_2(dba)_3$ (22.32 mg, 24.37 µmol, 0.03 eq), XPhos (46.47 mg, 97.48 µmol, 0.12 eq), and KOAc (239.16 mg, 2.44 mmol, 3 eq) at 25° C. under $N_2$ atmosphere. The mixture was stirred at 110° C. for 12 hours under $N_2$ atmosphere. The reaction mixture was filtered, and the filtrate was concentrated under reduced pressure to give a residue. The residue was purified by column chromatography ($SiO_2$, petroleum ether:ethyl acetate=1:0 to 4:1). Compound tert-butyl 8-[2-isopropyl-4-(4,4,5,5-tetramethyl-1,3,2-dioxaborolan-2-yl)phenyl]-2,8-diazaspiro[4.5]decane-2-carboxylate (365 mg, 668.26 µmol, 82.27% yield, 88.7% purity) was obtained as a yellow solid.

Step 3: Preparation of tert-butyl 8-[2-isopropyl-4-[(9S)-4,5,9,13-tetramethyl-3-thia-1,8,11,12-tetrazatricyclo[8.3.0.$0^{2,6}$]trideca2 (6),4,7,10,12-pentaen-7-yl]phenyl]-2,8-diazaspiro[4.5]decane-2-carboxylate. To a solution of tert-butyl 8-[2-isopropyl-4-(4,4,5,5-tetramethyl-1,3,2-dioxaborolan-2-yl)phenyl]-2,8-diazaspiro[4.5]decane-2-carboxylate (200 mg, 366.17 µmol, 1 eq) and (9S)-7-chloro-4,5,9,13-tetramethyl-3-thia1,8,11,12-tetrazatricyclo[8.3.0.$0^{2,6}$]trideca-2 (6), 4,7,10,12-pentaene (102.81 mg, 366.17 µmol, 1 eq) in THF (6 mL) and $H_2O$ (2 mL) was added $Cs_2CO_3$ (357.91 mg, 1.10 mmol, 3 eq) and $Pd(dppf)Cl_2 \cdot CH_2Cl_2$ (59.81 mg, 73.23 µmol, 0.2 eq). The mixture was stirred at 50° C. for 12 hours. The reaction mixture was filtered, and the filtrate was concentrated under reduced pressure to give a residue. The residue was purified by prep-TLC ($SiO_2$, petroleum ether: ethyl acetate=1:2). Compound tert-butyl 8-[2-isopropyl-4-[(9S)-4,5,9,13-tetramethyl-3-thia-1,8,11,12-tetrazatricyclo[8.3.0.$0^{2,6}$]trideca2 (6),4, 7,10,12-pentaen-7-yl]phenyl]-2,8-diazaspiro[4.5]decane-2-carboxylate (80 mg, 127.40 µmol, 34.79% yield, 96.0% purity) was obtained as a yellow oil.

Step 4: Preparation of (9S)-7-[4-(2,8-diazaspiro[4.5]decan-8-yl)-3-isopropyl-phenyl]-4,5,9,13-tetramethyl-3-thia-1,8,11,12-tetrazatricyclo[8.3.0.$0^{2,6}$]trideca-2 (6),4,7,10,12-pentaene. To a solution of tert-butyl 8-[2-isopropyl-4-[(9S)-4,5,9,13-tetramethyl-3-thia-1,8,11,12-tetrazatricyclo[8.3.0.$0^{2,6}$]trideca-2 (6),4,7,10,12-pentaen-7-yl]phenyl]-2,8-diazaspiro[4.5]decane-2-carboxylate (78 mg, 124.21 µmol, 1 eq) in DCM (1 mL) was added TFA (1.92 g, 16.80 mmol, 1.25 mL, 135.26 eq). The mixture was stirred at 25° C. for 1 hour. The reaction mixture was filtered, and the filtrate was concentrated under reduced pressure to give a residue. Compound (9S)-7-[4-(2,8-diazaspiro[4.5]decan-8-yl)-3-isopropyl-phenyl]-4,5,9,13-tetramethyl-3-thia-1,8,11,12-tetrazatricyclo[8.3.0.$0^{2,6}$]trideca-2 (6),4,7,10,12-pentaene (62 mg, crude) was obtained as a yellow solid.

Step 5: Preparation of N-[4-(4-cyano-3-methoxy-phenoxy)cyclohexyl]-6-[8-[2-isopropyl-4-[(9S)-4,5,9,13-tetramethyl-3-thia1,8,11,12-tetrazatricyclo[8.3.0.$0^{2,6}$]trideca-2 (6),4,7,10,12-pentaen-7-yl]phenyl]-2,8-diazaspiro[4.5]decan-2-yl]pyridazine-3-carboxamide. To a solution of (9S)-7-[4-(2,8-diazaspiro[4.5]decan-8-yl)-3-isopropyl-phenyl]-4,5,9,13-tetramethyl-3-thia-1,8,11,12-tetrazatricyclo[8.3.0.$0^{2,6}$]trideca-2 (6),4,7,10,12-pentaene (62 mg, 123.33 µmol, 1 eq) and 6-chloro-N-[4-(4-cyano-3-methoxy-phenoxy)cyclohexyl]pyridazine-3-carboxamide (47.71 mg, 123.33 µmol, 1 eq) in NMP (2 mL) was added DIEA (318.78 mg, 2.47 mmol, 429.63 µL, 20 eq). The mixture was stirred at 70° C. for 12 hours. The reaction mixture was concentrated under reduced pressure to give a residue. The residue was purified by prep-HPLC (column: Welch Xtimate C18 150 mm×25 mm×5 µm; mobile phase: [water (FA)-ACN]; gradient: 60%-80% B over 40 min). Compound N-[4-(4-cyano-3-methoxy-phenoxy)cyclohexyl]-6-[8-[2-isopropyl-4-[(9S)-4,5,9,13-tetramethyl-3-thia1,8,11,12-tetrazatricyclo[8.3.0.$0^{2,6}$]trideca-2 (6),4,7,10,12-pentaen-7-yl]phenyl]-2,8-diazaspiro[4.5]decan-2-yl]pyridazine-3-carboxamide (30.19 mg, 34.30 µmol, 27.81% yield, 96.92% purity) was obtained as a yellow solid. $^1$H NMR (400 MHz, $CDCl_3$): δ 8.00 (d, J=9.2 Hz, 1H), 7.90 (d, J=8.0 Hz, 1H), 7.47 (d, J=8.4 Hz, 1H), 7.36-7.28 (m, 2H), 7.05 (d, J=8.4 Hz, 1H), 6.73 (d, J=9.2 Hz, 1H), 6.54-6.50 (m, 1H), 6.47 (d, J=2.4 Hz, 1H), 4.42-4.27 (m, 1H), 4.22-4.11 (m, 1H), 4.10-4.02 (m, 1H), 3.91 (s, 3H), 3.86-3.45 (m, 4H), 3.45-3.37 (m, 1H), 2.98-2.80 (m, 4H), 2.69 (s, 3H), 2.42 (s, 3H), 2.23-2.15 (m, 4H), 2.10 (d, J=6.8 Hz, 3H), 2.07-2.03 (m, 2H), 1.82 (s, 4H), 1.71 (s, 3H), 1.69-1.67 (m, 2H), 1.51-1.44 (m, 2H), 1.24-1.16 (m, 6H). LC-MS: MS ($ES^+$): Rt=0530 min, m/z=853.5 $[M+H]^+$; LCMS method: 5-95.

Example 46—Synthesis of 6-[(3aR,6aS)-2-[4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenyl]-1,3,3a,4,6,6a-hexahydropyrrolo[3,4-c]pyrrol-5-yl]-N-[4-(4-cyano-3-methoxy-phenoxy)cyclohexyl]pyridazine-3-carboxamide (I-106)

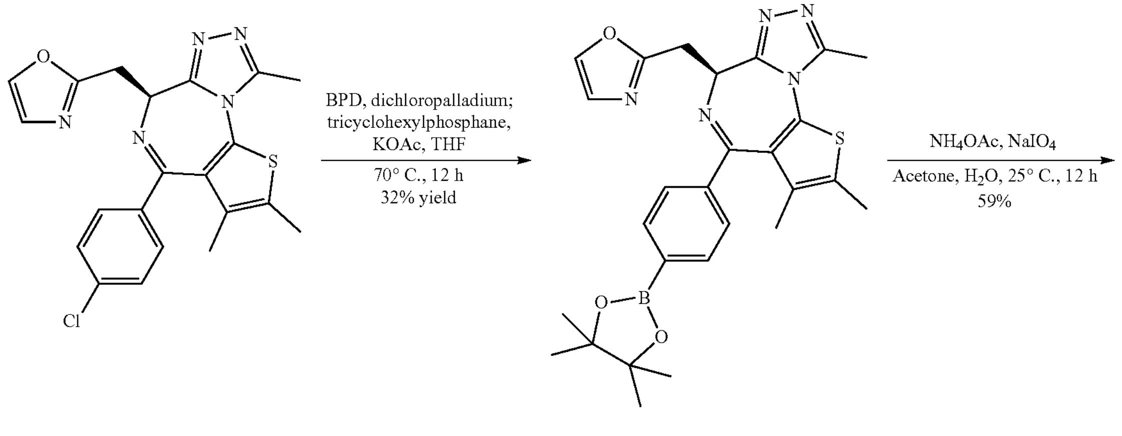

-continued

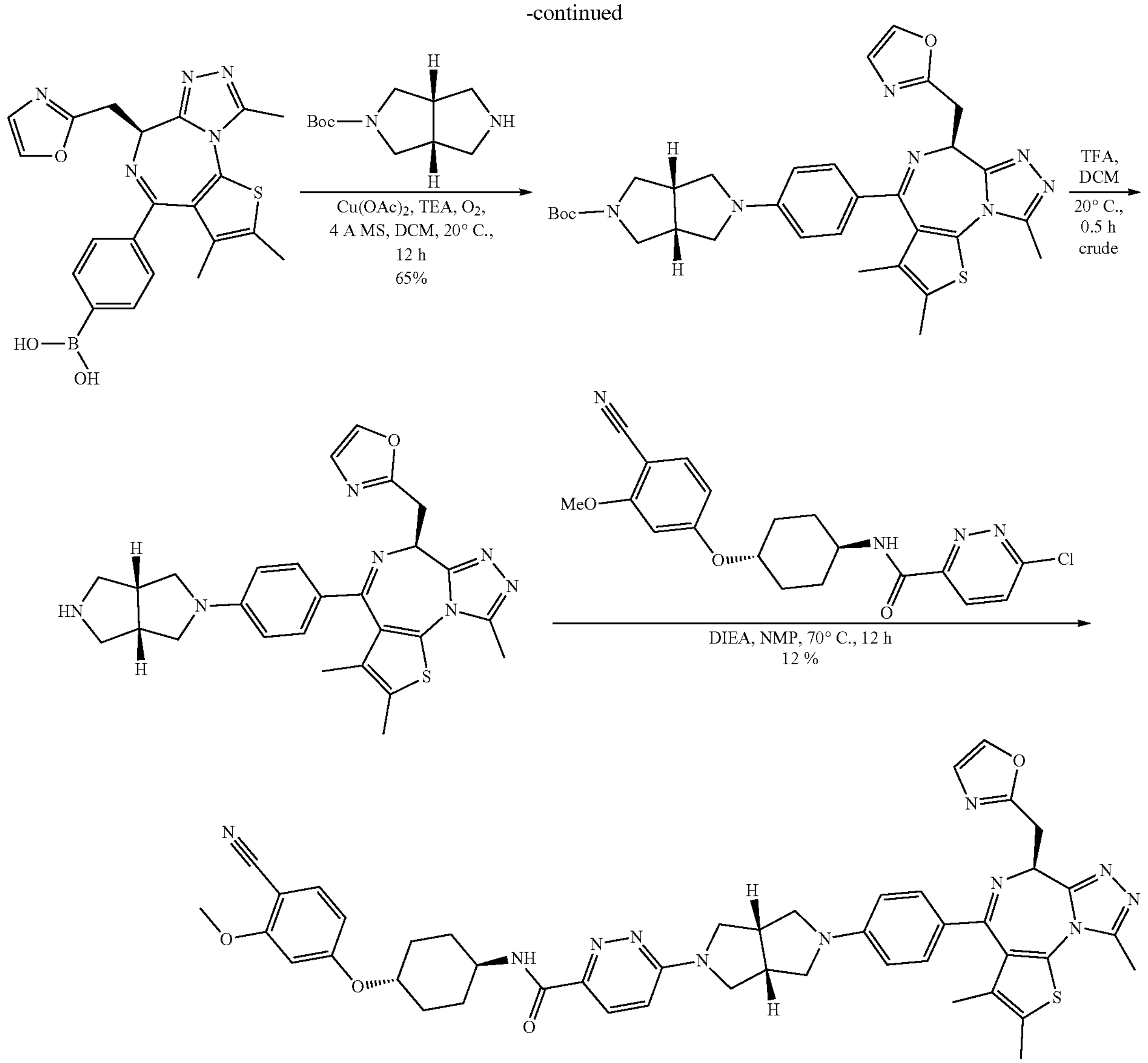

I-106

Step 1: Preparation of 2-[[(9S)-4,5,13-trimethyl-7-[4-(4,4,5,5-tetramethyl-1,3,2-dioxaborolan-2-yl)phenyl]-3-thia-1,8,11,12-tetrazatricyclo[8.3.0.0$^{2,6}$]trideca-2 (6),4,7,10,12-pentaen-9-yl]methyl]oxazole. A mixture of 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (3.0 g, 7.0 mmol, 1.0 equiv), BPD (5.4 g, 21.2 mmol, 3.0 equiv), dichloropalladium; tricyclohexylphosphane (1.0 g, 1.4 mmol, 0.2 equiv), and KOAc (1.5 g, 15.6 mmol, 2.2 equiv) in THF (60 mL) was degassed and purged with $N_2$ 3 times. The mixture was stirred at 70° C. for 12 hours under $N_2$ atmosphere. The reaction mixture was poured into EtOAc (100 mL). The crude mixture was filtered through a pad of Celatom® and poured into $H_2O$ (100 mL). The organic phase was separated, washed with brine (100 mL×3), dried over anhydrous sodium sulfate, filtered, and concentrated under reduced pressure to give a residue. The residue was purified by prep-TLC (silicon dioxide, dichloromethane:methanol=20:1) to give 2-[[(9S)-4,5,13-trimethyl-7-[4-(4,4,5,5-tetramethyl-1,3,2-dioxaborolan-2-yl)phenyl]-3-thia-1,8,11,12-tetrazatricyclo[8.3.0.0$^{2,6}$]trideca-2 (6),4,7,10,12-pentaen-9-yl]methyl]oxazole (1.2 g, 2.3 mmol, 33% yield) as a brown oil.

Step 2: Preparation of [4-[(9S)-4,5,13-trimethyl-9-(oxazol-2-ylmethyl)-3-thia-1,8,11,12-tetrazatricyclo[8.3.0.0$^{2,6}$] trideca-2 (6),4,7,10,12-pentaen-7-yl]phenyl]boronic acid. To a solution of 2-[[(9S)-4,5,13-trimethyl-7-[4-(4,4,5,5-tetramethyl-1,3,2-dioxaborolan-2-yl)phenyl]-3-thia-1,8,11,12-tetrazatricyclo[8.3.0.0$^{2,6}$]trideca-2 (6),4,7,10,12-pentaen-9-yl]methyl]oxazole (1 g, 1.94 mmol, 1.0 equiv) in acetone (12 mL) and $H_2O$ (12 mL) was added $NH_4OAc$ (748 mg, 9.70 mmol, 5.0 equiv) and $NaIO_4$ (2.07 g, 9.70 mmol, 5.0 equiv). The mixture was stirred at 25° C. for 12 hours. The reaction mixture was quenched with saturated aqueous $Na_2SO_3$ (30 mL) at 0° C. To the reaction mixture was added water (50 mL), and the mixture was extracted with EtOAc (50 mL). The combined organic phase was washed with brine (50 mL×3), dried over anhydrous $Na_2SO_4$, filtered, and concentrated to give [4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]boronic acid (500 mg, 59% yield) as a yellow solid.

Step 3: Preparation of tert-butyl (3aR,6aS)-2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-1,3,3a,4,6,6a -hexahydropyrrolo[3,4-c]pyrrole-5-carboxylate. To a solution of [4-[(9S)-4,5,13-trimethyl-9-(oxazol-2-ylmethyl)-3-thia-1,8,11,12-tetrazatricyclo[8.3.0.0$^{2,6}$]trideca-2 (6), 4,7,10,12-pentaen-7-yl]phenyl] boronic acid (300 mg, 692 μmol, 1 equiv) in DCM (8 mL) was added TEA (350 mg, 3.46 mmol, 5 equiv), Cu(OAc) 2 (252 mg, 1.38 mmol, 2 eq), tert-butyl (3aR,6aS)-2,3,3a,4,6,6a -hexahydro-1H-pyrrolo[3,4-c]pyrrole-5-carboxylate (441 mg, 2.08 mmol, 3 equiv), and 4 Å molecular sieves. The mixture was stirred at 20° C. for 12 hours. The residue was purified by prep-TLC ($SiO_2$, DCM:MeOH=10:1) to give tert-butyl (3aR,6aS)-2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-1,3,3a,4,6,6a -hexahydropyrrolo[3,4-c]pyrrole-5-carboxylate (270 mg, 65% yield) as a white solid.

Step 4: Preparation of 2-[[(9S)-7-[4-[(3aR,6aS)-2,3,3a,4,6,6a -hexahydro-1H-pyrrolo[3,4-c]pyrrol-5-yl]phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl (3aR,6aS)-2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-1,3,3a,4,6,6a -hexahydropyrrolo[3,4-c]pyrrole-5-carboxylate (100 mg, 167 μmol, 1 equiv) in DCM (2 mL) was added TFA (1 mL). The mixture was stirred at 20° C. for 0.5 hour. The reaction mixture was filtered and concentrated under reduced pressure to give crude 2-[[(9S)-7-[4-[(3aR,6aS)-2,3,3a,4,6,6a -hexahydro-1H-pyrrolo[3,4-c]pyrrol-5-yl]phenyl]-4,5,13-trimethyl-3-thia-1,8,11,12-tetrazatricyclo[8.3.0.0$^{2,6}$]trideca-2 (6),4,7,10,12-pentaen-9-yl]methyl] oxazole (166 mg) as a yellow oil.

Step 5: Preparation of 6-[(3aR,6aS)-2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-1,3,3a,4,6,6a -hexahydropyrrolo[3,4-c]pyrrol-5-yl]-N-[4-(4-cyano-3-methoxy-phenoxy)cyclohexyl]pyridazine-3-carboxamide. To a solution of 2-[[(9S)-7-[4-[(3aR,6aS)-2,3,3a,4,6,6a -hexahydro-1H-pyrrolo[3,4-c]pyrrol-5-yl]phenyl]-4,5,13-trimethyl-3-thia-1,8,11,12-tetrazatricyclo[8.3.0.0$^{2,6}$]trideca-2 (6),4,7,10,12-pentaen-9-yl]methyl] oxazole (83 mg, 166 μmol, 1 equiv) in NMP (1 mL) was added DIEA (64 mg, 498 μmol, 3 equiv) and 6-chloro-N-[4-(4-cyano-3-methoxy-phenoxy)cyclohexyl]pyridazine-3-carboxamide (71 mg, 183 μmol, 1.1 equiv). The mixture was stirred at 70° C. for 12 hours. The residue was purified by prep-HPLC (column: Waters xbridge 150 mm×25 mm×10 μm; mobile phase: [water ($NH_4HCO_3$)-ACN]; gradient: 47%-67% B over 8 min) to give 6-[(3aR,6aS)-2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-1,3,3a,4,6,6a -hexahydropyrrolo[3,4-c]pyrrol-5-yl]-N-[4-(4-cyano-3-methoxy-phenoxy) cyclohexyl] pyridazine-3-carboxamide (18 mg, 12% yield) as a white solid. $^1$H NMR (400 MHz, $CDCl_3$)$_8$ ppm 8.01 (d, J=9.28 Hz, 1 HOURS), 7.87 (d, J=8.20 Hz, 1H), 7.58-7.66 (m, 1H), 7.47 (d, J=8.56 Hz, 1H), 7.31 (d, J=8.20 Hz, 2H), 7.04 (s, 1H), 6.72 (d, J=9.40 Hz, 1H), 6.42-6.58 (m, 4H), 4.66-4.74 (m, 1H), 4.27-4.39 (m, 1H), 3.98-4.13 (m, 3H), 3.83-3.97 (m, 5H), 3.54-3.74 (m, 4H), 3.21-3.43 (m, 4H), 2.66 (s, 3H), 2.35-2.45 (m, 3H), 2.13-2.24 (m, 4H), 1.75 (s, 3H), 1.44-1.52 (m, 2H), 1.15-1.37 (m, 2H). LC-MS: MS (ES$^+$): RT=2.013 min, m/z=850.4 [M+H]$^+$; LCMS method: 10.

Example 47—Synthesis of N-[4-(4-cyano-3-methoxy-phenoxy)cyclohexyl]-6-[6-[2-[3-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-111)

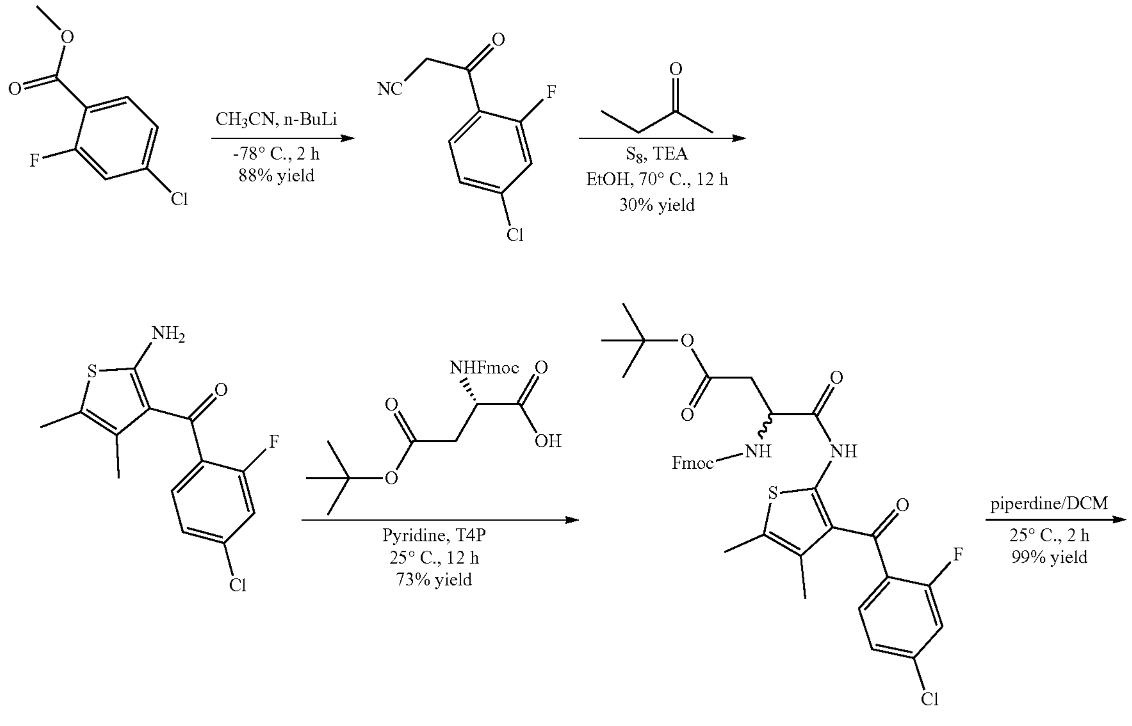

-continued
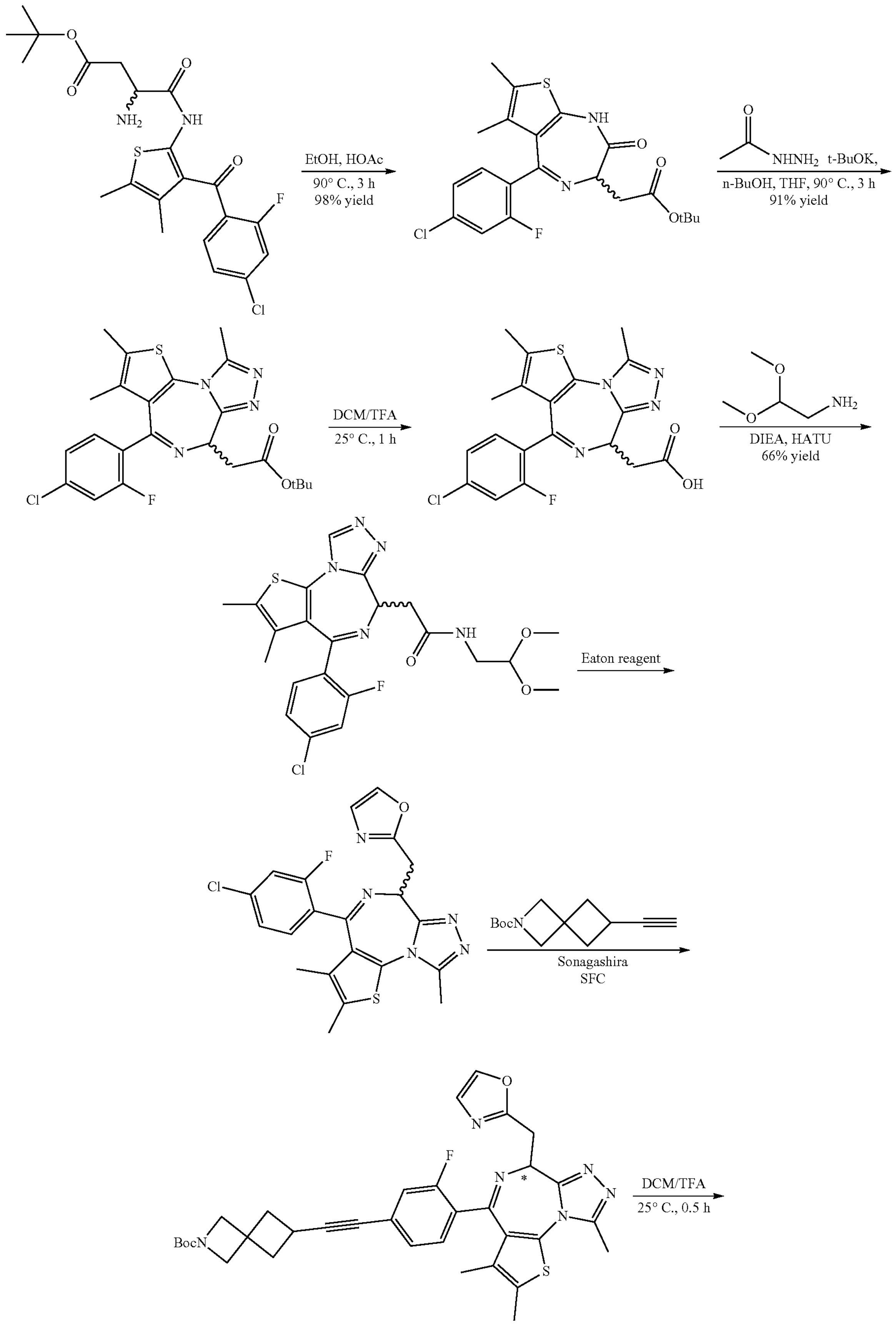

-continued

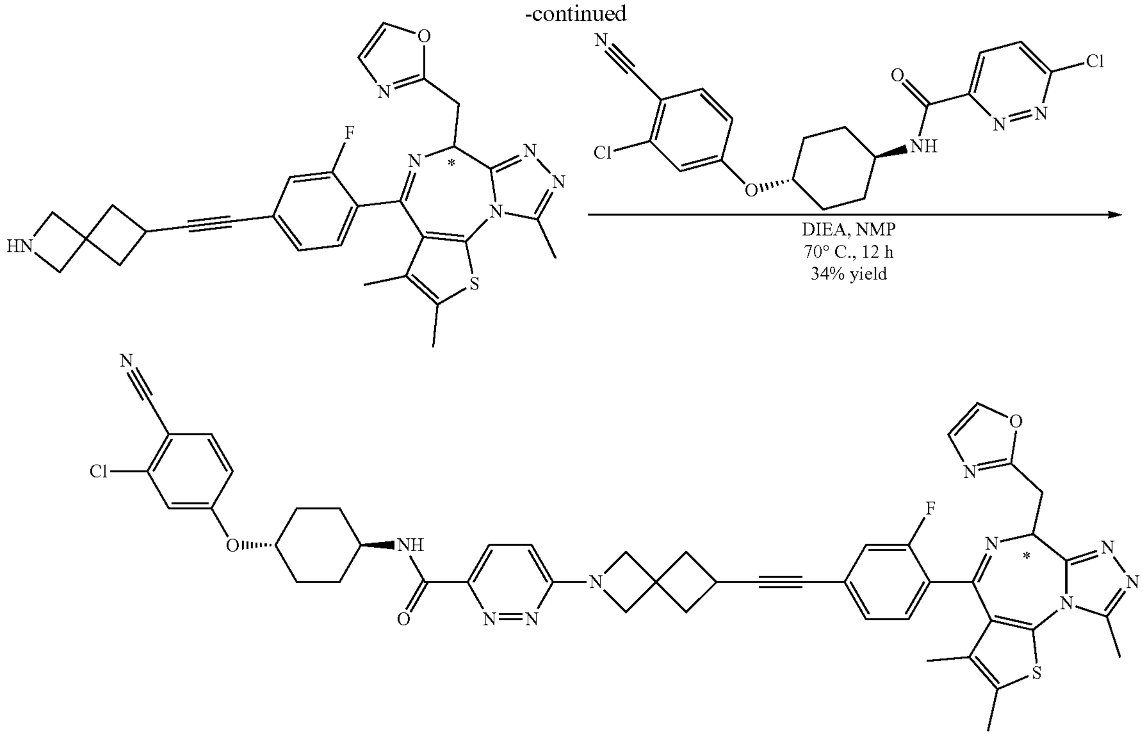

I-111
single stereoisomer of undetermined absolute configuration

Step 1: Preparation of 3-(4-chloro-2-fluoro-phenyl)-3-oxo-propanenitrile. A solution of acetonitrile (9.3 g, 225.3 mmol, 11.9 mL, 1.7 equiv) in THF (200 mL) was stirred at −78° C. under $N_2$ atmosphere. To the mixture was added n-BuLi (2.5 M, 106.0 mL, 2.0 equiv), and the mixture was stirred for 0.5 hour. Next, methyl 4-chloro-2-fluoro-benzoate (25.0 g, 132.5 mmol, 1.0 equiv) in THF (20 mL) was added dropwise, and the mixture was stirred for 1.5 hours under $N_2$ atmosphere. The reaction mixture was quenched with saturated aqueous $NH_4Cl$ (200 ml) at 0° C. The resultant mixture was extracted with ethyl acetate (100 mL×4). The combined organic layers were dried over anhydrous $Na_2SO_4$, filtered, and concentrated in vacuo. The crude product was triturated with petroleum ether:ethyl acetate=20:1 at 25° C. for 30 minutes to give 3-(4-chloro-2-fluoro-phenyl)-3-oxo-propanenitrile (23.0 g, 116.4 mmol, 87.80% yield) as a yellow solid.

Step 2: Preparation of (2-amino-4,5-dimethyl-3-thienyl)-(4-chloro-2-fluoro-phenyl) methanone. To a solution of 3-(4-chloro-2-fluoro-phenyl)-3-oxo-propanenitrile (23.0 g, 116.4 mmol, 1.0 equiv) and butan-2-one (8.4 g, 116.4 mmol, 10.4 mL, 1.0 equiv) in ethanol (200 mL) was added TEA (23.6 g, 232.8 mmol, 32.4 mL, 2.0 equiv) and sulfur flowers S8 (4.4 g, 17.3 mmol, 0.15 equiv). The mixture was stirred at 50° C. for 12 hours. To the reaction mixture was added water (500 mL), and the mixture was extracted with ethyl acetate (500 mL×3). The combined organic phase was washed with brine (500 mL), dried over anhydrous $Na_2SO_4$, filtered, and concentrated in vacuo. The residue was purified by column chromatography ($SiO_2$, petroleum ether:ethyl acetate=35:1 to 30:1) to give (2-amino-4,5-dimethyl-3-thienyl)-(4-chloro-2-fluoro-phenyl) methanone (10.0 g, 35.2 mmol, 30% yield) as a yellow oil.

Step 3: Preparation of tert-butyl (3S)-4-[[3-(4-chloro-2-fluoro-benzoyl)-4,5-dimethyl-2-thienyl]amino]-3-(9H-fluoren-9-ylmethoxycarbonylamino)-4-oxo-butanoate. To a solution of (2-amino-4,5-dimethyl-3-thienyl)-(4-chloro-2-fluoro-phenyl) methanone (8.8 g, 31.0 mmol, 1.0 equiv) and (2S)-4-tert-butoxy-2-(9H-fluoren-9-ylmethoxycarbonylamino)-4-oxo-butanoic acid (19.1 g, 46.5 mmol, 1.5 equiv) in EtOAc (40 mL) was added pyridine (9.8 g, 124.0 mmol, 10.0 mL, 4.0 equiv) and T4P (44.7 g, 62.0 mmol, 50% purity, 2.0 equiv). The mixture was stirred at 25° C. for 12 hours. To the reaction mixture was added water (300 mL), and the mixture was extracted with ethyl acetate (80 mL×3). The combined organic phase was washed with brine (100 mL), dried over anhydrous $Na_2SO_4$, filtered, and concentrated in vacuo. The residue was purified by column chromatography ($SiO_2$, petroleum ether:ethyl acetate=8:1 to 6:1) to give tert-butyl (3S)-4-[[3-(4-chloro-2-fluoro-benzoyl)-4,5-dimethyl-2-thienyl]amino]-3-(9H-fluoren-9-ylmethoxycarbonylamino)-4-oxo-butanoate (15.5 g, 22.9 mmol, 73% yield) as a yellow oil.

Step 4: Preparation of tert-butyl (3S)-3-amino-4-[[3-(4-chloro-2-fluoro-benzoyl)-4,5-dimethyl-2-thienyl]amino]-4-oxo-butanoate. To a solution of tert-butyl (3S)-4-[[3-(4-chloro-2-fluoro-benzoyl)-4,5-dimethyl-2-thienyl]amino]-3-(9H-fluoren-9-ylmethoxy-carbonylamino)-4-oxo-butanoate (14.0 g, 20.7 mmol, 1.0 equiv) in DCM (280 mL) was added piperidine (5.3 g, 62.0 mmol, 6.1 mL, 3.0 equiv). The mixture was stirred at 25° C. for 2 hours. To the reaction mixture was added water (300 mL), and the mixture was extracted with ethyl acetate (200 mL×3). The combined organic phase was washed with brine (350 mL), dried over anhydrous $Na_2SO_4$, filtered, and concentrated in vacuo. The residue was purified by column chromatography ($SiO_2$, petroleum ether:ethyl acetate=10:1 to 8:1) to give tert-butyl (3S)-3-amino-4-[[3-(4-chloro-2-fluoro-benzoyl)-4,5-dimethyl-2-thienyl]amino]-4-oxo-butanoate (9.4 g, 20.7 mmol, 99% yield) as a yellow oil.

Step 5: Preparation of racemic tert-butyl 2-(5-(4-chloro-2-fluorophenyl)-6,7-dimethyl-2-oxo-2,3-dihydro-1H-thieno[2,3-e][1,4]diazepin-3-yl) acetate. To a solution of tert-butyl (3S)-3-amino-4-[[3-(4-chloro-2-fluoro-benzoyl)-4,5-dimethyl-2-thienyl]amino]-4-oxo-butanoate (9.4 g, 20.6 mmol, 1.0 equiv) in EtOH (90 mL) was added AcOH (31.5 g, 524.0 mmol, 30.0 mL, 25.4 equiv). The mixture was stirred at 90° C. for 3 hours. To the reaction mixture was added water (100 mL), and the mixture was extracted with ethyl acetate (150 mL×3). The combined organic phase was washed with brine (150 mL), dried over anhydrous $Na_2SO_4$, filtered, and concentrated in vacuo. The residue was purified by column chromatography ($SiO_2$, petroleum ether:ethyl acetate=8:1 to 6:1) to give racemic tert-butyl 2-(5-(4-chloro-2-fluorophenyl)-6,7-dimethyl-2-oxo-2,3-dihydro-1H-thieno[2,3-e][1,4]diazepin-3-yl) acetate (8.9 g, 20.4 mmol, 98% yield) as a yellow oil.

Step 6: Preparation of tert-butyl 2-[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl]acetate. Potassium tert-butoxide (1.0 M, 22.4 mL, 1.1 equiv) was added to racemic tert-butyl 2-(5-(4-chloro-2-fluorophenyl)-6,7-dimethyl-2-oxo-2,3-dihydro-1H-thieno[2,3-e][1,4]diazepin-3-yl) (8.9 g, 20.4 mmol, 1.0 equiv) in THF (90 mL) at −78° C., and the reaction mixture was stirred at 25° C. for 30 minutes. The reaction mixture was cooled to −78° C. Diphenyl phosphorochloridate (6.6 g, 24.4 mmol, 5.1 mL, 1.2 equiv) was added to the reaction mixture. The resulting mixture was warmed to 25° C. over 45 minutes. Next, acetohydrazide (2.3 g, 30.6 mmol, 1.5 equiv) was added to the reaction mixture. After acetohydrazide was added, n-butanol (90 mL) was added immediately with stirring. The mixture was then heated at 90° C. for 1 hour. The reaction mixture was quenched with dropwise addition of saturated aqueous $NH_4Cl$ (100 mL) at 0° C. The resultant mixture was extracted with ethyl acetate (100 mL×2). The combined organic layers were dried over anhydrous $Na_2SO_4$, filtered, and concentrated in vacuo. The residue was purified by column chromatography ($SiO_2$, petroleum ether:ethyl acetate=8:1 to 6:1) to give racemic tert-butyl 2-(4-(4-chloro-2-fluorophenyl)-2,3,9-trimethyl-6H-thieno[3,2-f][1,2,4]triazolo[4,3-a][1,4]diazepin-6-yl) acetate (8.9 g, 18.74 mmol, 91% yield) as a yellow oil.

Step 7: Preparation of racemic 2-(4-(4-chloro-2-fluorophenyl)-2,3,9-trimethyl-6H-thieno[3,2-f][1,2,4]triazolo[4,3-a][1,4]diazepin-6-yl) acetic acid. To a solution of racemic tert-butyl 2-(4-(4-chloro-2-fluorophenyl)-2,3,9-trimethyl-6H-thieno[3,2-f][1,2,4]triazolo[4,3-a][1,4]diazepin-6-yl) acetate (8.9 g, 18.7 mmol, 1.0 equiv) in DCM (40 mL) was added TFA (20.0 mL). The mixture was stirred at 25° C. for 1 hour. The reaction mixture was filtered, and the filtrate was concentrated under reduced pressure to give racemic 2-(4-(4-chloro-2-fluorophenyl)-2,3,9-trimethyl-6H-thieno[3,2-f][1,2,4]triazolo[4,3-a][1,4]diazepin-6-yl) acetic acid (7.8 g, 18.6 mmol) as a yellow oil, which was used directly in the next step without purification.

Step 8: Preparation of racemic 2-(4-(4-chloro-2-fluorophenyl)-2,3-dimethyl-6H-thieno[3,2-f][1,2,4]triazolo[4,3-a][1,4]diazepin-6-yl)-N-(2,2-dimethoxyethyl) acetamide. To a solution of racemic 2-(4-(4-chloro-2-fluorophenyl)-2,3,9-trimethyl-6H-thieno[3,2-f][1,2,4]triazolo[4,3-a][1,4]diazepin-6-yl) acetic acid (7.8 g, 18.6 mmol, 1.0 equiv) and 2,2-dimethoxyethanamine (5.8 g, 55.8 mmol, 6.09 mL, 3.0 equiv) in DMF (70 mL) was added HATU (7.8 g, 20.5 mmol, 1.1 equiv) and DIEA (7.2 g, 55.8 mmol, 9.73 mL, 3.0 equiv). The mixture was stirred at 25° C. for 0.5 hour. To the reaction mixture was added water (20 mL), and the mixture was extracted with ethyl acetate (20 mL×3). The combined organic phase was washed with brine (50 mL), dried over anhydrous $Na_2SO_4$, filtered, and concentrated in vacuo. The residue was purified by column chromatography ($SiO_2$, DCM:MeOH=40:1 to 20:1) to give racemic 2-(4-(4-chloro-2-fluorophenyl)-2,3-dimethyl-6H-thieno[3,2-f][1,2,4]triazolo[4,3-a][1,4]diazepin-6-yl)-N-(2,2-dimethoxyethyl) acetamide (6.3 g, 12.5 mmol, 66% yield) as a yellow oil.

Step 9: Preparation of racemic 2-((4-(4-chloro-2-fluorophenyl)-2,3,9-trimethyl-6H-thieno[3,2-f][1,2,4]triazolo[4,3-a][1,4]diazepin-6-yl)methyl)oxazole. To a solution of racemic 2-(4-(4-chloro-2-fluorophenyl)-2,3-dimethyl-6H-thieno[3,2-f][1,2,4]triazolo[4,3-a][1,4]diazepin-6-yl)-N-(2,2-dimethoxyethyl) acetamide (2.0 g, 3.9 mmol, 1.0 equiv) in $P_2O_5$; methanesulfonic acid (20 mL). The mixture was stirred at 100° C. for 12 hours. The reaction mixture was quenched with dropwise addition of saturated aqueous $NaHCO_3$ (200 ml) at 0° C. The resulting mixture was extracted with ethyl acetate (50 mL×3). The combined organic layers were dried over anhydrous $Na_2SO_4$, filtered, and concentrated in vacuo. The residue was purified by column chromatography ($SiO_2$, DCM:MeOH=30:1 to 20:1). The residue was purified by prep-HPLC (column: Phenomenex luna C18 (250 mm×70 mm×10 μm); mobile phase: [water (FA)-ACN]; gradient: 40%-70% B over 20 min) to give racemic 2-((4-(4-chloro-2-fluorophenyl)-2,3,9-trimethyl-6H-thieno[3,2-f][1,2,4]triazolo[4,3-a][1,4]diazepin-6-yl)methyl)oxazole (3.0 g, 6.79 mmol, 57% yield) as a white solid.

Step 10: Preparation of tert-butyl 6-[2-[3-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. A mixture of tert-butyl 6-ethynyl-2-azaspiro[3.3]heptane-2-carboxylate (500 mg, 2.3 mmol, 2.5 equiv), racemic 2-((4-(4-chloro-2-fluorophenyl)-2,3,9-trimethyl-6H-thieno[3,2-f][1,2,4]triazolo[4,3-a][1,4]diazepin-6-yl)methyl) oxazole (400 mg, 905 μmol, 1.0 equiv), [2-(2-aminophenyl)phenyl]-methyl-sulfonyloxy-palladium; 2-(2-dicyclohexylphosphanylphenyl)-N,N-dimethyl-aniline (69 mg, 90 μmol, 0.1 equiv), and $Cs_2CO_3$ (589 mg, 1.8 mmol, 2.0 equiv) in MeCN (10 mL) was degassed and purged with $N_2$ 3 times. The reaction mixture was stirred at 90° C. for 2 hours under $N_2$ atmosphere. To the reaction mixture was added water (20 mL), and the mixture was extracted with ethyl acetate (30 mL×3). The combined organic phase was washed with brine (50 mL), dried over anhydrous $Na_2SO_4$, filtered, and concentrated in vacuo. The residue was purified by prep-HPLC (column: Phenomenex luna C18 150 mm×40 mm×15 μm; mobile phase: [water (FA)-ACN]; gradient: 55%-85% B over 15 min). The residue was purified by prep-SFC (column: DAICEL CHIRALPAK AS (250 mm×30 mm×10 μm); mobile phase: [$CO_2$-MeOH]; B %: 50%, isocratic elution mode) to give tert-butyl 6-[2-[3-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (140 mg, 223.38 μmol, 24.68% yield) as a yellow oil. The product is enantiopure of unknown absolute stereochemistry.

Step 11: Preparation of 2-[[7-[4-[2-(2-azaspiro[3.3]heptan-6-yl)ethynyl]-2-fluoro-phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 6-[2-[3-fluoro-4-[4,5,13-trimethyl-9-(oxazol-2-ylmethyl)-3- thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (140 mg, 223 μmol, 1.0 equiv) in DCM (3 mL) was added TFA (1.0 mL). The reaction mixture was stirred at 25° C. for 0.5 hour. The reaction mixture was quenched with dropwise addition of saturated aqueous $NaHCO_3$ (10 mL) at 0° C. The resultant mixture was extracted with ethyl acetate (10 mL×2). The combined organic layers were dried over anhydrous $Na_2SO_4$, filtered, and concentrated in vacuo to give 2-[[7-[4-[2-(2-azaspiro[3.3]heptan-6-yl)ethynyl]-2-fluoro-phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (120 mg, crude) as a yellow oil, which was used directly in the next step without purification.

Step 12: Preparation of N-[4-(4-cyano-3-methoxy-phenoxy)cyclohexyl]-6-[6-[2-[3-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-111). To a solution of 2-[[7-[4-[2-(2-azaspiro[3.3]heptan-6-yl)ethynyl]-2-fluoro-phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (60 mg, 113 μmol, 1.0 equiv) and 6-chloro-N-[4-(4-cyano-3-methoxy-phenoxy)cyclohexyl]pyridazine-3-carboxamide (44 mg, 113 μmol, 1.0 equiv) in NMP (1.0 mL) was added DIEA (29 mg, 227 μmol, 39 μL, 2.0 equiv). The reaction mixture was stirred at 70° C. for 12 hours. The reaction mixture was filtered, and the filtrate was concentrated under reduced pressure to give a residue. The residue was purified by prep-HPLC (column: Phenomenex luna C18 150 mm×25 mm×10 μm; mobile phase: [water (FA)-ACN]; gradient: 54%-84% B over 10 min) to give N-[4-(4-cyano-3-methoxy-phenoxy)cyclohexyl]-6-[6-[2-[3-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (56 mg, 55% yield) as a white solid. 1H NMR: (400 MHz, DMSO-$d_6$) δ=8.52 (d, J=8.4 Hz, 1H), 8.04 (s, 1H), 7.83-7.81 (m, 1H), 7.61-7.59 (m, 1H), 7.36-7.20 (m, 3H), 7.13 (s, 1H), 6.85-6.83 (m, 1H), 6.76-6.58 (m, 2H), 4.78-4.68 (m, 1H), 4.54-4.45 (m, 1H), 4.18 (s, 2H), 4.12 (s, 2H), 3.89 (s, 4H), 3.86-3.77 (m, 2H), 2.66-2.64 (m, 2H), 2.60 (s, 3H), 2.44-2.42 (m, 2H), 2.39 (s, 3H), 2.14-2.07 (m, 2H), 1.91-1.88 (m, 2H), 1.65-1.64 (m, 2H), 1.60 (s, 3H), 1.56-1.47 (m, 2H). LC-MS: MS ($ES^+$): RT=2.522 min, m/z=877.4 $[M+H]^+$.

Example 48—Synthesis of Additional Compounds

The following compounds were synthesized using procedures analogous to those described above: I-18, II-3, I-20, I-21, I-22, I-1, I-23, I-24, II-6, II-7, II-8, II-9, II-2, I-26, I-3, I-5, I-10, I-11, I-28, I-30, I-35, I-36, I-38, I-14, I-15, I-42, I-43, I-47, I-48, I-50, I-51, I-52, I-53, I-55, I-57, I-59, I-60, I-61, I-63, I-65, I-67, I-68, I-69, I-70, I-71, I-72, I-74, I-75, I-76, I-77, I-78, I-80, I-84, I-85, I-87, I-88, I-89, I-90, I-91, I-92, I-93, I-94, I-95, I-96, I-97, I-98, I-99, I-101, II-12, I-102, I-103, I-104, I-107, I-108, I-109, I-110, I-112, I-113, I-114, I-115, I-116, I-117, I-118, I-119, I-120, I-121, I-122, I-123, I-124, I-125, I-126, I-127, I-128, I-129, I-130, I-131, I-132, I-133, I-134, I-135, I-136, I-137, II-13, and II-14. Physical characterization data for exemplary compounds is provided in Table 4.

TABLE 4

| Compound No. | MW Exact | Observed Mass | LCMS Purity (UV 220) |
|---|---|---|---|
| I-18 | 824.39447 | 825.4 | 99.88 |
| II-3 | 852.42578 | 853.4 | 97.7 |
| I-20 | 809.38355 | 810.4 | 98.81 |
| I-21 | 809.38355 | 810.4 | 100 |
| I-22 | 809.38355 | 810.4 | 100 |
| I-1 | 930.36108 | 931.4 | 99.5 |
| I-23 | 810.37878 | 811.4 | 95.51 |
| I-24 | 823.39923 | 824.4 | 99.57 |
| II-6 | 836.41962 | 837.4 | 98.63 |
| II-7 | 837.41486 | 838.4 | 100 |
| II-8 | 837.41486 | 838.4 | 100 |
| II-9 | 946.43121 | 947.6 | 94.3 |
| II-2 | 960.37164 | 961.4 | 99.61 |
| I-26 | 823.39923 | 824.4 | 96.83 |
| I-3 | 893.36585 | 894.6 | 99.37 |
| I-5 | 907.38153 | 908.6 | 98.26 |
| I-10 | 863.35529 | 864.6 | 95.6 |
| I-11 | 864.35053 | 865.6 | 97.22 |
| I-28 | 839.3941 | 840.6 | 98.44 |
| I-30 | 853.40979 | 854.6 | 98.63 |
| I-35 | 809.38355 | 810.5 | 98.11 |
| I-36 | 808.38831 | 809.5 | 96.96 |
| I-38 | 809.38355 | 810.6 | 95.4 |
| I-14 | 877.37097 | 878.6 | 99.25 |
| I-15 | 878.36621 | 879.6 | 95.91 |
| I-42 | 823.39923 | 824.7 | 98.26 |
| I-43 | 810.37878 | 811.6 | 95.99 |
| I-47 | 782.34753 | 783.4 | 92.83 |
| I-48 | 810.37878 | 811.6 | 96.56 |
| I-50 | 811.36279 | 812.6 | 95.25 |
| I-51 | 811.36279 | 812.6 | 96.27 |
| I-52 | 811.36279 | 812.5 | 95.74 |
| I-53 | 808.38831 | 809.6 | 90.46 |
| I-55 | 807.39307 | 808.6 | 96.53 |
| I-57 | 827.37415 | 828.6 | 96.11 |
| I-59 | 827.37415 | 828.5 | 96.36 |
| I-60 | 823.39923 | 824.6 | 95.97 |
| I-61 | 823.39923 | 824.6 | 94.44 |
| I-63 | 823.39923 | 824.6 | 94.47 |
| I-65 | 843.3446 | 844.6 | 94.26 |
| I-67 | 839.3941 | 840.6 | 96.68 |
| I-68 | 839.3941 | 840.6 | 96.08 |
| I-69 | 839.3941 | 840.6 | 96.24 |
| I-70 | 809.38355 | 810.5 | 96.69 |
| I-71 | 808.38831 | 809.6 | 97.24 |
| I-72 | 824.39447 | 825.6 | 93.93 |
| I-74 | 844.33984 | 845.6 | 89.77 |
| I-75 | 840.38934 | 841.4 | 97.98 |
| I-76 | 800.33807 | 801.4 | 96.29 |
| I-77 | 800.33807 | 801.4 | 93.54 |
| I-78 | 836.39447 | 837.6 | 97.4 |
| I-80 | 814.35376 | 815.5 | 95.14 |
| I-84 | 843.3446 | 844.6 | 99.37 |
| I-85 | 843.3446 | 844.6 | 96.43 |
| I-87 | 810.37878 | 811.6 | 94.24 |
| I-88 | 810.37878 | 811.6 | 96.33 |
| I-89 | 810.37878 | 811.6 | 93.67 |
| I-90 | 840.38934 | 841.6 | 98 |
| I-91 | 818.32867 | 819.5 | 92.81 |
| I-92 | 814.35376 | 815.4 | 94.65 |
| I-93 | 814.35376 | 815.4 | 97.83 |
| I-94 | 795.36792 | 796.5 | 96.23 |
| I-95 | 795.36792 | 796.5 | 95.18 |
| I-96 | 795.36792 | 796.5 | 94.48 |
| I-97 | 795.36792 | 796.5 | 93.94 |
| I-98 | 810.37878 | 811.6 | 93.28 |
| I-99 | 810.37878 | 811.6 | 94.11 |
| I-101 | 876.38934 | 877.6 | 97.09 |
| II-12 | 904.42065 | 905.6 | 96.62 |
| I-102 | 809.38355 | 810.6 | 96.47 |
| I-103 | 832.3443 | 833.5 | 96.57 |
| I-104 | 832.3443 | 833.6 | 95.61 |
| I-107 | 846.35999 | 847.4 | 97.91 |
| I-108 | 778.31622 | 779.4 | 95.42 |
| I-109 | 826.37372 | 827.4 | 98.23 |
| I-110 | 812.35809 | 813.4 | 96.32 |
| I-112 | 876.33301 | 877.4 | 96.79 |
| I-113 | 846.35999 | 847.4 | 98.94 |

TABLE 4-continued
| Compound No. | MW Exact | Observed Mass | LCMS Purity (UV 220) |
|---|---|---|---|
| I-114 | 850.4101 | 851.4 | 96.59 |
| I-115 | 812.35809 | 813.4 | 96.59 |
| I-116 | 846.35999 | 847.4 | 96.19 |
| I-117 | 832.3443 | 833.6 | 95.19 |
| I-118 | 877.38464 | 878.4 | 94.57 |
| I-119 | 885.33447 | 886.4 | 92.18 |
| I-120 | 838.4101 | 839.6 | 97.33 |
| I-121 | 851.43048 | 852.7 | 95.98 |
| I-122 | 851.43048 | 852.7 | 99.83 |
| I-123 | 876.33301 | 877.4 | 99.46 |
| I-124 | 858.34241 | 859.4 | 99.22 |
| I-125 | 894.38 | 895.6 | 100 |
| I-126 | 945.372 | 946.6 | 100 |
| I-127 | 876.333 | 877.4 | 98.26 |
| I-128 | 896.359 | 897.4 | 98.83 |
| I-129 | 945.372 | 946.6 | 99.7 |
| I-130 | 850.41 | 851.6 | 97.42 |
| I-131 | 895.375 | 896.4 | 95.28 |
| I-132 | 850.41 | 851.6 | 98.75 |
| I-133 | 896.359 | 897.6 | 100 |
| I-134 | 895.375 | 896.2 | 100 |
| I-135 | 895.375 | 896.8 | 100 |
| I-136 | 945.372 | 946.4 | 98.77 |
| I-137 | 945.372 | 946.4 | 99.42 |
| II-13 | 922.411 | 923.6 | 99.71 |
| II-14 | 906.4 | 907.6 | 100 |
Example 49—Synthesis of N-[(1r,4r)-4-(4-cyano-3-methoxy-phenoxy)cyclohexyl]-6-[6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide (I-124)
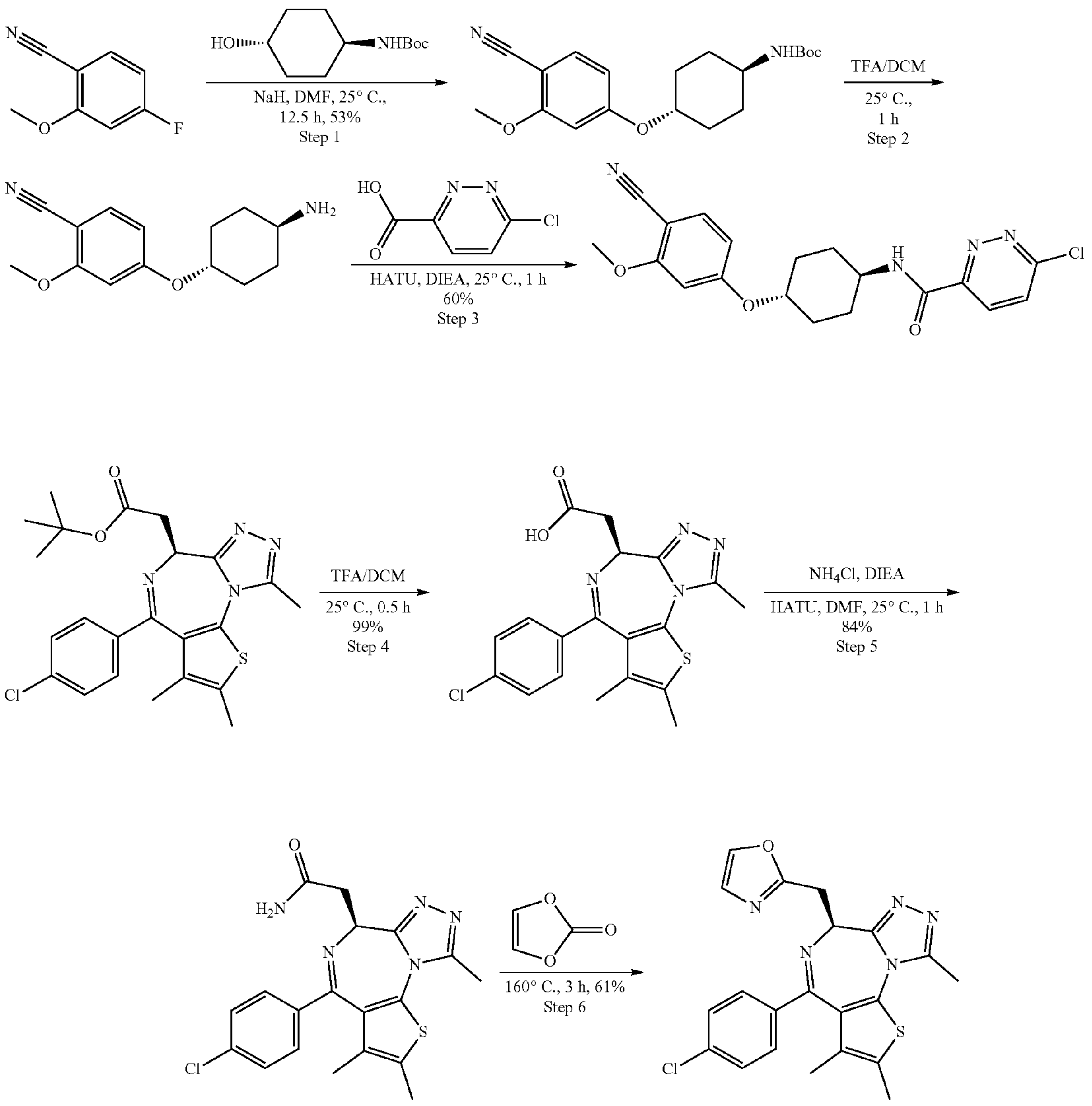

-continued

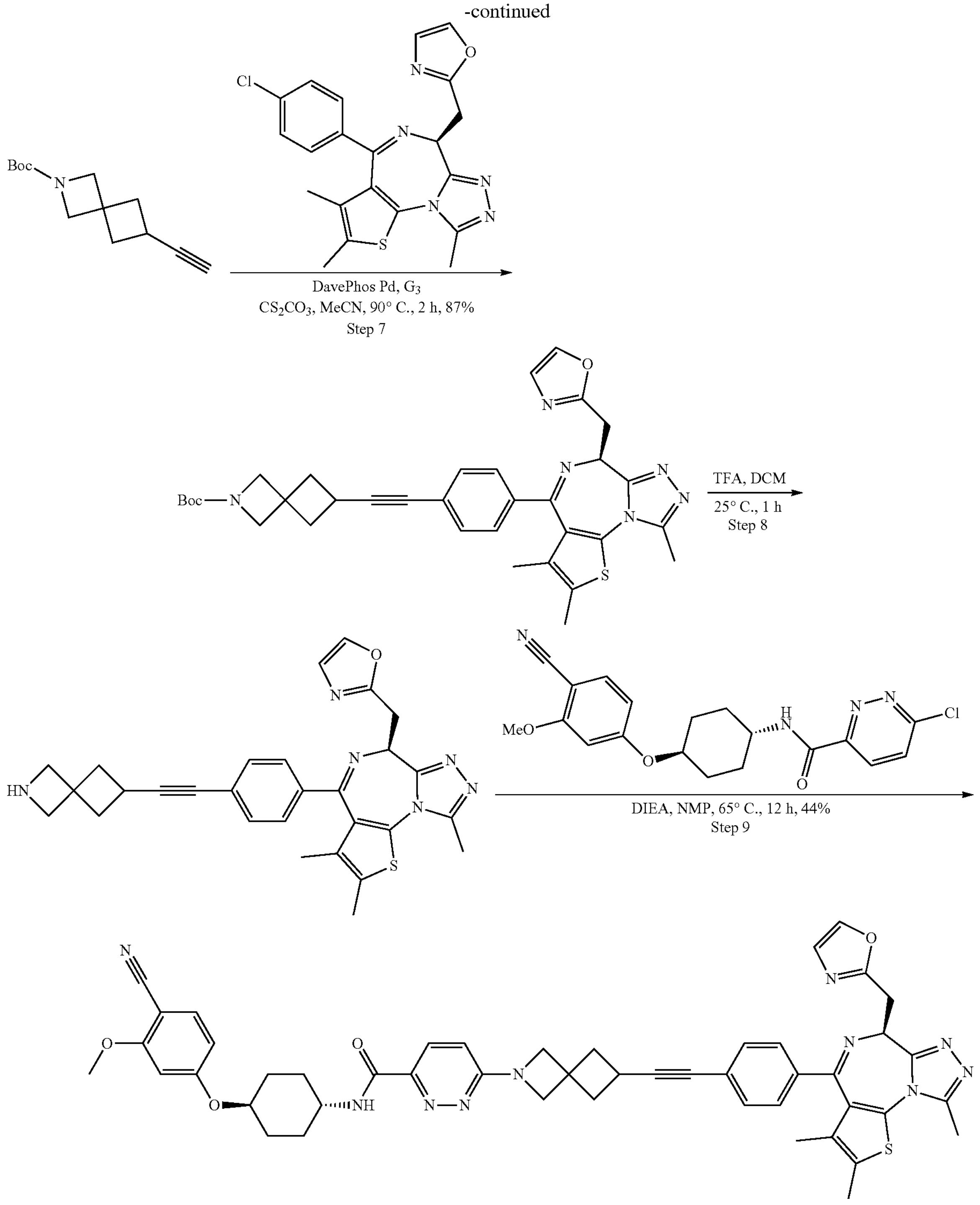

I-124

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxy-cyclohexyl) carbamate (5.6 g, 26.01 mmol, 1.0 equiv). After 30 minutes, 4-fluoro-2-methoxy-benzonitrile (3.93 g, 26.01 mmol, 1.0 equiv) was added. The reaction mixture was slowly allowed to warm to 25° C. and stirred for 12 h. The reaction mixture was quenched with a saturated solution of aqueous $NH_4Cl$ (100 mL) at 0° C., and the resulting mixture was extracted with ethyl acetate (100 mL×3). The combined organic layers were dried over anhydrous $Na_2SO_4$, filtered, and concentrated under vacuum. The residue was purified by column chromatography ($SiO_2$, petroleum ether/ethyl acetate=0/1 to 3/1) to afford compound tert-butyl ((1r,4r)-4-(4-cyano-3-methoxyphenoxy)cyclohexyl) carbamate (4.8 g, 13.86 mmol, 53% yield) as a white solid.

Step 2: Preparation of 4-(((1r,4r)-4-aminocyclohexyl) oxy)-2-methoxy-benzo nitrile. To a solution of tert-butyl ((1r,4r)-4-(4-cyano-3-methoxyphenoxy)cyclohexyl) carbamate (0.5 g, 1.44 mmol, 1.0 equiv) in DCM (2 mL) was added TFA (1 mL). The mixture was stirred at 25° C. for 1 h. The reaction mixture was concentrated under reduced pressure to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-((1r,4r)-4-(4-cyano-3-methoxyphenoxy) cyclohexyl) pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 µL, 3.0 equiv). The mixture was stirred at 25° C. for 1 h. The reaction mixture was concentrated under reduced pressure to remove solvent. The residue was purified by prep-HPLC (column: Waters xbridge 150×25 mm 10 µm; mobile phase: [water ($NH_4HCO_3$)-ACN]; gradient: 49%-69% B over 8 min) to afford 6-chloro-N-((1r,4r)-4-(4-cyano-3-methoxyphenoxy)cyclohexyl) pyridazine-3-carboxamide (337 mg, 871 µmol, 60% yield) as a white solid.

Step 4: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid. To a solution of tert-butyl 2-[(9S)-7-(4-chlorophenyl)-4,5,13-trimethyl-3-thia-1,8,11,12-tetraza tricyclo[8.3.0.0$^{2,6}$]trideca-2 (6),4,7,10,12-pentaen-9-yl]acetate (1.0 g, 2.1 mmol, 1.0 equiv) in DCM (10 mL) was added TFA (7.7 g, 67 mmol, 5.0 mL, 30 equiv). The mixture was stirred at 25° C. for 0.5 h. The reaction mixture was filtered and concentrated under reduced pressure to give 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 99% yield) as a residue, which was use directly in the next step.

Step 5: Preparation of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide. To a solution of 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetic acid (877 mg, 2.19 mmol, 1.0 equiv) and $NH_4Cl$ (351 mg, 6.56 mmol, 3.0 equiv) in DMF (8 mL) was added HATU (915 mg, 2.41 mmol, 1.1 equiv) and DIEA (848 mg, 6.56 mmol, 3.0 equiv). The mixture was stirred at 25° C. for 1 h. The mixture was filtered and concentrated. The residue was purified by prep-HPLC (column: Waters Xbridge C18 150×50 mm×10 µm; mobile phase: [water ($NH_4HCO_3$)-ACN]; B %: 24%-54%, 10 min) to give 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (740 mg, 84% yield).

Step 6: Preparation of 2-[[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole. A solution of 1,3-dioxol-2-one (103 mg, 1.20 mmol, 1.2 equiv) and 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]acetamide (400 mg, 1.00 mmol, 1.0 equiv) in PPA (4 mL) was stirred at 160° C. for 3 h. The mixture was quenched by addition of $H_2O$ (50 mL) at 0° C., and then diluted with EA (200 mL). The mixture was extracted with EtOAc (15 mL×2). The combined organic layers were washed with $H_2O$ (10 mL×3), dried over anhydrous $Na_2SO_4$, filtered, and concentrated. The residue was purified by column chromatography ($SiO_2$, petroleum ether/ethyl acetate=2/1 to 0/1) to give 2-[(9S)-7-(4-chlorophenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (260 mg, 61% yield).

Step 7: Preparation of tert-butyl 6-[2-[4-[(9S)-4,5,13-trimethyl-9-(oxazol-2-yl methyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate. A mixture of 2-[(9S)-7-(4-chloro phenyl)-4,5,13-trimethyl-3-thia-1,8,11,12-tetrazatricyclo[8.3.0.0$^{2,6}$]trideca-2 (6),4,7,10,12-penta en-9-yl]methyl]oxazole (600 mg, 1 mmol, 1.0 equiv), tert-butyl 6-ethynyl-2-azaspiro[3.3]heptane-2-carboxylate (783 mg, 3 mmol, 2.5 equiv), $Cs_2CO_3$ (922 mg, 2 mmol, 2.0 equiv), and [2-(2-aminophenyl)phenyl]-methylsulfonyloxy-palladium; 2-(2-dicyclohexyl-phosphanyl phenyl)-N,N-dimethyl-aniline (108 mg, 141 µmol, 0.1 equiv) in MeCN (12 mL) was degassed and purged with $N_2$ 3 times, then the mixture was stirred at 90° C. for 2 h under $N_2$ atmosphere. The mixture was concentrated to give a residue. The residue was purified by column chromatography ($SiO_2$, ethyl acetate: methanol=100/1 to 15/1) to give tert-butyl 6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6), 4,7,10,12-pentaen-7-yl]phenyl]ethynyl]-2-azaspiro[3.3]heptane-2-carboxylate (750 mg, 87% yield).

Step 8: Preparation of 2-[[(9S)-7-[4-[2-(2-azaspiro[3.3]heptan-6-yl)ethynyl]phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 6-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptane-2-carboxylate (750 mg, 1 mmol, 1.0 equiv) in DCM (6 mL) was added TFA (3.07 g, 26 mmol, 2 mL, 21.8 equiv). The mixture was stirred at 25° C. for 1 h. The reaction mixture was quenched with a saturated aqueous solution of $NaHCO_3$ dropwise. The residue was diluted with water (20 mL) and extracted with DCM (20 mL×3). The combined organic layers were dried over $Na_2SO_4$, filtered, and concentrated under reduced pressure to give a crude product. The crude product 2-[(9S)-7-[4-[2-(2-azaspiro[3.3]heptan-6-yl)ethynyl]phenyl]-4,5,13-trimethyl-3-thia-1,8,11,12-tetrazatricyclo[8.3.0.0$^{2,6}$]trideca-2 (6),4,7,10,12-pentaen-9-yl]methyl] oxazole (625 mg, crude) was used in the next step without further purification.

Step 9: Preparation of N-[(1r,4r)-4-(4-cyano-3-methoxyphenoxy)cyclohexyl]-6-[6-[2-[4-[(9S)-4,5,13-trimethyl-9-(oxazol-2-ylmethyl)-3-thia-1,8,11,12-tetrazatricyclo [8.3.0.0$^{2,6}$]trideca-2 (6),4,7,10,12-pentaen-7-yl]phenyl] ethynyl]-2-azaspiro[3.3]heptan-2-yl]pyridazine-3-carboxamide (I-124). To a solution of 2-[[(9S)-7-[4-[2-(2-azaspiro[3.3]heptan-6-yl)ethynyl]phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (358 mg, 704 µmol, 1.0 equiv) and 6-chloro-N-[(1r,4r)-4-(4-cyano-3-methoxy-phenoxy)cyclohexyl]pyridazine-3-carboxamide (300 mg, 774 µmol, 1.1 equiv) in NMP (1 mL) was added DIEA (273 mg, 2.11 mmol, 368 µL, 3.0 equiv). The mixture was stirred at 65° C. for 12 h. The residue was purified by prep-HPLC (column: Phenomenex luna C18 150×25 mm×10 µm; mobile phase: [water (FA)-ACN]; gradient: 54%-84% B over 10 min) to afford N-[(1r,4r)-4-(4-cyano-3-methoxyphenoxy)cyclohexyl]-6-[6-[2-[4-[(9S)-4,5,13-trimethyl-9-(oxazol-2-ylmethyl)-3-thia-1,8,11,12-tetrazatricyclo [8.3.0.0$^{2,6}$]trideca-2 (6),4,7,10,12-pentaen-7-yl]phenyl] ethynyl]-2-azaspiro[3.3]heptan-2-yl]pyridazine-3-carboxamide (I-124, 267 mg, 308 µmol, 44% yield) as a white solid. $^1H$ NMR (400 MHz, $CD_3OD$) δ 7.97-7.85 (m, 2H), 7.50 (d, J=9.2 Hz, 1H), 7.43-7.29 (m, 4H), 7.13 (s, 1H), 6.86 (d, J=9.4 Hz, 1H), 6.73-6.60 (m, 2H), 4.80-4.74 (m, 1H), 4.52-4.44 (m, 1H), 4.24 (d, J=6.7 Hz, 4H), 4.05-3.93 (m, 3H), 3.91 (s, 3H), 3.26-3.18 (m, 1H), 2.77-2.65 (m, 5H), 2.51-2.40 (m, 5H), 2.20 (d, J=3.5 Hz, 2H), 2.09 (d, J=4.6 Hz, 2H), 1.69 (s, 3H), 1.67-1.56 (m, 4H). LC-MS: MS ($ES^+$): RT=2.508 min, m/z=859.4 [$M+H^+$]; LCMS method: 10.

Example 50—Synthesis of N-[4-(4-cyano-3-methoxy-phenoxy)cyclohexyl]-6-[2-[[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5]nonan-7-yl]pyridazine-3-carboxamide (I-125)
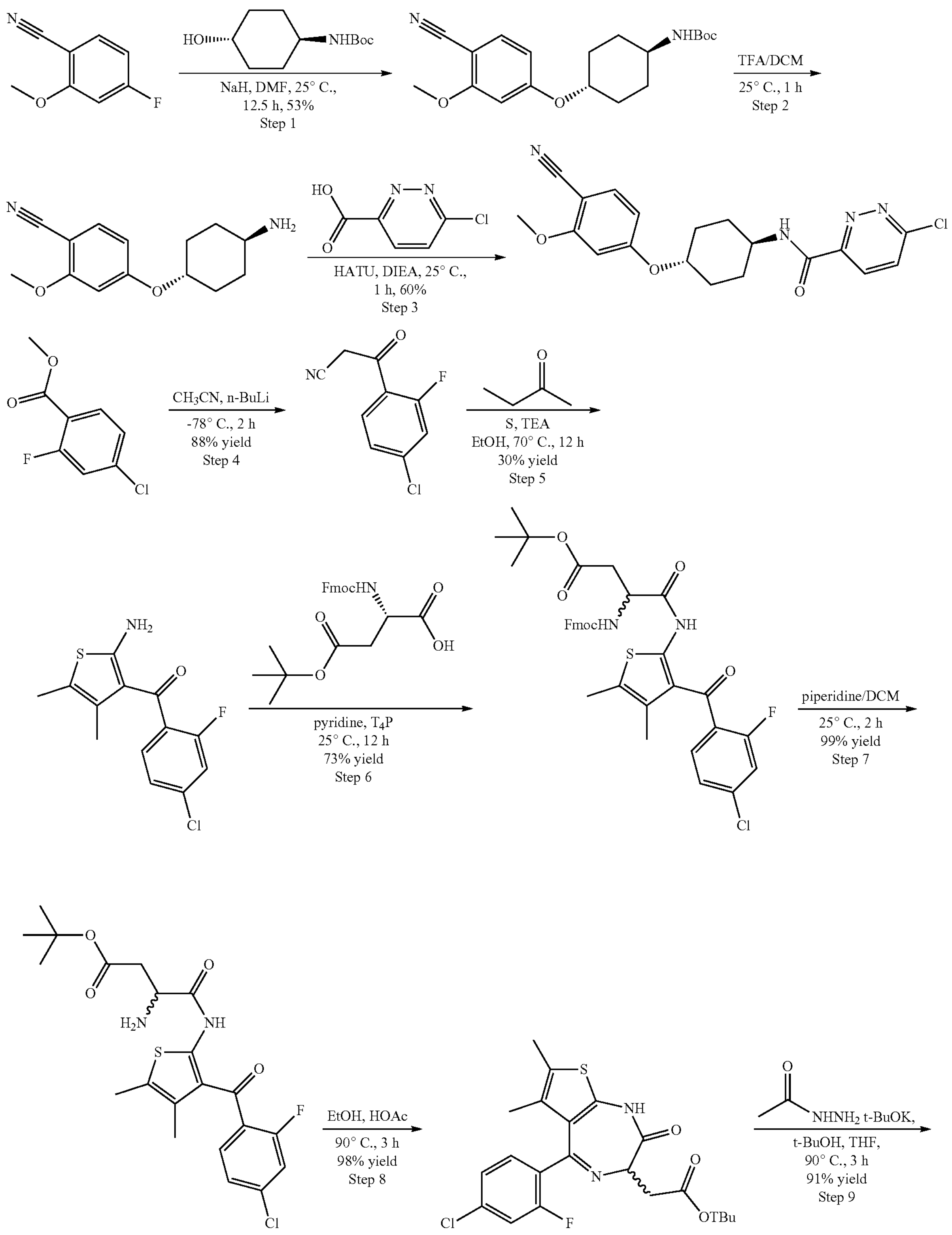

-continued
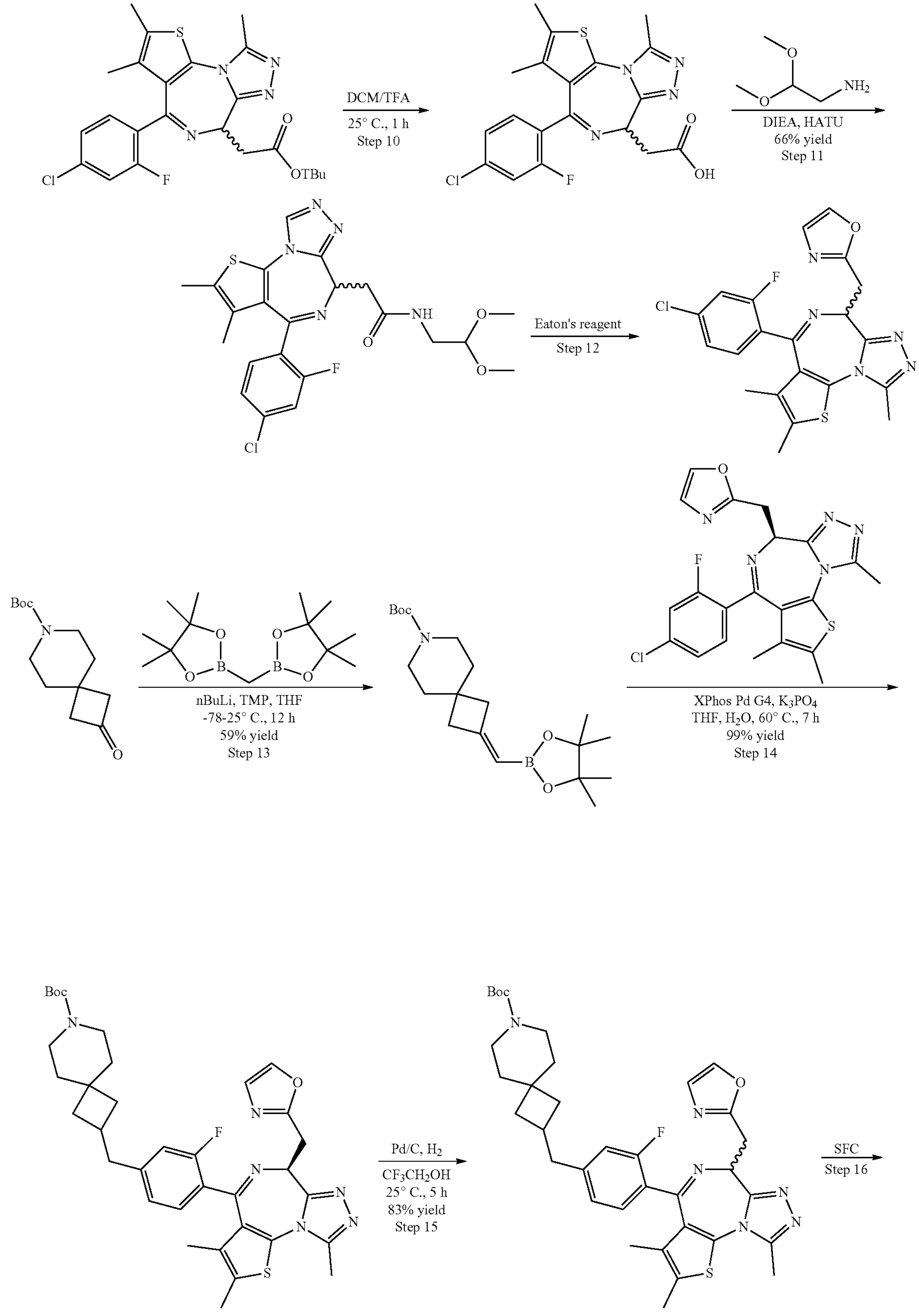

-continued

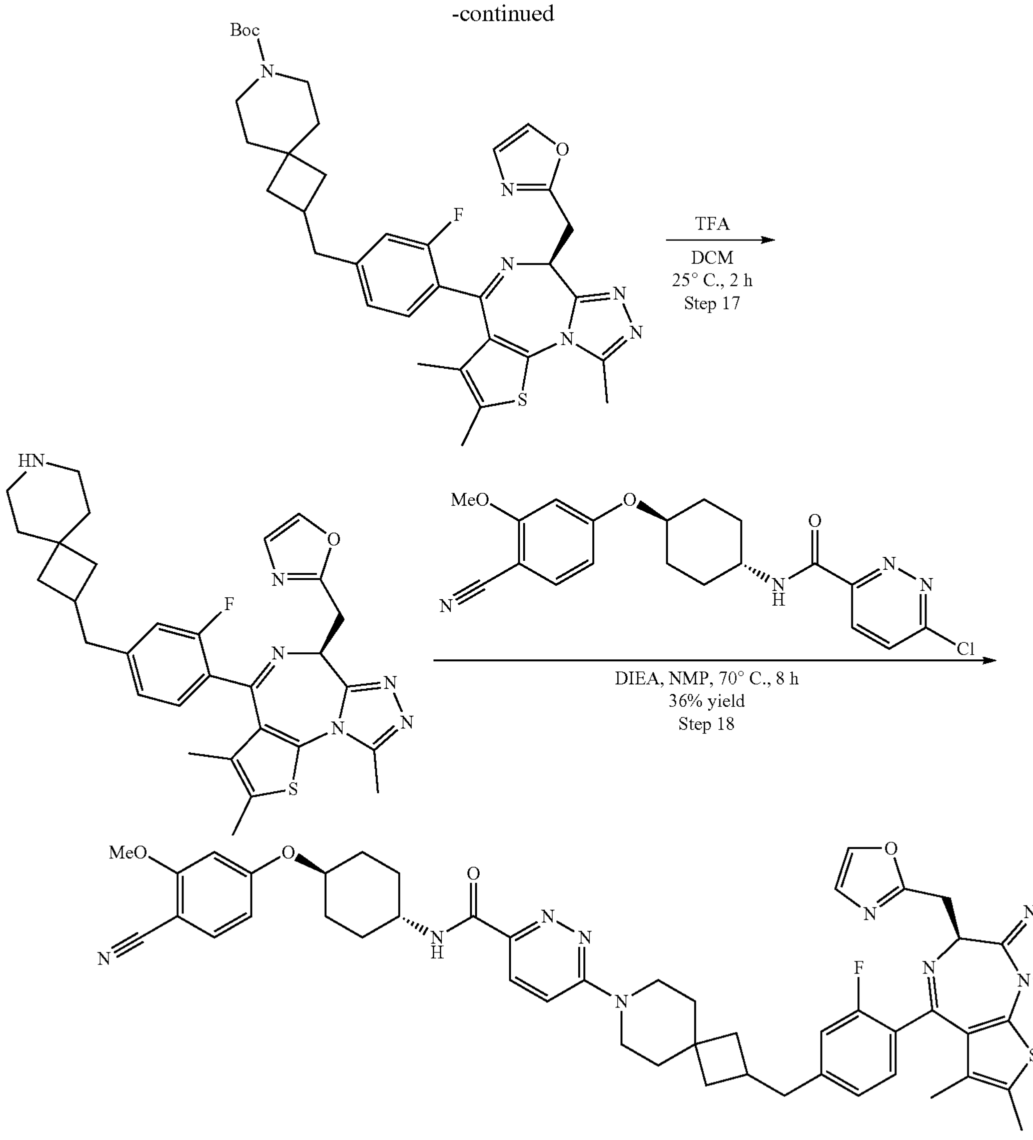

I-125

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxycyclohexyl) carbamate (5.6 g, 26.01 mmol, 1.0 equiv). After 30 minutes, 4-fluoro-2-methoxy-benzonitrile (3.93 g, 26.01 mmol, 1.0 equiv) was added. The reaction mixture was slowly allowed to attain to 25° C. and stirred for 12 h. The reaction mixture was quenched with a saturated aqueous $NH_4Cl$ (100 mL) solution at 0° C. And the resulting mixture was extracted with ethyl acetate (100 mL×3). The combined organic layers were dried over anhydrous $Na_2SO_4$, filtered and concentrated under vacuum. The residue was purified by column chromatography ($SiO_2$, petroleum ether/ethyl acetate=0/1 to 3/1) to afford tert-butyl ((1r,4r)-4-(4-cyano-3-methoxy-phenoxy)cyclohexyl) carbamate (4.8 g, 13.86 mmol, 53% yield) was obtained as a white solid.

Step 2: Preparation of 4-(((1r,4r)-4-aminocyclohexyl) oxy)-2-methoxy-benzonitrile. To a solution of tert-butyl ((1r,4r)-4-(4-cyano-3-methoxyphenoxy)cyclohexyl) carbamate (0.5 g, 1.44 mmol, 1.0 equiv) in DCM (2 mL) was added TFA (1 mL). The mixture was stirred at 25° C. for 1 h. The reaction mixture was concentrated under reduced pressure to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-((1r,4r)-4-(4-cyano-3-methoxy-phenoxy) cyclohexyl) pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 μL, 3.0 equiv). The mixture was stirred at 25° C. for 1 h. The reaction mixture was concentrated under reduced pressure to remove solvent. The residue was purified by prep-HPLC (column: Waters xbridge 150×25 mm 10 μm; mobile phase: [water ($NH_4HCO_3$)-ACN]; gradient: 49%-69% B over 8 min) to afford 6-chloro-N-((1r,4r) -4-

(4-cyano-3-methoxyphenoxy)cyclohexyl) pyridazine-3-carboxamide (337 mg, 871 μmol, 60% yield) as a white solid.

Step 4: Preparation of 3-(4-chloro-2-fluoro-phenyl)-3-oxo-propanenitrile. A solution of acetonitrile (9.3 g, 225.3 mmol, 11.9 mL, 1.7 equiv) in THF (200 mL) was stirred at −78° C. under $N_2$ protection. Then n-BuLi (2.5 M, 106.0 mL, 2.0 equiv) was added to the mixture and it was stirred for 0.5 h. Then, methyl 4-chloro-2-fluoro-benzoate (25.0 g, 132.5 mmol, 1.0 equiv) in THF (20 mL) was dropwise and the mixture was stirred for 1.5 h under $N_2$ protection. The reaction mixture was quenched with a saturated aqueous $NH_4Cl$ (200 ml) solution at 0° C. And the resulting mixture was extracted with ethyl acetate (100 mL×4). The combined organic layers were dried over anhydrous $Na_2SO_4$, filtered and concentrated under vacuum. The crude product was triturated with petroleum ether/ethyl acetate=20/1 at 25° C. for 30 min to give 3-(4-chloro-2-fluoro-phenyl)-3-oxo-propanenitrile (23.0 g, 116.4 mmol, 87.80% yield) as a yellow solid.

Step 5: Preparation of (2-amino-4,5-dimethyl-3-thienyl)-(4-chloro-2-fluoro-phenyl) methanone. To a solution of 3-(4-chloro-2-fluoro-phenyl)-3-oxo-propanenitrile (23.0 g, 116.4 mmol, 1.0 equiv) and butan-2-one (8.4 g, 116.4 mmol, 10.4 mL, 1.0 equiv) in EtOH (200 mL) was added TEA (23.6 g, 232.8 mmol, 32.4 mL, 2.0 equiv) and S (4.4 g, 138.5 mmol, 1.2 equiv). The mixture was stirred at 50° C. for 12 h. To the reaction mixture was added water (500 mL) and the mixture was extracted with ethyl acetate (500 mL×3). The combined organic phase was washed with brine (500 mL), dried over anhydrous $Na_2SO_4$, filtered and concentrated in vacuo. The residue was purified by column chromatography ($SiO_2$, petroleum ether/ethyl acetate=35/1 to 30/1) to give (2-amino-4,5-dimethyl-3-thienyl)-(4-chloro-2-fluoro-phenyl) methanone (10.0 g, 35.2 mmol, 30% yield) as a yellow oil.

Step 6: Preparation of tert-butyl (3S)-4-[[3-(4-chloro-2-fluoro-benzoyl)-4,5-dimethyl-2-thienyl]amino]-3-(9H-fluoren-9-ylmethoxycarbonylamino)-4-oxo-butanoate. To a solution of (2-amino-4,5-dimethyl-3-thienyl)-(4-chloro-2-fluoro-phenyl) methanone (8.8 g, 31.0 mmol, 1.0 equiv) and (2S)-4-tert-butoxy-2-(9H-fluoren-9-ylmethoxycarbonylamino)-4-oxo-butanoic acid (19.1 g, 46.5 mmol, 1.5 equiv) in EtOAc (40 mL) was added pyridine (9.8 g, 124.0 mmol, 10.0 mL, 4.0 equiv) and T4P (44.7 g, 62.0 mmol, 50% purity, 2.0 equiv). The mixture was stirred at 25° C. for 12 h. To the reaction mixture was added water (300 mL) and the mixture was extracted with ethyl acetate (80 mL×3). The combined organic phase was washed with brine (100 mL), dried over anhydrous $Na_2SO_4$, filtered and concentrated in vacuo. The residue was purified by column chromatography ($SiO_2$, petroleum ether/ethyl acetate=8/1 to 6/1) to give tert-butyl (3S)-4-[[3-(4-chloro-2-fluoro-benzoyl)-4,5-dimethyl-2-thienyl]amino]-3-(9H-fluoren-9-ylmethoxycarbonylamino)-4-oxo-butanoate (15.5 g, 22.9 mmol, 73% yield) as a yellow oil.

Step 7: Preparation of tert-butyl (3S)-3-amino-4-[[3-(4-chloro-2-fluoro-benzoyl)-4,5-dimethyl-2-thienyl]amino]-4-oxo-butanoate. To a solution of tert-butyl (3S)-4-[[3-(4-chloro-2-fluoro-benzoyl)-4,5-dimethyl-2-thienyl]amino]-3-(9H-fluoren-9-ylmethoxy-carbonyl amino)-4-oxo-butanoate (14.0 g, 20.7 mmol, 1.0 equiv) in DCM (280 mL) was added piperidine (5.3 g, 62.0 mmol, 6.1 mL, 3.0 equiv). The mixture was stirred at 25° C. for 2 h. To the reaction mixture was added water (300 mL) and the mixture was extracted with ethyl acetate (200 mL×3). The combined organic phase was washed with brine (350 mL), dried over anhydrous $Na_2SO_4$, filtered and concentrated in vacuo. The residue was purified by column chromatography ($SiO_2$, petroleum ether/ethyl acetate=10/1 to 8/1) to give the compound tert-butyl (3S)-3-amino-4-[[3-(4-chloro-2-fluoro-benzoyl)-4,5-dimethyl-2-thienyl]amino]-4-oxo-butanoate (9.4 g, 20.7 mmol, 99% yield) as a yellow oil.

Step 8: Preparation of tert-butyl 2-[(3S)-5-(4-chloro-2-fluoro-phenyl)-6,7-dimethyl-2-oxo-1,3-dihydrothieno[2,3-e][1,4]diazepin-3-yl]acetate. To a solution of tert-butyl (3S)-3-amino-4-[[3-(4-chloro-2-fluoro-benzoyl)-4,5-dimethyl-2-thienyl]amino]-4-oxo-butanoate (9.4 g, 20.6 mmol, 1.0 equiv) in EtOH (90 mL) was added AcOH (31.5 g, 524.0 mmol, 30.0 mL, 25.4 equiv). The mixture was stirred at 90° C. for 3 h. To the reaction mixture was added water (100 mL) and the mixture was extracted with ethyl acetate (150 mL×3). The combined organic phase was washed with brine (150 mL), dried over anhydrous $Na_2SO_4$, filtered and concentrated in vacuo. The residue was purified by column chromatography ($SiO_2$, petroleum ether/ethyl acetate=8/1 to 6/1) to give the tert-butyl 2-[(3S)-5-(4-chloro-2-fluoro-phenyl)-6,7-dimethyl-2-oxo-1,3-dihydrothieno[2,3-e][1,4]diazepin-3-yl]acetate (8.9 g, 20.4 mmol, 98% yield) as a yellow oil.

Step 9: Preparation of tert-butyl 2-[(9S)-7-(4-chloro-2-fluoro-phenyl)-4,5,13-trimethyl-3-thia-1,8,11,12-tetrazatricyclo[$8.3.0.0^{2,6}$]trideca-2 (6),4,7,10,12-pentaen-9-yl]acetate. t-BuOK (1.0 M, 22.4 mL, 1.1 equiv) was added to tert-butyl 2-[(3S)-5-(4-chloro-2-fluoro-phenyl)-6,7-dimethyl-2-oxo-1,3-dihydrothieno[2,3-e][1,4]diazepin-3-yl]acetate (8.9 g, 20.4 mmol, 1.0 equiv) in THF (90 mL) at −78° C., and stirred at 25° C. for 30 min. The reaction mixture was cooled to −78° C. [chloro(phenoxy) phosphoryl]oxybenzene (6.6 g, 24.4 mmol, 5.1 mL, 1.2 equiv) was added to the reaction mixture. The resulting mixture was warmed to 25° C. over 45 min. Then acetohydrazide (2.3 g, 30.6 mmol, 1.5 equiv) was added to the reaction mixture. The reaction mixture was stirred at 25° C., n-BuOH (90 mL) was added to the reaction mixture and it was heated to 90° C. for 1 h. The reaction mixture was quenched with a saturated aqueous $NH_4Cl$ (100 ml) solution at 0° C. dropwise. And the resulting mixture was extracted with ethyl acetate (100 mL×2). The combined organic layers were dried over anhydrous $Na_2SO_4$, filtered and concentrated in vacuum. The residue was purified by column chromatography ($SiO_2$, petroleum ether/ethyl acetate=8/1 to 6/1) to give the tert-butyl 2-[(9S)-7-(4-chloro-2-fluoro-phenyl)-4,5,13-trimethyl-3-thia-1,8,11,12-tetrazatricyclo[$8.3.0.0^{2,6}$]trideca-2 (6),4,7,10,12-pentaen-9-yl]acetate (8.9 g, 18.74 mmol, 91% yield) as a yellow oil.

Step 10: Preparation of 2-[(9S)-7-(4-chloro-2-fluoro-phenyl)-4,5,13-trimethyl-3-thia-1,8,11,12-tetrazatricyclo[$8.3.0.0^{2,6}$]trideca-2 (6),4,7,10,12-pentaen-9-yl]acetic acid. To a solution of tert-butyl 2-[(9S)-7-(4-chloro-2-fluoro-phenyl)-4,5,13-trimethyl-3-thia-1,8,11,12-tetrazatricyclo[$8.3.0.0^{2,6}$]trideca-2 (6),4,7,10,12-pentaen-9-yl]acetate (8.9 g, 18.7 mmol, 1.0 equiv) in DCM (40 mL) was added TFA (20.0 mL). The mixture was stirred at 25° C. for 1 h. The reaction mixture was filtered and concentrated under reduced pressure to give a residue. The residue was used for the next step directly. Compound 2-[(9S)-7-(4-chloro-2-fluoro-phenyl)-4,5,13-trimethyl-3-thia-1,8,11,12-tetrazatricyclo[$8.3.0.0^{2,6}$]trideca-2 (6),4,7,10,12-pentaen-9-yl]acetic acid (7.8 g, 18.6 mmol) was obtained as a yellow oil.

Step 11: Preparation of 2-[(9S)-7-(4-chloro-2-fluoro-phenyl)-4,5,13-trimethyl-3-thia-1,8,11,12-tetrazatricyclo[$8.3.0.0^{2,6}$]trideca-2 (6),4,7,10,12-pentaen-9-yl]-N-(2,2-dimethoxyethyl) acetamide. To a solution of 2-[(9S)-7-(4-chloro-2-fluoro-phenyl)-4,5,13-trimethyl-3-thia-1,8,11,12- tetrazatricyclo[8.3.0.0$^{2,6}$]trideca-2 (6),4,7,10,12-pentaen-9-yl]acetic acid (7.8 g, 18.6 mmol, 1.0 equiv) and 2,2-dimethoxyethanamine (5.8 g, 55.8 mmol, 6.09 mL, 3.0 equiv) in DMF (70 mL) was added HATU (7.8 g, 20.5 mmol, 1.1 equiv) and DIEA (7.2 g, 55.8 mmol, 9.73 mL, 3.0 equiv). The mixture was stirred at 25° C. for 0.5 h. To the reaction mixture was added water (20 mL) and the mixture was extracted with ethyl acetate (20 mL×3). The combined organic phase was washed with brine (50 mL), dried over anhydrous $Na_2SO_4$, filtered and concentrated in vacuo. The residue was purified by column chromatography ($SiO_2$, DCM/MeOH=40/1 to 20/1) to give 2-[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl]-N-(2,2-dimethoxyethyl) acetamide (6.3 g, 12.5 mmol, 66% yield) as a yellow oil.

Step 12: Preparation of 2-[[(9S)-7-(4-chloro-2-fluoro-phenyl)-4,5,13-trimethyl-3-thia-1,8,11,12-tetrazatricyclo [8.3.0.0$^{2,6}$]trideca-2 (6),4,7,10,12-pentaen-9-yl]methyl]oxazole. A solution of 2-[(9S)-7-(4-chloro-2-fluoro-phenyl)-4,5,13-trimethyl-3-thia-1,8,11,12-tetraza tricyclo[8.3.0.0$^{2,6}$] trideca-2 (6),4,7,10,12-pentaen-9-yl]-N-(2,2-dimethoxyethyl) acetamide (2.0 g, 3.9 mmol, 1.0 equiv) in Eaton's reagent (20 mL) was stirred at 100° C. for 12 h. The reaction mixture was quenched with a saturated aqueous $NaHCO_3$ (200 ml) solution at 0° C. dropwise. And the resulting mixture was extracted with ethyl acetate (50 mL×3). The combined organic layers were dried over anhydrous $Na_2SO_4$, filtered and concentrated under vacuum. The residue was purified by column chromatography ($SiO_2$, DCM:MeOH=30/1 to 20/1). The residue was purified by prep-HPLC (column: Phenomenex luna C18 (250×70 mm, 10 μm); mobile phase: [water (FA)-ACN]; gradient: 40%-70% B over 20 min) to give the 2-[[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl] methyl]oxazole (3.0 g, 6.79 mmol, 57% yield) as a white solid.

Step 13: Preparation of tert-butyl 2-[(4,4,5,5-tetramethyl-1,3,2-dioxaborolan-2-yl)methylene]-7-azaspiro[3.5] nonane-7-carboxylate. To the solution of TMP (2.4 g, 16.7 mmol, 2.8 mL, 2.0 equiv) in THF (20.0 mL) was added n-BuLi (2.5 M, 6.7 mL, 2.0 equiv) at −30° C. The solution was then stirred at −30° C. for 0.5 h. A solution of 4,4,5,5-tetramethyl-2-[(4,4,5,5-tetramethyl-1,3,2-dioxaborolan-2-yl)methyl]-1,3,2-dioxaborolane (3.36 g, 12.5 mmol, 1.5 equiv) in THF (5.0 mL) was added at −78° C. for 0.5 h. Then tert-butyl 2-oxo-7-azaspiro[3.5]nonane-7-carboxylate (2.0 g, 8.4 mmol, 1.0 equiv) in THF (5.0 mL) was added to the mixture at −78° C. and the mixture was stirred for 2 h, and then stirred at 25° C. for 9 h. The reaction mixture was quenched with a saturated aqueous $NH_4Cl$ (60 mL) solution at 0° C. by dropwise addition. The resulting mixture was extracted with ethyl acetate (40 mL×3). The combined organic layers were dried over anhydrous $Na_2SO_4$, filtered and concentrated under vacuum. The residue was purified by column chromatography ($SiO_2$, petroleum ether/ethyl acetate=8/1 to 5/1). Compound tert-butyl 2-[(4,4,5,5-tetramethyl-1,3,2-dioxaborolan-2-yl)methylene]-7-azaspiro[3.5] nonane-7-carboxylate (1.8 g, 5.0 mmol, 59% yield) was obtained as a yellow oil.

Step 14: Preparation of tert-butyl 2-[[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl] phenyl]methylene]-7-azaspiro[3.5]nonane-7-carboxylate. A mixture of tert-butyl 2-[(4,4,5,5-tetramethyl-1,3,2-dioxaborolan-2-yl)methylene]-7-azaspiro[3.5]nonane-7-carboxylate (370 mg, 1.0 mmol, 1.8 equiv), 2-[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl]methyl]oxazole (250 mg, 566 μmol, 1.0 equiv), Xphos Pd G4 (49 mg, 57 μmol, 0.1 equiv), and $K_3PO_4$ (360 mg, 1.7 mmol, 3.0 equiv) in THF (6.0 mL) and $H_2O$ (1.0 mL) was degassed and purged with $N_2$ 3 times, and then the mixture was stirred at 60° C. for 7 h under $N_2$ atmosphere. To the reaction mixture was added water (30 mL) and the mixture was extracted with ethyl acetate (10 mL×3). The combined organic phase was washed with brine (20 mL), dried over anhydrous $Na_2SO_4$, filtered and concentrated in vacuo. The residue was purified by column chromatography ($SiO_2$, petroleum ether/ethyl acetate=0/1). Compound tert-butyl 2-[[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methylene]-7-azaspiro [3.5]nonane-7-carboxylate (360 mg, 560 μmol, 99% yield) was obtained as a yellow solid.

Step 15: Preparation of tert-butyl 2-(3-fluoro-4-(2,3,9-trimethyl-6-(oxazol-2-ylmethyl)-6H-thieno[3,2-f][1,2,4]triazolo[4,3-a][1,4]diazepin-4-yl)benzyl)-7-azaspiro[3.5] nonane-7-carboxylate. Pd/C (500 mg, 470 μmol, 10% purity, 0.8 equiv) was added into a 100 mL single-necked round bottom flask under $N_2$, and then $CF_3CH_2OH$ (5.0 mL) was added at 25° C. under $N_2$ atmosphere. After addition, tert-butyl 2-[[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methylene]-7-azaspiro [3.5]nonane-7-carboxylate (360 mg, 560 μmol, 1.0 equiv) was added under $N_2$ atmosphere. The suspension was degassed under vacuum and purged with $H_2$ several times. The mixture was stirred under $H_2$ atmosphere at 25° C. for 5 h. The reaction mixture was filtered and the filtrate was concentrated. Compound tert-butyl 2-(3-fluoro-4-(2,3,9-trimethyl-6-(oxazol-2-ylmethyl)-6H-thieno[3,2-f][1,2,4]triazolo[4,3-a][1,4]diazepin-4-yl) benzyl)-7-azaspiro[3.5] nonane-7-carboxylate (300 mg, 489 μmol, 83% yield, 99% purity) was obtained as a colorless oil and used in the next step without further purification.

Step 16: Preparation of tert-butyl 2-[[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl] phenyl]methyl]-7-azaspiro[3.5]nonane-7-carboxylate. Compound tert-butyl 2-(3-fluoro-4-(2,3,9-trimethyl-6-(oxazol-2-ylmethyl)-6H-thieno[3,2-f][1,2,4]triazolo[4,3-a][1,4] diazepin-4-yl) benzyl)-7-azaspiro[3.5]nonane-7-carboxylate (300 mg, 489 μmol, 83% yield, 99% purity) was separated by SFC (column: DAICEL CHIRALPAK AS (250 mm×30 mm, 10 μm); mobile phase: [$CO_2$-ACN/i-PrOH (0.1% $NH_3H_2O$)]; B %: 50%, isocratic elution mode). Compound tert-butyl 2-[[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6), 4,7,10,12-pentaen-7-yl]phenyl]methyl]-7-azaspiro[3.5]nonane-7-carboxylate (236 mg, 361 μmol, 64% yield, 99% purity) was obtained as a colorless oil.

Step 17: Preparation of 2-[[(9S)-7-[4-(7-azaspiro[3.5] nonan-2-ylmethyl)-2-fluoro-phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 2-[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]methyl]-7-azaspiro[3.5] nonane-7-carboxylate (230 mg, 357 μmol, 1.0 equiv) in DCM (3.0 mL) was added TFA (1.5 mL). The mixture was stirred at 25° C. for 2 h. The reaction mixture was concentrated under reduced pressure to remove solvent. The pH of the aqueous phase was adjusted to 8-9 by addition of a saturated aqueous $NaHCO_3$ solution, then diluted with DCM (20 mL) and extracted with DCM 40 mL (20 mL×2). The combined organic layers were washed with water (10 mL), dried over anhydrous $Na_2SO_4$, filtered and concentrated under reduced pressure to give a residue. Compound 2-[(9S)-7-[4-(7-azaspiro[3.5]nonan-2-ylmethyl)-2-fluoro-phenyl]-4,5,13-trimethyl-3-thia-1,8,11,12-tetrazatricyclo [8.3.0.0$^{2,6}$]trideca-2 (6),4,7,10,12-pentaen-9-yl]methyl]oxazole (200 mg, crude) was obtained as a yellow oil and used for the next step without further purification.

Step 18: Preparation of N-[4-(4-cyano-3-methoxy-phenoxy)cyclohexyl]-6-[2-[[3-fluoro-4-[(9S)-4,5,13-trimethyl-9-(oxazol-2-ylmethyl)-3-thia-1,8,11,12-tetrazatricyclo [8.3.0.0$^{2,6}$]trideca-2 (6),4,7,10,12-pentaen-7-yl]phenyl] methyl]-7-azaspiro[3.5]nonan-7-yl]pyridazine-3-carboxamide (I-125). To a solution of 2-[[(9S)-7-[4-(7-azaspiro[3.5]nonan-2-ylmethyl)-2-fluoro-phenyl]-4,5,13-trimethyl-3-thia-1,8,11,12-tetrazatricyclo[8.3.0.0$^{2,6}$] trideca-2 (6), 4,7,10,12-pentaen-9-yl]methyl]oxazole (50 mg, 92 μmol, 1.0 equiv) in NMP (1.0 mL) was added DIEA (24 mg, 184 μmol, 32 μL, 2.0 equiv) and 6-chloro-N-[4-(4-cyano-3-methoxy-phenoxy)cyclohexyl]pyridazine-3-carboxamide (43 mg, 110 μmol, 1.2 equiv). The mixture was stirred at 70° C. for 8 h. The mixture was filtered and concentrated to give a residue. The residue was purified by prep-HPLC (column: Phenomenex luna C18 150×25 mm×10 μm; mobile phase: [water (FA)-ACN]; gradient: 60%-90% B over 10 min). N-[4-(4-cyano-3-methoxy-phenoxy) cyclohexyl]-6-[2-[[3-fluoro-4-[(9S)-4,5,13-trimethyl-9-(oxazol-2-ylmethyl)-3-thia-1,8,11,12-tetrazatricyclo [8.3.0.0$^{2,6}$]trideca-2 (6),4,7,10,12-pentaen-7-yl]phenyl] methyl]-7-azaspiro[3.5]nonan-7-yl]pyridazine-3-carboxamide (I-125, 29.8 mg, 33 μmol, 36% yield, 99% purity) was obtained as a white solid. $^1H$ NMR (400 MHz, $CD_3OD$) δ=7.93-7.84 (m, 2H), 7.53-7.47 (m, 1H), 7.31-7.23 (m, 2H), 7.16-7.10 (m, 1H), 7.08-7.02 (m, 1H), 6.96-6.89 (m, 1H), 6.68-6.63 (m, 2H), 4.81-4.78 (m, 1H), 4.54-4.44 (m, 1H), 4.06-3.93 (m, 3H), 3.92-3.89 (m, 3H), 3.74-3.68 (m, 2H), 3.67-3.61 (m, 2H), 2.82-2.76 (m, 2H), 2.72-2.68 (m, 3H), 2.66-2.55 (m, 1H), 2.46-2.39 (m, 3H), 2.27-2.16 (m, 2H), 2.14-2.06 (m, 2H), 2.05-1.97 (m, 2H), 1.76-1.70 (m, 2H), 1.68-1.54 (m, 11H). LC-MS: MS ($ES^+$): RT=2.518 min, m/z=895.6 $[M+H]^+$; LCMS method: 25.

Example 51—Synthesis of N-[4-(4-cyano-3-methoxy-phenoxy)cyclohexyl]-6-[6-[2-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide

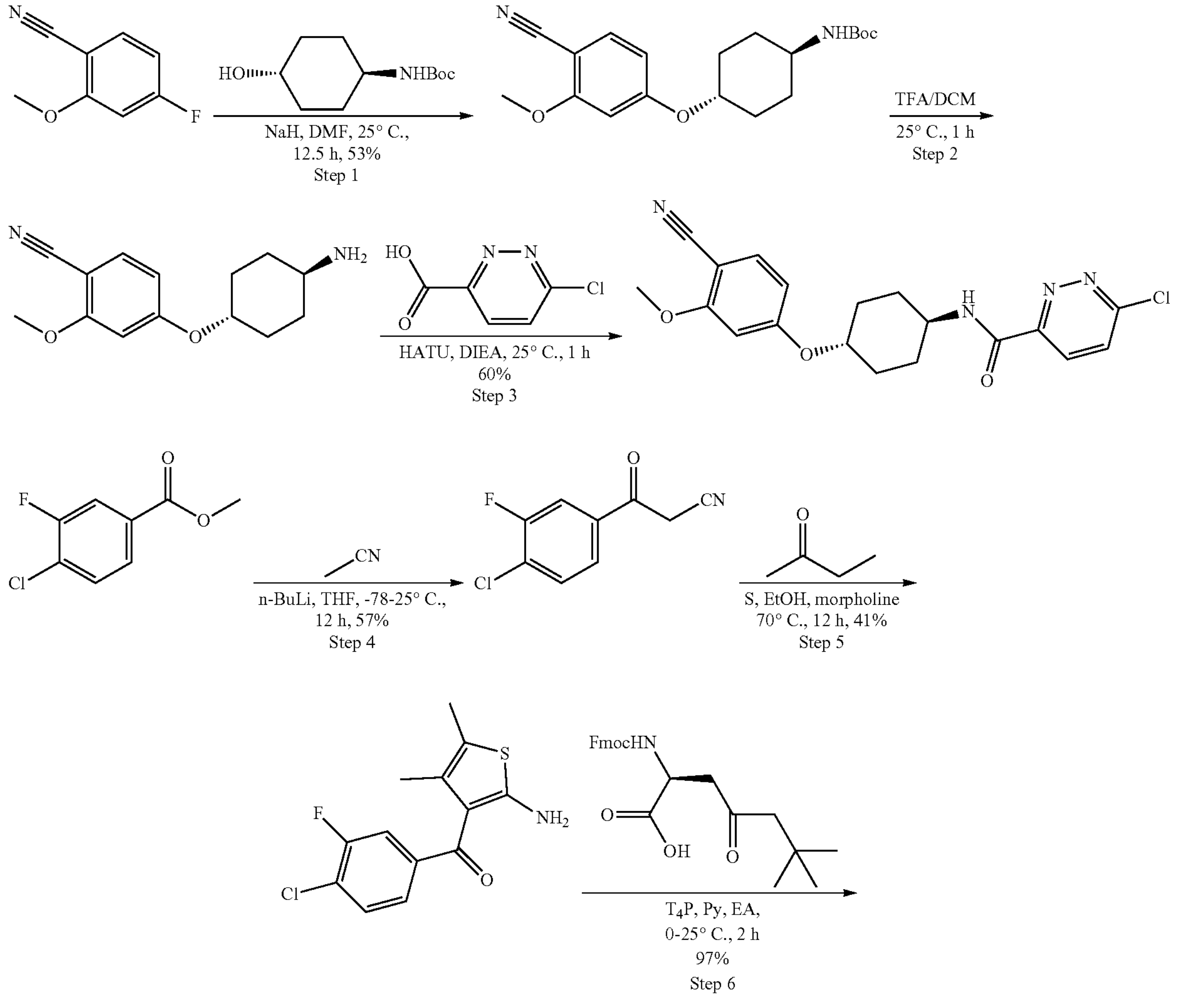

-continued
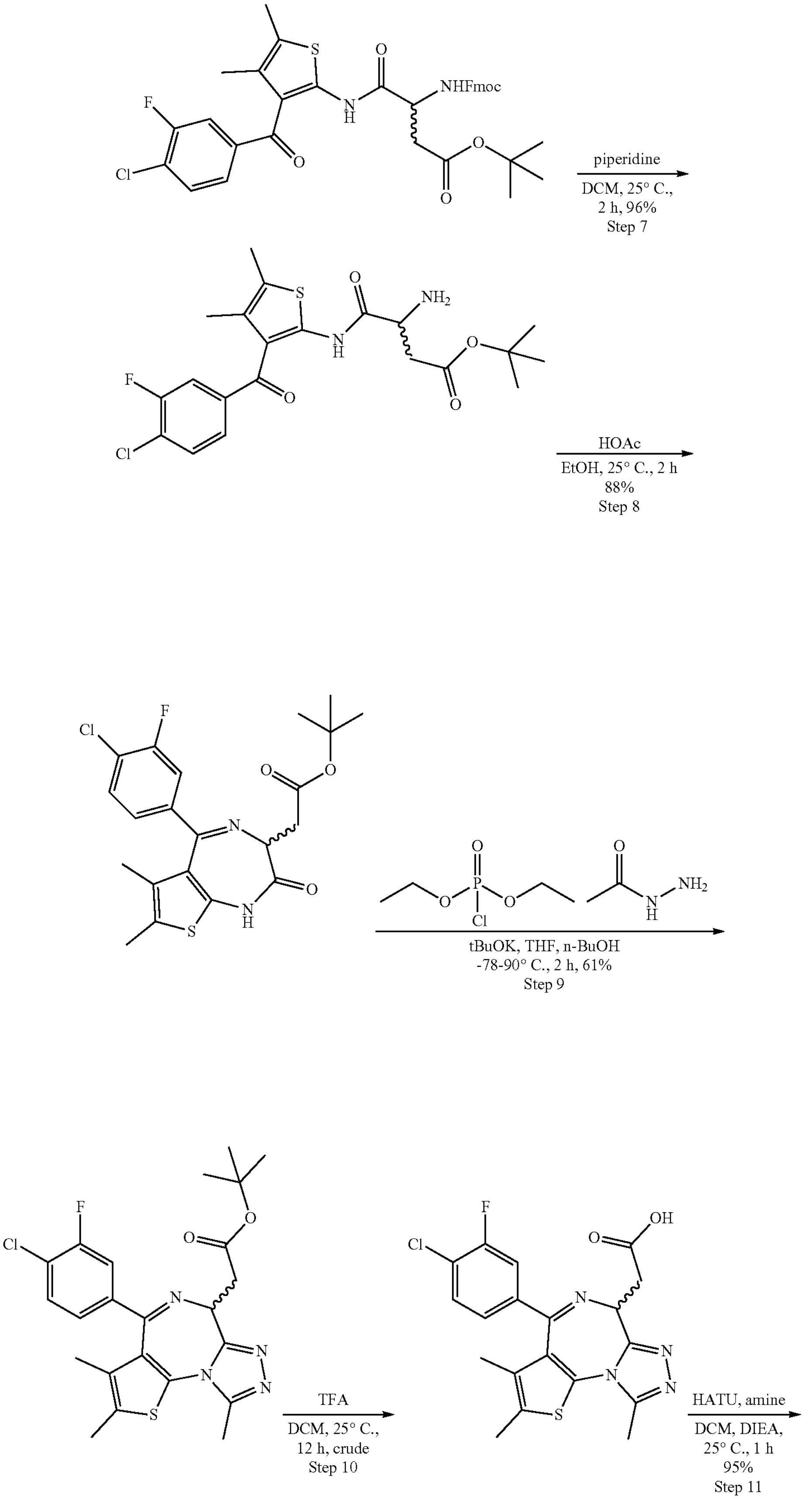

-continued

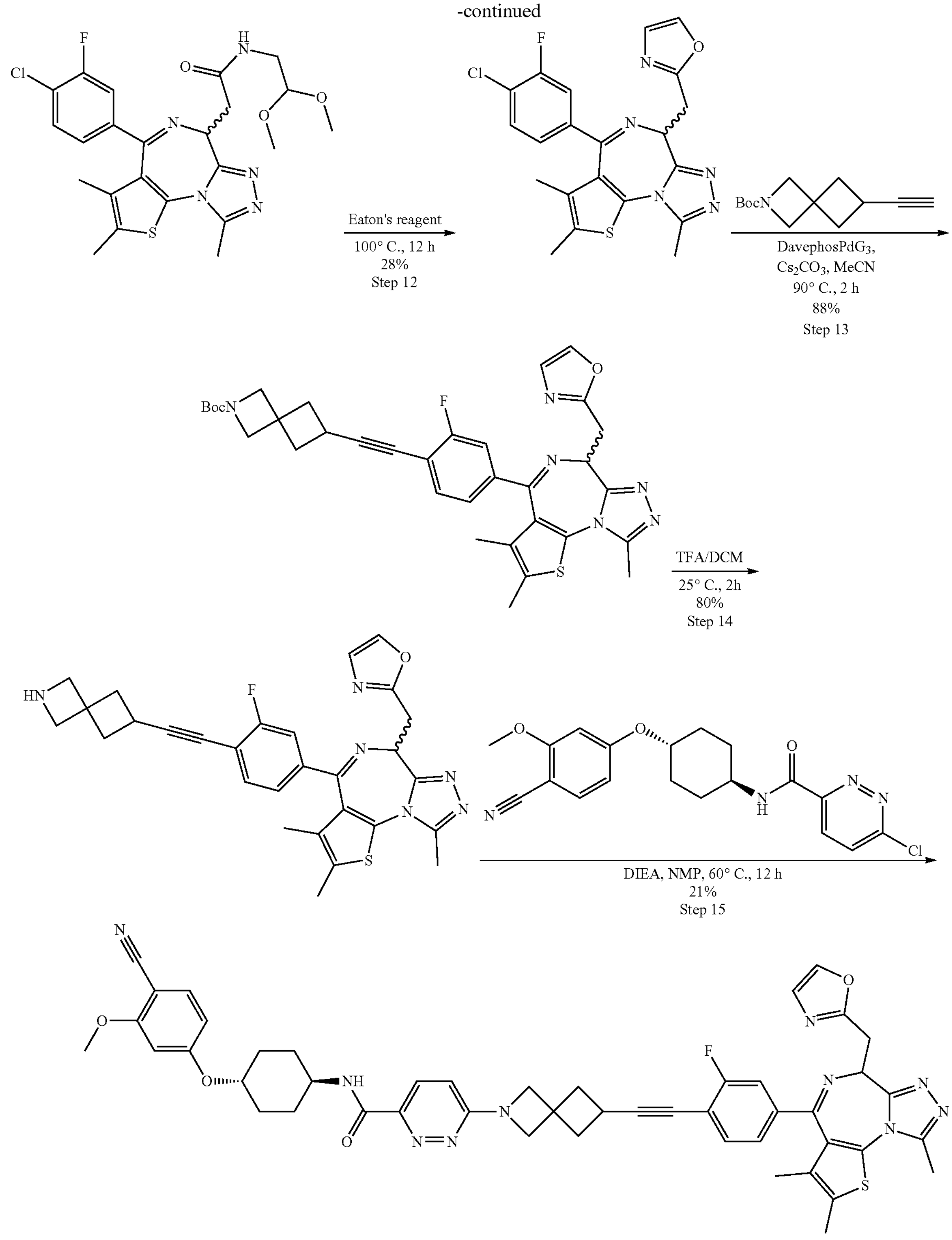

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxycyclohexyl) carbamate (5.6 g, 26.01 mmol, 1.0 equiv). After 30 minutes, 4-fluoro-2-methoxybenzonitrile (3.93 g, 26.01 mmol, 1.0 equiv) was added. The reaction mixture was slowly allowed to warm to 25° C. and was stirred for 12 h. The reaction mixture was quenched with a saturated aqueous $NH_4Cl$ (100 mL) solution at 0° C. The resulting mixture was extracted with ethyl acetate (100 mL×3). The combined organic layers were dried over anhydrous $Na_2SO_4$, filtered and concentrated under vacuum. The residue was purified by column chromatography ($SiO_2$, petroleum ether/ethyl acetate-0/1 to 3/1) to afford tert-butyl ((1r,4r)-4-(4-cyano-3-methoxy phenoxy)cyclohexyl) carbamate (4.8 g, 13.86 mmol, 53% yield) as a white solid.

Step 2: Preparation of 4-(((1r,4r)-4-aminocyclohexyl) oxy)-2-methoxy-benzo nitrile. To a solution of tert-butyl ((1r,4r)-4-(4-cyano-3-methoxyphenoxy)cyclohexyl) carbamate (0.5 g, 1.44 mmol, 1.0 equiv) in DCM (2 mL) was added TFA (1 mL). The mixture was stirred at 25° C. for 1 h. The reaction mixture was concentrated under reduced pressure to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-((1r,4r)-4-(4-cyano-3-methoxyphenoxy) cyclohexyl) pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 μL, 3.0 equiv). The mixture was stirred at 25° C. for 1 h. The reaction mixture was concentrated under reduced pressure to remove solvent. The residue was purified by prep-HPLC (column: Waters xbridge 150×25 mm 10 μm; mobile phase: [water ($NH_4HCO_3$)-CAN]; gradient: 49%-69% B over 8 min) to afford 6-chloro-N-((1r,4r)-4-(4-cyano-3-methoxyphenoxy)cyclohexyl) pyridazine-3-carboxamide (337 mg, 871 μmol, 60% yield) as a white solid.

Step 4: Preparation of 3-(4-chloro-3-fluoro-phenyl)-3-oxo-propanenitrile. To a solution of acetonitrile (11.9 g, 291 mmol, 15.3 mL, 2.2 equiv) in THF (200 mL) was added a solution of n-BuLi (2.5 M, 106 mL, 2.0 equiv) dropwise at −78° C. under $N_2$ and stirred at −78° C. for 1 h. Then methyl 4-chloro-3-fluoro-benzoate (25.0 g, 132 mmol, 1.0 equiv) in THF (100 mL) was added at −78° C. dropwise. The reaction mixture was warmed to 25° C. and stirred at 25° C. for 11 h. The reaction mixture was quenched with a saturated aqueous $NH_4Cl$ (50 mL) solution at 0° C. dropwise. The resulting mixture was extracted with ethyl acetate (200 mL×3). The combined organic layers were dried over anhydrous $Na_2SO_4$, filtered and concentrated under vacuum. The residue was purified by column chromatography ($SiO_2$, petroleum ether/ethyl acetate=20/1 to 1/1). Compound 3-(4-chloro-3-fluoro-phenyl)-3-oxo-propanenitrile (15 g, 75 mmol, 57% yield) was obtained as a white solid.

Step 5: Preparation of (2-amino-4,5-dimethyl-3-thienyl)-(4-chloro-3-fluoro-phenyl) methanone. To a solution of 3-(4-chloro-3-fluoro-phenyl)-3-oxo-propanenitrile (15 g, 75 mmol, 1.0 equiv), butan-2-one (5.47 g, 75.9 mmol, 6.79 mL, 1.0 equiv) in EtOH (200 mL) was added morpholine (6.61 g, 75.9 mmol, 6.68 mL, 1.0 equiv) and S (2.59 g, 80.7 mmol, 1.1 equiv). The mixture was stirred at 70° C. for 12 h. To the reaction mixture was added water (500 mL) and the mixture was extracted with ethyl acetate (500 mL×3). The combined organic phase was washed with brine (500 mL), dried over anhydrous $Na_2SO_4$, filtered and concentrated in vacuo. The residue was purified by column chromatography ($SiO_2$, petroleum ether/ethyl acetate=20/1 to 5/1). The crude was further purified by trituration (petroleum ether/ethyl acetate=3/1, 300 mL). Compound (2-amino-4,5-dimethyl-3-thienyl)-(4-chloro-3-fluoro-phenyl) methanone (9.0 g, 31 mmol, 41% yield) was obtained as a yellow solid.

Step 6: Preparation of tert-butyl 3-((((9H-fluoren-9-yl) methoxy) carbonyl) amino)-4-((3-(4-chloro-3-fluorobenzoyl)-4,5-dimethylthiophen-2-yl)amino)-4-oxobutanoate. To a solution of (2S)-4-tert-butoxy-2-(9H-fluoren-9-ylmethoxycarbonylamino)-4-oxo-butanoic acid (18.7 g, 45.4 mmol, 1.5 equiv) in EtOAc (86 mL) was added pyridine (9.59 g, 121 mmol, 9.79 mL, 4.0 equiv) and T4P (43.6 g, 60.6 mmol, 50% purity, 2.0 equiv) at 0° C. The mixture was stirred at 25° C. for 1 h, then (2-amino-4,5-dimethyl-3-thienyl)-(4-chloro-3-fluoro-phenyl) methanone (8.6 g, 30 mmol, 1.0 equiv) was added at 0° C., and then stirred at 25° C. for another 1 h. To the reaction mixture was added water (200 mL) and the mixture was extracted with ethyl acetate (200 mL×3). The combined organic phase was washed with brine (20 mL), dried over anhydrous $Na_2SO_4$, filtered and concentrated in vacuo. The residue was purified by column chromatography ($SiO_2$, petroleum ether/ethyl acetate=10/1 to 5/1). Compound tert-butyl 3-((((9H-fluoren-9-yl) methoxy) carbonyl)amino)-4-((3-(4-chloro-3-fluorobenzoyl)-4,5-dimethylthiophen-2-yl)amino)-4-oxobutanoate (20 g, 29 mmol, 97% yield) was obtained as a white solid.

Step 7: Preparation of tert-butyl 3-amino-4-((3-(4-chloro-3-fluorobenzoyl)-4,5-dimethylthiophen-2-yl)amino)-4-oxobutanoate. To a solution of tert-butyl 3-((((9H-fluoren-9-yl) methoxy) carbonyl)amino)-4-((3-(4-chloro-3-fluorobenzoyl)-4,5-dimethylthiophen-2-yl) amino)-4-oxobutanoate (20 g, 29 mmol, 1.0 equiv) in DCM (100 mL) was added piperidine (12.5 g, 147 mmol, 14.5 mL, 5.0 equiv). The mixture was stirred at 25° C. for 2 h. To the reaction mixture was added water (200 mL) and the mixture was extracted with ethyl acetate (200 mL×3). The combined organic phase was washed with brine (20 mL), dried over anhydrous $Na_2SO_4$, filtered and concentrated in vacuo. The residue was purified by column chromatography ($SiO_2$, petroleum ether/ethyl acetate=10/1 to 3/1). Compound tert-butyl 3-amino-4-((3-(4-chloro-3-fluorobenzoyl)-4,5-dimethylthiophen-2-yl)amino)-4-oxobutanoate (13 g, 28 mmol, 96% yield) was obtained as a white solid.

Step 8: Preparation of tert-butyl 2-(5-(4-chloro-3-fluorophenyl)-6,7-dimethyl-2-oxo-2,3-dihydro-1H-thieno[2,3-e][1,4]diazepin-3-yl) acetate. To a solution of tert-butyl 3-amino-4-((3-(4-chloro-3-fluorobenzoyl)-4,5-dimethylthiophen-2-yl)amino)-4-oxobutanoate (13 g, 28 mmol, 1.0 equiv) in EtOH (130 mL) was added AcOH (8.58 g, 142 mmol, 8.18 mL, 5.0 equiv). The mixture was stirred at 25° C. for 2 h. To the reaction mixture was added a saturated aqueous solution of $NaHCO_3$ (200 mL) and the mixture was extracted with ethyl acetate (200 mL×3). The combined organic phase was washed with brine (100 mL), dried over anhydrous $Na_2SO_4$, filtered and concentrated in vacuo. The residue was purified by column chromatography ($SiO_2$, petroleum ether/ethyl acetate=10/1 to 1/1). Compound tert-butyl 2-(5-(4-chloro-3-fluorophenyl)-6,7-dimethyl-2-oxo-2,3-dihydro-1H-thieno[2,3-e][1,4]diazepin-3-yl) acetate (11 g, 25 mmol, 88% yield) was obtained as a yellow solid.

Step 9: Preparation of tert-butyl 2-(4-(4-chloro-3-fluorophenyl)-2,3,9-trimethyl-6H-thieno[3,2-f][1,2,4]triazolo[4,3-a][1,4]diazepin-6-yl) acetate. Potassium tert-butoxide (1 M, 7.55 mL, 1.1 equiv) was added to a solution tert-butyl 2-(5-(4-chloro-3-fluorophenyl)-6,7-dimethyl-2-oxo-2,3-dihydro-1H-thieno[2,3-e][1,4]diazepin-3-yl) acetate (3.0 g, 6.8 mmol, 1.0 equiv) in THF (30 mL) at −78° C. The reaction mixture was warmed to 25° C., and then stirred at 25° C. for 30 min. The reaction mixture was then cooled to −78° C. [chloro(phenoxy) phosphoryl]oxybenzene (2.21 g, 8.24 mmol, 1.71 mL, 1.2 equiv) was added to the reaction mixture. The resulting mixture was warmed to 25° C. over 30 min. Then acetohydrazide (762 mg, 10.3 mmol, 1.5 equiv) was added to the reaction mixture. The reaction mixture was stirred at 25° C., n-BuOH (30 mL) was added to the reaction mixture and it was heated to 90° C. for 1 h. To the reaction mixture was added water (200 mL) and the mixture was extracted with ethyl acetate (200 mL×3). The combined organic phase was washed with brine (20 mL), dried over anhydrous $Na_2SO_4$, filtered and concentrated in vacuo. The residue was purified by column chromatography ($SiO_2$, petroleum ether/ethyl acetate=10/1 to 1/1). Compound tert-butyl 2-(4-(4-chloro-3-fluorophenyl)-2,3,9-trimethyl-6H-thieno[3,2-f][1,2,4]triazolo[4,3-a][1,4]diazepin-6-yl) acetate (2.0 g, 4.2 mmol, 61% yield) was obtained as a yellow solid.

Step 10: Preparation of 2-(4-(4-chloro-3-fluorophenyl)-2,3,9-trimethyl-6H-thieno[3,2-f][1,2,4]triazolo[4,3-a][1,4]diazepin-6-yl) acetic acid. To a solution of tert-butyl 2-(4-(4-chloro-3-fluorophenyl)-2,3,9-trimethyl-6H-thieno[3,2-f][1,2,4]triazolo[4,3-a][1,4]diazepin-6-yl) acetate (2.0 g, 4.2 mmol, 1.0 equiv) in DCM (20 mL) was added TFA (15.3 g, 134 mmol, 10 mL, 31.9 equiv). The mixture was stirred at 25° C. for 12 h. The reaction mixture was concentrated in vacuo to give the crude product. 2-(4-(4-chloro-3-fluorophenyl)-2,3,9-trimethyl-6H-thieno[3,2-f][1,2,4]triazolo[4,3-a][1,4]diazepin-6-yl) acetic acid (2.2 g, crude, TFA salt) was obtained as a brown solid.

Step 11: Preparation of 2-(4-(4-chloro-3-fluorophenyl)-2,3,9-trimethyl-6H-thieno[3,2-f][1,2,4]triazolo[4,3-a][1,4]diazepin-6-yl)-N-(2,2-dimethoxyethyl) acetamide. To a solution of 2-(4-(4-chloro-3-fluorophenyl)-2,3,9-trimethyl-6H-thieno[3,2-f][1,2,4]triazolo[4,3-a][1,4]diazepin-6-yl) acetic acid (2.2 g, 4.1 mmol, 1.0 equiv, TFA salt), 2,2-dimethoxy ethanamine (520 mg, 4.95 mmol, 539 μL, 1.2 equiv) in DCM (20 mL) was added DIEA (2.67 g, 20.6 mmol, 3.60 mL, 5.0 equiv) and HATU (2.35 g, 6.19 mmol, 1.5 equiv). The mixture was stirred at 25° C. for 1 h. The reaction mixture was concentrated in vacuo to give the crude product. The residue was purified by column chromatography ($SiO_2$, petroleum ether/ethyl acetate=10/1 to 1/1). Compound 2-(4-(4-chloro-3-fluorophenyl)-2,3,9-trimethyl-6H-thieno[3,2-f][1,2,4]triazolo[4,3-a][1,4]diazepin-6-yl)-N-(2,2-dimethoxyethyl) acetamide (2.0 g, 3.9 mmol, 95% yield) was obtained as a yellow solid.

Step 12: Preparation of 2-((4-(4-chloro-3-fluorophenyl)-2,3,9-trimethyl-6H-thieno[3,2-f][1,2,4]triazolo[4,3-a][1,4]diazepin-6-yl)methyl)oxazole. A mixture of 2-(4-(4-chloro-3-fluorophenyl)-2,3,9-trimethyl-6H-thieno[3,2-f][1,2,4]triazolo[4,3-a][1,4]diazepin-6-yl)-N-(2,2-dimethoxyethyl) acetamide (2.0 g, 3.9 mmol, 1.0 equiv) in Eaton's reagent (20 mL) was stirred at 100° C. for 12 h. The reaction mixture was added to ice/saturated aqueous solution of $NaHCO_3$ (200 mL) dropwise and the mixture was extracted with DCM (100 mL×3). The combined organic phase was washed with brine (100 mL), dried over anhydrous $Na_2SO_4$, filtered and concentrated in vacuo. The residue was purified by column chromatography ($SiO_2$, petroleum ether/ethyl acetate=10/1 to 0/1). Compound 2-((4-(4-chloro-3-fluorophenyl)-2,3,9-trimethyl-6H-thieno[3,2-f][1,2,4]triazolo[4,3-a][1,4]diazepin-6-yl)methyl)oxazole (0.5 g, 1.1 mmol, 28% yield) was obtained as a yellow solid.

Step 13: Preparation of tert-butyl 6-((2-fluoro-4-(2,3,9-trimethyl-6-(oxazol-2-ylmethyl)-6H-thieno[3,2-f][1,2,4]triazolo[4,3-a][1,4]diazepin-4-yl)phenyl)ethynyl)-2-aza spiro[3.3]heptane-2-carboxylate. A mixture of 2-((4-(4-chloro-3-fluorophenyl)-2,3,9-tri methyl-6H-thieno[3,2-f][1,2,4]triazolo[4,3-a][1,4]diazepin-6-yl)methyl)oxazole (400 mg, 905 μmol, 1.0 equiv), tert-butyl 6-ethynyl-2-azaspiro[3.3]heptane-2-carboxylate (500 mg, 2.26 mmol, 2.5 equiv), [2-(2-aminophenyl)phenyl]-methylsulfonyloxy-palladium; 2-(2-dicyclohexyl phosphanylphenyl)-N,N-dimethyl-aniline (69.0 mg, 90.5 μmol, 0.1 equiv), and $Cs_2CO_3$ (589 mg, 1.81 mmol, 2.0 equiv) in MeCN (16 mL) was degassed and purged with $N_2$ 3 times, and then the mixture was stirred at 90° C. for 2 h under $N_2$ atmosphere. The reaction mixture was concentrated in vacuo to give the crude product. The residue was purified by column chromatography ($SiO_2$, petroleum ether/ethyl acetate=10/1 to 0/1). Compound tert-butyl 6-((2-fluoro-4-(2,3,9-trimethyl-6-(oxazol-2-ylmethyl)-6H-thieno[3,2-f][1,2,4]triazolo[4,3-a][1,4]diazepin-4-yl)phenyl)ethynyl)-2-azaspiro[3.3]heptane-2-carboxylate (500 mg, 797 μmol, 88% yield) was obtained as a white solid.

Step 14: Preparation of 2-((4-(4-((2-azaspiro[3.3]heptan-6-yl)ethynyl)-3-fluorophenyl)-2,3,9-trimethyl-6H-thieno[3,2-f][1,2,4]triazolo[4,3-a][1,4]diazepin-6-yl)methyl)oxazole. To a solution of tert-butyl 6-((2-fluoro-4-(2,3,9-trimethyl-6-(oxazol-2-ylmethyl)-6H-thieno[3,2-f][1,2,4]triazolo[4,3-a][1,4]diazepin-4-yl)phenyl)ethynyl)-2-aza spiro[3.3]heptane-2-carboxylate (500 mg, 797 μmol, 1.0 equiv) in DCM (5 mL) was added TFA (3.07 g, 26.9 mmol, 2 mL, 33.7 equiv). The mixture was stirred at 25° C. for 2 h. To the reaction mixture was added water (20 mL) and the mixture was extracted with ethyl acetate (20 mL×3). The combined organic phase was washed with brine (20 mL), dried over anhydrous $Na_2SO_4$, filtered and concentrated in vacuo. The crude product was purified by preparative HPLC (column: Phenomenex luna C18 150×25 mm×10 μm; mobile phase: [water (FA)-ACN]; gradient: 12%-42% B over 10 min). The product was further purified by SFC (column: DAICEL CHIRALPAK AS (250 mm×30 mm, 10 μm); mobile phase: [$CO_2$-ACN/EtOH (0.1% $NH_3$ in $H_2O$)]; B %: 50%, isocratic elution mode). The product was further purified by preparative HPLC (column: REGIS(S,S)WHELK-01 (250 mm×25 mm, 10 μm); mobile phase: [$CO_2$-CAN/EtOH (0.1% $NH_3$ in $H_2O$)]; B %: 55%, isocratic elution mode) to yield compound 2-((4-(4-((2-azaspiro[3.3]heptan-6-yl)ethynyl)-3-fluorophenyl)-2,3,9-trimethyl-6H-thieno[3,2-f][1,2,4]triazolo[4,3-a][1,4]diazepin-6-yl)methyl)oxazole (80 mg, 0.15 mmol, 40% yield) as a white solid.

Step 15: Preparation of N-[4-(4-cyano-3-methoxy-phenoxy)cyclohexyl]-6-[6-[2-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]ethynyl]-2-azaspiro[3.3]heptan-2-yl]pyridazine-3-carboxamide. To a solution of 2-((4-(4-((2-azaspiro[3.3]heptan-6-yl)ethynyl)-3-fluorophenyl)-2,3,9-trimethyl-6H-thieno[3,2-f][1,2,4]triazolo[4,3-a][1,4]diazepin-6-yl)methyl)oxazole (40 mg, 75 μmol, 1.0 equiv) in NMP (0.5 mL) was added DIEA (29 mg, 0.22 mmol, 39 μL, 3.0 equiv) and 6-chloro-N-[4-(4-cyano-3-methoxy-phenoxy)cyclohexyl]pyridazine-3-carboxamide (29 mg, 75 μmol, 1.0 equiv). The mixture was stirred at 60° C. for 12 h. To the reaction mixture was added water (10 mL) and the mixture was extracted with ethyl acetate (20 mL×3). The combined organic phase was washed with brine (20 mL), dried over anhydrous $Na_2SO_4$, filtered and concentrated in vacuo. The crude product was purified by preparative HPLC (column: Waters xbridge 150×25 mm 10 μm; mobile phase: [water ($NH_4HCO_3$)-ACN]; gradient: 55%-75% B over 8 min). N-[4-(4-cyano-3-methoxy-phenoxy)cyclohexyl]-6-[6-[2-[2-fluoro-4-[4,5,13-trimethyl-9-(oxazol-2-ylmethyl)-3-thia-1,8,11,12-tetrazatricyclo[8.3.0.02,6]trideca-2 (6),4,7,10,12-pentaen-7-yl]phenyl]ethynyl]-2-azaspiro[3.3]heptan-2-yl]pyridazine-3-carboxamide (14 mg, 16 μmol, 21% yield, 98% purity) was obtained as a white solid. $^1$H NMR (400 MHz, $CD_3OD$-$d_4$) δ 7.96-7.91 (m, 2H), 7.52 (d, J=9.2 Hz, 1H), 7.44 (t, J=7.6 Hz, 1H), 7.24-7.14 (m, 3H), 6.87 (d, J=9.6 Hz, 1H), 6.72-6.65 (m, 2H), 4.83-4.79 (m, 2H), 4.26 (d, J=4.8 Hz, 4H), 4.08-3.95 (m, 3H), 3.94 (s, 3H), 3.31-3.28 (m, 1H), 2.81-2.70 (m, 5H), 2.55-2.46 (m, 5H), 2.27-2.19 (m, 2H), 2.11 (d, J=2.8 Hz, 2H), 1.75 (s, 3H), 1.65 (t, J=10.0 Hz, 4H). LC-MS: MS ($ES^+$): RT=2.558 min, m/z=877.4 [M+H$^+$]; LCMS method: 10.

Example 52—Synthesis of N-[4-(4-cyano-3-methoxy-phenoxy)cyclohexyl]-6-[2-[3-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyridazine-3-carboxamide (I-128)
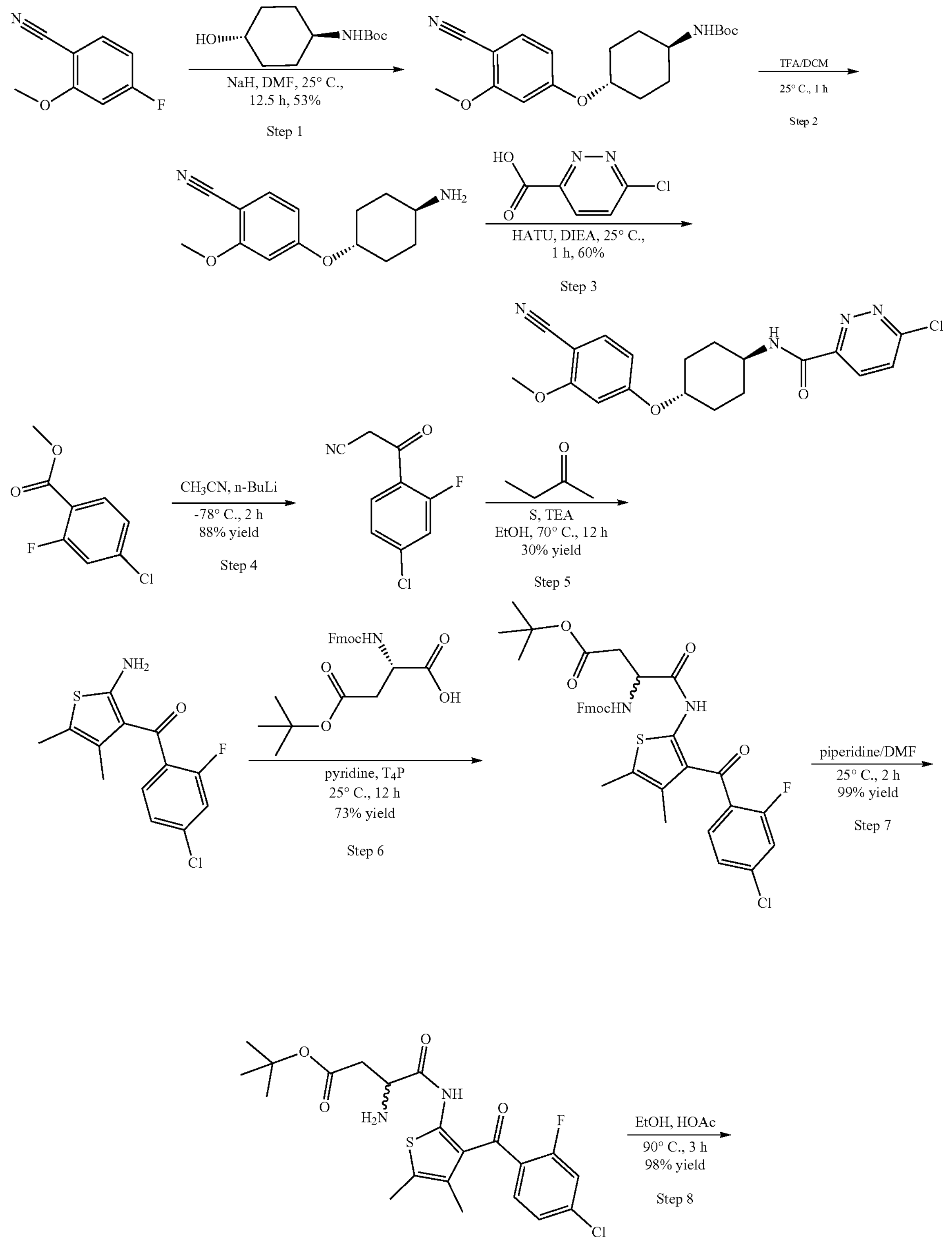

-continued
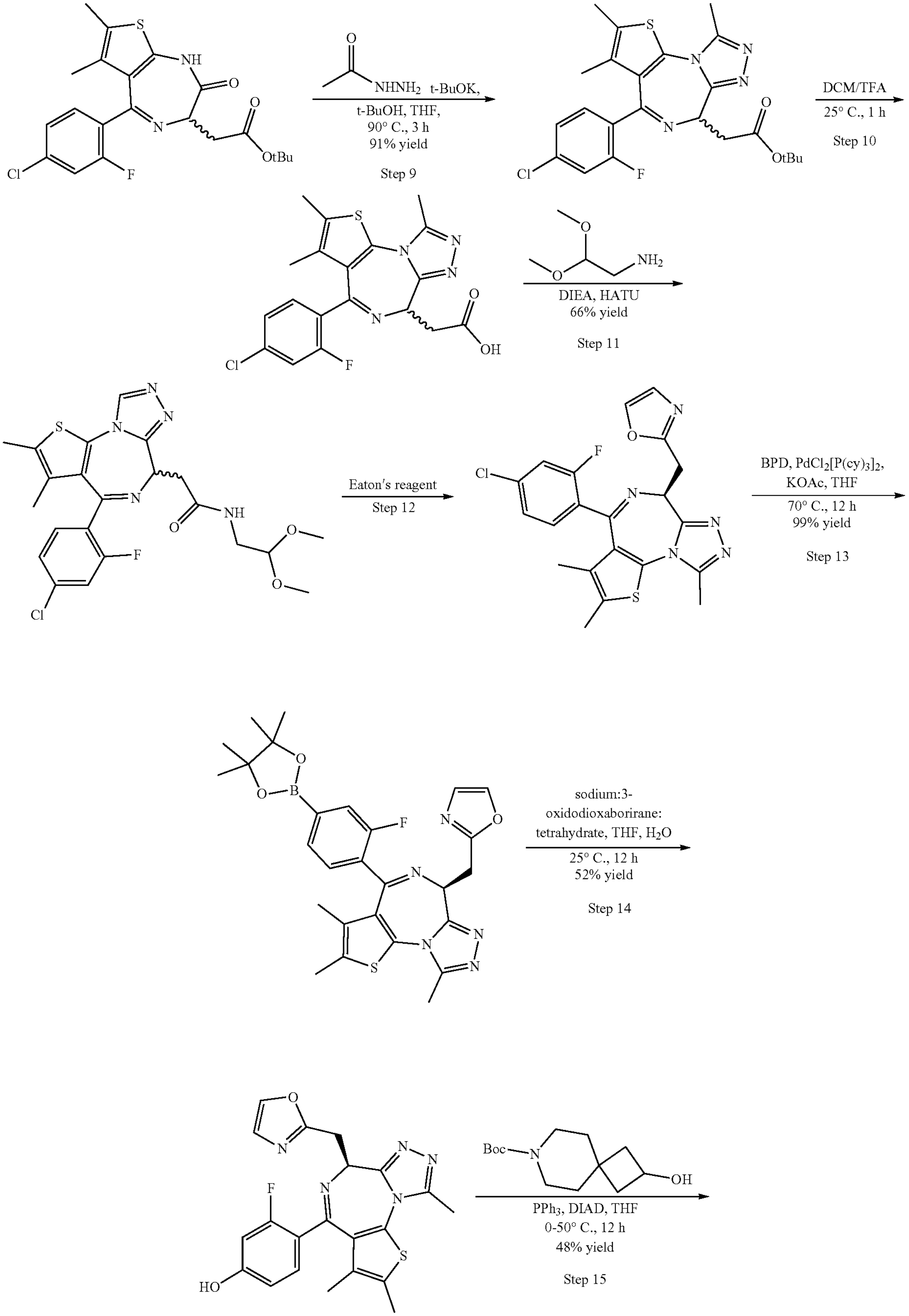

-continued

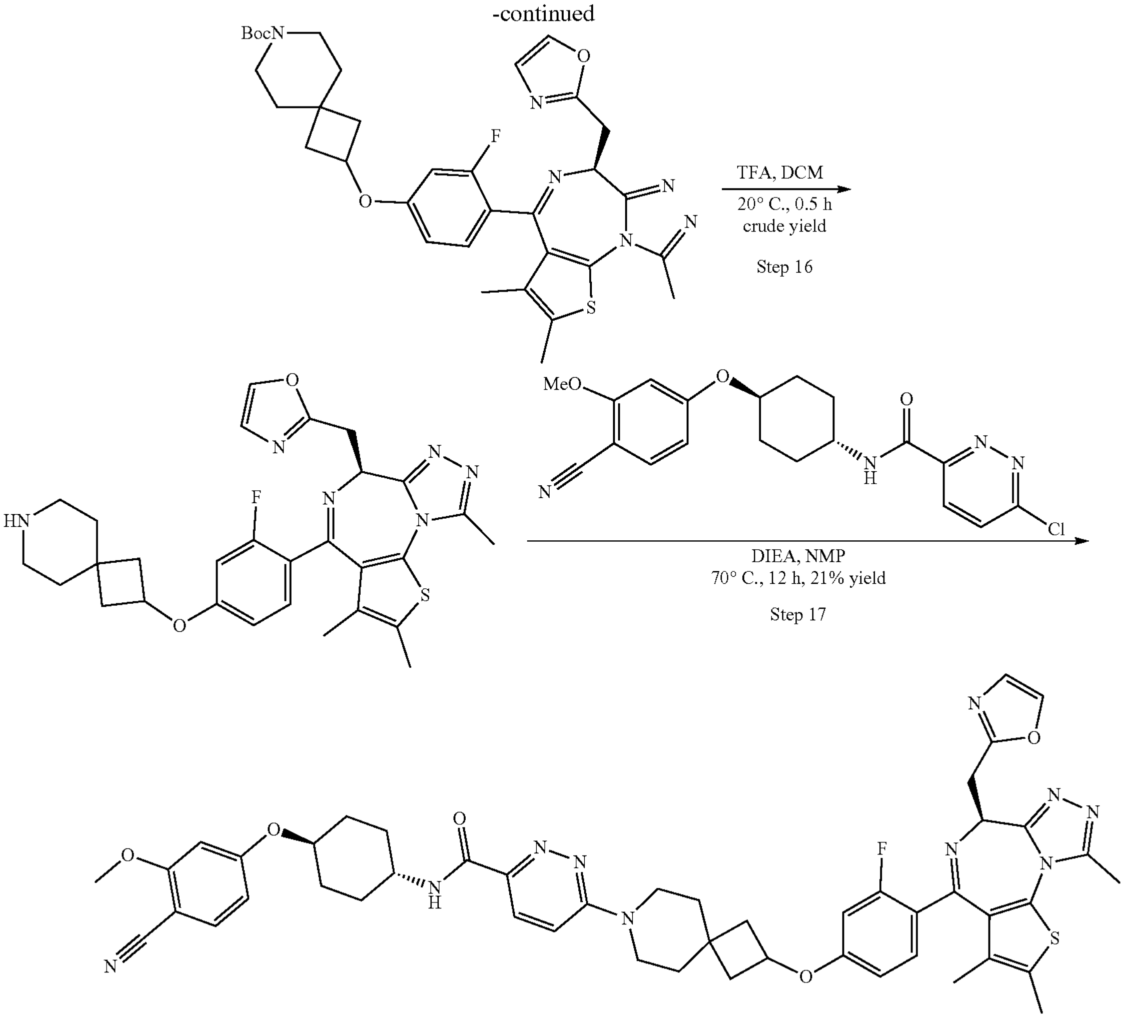

I-128

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxycyclohexyl) carbamate (5.6 g, 26.01 mmol, 1.0 equiv). After 30 minutes, 4-fluoro-2-methoxy-benzonitrile (3.93 g, 26.01 mmol, 1.0 equiv) was added. The reaction mixture was slowly allowed to warm to 25° C. and the mixture was stirred for 12 h. The reaction mixture was quenched with a saturated aqueous $NH_4Cl$ (100 mL) solution at 0° C. The resulting mixture was extracted with ethyl acetate (100 mL×3). The combined organic layers were dried over anhydrous $Na_2SO_4$, filtered and concentrated under vacuum. The residue was purified by column chromatography ($SiO_2$, petroleum ether/ethyl acetate-0/1 to 3/1) to afford tert-butyl ((1r,4r)-4-(4-cyano-3-methoxy phenoxy) cyclohexyl) carbamate (4.8 g, 13.86 mmol, 53% yield) as a white solid.

Step 2: Preparation of 4-(((1r,4r)-4-aminocyclohexyl) oxy)-2-methoxy-benzo nitrile. To a solution of tert-butyl ((1r,4r)-4-(4-cyano-3-methoxyphenoxy)cyclohexyl) carbamate (0.5 g, 1.44 mmol, 1.0 equiv) in DCM (2 mL) was added TFA (1 mL). The mixture was stirred at 25° C. for 1 h. The reaction mixture was concentrated under reduced pressure to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-((1r,4r)-4-(4-cyano-3-methoxyphenoxy)cyclo hexyl) pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 µL, 3.0 equiv). The mixture was stirred at 25° C. for 1 h. The reaction mixture was concentrated under reduced pressure. The residue was purified by prep-HPLC (column: Waters xbridge 150×25 mm 10 µm; mobile phase: [water ($NH_4HCO_3$) ACN]; gradient: 49%-69% B over 8 min) to afford 6-chloro-N-((1r,4r)-4-(4-cyano-3-methoxy-phenoxy)cyclohexyl) pyridazine-3-carboxamide (337 mg, 871 µmol, 60% yield) as a white solid.

Step 4: Preparation of 3-(4-chloro-2-fluoro-phenyl)-3-oxo-propanenitrile. A solution of acetonitrile (9.3 g, 225.3 mmol, 11.9 mL, 1.7 equiv) in THF (200 mL) was stirred at −78° C. under $N_2$ protection. Then n-BuLi (2.5 M, 106.0 mL, 2.0 equiv) was added to the mixture and it was stirred for 0.5 h. Then methyl 4-chloro-2-fluoro-benzoate (25.0 g, 132.5 mmol, 1.0 equiv) in THF (20 mL) was added dropwise and the mixture was stirred for 1.5 h under $N_2$ protection. The reaction mixture was quenched with a saturated aqueous $NH_4Cl$ (200 ml) solution at 0° C. The resulting mixture was extracted with ethyl acetate (100 mL×4). The combined organic layers were dried over anhydrous $Na_2SO_4$, filtered and concentrated under vacuum. The crude product was triturated with petroleum ether/ethyl acetate=20/1 at 25° C. for 30 min to give 3-(4-chloro-2-fluoro-phenyl)-3-oxo-propanenitrile (23.0 g, 116.4 mmol, 87.80% yield) as a yellow solid.

Step 5: Preparation of (2-amino-4,5-dimethyl-3-thienyl)-(4-chloro-2-fluoro-phenyl) methanone. To a solution of 3-(4-chloro-2-fluoro-phenyl)-3-oxo-propanenitrile (23.0 g, 116.4 mmol, 1.0 equiv) and butan-2-one (8.4 g, 116.4 mmol, 10.4 mL, 1.0 equiv) in EtOH (200 mL) was added TEA (23.6 g, 232.8 mmol, 32.4 mL, 2.0 equiv) and S (4.4 g, 138.5 mmol, 1.2 equiv). The mixture was stirred at 50° C. for 12 h. To the reaction mixture was added water (500 mL) and the mixture was extracted with ethyl acetate (500 mL×3). The combined organic phase was washed with brine (500 mL), dried over anhydrous $Na_2SO_4$, filtered and concentrated in vacuo. The residue was purified by column chromatography ($SiO_2$, petroleum ether/ethyl acetate=35/1 to 30/1) to give (2-amino-4,5-dimethyl-3-thienyl)-(4-chloro-2-fluoro-phenyl) methanone (10.0 g, 35.2 mmol, 30% yield) as a yellow oil.

Step 6: Preparation of tert-butyl (3S)-4-[[3-(4-chloro-2-fluoro-benzoyl)-4,5-dimethyl-2-thienyl]amino]-3-(9H-fluoren-9-ylmethoxycarbonylamino)-4-oxo-butanoate. To a solution of (2-amino-4,5-dimethyl-3-thienyl)-(4-chloro-2-fluoro-phenyl) methanone (8.8 g, 31.0 mmol, 1.0 equiv) and (2S)-4-tert-butoxy-2-(9H-fluoren-9-ylmethoxycarbonylamino)-4-oxo-butanoic acid (19.1 g, 46.5 mmol, 1.5 equiv) in EtOAc (40 mL) was added pyridine (9.8 g, 124.0 mmol, 10.0 mL, 4.0 equiv) and T4P (44.7 g, 62.0 mmol, 50% purity, 2.0 equiv). The mixture was stirred at 25° C. for 12 h. The reaction mixture was added to water (300 mL) and the mixture was extracted with ethyl acetate (80 mL×3). The combined organic phase was washed with brine (100 mL), dried over anhydrous $Na_2SO_4$, filtered and concentrated in vacuo. The residue was purified by column chromatography ($SiO_2$, petroleum ether/ethyl acetate=8/1 to 6/1) to give tert-butyl (3S)-4-[3-(4-chloro-2-fluoro-benzoyl)-4,5-dimethyl-2-thienyl]amino]-3-(9H-fluoren-9-ylmethoxycarbonylamino)-4-oxo-butanoate (15.5 g, 22.9 mmol, 73% yield) as a yellow oil.

Step 7: Preparation of tert-butyl (3S)-3-amino-4-[[3-(4-chloro-2-fluoro-benzoyl)-4,5-dimethyl-2-thienyl]amino]-4-oxo-butanoate. To a solution of tert-butyl (3S)-4-[[3-(4-chloro-2-fluoro-benzoyl)-4,5-dimethyl-2-thienyl]amino]-3-(9H-fluoren-9-ylmethoxy-carbonyl amino)-4-oxo-butanoate (14.0 g, 20.7 mmol, 1.0 equiv) in DCM (280 mL) was added piperidine (5.3 g, 62.0 mmol, 6.1 mL, 3.0 equiv). The mixture was stirred at 25° C. for 2 h. To the reaction mixture was added water (300 mL) and the mixture was extracted with ethyl acetate (200 mL×3). The combined organic phase was washed with brine (350 mL), dried over anhydrous $Na_2SO_4$, filtered and concentrated in vacuo. The residue was purified by column chromatography ($SiO_2$, petroleum ether/ethyl acetate=10/1 to 8/1) to give tert-butyl (3S)-3-amino-4-[[3-(4-chloro-2-fluoro-benzoyl)-4,5-dimethyl-2-thienyl] amino]-4-oxo-butanoate (9.4 g, 20.7 mmol, 99% yield) as a yellow oil.

Step 8: Preparation of tert-butyl 2-[(3S)-5-(4-chloro-2-fluoro-phenyl)-6,7-dimethyl-2-oxo-1,3-dihydrothieno[2,3-e][1,4]diazepin-3-yl]acetate. To a solution of tert-butyl (3S)-3-amino-4-[[3-(4-chloro-2-fluoro-benzoyl)-4,5-dimethyl-2-thienyl]amino]-4-oxo-butanoate (9.4 g, 20.6 mmol, 1.0 equiv) in EtOH (90 mL) was added AcOH (31.5 g, 524.0 mmol, 30.0 mL, 25.4 equiv). The mixture was stirred at 90° C. for 3 h. The reaction mixture was added to water (100 mL) and the mixture was extracted with ethyl acetate (150 mL×3). The combined organic phase was washed with brine (150 mL), dried over anhydrous $Na_2SO_4$, filtered and concentrated in vacuo. The residue was purified by column chromatography ($SiO_2$, petroleum ether/ethyl acetate=8/1 to 6/1) to give the tert-butyl 2-[(3S)-5-(4-chloro-2-fluoro-phenyl)-6,7-dimethyl-2-oxo-1,3-dihydrothieno[2,3-e][1,4]diazepin-3-yl]acetate (8.9 g, 20.4 mmol, 98% yield) as a yellow oil.

Step 9: Preparation of tert-butyl 2-[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl]acetate. t-BuOK (1.0 M, 22.4 mL, 1.1 equiv) was added to tert-butyl 2-[(3S)-5-(4-chloro-2-fluoro-phenyl)-6,7-dimethyl-2-oxo-1,3-dihydrothieno[2,3-e][1,4]diazepin-3-yl]acetate (8.9 g, 20.4 mmol, 1.0 equiv) in THF (90 mL) at −78° C., and stirred at 25° C. for 30 min. The reaction mixture was cooled to −78° C. [chloro(phenoxy) phosphoryl]oxybenzene (6.6 g, 24.4 mmol, 5.1 mL, 1.2 equiv) was added to reaction mixture. The resulting mixture was warmed to 25° C. over 45 min. Then acetohydrazide (2.3 g, 30.6 mmol, 1.5 equiv) was added to the reaction mixture. The reaction mixture was stirred at 25° C., n-BuOH (90 mL) was added to the reaction mixture and it was heated to 90° C. for 1 h. The reaction mixture was quenched with a saturated aqueous $NH_4Cl$ (100 ml) solution at 0° C. by dropwise addition. And the resulting mixture was extracted with ethyl acetate (100 mL×2). The combined organic layers were dried over anhydrous $Na_2SO_4$, filtered and concentrated under vacuum. The residue was purified by column chromatography ($SiO_2$, petroleum ether/ethyl acetate=8/1 to 6/1) to give the tert-butyl 2-[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl]acetate (8.9 g, 18.74 mmol, 91% yield) as a yellow oil.

Step 10: Preparation of 2-[(9S)-7-(4-chloro-2-fluoro-phenyl)-4,5,13-trimethyl-3-thia-1,8,11,12-tetrazatricyclo [8.3.0.0$^{2,6}$]trideca-2 (6),4,7,10,12-pentaen-9-yl]acetic acid. To a solution of tert-butyl 2-[(9S)-7-(4-chloro-2-fluoro-phenyl)-4,5,13-trimethyl-3-thia-1,8,11,12-tetrazatricyclo [8.3.0.0$^{2,6}$]trideca-2 (6),4,7,10,12-pentaen-9-yl]acetate (8.9 g, 18.7 mmol, 1.0 equiv) in DCM (40 mL) was added TFA (20.0 mL). The mixture was stirred at 25° C. for 1 h. The reaction mixture was filtered and concentrated under reduced pressure to give a residue. The residue was used for the next step directly. Compound 2-[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl]acetic acid (7.8 g, 18.6 mmol) was obtained as a yellow oil.

Step 11: Preparation of 2-[(9S)-7-(4-chloro-2-fluoro-phenyl)-4,5,13-trimethyl-3-thia-1,8,11,12-tetrazatricyclo [8.3.0.0$^{2,6}$]trideca-2 (6),4,7,10,12-pentaen-9-yl]-N-(2,2-di methoxyethyl) acetamide. To a solution of 2-[(9S)-7-(4-chloro-2-fluoro-phenyl)-4,5,13-trimethyl-3-thia-1,8,11,12-tetrazatricyclo[8.3.0.0$^{2,6}$]trideca-2 (6),4,7,10,12-pentaen-9-yl]acetic acid (7.8 g, 18.6 mmol, 1.0 equiv) and 2,2-dimethoxyethanamine (5.8 g, 55.8 mmol, 6.09 mL, 3.0 equiv) in DMF (70 mL) was added HATU (7.8 g, 20.5 mmol, 1.1 equiv) and DIEA (7.2 g, 55.8 mmol, 9.73 mL, 3.0 equiv). The mixture was stirred at 25° C. for 0.5 h. To the reaction mixture was added water (20 mL) and the mixture was extracted with ethyl acetate (20 mL×3). The combined organic phase was washed with brine (50 mL), dried over anhydrous $Na_2SO_4$, filtered and concentrated in vacuo. The residue was purified by column chromatography ($SiO_2$, DCM/MeOH=40/1 to 20/1) to give 2-[(9S)-7-(4-chloro-2-fluoro-phenyl)-4,5,13-trimethyl-3-thia-1,8,11,12-tetrazatricyclo[8.3.0.$0^{2,6}$]trideca-2 (6),4,7,10,12-pentaen-9-yl]-N-(2,2-dimethoxyethyl) acetamide (6.3 g, 12.5 mmol, 66% yield) as a yellow oil.

Step 12: Preparation of 2-[[(9S)-7-(4-chloro-2-fluoro-phenyl)-4,5,13-trimethyl-3-thia-1,8,11,12-tetrazatricyclo[8.3.0.$0^{2,6}$]trideca-2 (6),4,7,10,12-pentaen-9-yl]methyl]oxazole. A solution of 2-[(9S)-7-(4-chloro-2-fluoro-phenyl)-4,5,13-trimethyl-3-thia-1,8,11,12-tetraza tricyclo[8.3.0.$0^{2,6}$]trideca-2 (6),4,7,10,12-pentaen-9-yl]-N-(2,2-dimethoxyethyl) acetamide (2.0 g, 3.9 mmol, 1.0 equiv) in Eaton's reagent (20 mL) was stirred at 100° C. for 12 h. The reaction mixture was quenched with a saturated aqueous $NaHCO_3$ (200 ml) solution at 0° C. by dropwise addition. The resulting mixture was extracted with ethyl acetate (50 mL×3). The combined organic layers were dried over anhydrous $Na_2SO_4$, filtered and concentrated in vacuum. The residue was purified by column chromatography ($SiO_2$, DCM:MeOH=30/1 to 20/1). The product was further purified by prep-HPLC (column: Phenomenex luna C18 (250×70 mm, 10 μm); mobile phase: [water (FA)-ACN]; gradient: 40%-70% B over 20 min). To give 2-[[(9S)-7-(4-chloro-2-fluoro-phenyl)-4,5,13-trimethyl-3-thia-1,8,11,12-tetrazatricyclo[8.3.0.$0^{2,6}$]trideca-2 (6),4,7,10,12-pentaen-9-yl]methyl]oxazole (3.0 g, 6.79 mmol, 57% yield) as a white solid.

Step 13: Preparation of 2-[[(9S)-7-[2-fluoro-4-(4,4,5,5-tetramethyl-1,3,2-dioxa borolan-2-yl)phenyl]-4,5,13-trimethyl-3-thia-1,8,11,12-tetrazatricyclo[8.3.0.$0^{2,6}$]trideca-2 (6),4,7,10,12-pentaen-9-yl]methyl]oxazole. A mixture of 2-[(9S)-7-(4-chloro-2-fluoro-phenyl)-4,5,13-trimethyl-3-thia-1,8,11,12-tetrazatricyclo[8.3.0.$0^{2,6}$]trideca-2 (6),4,7,10,12-pentaen-9-yl]methyl]oxazole (550 mg, 1.2 mmol, 1.0 equiv), BPD (1.0 g, 3.9 mmol, 3.1 equiv), dichloropalladium; tricyclohexylphosphane (184 mg, 249 μmol, 0.2 equiv) and KOAc (269 mg, 2.7 mmol, 2.2 equiv) in THF (5 mL) was degassed and purged with $N_2$ 3 times, and then the mixture was stirred at 70° C. for 12 h under $N_2$ atmosphere. The reaction mixture was added to $H_2O$ (50 mL) and extracted with ethyl acetate (50 mL×3). The organic phase was separated, washed with brine (50 mL), dried over anhydrous sodium sulfate, filtered and concentrated under reduced pressure to give 2-[(9S)-7-[2-fluoro-4-(4,4,5,5-tetramethyl-1,3,2-dioxaborolan-2-yl)phenyl]-4,5,13-trimethyl-3-thia-1,8,11,12-tetrazatricyclo[8.3.0.$0^{2,6}$]trideca-2 (6),4,7,10,12-pentaen-9-yl]methyl]oxazole (660 mg, 1.2 mmol, 99% yield) as a yellow oil.

Step 14: Preparation of 3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenol. A mixture of 2-[(9S)-7-[2-fluoro-4-(4,4,5,5-tetramethyl-1,3,2-dioxaborolan-2-yl)phenyl]-4,5,13-trimethyl-3-thia-1,8,11,12-tetrazatricyclo[8.3.0.$0^{2,6}$]trideca-2 (6),4,7,10,12-pentaen-9-yl]methyl]oxazole (360 mg, 674 μmol, 1.0 equiv), and sodium; 3-oxidodioxaborirane; tetrahydrate (200 mg, 1.3 mmol, 1.9 equiv) in THF (3 mL) and $H_2O$ (1 mL) was degassed and purged with $N_2$ 3 times, and then the mixture was stirred at 25° C. for 12 h under $N_2$ atmosphere. The reaction mixture was added to water (20 mL) and extracted with ethyl acetate (20 mL×3). The combined organic phase was separated, washed with brine (20 mL), dried over anhydrous sodium sulfate, filtered and concentrated under reduced pressure to give a residue. The residue was purified by prep-HPLC (column: Phenomenex luna C18 150×25 mm×10 μm; mobile phase: [water (FA)-ACN]; gradient: 22%-52% B over 10 min) to give the 3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenol (150 mg, 354 μmol, 52% yield) as a yellow oil.

Step 15: Preparation of tert-butyl 2-[3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenoxy]-7-azaspiro[3.5]nonane-7-carboxylate. To a solution of $PPh_3$ (0.35 M, 2.0 mL, 2.1 equiv) in THF (2.0 mL) under $N_2$ protection was added DIAD (143 mg, 708 μmol, 2 equiv) was at 0° C. After addition, the mixture was stirred at this temperature for 0.5 h. Then tert-butyl 2-hydroxy-7-azaspiro[3.5]nonane-7-carboxylate (170 mg, 708 μmol, 2.0 equiv) and 3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6), 4,7,10,12-pentaen-7-yl]phenol (1 M, 354 μL, 1.0 equiv) in THF (2 mL) was added dropwise at 0° C. The resulting mixture was stirred at 50° C. for 11.5 h. The reaction mixture was concentrated under reduced pressure to give a residue. The residue was purified by prep-HPLC (column: Phenomenex Luna C18 150×25 mm×10 μm; mobile phase: [water (TFA)-ACN]; gradient: 53%-83% B over 10 min) to give tert-butyl 2-[3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenoxy]-7-azaspiro[3.5]nonane-7-carboxylate (110 mg, 170 μmol, 48% yield) as a white solid.

Step 16: Preparation of 2-[[(9S)-7-[4-(7-azaspiro[3.5]nonan-2-yloxy)-2-fluoro-phenyl]-4,5,13-trimethyl-3-thia-1,8,11,12-tetrazatricyclo[8.3.0.$0^{2,6}$]trideca-2 (6),4,7,10,12-pentaen-9-yl]methyl]oxazole. To a solution of tert-butyl 2-[3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenoxy]-7-azaspiro[3.5]nonane-7-carboxylate (110 mg, 170 μmol, 1.0 equiv) in DCM (3 mL) was added TFA (1.0 mL). The mixture was stirred at 20° C. for 0.5 h. The reaction mixture was concentrated under reduced pressure to give the 2-[[(9S)-7-[4-(7-azaspiro[3.5]nonan-2-yloxy)-2-fluoro-phenyl]-4,5,13-trimethyl-3-thia-1,8,11,12-tetrazatricyclo[8.3.0.$0^{2,6}$]trideca-2 (6), 4,7,10,12-pentaen-9-yl]methyl]oxazole (100 mg, crude) as a yellow oil.

Step 17: Preparation of N-[4-(4-cyano-3-methoxy-phenoxy)cyclohexyl]-6-[2-[3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenoxy]-7-azaspiro[3.5]nonan-7-yl]pyridazine-3-carboxamide (I-128). To a solution of 2-[[(9S)-7-[4-(7-azaspiro[3.5]nonan-2-yloxy)-2-fluoro-phenyl]-4,5,13-trimethyl-3-thia-1,8,11,12-tetrazatricyclo[8.3.0.$0^{2,6}$]trideca-2 (6), 4,7,10,12-pentaen-9-yl]methyl]oxazole (50 mg, 91 μmol, 1.0 equiv) in NMP (2 mL) was added DIEA (23 mg, 182 μmol, 2.0 equiv) and 6-chloro-N-[4-(4-cyano-3-methoxy-phenoxy) cyclohexyl]pyridazine-3-carboxamide (40 mg, 103 μmol, 1.1 equiv). The mixture was stirred at 70° C. for 12 h. The reaction mixture was purified by reversed-phase HPLC (column: Phenomenex luna C18 150×25 mm×10 μm; mobile phase: [water (FA)-CAN]; gradient: 54%-84% B over 10 min) to give N-[4-(4-cyano-3-methoxy-phenoxy)cyclohexyl]-6-[2-[3-fluoro-4-[(9S)-4,5,13-trimethyl-9-(oxazol-2-ylmethyl)-3-thia-1,8,11,12-tetrazatricyclo[8.3.0.$0^{2,6}$]trideca-2 (6),4,7,10,12-pentaen-7-yl]phenoxy]-7-azaspiro[3.5]nonan-7-yl]pyridazine-3-carboxamide (I-128, 18 mg, 19 μmol, 21% yield, 98% purity) as a white solid. $^1H$ NMR: (400 MHz, $CD_3OD$) &=7.95-7.86 (m, 2H), 7.53 (d, J=9.2 Hz, 1H), 7.38-7.25 (m, 2H), 7.15 (s, 1H), 6.81-6.56 (m, 4H), 4.02-3.93 (m, 6H), 3.82-3.70 (m, 4H), 2.72 (s, 3H), 2.63-2.52 (m, 2H), 2.45 (s, 3H), 2.27-2.20 (m, 2H), 2.17-2.08 (m, 2H), 2.06-1.97 (m, 2H), 1.85-1.61 (m, 12H). LC-MS: MS ($ES^+$): RT=2.692 min, m/z=897.4 [$M+H^+$].

Example 53—Synthesis of N-[4-(4-cyano-3-methoxy-phenoxy)cyclohexyl]-6-[8-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide
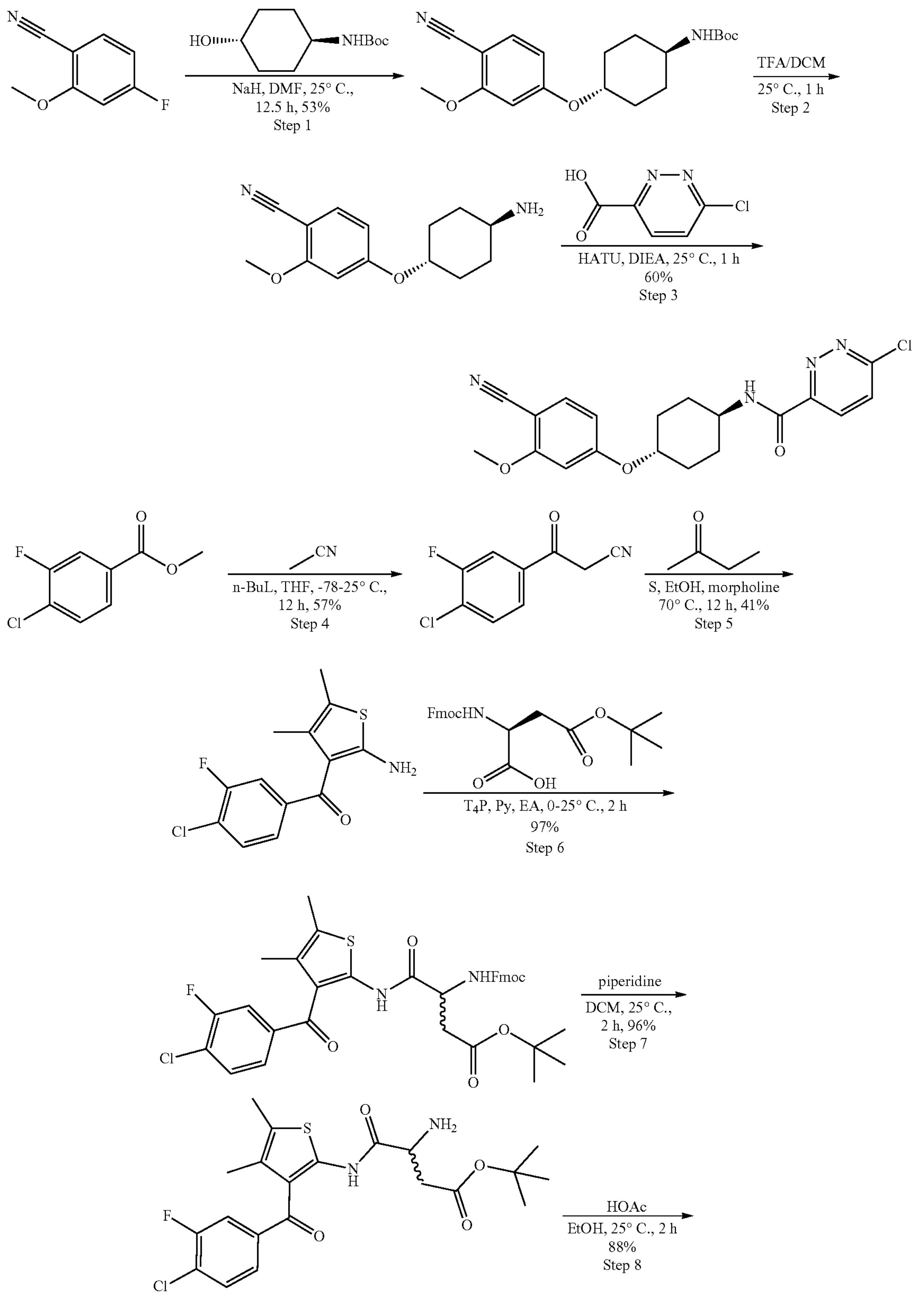

-continued
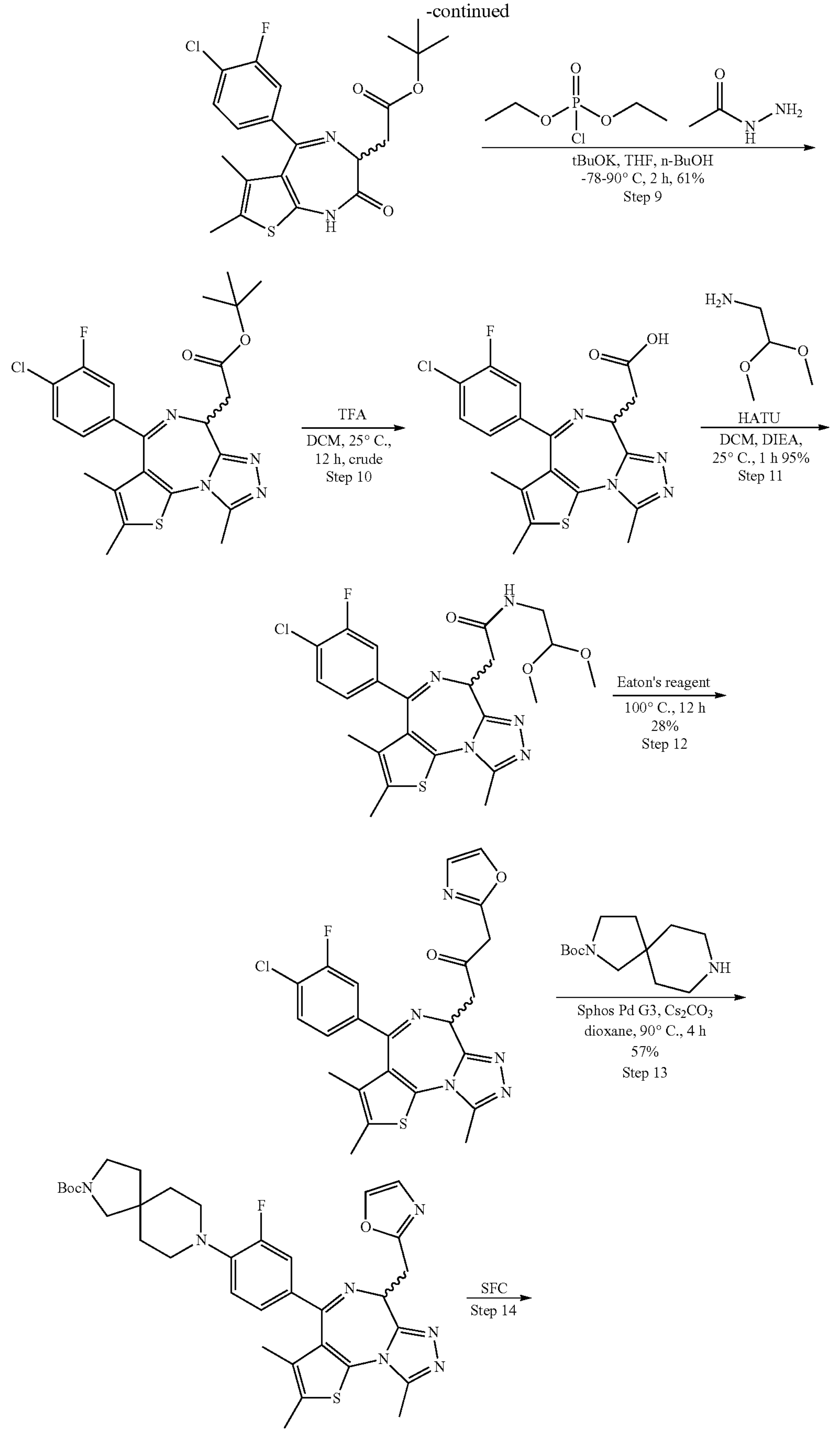

-continued

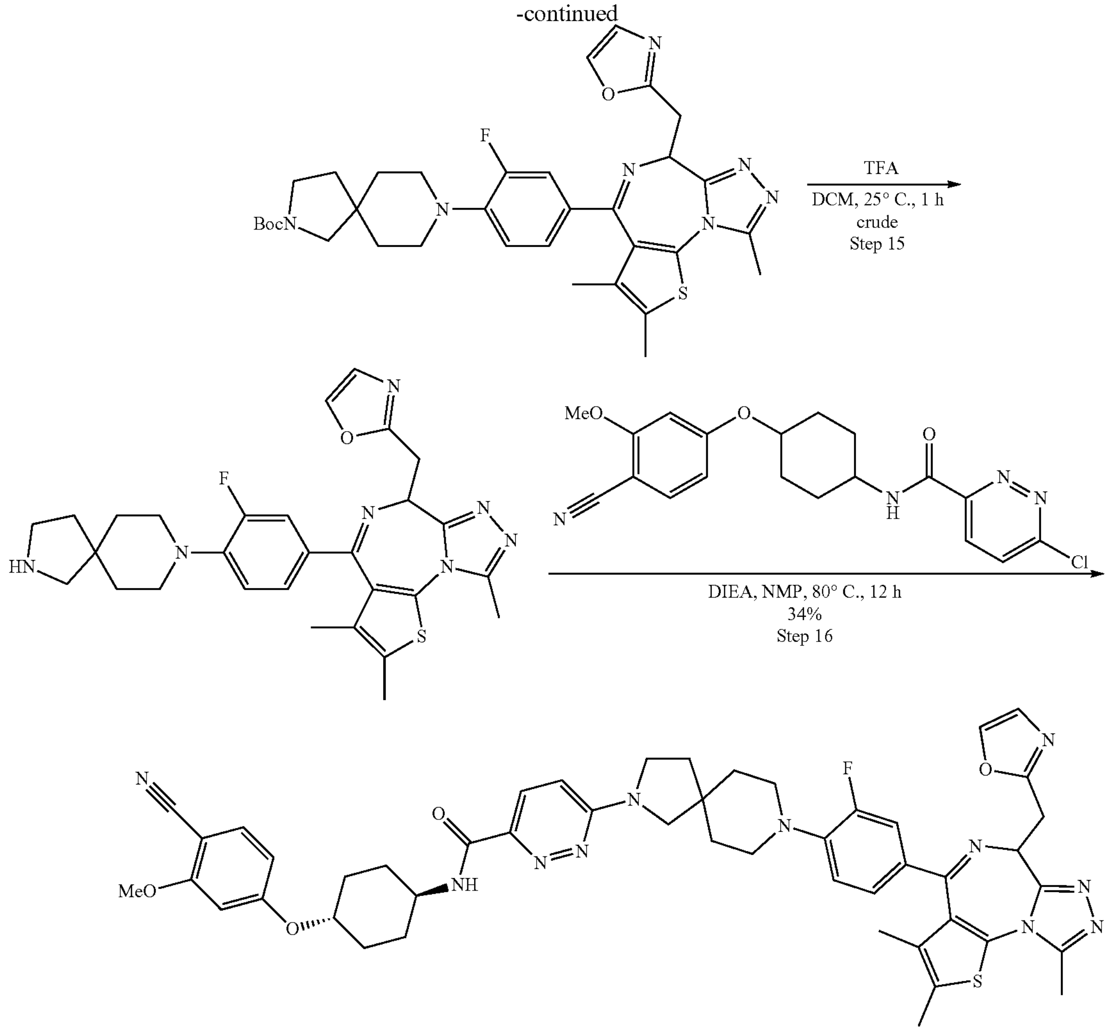

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxycyclohexyl) carbamate (5.6 g, 26.01 mmol, 1.0 equiv). After 30 minutes, 4-fluoro-2-methoxy-benzonitrile (3.93 g, 26.01 mmol, 1.0 equiv) was added. The reaction mixture was slowly allowed to warm to 25° C. and was stirred for 12 h. The reaction mixture was quenched with a saturated aqueous $NH_4Cl$ (100 mL) solution at 0° C. The resulting mixture was extracted with ethyl acetate (100 mL×3). The combined organic layers were dried over anhydrous $Na_2SO_4$, filtered and concentrated under vacuum. The residue was purified by column chromatography ($SiO_2$, petroleum ether/ethyl acetate=0/1 to 3/1) to afford tert-butyl ((1r,4r)-4-(4-cyano-3-methoxy-phenoxy)cyclohexyl) carbamate (4.8 g, 13.86 mmol, 53% yield) as a white solid.

Step 2: Preparation of 4-(((1r,4r)-4-aminocyclohexyl) oxy)-2-methoxy-benzo nitrile. To a solution of tert-butyl ((1r,4r)-4-(4-cyano-3-methoxyphenoxy)cyclohexyl) carbamate (0.5 g, 1.44 mmol, 1.0 equiv) in DCM (2 mL) was added TFA (1 mL). The mixture was stirred at 25° C. for 1 h. The reaction mixture was concentrated under reduced pressure to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-((1r,4r)-4-(4-cyano-3-methoxyphenoxy) cyclohexyl) pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 μL, 3.0 equiv). The mixture was stirred at 25° C. for 1 h. The reaction mixture was concentrated under reduced pressure to remove solvent. The residue was purified by prep-HPLC (column: Waters xbridge 150×25 mm 10 μm; mobile phase: [water ($NH_4HCO_3$)-ACN]; gradient: 49%-69% B over 8 min) to afford 6-chloro-N-((1r,4r) -4-(4-cyano-3-methoxyphenoxy)cyclohexyl) pyridazine-3-carboxamide (337 mg, 871 μmol, 60% yield) as a white solid.

Step 4: Preparation of 3-(4-chloro-3-fluoro-phenyl)-3-oxo-propanenitrile. To a solution of acetonitrile (11.9 g, 291 mmol, 15.3 mL, 2.2 equiv) in THF (200 mL) was added a solution of n-BuLi (2.5 M, 106 mL, 2.0 equiv) dropwise at −78° C. under $N_2$ and stirred at −78° C. for 1 h. Then methyl 4-chloro-3-fluoro-benzoate (25.0 g, 132 mmol, 1.0 equiv) in THF (100 mL) was added at −78° C. by dropwise addition. The reaction mixture was warmed to 25° C. and stirred at 25° C. for 11 h. The reaction mixture was quenched with a saturated aqueous $NH_4Cl$ (50 mL) solution at 0° C. by dropwise addition. The resulting mixture was extracted with ethyl acetate (200 mL×3). The combined organic layers were dried over anhydrous $Na_2SO_4$, filtered and concentrated under vacuum. The residue was purified by column chromatography ($SiO_2$, petroleum ether/ethyl acetate=20/1 to 1/1). Compound 3-(4-chloro-3-fluoro-phenyl)-3-oxo-propanenitrile (15 g, 75 mmol, 57% yield) was obtained as a white solid.

Step 5: Preparation of (2-amino-4,5-dimethyl-3-thienyl)-(4-chloro-3-fluoro-phenyl) methanone. To a solution of 3-(4-chloro-3-fluoro-phenyl)-3-oxo-propanenitrile (15 g, 75 mmol, 1.0 equiv) and butan-2-one (5.47 g, 75.9 mmol, 6.79 mL, 1.0 equiv) in EtOH (200 mL) was added morpholine (6.61 g, 75.9 mmol, 6.68 mL, 1.0 equiv) and S (2.59 g, 80.7 mmol, 1.1 equiv). The mixture was stirred at 70° C. for 12 h. To the reaction mixture was added water (500 mL) and the mixture was extracted with ethyl acetate (500 mL×3). The combined organic phase was washed with brine (500 mL), dried over anhydrous $Na_2SO_4$, filtered and concentrated in vacuo. The residue was purified by column chromatography ($SiO_2$, petroleum ether/ethyl acetate=20/1 to 5/1). The crude was further purified by trituration (petroleum ether/ethyl acetate=3/1, 300 mL). Compound (2-amino-4,5-dimethyl-3-thienyl)-(4-chloro-3-fluoro-phenyl) methanone (9.0 g, 31 mmol, 41% yield) was obtained as a yellow solid.

Step 6: Preparation of tert-butyl 3-((((9H-fluoren-9-yl) methoxy) carbonyl) amino)-4-((3-(4-chloro-3-fluorobenzoyl)-4,5-dimethylthiophen-2-yl)amino)-4-oxobutanoate. To a solution of (2S)-4-tert-butoxy-2-(9H-fluoren-9-ylmethoxycarbonylamino)-4-oxo-butanoic acid (18.7 g, 45.4 mmol, 1.5 equiv) in EtOAc (86 mL) was added pyridine (9.59 g, 121 mmol, 9.79 mL, 4.0 equiv) and T4P (43.6 g, 60.6 mmol, 50% purity, 2.0 equiv) at 0° C. The mixture was stirred at 25° C. for 1 h, then (2-amino-4,5-dimethyl-3-thienyl)-(4-chloro-3-fluoro-phenyl) methanone (8.6 g, 30 mmol, 1.0 equiv) was added at 0° C., and then the reaction mixture was stirred at 25° C. for another 1 h. To the reaction mixture was added water (200 mL) and the mixture was extracted with ethyl acetate (200 mL×3). The combined organic phase was washed with brine (20 mL), dried over anhydrous $Na_2SO_4$, filtered and concentrated in vacuo. The residue was purified by column chromatography ($SiO_2$, petroleum ether/ethyl acetate=10/1 to 5/1). Compound tert-butyl 3-((((9H-fluoren-9-yl) methoxy) carbonyl)amino)-4-((3-(4-chloro-3-fluoro benzoyl)-4,5-dimethylthiophen-2-yl) amino)-4-oxobutanoate (20 g, 29 mmol, 97% yield) was obtained as a white solid.

Step 7: Preparation of tert-butyl 3-amino-4-((3-(4-chloro-3-fluorobenzoyl)-4,5-dimethylthiophen-2-yl)amino)-4-oxobutanoate. To a solution of tert-butyl 3-((((9H-fluoren-9-yl) methoxy) carbonyl)amino)-4-((3-(4-chloro-3-fluorobenzoyl)-4,5-dimethylthiophen-2-yl) amino)-4-oxobutanoate (20 g, 29 mmol, 1.0 equiv) in DCM (100 mL) was added piperidine (12.5 g, 147 mmol, 14.5 mL, 5.0 equiv). The mixture was stirred at 25° C. for 2 h. To the reaction mixture was added water (200 mL) and the mixture was extracted with ethyl acetate (200 mL×3). The combined organic phase was washed with brine (20 mL), dried over anhydrous $Na_2SO_4$, filtered and concentrated in vacuo. The residue was purified by column chromatography ($SiO_2$, petroleum ether/ethyl acetate=10/1 to 3/1). Compound tert-butyl 3-amino-4-((3-(4-chloro-3-fluorobenzoyl)-4,5-dimethylthiophen-2-yl)amino)-4-oxobutanoate (13 g, 28 mmol, 96% yield) was obtained as a white solid.

Step 8: Preparation of tert-butyl 2-(5-(4-chloro-3-fluorophenyl)-6,7-dimethyl-2-oxo-2,3-dihydro-1H-thieno[2,3-e][1,4]diazepin-3-yl) acetate. To a solution of tert-butyl 3-amino-4-((3-(4-chloro-3-fluorobenzoyl)-4,5-dimethylthiophen-2-yl)amino)-4-oxobutanoate (13 g, 28 mmol, 1.0 equiv) in EtOH (130 mL) was added AcOH (8.58 g, 142 mmol, 8.18 mL, 5.0 equiv). The mixture was stirred at 25° C. for 2 h. To the reaction mixture was added $NaHCO_3$ (200 mL) and the mixture was extracted with ethyl acetate (200 mL×3). The combined organic phase was washed with brine (100 mL), dried over anhydrous $Na_2SO_4$, filtered and concentrated in vacuo. The residue was purified by column chromatography ($SiO_2$, petroleum ether/ethyl acetate=10/1 to 1/1). Compound tert-butyl 2-(5-(4-chloro-3-fluorophenyl)-6,7-dimethyl-2-oxo-2,3-dihydro-1H-thieno[2,3-e][1,4]diazepin-3-yl) acetate (11 g, 25 mmol, 88% yield) was obtained as a yellow solid.

Step 9: Preparation of tert-butyl 2-(4-(4-chloro-3-fluorophenyl)-2,3,9-trimethyl-6H-thieno[3,2-f][1,2,4]triazolo[4,3-a][1,4]diazepin-6-yl) acetate. Potassium tert-butoxide (1 M, 7.55 mL, 1.1 equiv) was added to a solution tert-butyl 2-(5-(4-chloro-3-fluorophenyl)-6,7-dimethyl-2-oxo-2,3-dihydro-1H-thieno[2,3-e][1,4]diazepin-3-yl) acetate (3.0 g, 6.8 mmol, 1.0 equiv) in THF (30 mL) at −78° C. The reaction mixture was warmed to 25° C., and stirred at 25° C. for 30 min. The reaction mixture was cooled to −78° C. [chloro(phenoxy) phosphoryl]oxybenzene (2.21 g, 8.24 mmol, 1.71 mL, 1.2 equiv) was added to the reaction mixture. The resulting mixture was warmed to 25° C. over 30 min. Then acetohydrazide (762 mg, 10.3 mmol, 1.5 equiv) was added to the reaction mixture. The reaction mixture was stirred at 25° C., n-BuOH (30 mL) was added to the reaction mixture and it was heated to 90° C. for 1 h. To the reaction mixture was added to water (200 mL) and the mixture was extracted with ethyl acetate (200 mL×3). The combined organic phase was washed with brine (20 mL), dried over anhydrous $Na_2SO_4$, filtered and concentrated in vacuo. The residue was purified by column chromatography ($SiO_2$, petroleum ether/ethyl acetate=10/1 to 1/1). Compound tert-butyl 2-(4-(4-chloro-3-fluorophenyl)-2,3,9-trimethyl-6H-thieno[3,2-f][1,2,4]triazolo[4,3-a][1,4]diazepin-6-yl) acetate (2.0 g, 4.2 mmol, 61% yield) was obtained as a yellow solid.

Step 10: Preparation of 2-(4-(4-chloro-3-fluorophenyl)-2,3,9-trimethyl-6H-thieno[3,2-f][1,2,4]triazolo[4,3-a][1,4]diazepin-6-yl) acetic acid. To a solution of tert-butyl 2-(4-(4-chloro-3-fluorophenyl)-2,3,9-trimethyl-6H-thieno[3,2-f][1,2,4]triazolo[4,3-a][1,4]diazepin-6-yl) acetate (2.0 g, 4.2 mmol, 1.0 equiv) in DCM (20 mL) was added TFA (15.3 g, 134 mmol, 10 mL, 31.9 equiv). The mixture was stirred at 25° C. for 12 h. The reaction mixture was concentrated in vacuo to give the crude product. Compound 2-(4-(4-chloro-3-fluorophenyl)-2,3,9-trimethyl-6H-thieno[3,2-f][1,2,4]triazolo[4,3-a][1,4]diazepin-6-yl) acetic acid (2.2 g, crude, TFA salt) was obtained as a brown solid.

Step 11: Preparation of 2-(4-(4-chloro-3-fluorophenyl)-2,3,9-trimethyl-6H-thieno[3,2-f][1,2,4]triazolo[4,3-a][1,4]diazepin-6-yl)-N-(2,2-dimethoxyethyl) acetamide. To a solution of 2-(4-(4-chloro-3-fluorophenyl)-2,3,9-trimethyl-6H-thieno[3,2-f][1,2,4]triazolo[4,3-a][1,4]diazepin-6-yl) acetic acid (2.2 g, 4.1 mmol, 1.0 equiv, TFA salt) and 2,2-dimethoxyethan amine (520 mg, 4.95 mmol, 539 μL, 1.2 equiv) in DCM (20 mL) was added DIEA (2.67 g, 20.6 mmol, 3.60 mL, 5.0 equiv) and HATU (2.35 g, 6.19 mmol, 1.5 equiv). The mixture was stirred at 25° C. for 1 h. The reaction mixture was concentrated in vacuo to give the crude product. The residue was purified by column chromatography ($SiO_2$, petroleum ether/ethyl acetate=10/1 to 1/1). Compound 2-(4-(4-chloro-3-fluorophenyl)-2,3,9-trimethyl-6H-thieno[3,2-f]

[1,2,4]triazolo[4,3-a][1,4]diazepin-6-yl)-N-(2,2-dimethoxyethyl) acetamide (2.0 g, 3.9 mmol, 95% yield) was obtained as a yellow solid.

Step 12: Preparation of 2-((4-(4-chloro-3-fluorophenyl)-2,3,9-trimethyl-6H-thieno[3,2-f][1,2,4]triazolo[4,3-a][1,4]diazepin-6-yl)methyl)oxazole. A mixture of 2-(4-(4-chloro-3-fluorophenyl)-2,3,9-trimethyl-6H-thieno[3,2-f][1,2,4]triazolo[4,3-a][1,4]diazepin-6-yl)-N-(2,2-dimethoxyethyl) acetamide (2.0 g, 3.9 mmol, 1.0 equiv) in Eaton's reagent (20 mL) was stirred at 100° C. for 12 h. The reaction mixture was added to ice/saturated aqueous $NaHCO_3$ (200 mL) by dropwise addition and the mixture was extracted with DCM (100 mL×3). The combined organic phase was washed with brine (100 mL), dried over anhydrous $Na_2SO_4$, filtered and concentrated in vacuo. The residue was purified by column chromatography ($SiO_2$, petroleum ether/ethyl acetate=10/1 to 0/1). Compound 2-((4-(4-chloro-3-fluorophenyl)-2,3,9-trimethyl-6H-thieno[3,2-f][1,2,4]triazolo[4,3-a][1,4]diazepin-6-yl)methyl)oxazole (0.5 g, 1.1 mmol, 28% yield) was obtained as a yellow solid.

Step 13: Preparation of tert-butyl 8-[2-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate. A solution of 2-((4-(4-chloro-3-fluoro phenyl)-2,3,9-trimethyl-6H-thieno[3,2-f][1,2,4]triazolo[4,3-a][1,4]diazepin-6-yl) methyl)oxazole (300 mg, 679 μmol, 1.0 equiv), tert-butyl 2,8-diazaspiro[4.5]decane-2-carboxylate (245 mg, 1.02 mmol, 1.5 equiv), SPhos Pd G3 (106 mg, 136 μmol, 0.20 equiv), and $Cs_2CO_3$ (664 mg, 2.04 mmol, 3.0 equiv) in dioxane (5.0 mL) was stirred at 90° C. for 4 h under $N_2$. The mixture was filtered and the filtrate was concentrated under reduced pressure to give a residue. The residue was purified by prep-HPLC (column: Phenomenex luna C18 150×25 mm×10 μm; mobile phase: [water (FA)-ACN]; gradient: 56%-86% B over 10 min) to give tert-butyl 8-[2-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6), 4,7,10,12-pentaen-7-yl]phenyl]-2,8-diazaspiro[4.5]decane-2-carboxylate (250 mg, 387 μmol, 57% yield) as a yellow solid.

Step 14: Preparation of tert-butyl 8-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate. tert-butyl 8-[2-fluoro-4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (260 mg, 301 μmol) was purified by SFC (column: DAICEL CHIRALPAK AS (250 mm×30 mm, 10 μm) ; mobile phase: [$CO_2$-EtOH (0.1% $NH_3$ in $H_2O$)]; B %: 45%, isocratic elution mode) to afford tert-butyl 8-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (130 mg, 201 μmol, 52% yield) as a yellow gum that was a single stereoisomer and tert-butyl 8-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (100 mg, 155 μmol, 40% yield) as a yellow gum that was a single stereoisomer.

Step 15: Preparation of 2-[[7-[4-(2,8-diazaspiro[4.5]decan-8-yl)-3-fluoro-phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 8-[2-fluoro-4-[4,5,13-trimethyl-9-(oxazol-2-yl methyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (100 mg, 155 μmol, 1.0 equiv) in DCM (2.0 mL) was added TFA (768 mg, 6.73 mmol, 0.50 mL, 43.5 equiv). The mixture was stirred at 25° C. for 1 h under $N_2$. The pH was adjusted with a saturated aqueous $NaHCO_3$ solution to neutral, then the mixture was extracted with methanol/dichloromethane (1/10) (60 mL×3). The organic phase was dried over anhydrous $Na_2SO_4$ and concentrated under vacuum to afford 2-[7-[4-(2,8-diaza spiro[4.5]decan-8-yl)-3-fluoro-phenyl]-4,5,13-trimethyl-3-thia-1,8,11,12-tetrazatricyclo[8.3.0.0$^{2,6}$]trideca-2 (6),4,7,10,12-pentaen-9-yl] methyl]oxazole (85.0 mg, crude) as a yellow gum.

Step 16: Preparation of N-[4-(4-cyano-3-methoxy-phenoxy)cyclohexyl]-6-[8-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide. To a solution of 2-[[7-[4-(2,8-diazaspiro[4.5]decan-8-yl)-3-fluoro-phenyl]-4,5,13-trimethyl-3-thia-1,8,11,12-tetrazatricyclo[8.3.0.0$^{2,6}$]trideca-2 (6),4,7,10,12-pentaen-9-yl] methyl]oxazole (42.0 mg, 77.0 μmol, 1.0 equiv) and 6-chloro-N-[4-(4-cyano-3-methoxy-phenoxy)cyclohexyl] pyridazine-3-carboxamide (29.8 mg, 77.0 μmol, 1.0 equiv) in NMP (0.75 mL) was added DIEA (99.5 mg, 769 μmol, 134 μL, 10.0 equiv). The mixture was stirred at 80° C. for 12 h under $N_2$. The reaction liquid was purified by prep-HPLC (column: Phenomenex luna C18 150×25 mm×10 μm; mobile phase: [water (FA)-ACN]; gradient: 50%-80% B over 10 min) to afford N-[4-(4-cyano-3-methoxy-phenoxy) cyclohexyl]-6-[8-[2-fluoro-4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenyl]-2,8-diazaspiro [4.5]decan-2-yl]pyridazine-3-carboxamide (23.1 mg, 25.8 μmol, 34% yield, 100% purity) as a white solid. $^1$H NMR (400 MHz, DMSO-$d_6$)$_{8=8.50}$ (br d, J=8.4 Hz, 1H), 8.04 (s, 1H), 7.82 (d, J=9.2 Hz, 1H), 7.61 (d, J=9.2 Hz, 1H), 7.18-7.01 (m, 4H), 6.97 (d, J=9.2 Hz, 1H), 6.76-6.62 (m, 2H), 4.63 (t, J=7.2 Hz, 1H), 4.49 (br s, 1H), 3.94-3.77 (m, 6H), 3.61 (br s, 2H), 3.46 (br s, 2H), 3.21-3.11 (m, 2H), 3.11-3.02 (m, 2H), 2.60 (s, 3H), 2.42 (s, 3H), 2.11 (br d, J=10.0 Hz, 2H), 2.00-1.86 (m, 4H), 1.72 (br s, 4H), 1.69 (s, 3H), 1.66-1.57 (m, 2H), 1.56-1.45 (m, 2H). LC-MS: MS (ES$^+$): RT=2.426 min, m/z=896.8 [M+H]$^+$; LCMS method: 10.

Example 54—Synthesis of N-[4-(4-cyano-3-methoxy-phenoxy)cyclohexyl]-6-[4,4-difluoro-8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decan-2-yl]pyridazine-3-carboxamide (I-107)
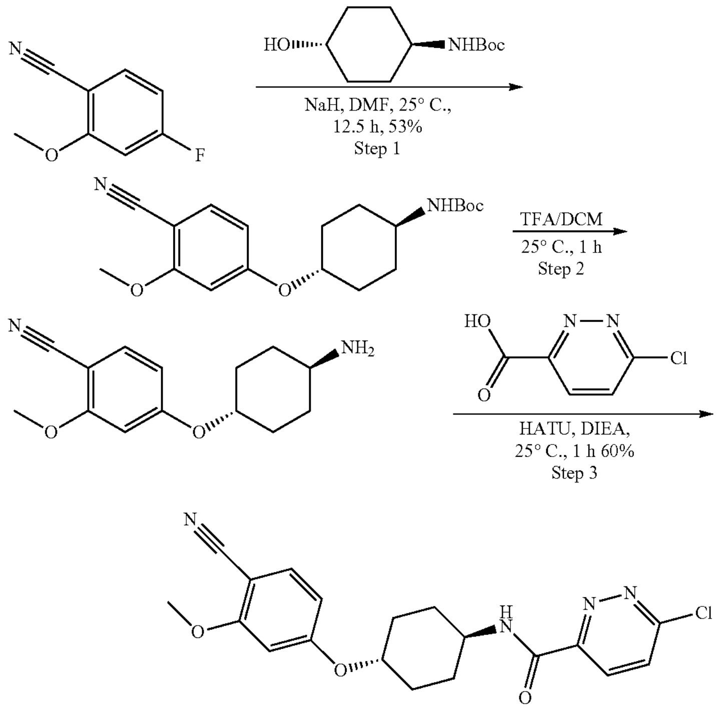
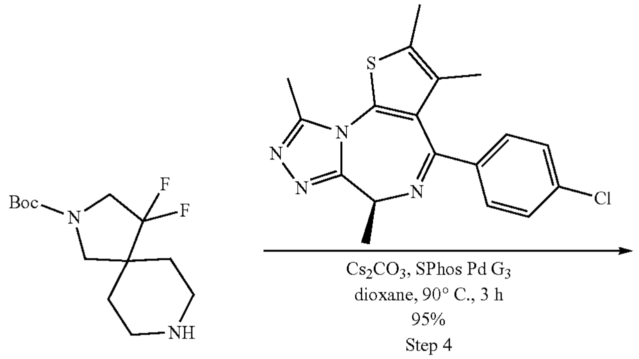
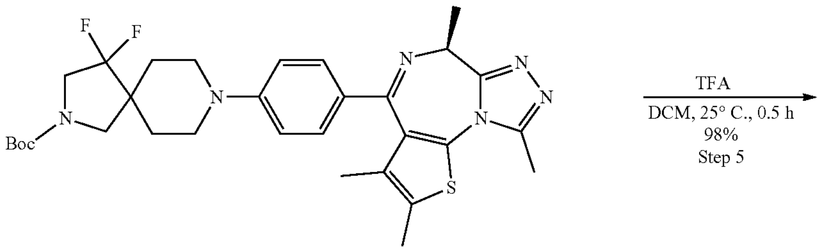

-continued

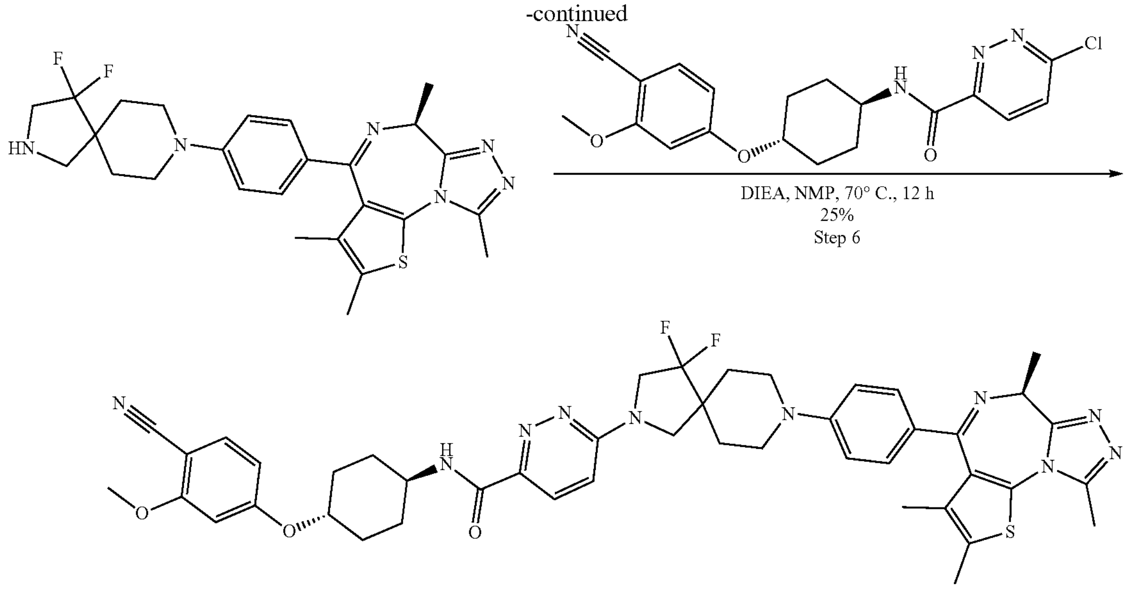

I-107

Step 1: Preparation of tert-butyl ((1r,4r)-4-(4-cyano-3-methoxyphenoxy) cyclohexyl) carbamate. To a solution of NaH (1.25 g, 31.21 mmol, 60% purity, 1.2 equiv) in DMF (60 mL) under $N_2$ atmosphere at 0° C. was added tert-butyl ((1r,4r)-4-hydroxycyclohexyl) carbamate (5.6 g, 26.01 mmol, 1.0 equiv). After 30 minutes, 4-fluoro-2-methoxy-benzonitrile (3.93 g, 26.01 mmol, 1.0 equiv) was added. The reaction mixture was slowly allowed to warm to 25° C. and then stirred for 12 h. The reaction mixture was quenched with a saturated aqueous $NH_4Cl$ (100 mL) solution at 0° C. The resulting mixture was extracted with ethyl acetate (100 mL×3). The combined organic layers were dried over anhydrous $Na_2SO_4$, filtered and concentrated in vacuum. The residue was purified by column chromatography ($SiO_2$, petroleum ether/ethyl acetate=0/1 to 3/1) to afford tert-butyl ((1r,4r)-4-(4-cyano-3-methoxy phenoxy)cyclohexyl) carbamate (4.8 g, 13.86 mmol, 53% yield) as a white solid.

Step 2: Preparation of 4-(((1r,4r)-4-aminocyclohexyl) oxy)-2-methoxy-benzo nitrile. To a solution of tert-butyl ((1r,4r)-4-(4-cyano-3-methoxyphenoxy)cyclohexyl) carbamate (0.5 g, 1.44 mmol, 1.0 equiv) in DCM (2 mL) was added TFA (1 mL). The mixture was stirred at 25° C. for 1 h. The reaction mixture was concentrated under reduced pressure to afford 4-(((1r,4r)-4-aminocyclohexyl)oxy)-2-methoxybenzonitrile (520 mg, 1.44 mmol, 99.99% yield, TFA salt) as a yellow oil.

Step 3: Preparation of 6-chloro-N-((1r,4r)-4-(4-cyano-3-methoxyphenoxy) cyclohexyl) pyridazine-3-carboxamide. To a solution of 4-(((1r,4r)-4-aminocyclohexyl)oxy)-2-methoxybenzonitrile (520 mg, 1.44 mmol, 1.0 equiv, TFA salt) and 6-chloropyridazine-3-carboxylic acid (229 mg, 1.44 mmol, 1.0 equiv) in DMF (2 mL) was added HATU (823 mg, 2.16 mmol, 1.5 equiv) and DIEA (560 mg, 4.33 mmol, 754 μL, 3.0 equiv). The mixture was stirred at 25° C. for 1 h. The reaction mixture was concentrated under reduced pressure to remove solvent. The residue was purified by prep-HPLC (column: Waters xbridge 150×25 mm 10 μm; mobile phase: [water ($NH_4HCO_3$)-ACN]; gradient: 49%-69% B over 8 min) to afford 6-chloro-N-((1r,4r) -4-(4-cyano-3-methoxyphenoxy)cyclohexyl) pyridazine-3-carboxamide (337 mg, 871 μmol, 60% yield) as a white solid.

Step 4: Preparation of tert-butyl 4,4-difluoro-8-[4-[(9S)-4,5,9,13-tetramethyl-3-thia-1,8,11,12-tetrazatricyclo [8.3.0.0$^{2,6}$]trideca-2 (6),4,7,10,12-pentaen-7-yl]phenyl]-2,8-diazaspiro[4.5]decane-2-carboxylate. To a solution of (9S)-7-(4-chlorophenyl)-4,5,9,13-tetra methyl-3-thia-1,8,11,12-tetrazatricyclo[8.3.0.0$^{2,6}$]trideca-2 (6),4,7,10,12-pentaene (200 mg, 560 μmol, 1.0 equiv) and tert-butyl 4,4-difluoro-2,8-diazaspiro[4.5]decane-2-carboxylate (263 mg, 952 μmol, 1.7 equiv) in dioxane (2 mL) was added $Cs_2CO_3$ (548 mg, 1.7 mmol, 3.0 equiv) and SPhos Pd G3 (43 mg, 56 μmol, 0.1 equiv). The mixture was stirred at 90° C. for 3 h under $N_2$ atmosphere. The mixture was diluted with water (10 mL) and extracted with ethyl acetate (3×20 mL). The combined organic layers were dried over anhydrous sodium sulfate, filtered and concentrated. The residue was purified by prep-TLC ($SiO_2$, petroleum ether:ethyl acetate=0:1) to give tert-butyl 4,4-difluoro-8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro[4.5]decane-2-carboxylate (320 mg, 95% yield) as a yellow oil.

Step 5: Preparation of (9S)-7-[4-(4,4-difluoro-2,8-diazaspiro[4.5]decan-8-yl)phenyl]-4,5,9,13-tetramethyl-3-thia-1,8,11,12-tetrazatricyclo[8.3.0.0$^{2,6}$]trideca-2 (6),4,7,10,12-pentaene. To a solution of tert-butyl 4,4-difluoro-8-[4-[(9S)-4,5,9,13-tetramethyl-3-thia-1,8,11,12-tetrazatricyclo [8.3.0.0$^{2,6}$]trideca-2 (6),4,7,10,12-pentaen-7-yl]phenyl]-2,8-diaza spiro[4.5]decane-2-carboxylate (390 mg, 653 μmol, 1.0 equiv) in DCM (3 mL) was added TFA (1 mL). The mixture was stirred at 25° C. for 0.5 h. The reaction mixture was concentrated under reduced pressure. The residue was diluted with a saturated aqueous solution of $NaHCO_3$ (5 mL) and extracted with DCM (20 mL×3). The combined organic layers were dried over $Na_2SO_4$, filtered and concentrated under reduced pressure to give (9S)-7-[4-(4,4-difluoro-2,8-diaza spiro[4.5]decan-8-yl)phenyl]-4,5,9,13-tetramethyl-3-thia-1,8,11,12-tetrazatricyclo[8.3.0.0$^{2,6}$]tri deca-2 (6),4,7,10,12-pentaene (320 mg, 98% yield) as a yellow solid.

Step 6: Preparation of N-[4-(4-cyano-3-methoxy-phenoxy)cyclohexyl]-6-[4,4-difluoro-8-[4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-2,8-diazaspiro [4.5]decan-2-yl]pyridazine-3-carboxamide (I-107). To a solution of (9S)-7-[4-(4,4-difluoro-2,8-diazaspiro[4.5]decan-8-yl)phenyl]-4,5,9,13-tetramethyl-3-thia-1,8,11,12-tetrazatricyclo[8.3.0.0$^{2,6}$]trideca-2 (6),4,7,10,12-pentaene (150 mg, 302 μmol, 1.0 equiv) in NMP (0.6 mL) was added DIEA (78 mg, 604 μmol, 105 μL, 2.0 equiv) and 6-chloro-N-[4-(4-cyano-3-methoxy-phenoxy)cyclohexyl]pyridazine-3-carboxamide (116 mg, 302 μmol, 1.0 equiv). The mixture was stirred at 70° C. for 12 h and concentrated. The residue was purified by prep-HPLC (column: Phenomenex luna C18 150×25 mm* 10 μm; mobile phase: [water (FA)-ACN]; gradient: 39%-69% B over 10 min) to give N-[4-(4-cyano-3-methoxy-phenoxy)cyclohexyl]-6-[4,4-difluoro-8-[4-[(9S)-4,5,9,13-tetramethyl-3-thia-1,8,11,12-tetrazatricyclo [8.3.0.0$^{2,6}$]trideca-2 (6),4,7,10,12-pentaen-7-yl]phenyl]-2,8-diaza spiro[4.5]decan-2-yl]pyridazine-3-carboxamide (I-107, 66 mg, 25% yield) as a yellow solid. 1H NMR (400 MHz, $CDCl_3$) δ 8.12-8.05 (m, 1H), 7.91-7.82 (m, 1H), 7.50-7.39 (m, 3H), 6.95-6.83 (m, 2H), 6.81-6.72 (m, 1H), 6.56-6.43 (m, 2H), 4.39-4.29 (m, 1H), 4.21-4.12 (m, 1H), 4.11-3.96 (m, 3H), 3.90 (s, 3H), 3.86-3.63 (m, 4H), 3.03-2.91 (m, 2H), 2.67 (s, 3H), 2.42 (s, 3H), 2.25-2.15 (m, 4H), 2.15-2.05 (m, 5H), 1.76 (s, 3H), 1.70-1.63 (m, 4H), 1.53-1.43 (m, 2H). LC-MS: MS ($ES^+$): RT=2.233 min, m/z=847.4 [$M+H^+$]; LCMS Method: 10.

Example 55—Synthesis of N-[(1r,3r)-3-(4-cyano-3-methoxy-phenoxy)-2,2,4,4-tetramethyl-cyclobutyl]-2-[2-[4-[(9S)-5-ethyl-13-methyl-9-(oxazol-2-ylmethyl)-3-thia-1,8,11,12-tetrazatricyclo[8.3.0.0$^{2,6}$] trideca-2 (6),4,7,10,12-pentaen-7-yl]phenoxy]-7-azaspiro[3.5]nonan-7-yl]pyrimidine-5-carboxamide (III-1)

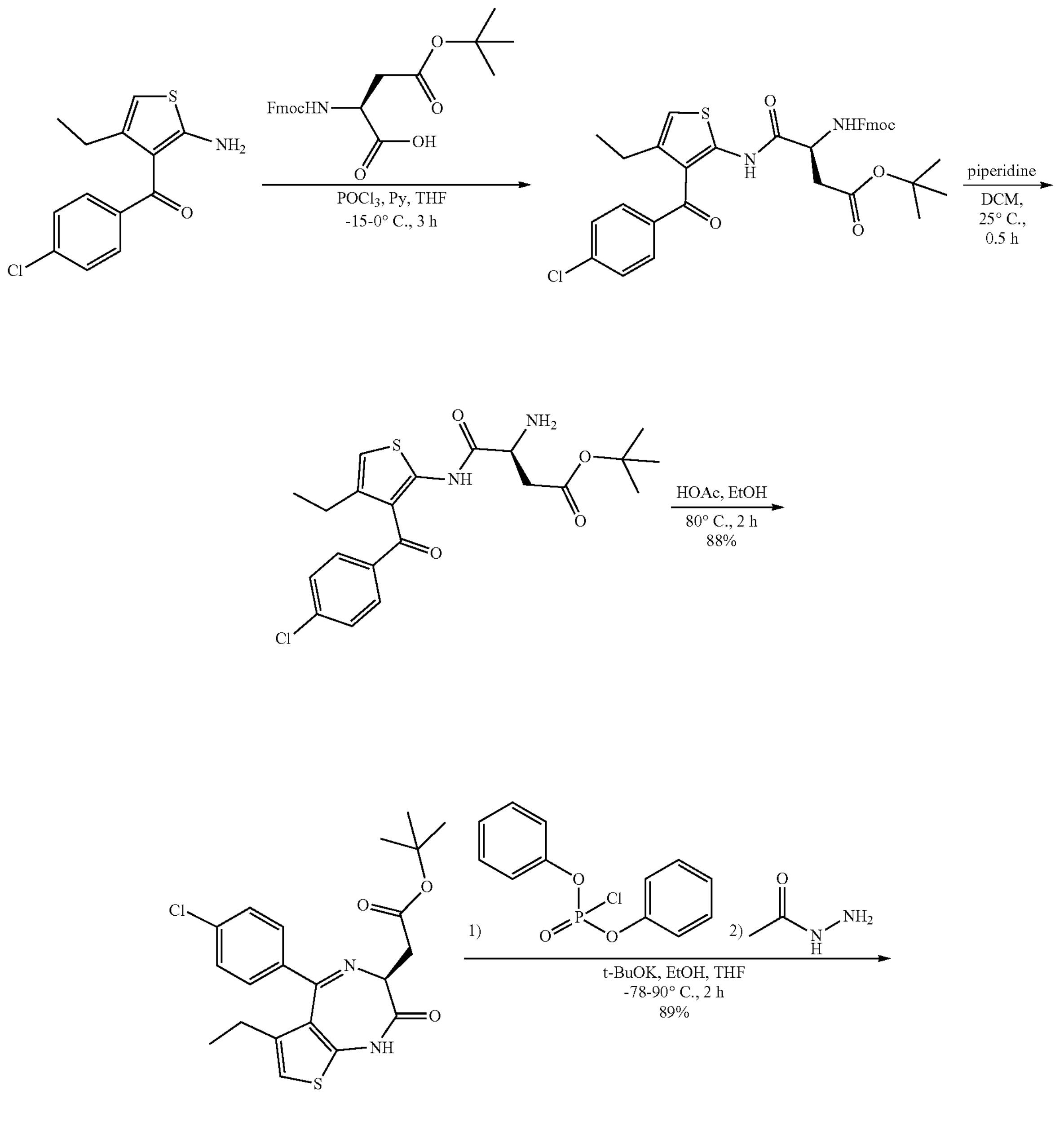

-continued
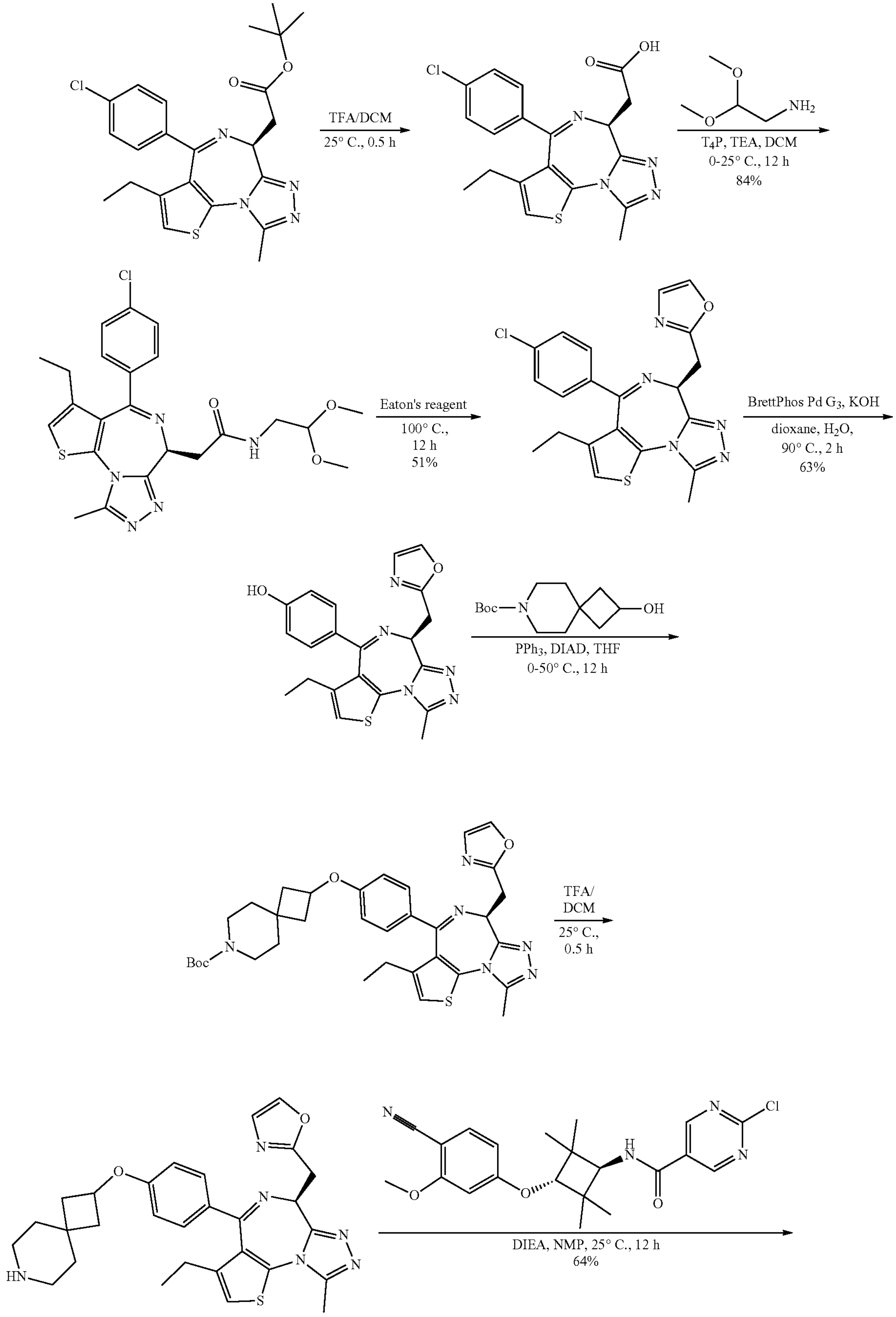

-continued

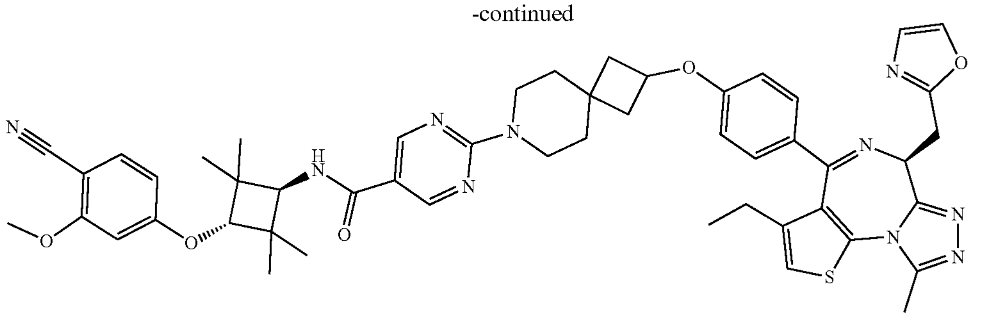

III-1

Step 1: Preparation of tert-butyl (3S)-4-[[3-(4-chlorobenzoyl)-4-ethyl-2-thienyl]amino]-3-(9H-fluoren-9-ylmethoxycarbonylamino)-4-oxo-butanoate. To a solution of (2-amino-4-ethyl-3-thienyl)-(4-chlorophenyl) methanone (4.72 g, 17.3 mmol, 1.0 equiv) in THF (40 mL) was added (2S)-4-tert-butoxy-2-(9H-fluoren-9-ylmethoxycarbonylamino)-4-oxo-butanoic acid (7.28 g, 17.6 mmol, 1.0 equiv) and pyridine (4.22 g, 53.1 mmol, 4.28 mL, 3.0 equiv), followed by $POCl_3$ (2.71 g, 17.6 mmol, 1.65 mL, 1.0 equiv) at −15° C. The mixture was stirred at 0° C. for 3 h. The mixture was concentrated, the residue was diluted with HCl (1 M, 150 mL), and the mixture was extracted with ethyl acetate (200 mL×3). The combined organic layers were washed with saturated sodium bicarbonate solution (200 mL), dried over sodium sulfate, filtered, and concentrated under reduced pressure to afford tert-butyl (3S)-4-[3-(4-chlorobenzoyl)-4-ethyl-2-thienyl]amino]-3-(9H-fluoren-9-ylmethoxycarbonylamino)-4-oxo-butanoate (11.6 g, 17.6 mmol, 100% yield) as a yellow solid.

Step 2: Preparation of tert-butyl (3S)-3-amino-4-[[3-(4-chlorobenzoyl)-4-ethyl-2-thienyl]amino]-4-oxo-butanoate. To a solution of tert-butyl (3S)-4-[[3-(4-chlorobenzoyl)-4-ethyl-2-thienyl]amino]-3-(9H-fluoren-9-ylmethoxycarbonylamino)-4-oxo-butanoate (11.6 g, 17.6 mmol, 1.0 equiv) in DCM (120 mL) was added piperidine (3.01 g, 35.8 mmol, 3.49 mL, 2.0 equiv). The mixture was stirred at 25° C. for 0.5 h. The reaction mixture was concentrated under reduced pressure to afford tert-butyl (3S)-3-amino-4-[3-(4-chlorobenzoyl)-4-ethyl-2-thienyl]amino]-4-oxo-butanoate (7.73 g, 17.6 mmol, 100% yield) as a colorless liquid.

Step 3: Preparation of tert-butyl 2-[(3S)-5-(4-chlorophenyl)-6-ethyl-2-oxo-1,3-dihydrothieno[2,3-e][1,4]diazepin-3-yl]acetate. To a solution of tert-butyl (3S)-3-amino-4-[[3-(4-chlorobenzoyl)-4-ethyl-2-thienyl]amino]-4-oxo-butanoate (7.73 g, 17.7 mmol, 1.0 equiv) in EtOH (50 mL) was added HOAc (5.25 g, 87.4 mmol, 5.55 mL, 4.9 equiv). The mixture was stirred at 80° C. for 2 h. The reaction mixture was concentrated under reduced pressure to remove solvent. The residue was made basic with aq. sodium bicarbonate solution (150 mL), and the mixture was extracted with ethyl acetate (100 mL×2). The combined organic layers were filtered and concentrated under reduced pressure to give a residue. The residue was purified by column chromatography ($SiO_2$, Petroleum ether/Ethyl acetate=22/1 to 3/1) to afford tert-butyl 2-[(3S)-5-(4-chlorophenyl)-6-ethyl-2-oxo-1,3-dihydrothieno[2,3-e][1,4]diazepin-3-yl]acetate (6.54 g, 15.5 mmol, 88% yield) as a yellow solid.

Step 4: Preparation of tert-butyl 2-[(9S)-7-(4-chlorophenyl)-5-ethyl-13-methyl-3-thia-1,8,11,12-tetrazatricyclo[8.3.0.$0^{2,6}$]trideca-2 (6),4,7,10,12-pentaen-9-yl]acetate. To a solution of tert-butyl 2-[(3S)-5-(4-chlorophenyl)-6-ethyl-2-oxo-1,3-dihydrothieno[2,3-e][1,4]diazepin-3-yl]acetate (7.21 g, 16.7 mmol, 1.0 equiv) in THF (70 mL) was added t-BuOK (1.0 M, 18 mL, 1.1 equiv) at −78° C. The reaction mixture was slowly warmed to 25° C. and stirred for 30 min. After cooling the mixture to −78° C., [chloro(phenoxy)phosphoryl]oxybenzene (5.39 g, 20.5 mmol, 4.16 mL, 1.2 equiv) was added to the reaction mixture, and the mixture was slowly warmed to 25° C. over 30 min. Acetohydrazide (1.97 g, 26.7 mmol, 1.6 equiv) and EtOH (35 mL) was added to reaction mixture, and it was stirred at 90° C. for 1 h. The reaction mixture was quenched by adding saturated $NH_4Cl$ solution (100 mL) at 0° C., and the mixture was diluted with $H_2O$ (200 mL) and extracted with ethyl acetate (250 mL×2). The combined organic layers were dried over $Na_2SO_4$, filtered, and concentrated under reduced pressure to give a residue. The residue was purified by column chromatography ($SiO_2$, Petroleum ether/Ethyl acetate=1/1 to 0/1) to afford tert-butyl 2-[(9S)-7-(4-chlorophenyl)-5-ethyl-13-methyl-3-thia-1,8,11,12-tetrazatricyclo[8.3.0.$0^{2,6}$]trideca-2 (6),4,7,10,12-pentaen-9-yl]acetate (6.82 g, 14.9 mmol, 89% yield) as a white solid.

Step 5: Preparation of 2-[(9S)-7-(4-chlorophenyl)-5-ethyl-13-methyl-3-thia-1,8,11,12-tetrazatricyclo[8.3.0.$0^{2,6}$]trideca-2 (6),4,7,10,12-pentaen-9-yl]acetic acid. To a solution of tert-butyl 2-[(9S)-7-(4-chlorophenyl)-5-ethyl-13-methyl-3-thia-1,8,11,12-tetrazatricyclo[8.3.0.$0^{2,6}$]trideca-2 (6),4,7,10,12-pentaen-9-yl]acetate (6.82 g, 14.8 mmol, 1.0 equiv) in DCM (40 mL) was added TFA (20 mL). The mixture was stirred at 25° C. for 0.5 h. The reaction mixture was concentrated under reduced pressure to afford 2-[(9S)-7-(4-chlorophenyl)-5-ethyl-13-methyl-3-thia-1,8,11,12-tetrazatricyclo[8.3.0.$0^{2,6}$]trideca-2 (6),4,7,10,12-pentaen-9-yl] acetic acid (7.66 g, 14.8 mmol, crude, TFA salt) as a yellow oil.

Step 6: Preparation of 2-[(9S)-7-(4-chlorophenyl)-5-ethyl-13-methyl-3-thia-1,8,11,12-tetrazatricyclo[8.3.0.$0^{2,6}$] trideca-2 (6),4,7,10,12-pentaen-9-yl]-N-(2,2-dimethoxyethyl) acetamide. To a solution of 2-[(9S)-7-(4-chlorophenyl)-5-ethyl-13-methyl-3-thia-1,8,11,12-tetrazatricyclo[8.3.0.$0^{2,6}$]trideca-2 (6),4,7,10,12-pentaen-9-yl]acetic acid (7.66 g, 14.8 mmol, 1.0 equiv, TFA salt), 2,2-dimethoxyethanamine (1.88 g, 17.8 mmol, 1.94 mL, 1.2 equiv) in DCM (40 mL) was added TEA (9.03 g, 89.6 mmol, 12.2 mL, 6.0 equiv) and T4P (16.1 g, 22.3 mmol, 50% purity, 1.5 equiv) at 0° C. The mixture was stirred at 25° C. for 12 h. The mixture was concentrated, and the residue was diluted with $H_2O$ (100 mL) and extracted with DCM (100 mL×2). The combined organic layers were filtered and concentrated under reduced pressure to give a residue. The residue was purified by column chromatography ($SiO_2$, Petroleum ether/Ethyl acetate=1/1 to 0/1) to afford 2-[(9S)-7-(4-chlorophenyl)-5-ethyl-13-methyl-3-thia-1,8,11,12-tetrazatricyclo[8.3.0.0$^{2,6}$]trideca-2 (6),4,7,10,12-pentaen-9-yl]-N-(2,2-dimethoxyethyl) acetamide (6.12 g, 12.5 mmol, 84% yield) as a yellow solid.

Step 7: Preparation of 2-[[(9S)-7-(4-chlorophenyl)-5-ethyl-13-methyl-3-thia-1,8,11,12-tetrazatricyclo[8.3.0.0$^{2,6}$]trideca-2 (6),4,7,10,12-pentaen-9-yl]methyl]oxazole. A solution of 2-[(9S)-7-(4-chlorophenyl)-5-ethyl-13-methyl-3-thia-1,8,11,12-tetrazatricyclo[8.3.0.0$^{2,6}$]trideca-2 (6),4,7,10,12-pentaen-9-yl]-N-(2,2-dimethoxyethyl) acetamide (6.11 g, 12.3 mmol, 1.0 equiv) in Eaton's reagent (90.9 g, 381 mmol, 60 mL, 31.0 equiv) was stirred at 100° C. for 12 h. The mixture was slowly poured into a mixture of $H_2O$ (3.5 L) and $NH_4OH$ (1 L) at 0° C., and the resulting mixture was extracted with ethyl acetate (200 mL×3). The combined organic layers were filtered and concentrated under reduced pressure to give a residue. The residue was purified by column chromatography ($SiO_2$, Petroleum ether/Ethyl acetate=1/1 to 0/1) to afford 2-[(9S)-7-(4-chlorophenyl)-5-ethyl-13-methyl-3-thia-1,8,11,12-tetrazatricyclo[8.3.0.0$^{2,6}$]trideca-2 (6),4,7,10,12-pentaen-9-yl]methyl]oxazole (2.65 g, 6.25 mmol, 51% yield) as a white solid.

Step 8: Preparation of 4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenol. To a solution of 2-[(9S)-7-(4-chlorophenyl)-5-ethyl-13-methyl-3-thia-1,8,11,12-tetrazatricyclo[8.3.0.0$^{2,6}$]trideca-2 (6),4,7,10,12-pentaen-9-yl]methyl]oxazole (2.55 g, 5.92 mmol, 1.0 equiv) in dioxane (20 mL) was added [2-(2-aminophenyl)phenyl]-methylsulfonyloxy-palladium; dicyclohexyl-[3,6-dimethoxy-2-(2,4,6-triisopropylphenyl)phenyl]phosphane (641 mg, 707 μmol, 0.1 equiv) and KOH (1.65 g, 29.4 mmol, 5.0 equiv) in $H_2O$ (4 mL). The mixture was stirred at 90° C. for 2 h. To the reaction mixture was added AcOH (4 mL), and the resulting mixture was concentrated under reduced pressure. The residue was purified by prep-HPLC (column: Phenomenex Synergi Max-RP 250*50 mm*10 μm; mobile phase: [water (FA)-ACN]; gradient: 1%-30% B over 20 min) to afford 4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenol (1.5 g, 3.7 mmol, 63% yield) as a yellow solid.

Step 9: Preparation of tert-butyl 2-[4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate. To a solution of $PPh_3$ (1.94 g, 7.42 mmol, 3.0 equiv) in THF (10 mL) was added DIAD (997 mg, 4.93 mmol, 956 μL, 2.0 equiv) at 0° C. The mixture was stirred at 25° C. for 0.5 h. The mixture was added to 4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenol (1.11 g, 2.47 mmol, 1.0 equiv) and tert-butyl 2-hydroxy-7-azaspiro[3.5]nonane-7-carboxylate (1.19 g, 4.93 mmol, 2.0 equiv) in THF (10 mL). The mixture was stirred at 50° C. for 11.5 h. The reaction mixture was concentrated under reduced pressure. The residue was purified by column chromatography ($SiO_2$, Petroleum ether/Ethyl acetate=1/1 to 0/1) to afford tert-butyl 2-[4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (1.55 g, 2.47 mmol, 100% yield) as a white solid.

Step 10: Preparation of 2-[[(9S)-7-[4-(7-azaspiro[3.5]nonan-2-yloxy)phenyl]-5-ethyl-13-methyl-3-thia-1,8,11,12-tetrazatricyclo[8.3.0.0$^{2,6}$]trideca-2 (6),4,7,10,12-pentaen-9-yl]methyl]oxazole. To a solution of tert-butyl 2-[4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (1.54 g, 2.45 mmol, 1.0 equiv) in DCM (20 mL) was added TFA (10 mL). The mixture was stirred at 25° C. for 0.5 h. The reaction mixture was concentrated under reduced pressure. The residue was made basic with aq. sodium bicarbonate solution and extracted with DCM/MeOH (10:1, 300 mL×2). The combined organic layers were filtered and concentrated under reduced pressure to afford 2-[(9S)-7-[4-(7-azaspiro[3.5]nonan-2-yloxy)phenyl]-5-ethyl-13-methyl-3-thia-1,8,11,12-tetrazatricyclo[8.3.0.0$^{2,6}$]trideca-2 (6),4,7,10,12-pentaen-9-yl]methyl]oxazole (1.29 g, 2.44 mmol, crude) as a yellow solid.

Step 11: Preparation of N-[(1r,3r)-3-(4-cyano-3-methoxy-phenoxy)-2,2,4,4-tetramethyl-cyclobutyl]-2-[2-[4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (III-1). To a solution of 2-[[(9S)-7-[4-(7-azaspiro[3.5]nonan-2-yloxy)phenyl]-5-ethyl-13-methyl-3-thia-1,8,11,12-tetrazatricyclo[8.3.0.0$^{2,6}$]trideca-2 (6),4,7,10,12-pentaen-9-yl]methyl]oxazole (1.28 g, 2.44 mmol, 1.0 equiv) and 2-chloro-N-[(1r,3r)-3-(4-cyano-3-methoxy-phenoxy)-2,2,4,4-tetramethyl-cyclobutyl]pyrimidine-5-carboxamide (1.21 g, 2.92 mmol, 1.2 equiv) in NMP (5 mL) was added DIEA (629 mg, 4.87 mmol, 848 μL, 2.0 equiv). The mixture was stirred at 25° C. for 12 h. The reaction mixture was concentrated under reduced pressure. The residue was purified by prep-HPLC (column: Waters Xbridge BEH C18 250*50 mm*10 μm; mobile phase: [water ($NH_4HCO_3$)-ACN]; gradient: 60%-90% B over 20 min) to afford N-[(1r,3r)-3-(4-cyano-3-methoxy-phenoxy)-2,2,4,4-tetramethyl-cyclobutyl]-2-[2-[4-[(9S)-5-ethyl-13-methyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (1.44 g, 1.57 mmol, 64% yield) as a white solid. 1H NMR (400 MHz, $CD_3OD$) & 8.72 (s, 2H), 7.89 (s, 1H), 7.52 (d, J=8.56 Hz, 1H), 7.27-7.42 (m, 3H), 7.12 (s, 1H), 6.83 (d, J=8.68 Hz, 2H), 6.62 (s, 1H), 6.55 (dd, J=8.68, 1.83 Hz, 1H), 4.77-4.84 (m, 1H), 4.70-4.76 (m, 1H), 4.24 (s, 1H), 4.12 (s, 1H), 3.88-4.02 (m, 7H), 3.81-3.87 (m, 2H), 2.73 (s, 3H), 2.48-2.58 (m, 2H), 2.21-2.32 (m, 1H), 2.02-2.12 (m, 1H), 1.97 (dd, J=12.78, 6.17 Hz, 2H), 1.66-1.71 (m, 4H), 1.28 (s, 6H), 1.22 (s, 6H), 0.97-1.01 (m, 3H). LC-MS: MS ($ES^+$): RT=2.750 min, m/z=907.6 [$M+H^+$]; LC-MS Method 25.

Example 56—Synthesis of N-[(1r,3r)-3-(4-cyano-3-methoxy-phenoxy)-2,2,4,4-tetramethyl-cyclobutyl]-2-[2-[4-[(9S)-4-(hydroxymethyl)-5,13-dimethyl-9-(oxazol-2-ylmethyl)-3-thia-1,8,11,12-tetrazatricyclo [8.3.0.0$^{2,6}$]trideca-2 (6),4,7,10,12-pentaen-7-yl] phenoxy]-7-azaspiro[3.5]nonan-7-yl]pyrimidine-5-carboxamide (III-2)
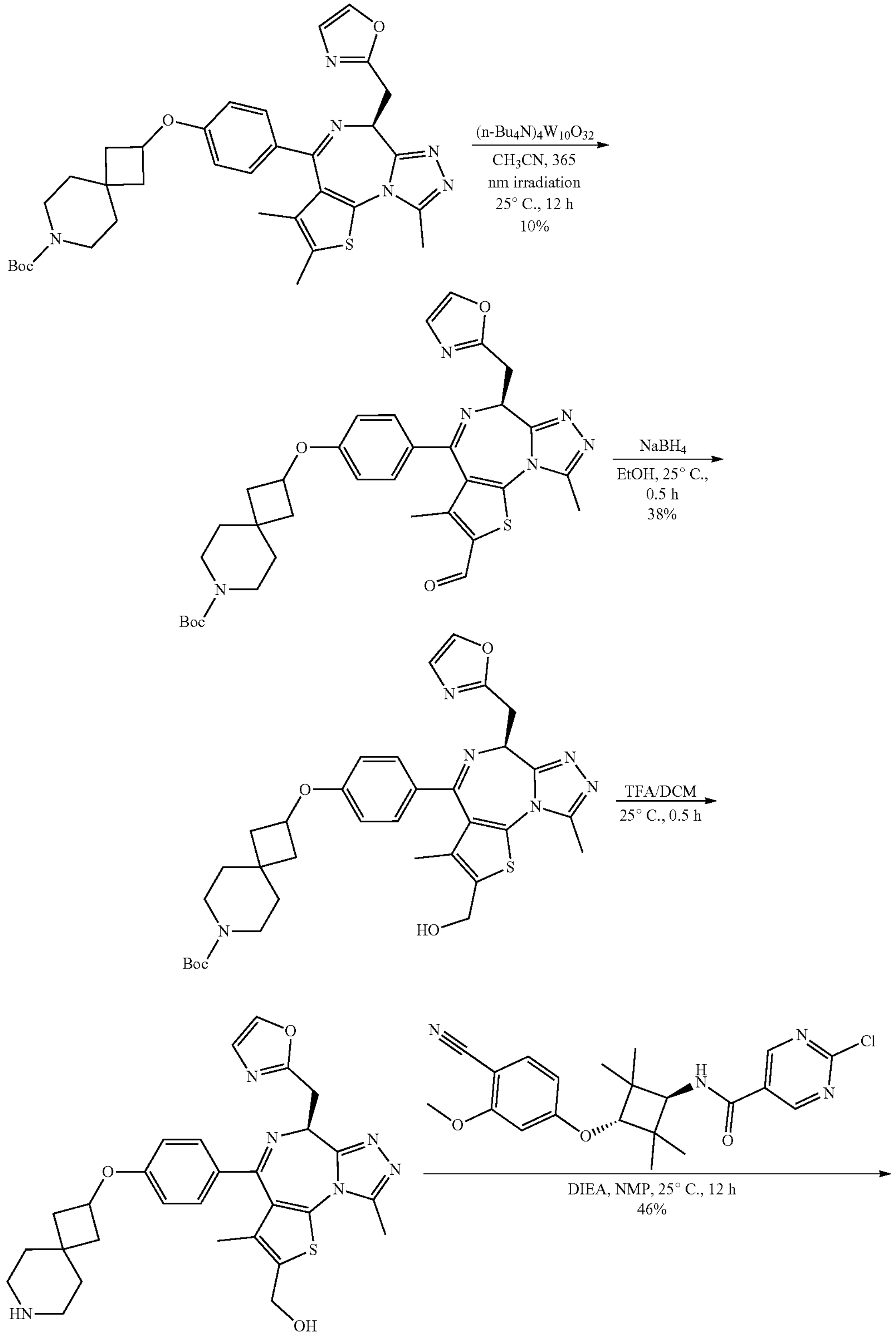

-continued

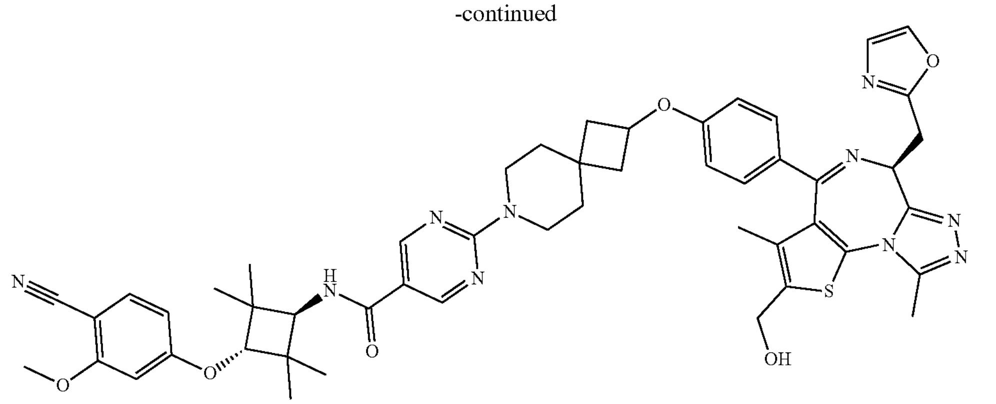

III-2

Step 1: Preparation of tert-butyl 2-[4-[(9S)-4-formyl-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate. To a 15-mL vial equipped with a stir bar was added tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (760 mg, 1.21 mmol, 1.0 equiv) in ACN (3 mL) and then $(n\text{-}Bu_4N)_4W_{10}O_{32}$ (803 mg, 242 μmol, 0.2 equiv). The mixture was stirred for 4 h and irradiated with a 365 nm LED lamp (7 cm away) with a cooling fan to keep the reaction temperature at 25° C. The mixture was filtered and concentrated. To the residue was added $(n\text{-}Bu_4N)_4W_{10}O_{32}$ (80.3 mg, 24.2 μmol, 0.02 equiv) and acetonitrile (3 mL), and the mixture was stirred for 4 h and irradiated with a 365 nm LED lamp (7 cm away) with a cooling fan to keep the reaction temperature at 25° C. The mixture was filtered, concentrated, and re-subjected the same way one additional time. The mixture was filtered and concentrated to give a residue. The residue was purified by prep-HPLC (column: Phenomenex luna C18 150×40 mm×15 μm; mobile phase: [water (FA)-ACN]; gradient: 58%-88% B over 10 min) to afford tert-butyl 2-[4-[(9S)-4-formyl-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (75 mg, 117 μmol, 10% yield) as a white solid.

Step 2: Preparation of tert-butyl 2-[4-[(9S)-4-(hydroxymethyl)-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate. To a solution tert-butyl 2-[4-[(9S)-4-formyl-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (200 mg, 311 μmol, 1.0 equiv) in EtOH (1 mL) was added $NaBH_4$ (23.3 mg, 618 μmol, 2.0 equiv). The mixture was stirred at 25° C. for 0.5 h. The mixture was quenched by $H_2O$ (20 mL). The mixture was extracted with DCM/MeOH (10:1, 20 mL×2), and the combined organic layers were concentrated to give a residue. The residue was purified by prep-TLC (DCM:MeOH=8:1) to afford tert-butyl 2-[4-[(9S)-4-(hydroxymethyl)-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (75.2 mg, 117 μmol, 38% yield) as a yellow foam.

Step 3: Preparation of [(9S)-7-[4-(7-azaspiro[3.5]nonan-2-yloxy)phenyl]-5,13-dimethyl-9-(oxazol-2-ylmethyl)-3-thia-1,8,11,12-tetraza-tricyclo[8.3.0.0$^{2,6}$]trideca-2 (6),4,7,10,12-pentaen-4-yl]methanol. To a solution tert-butyl 2-[4-[(9S)-4-(hydroxymethyl)-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (75.2 mg, 117 μmol, 1.0 equiv) in DCM (2 mL) was added TFA (1.0 mL). The mixture was stirred at 25° C. for 0.5 h. The mixture was quenched with aq. $NaHCO_3$ (10 mL), and the resulting mixture was extracted with DCM/MeOH (10:1, 10 mL×2). The combined organic layers were dried over $Na_2SO_4$, filtered, and concentrated to afford [(9S)-7-[4-(7-azaspiro[3.5]nonan-2-yloxy)phenyl]-5,13-dimethyl-9-(oxazol-2-ylmethyl)-3-thia-1,8,11,12-tetraza-tricyclo[8.3.0.0$^{2,6}$]trideca-2 (6), 4,7,10,12-pentaen-4-yl]methanol (63.6 mg, 116.70 μmol, 100% yield) as a white solid.

Step 4: Preparation of N-[(1r,3r)-3-(4-cyano-3-methoxy-phenoxy)-2,2,4,4-tetramethyl-cyclobutyl]-2-[2-[4-[(9S)-4-(hydroxymethyl)-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (III-2). To a solution of [(9S)-7-[4-(7-azaspiro[3.5]nonan-2-yloxy)phenyl]-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-4-yl]methanol (63.6 mg, 117 μmol, 1.0 equiv) and 2-chloro-N-[(1r,3r)-3-(4-cyano-3-methoxy-phenoxy)-2,2,4,4-tetramethyl-cyclobutyl]pyrimidine-5-carboxamide (48.4 mg, 116.7 μmol, 1.0 equiv) in NMP (2 mL) was added DIEA (45.3 mg, 350 μmol, 61.0 μL, 3.0 equiv). The reaction mixture was stirred at 25° C. for 12 h. The residue was purified by prep-HPLC (column: Phenomenex luna C18 150×25 mm×10 μm; mobile phase: [water (FA)-ACN]; gradient: 53%-83% B over 10 min) to afford N-[(1r,3r)-3-(4-cyano-3-methoxy-phenoxy)-2,2,4,4-tetramethyl-cyclobutyl]-2-[2-[4-[(9S)-4-(hydroxymethyl)-5,13-dimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (50 mg, 54.17 μmol, 46% yield) as a white solid. $^1$H NMR (400 MHz, $CD_3OD$ δ 8.72 (s, 2H), 7.89 (s, 1H), 7.52 (d, J=8.6 Hz, 1H), 7.36-7.29 (m, 2H), 7.12 (s, 1H), 6.85-6.80 (m, 2H), 6.62 (d, J=2.1 Hz, 1H), 6.57-6.53 (m, 1H), 4.81-4.71 (m, 4H), 4.24 (s, 1H), 4.17-4.08 (m, 1H), 4.03-3.82 (m, 9H), 2.72 (s, 3H), 2.58-2.46 (m, 2H), 2.03-1.89 (m, 2H), 1.74 (s, 3H), 1.73-1.64 (m, 4H), 1.28 (s, 6H), 1.22 (s, 6H). LC-MS: MS (ES$^+$): RT=2.45 min, m/z=923.6 [M+H$^+$]; LC-MS Method 10.

Example 57—Synthesis of N-[(1r,3s)-3-(4-cyano-3-methoxy-phenoxy)-2,2,4,4-tetramethyl-cyclobutyl]-2-[2-[4-[4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5] nonan-7-yl]pyrimidine-5-carboxamide (III-3)

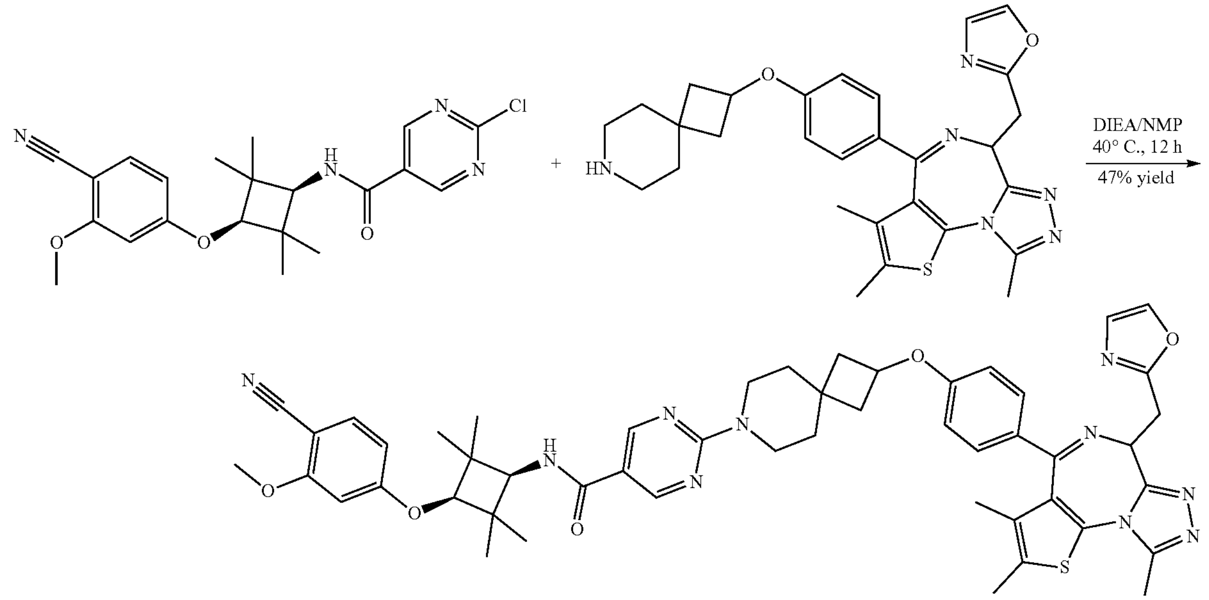

III-3

Starting materials were prepared by analogy to the procedures described herein. To a solution of 2-chloro-N-[(1r, 3s)-3-(4-cyano-3-methoxy-phenoxy)-2,2,4,4-tetramethyl-cyclobutyl]pyrimidine-5-carboxamide (540 mg, 1.04 mmol, 1.0 equiv) and 2-[7-[4-(7-azaspiro[3.5]nonan-2-yloxy)phenyl]-4,5,13-trimethyl-3-thia-1,8,11,12-tetrazatricyclo [8.3.0.0$^{2,6}$]trideca-2 (6),4,7,10,12-pentaen-9-yl]methyl]oxazole (550 mg, 1.04 mmol, 1.0 equiv) in NMP (5.0 mL) was added DIEA (269 mg, 2.08 mmol, 362 μL, 2.0 equiv). The mixture was stirred at 40° C. for 12 h. To the reaction mixture was added water (30 mL), and the mixture was extracted with ethyl acetate (50 mL×3). The combined organic phase was washed with brine (30 mL), dried over anhydrous $Na_2SO_4$, filtered, and concentrated in vacuo. The residue was purified by prep-HPLC (column: Waters Xbridge C18 150*50 mm*10 μm; mobile phase: [water ($NH_4HCO_3$)-ACN]; gradient: 57%-87% B over 10 min) to afford N-[(1r,3s)-3-(4-cyano-3-methoxy-phenoxy)-2,2,4,4-tetramethyl-cyclobutyl]-2-[2-[4-[4,5,13-trimethyl-9-(oxazol-2-ylmethyl)-3-thia-1,8,11,12-tetrazatricyclo[8.3.0.0$^{2,6}$] trideca-2 (6),4,7,10,12-pentaen-7-yl]phenoxy]-7-azaspiro [3.5]nonan-7-yl]pyrimidine-5-carboxamide (450 mg, 47% yield) as a white solid. $^1$H NMR (400 MHz, $CDCl_3$): δ=8.70 (s, 2H), 7.64 (s, 1H), 7.47-7.45 (m, 1H), 7.36-7.34 (m, 2H), 7.05 (s, 1H), 6.76-6.74 (m, 2H), 6.54-6.38 (m, 2H), 5.94-5.92 (m, 1H), 4.82-4.63 (m, 2H), 4.16-4.04 (m, 3H), 4.00-3.98 (m, 1H), 3.92 (s, 3H), 3.89 (s, 2H), 3.83-3.82 (m, 2H), 2.68 (s, 3H), 2.53-2.44 (m, 2H), 2.41 (s, 3H), 2.05-1.98 (m, 2H), 1.95-1.78 (m, 3H), 1.71 (s, 4H), 1.41 (s, 6H), 1.09 (s, 6H). LC-MS: MS (ES$^+$): RT=2.704 min, m/z=907.0 [M+H$^+$]; LC-MS Method 5-95.

Example 58—Synthesis of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$] trideca-2 (6),4,7,10,12-pentaen-7-yl]phenoxy]-7-azaspiro[3.5]nonan-7-yl]pyrimidine-5-carboxamide Crystal Form A (II-5 in Crystal Form

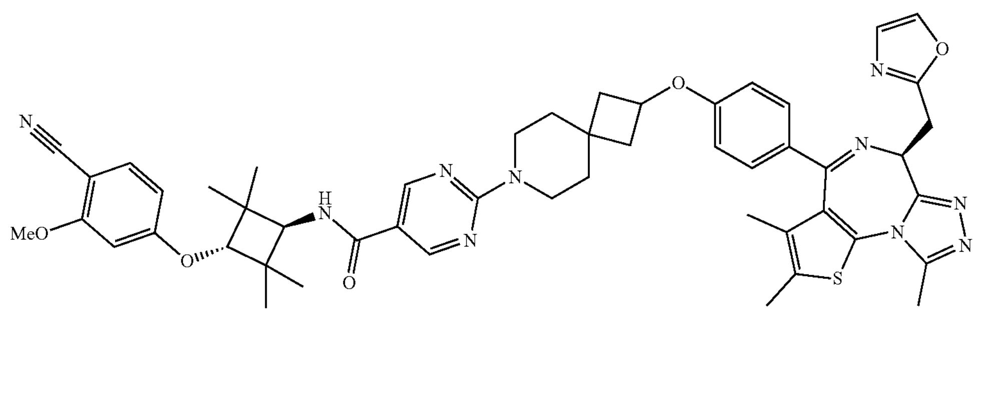 [SMILES: COc1cc(O[C@H]2C(C)(C)[C@H](NC(=O)c3cnc(N4CCC5(CC4)CC(Oc4ccc(C6=N[C@@H](Cc7ncco7)c7nnc(C)n7-c7sc(C)c(C)c76)cc4)C5)nc3)C2(C)C)ccc1C#N]

Part 1—Preparation of 2-[[(9S)-7-[4-(7-Azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole

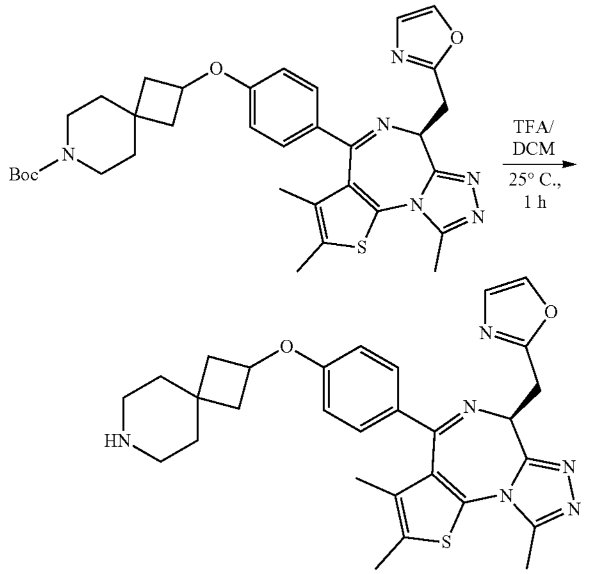

To a solution of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonane-7-carboxylate (22.5 g, 35.78 mmol, 1.0 equiv) in DCM (50 mL) was added TFA (31 mL). The mixture was stirred at 25° C. for 1 h. The reaction mixture was quenched by addition of $NaHCO_3$ (300 mL) at 0° C. The aqueous layer was washed with (DCM/MeOH=10:1; 300 mL×3), and then the combined organic layers were dried over $Na_2SO_4$, filtered, and concentrated under reduced pressure to afford 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (18.5 g, 35.0 mmol, 98% yield) as a yellow solid. LC-MS: MS (ES$^+$): RT=0.686 min, m/z=529.3 [M+H$^+$].

Part 2—Preparation of tert-Butyl N-[(1r,3r)-3-(4-Cyano-3-methoxy-phenoxy)-2,2,4,4-tetramethyl-cyclobutyl]carbamate

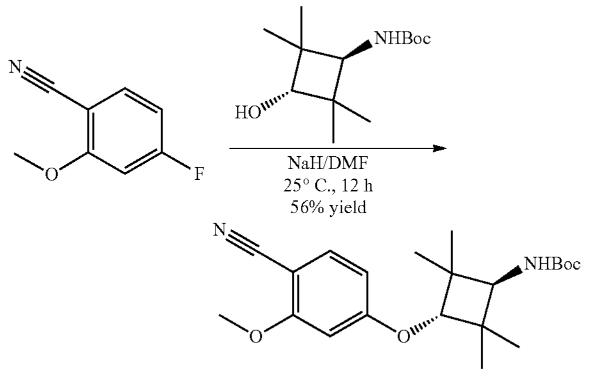

To a solution of tert-butyl N-((1r,3r)-3-hydroxy-2,2,4,4-tetramethyl-cyclobutyl) carbamate (65.0 g, 267 mmol, 1.0 equiv) in DMF (1 L) was added NaH (10.7 g, 267 mmol, 60% purity, 1.0 equiv) at 0° C. The reaction mixture was stirred at 0° C. for 0.5 h. Then 4-fluoro-2-methoxy-benzonitrile (40.4 g, 267 mmol, 1.0 equiv) was added. The reaction mixture was stirred at 25° C. for 12 h. The reaction mixture was quenched with saturated aqueous $NH_4Cl$ (20 mL) solution at 0° C. and diluted with water (5 L). The mixture was extracted with ethyl acetate (1 L×3). The combined organic layers were combined, washed with brine (1 L), dried over anhydrous $Na_2SO_4$, filtered, and concentrated in vacuum. The resulting residue was recrystallized from EtOH (1 L), and the resulting solid was filtered. The filter cake was dried to afford tert-butyl N-[(1r,3r)-3-(4-cyano-3-methoxy-phenoxy)-2,2,4,4-tetramethyl-cyclobutyl]carbamate (56.5 g, 151 mmol, 56% yield) as a white solid. LC-MS: MS (ES$^+$): RT=0.966 min, m/z=375.3 [M+H$^+$].

Part 3—Preparation of 4-((1r,3r)-3-Amino-2,2,4,4-tetramethyl-cyclobutoxy)-2-methoxy-benzonitrile

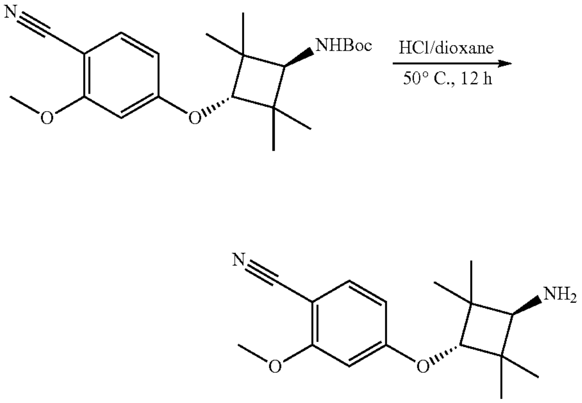

To a solution of tert-butyl N-[(1r,3r)-3-(4-cyano-3-methoxy-phenoxy)-2,2,4,4-tetramethyl-cyclobutyl]carbamate (50 g, 133.52 mmol, 1 equiv) in dioxane (125 mL) was added HCl/dioxane (4 M, 125 mL, 3.74 equiv). The mixture was stirred at 50° C. for 12 h. The reaction mixture was concentrated under reduced pressure to afford crude product 4-((1r,3r)-3-amino-2,2,4,4-tetramethyl-cyclobutoxy)-2-methoxy-benzonitrile (41.5 g, 134 mmol, 100% yield, HCl salt) as a white solid and it was used in the next step without further purification. LC-MS: MS (ES$^+$): RT=0.492 min, m/z=275.2 [M+H$^+$].

Part 4—Preparation of 2-Chloropyrimidine-5-carbonyl Chloride

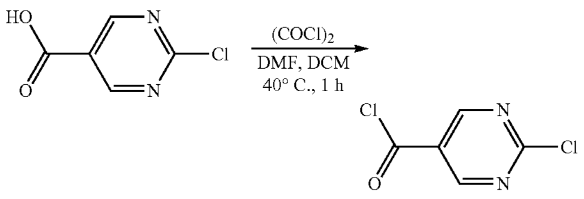

To a solution of 2-chloropyrimidine-5-carboxylic acid (32.0 g, 202 mmol, 1.0 equiv) in DCM (240 mL) was added oxalyl dichloride (76.9 g, 606 mmol, 53.0 mL, 3.0 equiv) and DMF (738 mg, 10.1 mmol, 776 μL, 0.1 equiv). The mixture was stirred at 40° C. for 1 h. The reaction mixture was concentrated under reduced pressure to afford 2-chloropyrimidine-5-carbonyl chloride (35.7 g, 202 mmol, 99.94% yield) as a yellow oil, which was used in the next step without further purification.

Part 5—Preparation of 2-Chloro-N-[(1r,3r)-3-(4-cyano-3-methoxy-phenoxy)-2,2,4,4-tetramethyl-cyclobutyl]pyrimidine-5-carboxamide

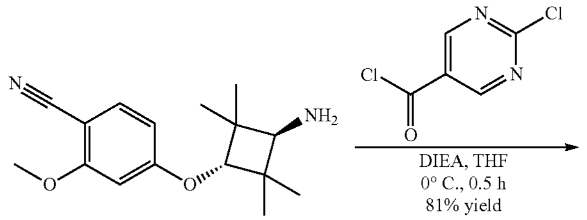

-continued

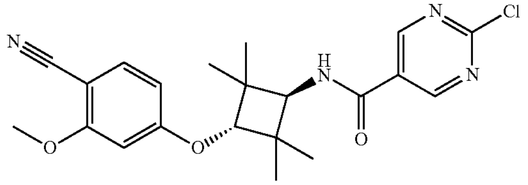

To a solution of 4-((1r,3r)-3-amino-2,2,4,4-tetramethyl-cyclobutoxy)-2-methoxy-benzonitrile (41.5 g, 134 mmol, 1.0 equiv, HCl salt) in THF (215 mL) was added DIEA (86.3 g, 668 mmol, 116 mL, 5.0 equiv), followed by 2-chloropyrimidine-5-carbonyl chloride (35.5 g, 200 mmol, 1.5 equiv) in THF (215 mL) at 0° C. The mixture was stirred at 0° C. for 0.5 h. The mixture was poured into ice water (2 L), and then extracted with EA (2 L×3). The combined organic layers were washed with brine (2 L), dried, filtered, and concentrated under reduced pressure to give a residue. The crude product was triturated with EA (500 mL) at 25° C. for 12 min to afford 2-chloro-N-[(1r,3r)-3-(4-cyano-3-methoxy-phenoxy)-2,2,4,4-tetramethyl-cyclobutyl]pyrimidine-5-carboxamide (45.0 g, 108 mmol, 81% yield) as a yellow solid.

Part 6—Preparation of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (II-5)

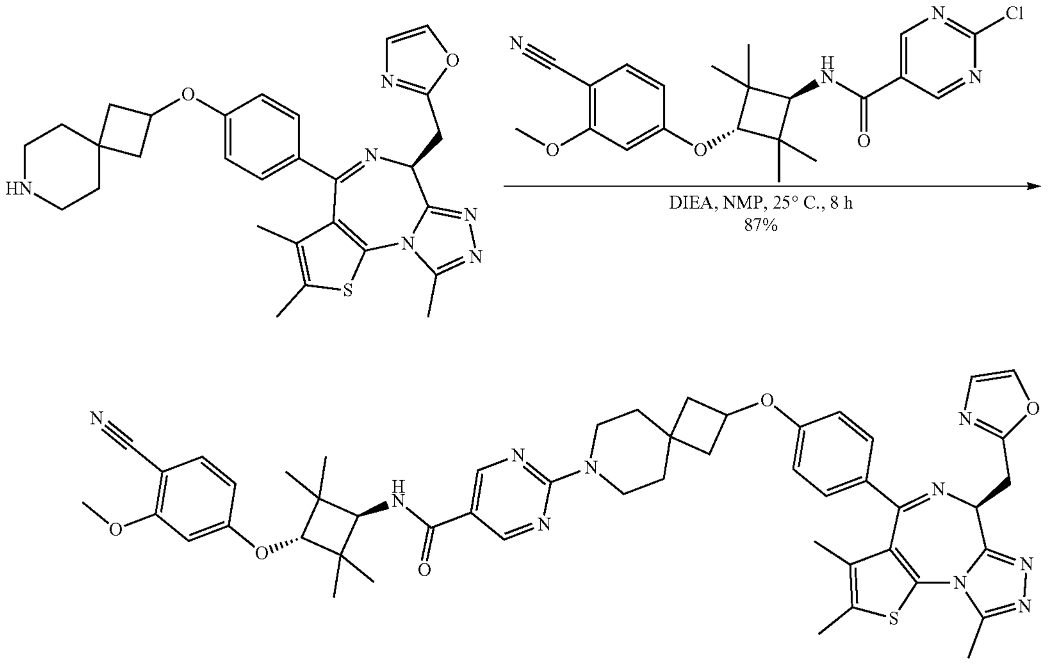

II-5

To a solution of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2 (6),4,7,10,12-pentaen-9-yl]methyl]oxazole (13.0 g, 24.6 mmol, 1.0 equiv) and 2-chloro-N-[(1r,3r)-3-(4-cyano-3-methoxy-phenoxy)-2,2,4,4-tetramethyl-cyclobutyl]pyrimidine-5-carboxamide (10.7 g, 25.8 mmol, 1.1 equiv) in NMP (30 mL) was added DIEA (9.53 g, 73.8 mmol, 12.9 mL, 3.0 equiv). The mixture was stirred at 25° C. for 8 h. The reaction mixture was diluted with DCM/MeOH (10:1, 300 mL) and washed with $H_2O$ (100 mL×3). The organic phase was dried and concentrated. The crude product was purified by column chromatography ($SiO_2$, $R_f$=0.4, EA/MeOH=10/1) to afford N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (19.5 g, 21.2 mmol, 87% yield, 98.5% purity) as a white solid. 1H NMR (400 MHz, $CD_3OD$) δ 8.74 (s, 2H), 7.91 (d, J=0.8 Hz, 1H), 7.54 (d, J=8.6 Hz, 1H), 7.34 (d, J=8.8 Hz, 2H), 7.14 (d, J=0.8 Hz, 1H), 6.85 (d, J=8.9 Hz, 2H), 6.64 (d, J=2.1 Hz, 1H), 6.57 (dd, J=2.1, 8.6 Hz, 1H), 4.79-4.71 (m, 2H), 4.27-4.25 (m, 1H), 4.16-4.12 (m, 1H), 3.95 (s, 7H), 3.90-3.83 (m, 2H), 2.72 (s, 3H), 2.61-2.50 (m, 2H), 2.48 (s, 3H), 2.03-1.92 (m, 2H), 1.72 (s, 7H), 1.30 (s, 6H), 1.24 (s, 6H). LC-MS: MS ($ES^+$): RT=2.698 min, m/z=907.4 [$M+H^+$].

Part 7—Preparation of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form A (II-5 in Crystal Form A)

To N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide (90.0 g, 99.2 mmol) was added $CH_3CN$ (450 mL), and then it was refluxed for 1 h until the reaction mixture turned clear. The mixture was slowly cooled to 25° C., and a white precipitate formed. After filtering, the filter cake was washed with $CH_3CN$ (50 mL×2) and dried to afford N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo [8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form A (77.0 g, 84.9 mmol, 86% yield, 99.7% purity) as a white crystalline solid. The filtrate was concentrated to afford a light brown foam (13.0 g, 13.5 mmol, 14% yield, 94% purity). LC-MS: MS ($ES^+$): RT=0.667 min, m/z=907.5 [$M+H^+$]. $^1H$ NMR (400 MHz, $CD_3OD$) δ 8.75-8.70 (m, 2H), 7.92-7.89 (m, 1H), 7.53 (d, J=8.6 Hz, 1H), 7.32 (d, J=8.7 Hz, 2H), 7.13 (s, 1H), 6.84 (d, J=8.8 Hz, 2H), 6.63 (d, J=2.2 Hz, 1H), 6.56 (dd, J=2.1, 8.6 Hz, 1H), 4.84-4.81 (m, 1H), 4.77-4.71 (m, 1H), 4.25 (s, 1H), 4.13 (s, 1H), 3.99-3.89 (m, 7H), 3.88-3.82 (m, 2H), 2.71 (s, 3H), 2.58-2.50 (m, 2H), 2.46 (s, 3H), 2.02-1.93 (m, 2H), 1.74-1.66 (m, 7H), 1.28 (s, 6H), 1.23 (s, 6H).

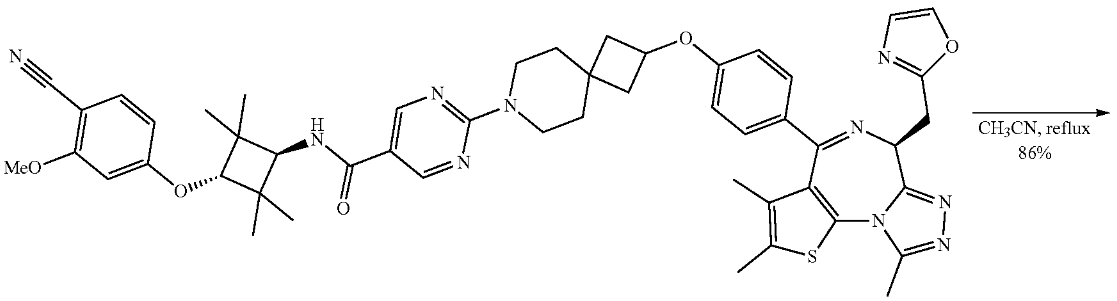

II-5

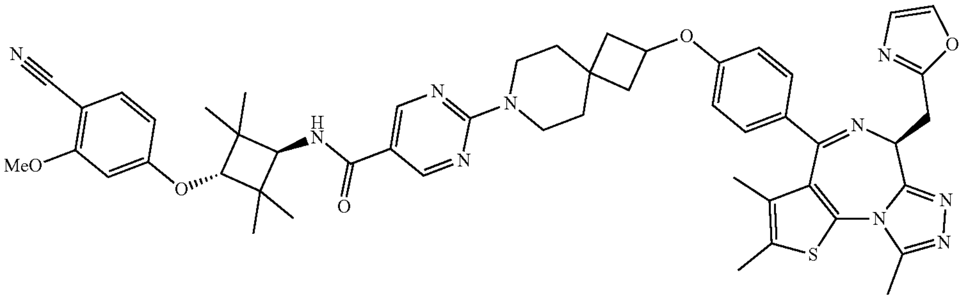

II-5 in Crystal Form A

Example 59—Physical Characterization of N-[(1r,3r)-3-(4-Cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form A (II-5 in Crystal Form A)

X-ray powder diffraction was performed using a LYNXEYE_XE_T detector operated in reflection mode. Samples were prepared on monocrystalline silicon, flat surface sample holders. Parameters for XRPD were:

| Parameter | Value |
|---|---|
| Open angle | 2.5° (max) |
| X-ray wavelength | Cu Kα1, 1.5406 Å |
| X-ray tube setting | 40 kV, 40 mA |
| Primary Beam Slit | 10.0 mm by sample length + 2.5° soller |
| Secondary Beam Slit | 2.5° soller |
| Scan mode | Continuous |
| Scan type | Locked coupled |
| Scan range (°2θ) | 3-40 |
| Step size (°2θ) | 0.02 |
| Dwell time (s/step) | 0.4 |
| Spin | Yes (15 rpm). |

An X-ray powder diffractogram taken on the title compound is provided in FIG. 14. Tabulated characteristics of the X-ray powder diffractogram in FIG. 14 are provided in the following table, which lists diffraction angle 2θ, interplanar distances d, and relative intensity (expressed as a percentage with respect to the most intense peak):

| X-Ray Powder Diffractogram Data | | |
|---|---|---|
| Angle [2θ] | d-spacing [Å] | Relative Intensity [%] |
| 8.1 | 11.0 | 28 |
| 8.3 | 10.6 | 13 |
| 8.6 | 10.2 | 22 |
| 9.5 | 9.3 | 8 |
| 9.9 | 8.9 | 34 |
| 10.5 | 8.4 | 31 |
| 11.7 | 7.6 | 9 |
| 12.1 | 7.3 | 8 |
| 13.1 | 6.8 | 81 |
| 13.5 | 6.5 | 9 |
| 15.5 | 5.7 | 10 |
| 15.8 | 5.6 | 28 |
| 16.1 | 5.5 | 14 |
| 16.6 | 5.3 | 9 |
| 17.6 | 5.0 | 39 |
| 18.0 | 4.9 | 14 |
| 18.3 | 4.9 | 38 |
| 18.7 | 4.7 | 37 |
| 19.5 | 4.5 | 100 |
| 19.8 | 4.5 | 37 |
| 20.4 | 4.4 | 11 |
| 21.6 | 4.1 | 22 |
| 22.7 | 3.9 | 5 |
| 23.3 | 3.8 | 9 |
| 23.5 | 3.8 | 21 |
| 23.8 | 3.7 | 56 |
| 24.3 | 3.7 | 22 |
| 25.1 | 3.5 | 20 |
| 25.3 | 3.5 | 30 |
| 25.6 | 3.5 | 64 |
| 26.2 | 3.4 | 7 |
| 27.0 | 3.3 | 6 |
| 27.5 | 3.2 | 7 |
| 28.8 | 3.1 | 6 |

-continued

| X-Ray Powder Diffractogram Data | | |
|---|---|---|
| Angle [2θ] | d-spacing [Å] | Relative Intensity [%] |
| 31.9 | 2.8 | 6 |
| 33.1 | 2.7 | 5 |
| 33.7 | 2.7 | 8. |

Differential scanning calorimetry analysis was performed on the title compound using a TA Discovery 2500 instrument with nitrogen gas flow of 50 mL/min. The sample (1-2 mg) was weighed into Tzero sample pan with a Tzero hermetic lid with a pinhole (0.7 mm diameter) and analyzed according to the following parameters: ramp method, heating rate 10° C./min, temperature range 30 to 250° C. or before decomposition. A differential scanning calorimetry curve of the title compound obtained according to this procedure is provided in FIG. 15. A melting peak was observed with an onset temperature of 192.0° C. and 38 J/g.

Figure 16:
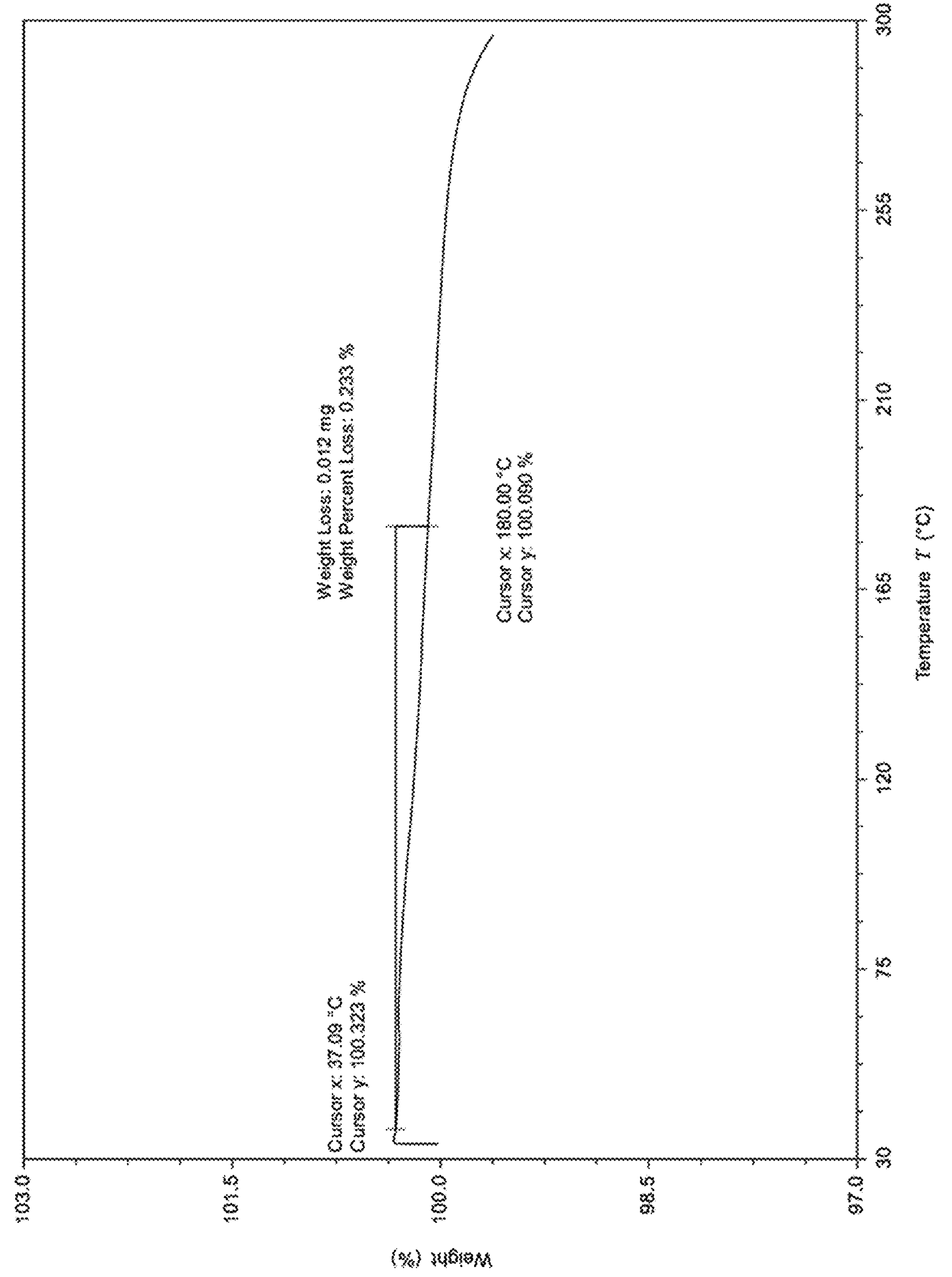
FIG. 16 depicts a thermogravimetric analysis curve of Compound II-5 in Crystal Form A, as further described in Example 59.

Thermogravimetric analysis on the title compound was performed using a TA Discovery 5500 instrument. Nitrogen flow rate was 10 mL/min at the balance and 25 mL/min in the sample chamber. The sample (2-10 mg) was weighed directly into an open aluminum pan and analyzed according to the following parameters: ramp method, heating rate 10.0° C./min, and temperature range ambient temperature (below 35° C.) to 300° C. (or until weight <80%). A thermogravimetric analysis curve of the title compound is provided in FIG. 16. A weight loss of 0.2% w/w was observed at 180° C.

The title compound was determined to be 99.7% pure by high-pressure liquid chromatography (HPLC).

Stability to Storage

To investigate the influence of relative humidity on the physical stability of Compound II-5 in Crystal Form A, a sample of Compound II-5 in Crystal Form A was held at a temperature of 23-25° C. in an environment with relative humidity levels (RH) ranging from 23% RH to 53% RH. After storage of Compound II-5 in Crystal Form A under the preceding conditions for a period of one week, no change in crystalline form was observed.

Example 60—Synthesis of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form B (II-5 in Crystal Form B)

About 50 mg of amorphous N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide was equilibrated in 0.15-0.35 mL of solvent that was EtOAc/MTBE (1/4, v/v) at 50° C. for 24 days with a stirring bar on a magnetic stirring plate at a rate of 600 rpm. On the sixth day, about 1 mg of a nucleating agent was added to the mixture to assist crystallization. On the twentieth day, about 1 mg of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form A was added to the mixture. On day 24, the resulting suspension was filtered through a 0.45 μm membrane filter by centrifugation. The isolated solid was collected and determined to be the title compound, Compound II-5 in Crystal Form B.

Example 61—Physical Characterization of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form B (II-5 in Crystal Form B)

The title compound was characterized using the instrumental methods described in Example 59.

An X-ray powder diffractogram taken on the title compound is provided in FIG. 17. Tabulated characteristics of the X-ray powder diffractogram in FIG. 17 are provided in the following table, which lists diffraction angle 2θ, interplanar distances d, and relative intensity (expressed as a percentage with respect to the most intense peak):

X-Ray Powder Diffractogram Data

| Angle [2θ] | d-spacing [Å] | Relative Intensity [%] |
|---|---|---|
| 5.9 | 15.0 | 19 |
| 8.0 | 11.0 | 10 |
| 8.5 | 10.3 | 47 |
| 9.1 | 9.7 | 24 |
| 9.4 | 9.4 | 61 |
| 11.7 | 7.5 | 34 |
| 12.5 | 7.1 | 32 |
| 12.8 | 6.9 | 50 |
| 14.5 | 6.1 | 6 |
| 14.8 | 6.0 | 9 |
| 15.4 | 5.8 | 100 |
| 15.9 | 5.6 | 6 |
| 17.1 | 5.2 | 15 |
| 17.6 | 5.0 | 44 |
| 18.2 | 4.9 | 57 |
| 18.7 | 4.7 | 85 |
| 19.6 | 4.5 | 36 |
| 20.2 | 4.4 | 91 |
| 20.8 | 4.3 | 11 |
| 21.0 | 4.2 | 12 |
| 21.4 | 4.2 | 10 |
| 21.9 | 4.1 | 38 |
| 22.3 | 4.0 | 22 |
| 22.9 | 3.9 | 10 |
| 23.5 | 3.8 | 34 |
| 23.9 | 3.7 | 20 |
| 24.6 | 3.6 | 74 |
| 25.1 | 3.5 | 21 |
| 25.4 | 3.5 | 5 |
| 26.1 | 3.4 | 23 |
| 26.5 | 3.4 | 5 |
| 27.1 | 3.3 | 22 |
| 27.4 | 3.3 | 5 |
| 28.7 | 3.1 | 14 |
| 29.8 | 3.0 | 11 |
| 31.0 | 2.9 | 6 |
| 32.4 | 2.8 | 7 |

Differential scanning calorimetry analysis was performed on the title compound using the method described in Example 59. A differential scanning calorimetry curve of the title compound obtained according to this procedure is provided in FIG. 18-A and FIG. 18-B. A melting peak, which presented with a shoulder, was observed with an onset temperature of 191.7° C. and 37 J/g.

Figure 19:
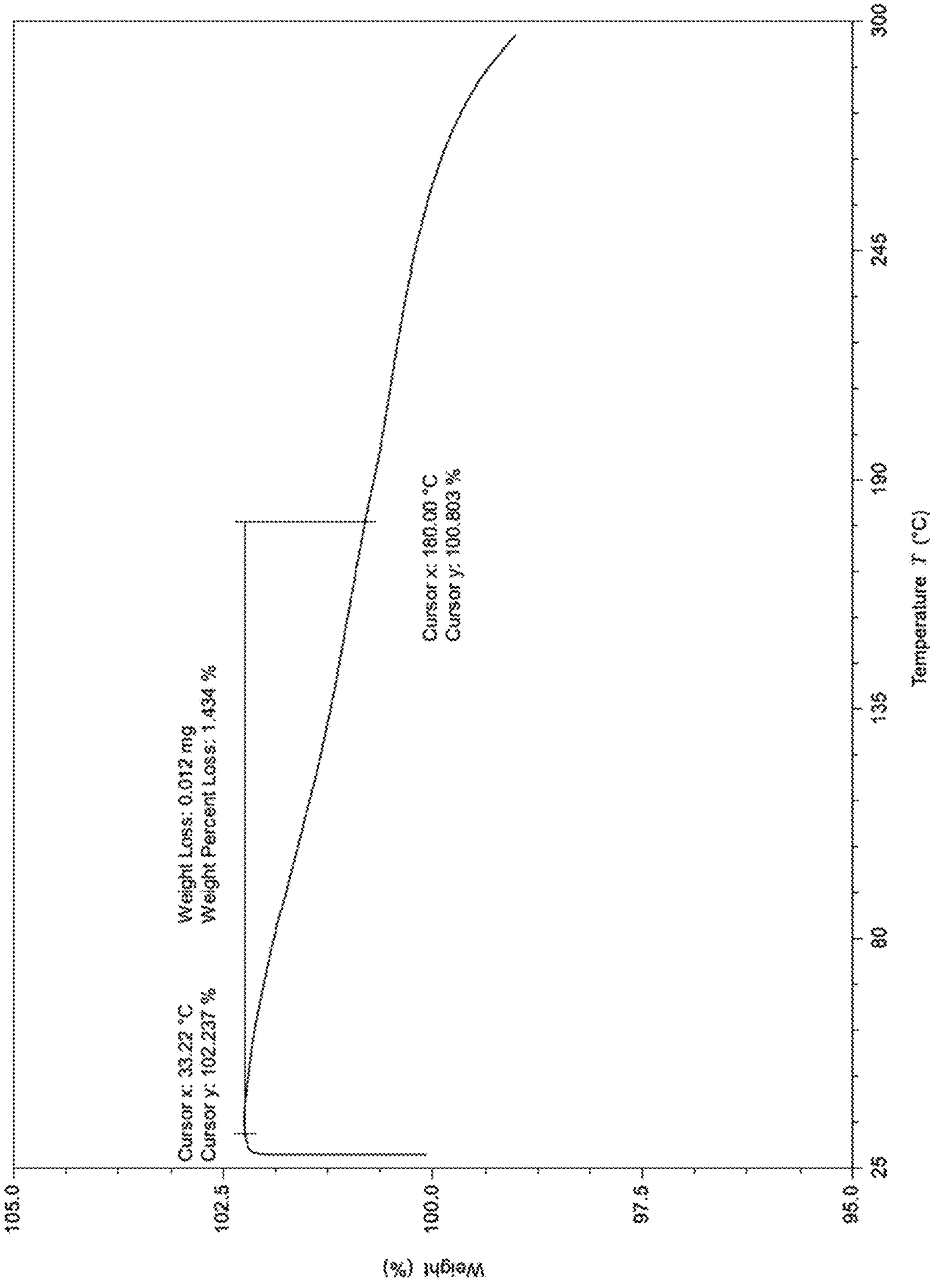
FIG. 19 depicts a thermogravimetric analysis curve of Compound II-5 in Crystal Form B, as further described in Example 61.

Thermogravimetric analysis on the title compound was performed using the method described in Example 59. A thermogravimetric analysis curve of the title compound is provided in FIG. 19. A weight loss of 1.4% w/w was observed at 180° C.

The title compound was determined to be 99.6% pure by high-pressure liquid chromatography (HPLC).

Example 62—Stability Analysis of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form A and N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form B About 3 mg of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form A and 3 mg of N-[(1r,3r)-3-(4-cyano-3-methoxy-phenoxy)-2,2,4,4-tetramethyl-cyclobutyl]-2-[2-[4-[(9S)-4,5,13-trimethyl-9-(oxazol-2-ylmethyl)-3-thia-1,8,11,12-tetrazatricyclo[8.3.0.0$^{2,6}$]trideca-2 (6),4,7,10,12-pentaen-7-yl]phenoxy]-7-azaspiro[3.5]nonan-7-yl]pyrimidine-5-carboxamide Crystal Form B were added to 0.18 mL saturated solutions of selected solvents. The obtained suspensions were stirred at 25° C. and 50° C. for 1 week, respectively. Solid parts (wet cakes) were isolated by centrifugation filtration at relative temperature and investigated by XRPD.

Results are provided in the following table. The results show that Compound II-5 in Crystal Form B converted to Compound II-5 in Crystal Form A under the stability study conditions in each solvent system listed in the following table. This demonstrates the superior stability of Compound II-5 in Crystal Form A relative to Compound II-5 in Crystal Form B.

| | XRPD | |
|---|---|---|
| Solvent | 25° C. for 1 week | 50° C. for 1 week |
| EtOH | Crystal Form A | Crystal Form A |
| Acetone | Crystal Form A | Crystal Form A |
| Acetonitrile | Crystal Form A | Crystal Form A |
| THF/Heptane (1/1, v/v) | Crystal Form A | Crystal Form A |

Example 63—Cellular Growth Inhibition Assay Using T-Rex 293 Cells

Exemplary compounds were tested for ability to inhibit the proliferation of the following types of cells: (i) a T-Rex 293 cell line having increased expression of androgen receptor protein due to exposure to doxycycline and (ii) a T-Rex 293 cell line lacking increased expression of androgen receptor protein. Experimental procedures and results are provided below.

Part I—Experimental Procedure

The following types of cells were prepared for this experiment: (i) a T-Rex 293 cell line having increased expression of androgen receptor protein due to exposure to doxycycline and (ii) a T-Rex 293 cell line lacking increased expression of androgen receptor protein. Ability of the test compounds to inhibit proliferation of the foregoing cell types was evaluated according to the procedures set forth below.

The doxycycline-inducible androgen receptor protein expressing cell line was established using the following protocol: T-Rex 293 cells were purchased from Invitrogen (Cat #R71007) and transfected using Lipofectamine 2000 with the wild-type androgen receptor protein sequence cloned into the pcDNA4/TO vector. Transfected cells were selected using 400 μg/mL Zeocin (Invitrogen Cat #R25001). Following selection, single clones were raised and maintained in Dulbecco's Modified Eagle Medium (DMEM) supplemented with 10% w/w Tetracycline-free fetal bovine serum (FBS) and 250 μg/mL Zeocin. Clones were analyzed for expression of androgen receptor protein in the presence and absence of 10 ng/ml doxycycline (Sigma Cat #D9891), and a single doxycycline-inducible clone (hereinafter "SC3") was selected for use in downstream assays.

The SC3 cells were seeded on poly-D-lysine coated, black clear-bottom 384-well plates at 2500/well, in 25 μL Phenol Red Free Dulbecco's Modified Eagle Medium (DMEM) supplemented with 10% w/w charcoal-dextran treated fetal bovine serum (FBS) and 1% w/w pen-strep, with or without 10 ng/ml doxycycline. Pen-Strep is a commercially available mixture of penicillin G and streptomycin, which is used in mammalian cell culture media to prevent bacterial contamination. Phenol Red Free Dulbecco's Modified Eagle Medium (DMEM) supplemented with 10% w/w charcoal-dextran treated fetal bovine serum (FBS) and 1% w/w pen-strep, with or without 10 ng/mL doxycycline is herein referred to as Treatment Medium. Following seeding of cells in the plates, the plates were spun at 300×g for 30 seconds, then equilibrated to room temperature for 30 minutes, and then deposited in a humidified tissue culture incubator maintained at 37° C. with 5% $CO_2$.

At 24 hours after seeding of the cells, dilutions of test compound were prepared in DMSO and dissolved in Treatment Medium, to achieve a final DMSO concentration of 0.5% w/w, thereby providing the Test Compound Solution. A 25 μL aliquot of the Test Compound Solution was added to cells in the well plates. An equal volume of a solution containing DMSO and Treatment Medium was used as a negative control. Following treatment of cells with Test Compound Solution or said equal volume of a solution containing DMSO and Treatment Medium, the plates were spun at 300×g for 30 seconds, and then left in an incubator for 72 hours.

At the end of the treatment duration, cell viability was quantified with CellTiter-Glo 2.0 reagent (Promega Cat #G9243). For this purpose, plates were equilibrated to room temperature for 30 minutes, and then 25 μL of CellTiter-Glo 2.0 reagent was added to cells in the plate wells. Plates were then agitated on a shaker for two minutes at 500 rpm and subsequently incubated at room temperature for 10 minutes. Following incubation, the plates were spun at 3000×g for 30 seconds, then sealed with an optical adhesive cover, and luminescence readings were measured with an En Vision Plate Reader.

Data was normalized using zero luminescence for baseline. A four-parameter non-linear regression curve fit was applied to dose-response data in GraphPad Prism data analysis software to determine the half-maximal growth inhibitory concentration ($GI_{50}$) for each test compound.

Part II—Results

The half-maximal growth inhibitory concentration ($GI_{50}$) results are provided in Tables 5 and 6 below for exemplary compounds. Table 5 provides results from the experiment analyzing ability of test compounds to inhibit proliferation of the T-Rex 293 cell line SC3 cells having increased expression of androgen receptor protein due to exposure to doxycycline. The symbol "++++" indicates a $GI_{50}$ less than 0.5 μM. The symbol "+++" indicates an $GI_{50}$ in the range of 0.5 μM to 1.5 μM. The symbol "++" indicates a $GI_{50}$ in the range of greater than 1.5 μM to 3 μM. The symbol "+" indicates a $GI_{50}$ greater than 3 μM.

TABLE 5

| Compound No. | $GI_{50}$ | Compound No. | $GI_{50}$ |
|---|---|---|---|
| I-17 | ++++ | I-38 | ++++ |
| I-18 | ++++ | I-39 | ++++ |
| II-4 | ++++ | I-40 | ++++ |
| I-19 | ++++ | I-13 | ++++ |
| I-20 | ++++ | I-14 | ++++ |
| I-21 | ++++ | I-15 | ++++ |
| I-22 | ++++ | I-41 | ++++ |
| II-5 | ++++ | I-42 | ++++ |
| I-1 | + | I-43 | ++++ |
| I-23 | + | I-44 | ++++ |
| I-24 | ++++ | I-45 | ++++ |
| I-25 | ++++ | I-46 | ++++ |
| II-7 | ++++ | I-47 | ++++ |
| I-26 | ++++ | I-48 | ++++ |
| I-2 | ++++ | I-49 | ++++ |
| I-3 | ++++ | I-50 | ++++ |
| I-4 | ++++ | I-51 | ++++ |
| I-5 | ++++ | I-52 | ++++ |
| I-6 | ++++ | I-16 | ++++ |
| I-7 | ++++ | I-53 | ++++ |
| I-8 | ++++ | I-54 | ++++ |
| I-9 | ++++ | I-55 | ++++ |
| I-10 | ++++ | I-56 | ++++ |
| I-11 | ++++ | I-57 | ++++ |
| I-12 | ++++ | I-58 | ++++ |
| I-27 | ++++ | I-59 | ++++ |
| I-28 | ++++ | I-60 | ++++ |
| I-29 | ++++ | I-61 | ++++ |
| I-30 | ++++ | I-62 | ++++ |
| I-31 | ++++ | I-63 | ++++ |
| I-32 | ++++ | I-64 | ++++ |
| I-33 | ++++ | I-65 | ++++ |
| I-34 | ++++ | I-66 | ++++ |
| I-35 | ++++ | I-67 | ++++ |
| I-36 | ++++ | I-68 | ++++ |
| I-37 | ++++ | I-69 | ++++ |
| I-70 | ++++ | I-104 | ++++ |
| I-71 | ++++ | I-105 | ++++ |
| I-72 | ++++ | I-106 | ++++ |
| I-73 | ++++ | I-107 | ++++ |
| I-74 | ++++ | I-108 | ++++ |
| I-75 | ++++ | I-109 | ++++ |
| I-76 | ++++ | I-110 | ++++ |
| I-77 | ++++ | I-111 | ++++ |
| I-78 | ++++ | I-112 | ++++ |
| I-79 | ++++ | I-113 | ++++ |
| I-80 | ++++ | I-114 | ++++ |
| I-81 | ++++ | I-115 | ++++ |
| I-82 | ++++ | I-116 | ++++ |
| I-83 | ++++ | I-117 | ++++ |
| II-1 | ++++ | I-118 | ++++ |
| II-10 | ++++ | I-119 | ++++ |
| I-84 | ++++ | I-120 | ++++ |
| I-85 | ++++ | I-121 | ++++ |
| I-86 | ++++ | I-122 | ++++ |
| I-87 | ++++ | I-123 | ++++ |
| I-88 | ++++ | I-124 | ++++ |
| I-89 | ++++ | I-125 | ++++ |
| I-90 | ++++ | I-126 | ++++ |
| I-91 | ++++ | I-127 | ++++ |
| I-92 | ++++ | II-13 | ++++ |
| I-93 | ++++ | I-128 | ++++ |

TABLE 5-continued

| Compound No. | $GI_{50}$ | Compound No. | $GI_{50}$ |
|---|---|---|---|
| I-94 | ++++ | I-129 | ++++ |
| I-95 | ++++ | I-130 | ++++ |
| I-96 | ++++ | I-131 | ++++ |
| I-97 | ++++ | I-132 | ++++ |
| I-98 | ++++ | II-14 | ++++ |
| I-99 | ++++ | I-133 | ++++ |
| I-100 | ++++ | I-134 | ++++ |
| I-101 | ++++ | I-135 | ++++ |
| II-11 | ++++ | I-136 | ++++ |
| II-12 | ++++ | I-137 | ++++ |
| I-102 | ++++ | III-2 | ++++ |
| I-103 | ++++ | III-3 | ++++ |
| III-1 | ++++ | | |

Table 6 provides results from the experiment analyzing ability of test compounds to inhibit proliferation of the T-Rex 293 cell line SC3 cells lacking increased expression of androgen receptor protein since such cells were not exposed to doxycycline. The symbol "++++" indicates a $GI_{50}$ less than 0.5 μM. The symbol "+++" indicates an $GI_{50}$ in the range of 0.5 μM to 1.5 μM. The symbol "++" indicates a $GI_{50}$ in the range of greater than 1.5 μM to 3 μM. The symbol "+" indicates a $GI_{50}$ greater than 3 μM.

TABLE 6

| Compound No. | $GI_{50}$ | Compound No. | $GI_{50}$ |
|---|---|---|---|
| I-17 | ++++ | I-29 | ++++ |
| I-18 | ++++ | I-30 | ++++ |
| II-4 | ++++ | I-31 | ++++ |
| I-19 | ++++ | I-32 | ++++ |
| I-20 | ++++ | I-33 | ++++ |
| I-21 | ++++ | I-34 | ++++ |
| I-22 | ++++ | I-35 | ++++ |
| II-5 | ++++ | I-36 | ++++ |
| I-1 | ++++ | I-37 | ++++ |
| I-23 | ++++ | I-38 | ++++ |
| I-24 | ++ | I-39 | ++++ |
| I-25 | ++++ | I-40 | ++++ |
| II-7 | ++++ | I-13 | ++++ |
| I-26 | ++++ | I-14 | + |
| I-2 | ++++ | I-15 | +++ |
| I-3 | + | I-41 | ++++ |
| I-4 | ++ | I-42 | ++++ |
| I-5 | + | I-43 | ++++ |
| I-6 | ++++ | I-44 | ++++ |
| I-7 | ++++ | I-45 | ++++ |
| I-8 | ++++ | I-46 | ++++ |
| I-9 | ++++ | I-47 | ++++ |
| I-10 | ++++ | I-48 | ++++ |
| I-11 | ++++ | I-49 | ++++ |
| I-12 | ++++ | I-50 | ++++ |
| I-27 | ++++ | I-51 | ++++ |
| I-28 | ++++ | I-52 | ++++ |
| I-16 | ++++ | I-88 | ++++ |
| I-53 | ++++ | I-89 | ++++ |
| I-54 | ++++ | I-90 | ++++ |
| I-55 | ++++ | I-91 | ++++ |
| I-56 | ++++ | I-92 | ++++ |
| I-57 | ++++ | I-93 | ++++ |
| I-58 | ++++ | I-94 | ++++ |
| I-59 | ++++ | I-95 | ++++ |
| I-60 | ++++ | I-96 | ++++ |
| I-61 | ++++ | I-97 | ++++ |
| I-62 | ++ | I-98 | ++++ |
| I-63 | ++++ | I-99 | ++++ |
| I-64 | ++++ | I-100 | ++++ |
| I-65 | + | I-101 | ++++ |
| I-66 | ++++ | II-11 | ++++ |
| I-67 | ++++ | II-12 | ++++ |
| I-68 | ++++ | I-102 | ++++ |
| I-69 | ++++ | I-103 | ++++ |
| I-70 | ++++ | I-104 | +++ |
| I-71 | ++++ | I-105 | + |

TABLE 6-continued

| Compound No. | $GI_{50}$ | Compound No. | $GI_{50}$ |
|---|---|---|---|
| I-72 | ++++ | I-106 | ++++ |
| I-73 | ++++ | I-107 | ++++ |
| I-74 | + | I-108 | ++++ |
| I-75 | ++++ | I-109 | ++++ |
| I-76 | ++++ | I-110 | ++++ |
| I-77 | ++++ | I-111 | ++++ |
| I-78 | ++++ | I-112 | + |
| I-79 | ++++ | I-113 | ++++ |
| I-80 | ++++ | I-114 | ++++ |
| I-81 | ++++ | I-115 | + |
| I-82 | ++++ | I-116 | ++++ |
| I-83 | ++++ | I-117 | ++++ |
| II-1 | ++++ | I-118 | ++++ |
| II-10 | +++ | I-119 | ++++ |
| I-84 | ++++ | I-120 | ++++ |
| I-85 | + | I-121 | + |
| I-86 | + | I-122 | ++ |
| I-87 | ++++ | I-123 | + |
| I-124 | ++++ | I-131 | ++++ |
| I-125 | ++++ | I-132 | ++++ |
| I-126 | + | II-14 | + |
| I-127 | ++++ | I-133 | ++++ |
| II-13 | ++++ | I-134 | + |
| I-128 | ++++ | I-135 | ++++ |
| I-129 | ++++ | I-136 | + |
| I-130 | ++++ | I-137 | + |
| III-1 | +++ | III-3 | ++++ |
| III-2 | ++++ | | |

Example 64—Cellular Growth Inhibition Assay for VCaP Cells

Exemplary compounds were tested for ability to inhibit the proliferation of VCaP cells. VCap cells are a commercially available human prostate cancer cell line. Experimental procedures and results are provided below.

Part I—Experimental Procedure

VCaP cells were purchased from American Type Cell Culture (ATCC Cat #CRL2876) and then seeded on poly-D-lysine coated, black clear-bottom 384-well plates at 5000/well in 25 μL Dulbecco's Modified Eagle Medium (DMEM) supplemented with 10% w/w Fetal bovine serum (FBS) and 1% w/w Pen-Strep. Pen-Strep is a commercially available mixture of penicillin G and streptomycin, which is used in mammalian cell culture media to prevent bacterial contamination. Dulbecco's Modified Eagle Medium (DMEM) supplemented with 10% w/w fetal bovine serum (FBS) and 1% w/w Pen-Strep is herein referred to as Treatment Medium. Following seeding of cells in the plates, the plates were spun at 300×g for 30 seconds, then equilibrated to room temperature for 30 minutes, and then deposited in a humidified tissue culture incubator maintained at 37° C. with 5% $CO_2$.

At 24 hours after seeding of the cells, dilutions of test compound were prepared in DMSO and dissolved in Treatment Medium, to achieve a final DMSO concentration of 0.5% w/w, thereby providing the Test Compound Solution. A 25 μL aliquot of the Test Compound Solution was added to cells in the well plates. An equal volume of a solution containing DMSO and Treatment Medium was used as a negative control. Following treatment of cells with Test Compound Solution or said equal volume of a solution containing DMSO and Treatment Medium, the plates were spun at 300×g for 30 seconds, and then left in an incubator for 72 hours.

At the end of the treatment duration, cell viability was quantified with CellTiter-Glo 2.0 reagent (Promega Cat

#G9243). For this purpose, plates were equilibrated to room temperature for 30 minutes, and then 25 μL of CellTiter-Glo 2.0 reagent was added to cells in the plate wells. Plates were then agitated on a shaker for two minutes at 500 rpm and subsequently incubated at room temperature for 10 minutes. Following incubation, the plates were spun at 3000×g for 30 seconds, then sealed with an optical adhesive cover, and luminescence readings were measured with an En Vision Plate Reader.

Data was normalized using zero luminescence for baseline. A four-parameter non-linear regression curve fit was applied to dose-response data in GraphPad Prism data analysis software to determine the half-maximal growth inhibitory concentration ($GI_{50}$) for each test compound.

Part II—Results

The half-maximal growth inhibitory concentration ($GI_{50}$) results are provided in Table 7 below for exemplary compounds. The symbol "++++" indicates a $GI_{50}$ less than 0.5 μM. The symbol "+++" indicates an $GI_{50}$ in the range of 0.5 μM to 1.5 μM. The symbol "++" indicates a $GI_{50}$ in the range of greater than 1.5 μM to 3 μM. The symbol "+" indicates a $GI_{50}$ greater than 3 μM.

TABLE 7

| Compound No. | $GI_{50}$ | Compound No. | $GI_{50}$ |
|---|---|---|---|
| I-17 | ++++ | I-1 | ++++ |
| I-18 | ++++ | I-23 | + |
| II-4 | ++++ | I-24 | ++++ |
| I-19 | ++++ | I-25 | ++++ |
| I-20 | ++++ | II-7 | ++ |
| I-21 | +++ | I-26 | ++++ |
| I-22 | +++ | I-2 | ++++ |
| II-5 | ++++ | I-3 | +++ |
| I-4 | ++++ | I-16 | ++++ |
| I-5 | ++++ | I-53 | ++++ |
| I-6 | ++++ | I-54 | ++++ |
| I-7 | ++++ | I-55 | ++++ |
| I-8 | ++++ | I-56 | ++++ |
| I-9 | ++++ | I-57 | ++++ |
| I-10 | ++++ | I-58 | ++++ |
| I-11 | ++++ | I-59 | ++++ |
| I-12 | ++++ | I-60 | ++++ |
| I-27 | ++++ | I-61 | ++++ |
| I-28 | ++++ | I-62 | ++++ |
| I-29 | ++++ | I-63 | ++++ |
| I-30 | ++++ | I-64 | +++ |
| I-31 | ++++ | I-65 | +++ |
| I-32 | ++++ | I-66 | ++++ |
| I-33 | ++++ | I-67 | ++++ |
| I-34 | ++++ | I-68 | ++++ |
| I-35 | ++++ | I-69 | ++++ |
| I-36 | ++++ | I-70 | ++++ |
| I-37 | ++++ | I-71 | ++++ |
| I-38 | ++++ | I-72 | ++++ |
| I-39 | ++++ | I-73 | ++++ |
| I-40 | ++++ | I-74 | ++++ |
| I-13 | ++++ | I-75 | ++++ |
| I-14 | ++ | I-76 | ++++ |
| I-15 | ++++ | I-77 | ++++ |
| I-41 | ++++ | I-78 | ++++ |
| I-42 | ++++ | I-79 | ++++ |
| I-43 | ++++ | I-80 | ++++ |
| I-44 | ++++ | I-81 | ++++ |
| I-45 | ++++ | I-82 | ++++ |
| I-46 | ++++ | I-83 | ++++ |
| I-47 | ++++ | II-1 | + |
| I-48 | ++++ | II-10 | ++++ |
| I-49 | ++++ | I-84 | ++++ |
| I-50 | ++++ | I-85 | ++++ |
| I-51 | ++++ | I-86 | ++++ |
| I-52 | ++++ | I-87 | ++++ |
| I-88 | ++++ | I-113 | ++++ |
| I-89 | +++ | I-114 | ++++ |
| I-90 | ++++ | I-115 | ++++ |

TABLE 7-continued

| Compound No. | $GI_{50}$ | Compound No. | $GI_{50}$ |
|---|---|---|---|
| I-91 | ++++ | I-116 | ++++ |
| I-92 | ++++ | I-117 | ++++ |
| I-93 | ++++ | I-118 | ++++ |
| I-94 | ++++ | I-119 | ++++ |
| I-95 | ++++ | I-120 | ++++ |
| I-96 | ++++ | I-121 | ++++ |
| I-97 | ++++ | I-122 | +++ |
| I-98 | ++++ | I-123 | ++++ |
| I-99 | ++++ | I-124 | ++++ |
| I-100 | ++++ | I-125 | ++++ |
| I-101 | ++++ | I-126 | + |
| II-11 | ++++ | I-127 | ++++ |
| II-12 | ++++ | II-13 | ++++ |
| I-102 | ++++ | I-128 | ++++ |
| I-103 | +++ | I-129 | ++++ |
| I-104 | +++ | I-130 | ++++ |
| I-105 | +++ | I-131 | ++++ |
| I-106 | ++++ | I-132 | ++++ |
| I-107 | ++++ | II-14 | + |
| I-108 | ++++ | I-133 | ++++ |
| I-109 | ++++ | I-134 | + |
| I-110 | ++++ | I-135 | ++++ |
| I-111 | ++++ | I-136 | + |
| I-112 | ++++ | I-137 | ++++ |
| III-1 | ++++ | III-3 | ++++ |
| III-2 | ++++ | | |

Example 65—Cellular Growth Inhibition Assay for T47D Cells

Exemplary compounds were tested for ability to inhibit the proliferation of T47D cells. T47D cells are a commercially available human breast cancer cell line. Experimental procedures and results are provided below.

Part I—Experimental Procedure

T47D cells were purchased from American Type Cell Culture (ATCC Cat #HTB-133) and then seeded on poly-D-lysine coated, black clear-bottom 384-well plates at 3000/well in 25 μL Dulbecco's Modified Eagle Medium (DMEM) supplemented with 10% w/w Fetal bovine serum (FBS), 0.2 units/mL recombinant human insulin (Gibco Cat #12585014), and 1% w/w Pen-Strep. Pen-Strep is a commercially available mixture of penicillin G and streptomycin, which is used in mammalian cell culture media to prevent bacterial contamination. Dulbecco's Modified Eagle Medium (DMEM) supplemented with 10% w/w fetal bovine serum (FBS), 0.2 units/mL recombinant human insulin, and 1% w/w Pen-Strep is herein referred to as Treatment Medium. Following seeding of cells in the plates, the plates were spun at 300×g for 30 seconds, then equilibrated to room temperature for 30 minutes, and then deposited in a humidified tissue culture incubator maintained at 37° C. with 5% $CO_2$.

At 24 hours after seeding of the cells, dilutions of test compound were prepared in DMSO and dissolved in Treatment Medium, to achieve a final DMSO concentration of 0.5% w/w, thereby providing the Test Compound Solution. A 25 μL aliquot of the Test Compound Solution was added to cells in the well plates. An equal volume of a solution containing DMSO and Treatment Medium was used as a negative control. Following treatment of cells with Test Compound Solution or said equal volume of a solution containing DMSO and Treatment Medium, the plates were spun at 300×g for 30 seconds, and then left in an incubator for 72 hours.

At the end of the treatment duration, cell viability was quantified with CellTiter-Glo 2.0 reagent (Promega Cat

#G9243). For this purpose, plates were equilibrated to room temperature for 30 minutes, and then 25 μL of CellTiter-Glo 2.0 reagent was added to cells in the plate wells. Plates were then agitated on a shaker for two minutes at 500 rpm and subsequently incubated at room temperature for 10 minutes. Following incubation, the plates were spun at 3000×g for 30 seconds, then sealed with an optical adhesive cover, and luminescence readings were measured with an En Vision Plate Reader (Perkin Elmer).

Data was normalized using zero luminescence for baseline. A four-parameter non-linear regression curve fit was applied to dose-response data in GraphPad Prism data analysis software to determine the half-maximal growth inhibitory concentration ($GI_{50}$) for each test compound.

Part II—Results

The half-maximal growth inhibitory concentration ($GI_{50}$) results are provided in Table 8 below for exemplary compounds. The symbol "++++" indicates a $GI_{50}$ less than 0.5 μM. The symbol "+++" indicates an $GI_{50}$ in the range of 0.5 μM to 1.5 μM. The symbol "++" indicates a $GI_{50}$ in the range of greater than 1.5 μM to 3 μM. The symbol "+" indicates a $GI_{50}$ greater than 3 UM.

TABLE 8

| Compound No. | $GI_{50}$ |
|---|---|
| II-3 | ++++ |
| II-4 | ++++ |
| II-5 | ++++ |
| II-6 | ++++ |
| II-7 | ++++ |
| II-8 | +++ |
| II-9 | ++++ |
| II-2 | ++++ |
| II-1 | ++++ |
| II-10 | ++++ |
| II-11 | ++++ |
| II-12 | ++++ |
| I-102 | ++++ |
| I-103 | +++ |
| I-104 | ++ |

Example 66—Cellular Growth Inhibition Assays with Additional Compounds

Exemplary compounds were tested for ability to inhibit the proliferation of the following types of cells: (i) a T-Rex 293 cell line having increased expression of androgen receptor protein due to exposure to doxycycline and (ii) VCap cells, a commercially available human prostate cancer cell line. Experimental procedures and results are provided below.

Part I—Experimental Procedure

The following types of cells were prepared for this experiment: (i) a T-Rex 293 cell line having increased expression of androgen receptor protein due to exposure to doxycycline and (ii) VCap cells, a commercially available human prostate cancer cell line. Ability of the test compounds to inhibit proliferation of the foregoing cell types was evaluated according to the procedures set forth in Examples 63 and 64, above.

Part II—Results

The ratio of the half-maximal growth inhibitory concentration ($GI_{50}$) results for exemplary pairs of compounds are provided in Tables 9 and 10 below. The ratios reported are the $GI_{50}$ of the top compound in the pair (e.g., Compound B, for the first pair of compounds) divided by the $GI_{50}$ of the lower compound in the pair (e.g., Compound II-5, for the first pair of compounds). To illustrate, Table 9-Part I reports a 5.3:1 ratio of the $GI_{50}$ for Compound B relative to the $GI_{50}$ for compound II-5. This shows that Compound II-5 is much more potent than Compound B, as the $GI_{50}$ value for Compound B is 5.3 times larger than the $GI_{50}$ value for Compound II-5. Table 9 provides results from the experiment analyzing ability of test compounds to inhibit proliferation of the T-Rex 293 cell line SC3 cells having increased expression of androgen receptor protein due to exposure to doxycycline. Table 10 provides results from the experiment analyzing ability of test compounds to inhibit proliferation of VCap cells, a commercially available human prostate cancer cell line.

TABLE 9

| Compound No. | Chemical Structure | Ratio of $GI_{50}$'s |
|---|---|---|
| | PART I | |
| B | 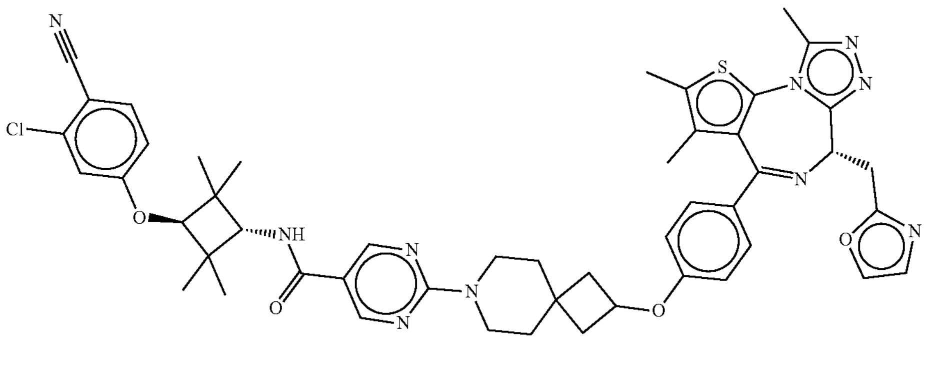 | 5.3 |

TABLE 9-continued
| Compound No. | Chemical Structure | Ratio of $GI_{50}$'s |
| --- | --- | --- |
| II-5 | 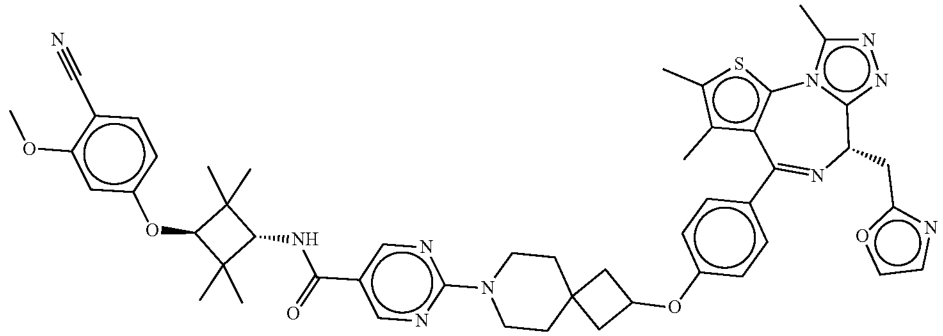 | 1 |
| | PART II | |
| C | 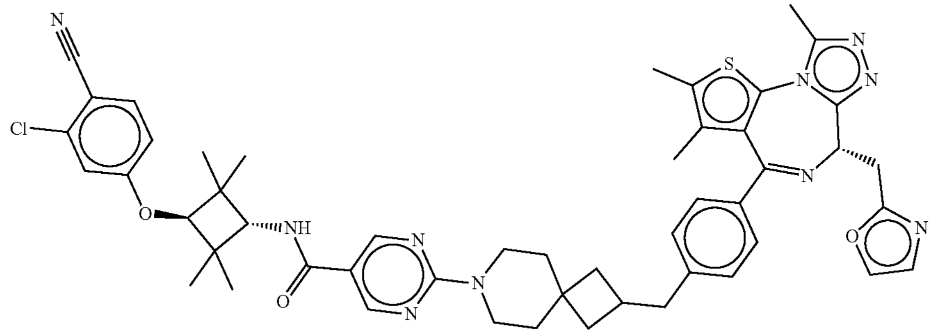 | 22.0 |
| II-10 | 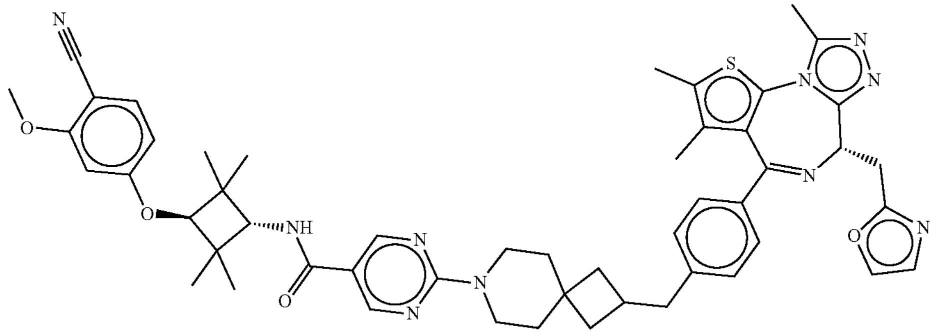 | 1 |
| | PART III | |
| D | 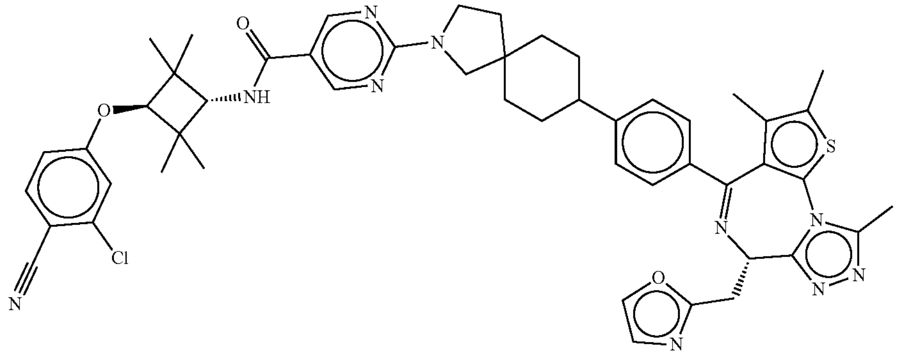 | 3.8 |

TABLE 9-continued
| Compound No. | Chemical Structure | Ratio of $GI_{50}$'s |
| --- | --- | --- |
| II-12 | 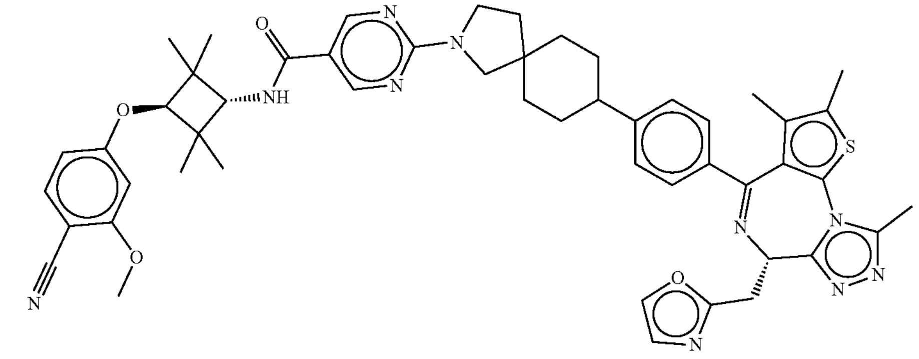 | 1 |
| | PART IV | |
| E | 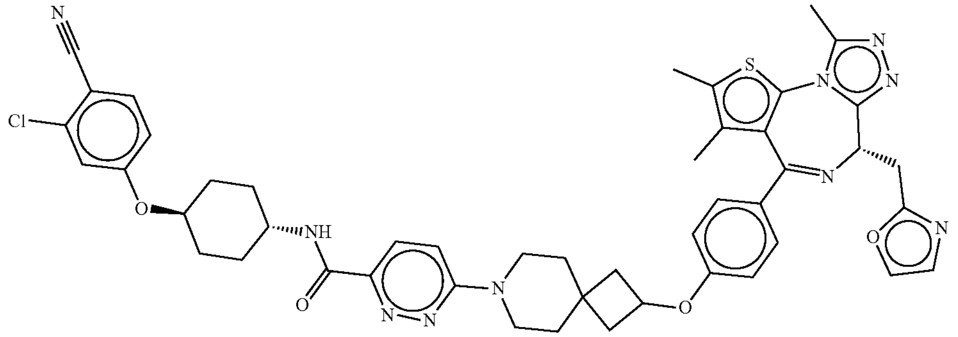 | 4.7 |
| I-83 | 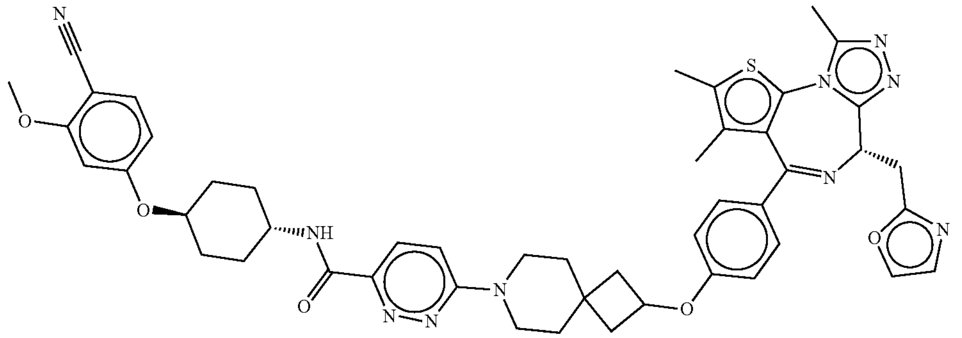 | 1 |
| | PART V | |
| F | 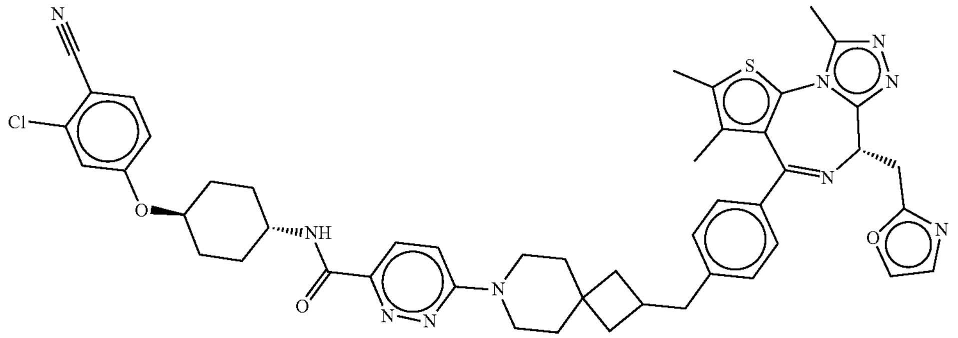 | 3.8 |

TABLE 9-continued
| Compound No. | Chemical Structure | Ratio of $GI_{50}$'s |
|---|---|---|
| I-25 | 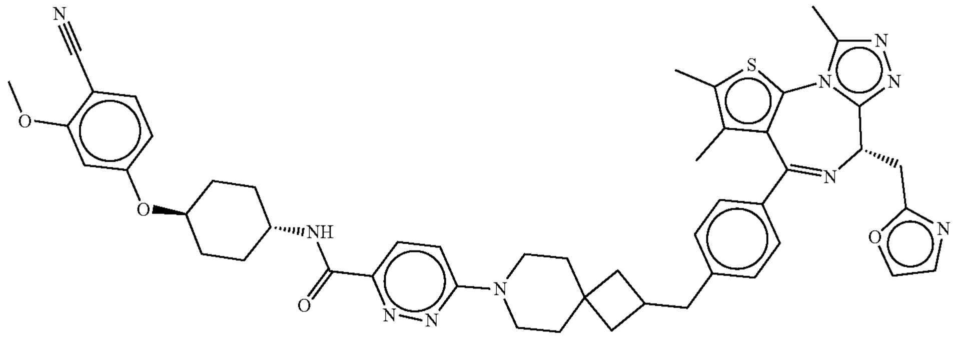 | 1 |
| | PART VI | |
| G | 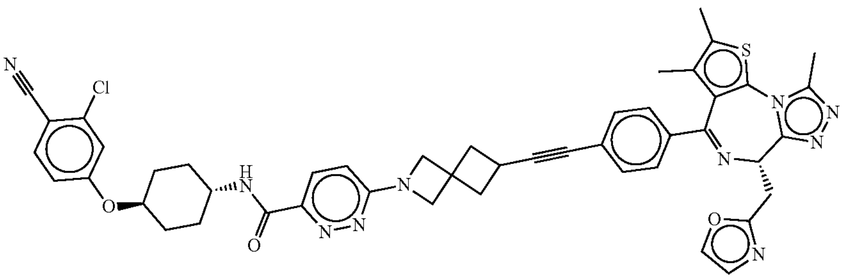 | 1.7 |
| I-124 | 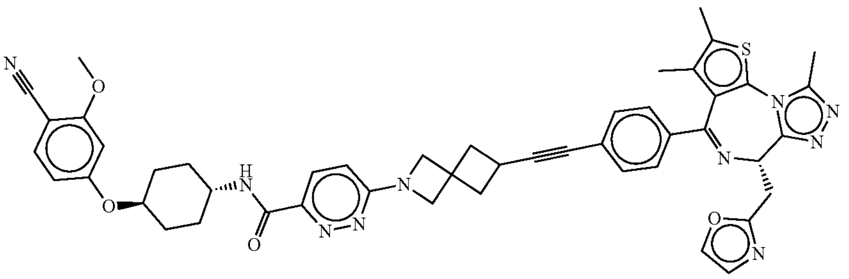 | 1 |
| | PART VII | |
| H | 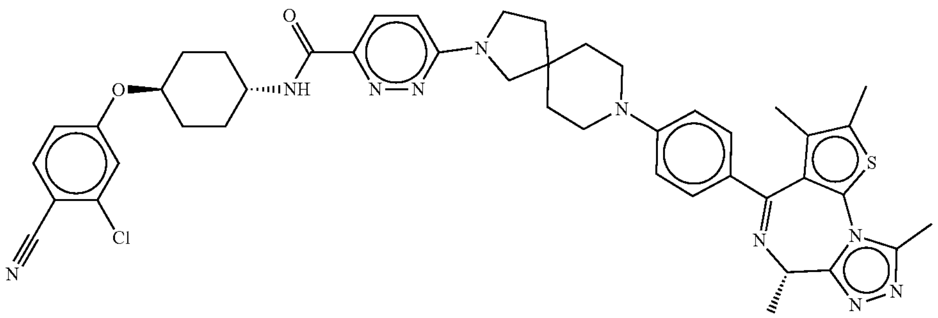 | 8.4 |

TABLE 9-continued
| Compound No. | Chemical Structure | Ratio of $GI_{50}$'s |
|---|---|---|
| I-17 | 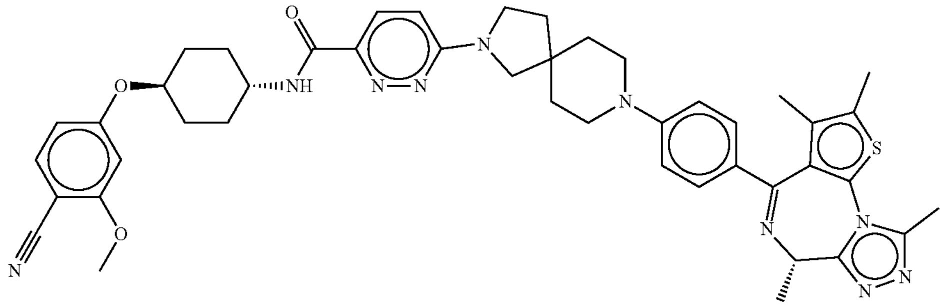 | 1 |
| | PART VIII | |
| J | 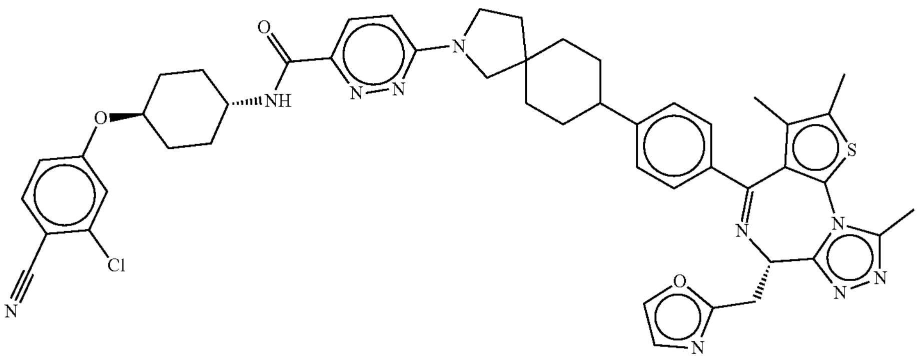 | 3.2 |
| I-101 | 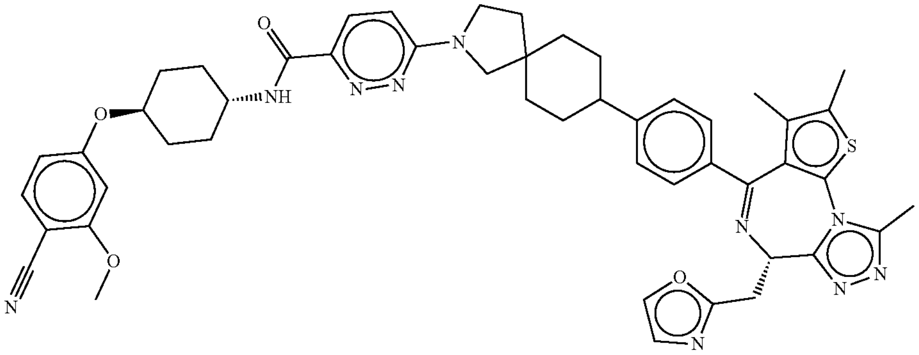 | 1 |
| | PART IX | |
| K | 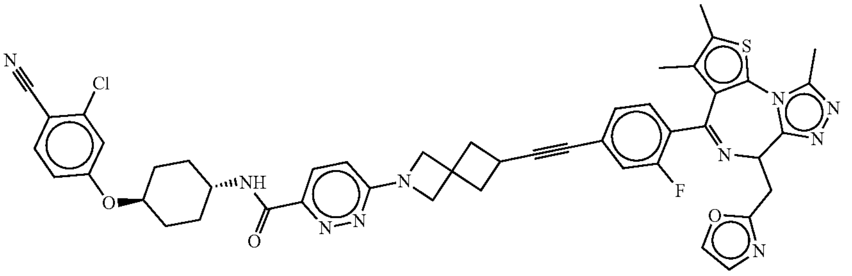 | 2.0 |

TABLE 9-continued

| Compound No. | Chemical Structure | Ratio of $GI_{50}$'s |
| --- | --- | --- |
| I-111 | 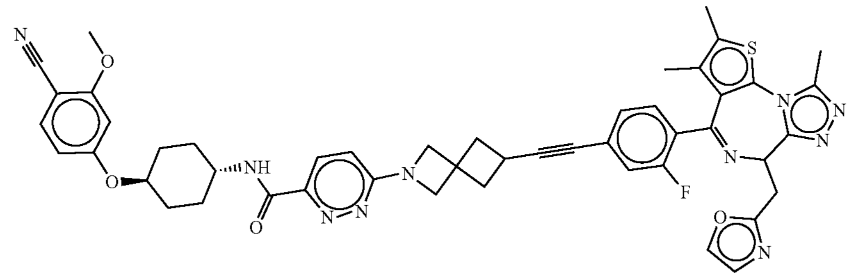 | 1 |

TABLE 10

| PART I. | |
| --- | --- |
| Compound No. | Ratio of $GI_{50}$'s |
| B | 1.3 |
| II-5 | 1 |
| PART II. | |
| Compound No. | Ratio of $GI_{50}$'s |
| C | 2.6 |
| II-10 | 1 |
| PART III. | |
| Compound No. | Ratio of $GI_{50}$'s |
| D | 6.5 |
| II-12 | 1 |
| PART IV. | |
| Compound No. | Ratio of $GI_{50}$'s |
| E | 4.4 |
| I-83 | 1 |
| PART V. | |
| Compound No. | Ratio of $GI_{50}$'s |
| F | 1.9 |
| I-25 | 1 |
| PART VI. | |
| Compound No. | Ratio of $GI_{50}$'s |
| G | 1.5 |
| I-124 | 1 |
| PART VII. | |
| Compound No. | Ratio of $GI_{50}$'s |
| H | 1.8 |
| I-17 | 1 |
| PART VIII. | |
| Compound No. | Ratio of $GI_{50}$'s |
| J | 3.0 |
| I-101 | 1 |

TABLE 10-continued

| PART IX. | |
| --- | --- |
| Compound No. | Ratio of $GI_{50}$'s |
| K | 1.5 |
| I-111 | 1 |

Example 67—Analysis of Ternary Complex Formation

Exemplary compounds were tested for ability to form a ternary complex containing a test compound, androgen receptor (AR), and bromodomain-containing protein 4 (BRD4) protein. Experimental procedures and results are provided below.

Part I—Experimental Procedure

VCaP cells were cultured in ATCC DMEM medium supplemented with 10% ATCC fetal bovine serum, and 1% pen-strep (culture medium). 5000 cells were seeded in 100 μL of culture medium, per well in a clear 96-well poly-D-lysine coated plate. Plates were equilibrated to room temperature for 30 minutes. After equilibration, plates were incubated at 37° C. with 5% $CO_2$ in a humidified tissue culture incubator. Black, opaque 96-well MaxiSorp plates were coated with 50 μL of a solution of androgen receptor antibody diluted in phosphate buffered saline (PBS). The coated plates were then quick-spun for 30 seconds before being sealed and placed in a fridge at 4° C. overnight. Test compounds were titrated in 100% DMSO the day before the experiment was performed and were left sealed in the dessicator overnight. QuantaRed™ Enhanced Chemifluorescent HRP Substrate Kit was taken out from 4° C. to warm up to room temperature. Plates coated with androgen receptor antibody were washed three times with 200 μL 1× Tris -Buffered Saline plus 0.1% Tween20 (TBST), then blocked with 200 μL 3% bovine serum albumin in TBST for approximately 2 hours on a room temperature plate shaker at 500 rpm for 1 hour. Test compound titrations were diluted in culture medium. 100 μL of the compound/media mixture was added to cells, bringing the total volume to 200 μL per well. DMSO was used as a negative control.

Test compounds used in this experiment were (i) Compound II-5, (ii) the component of Compound II-5 that binds androgen receptor, and (iii) the component of Compound II-5 that binds BRD4 protein.

Part II—Results

Detected ternary complex formation between test compound, androgen receptor, and BRD4 protein is shown in FIG. 1. The results in FIG. 1 show that ternary complex formation between test compound, androgen receptor, and BRD4 was detected when using Compound II-5, whereas no significant ternary complex formation was detected when the test compound was either of (a) the component of Compound II-5 that binds androgen receptor or (b) the component of Compound II-5 that binds BRD4 protein.

Example 68—Analysis of Ternary Complex Formation in TRex293 Cells

Compound II-5 was tested for ability to form a ternary complex containing Compound II-5, androgen receptor, and bromodomain-containing protein 4 (BRD4) protein using TRex293 cells induced to express elevated levels of androgen receptor. Experimental procedures and results are provided below.

Part I—Experimental Procedure

TRex293 cells expressing doxycycline inducible androgen receptor WT, T878A, L702H and H875Y were generated and cultured in DMEM medium supplemented with 10% heat inactivated fetal bovine serum, and 1% pen-strep (culture medium). 25,000 cells were seeded per well in 100 μL of phenol red free DMEM containing 10% CSS, 1% pen strep, and 10 ng/mL doxycycline in a clear 96-well poly-D-lysine coated plate. Plates were incubated at 37° C. Black, opaque 96-well MaxiSorp plates were coated with 50 μL of androgen receptor antibody diluted in phosphate buffered saline (PBS). The coated plates were sealed and placed at 4° C. overnight. Plates coated with androgen receptor antibody were washed three times with 200 μL 1× tris -buffered saline plus 0.1% Tween20 (TBST), then blocked with 200 μL of 3% bovine serum albumin in TBST for 1 hour at room temperature. Test compound titrations were diluted in culture medium. 100 μL of the test compound/media mixture was added to the cell plate. After treatment, plates were incubated for 1 hour. Then, cells were washed once with 250 μL 1× PBS. 50 μL of 1× cell signaling technology lysis buffer, phosphatase/protease inhibitor, and nuclease was added to each cell well, then put on a plate shaker in a 4° C. Fridge at 400 rpm for 20 minutes. Lysates were transferred into the black, MaxiSorp ELISA plate. The plate was covered with aluminum foil seal and placed onto a room temperature plate shaker at 500 rpm for 1 hour. Lysates were flicked from the plate and washed three times with TBST. 50 μL HRP-BRD4 antibody diluted in TBST was added to the black MaxiSorp plate. The plate was covered with an aluminum foil seal and placed onto a room temperature plate shaker at 500 rpm for 1 hour. The HRP-BRD4 antibody solution was flicked and washed three times with TBST. It was then washed three times with PBS. QuantaRed™ Enhanced Chemifluorescent HRP Substrate Kit solution was prepared and 100 μL was added to each well. The plate was covered with aluminum foil seal and incubated in a drawer for 1 hour. Fluorescent endpoint read was conducted on a SpectraMax plate reader.

Part II—Results

Figure 2:
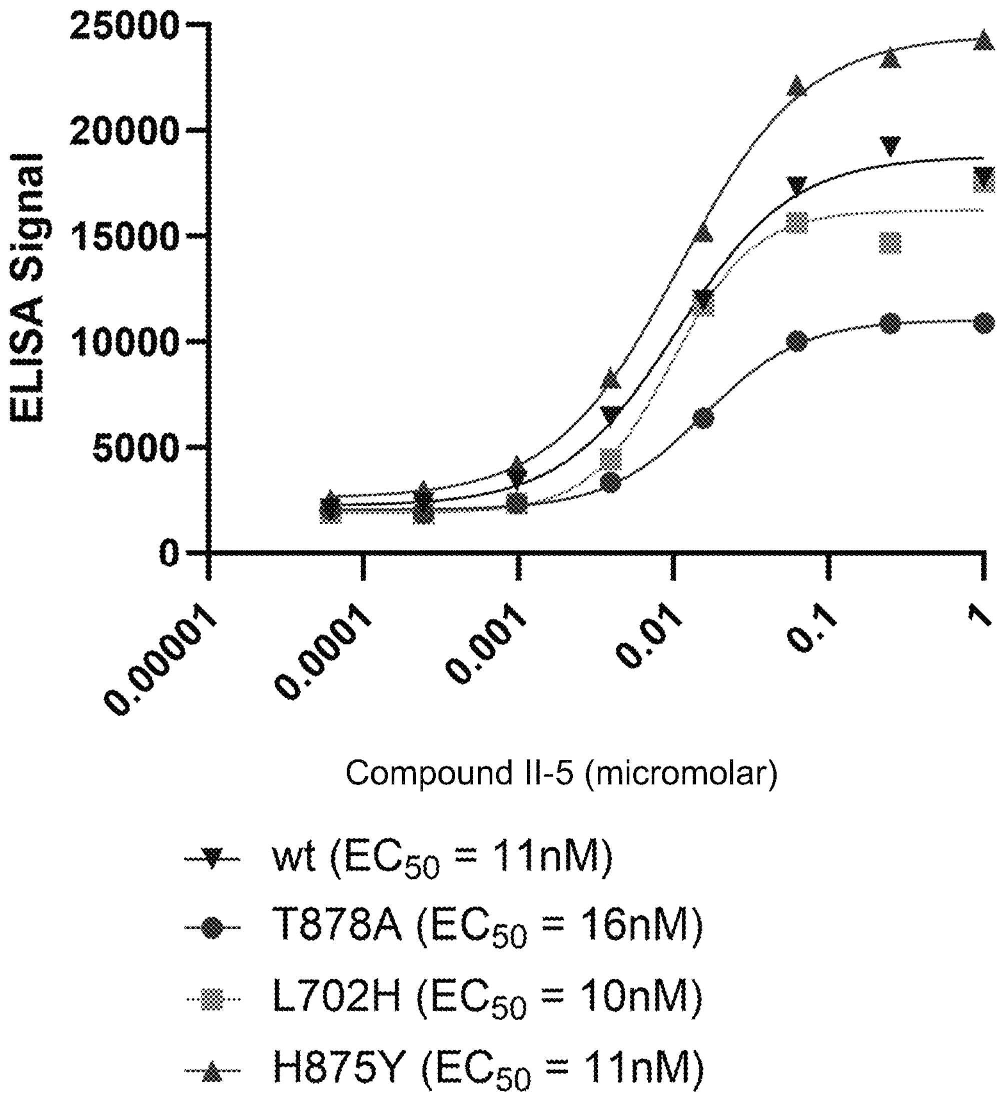
FIG. 2 is a graph showing detected ternary complex formation between Compound II-5, androgen receptor, and BRD4 protein, as further described in Example 68.

Detected ternary complex formation between Compound II-5, androgen receptor, and BRD4 protein is shown in FIG. 2. The results in FIG. 2 show that ternary complex formation between Compound II-5, androgen receptor, and BRD4 was detected using Trex293 cells engineered to express wtAR and the T878A, L702H and H875Y AR mutants.

Example 69—Assay for Inhibition of Growth of VCaP Cells

Compound II-5 was tested for ability to inhibit growth of VCaP cells. Experimental procedures and results are provided below.

Part I—Experimental Procedure

VCaP cells were maintained in standard culture media (ATCC DMEM plus 10% ATCC fetal bovine serum, and 1% pen-strep). Cells were seeded in 25 μL standard culture media in poly-D-lysine coated black clear-bottom 384-well plates at 3000 cells/well for continuous treatment. An additional plate under the same conditions was seeded as a Day 0 plate. Following seeding, plates were spun at 300×g for 30 seconds and cultured at 37° C. with 5% $CO_2$ in a humidified tissue culture incubator.

At 24 hours after seeding, Compound II-5 was titrated in 100% DMSO and diluted in standard culture media. 25 μL of the compound/media mixture was added to cells, bringing the total volume in each well to 50 μL. DMSO without Compound II-5 was used as a negative control. The day 0 plate was treated with the same percent DMSO as was used in the compound/media mixture but contained no compound. After treatment, plates were spun at 300×g for 30 seconds, then cultured at 37° C. with 5% $CO_2$ for 7 days in a humidified tissue culture incubator. The day 0 plate cell viability was quantified with CellTiter-Glo 2.0 reagent immediately following treatment under the same conditions as used below for measuring cell viability. On Day 7 of treatment, cell viability was quantified with CellTiter-Glo 2.0 reagent (Promega). Plates were equilibrated to room temperature for 30 minutes, then 25 μL of CellTiter-Glo 2.0 reagent was added to cells, bringing the total volume in each well to 75 μL. After reagent was added, plates were spun at 3000×g for 30 seconds then mixed on a shaker for two minutes at 500 rpm and then incubated at room temperature for 10 minutes. Following incubation, plates were spun at 300×g for 30 seconds, sealed with an optical adhesive cover, and luminescence was measured with an EnVision Plate Reader.

Data was normalized to the average Day 0 luminescence signal for a baseline. A four-parameter non-linear regression curve fit was applied to dose-response data in GraphPad Prism data analysis software to determine the half maximal growth inhibitory concentration ($GI_{50}$) for Compound II-5.

Part II—Results

Figure 3:
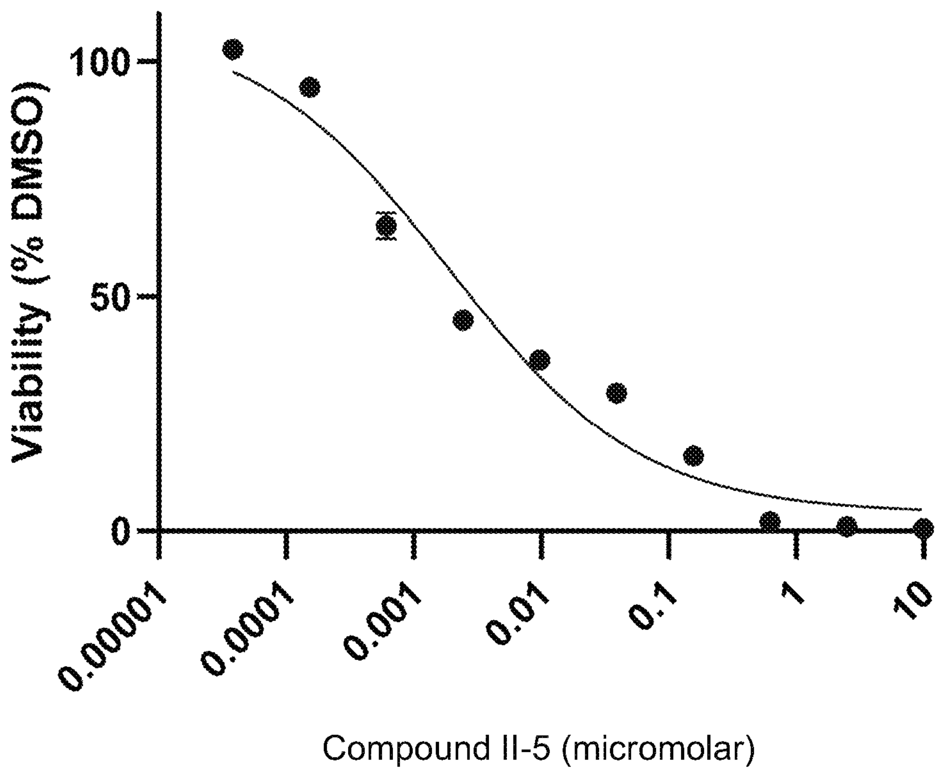
FIG. 3 is graph showing cell viability as a function of dose of Compound II-5, as further described in Example 69.

A cell viability dose-response curve obtained for Compound II-5 following the procedures above is provided in FIG. 3.

Example 70—Analysis of In Vivo Performance of an Exemplary Heterobifunctional Compound Compound II-5 was evaluated for in vivo performance when administered to CB17.SCID mice bearing VCaP cell tumors. Experimental procedures and results are provided below.

Part I—Experimental Procedure

A. VCaP Tumor Xenograft Studies

5M VCaP cells were subcutaneously implanted into CB17.SCID mice in 50% Matrigel (Corning). Mice were castrated under anesthesia once tumor volumes reached 100 $mm^3$. Tumors were then allowed to reach an average of approximately 150 $mm^3$ before randomization into efficacy arms. Tumors were measured twice weekly for Tumor Growth Inhibition (TGI) calculation. For PK/PD analysis, tumors were allowed to reach an average of 400 $mm^3$, before dosing the mice with test compound by oral gavage (n=5) for seven days. Mice were sacrificed 24 hours following the final dose, and tumors were harvested for downstream analysis. Plasma samples were collected from all dosed mice 2 hours following the final dose to determine test compound exposure by LC-MS/MS. Test compounds used in the experiment were (i) Compound II-5 and (ii) a commercially available nonsteroidal antiandrogen medication that has been approved by the United States Food and Drug Administration for treatment of prostate cancer (hereinafter "Compound A").

B. Tumor TR-FRET Trimer Assay

Tumors obtained from the Castrate VCaP Model were lysed in Cell Signaling Technology lysis buffer supplemented with protease/phosphatase inhibitors and nuclease. Each tumor was lysed in 10 μL of lysis buffer per mg of tumor and placed in a TissueLyser for 4 minutes at 20 Hz. Each sample was spun down at 16000×g for 10 minutes, the supernatant was removed, and a BCA assay was run to quantify the total protein concentration in each sample. In a white opaque 384 well plate each sample was diluted in supplemented CST lysis buffer to 48 and 24 μg of protein in a total volume of 16 μL. 4 μL of a 1:1 mixture of anti-androgen receptor and anti-BRD4 antibodies with donor and acceptor fluorophores were mixed into each well containing tumor samples. The plate was spun down at 300×g for one minute, placed on a plate shaker at 400 RPM for 10 minutes, spun down at 300×g for one minute, then sealed with a plate seal and stored overnight. Approximately 16 hours after adding antibodies, the plate was read on an Envision plate reader. The ratiometric value of each well was calculated by dividing the acceptor signal by the donor signal and multiplying by 10,000.

C. Determination of Amount of RNA by In Vivo qPCR

Tumors were lysed in 1.5 mL buffer RLT from the RNeasy Mini Kit (#74104, Qiagen) and pelleted. Total RNA was isolated using RNeasy Mini kit according to the manufacturers' instructions. After quantification, 1 μg RNA of each sample was used as a template for first strand C-DNA synthesis with Verso cDNA synthesis kit (#AB1453B, ThermoFisher) and the qRT-PCR reaction was performed using TaqMan Fast Advanced Master Mix (#4444964, ThermoFisher) with QuantStudio 5 Real Time PCR System (#A28570, Thermofisher) according to the manufacturers' instructions. The gene-specific TaqMan probes used in qRT-PCR were all purchased from Thermofisher and are HEXIM1 (#Hs00538918_s1), HPRT (#Hs99999909_m1), cMYC (#Hs00153408_m1), and TXNIP (#Hs0019-7750_m1). All PCR reactions were performed in technical triplicates.

D. Plasma PSA Analysis

All assay reagents were provided in the Human Prostate Specific Antigen (PSA) ELISA Kit (ab113327, Abcam). Plasma samples were collected at the end of the above-described Castrate VCaP Tumor Xenograft Model and diluted in assay diluent A for the absorbance signal to be in the linear range of the recombinant human PSA standard curve. Diluted samples and PSA standard were loaded into a pre-coated assay plate and incubated for 2.5 hours at ambient temperature. Samples and standards were flicked out, plate was washed, and biotinylated PSA detection antibody was added and incubated for 1 hour. Detection antibody was flicked out, plate was washed, and HRP-Streptavidin was added and incubated for 45 minutes. HRP-Streptavidin was flicked out, plate was washed, and TMB Substrate was added and incubated for 30 minutes while reading absorbance at 620 nm on the SpectraMax M5e, for up to 30 minutes. Stop solution was added directly on top of TMB Substrate. Endpoint read was obtained at an absorbance of 450 nm. During analysis, sample absorbances were multiplied by the dilution factor to calculate the concentration of PSA.

Part II—Results

Figure 4:
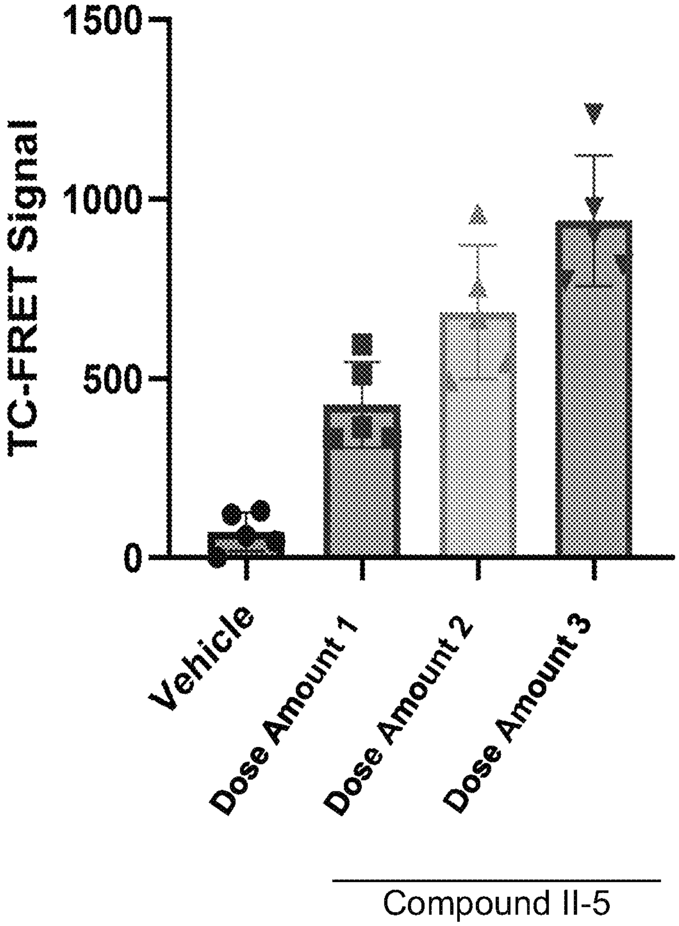
FIG. 4 is a graph that shows the relative ternary complex formation present with treatment of Compound II-5 at varying doses in samples collected at the end of the PK/PD Castrate VCaP Tumor Xenograft Model study, as further described in Example 70.

Ternary complex formation between Compound II-5, androgen receptor, and BRD4 protein was observed, and the results are provided in FIG. 4. FIG. 4 is a graph that shows the relative ternary complex formation present with treatment of Compound II-5 at varying doses in samples collected at the end of the PK/PD Castrate VCaP Tumor Xenograft Model study. In FIG. 4, Dose Amount 2 is two times greater than Dose Amount 1, and Dose Amount 3 is two times greater than Dose Amount 2.

Figure 5:
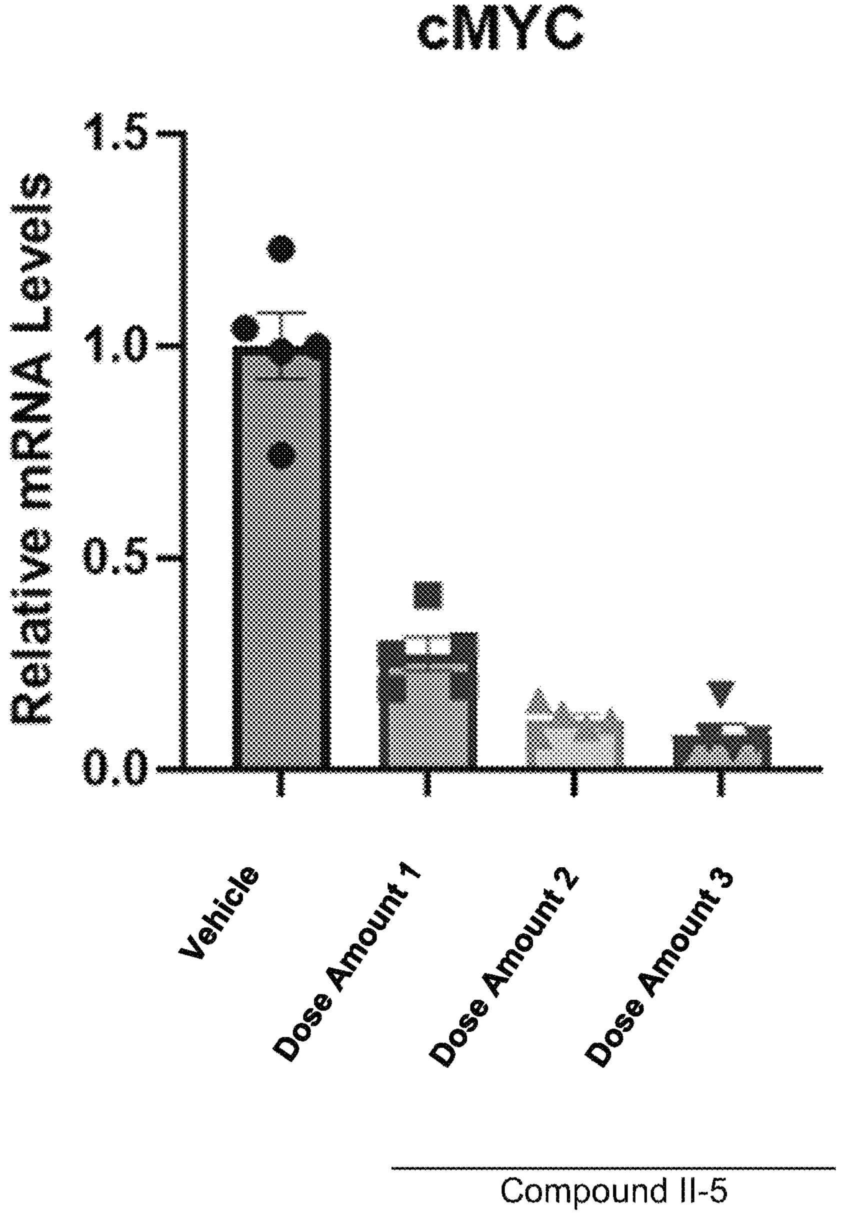
FIG. 5 is a graph that shows the relative total amount of cMYC mRNA present in tumors collected at the end of the PK/PD $Ar^{amp}$, $V7^{+}$ Castrate VcaP Model, for different dose amounts of Compound II-5, as further described in Example 70.

The relative total amount of cMYC mRNA present in tumors collected at the end of the PK/PD $Ar^{amp}$, $V7^{+}$ Castrate VcaP Model, for each of the different dose amounts of Compound II-5, is provided in FIG. 5. In FIG. 5, Dose Amount 2 is two times greater than Dose Amount 1, and Dose Amount 3 is two times greater than Dose Amount 2.

Figure 6:
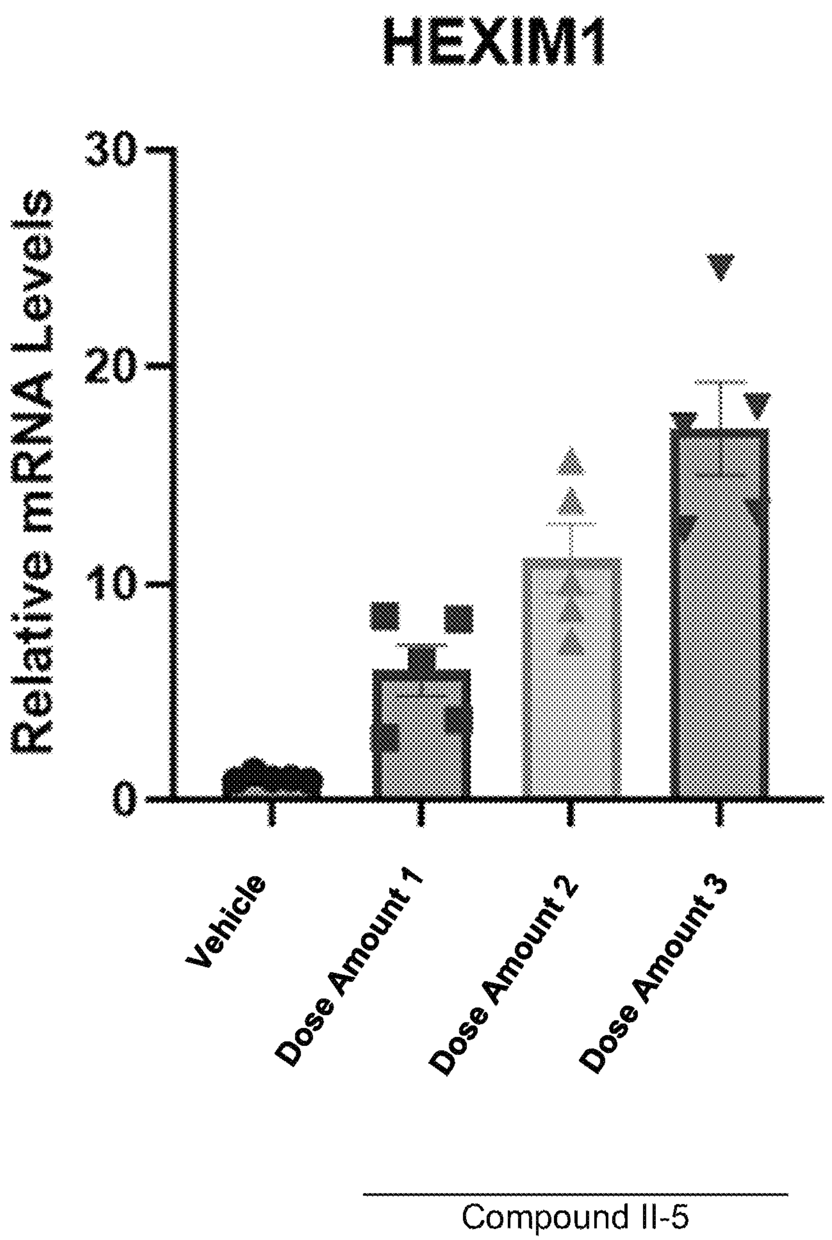
FIG. 6 is a graph that shows the relative total amount of HEXIM1 mRNA present in tumors collected at the end of the PK/PD $Ar^{amp}$, $V7^{+}$ Castrate VcaP Model, for each of the different dose amounts of Compound II-5, as further described in Example 70.
Figure 7:
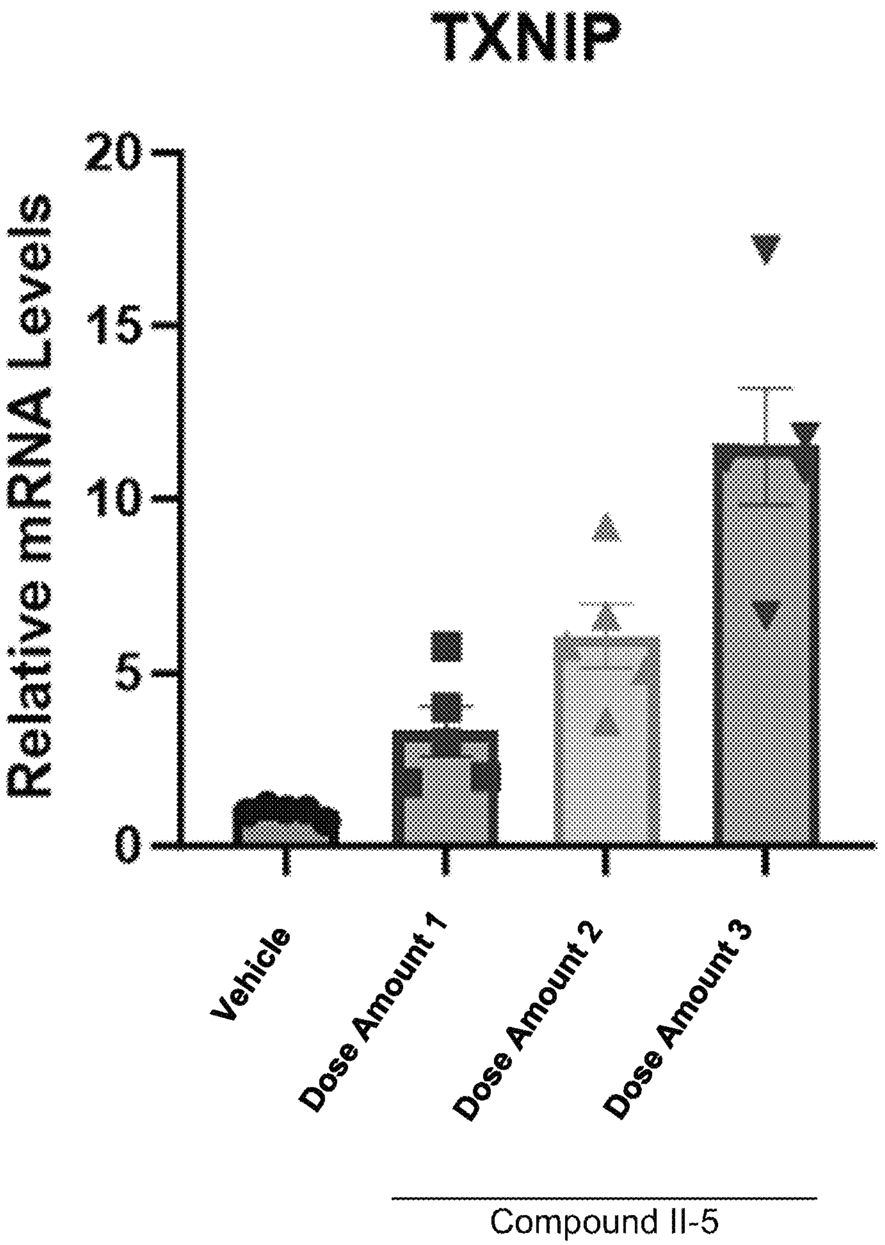
FIG. 7 is a graph that shows the relative total amount of TXNIP mRNA present in tumors collected at the end of the PK/PD $Ar^{amp}$, $V7^{+}$ Castrate VcaP Model, for each of the different dose amounts of Compound II-5, as further described in Example 70.

The relative total amount of HEXIM1 mRNA present in tumors collected at the end of the PK/PD $Ar^{amp}$, $V7^{+}$ Castrate VcaP Model, for each of the different dose amounts of Compound II-5, is provided in FIG. 6. In FIG. 6, Dose Amount 2 is two times greater than Dose Amount 1, and Dose Amount 3 is two times greater than Dose Amount 2. In FIG. 7, Dose Amount 2 is two times greater than Dose Amount 1, and Dose Amount 3 is two times greater than Dose Amount 2.

The relative total amount of TXNIP mRNA present in tumors collected at the end of the PK/PD $Ar^{amp}$, $V7^{+}$ Castrate VcaP Model, for each of the different dose amounts of Compound II-5, is provided in FIG. 7.

Figure 8:
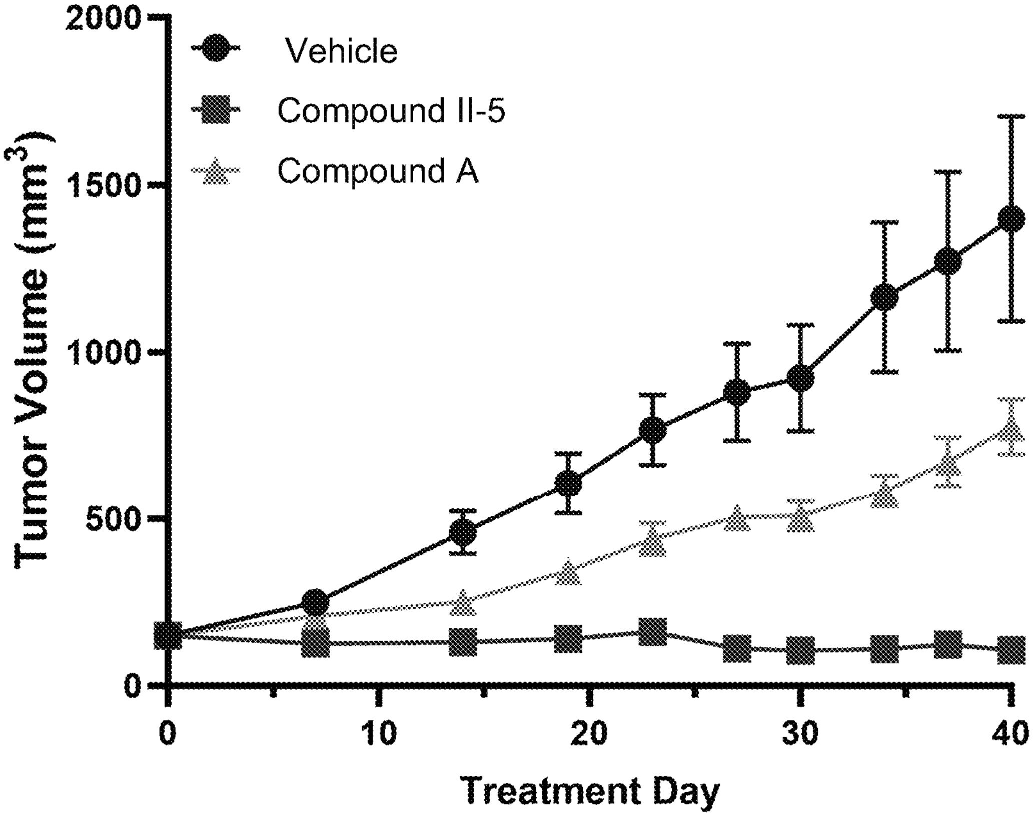
FIG. 8 is a graph that showing tumor growth in mice treated with either Compound II-5, Compound A, or vehicle, as further described in Example 70.
Figure 9:
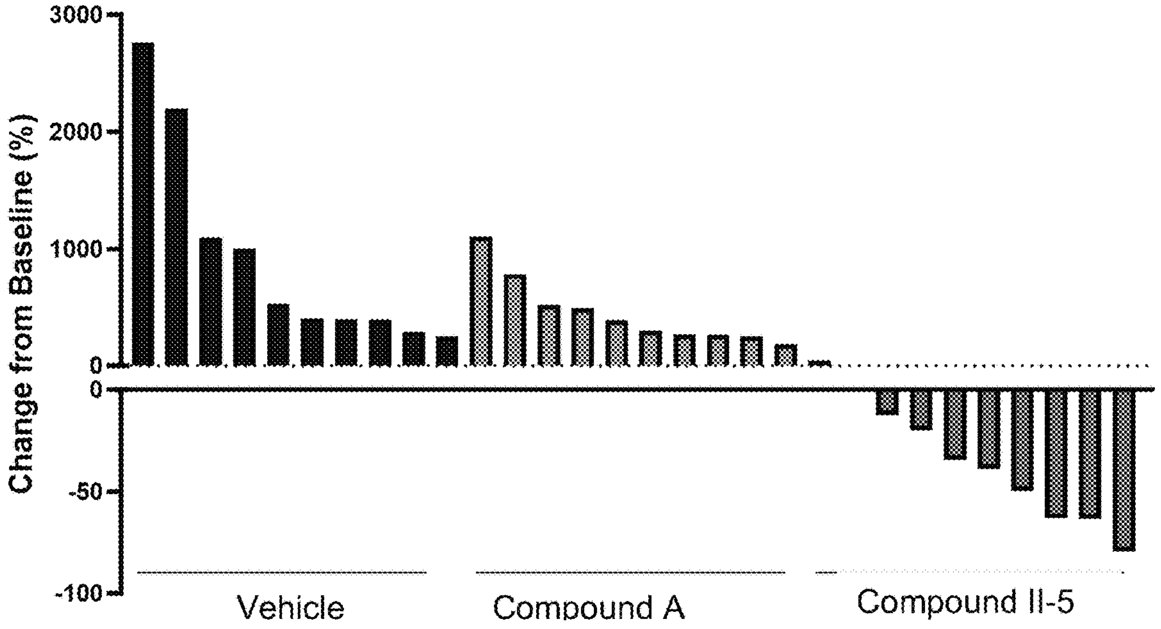
FIG. 9 is a waterfall plot that shows change in size of tumors at the end of study relative to baseline in mice treated with either Compound II-5, Compound A, or vehicle, as further described in Example 70.

Ability of Compound II-5 to inhibit tumor growth is demonstrated by results in FIG. 8, which is a graph showing tumor volume in mice that had been administered either Compound II-5, Compound A, or vehicle. The data in FIG. 8 were collected on mice in which the dose amount in mg/kg of Compound II-5 used in the experiment was the same dose amount used for Compound A, and the frequency of dosing was the same for each of Compound II-5 and Compound A. The results in FIG. 8 show that Compound II-5 was more effective in reducing tumor growth in this experiment than Compound A. A graph showing the change in size of tumors at the end of the study relative to baseline is shown in FIG. 9. The data in FIG. 9 were collected on mice in which the dose amount in mg/kg of Compound II-5 used in the experiment was the same dose amount used for Compound A, and the frequency of dosing was the same for each of Compound II-5 and Compound A.

Figure 10:
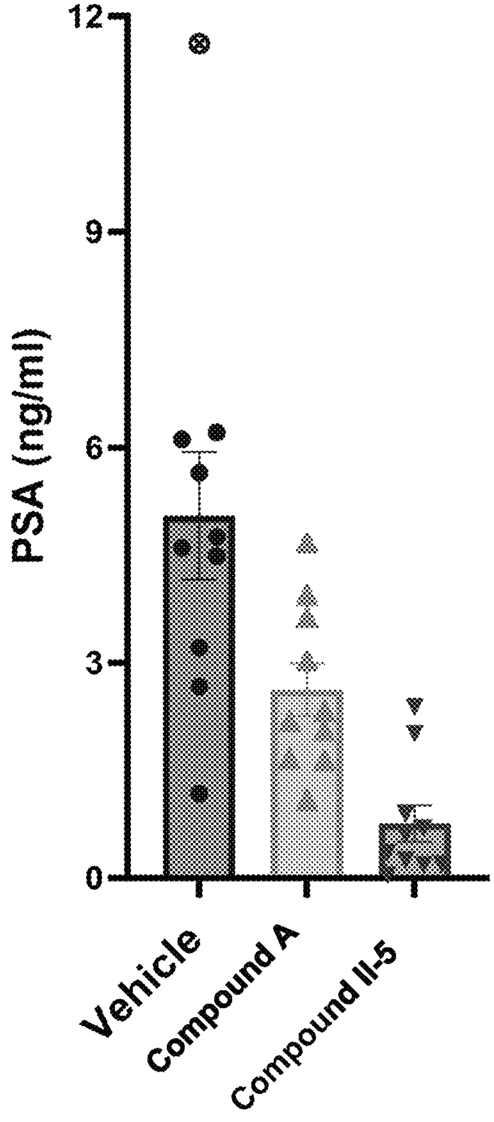
FIG. 10 is a graph that shows PSA plasma levels determined in mice at the end of the study treated with either Compound II-5, Compound A, or vehicle, as further described in Example 70.

PSA plasma levels determined in mice at the end of the study are shown in FIG. 10 for mice treated with either Compound II-5, Compound A, or vehicle. The data in FIG. 10 were collected on mice in which the dose amount in mg/kg of Compound II-5 used in the experiment was the same dose amount used for Compound A, and the frequency of dosing was the same for each of Compound II-5 and Compound A.

Example 71—Analysis of In Vivo Performance of an Exemplary Heterobifunctional Compound Compound II-5 was evaluated for in vivo performance when administered to NSG mice bearing LNCaP95 cell tumors. Experimental procedures and results are provided below.

Part I—Experimental Procedure

A. LNCaP95 Tumor Xenograft Studies

Male NSG mice were castrated under anesthesia, and then 7 days later 5M LNCaP95 cells in 50% Matrigel (Corning) were subcutaneously implanted into the right flank of the mice. Tumors were then allowed to reach an average of approximately 150 $mm^3$ before randomization into efficacy arms. Tumors were measured twice weekly for Tumor Growth Inhibition (TGI) calculation. Test compound was administered by mice by oral gavage. Test compounds used in the experiment were (i) Compound II-5 and (ii) a commercially available nonsteroidal antiandrogen medication that has been approved by the United States Food and Drug Administration for treatment of prostate cancer (hereinafter "Compound A").

In a first arm of the experiment, Compound II-5 was administered to mice according to a first dosing regimen in which the dosing frequency was the same as that used for vehicle and for Compound A. In a second arm of the experiment, Compound II-5 was administered to mice according to a second dosing regimen in which the dosing frequency was twice as often as that used for vehicle and for Compound A. In both the first arm and the second arm of the experiment, the amount of Compound II-5 administered at each dose event was 50% greater in mg/kg than the amount of Compound A administered at each dose event.

B. Plasma PSA Analysis

All assay reagents were provided in the Human Prostate Specific Antigen (PSA) ELISA Kit (ab113327, Abcam). Plasma samples were collected at the end of the above-described Tumor Xenograft Model and diluted in assay diluent A for the absorbance signal to be in the linear range of the recombinant human PSA standard curve. Diluted samples and PSA standard were loaded into a pre-coated assay plate and incubated for 2.5 hours at ambient temperature. Samples and standards were flicked out, plate was washed, and biotinylated PSA detection antibody was added and incubated for 1 hour. Detection antibody was flicked out, plate was washed, and HRP-Streptavidin was added and incubated for 45 minutes. HRP-Streptavidin was flicked out, plate was washed, and TMB Substrate was added and incubated for 30 minutes while reading absorbance at 620 nm on the SpectraMax M5e, for up to 30 minutes. Stop solution was added directly on top of TMB Substrate. Endpoint read was obtained at an absorbance of 450 nm. During analysis, sample absorbances were multiplied by the dilution factor to calculate the concentration of PSA.

Part II—Results

Figure 11:
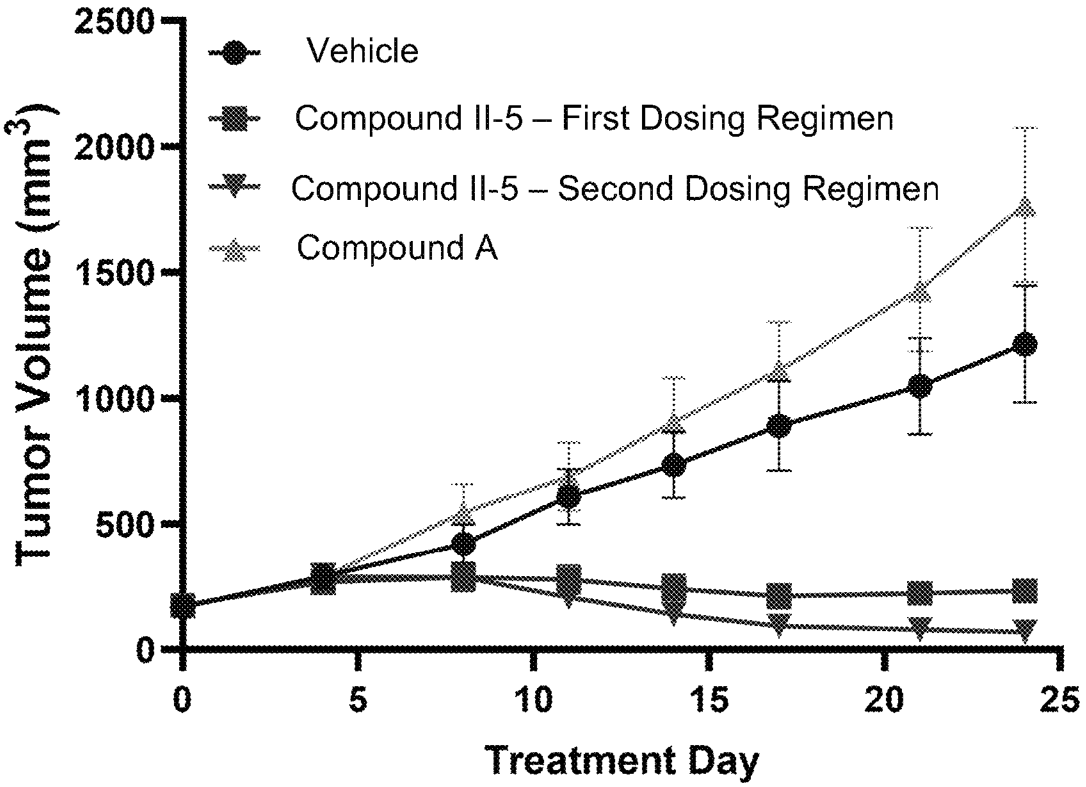
FIG. 11 is a graph showing tumor volume in mice treated with (i) vehicle, (ii) Compound II-5 according to a first dosing regimen in which the dosing frequency was the same as that used for vehicle and for Compound A, (iii) Compound II-5 according to a second dosing regimen in which the dosing frequency was twice as often as that used for vehicle and for Compound A, or (iv) Compound A, as further described in Example 71.
Figure 12:
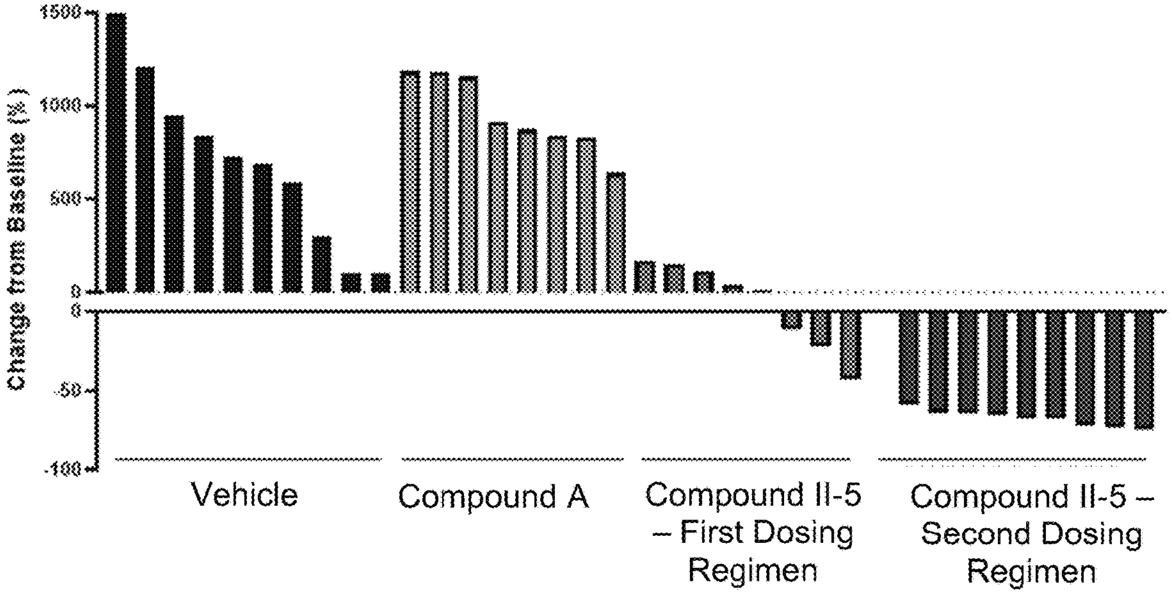
FIG. 12 is a waterfall plot that shows change in size of tumors at the end of study relative to baseline in mice treated with (i) vehicle, (ii) Compound II-5 according to a first dosing regimen in which the dosing frequency was the same as that used for vehicle and for Compound A, (iii) Compound II-5 according to a second dosing regimen in which the dosing frequency was twice as often as that used for vehicle and for Compound A, or (iv) Compound A, as further described in Example 71.
Figure 13:
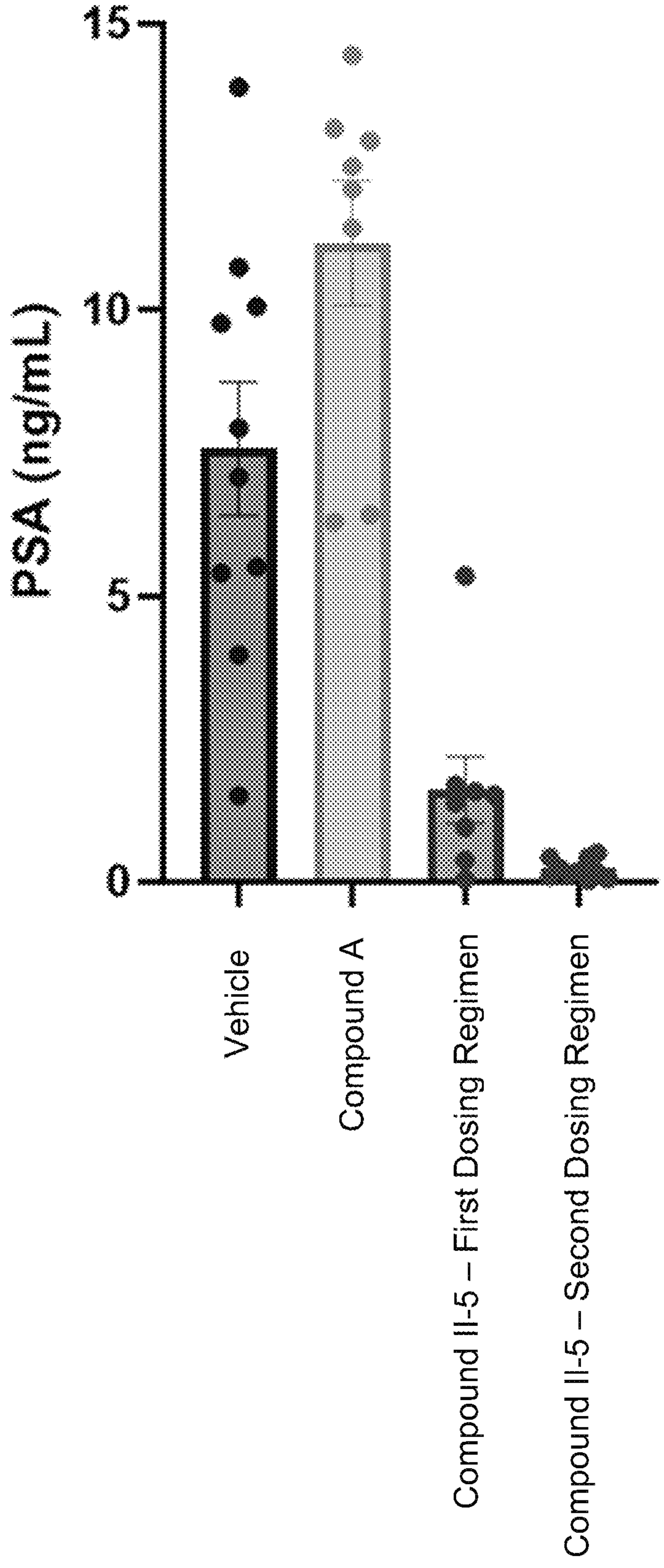
FIG. 13 is a graph that shows PSA plasma levels determined in mice at the end of the study treated with (i) vehicle, (ii) Compound II-5 according to a first dosing regimen in which the dosing frequency was the same as that used for vehicle and for Compound A, (iii) Compound II-5 according to a second dosing regimen in which the dosing frequency was twice as often as that used for vehicle and for Compound A, or (iv) Compound A, as further described in Example 71.

Results are provided in FIGS. 11,12, and 13. FIG. 11 provides a graph showing tumor volume in mice treated with (i) vehicle, (ii) Compound II-5 according to a first dosing regimen in which the dosing frequency was the same as that used for vehicle and for Compound A, (iii) Compound II-5 according to a second dosing regimen in which the dosing frequency was twice as often as that used for vehicle and for Compound A, or (iv) Compound A.

A graph showing the change in size of tumors at the end of the study relative to baseline is shown in FIG. 12 for mice treated with (i) vehicle, (ii) Compound II-5 according to a first dosing regimen in which the dosing frequency was the same as that used for vehicle and for Compound A, (iii) Compound II-5 according to a second dosing regimen in which the dosing frequency was twice as often as that used for vehicle and for Compound A, or (iv) Compound A.

PSA plasma levels determined in mice at the end of the study are shown in FIG. 13 for mice treated with (i) vehicle, (ii) Compound II-5 according to a first dosing regimen in which the dosing frequency was the same as that used for vehicle and for Compound A, (iii) Compound II-5 according to a second dosing regimen in which the dosing frequency was twice as often as that used for vehicle and for Compound A, or (iv) Compound A.

Example 72—Analysis of Relative In Vivo Performance of Exemplary Heterobifunctional Compounds Compound II-5 and Compound B (depicted in Example 66, above) were evaluated for in vivo performance when administered to CB17.SCID mice bearing VCaP cell tumors. Experimental procedures are described in Example 70, above. Compound II-5 and Compound B were both administered at the same dose and dosing frequency. Results are provided below.

Figure 20:
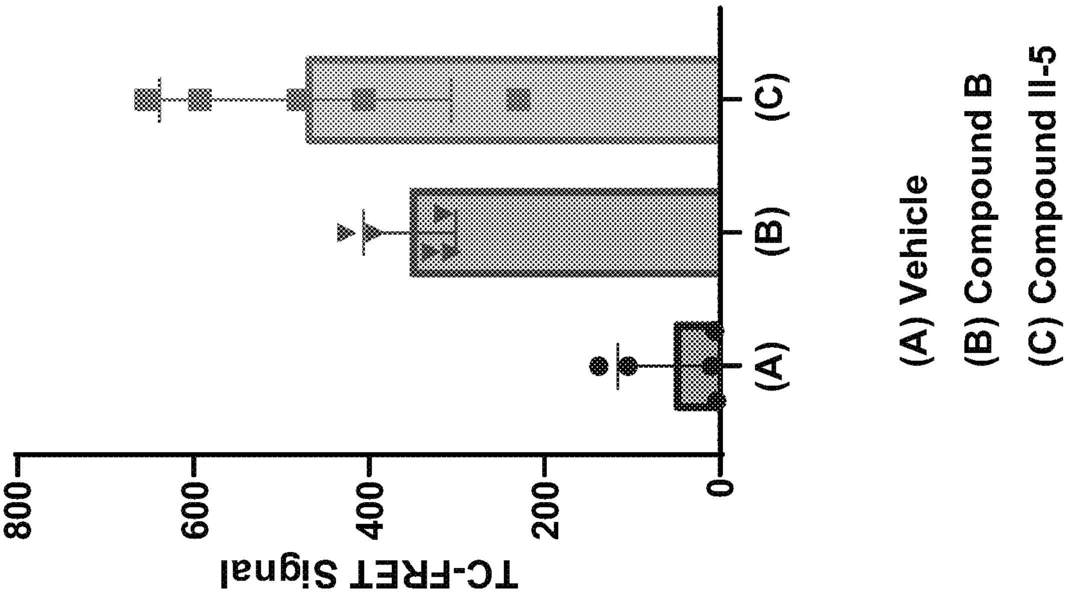
FIG. 20 is a graph that shows the relative ternary complex formation present in samples collected at the end of the PK/PD Castrate VCaP Tumor Xenograft Model study, for mice treated with Compound II-5, Compound B, or vehicle, as further described in Example 72.

Ternary complex formation between Compound II-5 (or Compound B), androgen receptor, and BRD4 protein was observed, and the results are provided in FIG. 20. FIG. 20 is a graph that shows the relative ternary complex formation present in samples collected at the end of the PK/PD Castrate VCaP Tumor Xenograft Model study, for mice treated with Compound II-5, Compound B, or vehicle.

Figure 21:
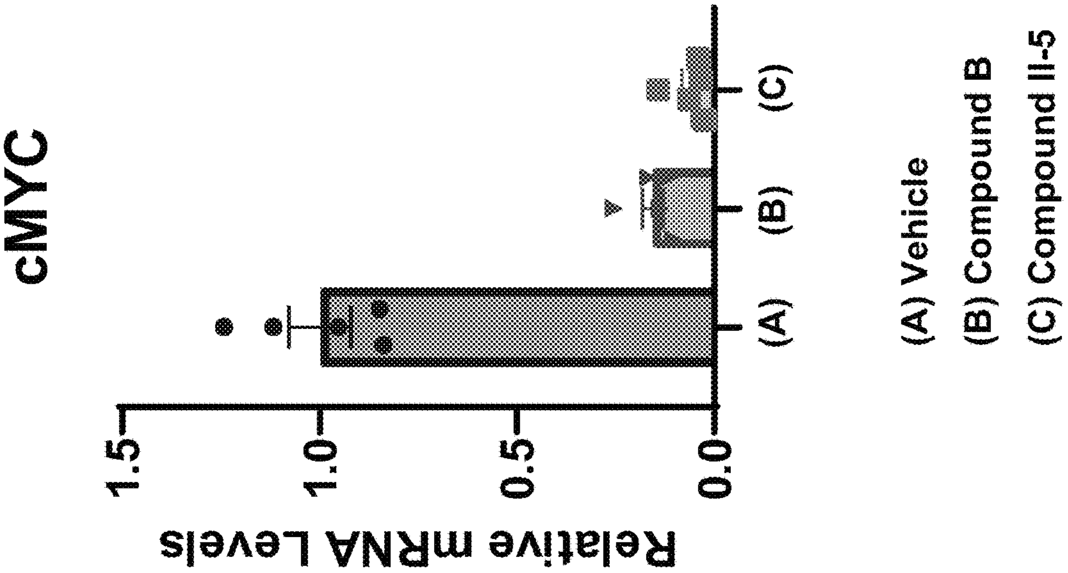
FIG. 21 is a graph that shows the relative total amount of cMYC mRNA present in tumors collected at the end of the PK/PD $Ar^{amp}$, $V7^{+}$ Castrate VcaP Model, for each of Compound II-5 and Compound B, as further described in Example 72.

The relative total amount of cMYC mRNA present in tumors collected at the end of the PK/PD $Ar^{amp}$, $V7^+$ Castrate VcaP Model, for each of Compound II-5 and Compound B, is provided in FIG. 21.

Figure 22:
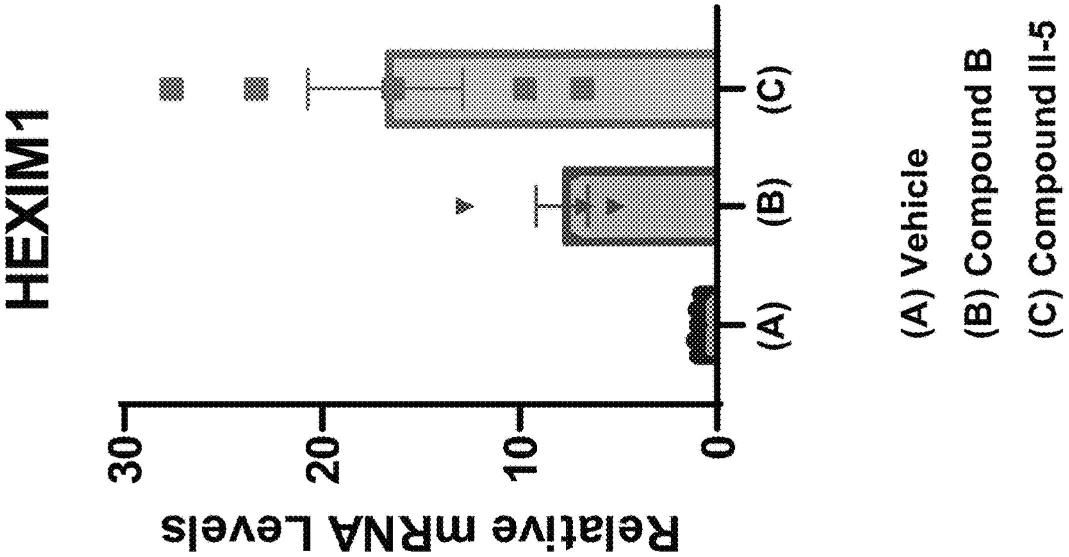
FIG. 22 is a graph that shows the relative total amount of HEXIM1 mRNA present in tumors collected at the end of the PK/PD $Ar^{amp}$, $V7^{+}$ Castrate VcaP Model, for each of Compound II-5 and Compound B, as further described in Example 72.

The relative total amount of HEXIM1 mRNA present in tumors collected at the end of the PK/PD $Ar^{amp}$, $V7^+$ Castrate VcaP Model, for each of Compound II-5 and Compound B, is provided in FIG. 22.

Figure 23:
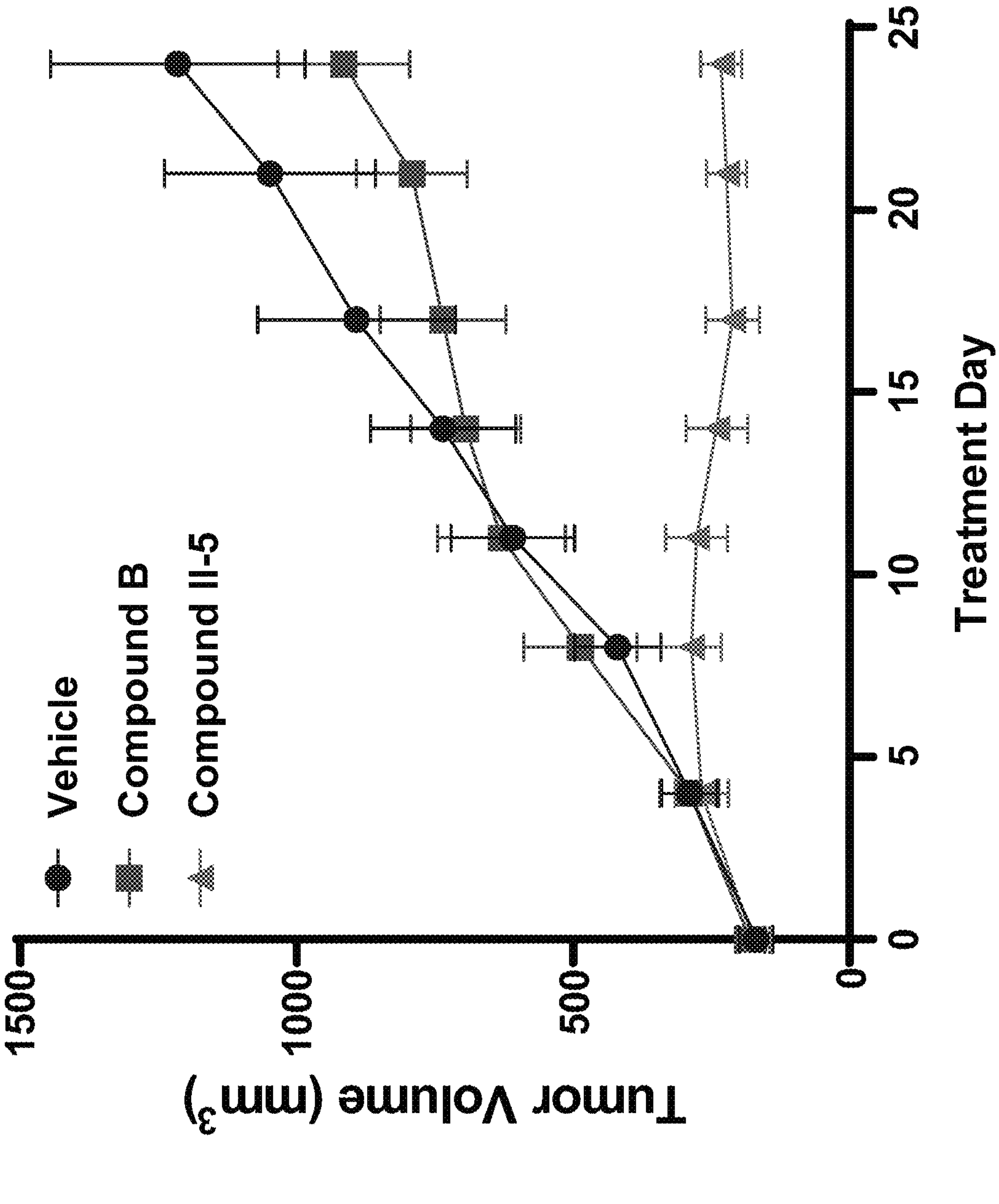
FIG. 23 is a graph showing tumor volume in mice treated with (i) vehicle, (ii) Compound II-5, or (iii) Compound B, as further described in Example 73.

Example 73—Analysis of Relative In Vivo Performance of Exemplary Heterobifunctional Compounds Compound II-5 and Compound B (depicted in Example 66, above) were evaluated for in vivo performance when administered to NSG mice bearing LNCaP95 cell tumors. Experimental procedures are described in Example 71, above. Compound II-5 and Compound B were both administered at the same dose and dosing frequency. Results are provided in FIG. 23, which provides a graph showing tumor volume in mice treated with (i) vehicle, (ii) Compound II-5, or (iii) Compound B.

Example 74—BRD4 Cellular TE Assay with Inducible Androgen Receptor

Compound II-5 and Compound B were tested in a BRD4 cellular TE assay with inducible androgen receptor (AR). Experimental procedures and results are provided below.

Part I-Experimental Procedure

HEK293 cells with NanoLuc knocked into endogenous BRD4 loci using CRISPR/Cas to create a BRD4nluc fusion protein were purchased from Promega. These cells were then stably transfected with doxycycline-inducible androgen receptor (AR). Cells were seeded at 10 million cells, with or without 100 ng/mL doxycycline, in T175 cm^2 flasks and incubated at 37° C. with 5% $CO_2$ in a humidified tissue culture incubator for 16 hours. The cells were cultured in DMEM medium supplemented with 10% Tet free FBS and 1% pen strep. After the 16-hour incubation, cells were collected and seeded in phenol red free Opti-MEM (Thermo 11058021) at 24,000 cells/well in a white 384 well Optiplate LBS (Revvity 6057480), then spun down for 30 seconds at 300 g. Cells were then treated with Compound II-5 or Compound B titrated in 100% DMSO and further diluted in phenol red free Opti-MEM. The plate was spun down at 300 g for 30 seconds, placed on a shaker for 30 seconds at 700 rpm, and placed in the incubator for 4 hours. After 4 hours, Promega BRD4 tracer was diluted in tracer dilution buffer and added to the plate (Nano BRET Kit: N2131 Promega). The plate was spun down, then placed at room temperature on a plate shaker, and returned to the incubator for 2 hours. Afterwards, the plate was cooled to room temperature for 15 minutes, then the substrate and extracellular inhibitor diluted in Opti-MEM was added to the plate according to manufacturer's instructions. The plate was placed on a shaker at 700 rpm for 30 seconds, incubated for 3 minutes, and placed on an Envision plate reader to capture the BRET signal. A ratio was calculated with the data according to the following: (Acceptor signal/Donor signal)×1000. Data was normalized to vehicle control.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A compound represented by Formula It or Iv, or a pharmaceutically acceptable salt thereof:

(It)

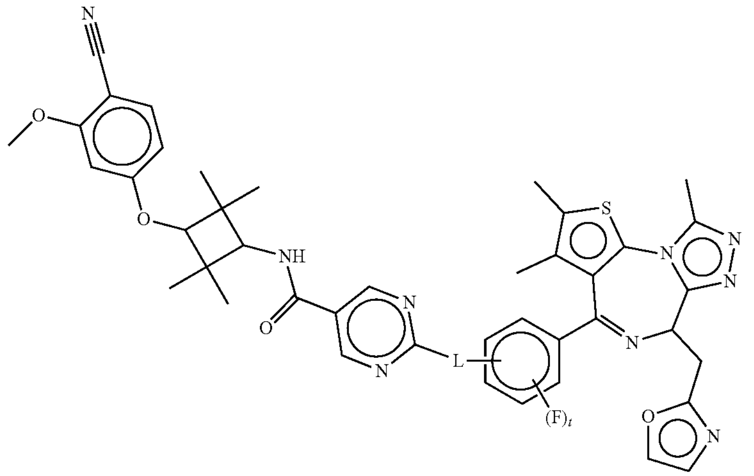

(Iv)

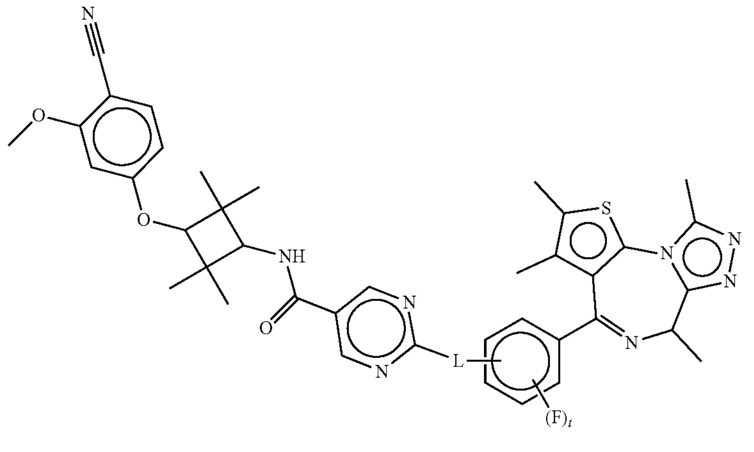

Part II—Results

Figure 24:
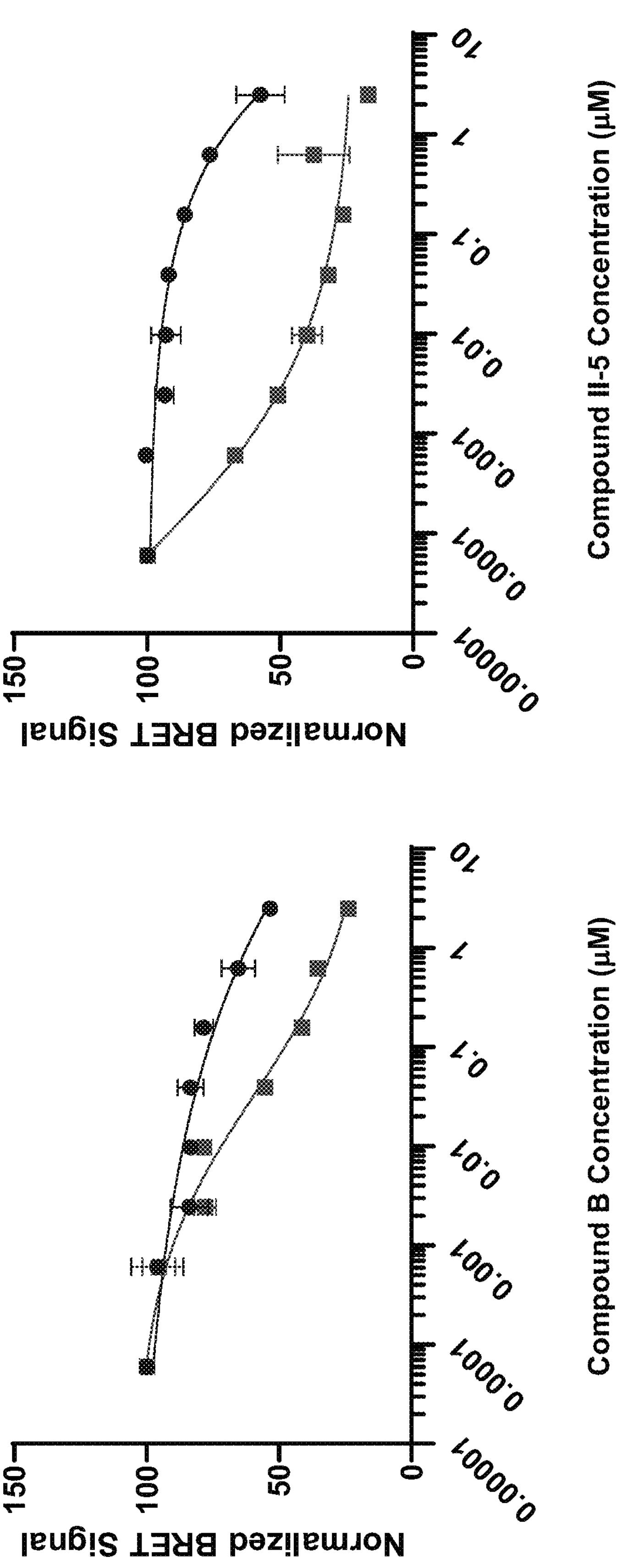
FIG. 24 provides graphs showing normalized BRET signal versus compound concentration for Compound II-5 and Compound B in the BRD4 cellular TE assay with inducible androgen receptor (AR), as further described in Example 74.

Dose-response curves obtained for each of Compound II-5 and Compound B, each with and without induction of androgen receptor (AR), following the procedures described above, is provided in FIG. 24.

INCORPORATION BY REFERENCE

The entire disclosure of each of the patent documents and scientific articles referred to herein is incorporated by reference for all purposes.

wherein

L is one of the following:

(i)-(7-11 membered spirocyclic or fused bicyclic saturated heterocyclic ring containing 1, 2, or 3 heteroatoms independently selected from nitrogen and oxygen)-O-*, wherein * is the point of attachment to the phenylene group in said formula;

(ii) a 7-11 membered spirocyclic or fused bicyclic saturated heterocyclic ring containing 1, 2, or 3 heteroatoms independently selected from nitrogen and oxygen; or (iii)-(7-11 membered spirocyclic saturated heterocyclic ring containing 1 or 2 heteroatoms selected from nitrogen)-($C_{2-4}$ alkynylene)-*, wherein * is the point of attachment to the phenylene group in said formula; and t is 0 or 1.

2. The compound of claim 1, wherein the compound is a compound of Formula It.

3. The compound of claim 2, wherein tis 0.

4. The compound of claim 3, wherein L is a -(7-11 membered spirocyclic or fused bicyclic saturated heterocyclic ring containing 1, 2, or 3 heteroatoms independently selected from nitrogen and oxygen)-O-***, wherein * is the point of attachment to the phenylene group in said formula.

5. The compound of claim 3, wherein L is -(7-11 membered spirocyclic saturated heterocyclic ring containing 1 or 2 heteroatoms selected from nitrogen)-($C_{2-4}$ alkynylene)-*, wherein * is the point of attachment to the phenylene group in said formula.

6. The compound of claim 1, wherein the compound is represented by Formula Iab or a pharmaceutically acceptable salt thereof:

(Iab)

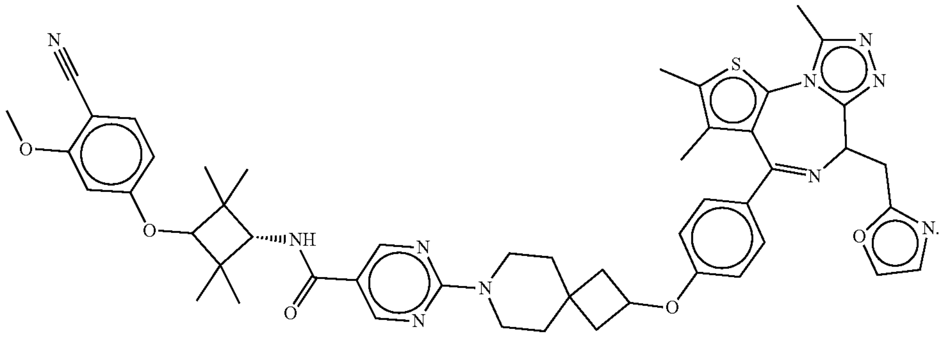

7. The compound of claim 1, wherein the compound is represented by Formula Iac or a pharmaceutically acceptable salt thereof:

(Iac)

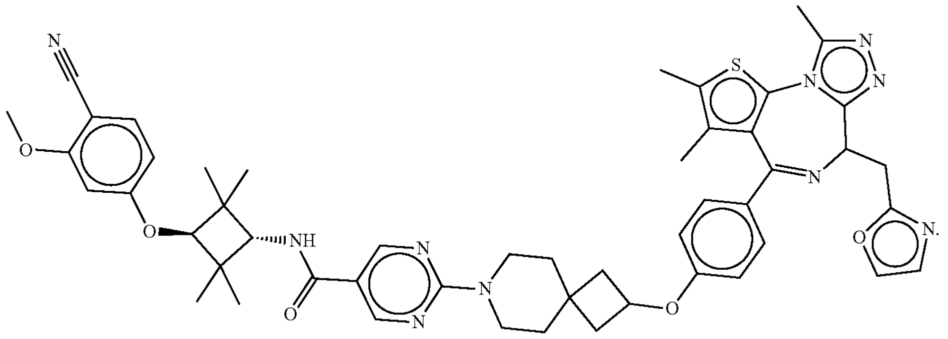

8. The compound of claim 1, wherein the compound is

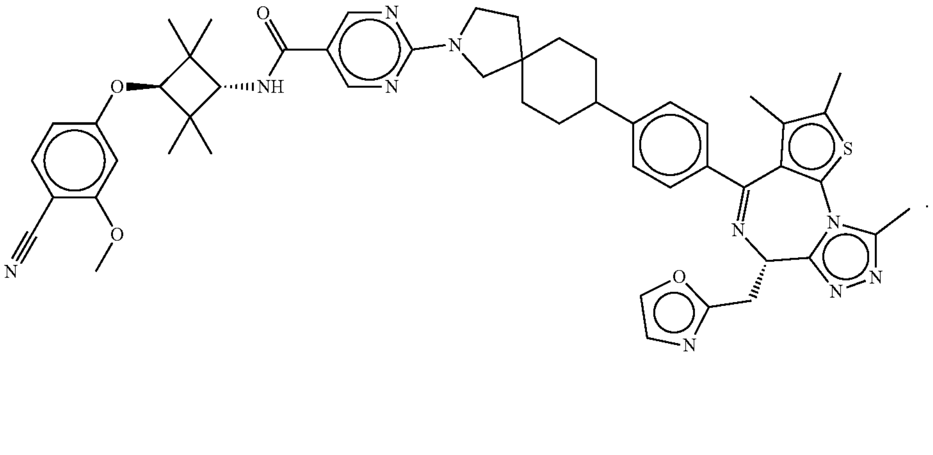

9. A compound represented by:
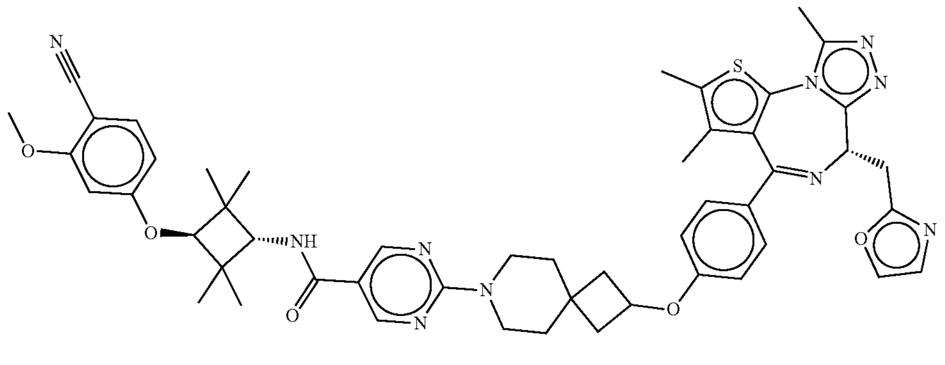
or a pharmaceutically acceptable salt thereof.
10. The compound of claim 9, wherein the compound is
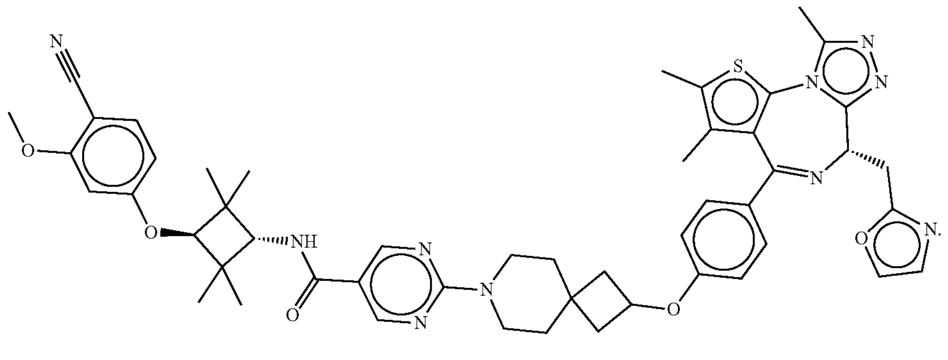
11. A compound selected from the following or a pharmaceutically acceptable salt thereof:
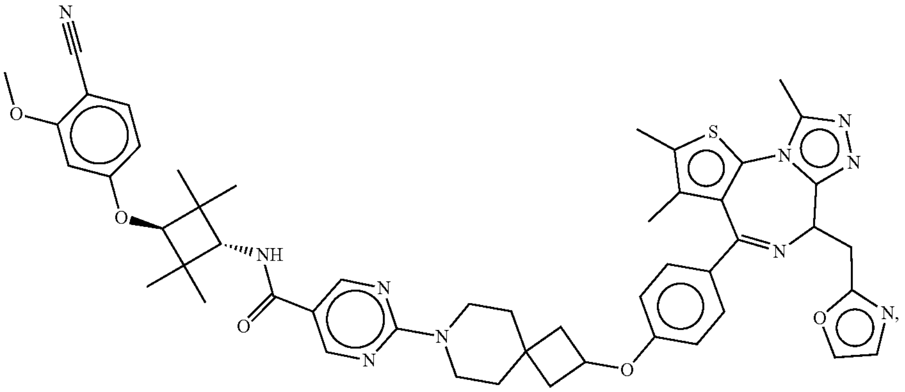
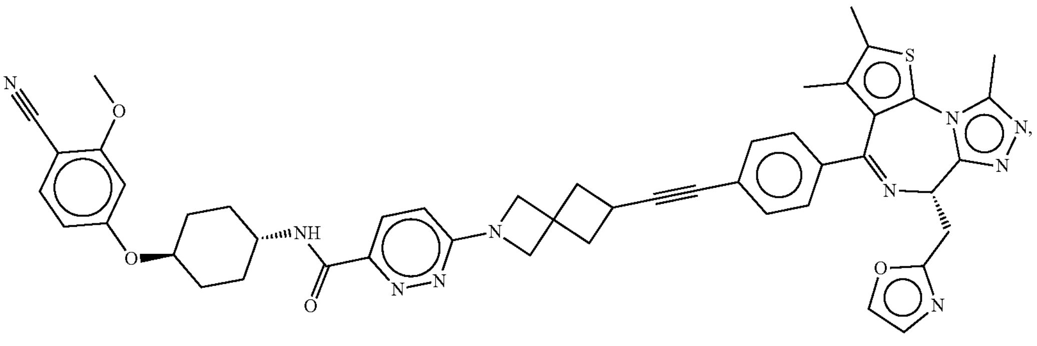
or -continued

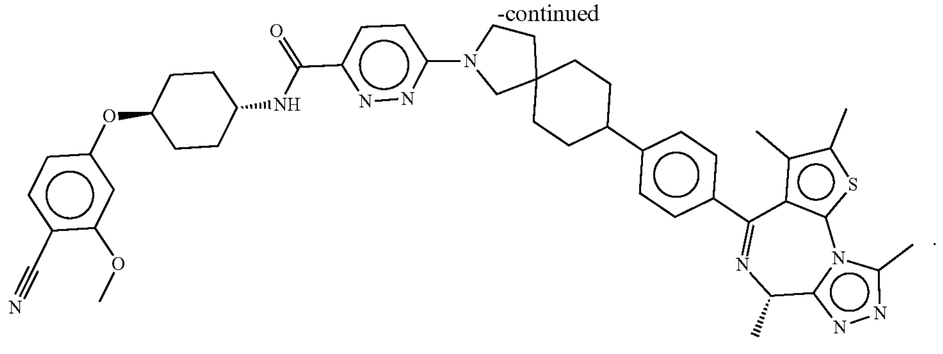

12. The compound of claim 11, wherein the compound is

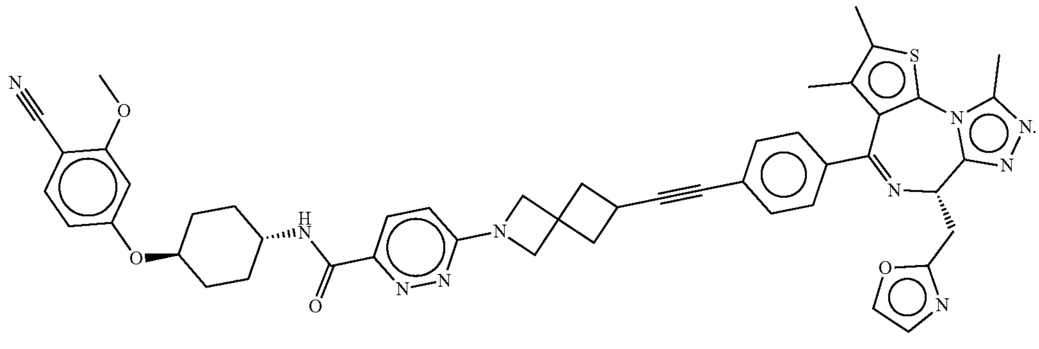

13. The compound of claim 11, wherein the compound is

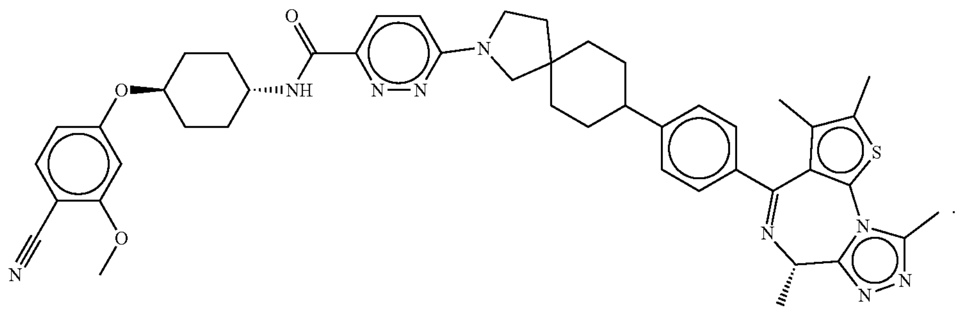

14. A pharmaceutical composition comprising a compound of claim 1 and a pharmaceutically acceptable carrier.

15. A pharmaceutical composition comprising a compound of claim 7 and a pharmaceutically acceptable carrier.

16. A pharmaceutical composition comprising a compound of claim 10 and a pharmaceutically acceptable carrier.

17. A pharmaceutical composition comprising a compound of claim 13 and a pharmaceutically acceptable carrier.

18. A method of treating cancer, comprising administering to a patient in need thereof a therapeutically effective amount of a compound of claim 1 to treat the cancer, wherein the cancer is prostate cancer or breast cancer.

19. The method of claim 18, wherein the compound is a compound of claim 10.

20. A method of treating cancer, comprising administering to a patient in need thereof a therapeutically effective amount of a compound of claim 13 to treat the cancer, wherein the cancer is prostate cancer, or breast cancer.

21. A method of treating prostate cancer, comprising administering to a patient in need thereof a therapeutically effective amount of a compound of claim 1 to treat the prostate cancer.

22. A method of treating prostate cancer, comprising administering to a patient in need thereof a therapeutically effective amount of a compound of claim 10 to treat the prostate cancer.

23. The method of claim 22, wherein the patient is a human.

24. A method of treating prostate cancer, comprising administering to a patient in need thereof a therapeutically effective amount of a compound of claim 13 to treat the prostate cancer.

25. A method of treating castrate resistant metastatic prostate cancer, comprising administering to a patient in need thereof a therapeutically effective amount of a compound of claim 1 to treat the castrate resistant metastatic prostate cancer.

26. A method of treating castrate resistant metastatic prostate cancer, comprising administering to a patient in need thereof a therapeutically effective amount of a compound of claim 10 to treat the castrate resistant metastatic prostate cancer.

27. The method of claim 26, wherein the patient is a human.

28. A method of causing death of a cancer cell, comprising contacting a cancer cell with an effective amount of a compound of claim 1 to cause death of the cancer cell, wherein the cancer cell is selected from a prostate cancer, or breast cancer cell.

29. A method of causing death of a prostate cancer cell, comprising contacting a prostate cancer cell with an effective amount of a compound of claim 1 to cause death of the prostate cancer cell.

30. A method of causing death of a prostate cancer cell, comprising contacting a prostate cancer cell with an effective amount of a compound of claim 10 to cause death of the prostate cancer cell.

* * * * *